(12) United States Patent
Norman et al.

(10) Patent No.: US 6,822,097 B1
(45) Date of Patent: Nov. 23, 2004

(54) COMPOUNDS AND METHODS OF USES

(75) Inventors: Mark H. Norman, Thousand Oaks, CA (US); Hui-Ling Wang, Thousand Oaks, CA (US); Robert Rzasa, Ventura, CA (US); Wenge Zhong, Thousand Oaks, CA (US); Thomas Nguyen, Thousand Oaks, CA (US); Matthew Kaller, Ventura, CA (US); Hu Liu, Brooklyn, NY (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 10/360,226

(22) Filed: Feb. 6, 2003

Related U.S. Application Data

(60) Provisional application No. 60/355,313, filed on Feb. 7, 2002.

(51) Int. Cl.[7] ............... C07D 215/16; C07D 215/20; C07D 215/36; A61K 31/47
(52) U.S. Cl. ............... 546/153; 546/155; 546/157; 546/158; 514/312; 514/314
(58) Field of Search ............... 546/153, 155, 546/157, 158; 514/312, 314

(56) References Cited

U.S. PATENT DOCUMENTS

| | | | |
|---|---|---|---|
| 4,127,574 A | 11/1978 | Hardtmann et al. | |
| 4,547,511 A | 10/1985 | Eriksoo et al. | |
| 5,252,584 A | 10/1993 | Carling et al. | |
| 5,480,883 A | 1/1996 | Spada et al. | |
| 5,643,932 A | 7/1997 | Chihiro et al. | |
| 5,945,422 A | 8/1999 | Doherty et al. | |
| 6,605,617 B2 * | 8/2003 | Renhowe et al. | ............ 514/312 |

FOREIGN PATENT DOCUMENTS

| | | |
|---|---|---|
| EP | 1295883 A1 | 3/2003 |
| WO | WO 92/18483 | 10/1992 |
| WO | WO 96/22990 A2 | 8/1996 |
| WO | WO 96/34867 A1 | 11/1996 |
| WO | WO 99/09030 A1 | 2/1999 |
| WO | WO 01/28993 A2 | 4/2001 |
| WO | WO 01/29025 A2 | 4/2001 |
| WO | WO 01/62251 A1 | 8/2001 |
| WO | WO 01/62252 A1 | 8/2001 |
| WO | WO 01/70227 A1 | 9/2001 |
| WO | WO 01/70228 A1 | 9/2001 |
| WO | WO 01/98300 A1 | 12/2001 |

OTHER PUBLICATIONS

M. Abass, "Chemistry of Substituted Quinolinones, Part II Synthesis of Novel 4–Pyrazolylquinolinone Derivatives", Synthetic Communications, 30(15): 2735–2757 (2000).

K. Ashok et al., "Synthesis of 1–aryl–4–ethoxypyrazolo–[4,3–c]quinolines and 3–(3–arylisoxazol–5–yl)–2/4–hydroxyquinolin–2/4–ones: Revision of the reported wrong structures", Indian Journal of Chemistry, 32B: 786–787 (1993).

A. Catania et al., "Expression and localization of cyclin–dependent kinase 5 in apoptotic human glioma cells", Neuro–Oncology, 89–98 (2001).

A. Doroshenko et al., "Physical Properties and Theoretical Considerations", Chem. Heterocycl. Compd., 33:1177–1184 (1998).

T. El–Emary et al., "New polycylic azines derived from pyrazolo[3,4–b]pyridine", Pharmazie, 55:356–358 (2000).

K. Gewald et al., Synthesis of New Substituted 1–(3–Pyridyl)pyridinium Salts and 3,4–Diamino–2(1H)–pyridinones, Liebigs Ann., 787–791 (1995).

S. Ibrahim, "Synthesis of Some Heterocyclic Rings as Substituents to Quinolone Moiety", Indian Journal of Heterocyclic Chemistry, 4:125–130 (1994).

R. Maccioni et al., "The protein kinase Cdk5: Structural aspects, roles in neurogenesis and involvement in Alzhelmer's pathology", Eur. J. Biochem., 268:1518–1527 (2001).

E. Mohamed et al., "Synthesis of 3–Heteroaryl–4–hydroxybenzocarbostyrils", J. Indian Chem. Soc., 69:82–84 (1992).

S. Naruto et al., "Photoylsis of 4–oxo–4H–Benzisoxazolo[2,3–a]pyridines", Chem. Pharm. Bull., 30(9):3421–3423 (1982).

T. Noguchi et al., "Involvement of Cyclins in Cell Proliferation and Their Clinical Implications in Soft Tissue Smooth Muscle Tumors", American Journal of Pathology, 156(6):2135–2147 (2000).

G. Paglini et al., "The role of the Cdk5–p35 kinase in neuronal development", Eur. J. Biochem., 268:1528–1533 (2001).

M. Rehwald et al., "Synthesis of Hetaryl–pyridinium Salts and Fused 3–Amino–pyrid–2–ones", J. Prakt. Chem., 342(4):371–378 (2000).

A. Sayed et al., "Some 3–Substituted–4–Hydroxycarbostyrils", Acta Chimica Academiae Scientiarum Hungaricae, Tomus 94(2):131–139 (1977).

A. Senderowicz et al., "Preclinical and Clinical Development of Cyclin–Dependent Kinase Modulators", Journal of the National Cancer Institute, 92(5):376–387 (2000).

G. Tennant et al., "Synthesis of 5–substituted imidazo[4,5–b]pyridinones by annelation of 4–amino–5–ethoxalyl–1 H–imidazole derivatives with active methylene compounds", J. Chem. Soc., Perkin Trans. 1, 827–832 (1999).

* cited by examiner

Primary Examiner—D. Margaret Seaman

(57) ABSTRACT

Selected compounds are effective for treatment of diseases, such as cell proliferation or apoptosis mediated diseases. The invention encompasses novel compounds, analogs, prodrugs and pharmaceutically acceptable derivatives thereof, pharmaceutical compositions and methods for prophylaxis and treatment of diseases and other maladies or conditions involving stroke, cancer and the like. The subject invention also relates to processes for making such compounds as well as to intermediates useful in such processes.

44 Claims, No Drawings

COMPOUNDS AND METHODS OF USES

This application claims the benefit of U.S. Provisional Application No. 60/355,313, filed Feb. 7, 2002, which is hereby incorporated by reference.

FIELD OF THE INVENTION

This invention is in the field of pharmaceutical agents and specifically relates to compounds, compositions, uses and methods for treating cell proliferation-related disorders, cell death and apoptosis-related disorders.

BACKGROUND OF THE INVENTION

Identification of therapeutic agents effective in the treatment of neoplastic diseases or for the treatment of neurological disorders is the subject of significant research efforts.

Protein kinases represent a large family of proteins which play a central role in the regulation of a wide variety of cellular processes and maintaining control over cellular function. A partial list of such kinases includes abl, Akt, bcr-abl, Blk, Brk, Btk, c-kit, c-met, c-src, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, FLK-4, flt-1, Fps, Frk, Fyn, Hck, IGF-1R, INS-R, Jak, KDR, Lck, Lyn, MEK, p38, PDCFR, PIK, PKC, PYK2, ros, tie, tie2, TRK, Yes, and Zap70. As such, inhibition of kinases has become an important therapeutic target.

Cell proliferation is the rapid reproduction of cells, such as by cell division. The cell cycle, which controls cell proliferation, is itself controlled by a family of serine-threonine kinases called cyclin dependent kinases (CDKs). The regulation of CDK activation is complex, and requires the association of the CDK with a member of the cyclin family of regulatory subunits. A further level of regulation occurs through both activating and inactivating phosphorylations of the CDK subunit. The coordinate activation and inactivation of different cyclin/CDK complexes is necessary for normal progression through the cell cycle. Both the critical G1-S and G2-M transitions are controlled by the activation of different cyclin/CDK activities. Loss of control of CDK regulation is a frequent event in hyperproliferative diseases and cancer. (T. Noguchi et al., Am. J. Pathol., 156, 2135–47 (2000)) As such, inhibition of CDKs has become an important target in the study of chemotherapeutics (A. Senderowicz and E. Sausville, J. Nat. Canc. Instit., 92, 376–87 (2000)).

Kinases have also been implicated in diseases and disorders of the central nervous system. For example, patients suffering from stroke, Alzheimer's disease or Parkinson's disease would benefit from the inhibition of kinases. Cdk5 has been shown to be involved in Alzheimer's pathology (R. Maccioni, et al., Eur. J. Biochem., 268, 1518–27 (2001)) and with neuronal development (G. Paglini and A. Caceres, Eur. J. Biochem., 268, 1528–33 (2001)).

Protein kinases also control programmed cell death, also known as apoptosis. Apoptosis is a ubiquitous physiological process used to eliminate damaged or unwanted cells in multicellular organisms. Disregulation of apoptosis is believed to be involved in the pathogenesis of many human diseases. The failure of apoptotic cell death has been implicated in various cancers, as well as autoimmune disorders. Conversely, increased apoptosis is associated with a variety of diseases involving cell loss such as neurodegenerative disorders and AIDS. As such, inhibition of apoptosis has become an important therapeutic target. Cdk5 has been shown to be involved in apoptosis pathology (A. Catania et al., Neuro-Oncology, 89–98 (April 2001)).

Quinolinones are known in the art. U.S. Pat. No. 4,127,574, issued Nov. 28, 1978, describes 3-sulfonyl-quinolinones as anti-allergic agents. U.S. Pat. No. 4,547,511, issued Oct. 15, 1985, describes 3-carboxamide-quinolinones as pharmaceuticals. S. Ibrahim et al., Ind. J. Het. Chem., 4, 125–130 (1994) describe 1-methylquinolinones. A. Sayed et al., Acta Chim. Acad. Sci. Hung., 94, 131–39 (1977), describes the preparation of 1-alkylquinolinones. M. Abass, Synth. Commun., 30, 2735–57 (2000), describes the preparation of 1-methylquinolinones. WO01/70227, published 27 Sep. 2001, describes 3-heterocyclylquinolinones as GnRH antagonists. WO01/70228, published 27 Sep. 2001, describes 3-phenylquinolinones as GnRH antagonists. WO01/62252, published 30 Aug. 2001, describes 3-pyrrolopyridinyl-quinolinones as tyrosine kinase inhibitors. WO01/29025, published 26 Apr. 2001, describes 3-(2-indolyl)quinolinones as tyrosine kinase inhibitors.

U.S. Pat. No. 5,252,584, issued Oct. 12, 1993, describes 4-hydroxy-quinolinones as NMDA antagonists. K. Ashok et al., Ind. J. Chem., 32B, 786–87 (1993), describe the preparation of 4-hydroxy-quinolinones. E. Mohamed et al., J. Ind. Chem. Soc, 69, 82–4 (1992), describe the preparation of 4-hydroxy-quinolinones. WO92/18483, published 29 Oct. 1992, describes 1-methyl-4-hydroxy-quinolinones as pharmaceuticals. WO01/28993, published 26 Apr. 2001, describes 6-(indazol-2-yl)-thieno[2,3-b]pyridones as kinase inhibitors. M. Rehwald et al., J. Prakt. Chem., 342, 371–78 (2000), describe preparation of heteroaryl pyridinium salts. G. Tenant et al., J. Chem. Soc., Perkin Trans. 1, 827–32 (1999), describe preparation of heterocyclyl-pyridinium salts. K. Gewald et al., Liebigs Ann., 787–91 (1995), describe preparation of heterocyclyl-pyridinium salts. T. El-Emary et al., Pharmazie, 55, 356–58 (2000), describe the preparation of pyrazolo[3,4-b]pyridin-2-ones. S. Naruto, et al., Chem. Pharm. Bull., 30, 3421–23 (1982), describe the preparation of benzofuro[3,2-b]pyridin-2-ones. WO01/62251, published 30 Aug. 2001, describes 3-pyrrolopyridinyl-quinolinones as tyrosine kinase inhibitors. WO01/29025, published 26 Apr. 2001, describes 3-(2-indolyl)quinolinones as tyrosine kinase inhibitors. WO01/28993, published 26 Apr. 2001, describes 3-(2-benzimidazolyl)quinolinones as tyrosine kinase inhibitors. WO01/62252, published 30 Aug. 2001, describes 3-pyrrolopyridinyl-quinolinones. U.S. Pat. No. 5,643,932, issued Jul. 1, 1997, describes thiazoles as superoxide radical inhibitors. A. Doroshenko et al. Chem. Heterocycl. Cmpd., 33, 1177–84 (1998) describes spectral properties of thiazolyl-coumarin derivatives.

However, compounds of the current invention have not been described as inhibitors of cell proliferation or apoptosis such as for the treatment of cancer or stroke.

DESCRIPTION OF THE INVENTION

A class of compounds useful in treating cell proliferative disorders, neurological disorders and apoptosis is defined by Formula I

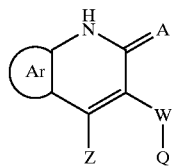

wherein

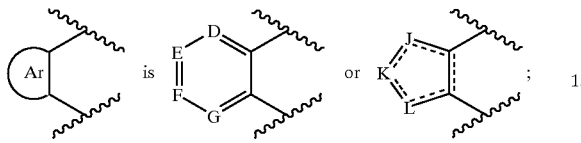

wherein A is O, S or NH;
wherein D is $CR^1$ or N;
wherein E is $CR^2$ or N;
wherein F is $CR^3$ or N;
wherein G is $CR^4$ or N;
wherein J is selected from $NR^6$, S, O, and $CR^1$;
wherein K is selected from $NR^6$, S, O, and $CR^2$;
wherein L is selected from $NR^6$, S, O, and $CR^3$;
wherein Q is selected from hydroxy, $-N(R^5)_2$, $-NR^5C(O)R^5$, $-(C_1-C_8)$alkyl-$OR^5$, $-(C_1-C_8)$alkyl-$S(O)_nR^5$, $-N(C_{1-C8}$-alkyl)-$S(O)_nR^5$, $-NHS(O)_nR^5$, aryl, a monocyclic or bicyclic, non-aromatic carbocyclic ring, heteroaryl and a monocyclic or bicyclic, non-aromatic heterocyclic ring; wherein the ring is unsubstituted or substituted with one or more groups selected from H, halo, aryl, alkynyl, alkenyl, $-OR^5$, $-N(R^5)_2$, $-(C_1-C_8)$alkyl-$N(R^5)_2$, lower alkoxyalkyl, $-O-C_1-C_2$-alkyl-O-, $-S(O)_nR^5$, cyano, $(C_1-C_8)$alkyl, lower cyanoalkyl, lower alkylaminoalkoxy, lower aminoalkoxyalkyl $(C_3-C_{10})$cycloalkyl, nitro, optionally substituted 4–7 membered heterocyclyl, optionally substituted phenoxyalkyl, optionally substituted heterocyclyloxyalkyl, $-SO_2NR^5R^5$, $-NR^5SO_2R^5$, $-C(O)N(R^5)_2$, $-CO_2R^5$, $-CO_2NR^5R^5$, $-SO_2NHC(O)R^5$, optionally substituted phenylalkyl, optionally substituted heterocyclylalkyl, $-NR^5C(O)N(R^5)_2$, $-NR^5C(O)R^5$, $-NR^5CO_2R^5$ and $-C(O)R^5$;
wherein W is an monocyclic aromatic or non-aromatic, heterocyclic ring that is unsubstituted or substituted with one or more groups selected from halo, aryl, cycloalkyl, $-OR^5$, $(C_2-C_8)$alkenyl, $(C_2-C_8)$alkynyl, $-N(R^5)_2$, $-(C_1-C_8)$alkyl-$N(R^5)_2$, $-SO_2NR^5R^5$, $-(C_2-C_8)$alkyl$SO_2R^5$, $-(C_1-C_8)$alkyl$SO_2-(C_1-C_8)$alkyl-$R^5$, $(C_1-C_8)$alkyl, $(C_3-C_{10})$cycloalkyl, nitro, cyano, optionally substituted 5–6 membered heterocyclyl, formyl, alkylcarbonyl, cycloalkylcarbonyl, heterocyclylcarbonyl, arylcarbonyl, $-NR^5SO_2R^5$, $-C(O)N(R^5)_2$, $-C(O)NR^5R^{5a}$, $-CO_2R^5$, optionally substituted phenylalkyl, optionally substituted heterocyclylalkyl, $-NR^5C(O)N(R^5)_2$, $-NR^5C(O)R^5$ and $-NR^5CO_2R^5$;
wherein Z is selected from H, $-N(R^5)_2$, $-SR^5$, $-OR^5$, $-C(R^5)_3$ and aryl;
wherein n is 0, 1 or 2;
wherein m is 0 or 1;

wherein $R^1$, $R^2$, $R^3$, and $R^4$ are independently selected from H, $-OR^5$, $-OR^{5a}$, halo, aryl, alkenyl, alkynyl, $-NR^5_2$, $-(C_1-C_8)$ alkyl-$N(R^5)_2$, $-S(O)_n-NR^5R^5$, $-S(O)_nR^5$, $(C_1-C_8)$alkyl, $(C_3-C_{10})$cycloalkyl, nitro, cyano, optionally substituted 4–10 membered heterocyclyl, $-C(O)R^5$, $-NR^5SO_2R^5$, $-C(O)N(R^5)_2$, $-CO_2R^5$, optionally substituted arylalkyl, optionally substituted 4–10 membered heterocyclylalkyl, $-NR^5C(O)N(R^5)_2$, $-NR^5C(O)R^5$ and $-NR^5CO_2R^5$; wherein $R^1$ and $R^2$ may be joined to form a 5–10 membered saturated or unsaturated carbocyclic or heterocyclic ring; wherein $R^2$ and $R^3$ may be joined to form a 5–10 membered saturated or unsaturated carbocyclic or heterocyclic ring; or wherein $R^3$ and $R^4$ may be joined to form a 5–10 membered saturated or unsaturated carbocyclic or heterocyclic ring;

wherein $R^5$ is independently selected from H, lower alkyl, optionally substituted aryl, optionally substituted aralkyl, optionally substituted heterocyclyl, optionally substituted heterocyclylalkyl, optionally substituted cycloalkyl, optionally substituted cycloalkyl-alkyl, and lower haloalkyl;

wherein $R^{5a}$ is alkylaminoalkyl; wherein $R^6$ is selected from H, $(C_1-C_2)$alkyl, and a lone pair of electrons;

wherein a solid line with a dashed line (- - -) represents either a single or a double bond;

wherein each alkyl, aryl, heteroaryl, heterocyclyl, cycloalkyl, alkynyl, alkynyl, and alkoxy moiety of any $R^1$, $R^2$, $R^3$, $R^4$, or $R^5$ can optionally join with another $R^1$, $R^2$, $R^3$, $R^4$, or $R^5$ to form a 3–7 membered ring; and wherein each alkyl, aryl, heteroaryl, cycloalkyl, alkynyl, alkynyl, heterocyclyl, and alkoxy moiety of any $R^1$, $R^2$, $R^3$, $R^4$, $R^5$, Q and W is optionally substituted with one or more groups selected from halo, $-NH_2$, $-OH$, $-CO_2H$, $(C_1-C_6)$alkylamino, $(C_1-C_6)$alkyl, $C_1-C_6$ alkoxy, $C_1-C_6$)haloalkyl, di$(C_1-C_6)$alkylamino, $(C_1-C_6)$alkylamino-$(C_1-C_6)$alkyl, $(C_1-C_6)$ hydroxyalkylamino, $(C_1-C_6)$alkylamino-$(C_1-C_6)$ alkylamino, phenyl, and heterocyclyl;

provided W is not pyridinium; further provided W is not dihydropyrazolyl or oxadiazolyl when Ar is aryl; further provided Z is not OH when Ar is aryl; further provided Z is not H when W is or pyrazol-3-yl, when Ar is phenyl and when Q is phenyl; further provided Q is not unsubstituted phenyl when W is thiazol-4-yl, when Z is H and when F is C—$OCH_3$; further provided Q is not 3,4-dimethoxyphenyl when W is thiazol-4-yl, when Z is H and when $R^1$, $R^2$, $R^3$ and $R^4$ are H; further provided Q is not 3,4-dihydroxyphenyl when W is thiazol-2-yl, when Z is H and when $R^1$, $R^2$, $R^3$ and $R^4$ are H; further provided Z is not phenyl when Q is phenyl, when W is tetrahydropyrazinyl and when Ar is phenyl; and further provided Z is not phenyl when Q is phenyl, when W is pyrazol-3-yl or dihydro-isoxazol-3-yl and when Ar is phenyl;

and pharmaceutically acceptable derivatives thereof.

The invention also relates to compounds of Formula I wherein,

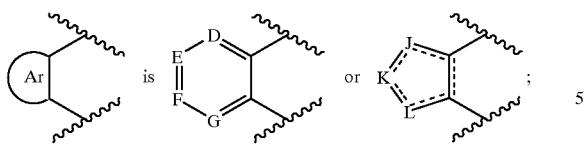

preferably phenyl, thienyl, pyrimidinyl, pyridyl and thiazolyl, more preferably phenyl, wherein Ar is optionally substituted with one or more radicals selected from —$OR^5$, halo, aryl, alkenyl, alkynyl, —$NR^5_2$, —$(C_1-C_8)$alkyl-$N(R^5)_2$, —$S(O)_n$—$NR^5R^5$, —$S(O)_nR^5$, $(C_1-C_8)$alkyl, $(C_3-C_{10})$cycloalkyl, nitro, cyano, optionally substituted 4–10 membered heterocyclyl, —$C(O)R^5$, —$NR^5SO_2R^5$, —$C(O)N(R^5)_2$, —$CO_2R^5$, optionally substituted arylalkyl, optionally substituted 4–10 membered heterocyclylalkyl, —$NR^5C(O)N(R^5)_2$, —$NR^5C(O)R^5$ and —$NR^5CO_2R^5$, preferably —$OR^5$, chloro, fluoro, phenyl, $C_2-C_6$ alkenyl, $C_2-C_6$ alkynyl, —$N(R^5)_2$, —$(C_1-C_6)$alkyl-$N(R^5)_2$, —$S(O)_n$—$NR^5R^5$, —$S(O)_nR^5$, $(C_1-C_6)$alkyl, $(C_3-C_6)$cycloalkyl, nitro, cyano, optionally substituted 4–6 membered heterocyclyl, —$C(O)R^5$, —$NR^5SO_2R^5$, —$C(O)N(R^5)_2$, —$CO_2R^5$, optionally substituted phenyl-$C_1-C_6$-alkyl, optionally substituted 4–6 membered heterocyclyl-$C_1-C_6$-alkyl, —$NR^5C(O)N(R^5)_2$, —$NR^5C(O)R^5$ and —$NR^5CO_2R^5$, more preferably —$OR^5$, chloro, fluoro, phenyl, —$N(R^5)_2$, —$(C_1-C_2)$alkyl-$N(R^5)_2$, —$S(O)_n$—$NR^5R^5$, —$S(O)_nR^5$, $(C_1-C_4)$alkyl, $(C_1-C_2)$ haloalkyl, hydroxy-$(C_1-C_2)$alkyl, hydroxy-$(C_1-C_4)$-alkylamino, $(C_1-C_2)$-alkylamino-$(C_1-C_2)$-alkylamino, $(C_1-C_2)$-alkylamino-$(C_1-C_2)$-alkoxy, optionally substituted $(C_3-C_6)$ cycloalkyl, optionally substituted heterocyclyl selected from pyrrolidinyl, piperazinyl, piperidinyl, and morpholinyl, —$C(O)R^5$, —$NR^5SO_2R^5$, —$C(O)N(R^5)_2$, —$CO_2R^5$, optionally substituted benzyl, optionally substituted 4–6 membered heterocyclyl-$C_1-C_2$-alkyl, —$NR^5C(O)R^5$ and —$NR^5CO_2R^5$, even more preferably cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, 4-methylpiperazin-1-yl, 3-aminopyrrolidin-1-yl, (diethylamino)ethylamino, 3,5-dimethylpiperazin-1-yl, (1-piperidylmethyl)amino, (2-methylbutyl)amino, 2-(dimethylamino)ethoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-morpholin-4-ylethoxy, hydroxy, benzyloxy, methoxy, chloro, fluoro, phenyl, amino, methylamino, diethylamino, aminomethyl, dimethylaminoethyl, aminosulfonyl, methylthio, methylsulfonyl, piperazinylsulfonyl, methyl, cyclopropyl, pyrrolidinyl, piperazinyl, 4-methylpiperazinyl, piperidinyl, morpholinyl, methylcarbonyl, phenylcarbonyl, piperidinylcarbonyl, trifluoromethyl, hydroxymethyl, hydroxyethyl, diethylaminocarbonyl, methoxycarbonyl, optionally substituted benzyl, piperazinylmethyl, 4-methylpiperazinylmethyl, piperidinylmethyl, and morpholinylmethyl;

wherein A is O, S or NH, and preferably O;
wherein D is $CR^1$, or N;
wherein E is $CR^2$, or N;
wherein F is $CR^3$, or N;
wherein G is $CR^4$ or N;
wherein J is selected from $NR^6$, S, O, and $CR^1$;
wherein K is selected from $NR^6$, S, O, and $CR^2$;
wherein L is selected from $NR^6$, S, O, and $CR^3$;
wherein Q is selected from hydroxy, —$N(R^5)_2$, —$NR^5C(O)R^5$, —$(C_1-C_8)$alkyl-$S(O)_nR^5$, —$N(C_1-C_8$-alkyl)-$S(O)_nR^5$, —$NHS(O)_nR^{11}$, aryl, a monocyclic or bicyclic, non-aromatic carbocyclic ring, heteroaryl and a monocyclic or bicyclic, non-aromatic heterocyclic ring, preferably hydroxy, $(R^5)_2N$—, $R^5$-carbonyl-HN—, $R^5$-carbonyl-N(CH$_3$)—, phenyl-O—$(C_1-C_2)$alkyl, $R^5SO_2$—$(C_1-C_6)$alkyl-, —$N(C_1-C_6$-alkyl)-$S(O)_nR^5$, substituted or unsubstituted phenyl, substituted or unsubstituted 5–6 membered heteroaryl, substituted or unsubstituted $C_3-C_6$ cycloalkyl, and substituted or unsubstituted non-aromatic heterocyclyl;

more preferably —$N(R^5)_2$, $R^5$ carbonyl-HN—, $R^5$-carbonyl-N(CH$_3$)—, phenyl-O-methyl, $R^5S(O)_n$—$(C_1-C_3)$alkyl, —$N(C_1-C_3$-alkyl)-$S(O)_nR^5$, substituted or unsubstituted phenyl, benzodioxolyl, and substituted or unsubstituted 6-membered heteroaryl;

even more preferably —$N(R^5)_2$, $R^5S(O)_n$—$(C_1-C_3)$alkyl, —$N(C_1-C_3$-alkyl)-$S(O)_nR^5$, —$NH$—$S(O)_nR^{11}$, substituted or unsubstituted phenyl, substituted or unsubstituted. pyridyl, substituted or unsubstituted pyrazinyl, substituted or unsubstituted pyrimidinyl and substituted or unsubstituted pyridazinyl;

particularly amino, 2-pyridylamino, 3-pyridylamino, 4-pyridylamino, phenylsulfonylamino, N-methyl-N-(2-pyridylsulfonyl)amino, N-methyl-N-(3-pyridylsulfonyl)amino, N-methyl-N-(4-pyridylsulfonyl)amino, N-methyl-N-(2-thienylsulfonyl)amino, N-methyl-N-(phenylsulfonyl)amino, 2-pyridylsulfonylmethyl, 3-pyridylsulfonylmethyl, 4-pyridylsulfonylmethyl, 2-thienylsulfonylmethyl, phenylsulfonylmethyl, 2-furylmethylsulfonylmethyl, 3-trifluoromethylbenzyl-sulfonylmethyl, methylsulfonylmethyl, tert-butyl-sulfonylmethyl, 4-fluorophenyl-methylsulfonylmethyl, 4-chlorophenyl-methylsulfonylmethyl, phenyl substituted with one or more substituents selected from H, hydroxyl, chloro, fluoro, methoxy, amino, aminomethyl, methylsulfonyl, methyl, cyano, trifluoromethyl, and pyrrolyl, unsubstituted pyridyl, and pyridyl substituted with one or more substituents selected from chloro, fluoro, —$NH_2$, —OH, —$CO_2H$, methylamino, methyl, ethyl, diethyl-amino, pyrrolidinyl, piperazinyl, piperidinyl, morpholinyl and azetidinyl;

more particularly substituted or unsubstituted pyridyl;

wherein the ring is unsubstituted or substituted with one or more groups selected from H, halo, aryl, alkynyl, alkenyl, —$OR^5$, —$N(R^5)_2$, —$(C_1-C_8)$alkyl-$N(R^5)_2$, lower alkoxyalkyl, —$S(O)_nR^5$, $(C_1-C_8)$alkyl, cyano, lower cyanoalkyl, lower alkylaminoalkoxy, lower aminoalkoxyalkyl $(C_3-C_{10})$cycloalkyl, nitro, optionally substituted 4–7 membered heterocyclyl, optionally substituted phenoxyalkyl, optionally substituted heterocyclyloxyalkyl, —$SO_2NR^5R^5$, —$NR^5SO_2R^5$, —$C(O)N(R^5)_2$, —$CO_2R^5$, —$CO_2NR^5R^5$, —$SO_2NHC(O)R^5$, optionally substituted phenylalkyl, optionally substituted heterocyclylalkyl, —$NR^5C(O)N(R^5)_2$, —$NR^5C(O)R^5$, —$NR^5CO_2R^5$ and —$C(O)R^5$;

preferably H, halo, phenyl, $(C_2-C_6)$-alkynyl, $(C_2-C_6)$-alkenyl, —$OR^5$, —$N(R^5)_2$, —$(C_1-C_8)$alkyl-$N(R^5)_2$, lower alkoxyalkyl, $R^5$-sulfonyl, $R^5$-sulfonyl-$(C_1-C_6)$-alkyl, $(C_1-C_8)$alkyl, cyano, lower cyanoalkyl, lower alkylaminoalkoxy, lower aminoalkoxyalkyl $(C_3-C_{10})$cycloalkyl, nitro, optionally substituted 4–7 membered heterocyclyl, optionally substituted phenoxyalkyl, optionally substituted heterocyclyloxyalkyl, —$SO_2NR^5R^5$, —$NR^5SO_2R^5$, —$C(O)N(R^5)_2$, —$CO_2R^5$, —$CO_2NR^5R^5$, —$SO_2NHC(O)R^5$, optionally substituted phenylalkyl, optionally substituted heterocyclylalkyl, —$NR^5C(O)N(R^5)_2$, —$NR^5C(O)R^5$, —$NR^5CO_2R^5$ and —$C(O)R^5$;

wherein W is a monocyclic, aromatic or non-aromatic, heterocyclic ring that is unsubstituted or substituted with one or more groups selected from halo, aryl, cycloalkyl, —$OR^5$, $(C_2-C_8)$alkenyl, $(C_2-C_8)$alkynyl, —$N(R^5)_2$, —$(C_1-C_8)$alkyl-$N(R^5)_2$, —$SO_2NR^5R^5$, $(C_1-C_8)$alkyl, $(C_3-C_{10})$cycloalkyl, nitro, cyano, optionally substituted 5–10 membered heterocyclyl, formyl, alkylcarbonyl, cycloalkylcarbonyl, heterocyclylcarbonyl, arylcarbonyl, —$NR^5SO_2R^5$, —$C(O)N(R^5)_2$, —$CO_2R^5$, optionally substituted phenylalkylenyl, optionally substituted heterocyclylalkylenyl, —$NR^5C(O)N(R^5)_2$, —$NR^5C(O)R^5$ and —$NR^5CO_2R^5$;

preferably 5–6 membered heterocyclyl;
more preferably 5-membered heteroaryl;
even more preferably thienyl, thiazolyl, oxazolyl, imidazolyl, pyrrolyl, furyl, pyrazolyl, isoxazolyl, thiadiazolyl, triazolyl and isothiazolyl;
particularly thienyl, thiazolyl, oxazolyl, furyl, isoxazolyl and isothiazolyl; more particularly thiazolyl, oxazolyl, and thienyl;

wherein Z is selected from H, —$N(R^5)_2$, —$SR^5$, —$OR^5$, —$C(R^5)_3$ and aryl;
preferably H, —$N(R^5)_2$, —$OR^5$, $(C_1-C_3)$alkyl and phenyl; more preferably H, —$N(R^5)_2$, and phenyl; even more preferably H, amino and phenyl;

wherein n is 0, 1 or 2;
preferably 2;

wherein $R^1$, $R^2$, $R^3$, and $R^4$ are independently selected from H, —$OR^5$, halo, aryl, alkenyl, alkynyl, —$NR^5_2$, —$(C_1-C_8)$alkyl-$N(R^5)_2$, —$S(O)_n$—$NR^5R^5$, $(C_1-C_8)$alkyl, $(C_3-C_{10})$cycloalkyl, nitro, cyano, optionally substituted 4–10 membered heterocyclyl, —$C(O)R^5$, —$NR^5SO_2R^5$, —$SO_2R^5$, —$C(O)N(R^5)_2$, —$CO_2R^5$, optionally substituted arylalkyl, optionally substituted 4–10 membered heterocyclylalkyl, —$NR^5C(O)N(R^5)_2$, —$NR^5C(O)R^5$ and —$NR^5CO_2R^5$; wherein $R^1$ and $R^2$ may be joined to form a 5–10 membered saturated or unsaturated carbocyclic or heterocyclic ring; wherein $R^2$ and $R^3$ may be joined to form a 5–10 membered saturated or unsaturated carbocyclic or heterocyclic ring; or wherein $R^3$ and $R^4$ may be joined to form a 5–10 membered saturated or unsaturated carbocyclic or heterocyclic ring;

wherein $R^5$ is independently selected from H, lower alkyl, optionally substituted aryl, optionally substituted aralkyl, optionally substituted heterocyclyl, optionally substituted heterocyclylalkyl, optionally substituted $C_3-C_6$ cycloalkyl, optionally substituted $C_3-C_6$ cycloalkylalkyl, and lower haloalkyl;

preferably H, $(C_1-C_6)$alkyl, optionally substituted phenyl, optionally substituted phenyl-$(C_1-C_4)$alkyl, optionally substituted 4–10 membered heterocyclyl, optionally substituted 4–10 membered heterocyclyl-$(C_1-C_4)$alkyl, optionally substituted $C_3-C_6$ cycloalkyl, optionally substituted $C_3-C_6$ cycloalkyl-$(C_1-C_4)$alkyl, and $(C_1-C_4)$haloalkyl;

more preferably H, $(C_1-C_6)$alkyl, optionally substituted $C_3-C_6$ cycloalkyl, $C_3-C_6$ cycloalkyl-$(C_1-C_4)$alkyl, optionally substituted phenyl, optionally substituted phenyl-$(C_1-C_3)$alkyl, optionally substituted 4–6 membered heterocyclyl-$(C_1-C_4)$alkyl, $(C_1-C_2)$haloalkyl, and optionally substituted 4–6 membered heterocyclyl;

even more preferably H, methyl, ethyl, propyl, tert-butyl, 2-methylbutyl, cyclopropyl, cyclopentyl, cyclobutyl, cyclohexyl, phenyl, benzyl, phenylethyl, 2-amino-3-phenylpropyl, cyclopropylmethyl, 4-piperidylmethyl, -(1-methylpyrrolidin-2-yl)methyl, (pyrrolidin-2-yl)methyl, piperidinylethyl, (pyrrolidin-1-yl)ethyl, (morpholin-4-yl)ethyl, piperidinylpropyl, (pyrrolidin-1-yl)propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl;

wherein $R^6$ is selected from H, $(C_1-C_2)$alkyl, and a lone pair of electrons;

wherein a solid line with a dashed line (- - -) represents either a single or a double bond;

wherein each alkyl, aryl, heteroaryl, heterocyclyl, cycloalkyl, alkynyl, alkynyl, and alkoxy moiety of any $R^1$, $R^2$, $R^3$, $R^4$, or $R^5$ can optionally join with another $R^1$, $R^2$, $R^3$, $R^4$, or $R^5$ to form a 3–7 membered ring; and wherein each alkyl, aryl, heteroaryl, cycloalkyl, alkynyl, alkynyl, heterocyclyl, and alkoxy moiety of any $R^1$, $R^2$, $R^3$, $R^4$, $R^5$, Q and W is optionally substituted with one or more groups selected from halo, —$NH_2$, —OH, —$CO_2H$, $(C_1-C_6)$alkylamino, $(C_1-C_6)$alkyl, $C_3-C_6$ alkoxy, $C_1-C_6$)haloalkyl, di$(C_1-C_6)$alkylamino, $(C_1-C_6)$alkylamino-$(C_1-C_6)$alkyl, $(C_1-C_6)$hydroxyalkylamino, $(C_1-C_6)$alkylamino-$(C_1-C_6)$alkylamino, phenyl, and heterocyclyl;

preferably halo, —NH₂, —OH, —CO₂H, (C₁–C₄) alkylamino, (C₁–C₄)alkyl, di(C₁–C₄)alkylamino, pyrrolidinyl, piperazinyl, piperidinyl, morpholinyl, and azetidinyl;
more preferably chloro, fluoro, —NH₂, —OH, methoxy, —CO₂H, (C₁–C₂)alkylamino, (C₁–C₂) alkyl, di(C₁–C₂)alkylamino, pyrrolidinyl, piperazinyl, piperidinyl, morpholinyl, and azetidinyl;

provided W is not pyridinium; further provided W is not dihydropyrazolyl or oxadiazolyl when Ar is aryl; further provided Z is not OH when Ar is aryl; further provided Z is not H when W is or pyrazol-3-yl, when Ar is phenyl and when Q is phenyl; further provided Q is not unsubstituted phenyl when W is thiazol-4-yl, when Z is H and when F is C—OCH₃; further provided Q is not 3,4-dimethoxyphenyl when W is thiazol-4-yl, when Z is H and when R¹, R², R³ and R⁴ are H; further provided Q is not 3,4-dihydroxyphenyl when W is thiazol-2-yl, when Z is H and when R¹, R², R³ and R⁴ are H; further provided Z is not phenyl when Q is phenyl, when W is tetrahydropyrazinyl and when Ar is phenyl; and further provided Z is not phenyl when Q is phenyl, when W is pyrazol-3-yl or dihydro-isoxazol-3-yl and when Ar is phenyl;

and pharmaceutically acceptable derivatives thereof.

The invention also relates to compounds of Formula I wherein W is thiazolyl, such as thiazol-4-yl or thiazol-2-yl.

The invention also relates to compounds of Formula I wherein Q is R⁵SO₂—(C₁–C₆)alkyl-, such as phenylsulfonylmethyl.

The invention also relates to compounds of Formula I wherein Q is —N(C₁–C₆-alkyl)-S(O)ₙR⁵, such as N-methyl-N-(phenylsulfonyl)amino.

The invention also relates to compounds of Formula I wherein Z is H.

The invention also relates to compounds of Formula I wherein Q is pyridyl, such as 4-pyridyl.

The invention also relates to compounds of Formula I wherein E is CR² and D, F and G are independently CH; and wherein R² is selected from H, cyclopropylmethylamino, 3-hydroxypropylamino, 2-(piperidin-1-yl)ethylamino, 2-(pyrrolidin-1-yl)ethylamino, 2-(morpholin-4-yl) ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino)ethylamino, aminomethyl, dimethylaminoethyl, isopropylaminomethyl, diethylaminomethyl, N-methyl-N-(isopropyl)aminomethyl, N-methyl-N-(diethylaminoethyl)aminomethyl, N-ethyl-N-(dimethylaminoethyl)aminomethyl, (1-hydroxymethyl-2-methylpropyl)amino, cyclopentylaminomethyl, 2-(dimethylamino)ethoxy, 3-(dimethylamino)propoxy, 2-(methylamino)ethoxy, ((2R)pyrrolidin-2-yl)methoxy, ((2R)-1-methylpyrrolidin-2-yl)methoxy, 2-(piperid-1-yl) ethoxy, 2-(piperazin-1-yl)ethoxy, 2-(morpholin-4-yl)ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4-ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl.

The invention also relates to compounds wherein W is —C(O)NR⁵R⁵ᵃ; wherein R¹, R², R³, and R⁴ are independently —OR⁵ᵃ; and wherein R⁵ᵃ is alkylaminoalkyl, such as (C₁–C₃)alkylamino-(C₁–C₆)alkyl, specifically dimethylaminomethyl, dimethylaminopropyl, dimethylaminoethyl, and diethylaminoethyl.

The invention also relates to compounds of Formula II

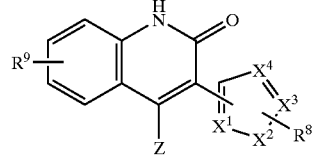

wherein X¹ is C, CR¹⁰ or N; wherein X² is selected from NH, N(CH₃), S and O ; wherein X³ is C, CR¹⁰ or N; wherein X⁴ is C, CR¹⁰ or N; provided at least one of X¹, X², X³ and X⁴ is not N, NH or N(CH₃);
preferably X² is S;
wherein Z is selected from H, —N(R¹¹)₂, —OR¹¹, (C₁–C₄)alkyl, and phenyl;
preferably H, amino, and phenyl;
wherein R⁸ is selected from —N(R¹¹)₂, R¹¹S(O)ₙ—(C₁–C₈)alkyl, N—(C₁–C₈-alkyl)-N—[R¹¹S(O)ₙ] amino, optionally substituted phenyl, benzodioxolyl, optionally substituted pyridyl, optionally substituted pyrazinyl, optionally substituted pyrimidinyl and optionally substituted pyridazinyl; wherein R⁸ is unsubstituted or substituted with one or more substituents selected from chloro, fluoro, —NH₂, —OH, —CO₂H, (C₁–C₂)alkylamino, (C₁–C₂)alkyl, di(C₁–C₂) alkylamino, pyrrolidinyl, piperazinyl, piperidinyl, morpholinyl and azetidinyl;
preferably amino, 2-pyridylamino, 3-pyridylamino, 4-pyridylamino, phenylsulfonylamino, N-methyl-N-(3-fluorobenzylsulfonyl)amino, N-methyl-N-(2-pyridylsulfonyl)amino, N-methyl-N-(3-pyridylsulfonyl)amino, N-methyl-N-(4-pyridylsulfonyl)amino, N-methyl-N-(2-thienylsulfonyl)amino, N-methyl-N-(phenylsulfonyl)amino, N-methyl-N-(1-methylimidazol-4-ylsulfonyl)amino, 2-pyridylsulfonylmethyl, 3-pyridylsulfonylmethyl, 4-pyridylsulfonylmethyl, 2-thienylsulfonylmethyl, phenylsulfonylmethyl, 1-phenylsulfonyl-1-methylethyl, 2-furylmethylsulfonylmethyl, 3-trifluoromethylphenylmethyl-sulfonylmethyl, methylsulfonylmethyl, tert-butylsulfonylmethyl, 4-fluorophenyl-methylsulfonylmethyl, 4-chlorophenyl-methylsulfonylmethyl, phenyl substituted with one or more substituents selected from H, hydroxyl, chloro, fluoro, methoxy, amino, aminomethyl, methylsulfonyl, methyl, cyano, trifluoromethyl, and pyrrolyl, unsubstituted pyridyl, and pyridyl substituted with one or more substituents selected from chloro, fluoro, —NH$_2$, —OH, —CO$_2$H, methylamino, methyl, ethyl, diethyl-amino, pyrrolidinyl, piperazinyl, piperidinyl, morpholinyl and azetidinyl;

wherein R$^9$ is one or more substituents selected from H, —OR$^{11}$, chloro, fluoro, phenyl, —N(R$^{11}$)$_2$, —(C$_1$–C$_2$) alkyl-N(R$^{11}$)$_2$, —S(O)$_n$—N(R$^{11}$)$_2$, —S(O)$_n$R$^{11}$, (C$_1$–C$_4$)alkyl, (C$_3$–C$_6$)cycloalkyl, hydroxy-(C$_1$–C$_4$)-alkylamino, (C$_1$–C$_2$)-alkylamino-(C$_1$–C$_2$)-alkylamino, (C$_1$–C$_2$)-alkylamino-(C$_1$–C$_2$)-alkoxy, optionally substituted heterocyclyl selected from pyrrolidinyl, piperazinyl, piperidinyl, and morpholinyl, —C(O)R$^{11}$, —NR$^{11}$SO$_2$R$^{11}$, —C(O)N(R$^{11}$)$_2$, —CO$_2$R$^{11}$, optionally substituted benzyl, optionally substituted 4–6 membered heterocyclyl-C$_1$–C$_2$-alkyl, —NR$^{11}$C(O)R$^{11}$ and —NR$^{11}$CO$_2$R$^{11}$;

preferably H, cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino)ethylamino, aminomethyl, dimethylaminoethyl, isopropylaminomethyl, diethylaminomethyl, N-methyl-N-(isopropyl)aminomethyl, N-methyl-N-(diethylaminoethyl)aminomethyl, N-ethyl-N-(dimethylaminoethyl)aminomethyl, (1-hydroxymethyl-2-methylpropyl)amino, cyclopentylaminomethyl, 2-(dimethylamino)ethoxy, 3-(dimethylamino)propoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-(morpholin-4-yl)ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4-ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl;

wherein R$^{10}$ is selected from H, halo, aryl, cycloalkyl, —OR$^{11}$, (C$_2$–C$_8$)alkenyl, (C$_2$–C$_8$)alkynyl, —N(R$^{11}$)$_2$, —(C$_1$–C$_8$)alkyl-N(R$^{11}$)$_2$, —SO$_2$NR$^{11}$R$^{11}$, (C$_1$–C$_8$) alkyl, cycloalkylalkyl, nitro, cyano, heteroaryl, optionally substituted 5–6 membered heterocyclyl, formyl, alkylcarbonyl, cycloalkylcarbonyl, arylcarbonyl, heterocyclylcarbonyl, —NR$^{11}$SO$_2$R$^{11}$, —C(O)N(R$^{11}$)$_2$, —CO$_2$R$^{11}$, optionally substituted phenylalkyl, optionally substituted heteroarylalkyl, —NR$^{11}$C(O)N(R$^{11}$)$_2$, —NR$^{11}$C(O)R$^{11}$ and —NR$^{11}$CO$_2$R$^{11}$;
preferably H;

wherein n is 0, 1 or 2;
preferably 2; and wherein R$^{11}$ is selected from H, (C$_1$–C$_6$)alkyl, optionally substituted phenyl, optionally substituted phenyl-(C$_1$–C$_4$)alkyl, optionally substituted 4–6 membered heterocyclyl, optionally substituted 4–6 membered heterocyclyl-(C$_1$–C$_4$)alkyl, C$_3$–C$_6$ cycloalkyl, C$_3$–C$_6$ cycloalkyl-(C$_1$–C$_4$)alkyl and (C$_1$–C$_2$)haloalkyl;
preferably H, methyl, ethyl, propyl, tert-butyl, 2-methylbutyl, cyclopropyl, cyclopentyl, cyclobutyl, cyclohexyl, phenyl, benzyl, phenylethyl, 2-amino-3-phenylpropyl, cyclopropylmethyl, 4-piperidylmethyl, -(1-methylpyrrolidin-2-yl)methyl, (pyrrolidin-2-yl)methyl, piperidinylethyl, (pyrrolidin-1-yl)ethyl, (morpholin-4-yl)ethyl, piperidinylpropyl, (pyrrolidin-1-yl)propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl;

wherein each alkyl, phenyl, cycloalkyl, and heterocyclyl moiety is optionally substituted with one or more groups selected from halo, —NH$_2$, —OH, —CO$_2$H, (C$_1$–C$_4$)alkylamino, (C$_1$–C$_4$)alkyl, di(C$_1$–C$_4$)alkylamino, (C$_1$–C$_4$)haloalkyl, pyrrolidinyl, piperazinyl, piperidinyl, morpholinyl, and azetidinyl; and pharmaceutically acceptable derivatives thereof;

provided Z is not OH; further provided ring W' is not oxadiazolyl or pyrazolyl; further provided R$^8$ is not unsubstituted 2-phenyl when Z is H, when ring W' is thiazol-4-yl and when R$^9$ is 6-methoxy; further provided R$^8$ is not 2-phenyl or 2-[3,4-dimethoxyphenyl] when Z is H, ring W' is thiazol-4-yl and when R$^9$ is H; and further provided R$^8$ is not 4-[3,4-dihydroxyphenyl] when Z is H, ring W' is thiazol-2-yl and when R$^9$ is H.

The invention also relates to compounds of Formula III

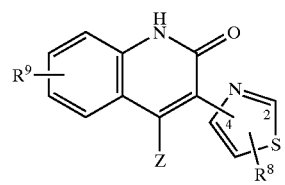

III wherein Z is selected from H, hydroxy, amino and phenyl;
preferably H, amino and phenyl;
wherein R$^8$ is selected from pyridyl, pyrazinyl, pyrimidinyl and pyridazinyl; wherein R$^8$ is unsubstituted or substituted with one or more substituents selected from chloro, fluoro, —NH$_2$, —OH, —CO$_2$H, (C$_1$–C$_2$)

alkylamino, $(C_1-C_2)$alkyl, di$(C_1-C_2)$alkylamino, $(C_1-C_2)$alkylamino$(C_1-C_2)$alkyl, hydroxy-$(C_1-C_2)$ alkylamino, 5–6-membered heterocyclyloxy, 5–6-membered heterocyclyl-$(C_1-C_2)$alkoxy, $[(C_1-C_2)$ alkoxy$]_{1-3}$, phenyl, pyrrolidinyl, piperazinyl, piperidinyl, morpholinyl and azetidinyl;

preferably unsubstituted pyridyl or pyridyl substituted with one or more substituents selected from chloro, fluoro, —$NH_2$, —OH, —$CO_2H$, methylamino, methyl, ethyl, diethyl-amino, pyrrolidinyl, piperazinyl, piperidinyl, morpholinyl and azetidinyl;

wherein $R^9$ is one or more radicals selected from H, —$OR^{11}$, chloro, fluoro, phenyl, —$N(R^{11})_2$, —$(C_1-C_2)$ alkyl-$N(R^{11})_2$, —$S(O)_n$—$N(R^{11})_2$, —$S(O)_nR^{11}$, $(C_1-C_4)$alkyl, $(C_3-C_6)$cycloalkyl, hydroxy-$(C_1-C_4)$-alkylamino, $(C_1-C_2)$-alkylamino-$(C_1-C_2)$-alkylamino, $(C_1-C_2)$-alkylamino-$(C_1-C_2)$-alkoxy, optionally substituted heterocyclyl selected from pyrrolidinyl, piperazinyl, piperidinyl, and morpholinyl, —$C(O)R^{11}$, —$NR^{11}SO_2R^{11}$, —$C(O)N(R^{11})_2$, —$CO_2R^{11}$, optionally substituted benzyl, optionally substituted 4–6 membered heterocyclyl-$C_1-C_2$-alkyl, —$NR^{11}C(O)R^{11}$ and —$NR^{11}CO_2R^{11}$;

preferably H, cyclopropylmethylamino, 3-hydroxypropylamino, 2-(piperidin-1-yl) ethylamino, 2-(pyrrolidin-1-yl)ethylamino, 2-(morpholin-4-yl)ethylamino, 3-(piperidin-1-yl) propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl) amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino) ethylamino, aminomethyl, dimethylaminoethyl, isopropylaminomethyl, diethylaminomethyl, N-methyl-N-(isopropyl)aminomethyl, N-methyl-N-(diethylaminoethyl)aminomethyl, N-ethyl-N-(dimethylaminoethyl)aminomethyl, (1-hydroxymethyl-2-methylpropyl)amino, cyclopentylaminomethyl, 2-(dimethylamino)ethoxy, 3-(dimethylamino)propoxy, 2-(methylamino)ethoxy, ((2R)pyrrolidin-2-yl)methoxy, ((2R)-1-methylpyrrolidin-2-yl)methoxy, 2-(piperid-1-yl) ethoxy, 2-(piperazin-1-yl)ethoxy, 2-(morpholin-4-yl) ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4-ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl;

wherein n is 0, 1 or 2;
preferably 2; and
wherein $R^{11}$ is selected from H, $(C_1-C_6)$alkyl, optionally substituted phenyl, optionally substituted phenyl-$(C_1-C_4)$alkyl, optionally substituted 4–6 membered heterocyclyl, optionally substituted 4–6 membered heterocyclyl-$(C_1-C_4)$alkyl, $C_3-C_6$ cycloalkyl, $C_3-C_6$ cycloalkyl-$(C_1-C_4)$alkyl and $(C_1-C_2)$haloalkyl; preferably H, methyl, ethyl, propyl, tert-butyl, 2-methylbutyl, cyclopropyl, cyclopentyl, cyclobutyl, cyclohexyl, phenyl, benzyl, phenylethyl, 2-amino-3-phenylpropyl, cyclopropylmethyl, 4-piperidylmethyl, -(1-methylpyrrolidin-2-yl)methyl, (pyrrolidin-2-yl)methyl, piperidinylethyl, (pyrrolidin-1-yl)ethyl, (morpholin-4-yl)ethyl, piperidinylpropyl, (pyrrolidin-1-yl propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl;

wherein each alkyl, phenyl, cycloalkyl, and heterocyclyl moiety is optionally substituted with one or more groups selected from halo, —$NH_2$, —OH, —$CO_2H$, $(C_1-C_4)$alkylamino, $(C_1-C_4)$alkyl, di$(C_1-C_4)$ alkylamino, $(C_1-C_4)$haloalkyl, pyrrolidinyl, piperazinyl, piperidinyl, morpholinyl, and azetidinyl;
and pharmaceutically acceptable derivatives thereof.

The invention also relates to compounds of Formula III wherein $R^8$ is pyridyl, such as 4-pyridyl or 3-pyridyl; wherein $R^8$ is unsubstituted or substituted.

The invention also relates to compounds of Formula III wherein Z is H.

The invention also relates to compounds of Formula III wherein the $R^8$ substituent is attached at thiazole ring position 2 and the quinolinone ring is attached at thiazole ring position 4.

The invention also relates to compounds of Formula III wherein the $R^8$ substituent is attached at thiazole ring position 4 and the quinolinone ring is attached at thiazole ring position 2.

The invention also relates to compounds of Formula III wherein $R^9$ is attached at quinolinone ring position 7.

The invention also relates to compounds of Formula IV

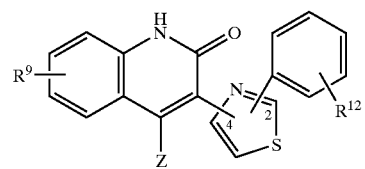

wherein Z is selected from H, hydroxy, amino and phenyl; preferably H, or amino;

wherein $R^9$ is one or more radicals selected from H, —$OR^{11}$, chloro, fluoro, phenyl, —$N(R^{11})_2$, —$(C_1-C_2)$ alkyl-$N(R^{11})_2$, —$S(O)_n$—$N(R^{11})_2$, —$S(O)_nR^{11}$, $(C_1-C_4)$alkyl, $(C_3-C_6)$cycloalkyl, hydroxy-$(C_1-C_4)$-alkylamino, $(C_1-C_2)$-alkylamino-$(C_1-C_2)$-alkylamino, $(C_1-C_2)$-alkylamino-$(C_1-C_2)$-alkoxy, optionally substituted heterocyclyl selected from pyrrolidinyl, piperazinyl, piperidinyl, and morpholinyl, —$C(O)R^{11}$, $NR^{11}SO_2R^{11}$, —$C(O)N(R^{11})_2$, —$CO_2R^{11}$, optionally substituted benzyl, optionally substituted 4–6 membered heterocyclyl-$C_1$–$C_2$-alkyl, —$NR^{11}C(O)R^{11}$ and —$NR^{11}CO_2R^{11}$;

preferably H, cyclopropylmethylamino, 3-hydroxypropylamino, 2-(piperidin-1-yl) ethylamino, 2-(pyrrolidin-1-yl)ethylamino, 2-(morpholin-4-yl)ethylamino, 3-(piperidin-1-yl) propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl) amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino) ethylamino, aminomethyl, dimethylaminoethyl, isopropylaminomethyl, diethylaminomethyl, N-methyl-N-(isopropyl)aminomethyl, N-methyl-N-(diethylaminoethyl)aminomethyl, N-ethyl-N-(dimethylaminoethyl)aminomethyl, (1-hydroxymethyl-2-methylpropyl)amino, cyclopentylaminomethyl, 2-(dimethylamino)ethoxy, 3-(dimethylamino)propoxy, 2-(methylamino)ethoxy, ((2R)pyrrolidin-2-yl)methoxy, ((2R)-1-methylpyrrolidin-2-yl)methoxy, 2-(piperid-1-yl) ethoxy, 2-(piperazin-1-yl)ethoxy, 2-(morpholin-4-yl) ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4-ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl;

wherein n is 0, 1 or 2; preferably 2; and wherein $R^{11}$ is selected from H, ($C_1$–$C_6$)alkyl, optionally substituted phenyl, optionally substituted phenyl-($C_1$–$C_4$)alkyl, optionally substituted 4–6 membered heterocyclyl, optionally substituted 4–6 membered heterocyclyl-($C_1$–$C_4$)alkyl, $C_3$–$C_6$ cycloalkyl, $C_3$–$C_6$ cycloalkyl-($C_1$–$C_4$)alkyl and ($C_1$–$C_2$)haloalkyl;

preferably H, methyl, ethyl, propyl, tert-butyl, 2-methylbutyl, cyclopropyl, cyclopentyl, cyclobutyl, cyclohexyl, phenyl, benzyl, phenylethyl, 2-amino-3-phenylpropyl, cyclopropylmethyl, 4-piperidylmethyl, -(1-methylpyrrolidin-2-yl) methyl, (pyrrolidin-2-yl)methyl, piperidinylethyl, (pyrrolidin-1-yl)ethyl, (morpholin-4-yl)ethyl, piperidinylpropyl, (pyrrolidin-1-yl)propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl;

wherein $R^{12}$ is one or more substituents selected from H, hydroxyl, halo, aryl, ($C_2$–$C_4$)alkynyl, ($C_2$–$C_4$)alkenyl, —$OR^{11}$, —$N(R^{11})_2$, —($C_1$–$C_4$)alkyl-$N(R^{11})_2$, lower alkoxyalkyl, $R^{11}$—$SO_2$—, ($C_1$–$C_4$)alkyl, cyano, nitro, lower cyanoalkyl, lower haloalkyl, lower hydroxyalkyl, lower aminoalkyl, lower alkylaminoalkyl, lower alkylaminoalkoxy, lower aminoalkoxyalkyl ($C_3$–$C_6$)cycloalkyl, optionally substituted 4–6 membered heterocyclyl, optionally substituted phenoxyalkyl, optionally substituted heterocyclyloxyalkyl, —$SO_2NR^{11}R^{11}$, —$NR^{11}SO_2R^{11}$, —$C(O)N(R^{11})_2$, —$CO_2R^{11}$, —$CO_2NR^{11}R^{11}$, —$SO_2NHC(O)R^{11}$, optionally substituted phenyl-($C_1$–$C_4$)alkyl, optionally substituted heterocyclyl-($C_1$–$C_4$)alkyl, —$NR^{11}C(O)N(R^{11})_2$, —$NR^{11}C(O)R^{11}$, —$NR^{11}CO_2R^{11}$ and —$C(O)R^{11}$;

preferably H, hydroxyl, chloro, fluoro, methoxy, amino, aminomethyl, methylsulfonyl, methyl, cyano, trifluoromethyl, and pyrrolyl; and wherein each alkyl, phenyl, cycloalkyl, and heterocyclyl moiety is optionally substituted with one or more groups selected from halo, —$NH_2$, —OH, —$CO_2H$, ($C_1$–$C_4$)alkylamino, ($C_1$–$C_4$)alkyl, di($C_1$–$C_4$) alkylamino, ($C_1$–$C_4$)haloalkyl, pyrrolidinyl, piperazinyl, piperidinyl, morpholinyl, and azetidinyl;

provided the compound of Formula IV is not 6-methoxy-3-(2-phenyl-thiazol-4-yl)-1H-quinolin-2-one, 3-(2-phenyl-thiazol-4-yl)-1H-quinolin-2-one, 3-(4-(3,4-dihydroxyphenyl)thiazol-2-yl)-1H-quinolin-2-one or 3-(2-(3,4-dimethoxyphenyl)thiazol-4-yl)-1H-quinolin-2-one;

and pharmaceutically acceptable derivatives thereof.

The invention also relates to compounds of Formula IV wherein Z is H.

The invention also relates to compounds of Formula IV wherein the phenyl substituent is attached at thiazole ring position 2 and the quinolinone ring is attached at thiazole ring position 4.

The invention also relates to compounds of Formula IV wherein the phenyl substituent is attached at thiazole ring position 4 and the quinolinone ring is attached at thiazole ring position 2.

The invention also relates to compounds of Formula IV wherein $R^9$ is attached at quinolinone ring position 7.

The invention also relates to compounds of Formula V

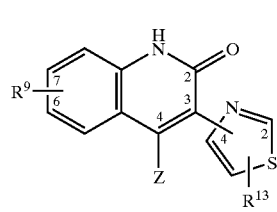

wherein Z is selected from H, amino, —OH and phenyl; preferably H, or amino;

wherein $R^9$ is one or more radicals selected from H, —$OR^{11}$, chloro, fluoro, phenyl, —$N(R^{11})_2$, —($C_1$–$C_2$) alkyl-$N(R^{11})_2$, —$S(O)_n$—$N(R^{11})_2$, —$S(O)_nR^{11}$, ($C_1$–$C_4$)alkyl, ($C_3$–$C_6$)cycloalkyl, hydroxy-($C_1$–$C_4$)-alkylamino, ($C_1$–$C_2$)-alkylamino-($C_1$–$C_2$)-alkylamino, ($C_1$–$C_2$)-alkylamino-($C_1$–$C_2$)-alkoxy, optionally substituted heterocyclyl selected from pyrrolidinyl, piperazinyl, piperidinyl, and morpholinyl, —C(O)$R^{11}$, —$NR^{11}SO_2R^{11}$, —C(O)N($R^{11}$)$_2$, —$CO_2R^{11}$, optionally substituted benzyl, optionally substituted 4–6 membered heterocyclyl-$C_1$–$C_2$-alkyl, —$NR^{11}$C(O)$R^{11}$ and —$NR^{11}CO_2R^{11}$;

preferably H, cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino)ethylamino, aminomethyl, dimethylaminoethyl, isopropylaminomethyl, diethylaminomethyl, N-methyl-N-(isopropyl)aminomethyl, N-methyl-N-(diethylaminoethyl)aminomethyl, N-ethyl-N-(dimethylaminoethyl)aminomethyl, (1-hydroxymethyl-2-methylpropyl)amino, cyclopentylaminomethyl, 2-(dimethylamino)ethoxy, 3-(dimethylamino)propoxy, 2-(methylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-(morpholin-4-yl)ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4-ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl;

wherein $R^{11}$ is selected from H, ($C_1$–$C_6$)alkyl, $C_1$–$C_6$-alkylamino-$C_1$–$C_6$-alkyl, optionally substituted $C_3$–$C_6$ cycloalkyl, $C_3$–$C_6$ cycloalkyl-($C_1$–$C_4$)alkyl, optionally substituted phenyl, optionally substituted phenyl-($C_1$–$C_3$)alkyl, optionally substituted 4–6 membered heterocyclyl-($C_1$–$C_4$)alkyl, ($C_1$–$C_2$)haloalkyl, and optionally substituted 4–6 membered heterocyclyl;

preferably H, methyl, ethyl, propyl, isopropyl, tert-butyl, 2-methylbutyl, cyclopropyl, cyclopentyl, cyclobutyl, cyclohexyl, phenyl, benzyl, phenylethyl, diethylaminoethyl, dimethylaminoethyl, 2-amino-3-phenylpropyl, cyclopropylmethyl, (tetrahydrofur-2-yl)methyl, 4-piperidinylmethyl, (1-methylpyrrolidin-2-yl)methyl, (pyrrolidin-2-yl)methyl, piperidinylethyl, (pyrrolidin-1-yl)ethyl, (morpholin-4-yl)ethyl, piperidinylpropyl, (pyrrolidin-1-yl)propyl, (morpholin-4-yl)propyl, trifluoromethyl, 2-furylmethyl, pyridyl, 2-thienyl, piperazinyl, 3,5-dimethylpiperazin-1-yl, 3-aminopyrrolidin-1-yl and 4-methylpiperazin-1-yl;

wherein $R^{13}$ is selected from amino, 5–6-membered heteroarylamino, $R^{11}$sulfonyl-$C_{1-2}$-alkyl and N—($R^{11}$sulfonyl)-N—($R^{14}$)amino;

preferably amino, 2-pyridylamino, 3-pyridylamino, 4-pyridylamino, phenylsulfonylamino, N-methyl-N-(3-fluorobenzylsulfonyl)amino, N-methyl-N-(2-pyridylsulfonyl)amino, N-methyl-N-(3-pyridylsulfonyl)amino, N-methyl-N-(4-pyridylsulfonyl)amino, N-methyl-N-(2-thienylsulfonyl)amino, N-methyl-N-(phenylsulfonyl)amino, N-methyl-N-(1-methylimidazol-4-ylsulfonyl)amino, 2-pyridylsulfonylmethyl, 3-pyridylsulfonylmethyl, 4-pyridylsulfonylmethyl, 2-thienylsulfonylmethyl, phenylsulfonylmethyl, 1-phenylsulfonyl-1-methylethyl, 2-furylmethylsulfonylmethyl, 3trifluoromethylphenylmethyl-sulfonylmethyl, methylsulfonylmethyl, tert-butylsulfonylmethyl, 4-fluorophenyl-methylsulfonylmethyl and 4-chlorophenyl-methylsulfonylmethyl;

wherein $R^{14}$ is $C_{1-3}$ alkyl;
preferably methyl;
wherein n is 0, 1 or 2; and
wherein each alkyl, phenyl, cycloalkyl, and heterocyclyl moiety is optionally substituted with one or more groups selected from halo, —$NH_2$, —OH, —$CO_2H$, ($C_1$–$C_4$)alkylamino, ($C_1$–$C_4$)alkyl, di($C_1$–$C_4$)alkylamino, ($C_1$–$C_4$)haloalkyl, pyrrolidinyl, piperazinyl, piperidinyl, morpholinyl, and azetidinyl;
and pharmaceutically acceptable derivatives thereof.

The invention also relates to compounds of Formula V wherein the $R^{13}$ substituent is attached at thiazole ring position 4 and the quinolinone ring is attached at thiazole ring position 2.

The invention also relates to compounds of Formula V wherein the $R^{13}$ substituent is attached at thiazole ring position 2 and the quinolinone ring is attached at thiazole ring position 4.

The invention also relates to compounds of Formula V wherein $R^{13}$ is $R^{11}SO_2$—($C_1$–$C_6$)alkyl-, such as phenylsulfonylmethyl.

The invention also relates to compounds of Formula V wherein $R^{13}$ is —N($C_1$–$C_6$-alkyl)-S(O)$_n$$R^{11}$, such as N-methyl-N-(phenylsulfonyl)amino.

The invention also relates to compounds of Formula V wherein Z is H.

The invention also relates to compounds of Formula V wherein the $R^9$ substituent is attached at quinolinone ring position 7.

A family of specific compounds of particular interest within Formula I consists of compounds and pharmaceutically-acceptable salts thereof as follows:

3-[2-(6-methoxy-3-pyridyl)-1,3-thiazol-4-yl]hydroquinolin-2-one;

6-chloro-3-[2-(2-ethyl(4-pyridyl))(1,3-thiazol-4-yl)]hydroquinolin-2-one;

3-[2-(4-(1,2,3-thiadiazol-4-yl)phenyl)-1,3-thiazol-4-yl]hydroquinolin-2-one;

3-[2-(2,3-dichlorophenyl)-1,3-thiazol-4-yl]hydroquinolin-2-one;

3-(2-benzenesulfonylmethyl-thiazol-4-yl)-7-trifluoromethyl-1H-quinolin-2-one;
3-[2-(4-chloro-benzenesulfonylmethyl)-thiazol-4-yl]-7-trifluoromethyl-1H-quinolin-2-one;
3-[2-(thienyl-2-sulfonylmethyl)-thiazol-4-yl]-7-trifluoromethyl-1H-quinolin-2-one;
7-piperidin-1-ylmethyl-3-(2-pyridin-4-yl-thiazol-4-yl)-1H-quinolin-2-one;
7-(4-methyl-piperazin-1-ylmethyl)-3-(2-pyridin-4-yl-thiazol-4-yl)-1H-quinolin-2-one;
3-[2-(3,4,5,6-tetrahydro-2H-[1,2']bipyridinyl-4'-yl)-thiazol-4-yl]-1H-quinolin-2-one;
3-{2-[2-(3-hydroxy-propylamino)-pyridin-4-yl]-thiazol-4-yl}-1H-quinolin-2-one;
7-hydroxymethyl-3-(2-pyridin-4-yl-thiazol-4-yl)-1H-quinolin-2-one;
3-[2-(4-amino-phenyl)-thiazol-4-yl]-1H-quinolin-2-one;
3-{2-[2-(2-piperidin-1-yl-ethoxy)-pyridin-4-yl]-thiazol-4-yl}-1H-quinolin-2-one;
3-{2-[2-(2-morpholin-4-yl-ethoxy)-pyridin-4-yl]-thiazol-4-yl}-1H-quinolin-2-one;
3-{2-[2-(2-diethylamino-ethoxy)-pyridin-4-yl]-thiazol-4-yl}-1H-quinolin-2-one;
3-{2-[2-(1-ethyl-pyrrolidin-3-yloxy)-pyridin-4-yl]-thiazol-4-yl}-1H-quinolin-2-one;
2-methylene-3-{2-[2-(5-methyl-tetrahydro-furan-2-ylmethoxy)-pyridin-4-yl]-thiazol-4-yl}-1,2-dihydroquinoline;
3-{2-[2-(tetrahydro-furan-2-ylmethoxy)-pyridin-4-yl]-thiazol-4-yl}-1H-quinolin-2-one;
3-(2-(2-[2-(2-ethoxy-ethoxy)-ethoxy]-pyridin-4-yl)-thiazol-4-yl)-1H-quinolin-2-one;
3-[2-(2-chloro-pyridin-4-yl)-thiazol-4-yl]-1H-quinolin-2-one;
3-[2-(4-hydroxy-phenyl)-thiazol-4-yl]-1H-quinolin-2-one;
5-(piperidine-1-carbonyl)-3-(2-pyridin-4-yl-thiazol-4-yl)-1H-quinolin-2-one;
3-(4-pyridin-4-yl-thiazol-2-yl)-1H-quinolin-2-one;
3-[4-(3-nitro-phenyl)-thiazol-2-yl]-1H-quinolin-2-one;
3-[2-(4-pyridyl)-4-thiazolyl]-2(1H)-quinolinone;
3-[2-(3-pyridyl)-4-thiazolyl]-2(1H)-quinolinone;
3-[2-(4-pyridyl)-4-thiazolyl]-4-phenyl-2(1H)-quinolinone;
4-hydroxy-3-(2-pyridin-4-yl-thiazol-4-yl)-1H-quinolin-2-one;
3-[2-(4-pyridyl)-4-thiazolyl]-4-amino-2(1H)-quinolinone;
3-[2-(4-pyridyl)-4-thiazolyl]-4-amino-6-(1-piperidinyl)-2(1H)-quinolinone;
1,2-dihydro-2-oxo-3-[2-(4-pyridyl)-4-thiazolyl]-5-quinolinecarboxylic acid methyl ester;
3-[2-(3-pyridyl)-4-thiazolyl]-6,7-(methylenedioxyl)-2(1H)-quinolinone;
N,N-diethyl-1,2-dihydro-2-oxo-3-[2-(4-pyridyl)-4-thiazolyl]-5-quinolinecarboxamide;
3-[2-(2-ethyl-4-pyridyl)-1,3-thiazol-4-yl]hydroquinolin-2-one;
3-[2-(6-oxo-3-hydropyridyl)-1,3-thiazol-4-yl]hydroquinolin-2-one;
6-chloro-3-(2-(4-pyridyl)(1,3-thiazol-4-yl))hydroquinolin-2-one;
3-[2-(4-pyridyl)-4-thiazolyl]-6,7-(methylenedioxyl)-2(1H)-quinolinone;
3-[2-(4-pyridyl)-4-thiazolyl]-4-amino-6,7-dimethoxy-2(1H)-quinolinone;
3-[2-(3-oyridyl)-4-thiazolyl]-4-amino-6,7-dimethoxy-2(1H)-quinolinone;
3-[2-(4-pyridyl)-4-thiazolyl]-4-amino-6-chloro-2(1H)-quinolinone;
3-[2-(4-pyridyl)-4-thiazolyl]-4-amino-6-(4-methyl-1-piperazinyl)-2(1H)-quinolinone;
3-[2-(2-ethyl(4-pyridyl))(1,3-thiazol-4-yl)]-6-fluorohydroquinolin-2-one;
6-fluoro-3-(2-(4-pyridyl)(1,3-thiazol-4-yl))hydroquinolin-2-one;
3-(2-(4-pyridyl)(1,3-thiazol-4-yl))-7-(trifluoromethyl)hydroquinolin-2-one;
3-[2-(2,6-dichlorophenyl)-1,3-thiazol-4-yl]hydroquinolin-2-one;
3-(2-(2,3-dihydrobenzo[b]furan-5-yl)-1,3-thiazol-4-yl)hydroquinolin-2-one;
3-(2-(3-thienyl)-1,3-thiazol-4-yl)hydroquinolin-2-one;
3-[2-(3,5-dichloro-4-pyridyl)-1,3-thiazol-4-yl]hydroquinolin-2-one;
3-{2-[(2-pyridylsulfonyl)methyl]-1,3-thiazol-4-yl}hydroquinolin-2-one;
3-(2-{[(2-furylmethyl)sulfonyl]methyl}-1,3-thiazol-4-yl)hydroquinolin-2-one;
3-{2-[({[3-(trifluoromethyl)phenyl]methyl}sulfonyl)methyl]-1,3-thiazol-4-yl}hydroquinolin-2-one;
3-[2-({[(4-fluorophenyl)methyl]sulfonyl}methyl)-1,3-thiazol-4-yl]hydroquinolin-2-one;
3-(2-(2-thienyl)-1,3-thiazol-4-yl)hydroquinolin-2-one;
3-(2-{[(4-chlorophenyl)sulfonyl]methyl}-1,3-thiazol-4-yl)hydroquinolin-2-one;
3-{2-[(2-thienylsulfonyl)methyl]-1,3-thiazol-4-yl}hydroquinolin-2-one;
3-{2-[(methylsulfonyl)methyl]-1,3-thiazol-4-yl}hydroquinolin-2-one;
3-{2-[(phenylsulfonyl)methyl]-1,3-thiazol-4-yl}hydroquinolin-2-one;
3-[2-(2-pyridylamino)-1,3-thiazol-4-yl]hydroquinolin-2-one hydrobromide;
3-[2-(3-pyridylamino)-1,3-thiazol-4-yl]hydroquinolin-2-one hydrobromide;
N-methyl-N-(4-(2-oxo-1,2-dihydro-3-quinolinyl)-1,3-thiazol-2-yl)benzenesulfonamide;
7-(Hydroxymethyl)-3-(2-((phenylsulfonyl)methyl)-1,3-thiazol-4-yl)-2(1H)-quinolinone;
3-(2-(3-Pyridinyl)-1,3-thiazol-4-yl)-7-(trifluoromethyl)-2(1H)-quinolinone;
3-(2-(1,3-Benzodioxol-5-yl)-1,3-thiazol-4-yl)-7-(trifluoromethyl)-2(1H)-quinolinone;
3-(2-Phenylthiomethyl-thiazol-4-yl)-1H-quinolin-2-one;
3-(2-Benzenesulfinylmethyl-thiazol-4-yl)-1H-quinolin-2-one;
N-Allyl-N-[4-(2-oxo-1,2-dihydro-quinolin-3-yl)-thiazol-2-yl]-benzenesulfonamide;
4-Bromo-N-methyl-N-[4-(2-oxo-1,2-dihydro-quinolin-3-yl)-thiazol-2-yl]-benzenesulfonamide;
3-Fluoro-N-methyl-N-[4-(2-oxo-1,2-dihydro-quinolin-3-yl)-thiazol-2-yl]-benzenesulfonamide;
N,1-Dimethyl-N-(4-(2-oxo-1,2-dihydro-3-quinolinyl)-1,3-thiazol-2-yl)-1H-imidazole-4-sulfonamide;
7-((4-Methyl-1-piperazinyl)carbonyl)-3-(2-((phenylsulfonyl)methyl)-1,3-thiazol-4-yl)-2(1H)-quinolinone;
3-(2-((Phenylsulfonyl)methyl)-1,3-thiazol-4-yl)-7-(1-piperidinylcarbonyl)-2(1H)-quinolinone
7-(Methoxy)-3-(2-((phenylsulfonyl)methyl)-1,3-thiazol-4-yl)-2(1H)-quinolinone;
3-(2-(1-Methyl-1-(phenylsulfonyl)ethyl)-1,3-thiazol-4-yl)-2(1H)-quinolinone;
3-(2-(1-Methyl-1-(phenylsulfonyl)ethyl)-1,3-thiazol-4-yl)-7-(trifluoromethyl)-2(1H)-quinolinone;
7-(4-Morpholinylcarbonyl)-3-(2-((phenylsulfonyl)methyl)-1,3-thiazol-4-yl)-2(1H)-quinolinone;

7-hydroxy-3-(2-((phenylsulfonyl)methyl)-1,3-thiazol-4-yl)-2(1H)-quinolinone;
7-(Methoxy)-3-(2-(1-methyl-1-(phenylsulfonyl)ethyl)-1,3-thiazol-4-yl)-2(1H)-quinolinone;
7-(((2R)-2-(((1-Methylethyl)amino)methyl)-1-pyrrolidinyl)methyl)-3-(2-((phenylsulfonyl)methyl)-1,3-thiazol-4-yl)-2(1H)-quinolinone;
7-(((3S)-3-(1-Methylethyl)-1-piperazinyl)methyl)-3-(2-((phenylsulfonyl)methyl)-1,3-thiazol-4-yl)-2(1H)-quinolinone;
7-((4-Methyl-1-piperazinyl)methyl)-3-(2-((phenylsulfonyl)methyl)-1,3-thiazol-4-yl)-2(1H)-quinolinone;
7-((3,5-Dimethyl-1-piperidinyl)methyl)-3-(2-((phenylsulfonyl)methyl)-1,3-thiazol-4-yl)-2(1H)-quinolinone;
7-((3-Methyl-1-piperidinyl)methyl)-3-(2-((phenylsulfonyl)methyl)-1,3-thiazol-4-yl)-2(1H)-quinolinone;
7-((3-methyl-1-piperazinyl)methyl)-3-(2-((phenylsulfonyl)methyl)-1,3-thiazol-4-yl)-2(1H)-quinolinone;
7-(3,6-Dihydro-1(2H)-pyridinylmethyl)-3-(2-((phenylsulfonyl)methyl)-1,3-thiazol-4-yl)-2(1H)-quinolinone;
7-((3,5-Dimethyl-1-piperazinyl)methyl)-3-(2-((phenylsulfonyl)methyl)-1,3-thiazol-4-yl)-2(1H)-quinolinone;
7-(((2-(Diethylamino)ethyl)(methyl)amino)methyl)-3-(2-((phenylsulfonyl)methyl)-1,3-thiazol-4-yl)-2(1H)-quinolinone;
7-((Methyl(1-methylethyl)amino)methyl)-3-(2-((phenylsulfonyl)methyl)-1,3-thiazol-4-yl)-2(1H)-quinolinone;
3-(2-((Phenylsulfonyl)methyl)-1,3-thiazol-4-yl)-7-(1-piperidinylmethyl)-2(1H)-quinolinone;
3-(2-((Phenylsulfonyl)methyl)-1,3-thiazol-4-yl)-7-(1-pyrrolidinylmethyl)-2(1H)-quinolinone;
7-((Diethylamino)methyl)-3-(2-((phenylsulfonyl)methyl)-1,3-thiazol-4-yl)-2(1H)-quinolinone;
7-((2,6-Dimethyl-4-morpholinyl)methyl)-3-(2-((phenylsulfonyl)methyl)-1,3-thiazol-4-yl)-2(1H)-quinolinone;
7-((4-Methyl-1-piperazinyl)carbonyl)-3-(2-(4-pyridinyl)-1,3-thiazol-4-yl)-2(1H)-quinolinone;
7-(3-Methyl-piperidin-1-ylmethyl)-3-(2-pyridin-4-yl-thiazol-4-yl)-1H-quinolin-2-one;
7-[(Isopropyl-methyl-amino)-methyl]-3-(2-pyridin-4-yl-thiazol-4-yl)-1H-quinolin-2-one;
2-Oxo-3-(2-pyridin-4-yl-thiazol-4-yl)-1,2-dihydro-quinoline-7-carboxylic acid (2-dimethylamino-ethyl)-ethyl-amide;
7-(Piperidine-1-carbonyl)-3-(2-pyridin-4-yl-thiazol-4-yl)-1H-quinolin-2-one;
3-(2-(2-Chloro-4-pyridinyl)-1,3-thiazol-4-yl)-7-(methoxy)-2(1H)-quinolinone;
Methyl 3-(2-(methyl(phenylsulfonyl)amino)-1,3-thiazol-4-yl)-2-oxo-1,2-dihydro-7-quinolinecarboxylate;
3-(2-(Methyl(phenylsulfonyl)amino)-1,3-thiazol-4-yl)-2-oxo-1,2-dihydro-7-quinolinecarboxylic acid;
N-Methyl-N-{4-[7-(4-methyl-piperazine-1-carbonyl)-2-oxo-1,2-dihydro-quinolin-3-yl]-thiazol-2-yl}-benzenesulfonamide;
3-[2-(Benzenesulfonyl-methyl-amino)-thiazol-4-yl]-2-oxo-1,2-dihydro-quinoline-7-carboxylic acid ethylamide;
N,N-Diethyl-3-(2-(methyl(phenylsulfonyl)amino)-1,3-thiazol-4-yl)-2-oxo-1,2-dihydro-7-quinolinecarboxamide;
7-(Isopropylamino-methyl)-3-(2-pyridin-4-yl-thiazol-4-yl)-1H-quinolin-2-one;
3-(2-Pyridin-4-yl-thiazol-4-yl)-7-pyzrolidin-1-ylmethyl-1H-quinolin-2-one;
7-Diethylaminomethyl-3-(2-pyridin-4-yl-thiazol-4-yl)-1H-quinolin-2-one;
7-Azetidin-1-ylmethyl-3-(2-pyridin-4-yl-thiazol-4-yl)-1H-quinolin-2-one;
7-(3-Hydroxy-pyrrolidin-1-ylmethyl)-3-(2-pyridin-4-yl-thiazol-4-yl)-1H-quinolin-2-one;
7-((3-(Dimethylamino)propyl)oxy)-3-(2-(4-pyridinyl)-1,3-thiazol-4-yl)-2(1H)-quinolinone;
7-((2-(Dimethylamino)ethyl)oxy)-3-(2-(4-pyridinyl)-1,3-thiazol-4-yl)-2(1H)-quinolinone;
7-((2-(4-Morpholinyl)ethyl)oxy)-3-(2-(4-pyridinyl)-1,3-thiazol-4-yl)-2(1H)-quinolinone;
7-(4-Hydroxy-piperidin-1-ylmethyl)-3-(2-pyridin-4-yl-thiazol-4-yl)-1H-quinolin-2-one;
7-(2,6-Dimethyl-morpholin-4-ylmethyl)-3-(2-pyridin-4-yl-thiazol-4-yl)-1H-quinolin-2-one;
7-(3,5-Dimethyl-piperidin-1-ylmethyl)-3-(2-pyridin-4-yl-thiazol-4-yl)-1H-quinolin-2-one;
7-Morpholin-4-ylmethyl-3-(2-pyridin-4-yl-thiazol-4-yl)-1H-quinolin-2-one;
7-(3-Hydroxy-piperidin-1-ylmethyl)-3-(2-pyridin-4-yl-thiazol-4-yl)-1H-quinolin-2-one;
7-{[(2-Diethylamino-ethyl)-methyl-amino]-methyl}-3-(2-pyridin-4-yl-thiazol-4-yl)-1H-quinolin-2-one;
7-Cyclopentylaminomethyl-3-(2-pyridin-4-yl-thiazol-4-yl)-1H-quinolin-2-one;
7-(3-Methyl-piperazin-1-ylmethyl)-3-(2-pyridin-4-yl-thiazol-4-yl)-1H-quinolin-2-one;
7-{[(2-Dimethylamino-ethyl)-ethyl-amino]-methyl}-3-(2-pyridin-4-yl-thiazol-4-yl)-1H-quinolin-2-one;
7-(Isobutylamino-methyl)-3-(2-pyridin-4-yl-thiazol-4-yl)-1H-quinolin-2-one; and
7-[(1-Hydroxymethyl-2-methyl-propylamino)-methyl]-3-(2-pyridin-4-yl-thiazol-4-yl)-1H-quinolin-2-one.

Indications

Compounds of the present invention would be useful for, but not limited to, the treatment of cell proliferative diseases, cell death or of apoptosis.

The compounds of the invention are endowed with serine-threonine kinase inhibitory activity, such as CDK/cyclin kinase inhibitory activity.

The compounds of the invention are useful in therapy as antineoplasia agents.

Compounds of the invention would be useful for the treatment of neoplasia including cancer, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-Lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of neoplasia selected from lung cancer, colon cancer and breast cancer.

Due to the key role of CDKs in the regulation of cellular proliferation, these compounds are also useful in the treatment of a variety of cell proliferative disorders such as, for instance, blood vessel proliferative disorders including arthritis and restenosis; fibrotic disorders including hepatic cirrhosis and atherosclerosis; mesangial cell proliferative disorders including glomerulonephritis, diabetic nephropathy, malignant nephrosclerosis, thrombotic microangiopathy syndromes, transplant rejection and glomerulopathies; metabolic disorders including psoriasis, diabetes mellitus, chronic wound healing, inflammation, and diabetic retinopathy and other vision disorders; and others including benign prostate hyperplasia, familial adenomatosis polyposis, neuro-fibromatosis, pulmonary fibrosis, angiogenesis, metastasis, vascular smooth cell proliferation, post-surgical stenosis and hypertrophic scar formation, eczema, inflammatory bowel disease, endotoxic shock, and fungal infections.

The compounds of the invention are useful to prevent the phosphorylation of tau protein.

The compounds of the invention are useful in the treatment of neurological disorders, including neurological injuries and neurodegenerative diseases, such as, but not limited to, stroke, brain trauma, epilepsy, spinal cord injury, ischemia, multiple sclerosis, vision related disorders including but not limited to glaucoma and macular degeneration, hearing loss, AIDS-related dementia, retinitis pigmentosa, spinal muscular atrophy, cerebellar degeneration, amyotrophic lateral sclerosis, Parkinson's disease, Huntington's disease and Alzheimer's disease.

Compounds of Formula I–V, as inhibitors of the CDKs, can modulate the level of cellular RNA and DNA synthesis. These agents would therefore be useful in the treatment of viral infections, including but not limited to HIV, human papilloma virus, herpesvirus, poxvirus, Epstein-Barr virus, Sindbis virus and adenovirus.

The compounds of this invention may also act as inhibitors of other protein kinases, e.g. GSK, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

Inhibitors of certain kinases may have utility in the treatment of diseases when the kinase is not misregulated, but is nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle. Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents. Inhibition of CDK2 or CDK4 will prevent progression into the cycle in normal cells and limit the toxicity of cytotoxics which act in S-phase, G2 or mitosis. Furthermore, CDK2/cyclin E activity has also been shown to regulate NF-κB: Inhibition of CDK2 activity stimulates NF-κB-dependent gene expression, an event mediated through interactions with the p300 coactivator. NF-κB regulates genes involved in inflammatory responses, (such as hematopoietic growth factors chemokines and leukocyte adhesion molecules) and may be involved in the suppression of apoptotic signals within the cell. Thus, inhibition of CDK2 may suppress apoptosis induced by cytotoxic drugs via a mechanism which involves NF-κB. Inhibition of CDK2 activity may also have utility in other cases where regulation of NF-κB plays a role in etiology of disease. A further example may be taken from fungal infections: Inhibition of the Aspergillus kinases Cdc2/CDC28 or Nim A may cause arrest or death in the fungi, improving the therapeutic outcome for patients with these infections.

The compounds of the invention are useful as modulators of apoptosis. As such they are useful in the prevention of AIDS development in HIV-infected individuals, autoimmune diseases (including but not limited to systemic lupus, erythematosus, autoimmune mediated glomerulonephritis, rheumatoid arthritis and autoimmune diabetes mellitus), myelodysplastic syndromes, aplastic anemia, ischemic injury associated with myocardial infarctions, stroke and reperfusion injury, vision related disorders including but not limited to glaucoma and macular degeneration, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis) aspirin-sensitive rhinosinusitis, cystic fibrosis, kidney diseases and cancer pain.

Definitions

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neuroplastic therapeutic agents prolong the survivability of the patient, inhibit the rapidly-proliferating cell growth associated with the neoplasm, or effect a regression of the neoplasm. Alternatively, effective therapeutic agents for the treatment of neurological disorders minimize the damage from injury, improve cognitive functions, and the like.

The term "treatment" includes therapeutic treatment as well as prophylactic treatment (either preventing the onset of disorders altogether or delaying the onset of a preclinically evident stage of disorders in individuals).

The term "H" denotes a single hydrogen atom. This radical may be attached, for example, to an oxygen atom to form a hydroxyl radical.

Where the term "alkyl" is used, either alone or within other terms such as "haloalkyl", "cyanoalkyl" and "alkylamino", it embraces linear or branched radicals having one to about twenty carbon atoms or, preferably, one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to four carbon atoms. The term "alkylenyl" embraces bridging divalent alkyl radicals such as methylenyl and ethyleneyl.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations.

The term "alkynyl" denotes linear or branched radicals having at least one carbon-carbon triple bond and having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about four carbon atoms. Examples of such radicals include propargyl, butynyl, and the like.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy, and fluoropropoxy.

The term "aryl", alone or in combination, means a carbocyclic aromatic system containing one or two rings wherein such rings may be attached together in a pendent manner or may be fused. The term "aryl" embraces aromatic radicals such as phenyl, naphthyl, tetrahydronaphthyl, indane and biphenyl. More preferred aryl is phenyl. Said "aryl" group may have 1 to 3 substituents such as lower alkyl, hydroxyl, halo, haloalkyl, nitro, cyano, alkoxy, and lower alkylamino. Benzodioxolyl is considered aryl.

The term "heterocyclyl" embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, halo, haloalkyl, cyano, lower alkyl, lower aralkyl, oxo, lower alkoxy, amino, and lower alkylamino.

Examples of saturated heterocyclic radicals include saturated 3 to 6-membered heteromonocyclic group containing 1 to 4 nitrogen atoms [e.g. pyrrolidinyl, imidazolidinyl, piperidino, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole.

Examples of unsaturated heterocyclic radicals, also termed "heteroaryl" radicals, include unsaturated 5 to 6 membered heteromonocyclyl groups containing 1 to 4 nitrogen atoms, for example, pyrrolyl, pyrrolinyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 3 to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b] pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms (e.g., benzothiazolyl, benzothiadiazolyl].

The term also includes bridged, spiro and oxo-containing heterocyclic rings, such as 1,4-dioxa-8-aza-spiro[4.5]decyl, phthalimidyl, 1,4-dioxa-8-aza-spiro[4.5]decyl, and (1-azabicyclo[2.2.2]oct-3-yl).

Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, and pyrazinyl. Even more preferred heteroaryl radicals are 5- or 6-membered heteroaryl, containing one or two heteroatoms selected from sulfur nitrogen and oxygen, selected from thienyl, furanyl, pyrrolyl, thiazolyl, oxazolyl, imidazolyl, pyrazolyl, isoxazolyl, isothiazolyl, pyridyl, piperidinyl and pyrazinyl.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," whether alone or used with terms such as "N-alkylaminosulfonyl", "N-arylaminosulfonyl", "N,N- dialkylaminosulfonyl" and "N-alkyl-N-arylaminosulfonyl", denotes a sulfonyl radical substituted with an amine radical, forming a sulfonamide (—SO$_2$NH$_2$).

The term "alkylaminosulfonyl" includes "N-alkylaminosulfonyl" and "N,N-dialkylaminosulfonyl" where sulfamyl radicals are independently substituted, respectively, with one alkyl radical, or two alkyl radicals. More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, N-ethylaminosulfonyl and N-methyl-N-ethylaminosulfonyl.

The terms "N-arylaminosulfonyl" and "N-alkyl-N-arylaminosulfonyl" denote sulfamyl radicals substituted, respectively, with one aryl radical, or one alkyl and one aryl radical. More preferred N-alkyl-N-arylaminosulfonyl radicals are "lower N-alkyl-N-arylsulfonyl" radicals having alkyl radicals of one to six carbon atoms. Even more preferred are lower N-alkyl-N-arylsulfonyl radicals having one to three carbon atoms. Examples of such lower N-alkyl-N-aryl-aminosulfonyl radicals include N-methyl-N-phenylaminosulfonyl and N-ethyl-N-phenylaminosulfonyl. Examples of such N-aryl-aminosulfonyl radicals include N-phenylaminosulfonyl.

The term "arylalkylaminosulfonyl" embraces aralkyl radicals as described above, attached to an aminosulfonyl radical. More preferred are lower arylalkylaminosulfonyl radicals having one to three carbon atoms.

The term "heterocyclylaminosulfonyl" embraces heterocyclyl radicals as described above, attached to an aminosulfonyl radical.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The terms "alkylcarbonyl" denotes carbonyl radicals which have been substituted with an alkyl radical. More preferred are "lower alkylcarbonyl" having lower alkyl radicals as described above attached to a carbonyl radical.

The terms "arylcarbonyl" denotes carbonyl radicals substituted with an aryl radical. More preferred are "optionally substituted phenylcarbonyl" radicals.

The terms "cycloalkylcarbonyl" denotes carbonyl radicals substituted with an cycloalkyl radical. More preferred are "optionally substituted cycloalkylcarbonyl" radicals, even more preferably containing C$_{3-6}$ cycloalkyl.

The terms "heterocyclylcarbonyl" denotes carbonyl radicals substituted with an heterocyclyl radical. More preferred are "optionally substituted 5–6 membered heterocyclylcarbonyl" radicals.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula —C(=O)NH$_2$.

The terms "N-alkylaminocarbonyl" and "N,N-dialkylaminocarbonyl", denote aminocarbonyl radicals which have been substituted with one alkyl radical and independently with two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces aminoalkyl radicals having the nitrogen atom independently substituted with an alkyl radical. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "arylalkenyl" embraces aryl-substituted. alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, halkoalkyl and haloalkoxy.

The term "arylalkynyl" embraces aryl-substituted alkynyl radicals. Preferable arylalkynyl radicals are "lower arylalkynyl" radicals having aryl radicals attached to alkynyl radicals having two to six carbon atoms. Examples of such radicals include phenylethynyl. The aryl in said aralkyl may be additionally substituted with halo, alkyl, alkoxy, halkoalkyl and haloalkoxy. The terms benzyl and phenylmethyl are interchangeable.

The term "alkylthiol" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$S—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylsulfinyl" embraces radicals containing a linear or branched alkyl radical, of one to ten carbon atoms, attached to a divalent —S(=O)— atom. More preferred are lower alkylsulfinyl radicals having one to three carbon atoms.

The term "arylsulfinyl" embraces radicals containing an aryl radical, attached to a divalent —S(=O)— atom. Even more preferred are optionally substituted phenylsulfinyl radicals.

The term "haloalkylsulfinyl" embraces radicals containing a haloalkyl radical, of one to ten carbon atoms, attached to a divalent —S(=O)— atom. Even more preferred are lower haloalkylsulfinyl radicals having one to three carbon atoms.

The term "alkylamino" denotes amino groups which have been substituted with one alkyl radical and with two alkyl radicals, including terms "N-alkylamino" and "N,N-dialkylamino". More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The "arylamino" radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$–$C_3$-alkylamino radicals, such as N-benzylamino. The "aralkylamino" radicals may be further substituted on the aryl ring portion of the radical.

The term "alkylaminoalkylamino" denotes alkylamino groups which have been substituted with one or two alkylamino radicals. More preferred are $C_1$–$C_3$-alkylamino-$C_1$–$C_3$-alkylamino radicals.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The terms "N-alkyl-N-arylamino" and "N-aralkyl-N-alkylamino" denote amino groups which have been substituted with one aralkyl and one alkyl radical, or one aryl and one alkyl radical, respectively, to an amino group.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$–$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heterocyclylalkoxy" embraces oxy-containing heterocyclylalkyl radicals attached through an oxygen atom to other radicals. More preferred heterocyclylalkoxy radicals are "lower heteroarylalkoxy" radicals having optionally substituted heteroaryl radicals attached to lower alkoxy radical as described above.

The term "heterocyclyloxyalkyl" embraces heteroaryl radicals attached through an ether oxygen atom to an alkyl radical. More preferred heterocyclyloxyalkyl radicals are "lower heteroaryloxyalkyl" radicals having optionally substituted heteroaryl radicals attached to an —O—$C_{1-6}$ alkyl radical.

The term "cycloalkyl" includes saturated carbocyclic groups. Preferred cycloalkyl groups include $C_3$–$C_6$ rings. More preferred compounds include, cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$–$C_6$ rings. More preferred compounds include, for example, cyclopentenyl, cyclopentadienyl, cyclohexenyl and cycloheptadienyl.

The term "comprising" is meant to be open ended, including the indicated component but not excluding other elements.

The present invention preferably includes compounds that selectively inhibit CDK2 and/or CDK5.

The present invention also comprises the use of a compound of the invention, or pharmaceutically acceptable salt thereof, in the manufacture of a medicament for the treatment either acutely or chronically of a cell proliferation or apoptosis mediated disease state, including those described previously. The compounds of the present invention are also useful in the manufacture of an anti-cancer medicament. The compounds of the present invention are also useful in the manufacture of a medicament to attenuate or prevent disorders through inhibition of CDKs and other kinases. The compounds of the present invention are also useful in the manufacture of a medicament to treat neurological disorders.

The present invention comprises a pharmaceutical composition comprising a therapeutically-effective amount of a compound of Formulas I–V in association with a least one pharmaceutically-acceptable carrier, adjuvant or diluent.

The present invention also comprises a method of treating cell proliferative disorders, apoptosis mediated disorders, cancer, CDK mediated disorder or neurological disorders, in a subject, the method comprising treating the subject having or susceptible to such disorder with a therapeutically-effective amount of a compound of Formulas I–V.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the treatment of neoplasia, such as with radiation therapy or with cytostatic or cytotoxic agents; or in the treatment of neurological disorders, such as with thrombolytic and anticoagulant agents, anti-inflammatory agents, NMDA inhibitors, antiparkinsonian agents, and inhibitors of lipid peroxidation.

If formulated as a fixed dose, such combination products employ the compounds of this invention within the accepted dosage ranges. Compounds of Formula I–V may also be administered sequentially with known agents when a combination formulation is inappropriate. The invention is not limited in the sequence of administration; compounds of the invention may be administered either prior to, at the same time with or after administration of the other agent.

Currently, standard treatment of primary tumors consists of surgical excision followed by either radiation or IV administered chemotherapy. The typical chemotherapy regime consists of either DNA alkylating agents, DNA intercalating agents or microtubule poisons. The chemotherapy doses used are just below the maximal tolerated dose and therefore dose limiting toxicities typically include, nausea, vomiting, diarrhea, hair loss, neutropenia and the like. Experiments performed in in vivo animal models and in in vitro cell based assays have demonstrated that combining chemotherapeutic agents with cell cycle inhibitors, such as CDK inhibitors, typically results in either decreased rate of tumor growth or, in some cases, tumor regression. Combining chemotherapy with a CDK inhibitor typically results in an increased therapeutic index and lower levels of both agents are required. This ultimately results in a decrease in toxicity and an increase in efficacy.

Schwartz et al, Clin. Can. Res., 3,1467–1472 (1997) have demonstrated that combining the CDK inhibitor flavopiridol with mitomycin-C (DNA alkylating agent) resulted in an increased rate of apoptosis in gastric and breast cancer cells. Bible et al (Bible et al., Cancer Res., 57, 3375–3380 (1997) have also demonstrated therapeutic synergy exists between flavopiridol and paclitaxel, cytarabine, topotecan, doxorubicin, and etoposide (all standard chemotherapeutic agents) when tested in cell based assays using human non-small cell lung cancer cells. Preclinical models (cell culture) suggest that a cell cycle inhibitor potentiates the effect of a cytotoxic agent when administered after the chemotherapeutic agent. The chemotherapeutic agent will induce specific DNA/mitotic damage checkpoints in normal cells which in combination with a CDK inhibitor will cause a cell cycle arrest or cytostatic effect. In contrast, tumor cells will be driven into apoptosis or cell death when a chemotherapeutic agent and a CDK inhibitor are combined due to tumor cells attempting to activate defective DNA damage and cell cycle checkpoints. In addition, scheduling of a CDK inhibitor for clinical trials should include a rest period to allow the patients normal cells to recover and reduce the potential for cytotoxic side effects.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine protein kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celecoxib, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit anti-thymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with other anti-neoplastic agents, such as other kinase inhibitors including KDR inhibitors, p38 inhibitors, TNF inhibitors, metallomatrix proteases inhibitors (MMP), COX-2 inhibitors, NSAID's, SOD mimics or $\alpha_v\beta_3$ inhibitors.

Alternatively, the present compounds may also be used in co-therapies with other treatments for neurological treatments such as thrombolytic and anticoagulant agents including tPA, urokinase and inhibitors of platelet aggregation, p38 inhibitors, IL1ra, NMDA inhibitors, antiparkinsonian agents including carbidopa and levodopa, and inhibitors of lipid peroxidation, for example.

The present invention comprises a process for the preparation of a compound of Formula I–V.

Compounds of the present invention can possess, in general, one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

Compounds of the present invention can possess, in general, tautomeric forms, which are included in the family of compounds in Formula I–V.

Also included in the family of compounds of Formula I–V are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I–V may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I–V include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I–V.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl, $H_2SO_4$ and $H_3PO_4$ and such organic acids as oxalic acid, maleic acid, succinic acid and citric acid. Other examples include salts with alkali metals or alkaline earth metals, such as sodium, potassium, calcium or magnesium or with organic bases.

Additional examples of such salts can be found in Berge et al., J. Pharm. Sci., 66, 1 (1977).

General Synthetic Procedures

The compounds of the invention can be synthesized according to the following procedures of Schemes 1–5, wherein the substituents are as defined for Formulas I–V, above, except where further noted.

Scheme 1

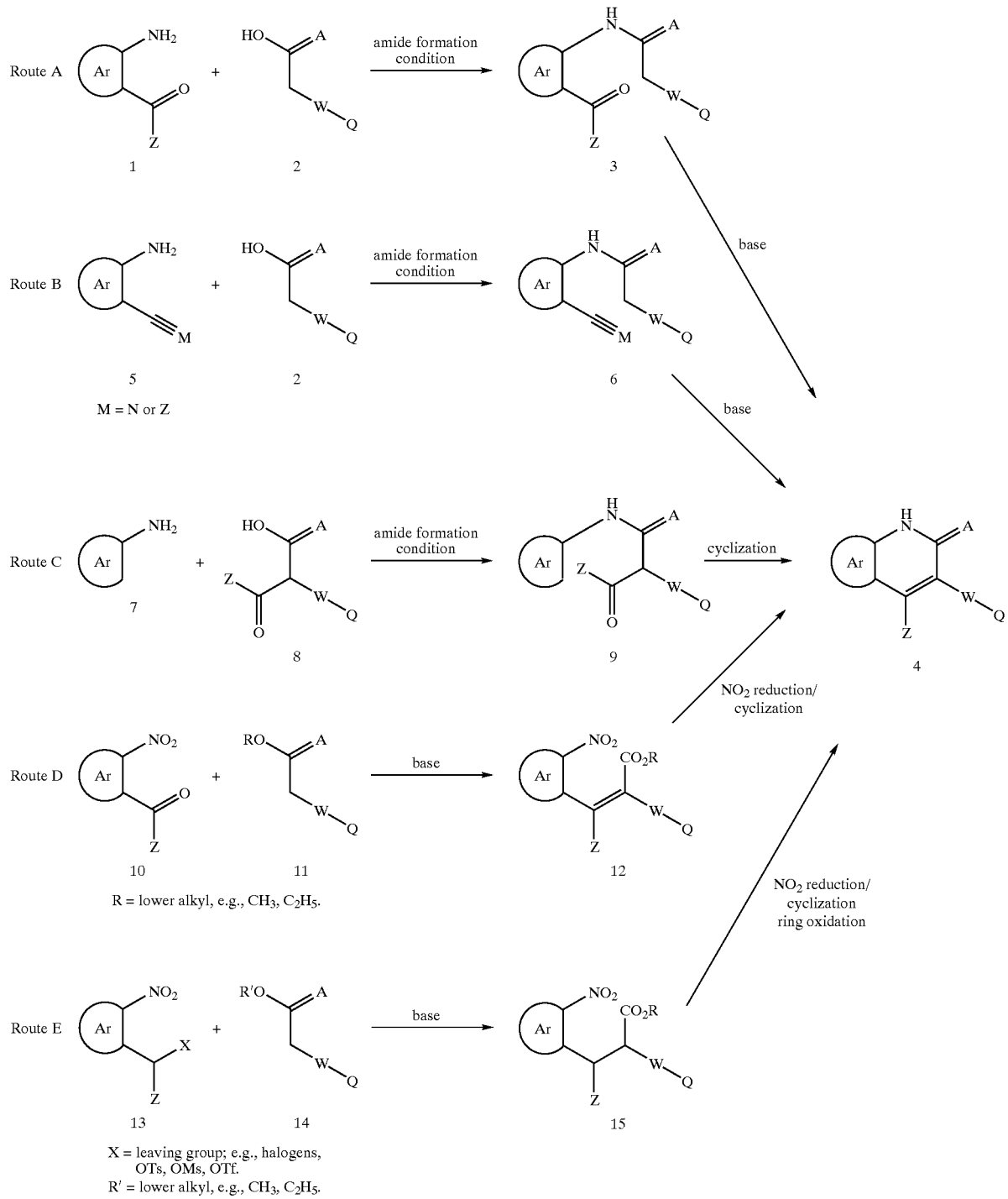

Substituted bicyclic pyridones 4 can be prepared according to the cyclization methods set out in Scheme 1. Substituted acids 2 are coupled with aromatic aldehydes or ketones 1, such as optionally substituted aminobenzaldehydes, under standard amino coupling chemistry to afford the amides 3 (Route A). Such coupling occurs in the presence of a coupling agent such as EDC and base, such as DIEA, in an appropriate organic solvent, such as $CH_2Cl_2$. The aromatic amides 3 are cyclized with base, such as with potassium tert-butoxide, to form the bicyclic pyridones 4.

Substituted bicyclic pyridones 4 can also be prepared by coupling substituted acids 2 with aromatic nitriles 5, such as optionally substituted aminobenzonitriles, under standard amino coupling chemistry to afford the amides 6 (Route B). Such coupling occurs in the presence of a coupling agent such as EDC and base, such as DIEA, in an appropriate organic solvent, such as $CH_2Cl_2$. The aromatic amides 6 are cyclized with base, such as with potassium tert-butoxide, to form the substituted bicyclic pyridones 4.

Likewise, aromatic amines 7 may be coupled with substituted acids 8 under standard amino coupling conditions to provide amides 9 (Route C). Cyclization affords the substituted bicyclic pyridones 4.

Alternatively, treatment of nitroaryls 10, such as a keto-nitrobenzene, with substituted esters 11 in the presence of base provides esters 12 (Route D). Reduction of the nitro moiety of ester 12 followed by cyclization provides the substituted bicyclic pyridones 4.

Alternatively, bicyclic pyridones 4 can be prepared from esters 14 by treatment with base, such as with LHMDS, at a temperature below about RT, preferably below about −45° C. and even more preferably at about −78° C. Reaction with a nitro aryl 13 at a temperature below about RT, preferably below about −45° C., yielded the addition product 15 (Route E). Reduction and cyclization of the nitro-aryl ester, such as with iron or tin chloride, yielded the saturated bicyclic pyridones. Oxidation, such as with NBS and AIBN, in the presence of a non-protic co-solvent, such as $CCl_4$, at a temperature above about RT, preferably above about 50° C., more preferably at about 85° C., provides the bicyclic pyridones 4.

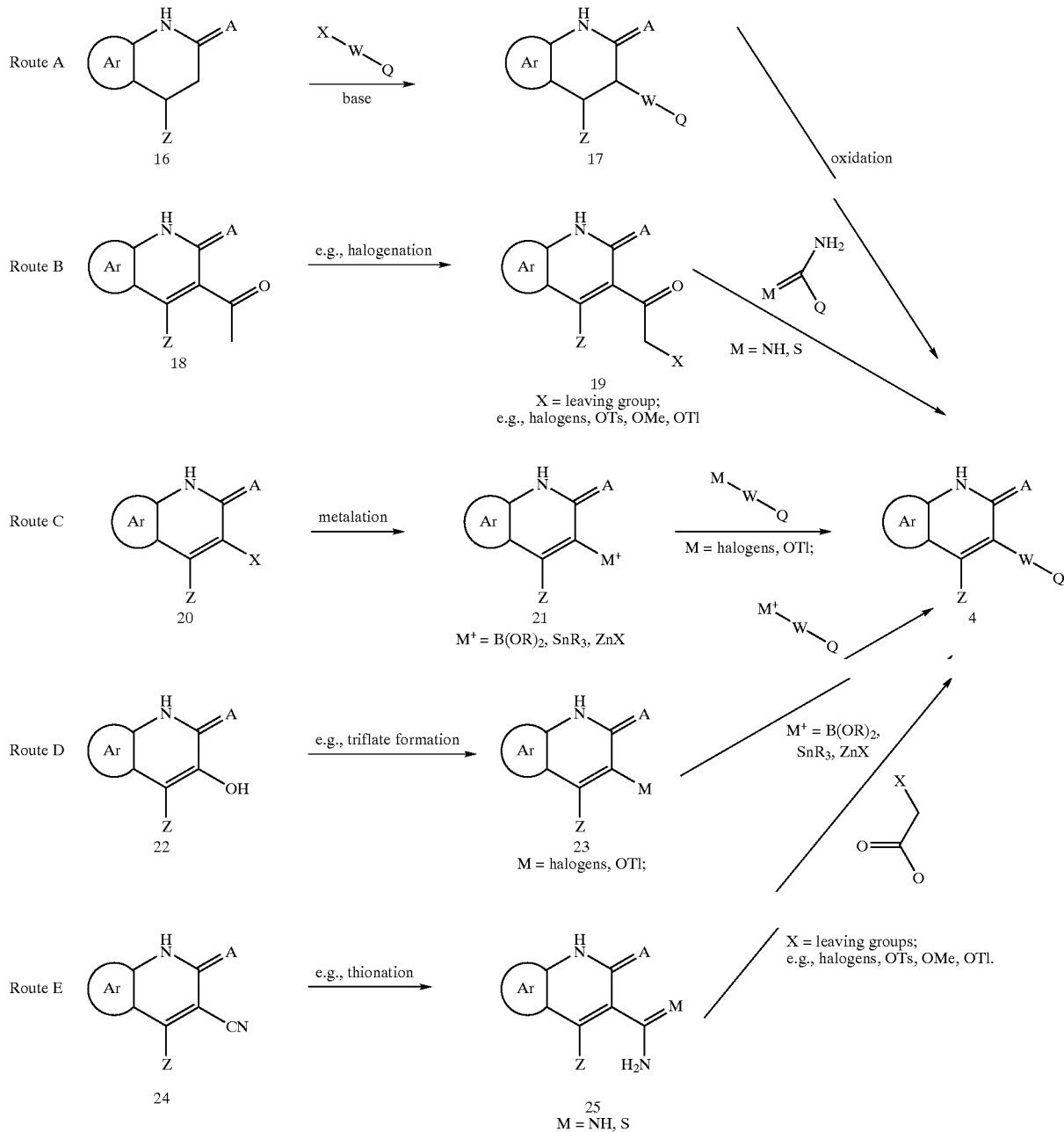

Scheme 2

Substituted bicyclic pyridones 4 alternatively can be prepared according to the methods set out in Scheme 2. Dihydro-pyridone 17 can be prepared from pyridone 16 and an appropriate halide, tosylate, triflate or mesylate in the presence of base (Route A). Oxidation of the bicyclic ring system affords the substituted bicyclic pyridones 4.

The haloacetyl-bicyclic pyridones 19 were prepared by halogenation of the corresponding acetyl-bicyclic-pyridones 18, such as with 5,5-dibromobarbituric acid in anhydrous solvent, such as THF, at a temperature above about RT, preferably above about 50° C., more preferably at about reflux (Route B). Condensation with an appropriate urea, thiourea or thioamide in anhydrous solvent, such as an alcohol including MeOH, at a temperature above about RT, preferably above about 50° C., more preferably at about reflux, provides the heterocyclic substituted bicyclic pyridones 4. Alternatively, a microwave synthetic apparatus (such as a Smith synthesizer) can be utilized.

Additionally, bicyclic pyridone 20 may be converted, via lithiation or metal catalyzed coupling, to pyridones 21 (Route C). Metal catalyzed coupling of 21 with an appropriate halogen or triflate would then afford substituted bicyclic pyridones 4. Alternatively, hydroxy-pyridone 22 may be converted to either halide or triflate 23 and subjected to metal catalyzed coupling with an appropriate metalo-aryl, such as a boronic acid, a stannane or an organozinc, to yield substituted bicyclic pyridones 4 (Route D).

In addition, substituted nitriles 24 are added to base at about RT and $H_2S$ is bubbled through the solution, to yield the thioamide 25 (Route E). Treatment of thioamides 25 (M=S) with an appropriate ketone in a polar protic solvent, such as MeOH, yields the substituted bicyclic pyridones 4.

Scheme 3

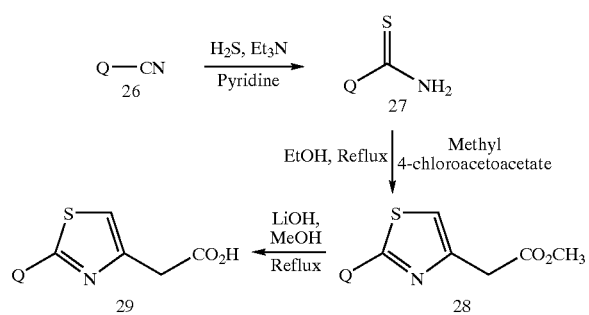

Substituted thiazolyl acetic acids 29 are prepared from the corresponding nitriles 26 according to the method set out in Scheme 3. Substituted nitriles 26 are added to base at about RT and $H_2S$ is bubbled through the solution, to yield the thioamide 27. The thioamide 27 is combined with methyl 4-chloroacetoacetate and heated at a temperature above about RT, preferably above about 50° C., more preferably at about 75° C., to form the thiazolyl acetate ester 28. Hydrolysis of the ester 28, such as with a base, such as LiOH, at a temperature above about RT, preferably above about 50° C., more preferably at about 75° C., provides the substituted thiazole acetic acid 29.

Scheme 4

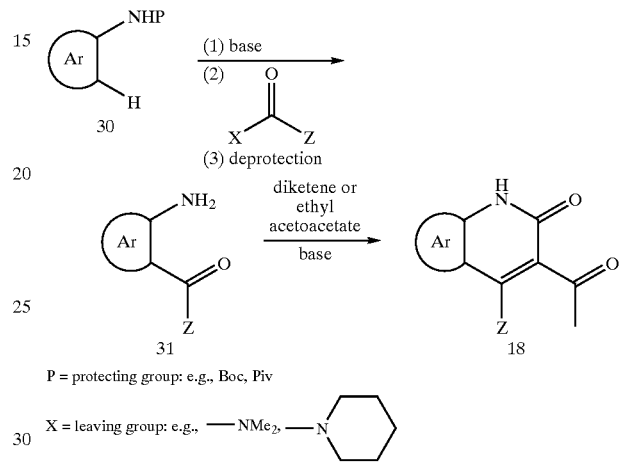

P = protecting group: e.g., Boc, Piv

X = leaving group: e.g., —NMe₂, —N(piperidine)

Acetyl-bicyclic-pyridones 18 are prepared from the corresponding aldehydes 31 according to the method set out in Scheme 4. Protected aromatic amine 30 may be treated with a base, and quenched with a formylating reagent, such as DMF or 1-formylpiperidine, to provide the aromatic aldehyde. Removal of the protecting group provides the amine 31. A mixture of arylaldehyde 31 and ethyl acetoacetate in the presence of base, such as piperidine, and a suitable solvent, such as o-xylene is heated at a temperature above about RT, preferably above about 50° C., more preferably at about reflux to provide the acetyl-bicyclic-pyridones 18. Alternatively, a mixture of aryl aldehyde 31 and diketene in the presence of a catalyst, such as DMAP, and a suitable solvent, such as 1,2-dichloroethane is heated at a temperature above about RT, preferably above about 50° C., more preferably at about reflux to provide the acetyl-bicyclic-pyridones 18.

Scheme 5

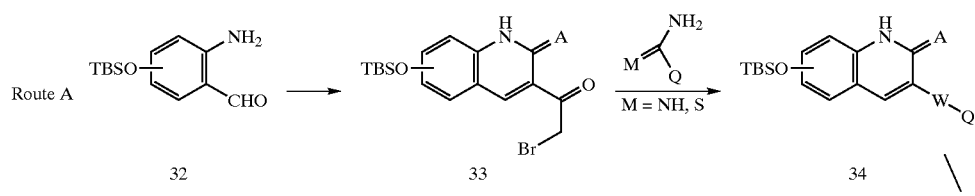

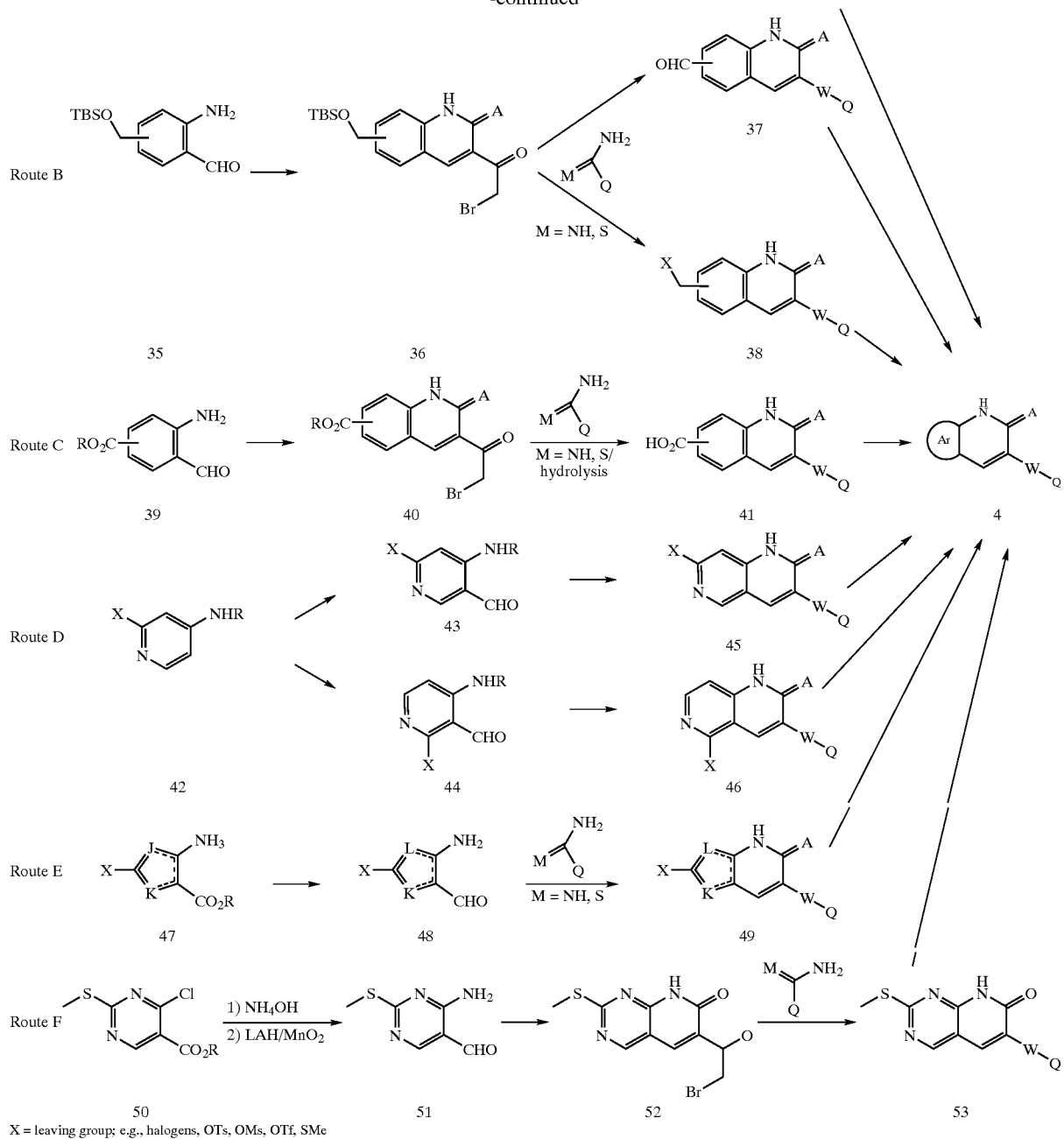

X = leaving group; e.g., halogens, OTs, OMs, OTf, SMe
R = lower alkyl, eg., CH$_3$, C$_2$H$_5$.

Substituted bicyclic pyridones 4 may be prepared according to Scheme 5. Amino-benzaldehyde 32 may be converted to the acetyl quinolone and subsequently brominated to provide quinolone 33 (Route A). Pyridone 33 may be condensed with an appropriate urea, thiourea, or thioamide to yield pyridone 34. Following removal of the TBS group the resulting phenol may be acylated or alkylated to afford substituted bicyclic pyridones 4.

In a similar manner, amino benzaldehydes 35 are converted to bromoketone 36 (Route B). Treatment with an appropriate urea, thiourea, or thioamide followed by deprotection and oxidation afforded pyridones 37. Pyridones 37 are subjected to reductive amination conditions to afford substituted bicyclic pyridones 4. Likewise, bromoketones 36 are treated with an appropriate urea, thiourea, or thioamide and deprotected providing pyridones 38 (X=OH). Conversion of alcohol 38 (X=OH) to a leaving group (where X is, for example, a halogen, OTs, OMs, OTf) and displacement with an appropriate amine provided substituted bicyclic pyridones 4.

In addition, benzaldehydes 39 are converted to bromoketones 40 (Route C). Treatment of bromoketone 40 with an appropriate urea, thiourea, or thioamide followed by hydrolysis of the ester affords substituted acids 41. Acid 41 can be converted to substituted bicyclic pyridones 4 using standard coupling conditions.

Pyridine 42 may be lithiated and treated with a formyl-quenching reagent, such as DMF or 1-formylpiperidine, to afford either pyridines 43 (R=Boc) or 44 (R=Boc) (Route D). Following deprotection of the amine, the pyridines 43

(R=H) or 44 (R=H) may be converted to the bromoketone and treated with an appropriate urea, thiourea, or thioamide to yield provides the substituted bicyclic pyridones 4.

In addition, ester 47 may be converted to aldehyde 48 (Route E). Aldehyde 48 is converted to the bromoketone and subsequently treated with an appropriate urea, thiourea, or thioamide to afford pyridone 49. Displacement of the leaving group provides substituted bicyclic pyridones 4.

In a similar fashion, chloropyrimidine 50 could be converted to the corresponding aminopyrimidine which can be further transformed to aldehyde 51 following a reduction (such as with LAH) and oxidation (such as with $MnO_2$) reaction sequence. Aldehyde 51 is converted to bromoketone 52 and subsequently treated with an appropriate urea, thiourea, or thioamide to afford pyridone 53. Displacement of the methylthio group with or without prior oxidation, such as with mCPBA, provides substituted bicyclic pyridone 4.

N-Oxides can be obtained in a known matter by reacting a compound of Formula I–V with hydrogen peroxide or a peracid, e.g. 3-chloroperoxy-benzoic acid, in an inert solvent, e.g. $CH_2Cl_2$, at a temperature between about −10 to about 35° C., such as about 0° C. to about RT.

In the preparation of starting materials, existing functional groups, for example carboxy, hydroxy, amino, or mercapto, which do not participate in the reaction should, if necessary, be protected. Such protecting groups are those or similar to those usually used in the synthesis of peptide compounds, cephalosporins, penicillins, nucleic acid derivatives or sugars. Preferred protecting groups, their introduction and their removal are described above or in the examples.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves ready removal, i.e. without undesired secondary reactions, typically by solvolysis, reduction, photolysis or also by enzyme activity, for example under conditions analogous to physiological conditions, and that they are not present in the end-products. One skilled in the art knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

In certain cases, typically in hydrogenation processes, it is possible to achieve stereoselective reactions, allowing for example easier recovery of individual isomers.

The solvents from which those can be selected which are suitable for the reaction in question include, for example, water, esters, typically lower alkyl-lower alkanoates, e.g EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH or 1-propanol or iPrOH, nitrites, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. AcOH, carboxylic acid anhydrides, typically lower alkane acid anhydrides, e.g. $Ac_2O$, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I–V, including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

All remaining starting materials are known, capable of being prepared according to known processes, or commercially obtainable; in particular, they can be prepared using processes as described above or as in the examples.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention.

The compounds of this invention may also be represented in multiple tautomeric forms, for example, as illustrated below:

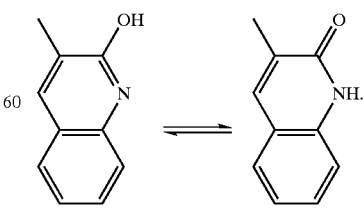

The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thiazolyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

A compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, simulated moving bed ("SMB")), extraction, distillation, trituration, reverse phase HPLC and the like. Reactions conditions such as temperature, duration, pressure, and atmosphere (inert gas, ambient) are known in the art and may be adjusted as appropriate for the reaction. Additionally, the compounds can be produced metabolically.

As can be appreciated by one skilled in the art, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. Greene and P. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995); P. Lopez et al., Synthesis 2, 186 (1998); A. Mikhalev, et al., Khim. Geterotsikl Soedin, 5, 697 (1997); M. Fernandez, et al., Synthesis, 11, 1362 (1995); P. Desos, et al., J. Med. Chem, 39, 197 (1996); G. Timari, et al., Synlett, 9, 1067 (1997); Y. Tagawa, et al., J. Heterocycl. Chem., 34, 1677 (1997); A. Fuerstner, et al., Chem. Sci. 50, 326 (1995); A. Katritzky and A. Pozharski, Handbook of Heterocyclic Chemistry, $2^{nd}$ Ed. (2001); and WO01/132658.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The following examples contain detailed descriptions of the methods of preparation of compounds of Formulas I–V. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

The following abbreviations are used:

| | |
|---|---|
| AcOH, HOAc - | acetic acid |
| $Ac_2O$ - | acetic anhydride |
| $CH_3CN$ - | acetonitrile |
| ATP - | adenosine triphosphate |
| $NH_3$ - | ammonia |
| $NH_4Cl$ - | ammonium chloride |
| AIBN - | 2,2'-azobisisobutyronitrile |
| $BH_3$ - | borane |
| BSA - | bovine serum albumin |
| $CCl_4$ - | carbon tetrachloride |
| d - | day |
| $CH_2Cl_2$ - | dichloromethane |
| $Et_2O$ - | diethyl ether |
| DEA - | diethylamine |
| DIBAL-H - | diisobutylaluminum hydride |
| DIEA - | diisopropylethylamine |
| DMAP - | 4-(dimethylamino)pyridine |
| EDC - | 1-(3-dimethylaminopropyl)-3-ethylcarbodiimide hydrochloride |
| DMF - | dimethylformamide |
| DMSO - | dimethylsulfoxide |
| DTT - | dithiothreitol |
| EtOH - | ethanol |
| EtOAc - | ethyl acetate |
| EGTA - | ethylene glycol-bis(β-aminoethyl ether)-N,N,N', N'-tetraacetic acid |
| EDTA - | ethylenediaminetetraacetic acid |
| g - | gram |
| h - | hour |
| HCl - | hydrochloric acid |
| $H_2$ - | hydrogen |
| $H_2S$ - | hydrogen sulfide |
| HOBt - | hydroxybenzotriazole |
| HEPES - | [4-(2-hydroxyethyl)-1-piperzine-ethanesulfonic acid |
| Fe - | iron |
| iPrOH - | isopropanol |
| IPEA - | isopropylethylamine |
| LDA - | lithium diisopropylamide |
| LiOH - | lithium hydroxide |
| LHMDS - | lithium bis(trimethylsilyl)amide |
| $MgSO_4$ - | magnesium sulfate |
| $MgCl_2$ - | magnesium chloride |
| $MnCl_2$ - | manganese chloride |
| $MnO_2$ - | manganese oxide |
| MeOH - | methanol |
| mg - | milligram |
| mL - | milliliter |
| min - | minutes |
| NBS - | N-bromosuccinimide |
| $N_2$ - | nitrogen |
| Pd/C - | palladium on carbon |
| $H_3PO_4$ - | phosphoric acid |
| $K_2CO_3$ - | potassium chromate |
| RT - | room temperature |
| $NaN_3$ - | sodium azide |
| $Na_2SO_4$ - | sodium sulfate |
| $NaHCO_3$ - | sodium bicarbonate |
| $NaBH(OAc)_3$ - | sodium triacetoxyborohydride |
| NaCl - | sodium chloride |
| NaH - | sodium hydride |
| NaI - | sodium iodide |
| SOV - | sodium orthovanadate |
| $H_2SO_4$ - | sulfuric acid |

-continued

| | |
|---|---|
| TBS-Cl - | tert-butyldimethylsilyl chloride |
| THF - | tetrahydrofuran |
| TPAP - | tetrapropylammonium perruthenate |
| TEA - | triethylamine |
| TFA - | trifluoroacetic acid |
| Tris-HCl - | tris(hydroxymethyl)aminomethane hydrochloride salt |
| $H_2O$ - | water |

EXAMPLE 1

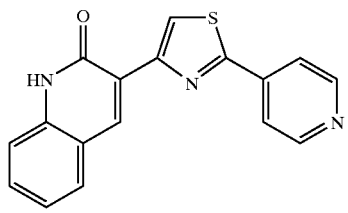

3-[2-(4-Pyridyl)-4-thiazolyl]-2(1H)-quinolinone

Step (a) Preparation of 2-(4-pyridyl)-thiazole acetic acid methyl ester

In an oven-dried, 100-mL, round-bottomed flask was placed thioisonicotinamide (Pflaltz-Bauer) (2.9 g, 21 mmol) in 1,4-dioxane (60 mL). Methyl 4-chloroacetoacetate (Aldrich, 3.16 g, 2.4 mL, 21 mmol) was added at RT. The flask was purged with $N_2$ and the solution was heated to 75° C. for 12 h. The mixture was cooled to RT, quenched with 2N $NH_3$ in MeOH (10 mL), and concentrated. The material was purified by flash chromatography on silica gel (EtOAc/hexane, 50:50) to afford 2-(4-pyridyl)-thiazole acetic acid methyl ester as a light yellow solid. Mp: 78–79° C. MS m/z: 235 (M+1). Calc'd for $C_{11}H_{10}N_2O_2S$: 234.05.

Step (b) Preparation of 2-(4-pyridyl)-thiazole acetic acid

In a 100-mL, round-bottomed flask was placed 2-(4-pyridyl)-thiazole acetic acid methyl ester (Step a, 818 mg, 3.5 mmol), LiOH monohydrate (154 mg, 3.67 mmol) in MeOH (20 mL), and $H_2O$ (2 mL). The solution was heated to 75° C. for 2 h, cooled to RT, and concentrated. The resulting yellow solid was dissolved in $H_2O$ (10 mL) and extracted with EtOAc (15 mL). The aqueous layer was acidified with 1N aqueous HCl (3.67 mL). The resulting precipitate was filtered, and washed with $H_2O$ (10 mL) to afford 2-(4-pyridyl)-thiazole acetic acid as a light yellow solid. Mp: >240° C. MS m/z: 221 (M+1). Calc'd for $C_{10}H_8N_2O_2S$: 220.03.

Step (c) Preparation of N-(2-formylphenyl)-2-(4-pyridyl)-thiazole acetamide

In an oven-dried, 50-mL, round-bottomed flask were placed 2-(4-pyridyl)-thiazole acetic acid (Step b, 140 mg, 0.64 mmol), 2-aminobenzaldehyde (Aldrich, 270 mg, 2.22 mmol), EDC (Aldrich, 244 mg, 1.27 mmol), and DIEA (Aldrich, 148 mg, 0.20 mL, 1.15 mmol) in $CH_2Cl_2$ (20 mL). The mixture was cooled to 0° C., and 1-hydroxy-7-azabenzotriazole (Aldrich, 173 mg, 1.27 mmol) was added in one portion. The reaction was warmed to RT slowly, stirred for 12 h, and concentrated in vacuo. The resulting crude product was purified by flash chromatography (EtOAc/hexanes, 50:50) to afford N-(2-formylphenyl)-2-(4-pyridyl)-thiazole acetamide as a white solid. Mp: 136–137° C. MS m/z: 324 (M+1). Calc'd for $C_{17}H_{13}N_3O_2S$: 323.07.

Step (d) Preparation of 3-[2-(4-pyridyl)-4-thiazolyl]-2(1H)-quinolinone

In an oven-dried, 100-mL, round-bottomed flask was placed N-(2-formylphenyl)-2-(4-pyridyl)-thiazole acetamide (Step c, 111 mg, 0.35 mmol) in THF (20 mL). The mixture was cooled to 0° C., and potassium tert-butoxide (Aldrich, 1.0 M in THF, 1.03 mL) was added slowly. The reaction was warmed to RT, stirred for 12 h, cooled to 0° C., and HCl (Aldrich, 1.0 M in $Et_2O$, 1.03 mL) was added slowly. The crude product was concentrated in vacuo, and the resulting solid was filtered, washed with $H_2O$ (3×5 mL), $Et_2O$ (3×5 mL) to afford 3-[2-(4-pyridyl)-4-thiazolyl]-2(1H)-quinolinone as a yellow solid. Mp: 241–243° C. MS m/z: 306 (M+1). Anal. Calc'd for $C_{17}H_{11}N_3OS \cdot 0.5 CH_3OH$: 65.40; H, 4.08; N, 13.08. Found: C, 65.05; H, 3.89; N, 12.73. MALDIFTMS (DHB) m/z: 306.0692 (M+H$^+$, $C_{17}H_{11}N_3OS$ Calc'd 306.0696).

EXAMPLE 2

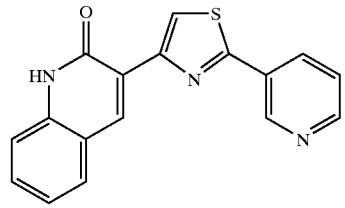

3-[2-(3-Pyridyl)-4-thiazolyl]-2(1H)-quinolinone

Step (a) Preparation of 2-(3-pyridyl)-thiazole acetic acid methyl ester

This compound was prepared according to the method described in Example 1a by employing thionicotinamide (Aldrich). Mp: 74–75° C. MS m/z: 235 (M+1). Calc'd for $C_{11}H_{10}N_2O_2S$: 234.05.

Step (b) Preparation of 2-(3-pyridyl)-thiazole acetic acid

This compound was prepared according to the method described in Example 1b by employing 2-(3-pyridyl)-thiazole acetic acid methyl ester (Step a). Mp: 197–198° C. MS m/z: 221 (M+1). Calc'd for $C_{10}H_8N_2O_2S$: 220.03.

Step (c) Preparation of N-(2-formylphenyl)-2-(3-pyridyl)-thiazole acetamide

This compound was prepared according to the method described in Example 1c by employing 2-(3-pyridyl)-thiazole acetic acid (Step b) and o-aminobenzaldehyde (Aldrich). Mp: 70–73° C. MS m/z: 324 (M+1). Calc'd for $C_{17}H_{13}N_3O_2S$: 323.07.

Step (d) Preparation of 3-[2-(3-pyridyl)-4-thiazolyl]-2(1H)-quinolinone

This compound was prepared by the method described in Example 1d by employing N-(2-formylphenyl)-2-(3-pyridyl)-thiazole acetamide (Step c). Mp: 230–232° C. MS m/z: 306 (M+1). MALDIFTMS (DHB) m/z: 306.0695 (M+H$^+$, Calc'd 306.0696).

EXAMPLE 3

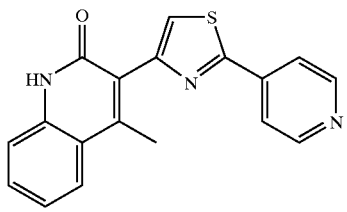

3-[2-(4-Pyridyl)-4-thiazolyl]-4-methyl-2(1H)-quinolinone

Step (a) Preparation of N-(2-acetylphenyl)-2-(4-pyridyl)-thiazole acetamide

This compound was prepared according to the method described in Example 1c by employing 2-aminoacetophenone (Aldrich). Mp: 188–189° C. MS m/z: 338 (M+1). Anal. Calc'd for $C_{18}H_{15}N_3O_2S$: C, 64.08; H, 4.48; N, 12.45. Found: C, 63.95; H, 4.32; N, 12.55. Calc'd for $C_{18}H_{15}N_3O_2S$: 337.09.

Step (b) Preparation of 3-[2-(4-pyridyl)-4-thiazolyl]-4-methyl-2(1H)-quinolinone This compound was prepared according to the method described in Example 1d by employing N-(2-acetylphenyl)-2-(4-pyridyl)-thiazole acetamide (Step a). Mp: >250° C.; MS m/z: 320 (M+1). MALDIFTMS (DHB) m/z: 320.0875 (M+H+, Calc'd 320.0852).

EXAMPLE 4

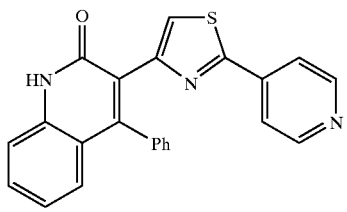

3-[2-(4-Pyridyl)-4-thiazolyl]-4-phenyl-2(1H)-quinolinone

Step (a) Preparation of N-(2-benzoylphenyl)-2-(4-pyridyl)-thiazole acetamide

This compound was prepared according to the method described in Example 1c by employing 2-aminobenzophenone. Mp: 196–198° C. MS m/z: 400 (M+1). Calc'd for $C_{23}H_{17}N_3O_2S$: 399.10. Anal. Calc'd for $C_{23}H_{17}N_3O_2S$: C, 69.15; H, 4.29; N, 10.52. Found: C, 68.94; H, 4.13; N, 10.77.

Step (b) Preparation of 3-[2-(4-pyridyl)-4-thiazolyl]-4-phenyl-2(1H)-quinolinone This compound was prepared according to the method described in Example 1d by employing N-(2-benzoylphenyl)-2-(4-pyridyl)-thiazole acetamide. Mp: >250° C. MS m/z: 382 (M+1). Anal. Calc'd for $C_{23}H_{15}N_3OS \cdot 0.1H_2O$: C, 72.08; H, 4.00; N, 10.97. Found: C, 72.08; H, 4.06; N, 10.57.

EXAMPLE 5

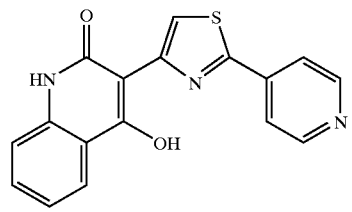

Step (a) Preparation of N-(2-carbomethoxphenyl)-2-(4-pyridyl)-thiazole acetamide This compound was prepared by the method described in Example 1c by employing methyl anthranilate (Aldrich). Mp: 211–213° C. MS m/z: 354 (M+1). Calc'd for $C_{18}H_{15}N_3O_3S$: 353.08.

Step (b) Preparation of 3-[2-(4-pyridyl)-4-thiazolyl]-4-hydroxy-2(1H)-quinolinone This compound was prepared by the method described in Example 1d by employing N-(2-carbomethoxyphenyl)-2-(4-pyridyl)-thiazole acetamide. Mp: >250° C.; MS m/z: 322 (M+1). Anal. Calc'd for $C_{17}H_{11}N_3O_2S \cdot 1.75H_2O$: C, 57.86; H, 4.14; N, 11.91. Found: C, 58.22; H, 3.80; N, 11.54. MALDIFTMS (DHB) m/z: 322.0649 (M+H+, $C_{17}H_{11}N_3O_2S$ Calc'd 322.0645).

EXAMPLE 6

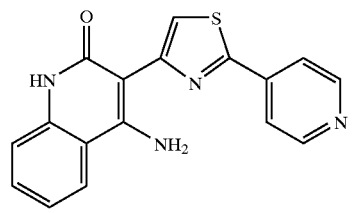

3-[2-(4-Pyridyl)-4-thiazolyl]-4-amino-2(1H)-quinolinone

Step (a) Preparation of N-(2-cyanophenyl)-2-(4-pyridyl)-thiazole acetamide

This compound was prepared by the method described in Example 1c by employing 2-aminobenzonitrile (Aldrich). Mp: 188–190° C. MS m/z: 321 (M+1). Calc'd for $C_{17}H_{12}N_4OS$: 320.07.

Step (b) Preparation of 3-[2-(4-pyridyl)-4-thiazolyl]-4-amino-2(1H)-quinolinone

This compound was prepared according to the method described in Example 1d by employing N-(2-cyanophenyl)-2-(4-pyridyl)-thiazole acetamide (Step a). Mp: >250° C.; MS m/z: 321 (M+1). Anal. Calc'd for $C_{17}H_{12}N_4OS \cdot 2HCl$: C, 51.91; H, 3.59; N, 14.25. Found: C, 52.16; H, 3.53; N, 14.17.

EXAMPLE 7

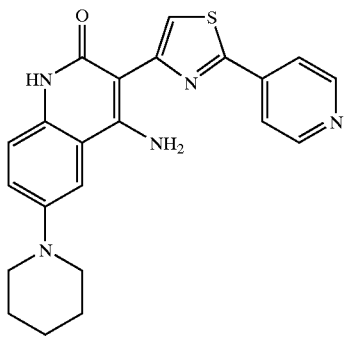

3-[2-(4-Pyridyl)-4-thiazolyl]-4-amino-6-(1-piperidinyl)-2(1H)-quinolinone

Step (a) Preparation of N-[2-cyano-4-(1-piperidinyl)-phenyl]-2-(4-pyridyl)-thiazole acetamide This compound was prepared by the method described in Example 1c by employing 2-amino-5-(1-piperidinyl) benzonitrile. Mp: 180–182° C. MS m/z: 404 (M+1). Calc'd for $C_{22}H_{21}N_5OS$: 403.15. Anal. Calc'd for $C_{22}H_{21}N_5OS$: C, 65.49; H, 5.25; N, 17.36. Found: C, 65.38; H, 5.60; N, 17.01.

Step (b) Preparation of 3-[2-(4-pyridyl)-4-thiazolyl]-4-amino-6-(1-piperidinyl)-2(1H)-quinolinone This compound was prepared according to the method described in Example 1d by employing N-[2-cyano-4-(1-piperidinyl)-phenyl]-2-(4-pyridyl)-thiazole acetamide (Step a). Mp: 199–202° C.; MS m/z: 404 (M+1). MALDIFTMS (DHB) m/z: 404.1535 (M+H+, Calc'd 404.1540).

EXAMPLE 8

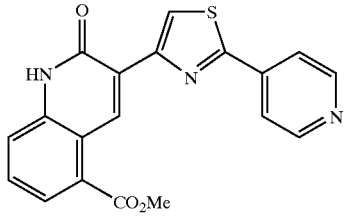

1,2-Dihydro-2-oxo-3-[2-(4-pyridyl)-4-thiazolyl]-5-quinolinecarboxylic acid methyl ester Step (a) Preparation of 1,2,3,4-tetrahydro-2-oxo-3-[2-(4-pyridyl)-4-thiazolyl]-5-quinolinecarboxylic acid methyl ester In an oven-dried, 25-mL, round-bottomed flask was placed 2-(4-pyridyl)-thiazole acetic acid methyl ester (Example 1a, 380 mg, 1.62 mmol) in THF (10 mL). The mixture was cooled to −78° C. and LHMDS (Aldrich, 1.0 M in THF, 1.62 mL) was added slowly. The reaction was stirred for 5 min, and the resulting enolate was added to a pre-cooled (−45° C.) solution of 2-bromomethyl-3-nitro-benzoic acid methyl ester in THF (10 mL) via a cannula over a period of 5 min. The reaction was stirred for additional 1.5 h, and quenched by saturated aq. $NH_4Cl$ (5 mL). The phases were separated, and the aqueous phase was extracted with EtOAc (50 mL). The combined organic layers were washed with brine (15 mL), dried over $MgSO_4$, and concentrated in vacuo to afford the crude addition product. This material was employed in the next step without further purification. In a 50-mL, round-bottomed flask were placed the crude addition product, Fe powder (Aldrich, 454 mg, 8.0 mmol), and $NH_4Cl$ (70 mg, 1.3 mmol) in $H_2O$ (8 mL) and EtOH (8 mL). The mixture was heated at 80° C. for 12 h, and filtered while hot. The filtrate was concentrated in vacuo, and purified by flash chromatography (EtOAc) to afford 1,2,3,4-tetrahydro-2-oxo-3-[2-(4-pyridyl)-4-thiazolyl]-5-quinolinecarboxylic acid methyl ester as a yellow solid. Mp: 230–231° C. MS m/z: 366 (M+1). Calc'd for $C_{19}H_{15}N_3O_3S$: 365.08.

Step (b) Preparation of 1,2-Dihydro-2-oxo-3-[2-(4-pyridyl)-4-thiazolyl]-5-quinolinecarboxylic acid methyl ester In an oven-dried, 100-mL, round-bottomed flask was placed 1,2,3,4-tetrahydro-2-oxo-3-[2-(4-pyridyl)-4-thiazolyl]-5-quinolinecarboxylic acid methyl ester (Step a, 60 mg, 0.16 mmol), NBS (Aldrich, 32 mg, 0.18 mmol), and AIBN (Aldrich, 5 mg, 0.03 mmol) in $CCl_4$ (10 mL). The mixture was heated to 85° C. for 2 h, cooled to RT, and quenched with 2N $NH_3$ in MeOH (5 mL). The crude product was concentrated in vacuo, and the resulting solid was filtered, washed with $H_2O$ (3×5 mL), and MeOH (1×2 mL) to afford 1,2-dihydro-2-oxo-3-[2-(4-pyridyl)-4-thiazolyl]-5-quinoline carboxylic acid methyl ester as a yellow solid: Mp: >250° C. MS m/z: 364 (M+1).

EXAMPLE 9

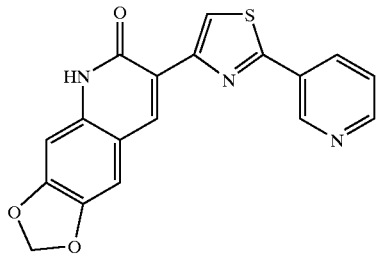

3-[2-(3-Pyridyl)-4-thiazolyl]-6,7-(methylenedioxyl)-2(1H)-quinolinone

Step (a) Preparation of N-[6-hydroxymethyl-4,5-(methylenedioxyl)phenyl]-2-(3-pyridyl)-thiazole acetamide This compound was prepared according to the method described in Example 1c by employing 6-amino-piperonylalcohol (Aldrich) and 2-(3-pyridyl)-thiazole acetic acid (Example 2, Step b). Mp: 168–170° C. MS m/z: 369.9 (M+1). Calc'd for $C_{18}H_{15}N_3O_4S$: 369.08.

Step (b) Preparation of N-[6-formyl-4,5-(methylenedioxyl)phenyl]-2-(3-pyridyl)-thiazole acetamide In an oven-dried, 50-mL, round-bottomed flask were placed N-[6-hydroxymethyl-4,5-(methylenedioxyl)phenyl]-2-(3-pyridyl)-thiazole acetamide (Step a, 47 mg, 0.13 mmol), TEA (Aldrich, 0.3 mL, 2.1 mmol) in DMSO (2 mL). To this mixture was added sulfur trioxide pyridine complex (Aldrich, 160 mg, 1.0 mmol). The reaction was stirred for 1 h, quenched with $H_2O$ (5 mL), and diluted with EtOAc (25 mL). The phases were separated, and the aqueous phase was extracted with EtOAc (2×25 mL). The combined organic layers were washed with $H_2O$ (2×5 mL), brine (15 mL), dried over $MgSO_4$, and concentrated in vacuo to afford the crude compound which was purified by flash chromatography (EtOAc/hexanes, 50:50) to afford N-[6-formyl-4,5-(methylenedioxyl)phenyl]-2-(3-pyridyl)-thiazole acetamide as an oily solid. MS m/z: 367.9 (M+1). Calc'd for $C_{18}H_{13}N_3O_4S$: 367.06.

Step (c) Preparation of 3-[2-(3-Pyridyl)-4-thiazolyl]-6,7-(methylenedioxyl)-2(1H)-quinolinone This compound was prepared according to the method described in Example 1d by employing N-[6-formyl-4,5-

(methylenedioxyl)phenyl]-2-(3-pyridyl)-thiazole acetamide (Step b). Mp: >220° C. MS m/z: 350 (M+1). Anal. Calc'd for $C_{18}H_{11}N_3O_3S \cdot 0.25$ $CH_3OH$: C, 61.33; H, 3.38; N, 11.76. Found: C, 61.21; H, 3.56; N, 11.43. MALDIFTMS (DHB) m/z: 350.0611 (M+H$^+$, Calc'd 350.0594).

EXAMPLE 10

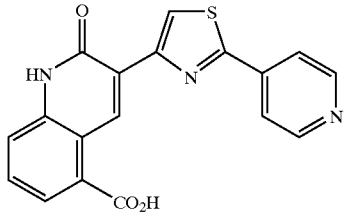

1,2-Dihydro-2-oxo-3-[2-(4-pyridyl)-4-thiazolyl]-5-quinolinecarboxylic acid

This compound was prepared according to the method described in Example 1b by employing 1,2-dihydro-2-oxo-3-[2-(4-pyridyl)-4-thiazolyl]-5-quinolinecarboxylic acid methyl ester (Example 8). Mp: >250° C. MS m/z: 350 (M+1). MALDIFTMS (DHB) m/z: 350.0606 (M+H$^+$, Calc'd 350.0594).

EXAMPLE 11

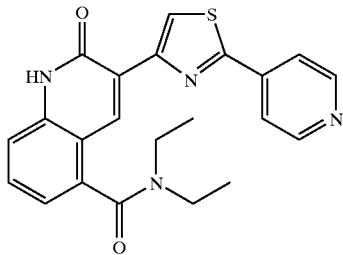

N,N-Diethyl-1,2-dihydro-2-oxo-3-[2-(4-pyridyl)-4-thiazolyl]-5-quinolinecarboxamide Step (a) Preparation of 1,2,3,4-tetrahydro-2-oxo-3-[2-(4-pyridyl)-4-thiazolyl]-5-quinolinecarboxylic acid This compound was prepared according to the method described in Example 1b by employing 1,2,3,4-tetrahydro-2-oxo-3-[2-(4-pyridyl)-4-thiazolyl]-5-quinolinecarboxylic acid methyl ester (Example 8). Mp: >250° C. MS m/z: 352 (M+1). Calc'd for $C_{18}H_{13}N_3O_3S$: 351.07.

Step (b) Preparation of N,N-diethyl-1,2,3,4-tetrahydro-2-oxo-3-[2-(4-pyridyl)-4-thiazolyl]-5-quinolinecarboxamide This compound was prepared by the method described in Example 1c by employing 1,2,3,4-tetrahydro-2-oxo-3-[2-(4-pyridyl)-4-thiazolyl]-5-quinolinecarboxylic acid (Step a) and DEA to give an oil. MS m/z: 407 (M+1). Calc'd for $C_{22}H_{22}N_4O_2S$: 406.15.

Step (c) Preparation of N,N-diethyl-1,2-dihydro-2-oxo-3-[2-(4-pyridyl)-4-thiazolyl]-5-quinolinecarboxamide This compound was prepared by the method described in Example 8b by employing N,N-diethyl-1,2,3,4-tetrahydro-2-oxo-3-[2-(4-pyridyl)-4-thiazolyl]-5-quinolinecarboxamide (Step b). Mp: 210° C. (dec); MS m/z: 405 (M+1).

EXAMPLE 12

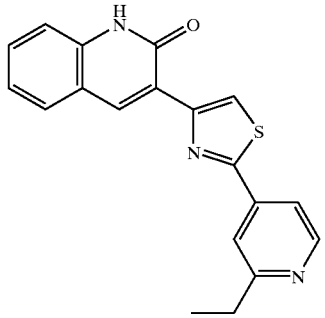

3-[2-(2-Ethyl-4-pyridyl)-1,3-thiazol-4-yl]hydroquinolin-2-one

Step (a) Preparation of methyl 2-[2-(2-ethyl-4-pyridyl)-1,3-thiazol-4-yl]acetate A mixture of ethionamide (Aldrich) (1.65 g, 10.0 mmol) and methyl 4-chloroacetoacetate (Fluka) (1.41 g, 10.0 mmol) in 50 mL of anhydrous MeOH was heated at reflux for 18 h. The solvent was evaporated to give an oily residue that was purified by chromatography (gradient elution: 10–50% EtOAc in hexanes) to afford the title compound as a light brown oil. MS m/z: 263 (M+1). Calc'd for $C_{13}H_{14}N_2O_2S$: 262.08.

Step (b) Preparation of 2-[2-(2-ethyl-4-pyridyl)-1,3-thiazol-4-yl]acetic acid

A mixture of methyl 2-[2-(2-ethyl-4-pyridyl)-1,3-thiazol-4-yl]acetate (Step a, 0.5 g, 1.9 mmol) and LiOH (2 N, 5.0 mL) in THF (5 mL) and MeOH (2 mL) was stirred at RT for 7 h. HCl (aq. 1 N) was added to adjust the reaction mixture to pH ~2. The solution was evaporated and the resulting residue was partitioned between EtOAc (20 mL) and $H_2O$ (20 mL). The layers were separated and the aqueous layer was extracted again with EtOAc (2×20 mL). The organic layers were combined, dried ($Na_2SO_4$), and concentrated to afford a solid, which was suspended in $CH_2Cl_2$ and filtered to give the compound as a white solid. MS m/z: 249 (M+1). Calc'd for $C_{12}H_{12}N_2O_2S$. 248.06.

Step (c) 3-[2-(2-Ethyl-4-pyridyl)-1,3-thiazol-4-yl]hydroquinolin-2-one

To a solution of 2-[2-(2-ethyl-4-pyridyl)-1,3-thiazol-4-yl] acetic acid (Step b, 124 mg, 0.5 mmol), 1-hydroxy-8-azabenzotriazole (70 mg, 0.51 mmol), DIEA (1.0 mL, 5.8 mmol), and o-aminobenzaldehyde (Aldrich) (180 mg, 1.5 mmol) in anhydrous $CH_2Cl_2$ (15 mL) was added EDC (190 mg, 1.0 mmol). The reaction mixture was stirred at RT for 48 h. $CH_2Cl_2$ (30 mL) was added and the solution was washed with saturated aq. $NaHCO_3$ (30 mL). The organic layer was dried ($Na_2SO_4$) and concentrated. Flash chromatography (gradient elution: 10–50% EtOAc in hexanes) afforded the coupled intermediate as an oil that was used directly in the next step.

To the solution of the intermediate in anhydrous THF (5 mL) was added potassium t-butoxide (0.18 mL, 1.0 M in THF) at −15° C. The reaction mixture was warmed slowly to RT and stirred overnight. HCl (0.2 mL, 1.0 M in $Et_2O$) was added and the solvents were evaporated. The residue was suspended in MeOH, filtered, and washed successively with $H_2O$, MeOH, EtOAc, and hexanes to afford the title compound as a light yellow solid. MS m/z: 334 (M+1). MALDIFTMS (DHB) m/z: 334.1020 (M+H; $C_{19}H_{15}N_3OS$, Calc'd 334.1009).

EXAMPLE 13

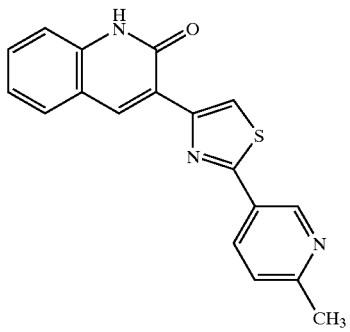

3-[2-(6-Methyl-3-pyridyl)-1,3-thiazol-4-yl]hydroquinolin-2-one

Step (a) Preparation of methyl 2-[2-(6-methyl-3-pyridyl)-1,3-thiazol-4-yl]acetate This material was prepared by the procedure described for Example 24(a) using 6-methyl-thionicotinamide (Maybridge) (1.52 g, 10.0 mmol) and methyl 4-chloroacetoacetate (Fluka) (1.42 g, 10.0 mmol). Chromatography (gradient elution: 10–50% EtOAc in hexanes) of the crude material afforded the title compound as an off-white solid. MS m/z: 249 (M+1). Calc'd for $C_{12}H_{12}N_2O_2S$: 248.06.

Step (b) Preparation of 2-[2-(6-methyl-3-pyridyl)-1,3-thiazol-4-yl]acetic acid. This material was prepared according to the procedure described for Example 24(b) using methyl 2-[2-(6-methyl-3-pyridyl)-1,3-thiazol-4-yl]acetate (Step a, 0.5 g, 2.0 mmol) and LiOH (2 N, 5.0 mL). The product was filtered and washed successively with $CH_2Cl_2$, EtOAc, and hexanes to afford the title compound as a white solid. MS m/z: 235 (M+1). Calc'd for $C_{11}H_{10}N_2O_2S$: 234.05.

Step (c) Preparation of 3-[2-(6-methyl-3-pyridyl)-1,3-thiazol-4-yl]hydroquinolin-2-one This material was prepared according to the procedure described for Example 24(c) using 2-[2-(6-methyl-3-pyridyl)-1,3-thiazol-4-yl]acetic acid (Step b, 230 mg, 1.0 mmol). The product was filtered and washed successively with $H_2O$, $CH_2Cl_2$, EtOAc, and hexanes to afford the title compound as a light yellow solid. MS m/z: 320 (M+1). MALDIFTMS (DHB) m/z: 320.0853 (M+H; $C_{18}H_{13}N_3OS$, Calc'd 320.0852).

EXAMPLE 14

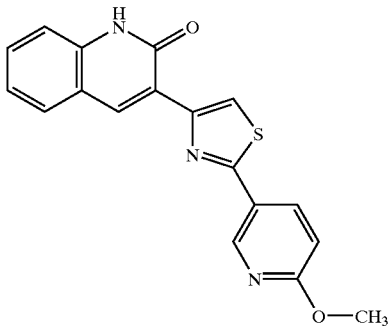

3-[2-(6-Methoxy-3-pyridyl)-1,3-thiazol-4-yl]hydroquinolin-2-one

Step (a) Preparation of methyl 2-[2-(6-methoxy-3-pyridyl)-1,3-thiazol-4-yl]acetate This material was prepared according to the procedure described for Example 24(a) using 6-methoxythionicotinamide (Maybridge) (1.68 g, 10.0 mmol) and methyl 4-chloroacetoacetate (1.42 g, 10.0 mmol). Chromatography (gradient elution: 0–20% EtOAc in hexanes) of the crude material afforded the compound as an off-white solid. MS m/z: 265 (M+1). Calc'd for $C_{12}H_{12}N_2O_3S$: 264.06.

Step (b) Preparation of 2-[2-(6-methoxy-3-pyridyl)-1,3-thiazol-4-yl]acetic acid

This material was prepared according to the procedure described for Example 24(b) using methyl 2-[2-(6-methoxy-3-pyridyl)-1,3-thiazol-4-yl]acetate (Step a, 1.1 g, 4.2 mmol) and LiOH (2 N, 7.0 mL) in THF (10 mL) and MeOH (3 mL). The solution was stirred at RT for 18 h, and HCl (aq. 1 N) was added to adjust the reaction mixture to pH ~2. The solvents were evaporated and the resulting residue was partitioned between EtOAc (75 mL) and $H_2O$ (75 mL). The layers were separated and the aqueous layer was extracted again with EtOAc (75 mL). The organic layers were combined, dried ($Na_2SO_4$) and concentrated to afford the title compound as a light yellow solid. MS m/z: 251 (M+1). Calc'd for $C_{11}H_{10}N_2O_3S$: 250.04.

Step (c) Preparation of 3-[2-(6-methoxy-3-pyridyl)-1,3-thiazol-4-yl]hydroquinolin-2-one This material was prepared according to the procedure described for Example 24(c) using 2-[2-(6-methoxy-3-pyridyl)-1,3-thiazol-4-yl]acetic acid (Step b, 250 mg, 1.0 mmol). The product was filtered and washed successively with $H_2O$, MeOH, EtOAc, and hexanes afforded the title compound as a white solid. MS m/z: 336 (M+1). MALDIFTMS (DHB) m/z: 336.0791 (M+H; $C_{18}H_{13}N_1O_2S$, Calc'd 336.0801).

EXAMPLE 15

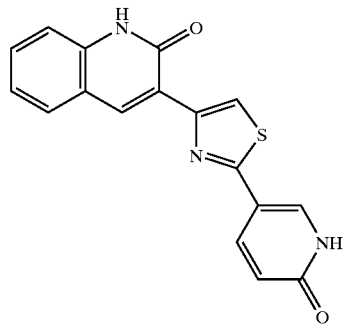

3-[2-(6-Oxo-3-hydropyridyl)-1,3-thiazol-4-yl]hydroquinolin-2-one

A suspension of 3-[2-(6-methoxy-3-pyridyl)-1,3-thiazol-4-yl]hydroquinolin-2-one (Example 14, 50 mg, 0.15 mmol) in DMSO (5 mL) and aq. HCl (10 mL, 3 N) was heated at reflux for 3 h. The material was filtered and washed by MeOH and $CH_2Cl_2$. The solids were re-suspended in hot DMSO, cooled and filtered to afford the title compound as an off-white solid. MS m/z: 322 (M+1). MALDIFTMS (DHB) m/z: 322.0637 (M+H; $C_{17}H_{11}N_3O_2S$, Calc'd 322.0645).

EXAMPLE 16

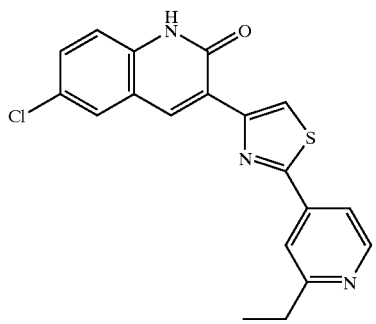

6-Chloro-3-[2-(2-ethyl(4-pyridyl))(1,3-thiazol-4-yl)]hydroquinolin-2-one

To a solution of 2-[2-(2-ethyl-4-pyridyl)-1,3-thiazol-4-yl] acetic acid (Example 12, 220 mg, 0.89 mmol), 1-hydroxy-8-aza-benzotriazole (137 mg, 1.0 mmol), DIEA (3.0 mL, 17.4 mmol), and 5-chloro-2-aminobenzaldehyde (310 mg, 2.0 mmol) in anhydrous $CH_2Cl_2$ (30 mL) was added EDC (380 mg, 2.0 mmol). The reaction mixture was stirred at RT for 48 h. The resulting precipitates were filtered and washed with MeOH, $CH_2Cl_2$, and hexanes to provide a crude material. The mother liquid was concentrated and resulting residue was purified by prep TLC (EtOAc: hexanes=80:20) to afford the coupled intermediate, which was heated at reflux in DIEA (15 mL) for 24 h. The title compound precipitated and was filtered and combined with the original crude product. The solids were recrystallized from DMSO-MeOH—$CH_2Cl_2$ in the presence of TFA (15 μL) to afford the title compound, as the TFA salt, as a light yellow solid. MS m/z: 368 (M+1). MALDIFTMS (DHB) m/z: 368.0616 (M+H; $C_{19}H_{14}N_3OSCl$, Calc'd 368.0619).

EXAMPLE 17

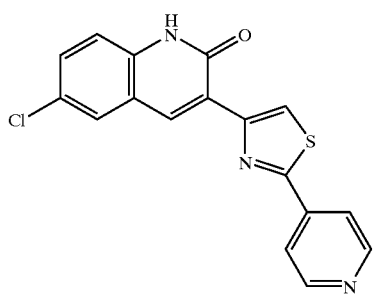

6-Chloro-3-(2-(4-pyridyl)(1,3-thiazol-4-yl))hydroquinolin-2-one

To a solution of 2-[2-(4-pyridyl)-1,3-thiazol-4-yl]acetic acid (Example 1, 160 mg, 0.73 mmol), 1-hydroxy-8-azabenzotriazole (137 mg, 1.0 mmol), DIEA (3.0 mL, 17.4 mmol), and 5-chloro-2-aminobenzaldehyde (310 mg, 2.0 mmol) in anhydrous $CH_2Cl_2$ (30 mL) was added EDC (380 mg, 2.0 mmol). The reaction mixture was stirred at RT for 48 h. The resulting precipitates were filtered and washed with MeOH, $CH_2Cl_2$, and hexanes to provide the title compound as an off-white solid. MS m/z: 340 (M+1). MALDIFTMS (DHB) m/z: 340.0312 (M+H; $C_{17}H_{10}N_3O_2SCl$, Calc'd 340.0306).

EXAMPLE 18

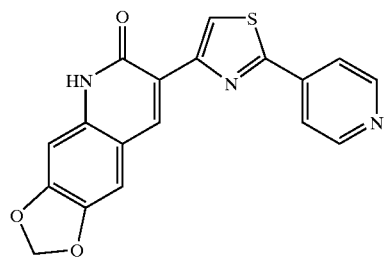

7-(2-(4-Pyridinyl)-1,3-thiazol-4-yl)[1,3]dioxolo[4,5-g]quinolin-6(5H)-one

Step (a) Preparation of N-[6-hydroxymethyl-4,5-(methylenedioxy)phenyl]-2-(4-pyridyl)-thiazole acetamide This compound was prepared according to the method described in Example 1c by employing 2-(4-pyridyl)-thiazole acetic acid (Example 1, Step b) and 6-amino-piperonylalcohol (Aldrich). Mp: 133–135° C. MS m/z: 370.1 (M+1). Calc'd for $C_{18}H_{15}N_3O_4S$: 369.08.

Step (b) Preparation of N-[6-formyl-4,5-(methylenedioxyl)phenyl]-2-(4-pyridyl)-thiazole acetamide This compound was prepared according to the method described in Example 9b by employing N-[6-hydroxymethyl-4,5-(methylenedioxyl)phenyl]-2-(4-pyridyl)-thiazole acetamide (Step a). Mp: 167–169° C. MS m/z: 368.1 (M+1). Calc'd for $C_{18}H_{13}N_3O_4S$: 367.06.

Step (c) Preparation of 3-[2-(4-pyridyl)-4-thiazolyl]-6,7-(methylenedioxy)-2(1H)-quinolinone This compound was prepared by the method described in Example 1d by employing N-[6-formyl-4,5-(methylenedioxy)phenyl]-2-(4-pyridyl)-thiazole acetamide (Step b). Mp: >220° C. MS m/z: 350.1 (M+1). Anal. Calc'd for $C_{18}H_{11}N_3O_3 \cdot 1.75HCl$: C, 52.32; H, 3.11; N, 10.17. Found: C, 52.09; H, 3.05; N, 9.77. MALDIFTMS (DHB) m/z: 350.0603 (M+H; $C_{18}H_{11}N_3O_3$, Calc'd 350.0594).

EXAMPLE 19

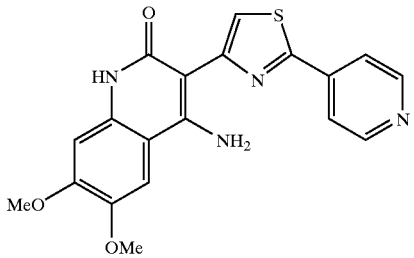

3-[2-(4-pyridyl)-4-thiazolyl]-4-amino-6,7-dimethoxy-2(1H)-quinolinone

Step (a) Preparation of N-(2-cyano-4,5-dimethoxyphenyl)-2-(4-pyridyl)-thiazole acetamide This compound was prepared according to the method described in Example 1c by employing 2-amino-4,5-dimethoxybenzonitrile (Aldrich) and 2-(4-pyridyl)-thiazole acetic acid (Example 1, Step b). Mp: 165–167° C. MS m/z: 381.1 (M+1). Calc'd for $C_{19}H_{16}N_4O_3S$: 380.09.

Step (b) Preparation of 3-[2-(4-pyridyl)-4-thiazolyl]-4-amino-6,7-dimethoxy-2(1H)-quinolinone This compound was prepared by the method described in Example 1d by employing N-(2-cyano-4,5-dimethoxyphenyl)-2-(4-pyridyl)-thiazole acetamide (Step a). Mp: >250° C. MS m/z: 381.1 (M+1). Anal. Calc'd for $C_{19}H_{16}N_4O_3S \cdot 1.25H_2O$: C, 56.64; H, 4.63; N, 13.91. Found: C, 56.84; H, 4.70; N, 13.66. MALDIFTMS (DHB) m/z: 381.1024 (M+H; $C_{19}H_{16}N_4O_3S$, Calc'd 381.1016).

EXAMPLE 20

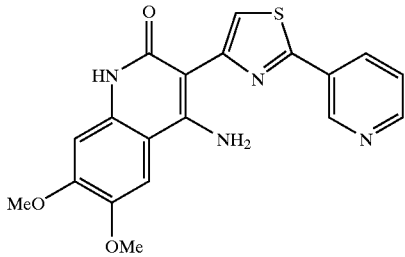

3-[2-(3-Pyridyl)-4-thiazolyl]-4-amino-6,7-dimethoxy-2(1H)-quinolinone

Step (a) Preparation of N-(2-cyano-4,5-dimethoxyphenyl)-2-(3-pyridyl)-thiazole acetamide This compound was prepared according to the method described in Example 1c by employing 2-amino-4,5-dimethoxybenzonitrile (Aldrich) and 2-(3-pyridyl)-thiazole acetic acid (Example 2, Step b). Mp: 65–67° C. MS m/z: 381.1 (M+1). Calc'd for $C_{19}H_{16}N_4O_3S$: 380.09.

Step (b) Preparation of 3-[2-(3-pyridyl)-4-thiazolyl]-4-amino-6,7-dimethoxy-2(1H)-quinolinone This compound was prepared by the method described in Example 1d by employing N-(2-cyano-4,5-dimethoxyphenyl)-2-(3-pyridyl)-thiazole acetamide (Step a). Mp: >250° C. MS m/z: 381.1 (M+1). MALDIFTMS (DHB) m/z: 381.1016 (M+H; Calc'd 381.1016).

EXAMPLE 21

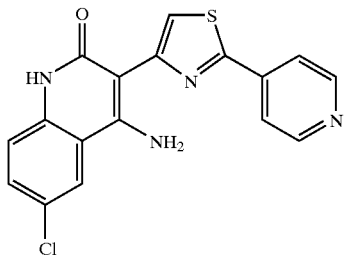

3-[2-(4-Pyridyl)-4-thiazolyl]-4-amino-6-chloro-2(1H)-quinolinone

Step (a) Preparation of N-(2-cyano-4-chlorophenyl)-2-(4-pyridyl)-thiazole acetamide This compound was prepared according to the method described in Example 1c by employing 2-amino-5-chlorobenzonitrile (Aldrich) and 2-(4-pyridyl)-thiazole acetic acid (Example 1, Step b). Mp: 164–166° C. MS m/z: 355.0 (M+1). Calc'd for $C_{17}H_{11}ClN_4OS$: 354.03.

Step (b) Preparation of 3-[2-(4-Pyridyl)-4-thiazolyl]-4-amino-6-chloro-2(1H)-quinolinone This compound was prepared according to the method described in Example 1d by employing N-(2-cyano-4-chlorophenyl)-2-(4-pyridyl)-thiazole acetamide (Step a). Mp: >220° C.; MS m/z: 355.0 (M+1).

EXAMPLE 22

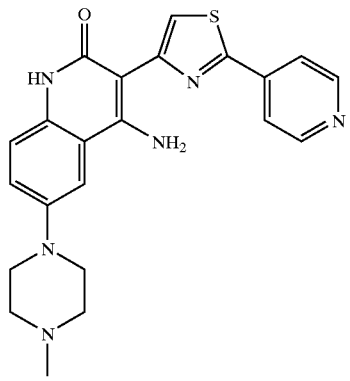

3-[2-(4-Pyridyl)-4-thiazolyl]-4-amino-6-(4-methyl-1-piperazinyl)-2(1H)-quinolinone Step (a) Preparation of N-[2-cyano-4-(4-methyl-1-piperazinyl)phenyl]-2-(4-pyridyl)-thiazole acetamide This compound was prepared by the method described in Example 1c by employing 2-amino-5-(4-methyl-1-piperazinyl)-benzonitrile. Mp: 191–193° C. MS m/z: 419.2 (M+1). Calc'd for $C_{22}H_{22}N_6OS$: 418.16.

Step (b) Preparation of 3-[2-(4-pyridyl)-4-thiazolyl]-4-amino-6-(4-methyl-1-piperazinyl)-2(1H)-quinolinone This compound was prepared according to the method described in Example 1d by employing N-[2-cyano-4-(4-methyl-1-piperazinyl)phenyl]-2-(4-pyridyl)-thiazole acetamide (Step a). Mp: >220° C.; MS m/z: 419.2 (M+1). MALDIFTMS (DHB) m/z: 419.1648 (M+H; Calc'd 419.1649).

EXAMPLE 23

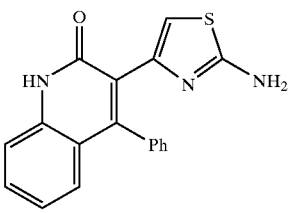

3-(2-Amino-4-thiazolyl)-4-phenyl-2(1H)-quinolinone

Step (a) Preparation of N-(2-benzoylphenyl)-2-aminothiazole acetamide

This compound was prepared according to the method described in Example 1c by employing 2-aminobenzophenone (Aldrich) and (2-amino-4-thiazoly) acetic acid (Aldrich). MS m/z: 338.0 (M+1). Calc'd for $C_{18}H_{15}N_3O_2S$: 337.09.

Step (b) Preparation of 3-(2-amino-4-thiazolyl)-4-phenyl-2(1H)-quinolinone

This compound was prepared according to the method described in Example 1d by employing N-(2-benzoylphenyl)-2-amino-thiazole acetamide (Step b). Mp: >220° C. MS m/z: 320.2 (M+1). MALDIFTMS (DHB) m/z: 320.0823 (M+H; Calc'd 320.0852).

EXAMPLE 24

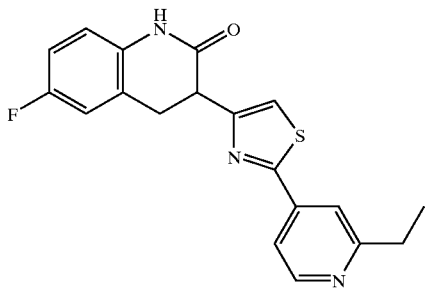

3-[2-(2-Ethyl(4-pyridyl))(1,3-thiazol-4-yl)]-6-fluorohydroquinolin-2-one

Step (a) Preparation of methyl 2-[2-(2-ethyl(4-pyridyl))(1,3-thiazol-4-yl)]-3-(5-fluoro-2-nitrophenyl)propanoate Methyl 2-[2-(2-ethyl-4-pyridyl)-1,3-thiazole-4-yl]acetate (520 mg, 2.0 mmol) (Example 12(a)) was dissolved in toluene and the solution was concentrated by rotary evaporation. This procedure was repeated, and the dry residue was dissolved in 18 mL anhydrous THF (18 mL). The solution was cooled to −78° C., and LHMDS (2.1 mL, 1.0 M in THF, Aldrich) was added slowly via a syringe. To the resulting red solution, 5-fluoro-2-nitrobenzyl bromide (400 mg, 1.7 mmol) was added as a solid in one portion. The reaction was warmed slowly to RT over 4 h. Saturated aqueous $NH_4Cl$ (50 mL) was added, and the mixture was extracted with 100 mL of EtOAc. The organic layer was separated, washed with $H_2O$ (100 mL), dried ($Na_2SO_4$), and concentrated. Flash chromatography (gradient elution: 10–40% EtOAc in hexanes) of the crude material afforded the title compound as a clear oil. MS m/z: 416 (M+1). Calc'd for $C_{20}H_{18}FN_3O_4S$: 415.10.

Step (b) Preparation of 3-[2-(2-ethyl(4-pyridyl))(1,3-thiazol-4-yl)]-6-fluoro-1,3,4-trihydroquinolin-2-one A mixture of methyl 2-[2-(2-ethyl(4-pyridyl))(1,3-thiazol-4-yl)]-3-(5-fluoro-2-nitrophenyl) propanoate (Step a, 540 mg, 1.3 mmol), Fe powder (364 mg, 6.5 mmol), and $NH_4Cl$ (75 mg, 1.3 mmol) in 40 mL of $EtOH-H_2O$ (1:1) was heated at reflux for 3 h. Insoluble solids were removed by filtration of the solution through a Celite® pad while the reaction mixture was still hot. The filtrate was concentrated, and precipitates formed upon cooling. The solution was filtered to provide a white solid. The filtrate was concentrated to dryness to yield additional compound. MS m/z: 354 (M+1). MALDIFTMS (DHB) m/z: 354.1061 (M+H$^+$, $C_{19}H_{16}FN_3OS$ Calc'd 354.1071).

Step (c) Preparation of 3-[2-(2-ethyl(4-pyridyl))(1,3-thiazol-4-yl)]-6-fluorohydroquinolin-2-one To a suspension of 3-[2-(2-ethyl(4-pyridyl))(1,3-thiazol-4-yl)]-6-fluoro-1,3,4-trihydroquinolin-2-one (Step b, 85 mg, 0.24 mmol) in 50 mL of $CCl_4$ was added NBS (Aldrich) (52 mg, 0.29 mmol) and a catalytic amount of AIBN. The mixture was heated at reflux for 3 h. Another portion of NBS (52 mg, 0.29 mmol) and a catalytic amount of AIBN were added and the reaction was heated at reflux overnight. The solvent was removed and the residue was dissolved in minimal amount of DMSO and purified by HPLC to afford a yellow solid after lyophilization. MS m/z: 352 (M+1). MALDIFTMS (DHB) m/z: 352.0901 (M+H$^+$, $C_{19}H_{14}FN_3OS$ Calc'd 352.0914).

EXAMPLE 25

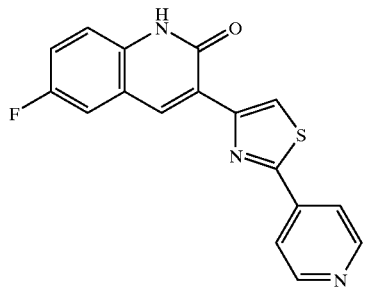

6-Fluoro-3-(2-(4-pyridyl)(1,3-thiazol-4-yl))hydroquinolin-2-one

The title compound was synthesized according to the procedures described for Examples 24(a), (b), and (c) starting from 5-fluoro-2-nitrobenzyl bromide and methyl 2-(4-pyridyl)-thiazole acetate. Purification of the crude product by HPLC afforded the title compound as a yellow solid after lyophilization. MS m/z: 324 (M+1). MALDIFTMS (DHB) m/z: 324.0613 (M+H; $C_{17}H_{10}N_3O_2SF$, Calc'd 324.0601).

EXAMPLE 26

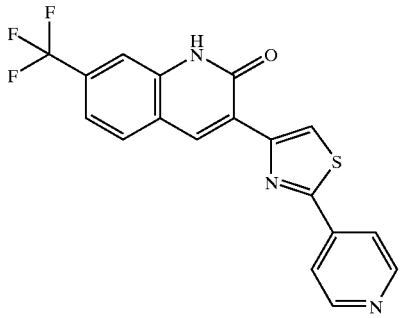

3-(2-(4-Pyridyl)(1,3-thiazol-4-yl))-7-(trifluoromethyl)hydroquinolin-2-one

The title compound was synthesized according to the procedures described for Example 24 (a). (b) and (c) starting from 4-trifluoromethyl-2-nitrobenzyl iodide (obtained from 4-trifluoromethyl-2-nitrobenzyl chloride by treating with NaI in acetone overnight) and methyl 2-(4-pyridyl)-thiazole acetate. Purification of the crude material by HPLC afforded the title compound as a yellow solid after lyophilization. MS m/z: 374 (M+1). MALDIFTMS (DHB) m/z: 374.0563 (M+H$^+$, $C_{18}H_{10}F_3N_3OS$ Calc'd 374.0569).

EXAMPLE 27

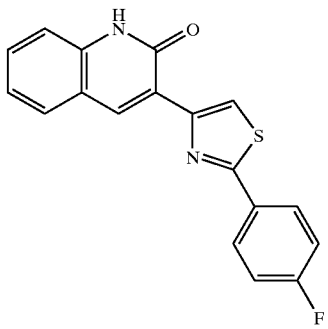

3-[2-(4-Fluorophenyl)-1,3-thiazol-4-yl]hydroquinolin-2-one

Step (a) Preparation of 3-acetylhydroquinolin-2-one

A mixture of o-aminobenzaldehyde (Aldrich) (9.6 g, 80 mmol), ethyl acetoacetate (10.6 g, 80 mmol) and piperidine (0.79 ML, 8 mmol) in 300 mL of o-xylene was heated at reflux overnight. The reaction mixture was cooled to RT, and the resulting precipitates were filtered and washed with $CH_2Cl_2$ and hexanes to provide the title compound as light yellow needles. MS m/z: 188 (M+1). Calc'd for $C_{11}H_9NO_2$: 187.06.

Step (b) Preparation of 3-(2-bromoacetyl)hydroquinolin-2-one

A mixture of 3-acetylhydroquinolin-2-one (Step a, 3.6 g, 19.3 mmol) and 5,5-dibromobarbituric acid (Aldrich) (3.3 g, 11.5 mmol) in 250 mL of anhydrous THF was heated at reflux for 3.5 h. The reaction mixture was cooled to RT. The precipitates were filtered and washed with THF, $CH_2Cl_2$ and hexanes to provide the title compound as a light yellow solid. MS m/z: 266, 268 (M+1). Calc'd for $C_{11}H_8BrNO_2$: 264.97.

Step (c) Preparation of 3-[2-(4-fluorophenyl)-1,3-thiazol-4-yl]hydroquinolin-2-one A mixture of 3-(2-bromoacetyl)hydroquinolin-2-one (Step b, 102 mg, 0.37 mmol) and 4-fluorothiobenzamide (Maybridge) (65 mg, 0.42 mmol) in 25 mL of anhydrous MeOH was heated at reflux for 3 h. Precipitates formed, and the reaction mixture was cooled to RT. The solution was filtered and the solids were washed with MeOH, $CH_2Cl_2$, and hexanes to provide the title compound as a white solid. MS m/z: 323 (M+1). MALDIFTMS (DHB) m/z: 323.0642 (M+H; $C_{18}H_{11}N_2OSF$, Calc'd 323.0649).

EXAMPLE 28

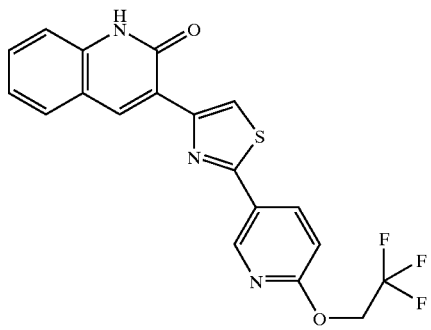

3-{2-[6-(2,2,2-Trifluoroethoxy)-3-pyridyl]-1,3-thiazol-4-yl}hydroquinolin-2-one

This material was prepared according the procedure described for Example 27 using 3-(2-bromoacetyl) hydroquinolin-2-one (78 mg, 0.29 mmol) and 6-(2,2,2-trifluoroethoxy)-pyridine-3-thiocarboxamide (Maybridge) (69 mg, 0.29 mmol) to give a pink solid. MS m/z: 404 (M+1). Anal. Calc'd for $C_{19}H_{12}F_3N_3O_2S$: C, 56.57; H, 3.00; F, 14.13; N, 10.42; O, 7.93; S, 7.95; Found: C, 56.22; H, 2.93; F, 13.88; N, 10.21; O, 8.37; S, 7.64.

EXAMPLE 29

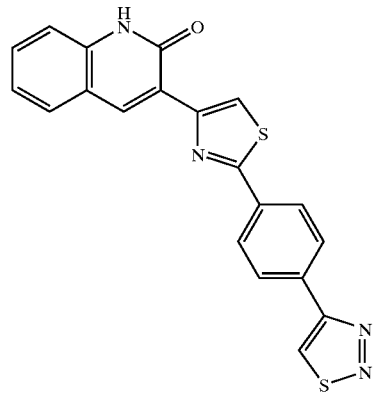

3-[2-(4-(1,2,3-Thiadiazol-4-yl)phenyl)-1,3-thiazol-4-yl]hydroquinolin-2-one

This material was prepared according to the procedure described for Example 27 using 3-(2-bromoacetyl)-hydroquinolin-2-one (78 mg, 0.29 mmol) and 4-(1,2,3-thiadiazol-4-yl)-thiobenzamide (Maybridge) (65 mg, 0.29 mmol) to give an off-white solid. MS m/z: 389 (M+1). MALDIFTMS (DHB) m/z: 389.0514 (M+H; $C_{20}H_{12}N_4OS_2$, Calc'd 389.0525).

General Procedure for the Preparation of Examples 30–63

A mixture of 3-(2-bromoacetyl)hydroquinolin-2-one (50 mg, 0.19 mmol) (Example 27(b)) and the corresponding thioamide (0.19 mmol) in 30 mL of anhydrous MeOH was kept on a Büchi Syncore synthesizer at 65° C. overnight. Precipitates formed, and the reaction mixture was cooled to RT. The solutions were filtered and the solids were washed with MeOH, $CH_2Cl_2$, and hexanes to provide the title compounds.

EXAMPLE 30

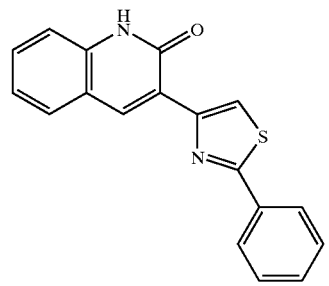

3-(2-Phenyl-1,3-thiazol-4-yl)hydroquinolin-2-one

White solid. MS m/z: 305 (M+1). Anal. Calc'd for $C_{18}H_{12}N_2OS$: C, 71.03; H, 3.97; N, 9.20; O, 5.26; S, 10.54. Found: C, 70.86; H, 3.95; N, 9.04; O, 5.25; S, 10.39.

EXAMPLE 31

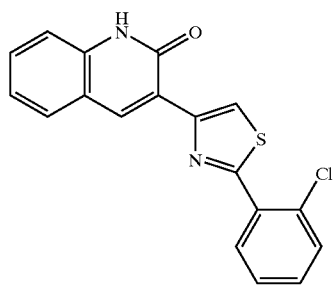

3-[2-(2-Chlorophenyl)-1,3-thiazol-4-yl]
hydroquinolin-2-one

White solid. MS m/z: 339 (M+1). Anal. Calc'd for C$_{18}$H$_{11}$ClN$_2$OS: C, 63.81; H, 3.27; Cl, 10.46; N, 8.27; O, 4.72; S, 9.46. Found: C, 63.51; H, 3.21; Cl, 10.69; N, 8.18; O, 4.73; S, 9.35.

EXAMPLE 32

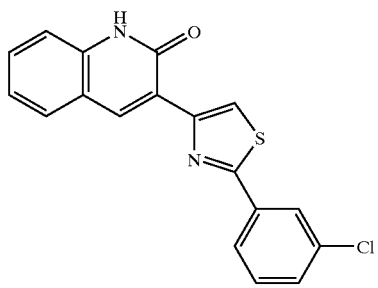

3-[2-(3-Chlorophenyl)-1,3-thiazol-4-yl]
hydroquinolin-2-one

White solid. MS m/z: 339 (M+1). Anal. Calc'd for C$_{18}$H$_{11}$ClN$_2$OS: C, 63.81; H, 3.27; Cl, 10.46; N, 8.27; O, 4.72; S, 9.46. Found: C, 63.55; H, 3.52; Cl, 10.57; N, 8.10; O, 4.91; S, 9.21.

EXAMPLE 33

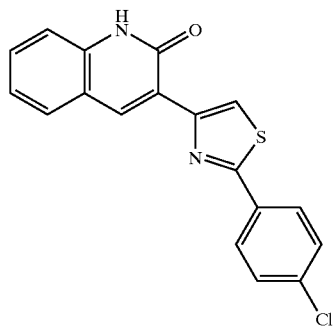

3-[2-(4-Chlorophenyl)-1,3-thiazol-4-yl]
hydroquinolin-2-one

Off-white solid. MS m/z: 339 (M+1). Anal. Calc'd for C$_{18}$H$_{11}$ClN$_2$OS—H$_2$O: C, 63.47; H, 3.31; Cl, 10.40; N, 8.22; O, 5.16; S, 9.41. Found: C, 63.24; H, 3.32; Cl, 10.51; N, 8.28; O, 5.03; S, 9.29.

EXAMPLE 34

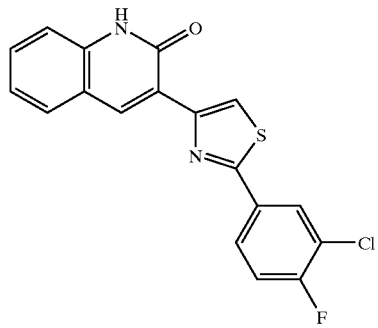

3-[2-(3-Chloro-4-fluorophenyl)-1,3-thiazol-4-yl]
hydroquinolin-2-one

White solid. MS m/z: 357 (M+1). Anal. Calc'd for C$_{18}$H$_{10}$ClFN$_2$OS: C, 60.59; H, 2.82; Cl, 9.94; F, 5.32; N, 7.85; O, 4.48. Found: C, 60.29; H, 2.92; Cl, 9.70; F, 5.39; N, 7.67; O, 4.74.

EXAMPLE 35

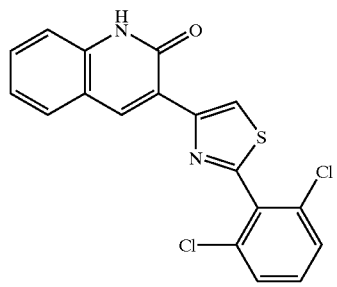

3-[2-(2,6-Dichlorophenyl)-1,3-thiazol-4-yl]
hydroquinolin-2-one

White solid. MS m/z: 373 (M+1). MALDIFTMS (DHB) m/z: 372.9977 (M+H$^+$, C$_{18}$H$_{10}$Cl$_2$N$_2$OS Calc'd 372.9964).

EXAMPLE 36

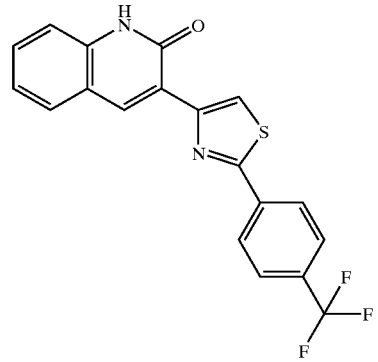

3-{2-[4-(Trifluoromethyl)phenyl]-1,3-thiazol-4-yl}hydroquinolin-2-one

White solid. MS m/z: 373 (M+1). Anal. Calc'd for C$_{19}$H$_{11}$F$_3$N$_2$OS; C, 61.28; H, 2.98; N, 7.52; S, 8.61. Found: C, 61.68; H, 3.28; N, 7.49; S, 8.44.

EXAMPLE 37

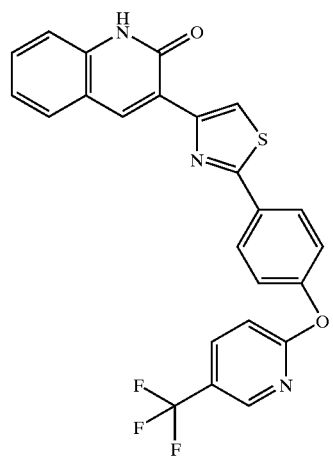

3-(2-{4-[5-(Trifluoromethyl)-2-pyridyloxy]phenyl}-1,3-thiazol-4-yl)hydroquinolin-2-one White solid. MS m/z: 466 (M+1). MALDIFTMS (DHB) m/z: 466.0850 (M+H$^+$, C$_{24}$H$_{14}$F$_3$N$_3$O$_2$S Calc'd 466.0832).

EXAMPLE 38

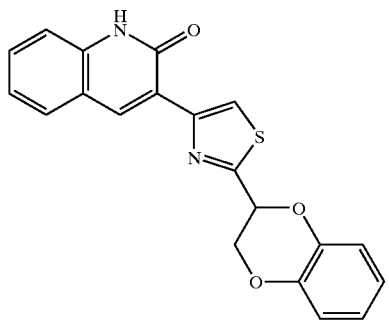

3-(2-(2H,3H-Benzo[e]1,4-dioxin-2-yl)-1,3-thiazol-4-yl)hydroquinolin-2-one

Tan Solid. MS m/z: 363 (M+1). MALDIFTMS (DHB) m/z: 363.0791 (M+H$^+$, C$_{20}$H$_{14}$N$_2$O$_3$S Calc'd 363.0798).

EXAMPLE 39

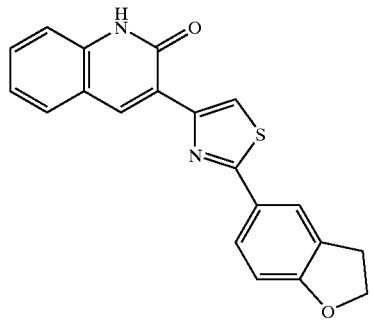

3-(2-(2,3-Dihydrobenzo[b]furan-5-yl)-1,3-thiazol-4-yl)hydroquinolin-2-one

Off-white solid. MS m/z: 347 (M+1). Anal. Calc'd for C$_{20}$H$_{14}$N$_2$O$_2$S: C, 69.35; H, 4.07; N, 8.09; O, 9.24; S, 9.26 Found: C, 68.99; H, 4.26; N, 8.01; O, 9.18; S, 9.16.

EXAMPLE 40

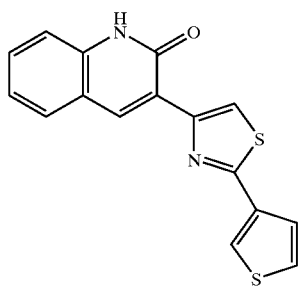

3-(2-(3-Thienyl)-1,3-thiazol-4-yl)hydroquinolin-2-one

Light yellow solid. MS m/z: 311 (M+1). Anal. Calc'd for C$_{16}$H$_{10}$N$_2$OS$_2$·0.4H$_2$O: C, 60.50; H, 3.43; N, 8.82. Found: C, 60.88; H, 3.43; N, 8.68.

EXAMPLE 41

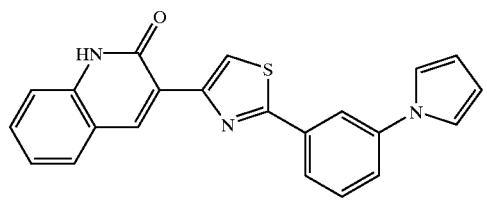

3-[2-(3-Pyrrolylphenyl)-1,3-thiazol-4-yl]hydroquinolin-2-one

Yellow solid. MS m/z: 370 (M+1). MALDIFTMS (DHB) m/z: 370.0998 (M+H$^+$, C$_{22}$H$_{15}$N$_3$OS Calc'd 370.1009).

EXAMPLE 42

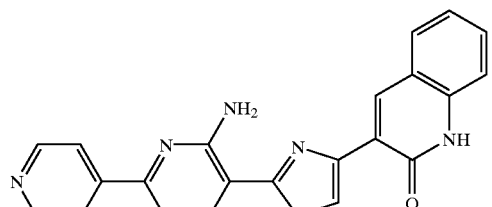

3-[2-(4-Amino-2-(4-pyridyl)pyrimidin-5-yl)-1,3-thiazol-4-yl]hydroquinolin-2-one

Orange solid. MS m/z: 399 (M+1). MALDIFTMS (DHB) m/z: 399.1013 (M+H$^+$, C$_{21}$H$_{14}$N$_6$OS Calc'd 399.1023).

EXAMPLE 43

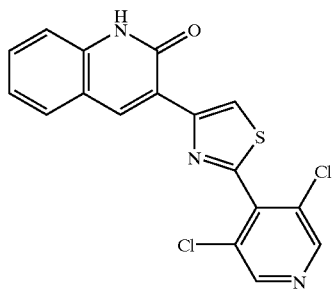

3-[2-(3,5-Dichloro-4-pyridyl)-1,3-thiazol-4-yl]hydroquinolin-2-one

Pink solid. MS m/z: 374 (M+1). MALDIFTMS (DHB) m/z: 373.9915 (M+H⁺, $C_{17}H_9Cl_2N_3OS$ Calc'd 373.9916).

EXAMPLE 44

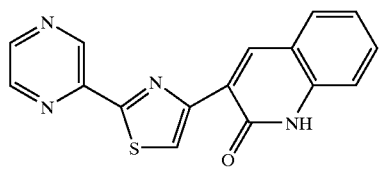

3-(2-Pyrazin-2-yl-1,3-thiazol-4-yl)hydroquinolin-2-one

Pink solid. MS m/z: 307 (M+1). Anal. Calc'd for $C_{16}H_{10}N_4OS$: C, 62.73; H, 3.29; N, 18.29; O, 5.22; S, 10.47. Found: C, 62.40; H, 3.43; N, 17.95; O, 5.70; S, 10.35.

EXAMPLE 45

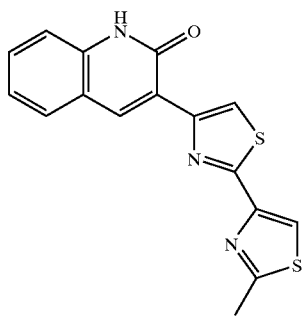

3-[2-(2-Methyl-1,3-thiazol-4-yl)-1,3-thiazol-4-yl]hydroquinolin-2-one

Off-white solid. MS m/z: 326 (M+1). MALDIFTMS (DHB) m/z: 326.0405 (M+H⁺, $C_{16}H_{11}N_3OS_2$ Calc'd 326.0416).

EXAMPLE 46

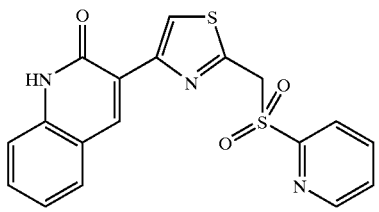

3-{2-[(2-Pyridylsulfonyl)methyl]-1,3-thiazol-4-yl}hydroquinolin-2-one

White solid. MS m/z: 384 (M+1). Anal. Calc'd for $C_{18}H_{13}N_3O_3S_2$: C, 56.38; H, 3.42; N, 10.96; O, 12.52; S, 16.73. Found: C, 56.30; H, 3.52; N, 10.98; O, 12.46; S, 16.78.

EXAMPLE 47

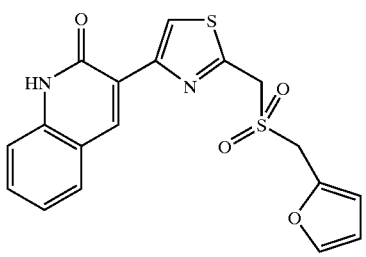

3-(2-{[((2-Furylmethyl)sulfonyl]methyl}-1,3-thiazol-4-yl)hydroquinolin-2-one

White solid. MS m/z: 387 (M+1). Anal. Calc'd for $C_{18}H_{14}N_2O_4S_2$: C, 55.94; H, 3.65; N, 7.25; O, 16.56; S, 16.60. Found: C, 55.90; H, 3.60; N, 7.14; O, 16.71; S, 16.44.

EXAMPLE 48

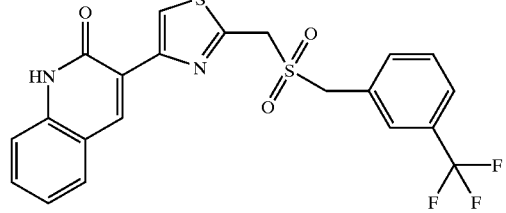

3-{2-[3 ({[(trifluoromethyl)phenyl]methyl}sulfonyl)methyl]-1,3-thiazol-4-yl}hydroquinolin-2-one White solid. MS m/z: 465 (M+1). Anal. Calc'd for $C_{21}H_{15}F_3N_2O_3S_2$: C, 54.30; H, 3.26; F, 12.27; N, 6.03; O, 10.33; S, 13.81. Found: C, 54.40; H, 3.21; F, 12.39; N, 6.09; O, 10.42; S, 13.85.

EXAMPLE 49

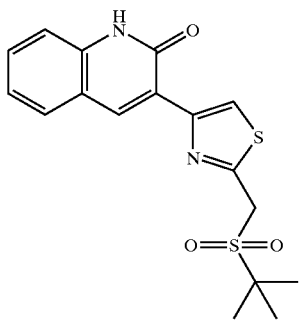

3-(2-{[(tert-Butyl)sulfonyl]methyl}-1,3-thiazol-4-yl)hydroquinolin-2-one

White solid. MS m/z: 363 (M+1). MALDIFTMS (DHB) m/z: 363.0843 (M+H$^+$, $C_{17}H_{18}N_2O_3S_2$ Calc'd 363.0832).

EXAMPLE 50

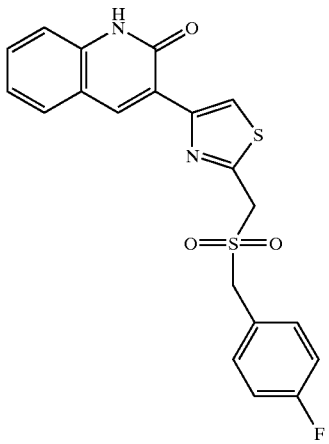

3-[2-({[(4-Fluorophenyl)methyl]sulfonyl}methyl)-1,3-thiazol-4-yl]hydroquinolin-2-one White solid. MS m/z: 415 (M+1). MALDIFTMS (DHB) m/z: 415.0596 (M+H$^+$, $C_{20}H_{15}FN_2O_3S_2$ Calc'd 415.0581).

EXAMPLE 51

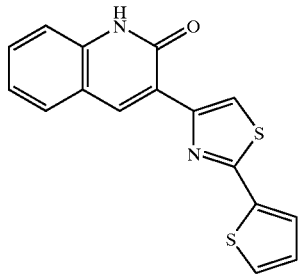

3-(2-(2-Thienyl)-1,3-thiazol-4-yl)hydroquinolin-2-one

Light yellow solid. MS m/z: 311 (M+1). Anal. Calc'd for $C_{16}H_{10}N_2OS_2$: C, 61.91; H, 3.25; N, 9.03; O, 5.15; S, 20.66. Found: C, 61.68; H, 3.17; N, 9.14; O, 5.34; S, 20.43.

EXAMPLE 52

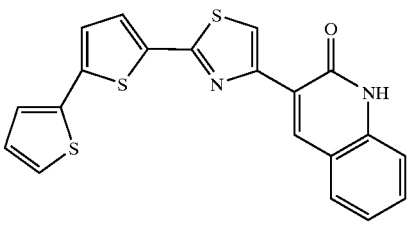

3-[2-(5-(2-Thienyl)-2-thienyl)-1,3-thiazol-4-yl]hydroquinolin-2-one

Yellow solid. MS m/z: 393 (M+1). Anal. Calc'd for $C_{20}H_{12}N_2OS_3$: C, 61.20; H, 3.08; N, 7.14; O, 4.08; S, 24.51. Found; C, 60.96; H, 3.19; N, 7.12; O, 4.24; S, 24.50.

EXAMPLE 53

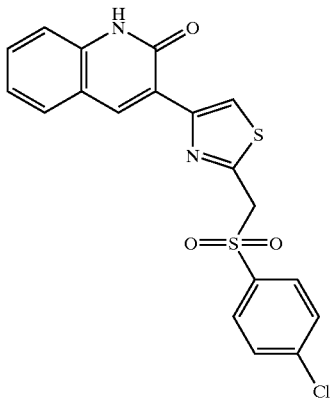

3-(2-{[(4-Chlorophenyl)sulfonyl]methyl}-1,3-thiazol-4-yl)hydroquinolin-2-one

The reaction was conducted at 0.37 mmol scale. White solid. MS m/z: 417 (M+1). Anal. Calc'd for $C_{19}H_{13}ClN_2O_3S_2$: C, 54.74; H, 3.14; Cl, 8.50; N, 6.72; O, 11.51; S, 15.38. Found: C, 54.62; H, 3.16; Cl, 8.70; N, 6.81; O, 11.16; S, 15.16.

EXAMPLE 54

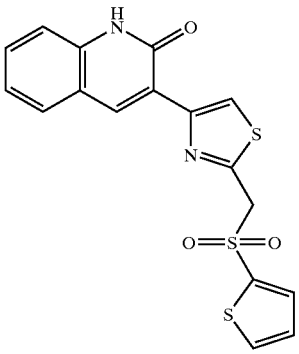

3-{2-[(2-Thienylsulfonyl)methyl]-1,3-thiazol-4-yl}hydroquinolin-2-one

The reaction was conducted at 0.37 mmol scale. Tan solid. MS m/z: 389 (M+1). Anal. Calc'd for $C_{17}H_{12}N_2O_3S_3$: C,

EXAMPLE 55

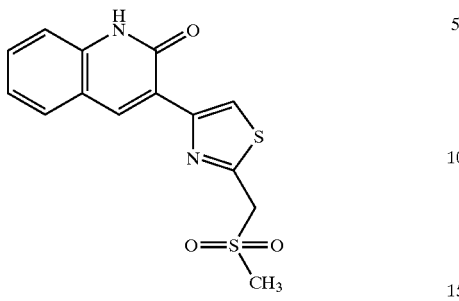

3-{2-[(Methylsulfonyl)methyl]-1,3-thiazol-4-yl}hydroquinolin-2-one

White solid. MS m/z: 321 (M+1). Anal. Calc'd for $C_{14}H_{12}N_2O_3S_2$: C, 52.48; H, 3.78; N, 8.74; O, 14.98; S, 20.02. Found: C, 52.63; H, 3.91; N, 8.65; O, 15.11; S, 19.93.

EXAMPLE 56

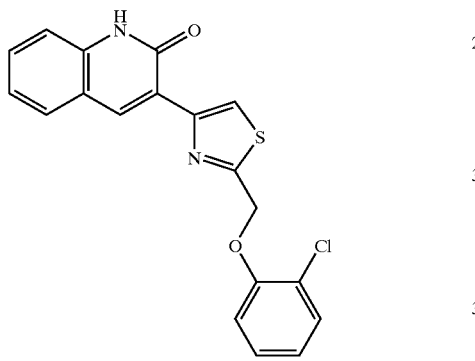

3-{2-[(2-Chlorophenoxy)methyl]-1,3-thiazol-4-yl}hydroquinolin-2-one

White solid. MS m/z: 369 (M+1). Anal. Calc'd for $C_{19}H_{13}ClN_2O_2S$: C, 61.87; H, 3.55; Cl, 9.61; N, 7.60; O, 8.68; S, 8.69. Found: C, 61.65; H, 3.49; Cl, 9.50; N, 7.65; O, 8.54; S, 8.65.

EXAMPLE 57

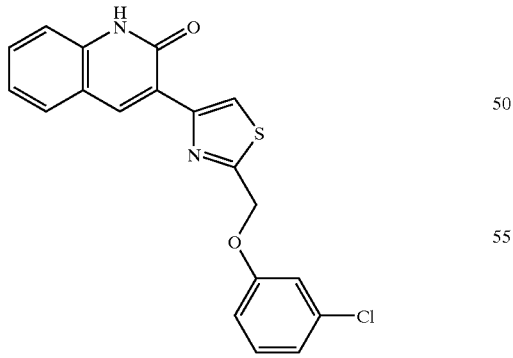

3-{2-[(3-Chlorophenoxy)methyl]-1,3-thiazol-4-yl}hydroquinolin-2-one

White solid. MS m/z: 369 (M+1). Anal. Calc'd for $C_{19}H_{13}ClN_2O_2S \cdot 0.1H_2O$: C, 61.32; H, 3.55; Cl, 9.53; N, 7.53; S, 8.62. Found: C, 61.41; H, 3.54; Cl, 9.64; N, 7.47; S, 8.57.

EXAMPLE 58

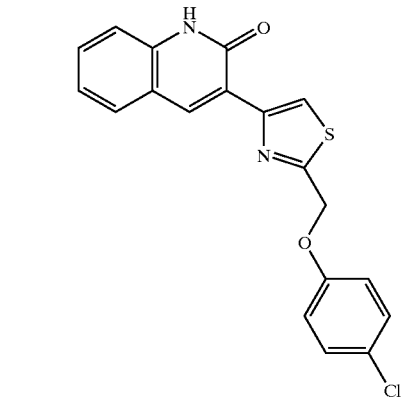

3-{2-[(4-Chlorophenoxy)methyl]-1,3-thiazol-4-yl}hydroquinolin-2-one

White solid. MS m/z: 369 (M+1). Anal. Calc'd for $C_{19}H_{13}ClN_2O_2S$: C, 61.87; H, 3.55; Cl, 9.61; N, 7.60; O, 8.68; S, 8.69. Found: C, 61.56; H, 3.54; Cl, 9.40; N, 7.53; O, 8.91; S, 8.51.

EXAMPLE 59

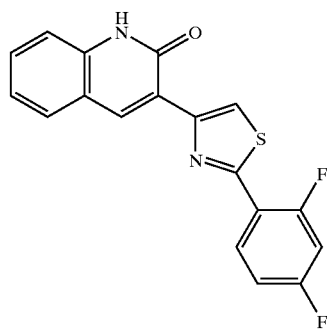

3-[2-(2,4-Difluorophenyl)-1,3-thiazol-4-yl]hydroquinolin-2-one

Reaction was conducted at 0.37 mmol scale. White solid. MS m/z: 341 (M+1). Anal. Calc'd for $C_{18}H_{10}F_2N_2OS$: C, 63.52; H, 2.96; F, 11.16; N, 8.23; O, 4.70; S, 9.42. Found: C, 63.65; H, 3.26; F, 11.25; N, 8.20; O, 4.93; S, 9.33.

EXAMPLE 60

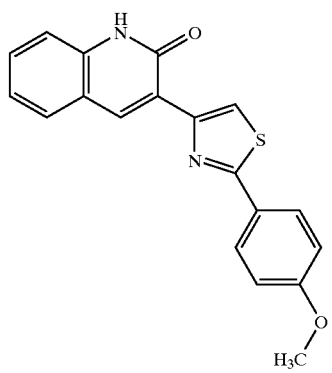

3-[2-(4-Methoxyphenyl)-1,3-thiazol-4-yl]hydroquinolin-2-one

Reaction was conducted at 0.37 mmol scale. White solid. MS m/z: 335 (M+1). Anal. Calc'd for $C_{19}H_{14}N_2O_2S$: C, 68.24; H, 4.22; N, 8.38; O, 9.57; S, 9.59. Found: C, 67.98; H, 4.20; N, 8.40; O, 9.67; S, 9.51.

EXAMPLE 61

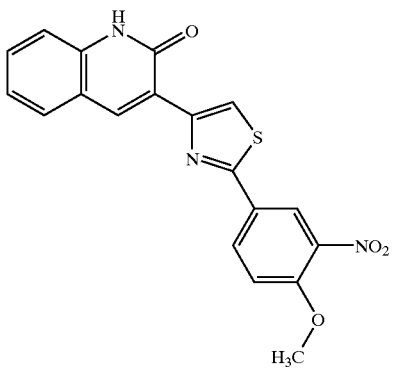

3-[2-(4-Methoxy-3-nitrophenyl)-1,3-thiazol-4-yl]hydroquinolin-2-one

Reaction was conducted at 0.37 mmol scale. Light yellow solid. MS m/z: 380 (M+1). Anal. Calc'd for $C_{19}H_{13}N_3O_4S \cdot H_2O$: C, 59.86; H, 3.49; N, 11.02; O, 17.20; S, 8.41. Found: C, 59.55; H, 3.52; N, 11.05; O, 17.30; S, 8.36.

EXAMPLE 62

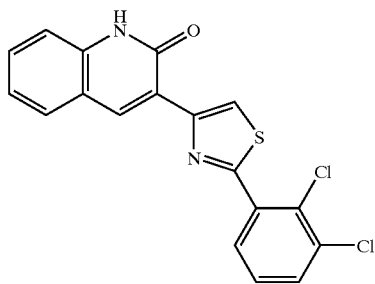

3-[2-(2,3-Dichlorophenyl)-1,3-thiazol-4-yl]hydroquinolin-2-one

Reaction was conducted at 0.37 mmol scale. White solid. MS m/z: 373 (M+1). Anal. Calc'd for $C_{18}H_{10}Cl_2N_2OS$: C, 57.92; H, 2.70; Cl, 19.00; N, 7.51; O, 4.29; S, 8.59. Found: C, 57.95; H, 2.86; Cl, 19.05; N, 7.44; O, 4.38; S, 8.53.

EXAMPLE 63

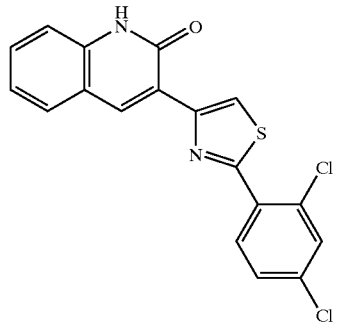

3-[2-(2,4-Dichlorophenyl)-1,3-thiazol-4-yl]hydroquinolin-2-one

Reaction was conducted at 0.37 mmol scale. White solid. MS m/z: 373 (M+1). Anal. Calc'd for $C_{18}H_{10}Cl_2N_2OS$: C, 57.92; H, 2.70; Cl, 19.00; N, 7.51; O, 4.29; S, 8.59. Found: C, 57.75; H, 2.76; Cl, 18.87; N, 7.48; O, 4.42; S, 8.52.

EXAMPLE 64

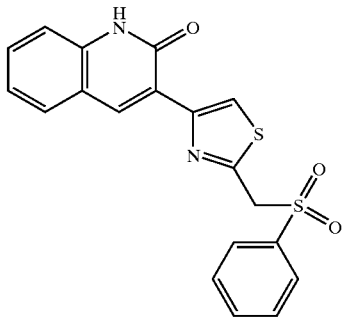

3-{2-[(Phenylsulfonyl)methyl]-1,3-thiazol-4-yl}hydroquinolin-2-one

A mixture of 3-(2-{[(4-chlorophenyl)sulfonyl]-methyl}-1,3-thiazol-4-yl)hydroquinolin-2-one (Example 57) (147 mg, 0.35 mmol), 0.12 g of Pd/C (10%), and 0.3 mL of DIEA in 45 mL of anhydrous DMF was purged with 1 L of $H_2$. The reaction mixture was stirred at RT overnight under $H_2$. The catalyst was filtered off through a Celite®-pad and the filtrate concentrated to 5 mL in volume. Anhydrous MeOH (20 mL) was added and precipitates formed. Filtration and washing with MeOH, $CH_2Cl_2$, and hexanes afforded the title compound as a white solid. MS m/z: 383 (M+1). Anal. Calc'd for $C_{19}H_{14}N_2O_3S_2$: C, 59.67; H, 3.69; N, 7.32; O, 12.55; S, 16.77. Found: C. 59.39; H, 3.86; N, 7.40; O, 12.57; S, 16.67.

EXAMPLE 65

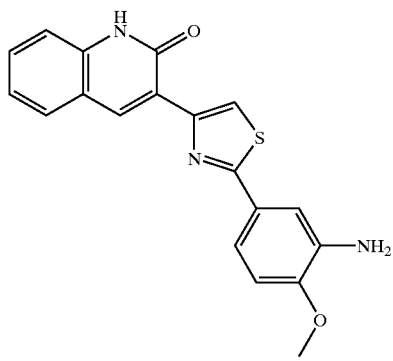

3-[2-(3-Amino-4-methoxyphenyl)-1,3-thiazol-4-yl]hydroquinolin-2-one

A mixture of 3-[2-(4-methoxy-3-nitrophenyl)-1,3-thiazol-4-yl]hydroquinolin-2-one (Example 61) (76 mg, 0.20 mmol) and 0.1 g of Pd/C (10%) in 75 mL of anhydrous DMF was purged with 1.5 L of $H_2$. The reaction mixture was stirred at RT overnight under $H_2$. The catalyst was filtered off through a Celite®-pad and the filtrate concentrated to 7 mL in volume. Anhydrous MeOH (20 mL) was added and precipitates formed. Filtration and washing with MeOH, $CH_2Cl_2$, and hexanes afforded the title compound as a light yellow solid. MS m/z: 350 (M+1). Anal. Calc'd for $C_{19}H_{15}N_3O_2S$: C, 65.31; H, 4.33; N, 12.03; O, 9.16; S, 9.18. Found: C, 65.08; H, 4.35; N, 11.99; O, 9.25; S, 9.15.

EXAMPLE 66

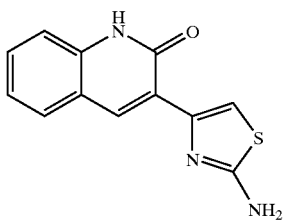

3-(2-Amino-1,3-thiazol-4-yl)hydroquinolin-2-one

To a suspension of 3-(2-bromoacetyl)hydroquinolin-2-one (Example 27, Step b, 266 mg, 1 mmol) in 15 mL MeOH was added thiourea (Aldrich) (79 mg, 1.0 mmol). The reaction was heated at 63° C. for 16 h, then cooled to RT. The resulting precipitate was filtered, washed with MeOH, and dried in vacuo to afford the hydrobromide salt as a yellow amorphous solid. Mp: >300° C. MS m/z: 244 (M+1). Calc'd for $C_{12}H_{10}N_3OS$: $C_{12}H_9N_3OS$: 243.05. Anal. Calc'd for $C_{12}H_{10}N_3OS$.HBr: C, 44.45; H, 3.11; N, 12.96. Found: C, 44.53; H, 3.09; N, 13.01.

EXAMPLE 67

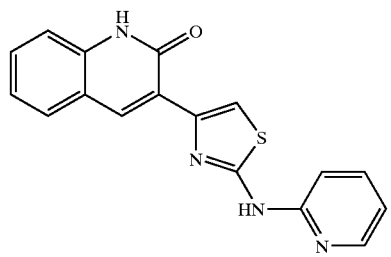

3-[2-(2-pyridylamino)-1,3-thiazol-4-yl]hydroquinolin-2-one

To a suspension of 3-(2-bromoacetyl)hydroquinolin-2-one (Example 27(b)) (133 mg, 0.5 mmol) in 6 mL MeOH was added 2-pyridyl thiourea (Lancaster) (78 mg, 0.5 mmol). The reaction mixture was heated at 63° C. for 17 h and then cooled to RT. The precipitate was filtered, washed with MeOH, and dried in vacuo to afford the hydrobromide salt as a yellow amorphous solid. Mp: 307–312° C. (dec). MS m/z: 321 (M+1); 319 (M−1). Anal. Calc'd for $C_{17}H_{12}N_4OS.0.7$ HBr.1.1 $H_2O$: C, 51.45; H, 3.78; Br, 14.10; N, 14.12. Found: C, 51.38; H, 3.60; Br, 14.09; N, 14.15.

EXAMPLE 68

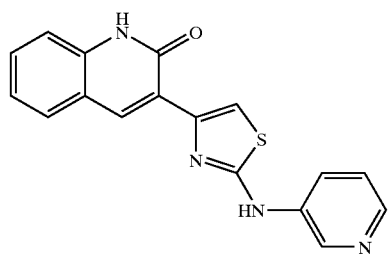

3-[2-(3-Pyridylamino)-1,3-thiazol-4-yl]hydroquinolin-2-one

To a suspension of 3-(2-bromoacetyl)hydroquinolin-2-one (122 mg, 0.5 mmol) in 6 mL MeOH was added 3-pyridyl thiourea (Lancaster) (72 mg, 0.5 mmol). The reaction was heated at 63° C. for 17 h, then cooled to RT. The precipitate was filtered, washed with MeOH, and dried in vacuo to afford the hydrobromide salt as a yellow amorphous solid. Mp: >300° C. MS m/z: 321 (M+1); 319 (M−1). Anal. Calc'd for $C_{17}H_{12}N_4OS.HBr.H_2O$: C, 48.69; H, 3.61; Br, 19.06; N, 13.36. Found: C, 48.67; H, 3.84; Br, 18.80; N, 13.19.

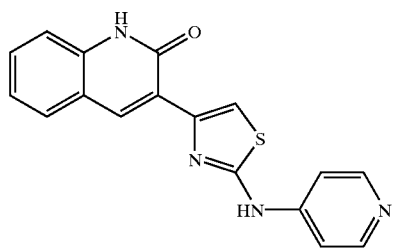

EXAMPLE 69

3-[2-(4-Pyridylamino)-1,3-thiazol-4-yl]hydroquinolin-2-one

To a suspension of 3-(2-bromoacetyl)hydroquinolin-2-one (Example 27(b)) (132 mg, 0.5 mmol) in 6 mL MeOH was added 4-pyridyl thiourea (Lancaster) (78 mg, 0.5 mmol). The reaction was heated at 63° C. for 16 h, then cooled to RT. The precipitate was filtered, washed with MeOH, and dried in vacuo to afford the hydrobromide salt as a yellow amorphous solid. Mp: >300° C. MS m/z: 321 (M+1); 319 (M−1). Anal. Calc'd for $C_{17}H_{12}N_4OS.HBr.2H_2O$: C, 46.69; H, 3.92; Br, 18.27; N, 12.81. Found: C, 46.47; H, 3.91; Br, 18.49; N, 12.60.

EXAMPLE 70

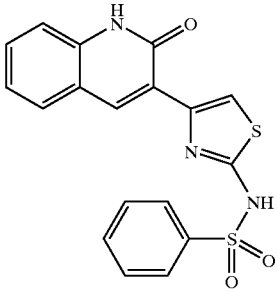

3-{2-[(Phenylsulfonyl)amino]-1,3-thiazol-4-yl}hydroquinolin-2-one

To a suspension of 3-(2-amino-1,3-thiazol-4-yl)hydroquinolin-2-one hydrobromide (Example 66) (51 mg, 0.16 mol) in 1 mL pyridine was added a solution of benzenesulfonyl chloride (Aldrich) (37 mg, 0.21 mmol) in 1 mL pyridine at RT. After 2 h the reaction was heated to 60° C. After 1.5 h, the reaction was cooled to RT and the resulting precipitate was filtered, washed with MeOH, and dried in vacuo to give a tan amorphous solid. Mp: >300° C. MS m/z: 384 (M+1); 382 (M−1). Anal. Calc'd for $C_{18}H_{13}N_3O_3S_2.0.1\ H_2O$: C, 56.12; H, 3.45; N, 10.91. Found: C, 55.91; H, 3.46; N, 10.68.

EXAMPLE 71

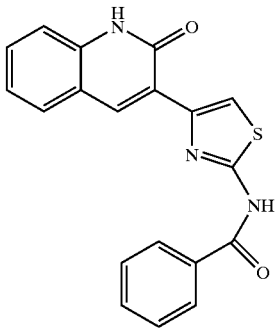

N-[4-(2-Oxo(3-hydroquinolyl))(1,3-thiazol-2-yl)]benzamide

To a suspension of 3-(2-amino-1,3-thiazol-4-yl)hydroquinolin-2-one hydrobromide (Example 66) (52 mg, 0.16 mmol) in 1 mL pyridine was added a solution of benzoyl chloride (Aldrich) (33 mg, 0.23 mmol) in 1 mL pyridine at RT. After 2 h the reaction was heated to 60° C. After 1.5 h the reaction was cooled to RT and the resulting precipitate was filtered, washed with MeOH, and dried in vacuo to give a the HCl salt as a white amorphous solid. Mp: 309–311° C. (dec.). MS m/z: 348 (M+1), 346 (M−1). Anal.

Calc'd for $C_{19}H_{13}N_3O_2S.HCl$: C, 62.03; H, 3.84; N, 11.43. Found: C, 61.67; H, 4.00; N, 11.22.

EXAMPLE 72

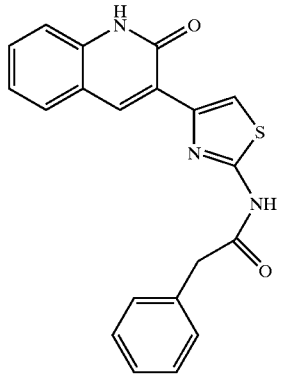

N-[4-(2-Oxo(3-hydroquinolyl))(1,3-thiazol-2-yl)]-2-phenylacetamide

To a suspension of 3-(2-amino-1,3-thiazol-4-yl)hydroquinolin-2-one hydrobromide (Example 66) (52 mg, 0.16 mmol) in 2 mL pyridine was added phenylacetyl chloride (Aldrich, 245 mg, 0.21 mL, 1.6 mmol) followed by a few crystals of DMAP (Aldrich). The reaction was heated at 60° C. for 7 h then cooled to RT. The precipitate was filtered, washed with MeOH and dried in vacuo to give a white crystalline solid. Mp: 272–278° C. MS m/z: 362 (M+1), 360 (M−1). Anal. Calc'd for $C_{20}H_{15}N_3O_2S.0.50\ H_2O$: C, 64.85; H, 4.35; N, 11.35. Found: C, 64.71; H, 4.08; N, 11.28.

EXAMPLE 73

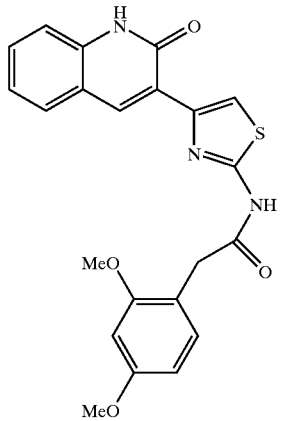

2-(2,4-Dimethoxyphenyl)-N-[4-(2-oxo(3-hydroquinolyl))(1,3-thiazol-2-yl)]acetamide To a suspension of 3-(2-amino-1,3-thiazol-4-yl)hydroquinolin-2-one hydrobromide (Example 66) (49 mg, 0.15 mmol) in 2 mL pyridine was added (2,5-dimethoxyphenyl)acetyl chloride (Aldrich, 117 mg, 0.095 mL, 0.54 mmol) followed by a few crystals of DMAP (Aldrich). The reaction was heated at 60° C. for 9 h and then cooled to RT. The reaction was diluted with MeOH and stirred for 2 h. The solids were filtered, washed with MeOH and dried in vacuo to yield a gray amorphous solid. Mp:

295–300° C. (dec.). MS m/z: 422 (M+1), 420 (M−1). Anal. Calc'd for $C_{22}H_{19}N_3O_4S.0.30$ MeOH: C, 62.13; H, 4.72; N, 9.75. Found: C, 62.53; H, 4.75; N, 9.38.

EXAMPLE 74

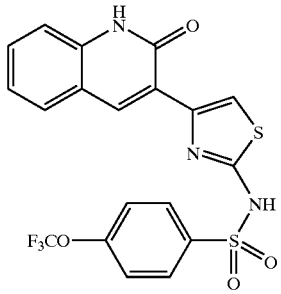

3-[2-({[4-(Trifluoromethoxy)phenyl]sulfonyl}amino)-1,3-thiazol-4-yl]hydroquinolin-2-one To a suspension of 3-(2-amino-1,3-thiazol-4-yl)-hydroquinolin-2-one hydrobromide (Example 66) (47 mg, 0.15 mmol) in 2 mL pyridine was added 4-(trifluoromethoxy) benzenesulfonyl chloride (Aldrich) (126 mg, 0.082 mL, 0.48 mmol) followed by a few crystals of DMAP (Aldrich). The reaction was heated at 63° C. for 10 h then cooled to RT. The solvent was removed in vacuo and the residue was stirred with MeOH for 2 h. The solids were filtered, washed with MeOH and dried in vacuo to give a pink amorphous solid. Mp: >300° C. MS m/z: 468 (M+1), 466 (M−1). Anal. Calc'd for $C_{19}H_{12}N_3O_4S_2.0.30$ $H_2O$: C, 48.26; H, 2.69; N, 8.89. Found: C, 48.27; H, 2.58; N, 8.81.

EXAMPLE 75

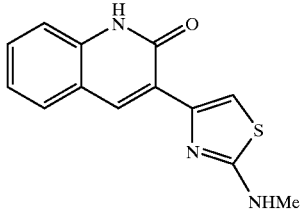

3-[2-(Methylamino)-1,3-thiazol-4-yl]hydroquinolin-2-one hydrobromide

To a suspension of 3-(2-bromoacetyl)hydroquinolin-2-one (Example 27(b)) (395 mg, 1.5 mmol) in 14 mL MeOH was added N-methylthiourea (Aldrich) (137 mg, 1.5 mmol). The reaction was heated at 63° C. for 16 h and then cooled to RT. The precipitate was filtered, washed with MeOH, and dried in vacuo to afford a pale yellow amorphous solid. Mp: 292–293° C. MS m/z: 258 (M+1), 256 (M−1). Anal. Calc'd for $C_{13}H_{11}N_3OS.H_2O.HBr$: C, 43.83; H, 3.96; N, 11.80; Br, 22.43. Found: C, 43.68; H, 3.81; N, 11.77; Br, 22.54.

EXAMPLE 76

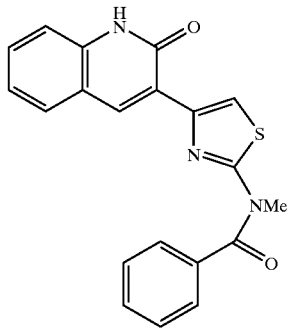

N-Methyl-N-[4-(2-oxo(3-hydroquinolyl))(1,3-thiazol-2-yl)]benzamide

To a solution of 3-[2-(methylamino)-1,3-thiazol-4-yl]hydroquinolin-2-one (Example 75) (63 mg, 0.24 mmol) in 1 mL pyridine was added benzoyl chloride (Aldrich) (85 mg, 0.070 mL, 0.60 mmol) followed by a few crystals of DMAP (Aldrich). The reaction was heated to 63° C. for 6 h then cooled to RT. The reaction was diluted to 3 times volume with MeOH and heating proceeded at 63° C. for an additional 4 h. The solution was cooled to RT and the solids were filtered, washed with MeOH and dried in vacuo to give a pale yellow amorphous solid. Mp: >300° C. MS m/z: 362 (M+1). Anal. Calc'd for $C_{20}H_{15}N_3O_2S$: C, 66.45; H, 4.18; N, 11.63. Found: C, 66.45; H, 4.17; N, 11.77.

EXAMPLE 77

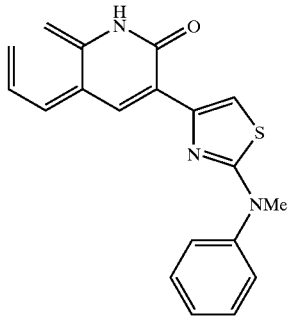

3-[2-(Methylphenylamino)-1,3-thiazol-4-yl]hydroquinolin-2-one

To a suspension of 3-(2-bromoacetyl)hydroquinolin-2-one (Example 27(b)) (67 mg, 0.25 mmol) in 5 mL MeOH was added N-methyl-N-phenylthiourea (Maybridge) (42 mg, 0.25 mmol). The reaction was heated to 63° C. for 15 h and cooled to RT. The precipitate was filtered, washed with MeOH, and dried in vacuo to afford a yellow amorphous solid. Mp: 283–285° C. MS m/z: 334 (M+1), 332 (M−1). Anal. Calc'd for $C_{19}H_{15}N_3OS.0.1$ $H_2O$: C, 68.08; H, 4.57; N, 12.54. Found: C, 67.79; H, 4.66; N, 12.53.

EXAMPLE 78

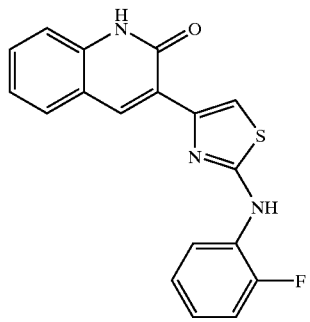

3-{2-[(2-Fluorophenyl)amino]-1,3-thiazol-4-yl}hydroquinolin-2-one

To a suspension of 3-(2-bromoacetyl)hydroquinolin-2-one (Example 27(b)) (91 mg, 0.34 mmol) in 5 mL MeOH was added 2-(fluorophenyl)thiourea (Lancaster) (59 mg, 0.34 mmol). The reaction was heated to 63° C. for 18 h and cooled to RT. The precipitate was filtered, washed with MeOH, and dried in vacuo to afford a white amorphous solid. Mp: 277–278° C. (dec.). MS m/z: 338 (M+1), 336 (M−1). Anal. Calc'd for $C_{18}H_{12}FN_3OS$: C, 64.08; H, 3.59; N, 12.46. Found: C, 63.90; H, 3.54; N, 12.41.

EXAMPLE 79

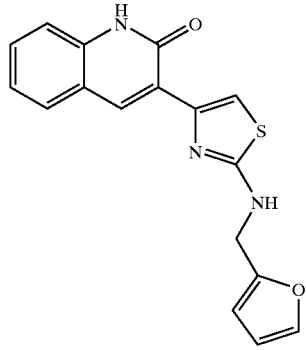

3-{2-[(2-Furylmethyl)amino]-1,3-thiazol-4-yl}hydroquinolin-2-one hydrobromide

To a suspension of 3-(2-bromoacetyl)hydroquinolin-2-one (Example 27(b)) (105 mg, 0.4 mmol) in 5 mL MeOH was added 1-(2-furfuryl)-2-thiourea (Transworld) (63 mg, 0.4 mmol). The reaction was heated to 63° C. for 18 h and then cooled to RT. The precipitate was filtered, washed with MeOH, and dried in vacuo to afford a pale yellow amorphous solid. Mp: 221–224° C. (dec.). MS m/z: 324 (M+1), 322 (M−1). Anal. Calc'd for $C_{17}H_{13}N_3O_2S \cdot HBr$: C, 50.50; H, 3.49; N, 10.39; Br, 19.76. Found: C, 50.22; H, 3.59; N, 10.26; Br, 19.76.

EXAMPLE 80

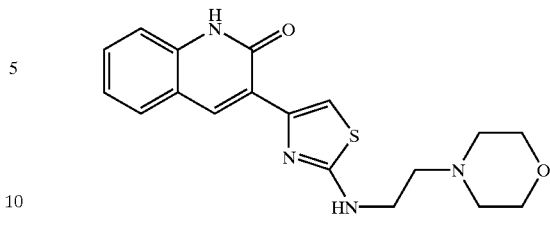

3-{2-[(2-Morpholin-4-ylethyl)amino]-1,3-thiazol-4-yl}hydroquinolin-2-one hydrobromide To a suspension of 3-(2-bromoacetyl)hydroquinolin-2-one (Example 27(b)) (84 mg, 0.32 mmol) in 5 mL MeOH was added 1-(2-morpholinoethyl)-2-thiourea (Transworld) (60 mg, 0.32 mmol). The reaction was heated to 63° C. for 18 h and then cooled to RT. The precipitate was filtered, washed with MeOH, and dried in vacuo to afford a yellow crystalline solid. Mp: 237–239° C. MS m/z: 357 (M+1), 355 (M−1). Anal. Calc'd for $C_{18}H_{20}N_4O_2S \cdot HBr$: C, 49.43; H, 4.84; N, 12.81; Br, 18.27. Found: C, 49.30; H, 4.80; N, 12.81; Br, 18.12.

EXAMPLE 81

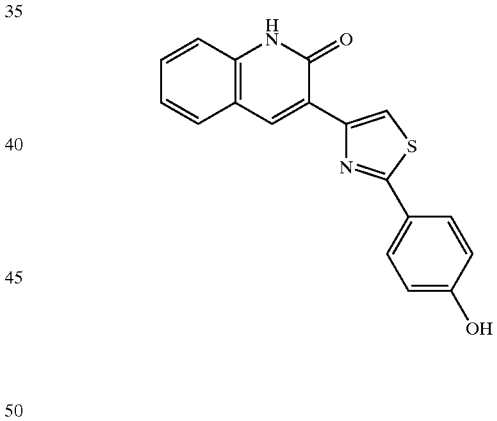

3-[2-(4-Hydroxyphenyl)-1,3-thiazol-4-yl]hydroquinolin-2-one

A mixture of 3-(2-{4-[5-(trifluoromethyl)-2-pyridyloxy]phenyl}-1,3-thiazol-4-yl)hydroquinolin-2-one (Example 37) (65 mg, 0.14 mmol) and 5 mL of aqueous HCl (5 N) in 40 mL of DMSO was heated at reflux for 6 d. Additional 2 mL of HCl (5 N) was added to the reaction mixture every 24 h. Solvents were evaporated under vacuum. The residue was purified by HPLC to provide the title compound as a light yellow solid which turned into light gray color upon standing at RT overnight. MS m/z: 321 (M+1). MALDIFTMS (DHB) m/z: 321.0707 (M+H$^+$, $C_{18}H_{12}N_2O_2S$ Calc'd 321.0692).

EXAMPLE 82

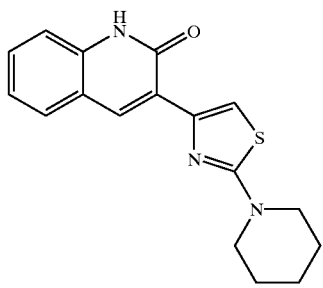

3-(2-Piperidyl-1,3-thiazol-4-yl)hydroquinolin-2-one

The reaction was conducted as described for Example 27c starting from aminopiperidylmethane-1-thione. (Aldrich). Light yellow solid. MS m/z: 312 (M+1). HRMS m/z: 312.1156 (M+H$^+$, C$_{17}$H$_{17}$N$_3$OS Calc'd 312.1165).

EXAMPLE 83

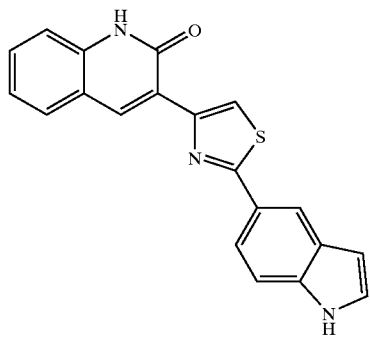

3-(2-Indol-5-yl-1,3-thiazol-4-yl)hydroquinolin-2-one

A solution of 5-cyanoindole (Aldrich) (2.84 g, 20.0 mmol) in 20 mL of pyridine and 8.35 mL of TEA was purged with H$_2$S gas for 1.5 h. Solvents were removed under vacuum. The residue was dissolved in 100 mL of EtOAc, washed with H$_2$O, 0.3 N HCl (aq.), and H$_2$O. The EtOAc layer was separated, dried (Na$_2$SO$_4$), and concentrated to yield the corresponding 5-indole-thiocarboxamide that was used directly in the next step. A solution of 5-indole-thiocarboxamide (150 mg, 0.85 mmol) and 3-(2-bromoacetyl)hydroquinolin-2-one (Example 27, 120 mg, 0.45 mmol) in 50 mL of MeOH was heated at reflux for 4 h. The mixture was then concentrated. The residue was treated with CH$_2$Cl$_2$ and the precipitates were collected by filtration to provide the title compound as a pale orange solid. MS m/z: 344 (M+1). Anal. Calc'd for C$_{20}$H$_{13}$N$_3$OS.H$_2$O.0.8HBr: C, 56.37; H, 3.74; N, 9.86; O, 7.51; S, 7.52. Found: C, 56.64; H, 3.80; N, 9.64; O, 7.30; S, 7.44.

EXAMPLE 84

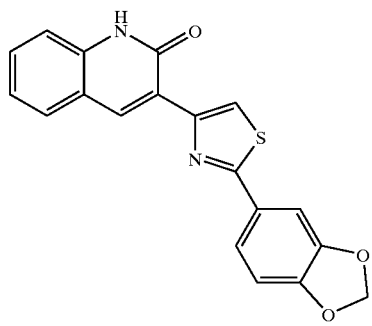

3-(2-(2H-Benzo[d]1,3-dioxolan-5-yl)-1,3-thiazol-4-yl)hydroquinolin-2-one

This compound was prepared according to the procedure described for Example 83 starting from 2H-benzo[d]1,3-dioxolane-5-carbonitrile (Aldrich). Off-white solid. MS m/z: 349 (M+1). Anal. Calc'd for C$_{19}$H$_{12}$N$_2$O$_3$S: C, 65.50; H, 3.47; N, 8.04; O, 13.78; S, 9.20. Found: C, 65.66; H, 3.62; N, 8.05; O, 13.51; S, 9.24.

EXAMPLE 85

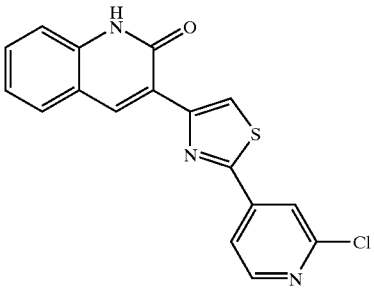

3-[2-(2-Chloro-pyridin-4-yl)-thiazol-4-yl]-1H-quinolin-2-one

This compound was prepared according to the procedure described for Example 83 starting from 2-chloropyridine-4-carbonitrile (Aldrich). Off-white solid. MS m/z: 339, 341 (M+1). HRMS m/z: 340.0338 (M+H$^+$, C$_{17}$H$_{10}$ClN$_3$OS Calc'd 340.0306).

General procedure for the preparation of Examples 86–96

The mixture of 3-[2-(2-chloro-4-pyridyl)-1,3-thiazol-4-yl]hydroquinolin-2-one (Example 85) (100 mg, 0.29 mmol) and the corresponding alcohols (4.5 mmol) in 30 mL of anhydrous DMF was treated carefully with 120 mg of NaH (60%, 3.0 mmol). Bubbles were generated. The resulting solutions were placed on a Büchi Syncore synthesizer at 100° C. for 2 days. Solvents were removed under vacuum and the residue was treated with 30 mL of H$_2$O. The precipitates were collected by filtration, and the compounds were purified by Prep-HPLC as solids after lyophilization.

EXAMPLE 86

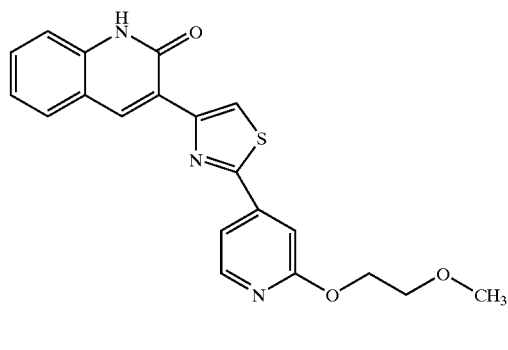

3-{2-[2-(2-Methoxyethoxy)-4-pyridyl]-1,3-thiazol-4-yl}hydroquinolin-2-one

Light yellow solid. MS m/z: 380 (M+1). HRMS m/z: 380.1115 (M+H$^+$, C$_{20}$H$_{17}$N$_3$O$_3$S Calc'd 380.1063).

EXAMPLE 87

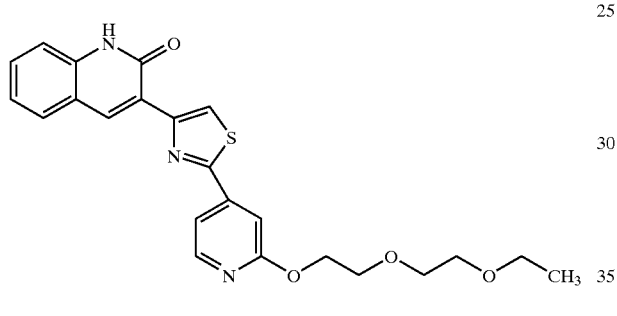

3-(2-{2-[2-(2-Ethoxyethoxy)ethoxy]-4-pyridyl}-1,3-thiazol-4-yl)hydroquinolin-2-one.

Light yellow solid. MS m/z: 438 (M+1). HRMS m/z: 438.1520 (M+H$^+$, C$_{23}$H$_{23}$N$_3$O$_4$S Calc'd 438.1482).

EXAMPLE 88

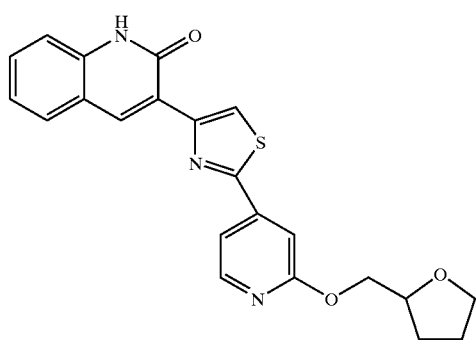

3-{2-[2-(Oxolan-2-ylmethoxy)-4-pyridyl]-1,3-thiazol-4-yl}hydroquinolin-2-one

Off-white solid. MS m/z: 406 (M+1). HRMS m/z: 406.1237 (M+H$^+$, C$_{22}$H$_{19}$N$_3$O$_3$S Calc'd 406.1220).

EXAMPLE 89

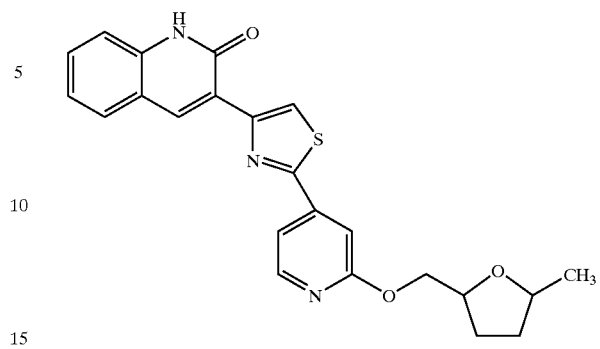

3-(2-{2-[(5-Methyloxolan-2-yl)methoxy]-4-pyridyl}-1,3-thiazol-4-yl)hydroquinolin-2-one Light yellow solid. MS m/z: 420 (M+1). HRMS m/z: 420.1367 (M+H$^+$, C$_{23}$H$_{21}$N$_3$O$_3$S Calc'd 420.1376).

EXAMPLE 90

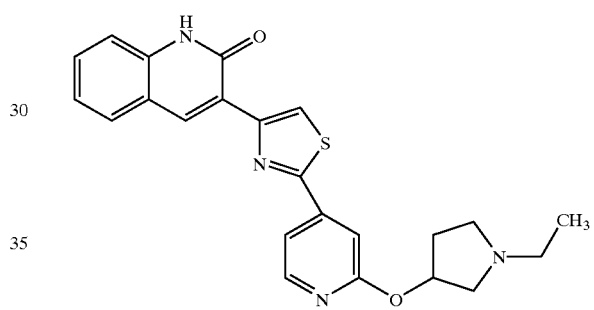

3-{2-[2-(1-Ethylpyrrolidin-3-yloxy)-4-pyridyl]-1,3-thiazol-4-yl}hydroquinolin-2-one Brown solid. MS m/z: 419 (M+1). HRMS m/z: 419.1532 (M+H$^+$, C$_{23}$H$_{22}$N$_4$O$_2$S Calc'd 419.1536).

EXAMPLE 91

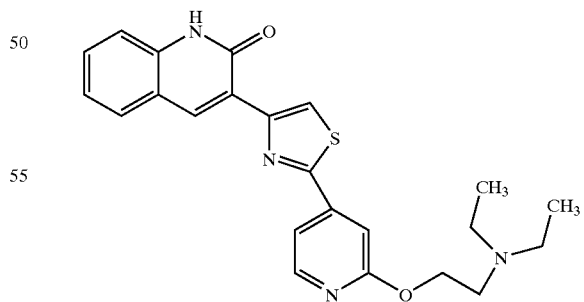

3-(2-{2-[2-(Diethylamino)ethoxy]-4-pyridyl}-1,3-thiazol-4-yl)hydroquinolin-2-one.

Light yellow solid. MS m/z: 421 (M+1). HRMS m/z: 421.1730 (M+H$^+$, C$_{23}$H$_{24}$N$_4$O$_2$S Calc'd 421.1693).

EXAMPLE 92

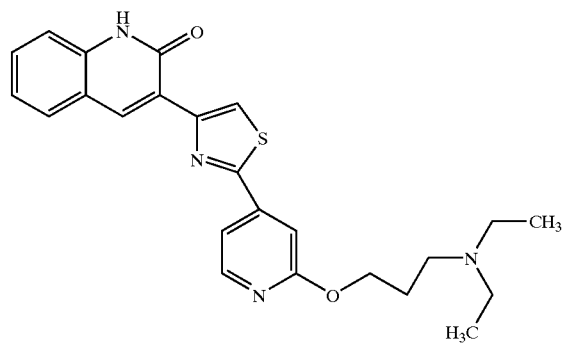

3-(2-{2-[3-(Diethylamino)propoxy]-4-pyridyl}-1,3-thiazol-4-yl)hydroquinolin-2-one Yellow solid. MS m/z: 435 (M+1). HRMS m/z: 435.1857 (M+H$^+$, C$_{24}$H$_{26}$N$_4$O$_2$S Calc'd 435.1849).

EXAMPLE 93

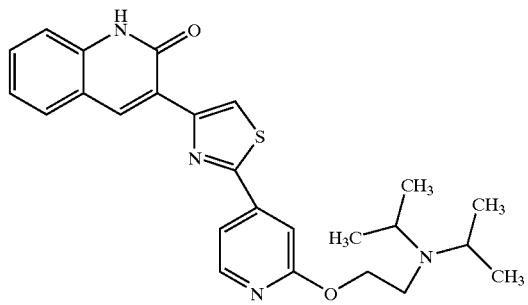

3-[2-(2-{2-[Bis(methylethyl)amino]ethoxy}-4-pyridyl)-1,3-thiazol-4-yl]hydroquinolin-2-one Light yellow solid. MS m/z: 449 (M+1). HRMS m/z: 449.2010 (M+H$^+$, C$_{25}$H$_{28}$N$_4$O$_2$S Calc'd 449.2006).

EXAMPLE 94

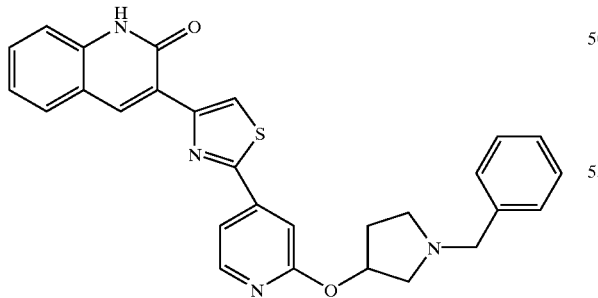

3-(2-{2-[1-Benzylpyrrolidin-3-yloxy]-4-pyridyl}-1,3-thiazol-4-yl)hydroquinolin-2-one Rust solid. MS m/z: 481 (M+1). HRMS m/z: 481.1690 (M+H$^+$, C$_{28}$H$_{24}$N$_4$O$_2$S Calc'd 481.1693).

EXAMPLE 95

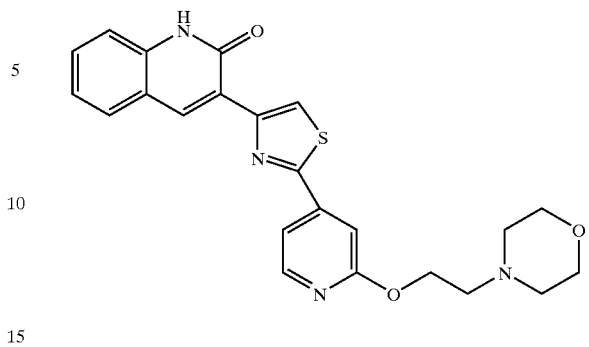

3-{2-[2-(2-Morpholin-4-ylethoxy)-4-pyridyl]-1,3-thiazol-4-yl}hydroquinolin-2-one Yellow solid. MS m/z: 435 (M+1). HRMS m/z: 435.1478 (M+H$^+$, C$_{23}$H$_{22}$N$_4$O$_3$S Calc'd 435.1485).

EXAMPLE 96

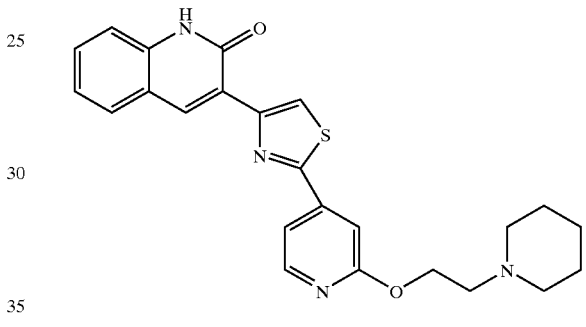

3-{2-[2-(2-Piperidylethoxy)-4-pyridyl]-1,3-thiazol-4-yl}hydroquinolin-2-one

Light yellow solid. MS m/z: 433 (M+1). HRMS m/z: 433.1710 (M+H$^+$, C$_{24}$H$_{24}$N$_4$O$_2$S Calc'd 433.1693).

EXAMPLE 97

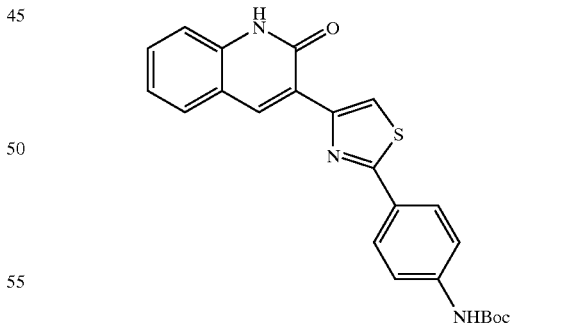

{4-[4-(2-Oxo-1,2-dihydro-quinolin-3-yl)-thiazol-2-yl]-phenyl}-carbamic acid tert-butyl ester A solution of 4-cyano-tert-butyloxycarbonylaniline (2.20 g, 10.0 mmol) in 20 mL of pyridine and 5 mL of TEA was purged with H$_2$S gas for 7.0 h. Solvents were removed under vacuum. The resulting crude 4-Boc-aminobenzene-thiocarboxamide (yellow residue, 70% purity) was used directly in the next step. A solution of 4-Bocaminobenzenethiocarboxamide (205 mg, 70% pure, 0.57 mmol) and 3-(2-bromoacetyl)hydroquinolin-2-one (Example 27b, 78 mg, 0.29 mmol) in 50 mL of MeOH was heated at reflux for 4 h. After cooling to RT, the precipitates were collected by filtration to provide the title compound as an off-white solid. MS m/z: 420.2 (M+1). HRMS m/z: 420.1358 (M+H$^+$, $C_{23}H_{21}N_3O_3S$ Calc'd 420.1376).

EXAMPLE 98

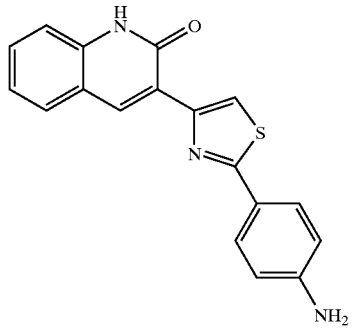

3-[2-(4-Amino-phenyl)-thiazol-4-yl]-1H-quinolin-2-one

A solution of {4-[4-(2-oxo-1,2-dihydro-quinolin-3-yl)-thiazol-2-yl]-phenyl}-carbamic acid tert-butyl ester (Example 97, 70 mg, 0.17 mmol) in 0.8 mL of $CH_2Cl_2$ and 0.8 mL of TFA was stirred at RT for 1 h. Solvents were removed under vacuum and the residue was azeotroped twice with toluene. To the flask, 4.0 mL of aqueous HCl (1 M) was added and solids formed. The solvent was removed again and the solid was azeotroped with toluene twice. The solid was dried under vacuum overnight to afford the title compound as a light yellow solid. MS m/z: 320.2 (M+1). Anal. Calc'd for $C_{18}H_{13}N_3OS \cdot 0.8H_2O \cdot 1.6HBr$: C, 55.13; H, 4.16; N, 10.72; O, 7.34; S, 8.18. Found: C, 55.24; H, 4.15; N, 10.66; O, 7.45; S, 8.21.

EXAMPLE 99

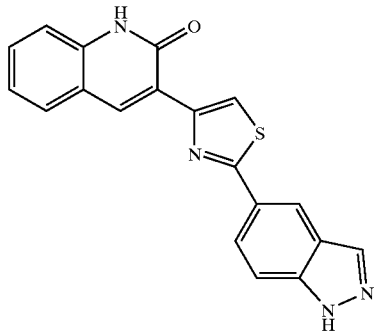

3-[2-(1H-Indazol-5-yl)-thiazol-4-yl]-1H-quinolin-2-one

A mixture of 1-acetyl-indazol-5-thiocarboxamide (60 mg, 0.27 mmol) and 3-(2-bromoacetyl)hydroquinolin-2-one (Example 27b, 87 mg, 0.32 mmol) in 15 mL of MeOH was heated at reflux for 5 h. After cooling down to RT, the precipitates were collected by filtration. The solid was heated at reflux in 35 mL of MeOH and 1 mL of aqueous HCl (1 M) and 1 mL of 1-methylpiperizine for 8 h. The precipitates were filtered and washed successively with MeOH, $CH_2Cl_2$ and hexanes to provide the title compound as an off-white solid. MS m/z: 345.1 (M+1). HRMS m/z: 345.0784 (M+H$^+$, $C_{19}H_{12}N_4OS$ Calc'd 345.0805).

EXAMPLE 100

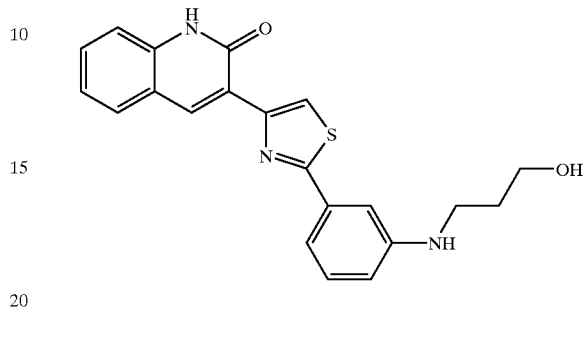

3-{2-[2-(3-Hydroxy-propylamino)-pyridin-4-yl]-thiazol-4-yl}-1H-quinolin-2-one

A mixture of 3-[2-(2-chloro-pyridin-4-yl)-thiazol-4-yl]-1H-quinolin-2-one (Example 85, 78 mg, 0.23 mmol) and 3-hydroxypropyl-1-amine (Aldrich, 3 mL) was heated at 128° C. for 48 h. The reaction was quenched by addition of 5 mL of $H_2O$. The precipitates were collected by filtration and purified by Gilson preparative HPLC to provide the title compound as a brown solid after lyophilization MS m/z: 379.4 (M+1). HRMS m/z: 379.1238 (M+H$^+$, $C_{20}H_{18}N_4O_2S$ Calc'd 379.1223).

EXAMPLE 101

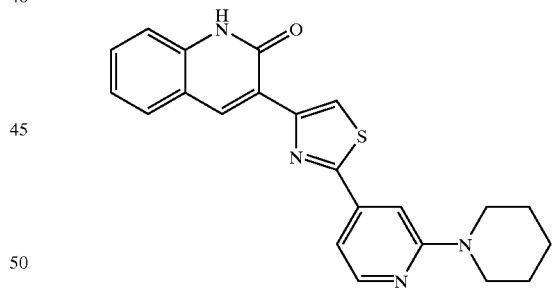

3-[2-(3,4,5,6-Tetrahydro-2H-[1,2']bipyridinyl-4'-yl)-thiazol-4-yl]-1H-quinolin-2-one A mixture of 3-[2-(2-chloro-pyridin-4-yl)-thiazol-4-yl]-1H-quinolin-2-one (Example 85, 60 mg, 0.18 mmol) and 1-(2-aminoethyl)piperidine (Aldrich-Sigma Company, 2 mL) was heated at 128° C. for 48 h. The reaction was quenched by addition of 10 mL of $H_2O$. The precipitates were collected by filtration and purified by Gilson preparative HPLC to provide the title compound as a yellow solid after lyophilization. MS m/z: 389.3 (M+1). HRMS m/z: 389.1398 (M+H$^+$, $C_{22}H_{20}N_4OS$ Calc'd 389.1431).

EXAMPLE 102

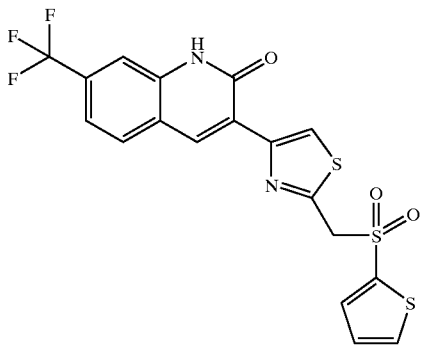

3-[2-(Thiophene-2-sulfonylmethyl)-thiazol-4-yl]-7-trifluoromethyl-1H-quinolin-2-one Step (a) 4-(α,α,α-Trifluoromethyl)-2-aminobenzyl alcohol A solution of 4-(α,α,α-trifluoromethyl)-2-nitrobenzoic acid (Aldrich, 30.0 g, 125 mmol) in 150 mL of anhydrous THF was treated slowly with 250 mL of $BH_3$ (1.0 M in THF, 250 mmol) over 30 min. Bubbles were generated. The resulting mixture was stirred at RT overnight. The reaction was carefully quenched with the addition of 100 mL of anhydrous MeOH and all the solvents were removed under vacuum. The residue was dissolved in 100 mL of MeOH and dried again. This was repeated two more times and the residue thus obtained was used directly in the next step.

The oily residue was dissolved in 200 mL of EtOH and 100 mL of $H_2O$. To this solution, 33.5 g $NH_4Cl$ and 14.0 g of Fe were added and the resulting mixture was heated at reflux for 4.5 h with vigorous stirring. The solids were filtered off through Celite and the filtrate was concentrated to minimal volume. EtOAc (300 mL) was added and the solution was washed with $H_2O$ (300 mL), then saturated aqueous $NaHCO_3$ (300 mL). The organic layer was dried ($Na_2SO_4$) and concentrated to afford the title compound as a yellow solid upon drying under vacuum. MS m/z: 174.3 (M+1).

Step (b) 5-(α,α,α-Trifluoromethyl)-2-hydroxymethyl acetoacetanilinamide

To a solution of 4-(α,α,α-trifluoromethyl)-2-aminobenzyl alcohol (7.0 g, 40 mmol) in 200 mL of anhydrous $CH_2Cl_2$ was added 0.1 g of DMAP, followed by slow addition of diketene (7.8 mL, 0.100 mmol) via a syringe. An exothermic reaction resulted. 30 min later, the reaction was quenched by the addition of saturated aqueous $NaHCO_3$ (200 mL). After stirring vigorously for 10 min, the layers were separated and the $CH_2Cl_2$ layer was dried ($Na_2SO_4$) and concentrated to give an oily residue, which was dissolved in THF:MeOH:$H_2O$ and treated with 80 mL NaOH (1 M) for 2.5 h. The reaction mixture was acidified with 1M HCl to pH 2. The solvents were removed under vacuum. The residue was taken into 300 mL of EtOAc and washed 200 mL of $H_2O$. The EtOAc layer was dried ($Na_2SO_4$) and concentrated to afford the title compound as a light yellow solid upon drying under vacuum (10.6 g, 95%). MS m/z: 276.2 (M+1).

Step (c) 7-(α,α,α-Trifluoromethyl)-3-acetyl-1H-quinolin-2-one

To a solution of 5-(α,α,α-trifluoromethyl)-2-hydroxymethyl acetoacetanilinamide (7.5 g, 27.0 mmol) in 150 mL of anhydrous $CH_2Cl_2$ was added N-methylmorpholine-N-oxide (Aldrich-Sigma Company, 3.95 g, 33.7 mmol), followed by TPAP (0.1 g). The reaction mixture became a dark solution. The reaction was stirred at RT for 3 d. White solids formed. Filtration and washing carefully with $CH_2Cl_2$ afforded the title compound as a white solid (4.1 g, 59%). MS m/z: 256.1 (M+1).

Step (d) 7-(α,α,α-Trifluoromethyl)-3-(2-bromoacetyl)-1H-quinolin-2-one

A mixture of 7-(α,α,α-trifluoromethyl)-3-acetylhydroquinolin-2-one (4.0 g, 15.7 mmol) and 5,5-dibromobarbituric acid (Aldrich-Sigma Company, 2.69 g, 9.4 mmol) in 175 mL of anhydrous THF was heated at reflux for 3 h. The reaction mixture cooled to RT and the precipitates were filtered to afford the title compound as an off-white solid. MS m/z: 333.9, 335.9 (M+1, equal intensity).

Step (e) 3-[2-(Thiophene-2-sulfonylmethyl)-thiazol-4-yl]-7-trifluoromethyl-1H-quinolin-2-one A mixture of 7-(α,α,α-trifluoromethyl)-3-(2-bromoacetyl)-1H-quinolin-2-one (180 mg, 0.54 mmol) and 2-(2-thienylsulfonyl)ethanethioamide (Maybridge, 110 mg, 0.50 mmol) in 30 mL of anhydrous MeOH was heated at reflux for 3 h. The reaction mixture was cooled to RT. The precipitates were filtered, washed with MeOH, 10% $Et_3N$ in MeOH, $CH_2Cl_2$ to afford the title compound as a white solid. MS m/z: 457.3 (M+1). HRMS m/z: 456.9980 (M+H+, $C_{18}H_{11}F_3N_2O_3S_3$ Calc'd 456.9957).

EXAMPLE 103

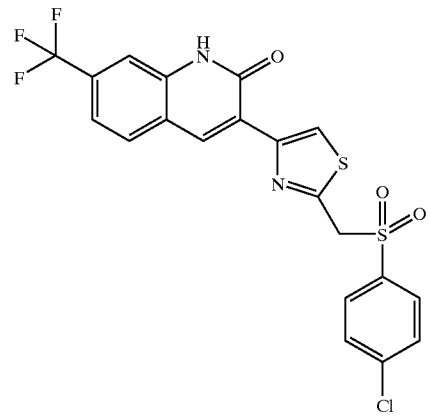

3-[2-(4-Chloro-benzenesulfonylmethyl)-thiazol-4-yl]-7-trifluoromethyl-1H-quinolin-2-one A mixture of 7-(α,α,α-trifluoromethyl)-3-(2-bromoacetyl)-1H-quinolin-2-one (Example 102d, 180 mg, 0.54 mmol) and 2-(4-chlorophenylsulfonyl)ethanethioamide (Maybridge, 126 mg, 0.50 mmol) in 35 mL of anhydrous MEOH was heated at reflux for 3 h. The reaction mixture was cooled to RT. The precipitates were filtered, washed with MeOH, 10% TEA in MeOH, $CH_2Cl_2$ to afford the title compound as a white solid. MS m/z: 485.3 (M+1). HRMS m/z: 485.0028 (M+H+, $C_{20}H_{12}ClF_3N_2O_3S_2$ Calc'd 485.0003).

EXAMPLE 104

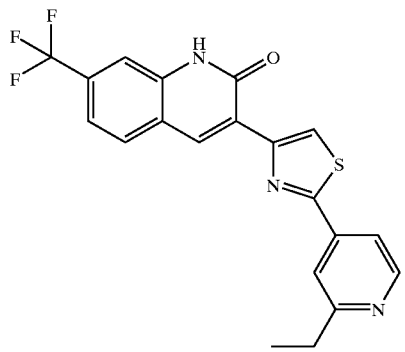

3-[2-(2-Ethyl-pyridin-4-yl)-thiazol-4-yl]-7-trifluoromethyl-1H-quinolin-2-one

A mixture of 7-(α,α,α-trifluoromethyl)-3-(2-bromoacetyl)-1H-quinolin-2-one (Example 102d, 180 mg, 0.54 mmol) and ethionamide (Aldrich, 84 mg, 0.50 mmol) in 35 mL of anhydrous MeOH was heated at reflux for 3 h. The reaction mixture was cooled to RT. The precipitates were filtered, washed with MeOH, 10% TEA in MeOH, CH$_2$Cl$_2$ to afford the title compound as a pink solid. MS m/z: 402.2 (M+1). HRMS m/z: 402.0903 (M+H$^+$, C$_{20}$H$_{14}$F$_3$N$_3$OS Calc'd 402.0882).

EXAMPLE 105

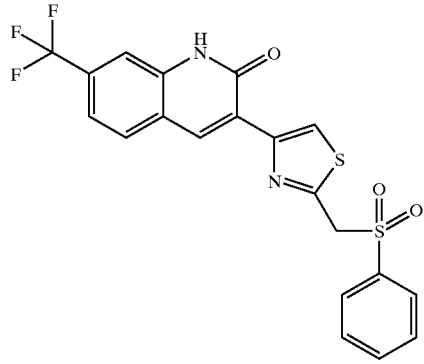

3-(2-Benzenesulfonylmethyl-thiazol-4-yl)-7-trifluoromethyl-1H-quinolin-2-one

A mixture of 3-[2-(4-chloro-benzenesulfonylmethyl)-thiazol-4-yl]-7-trifluoromethyl-1H-quinolin-2-one (Example 103, 67 mg, 0.14 mmol), 0.5 mL of IPEA, and 0.1 g of Pd-C (10%) in anhydrous DMF (10 mL) was stirred under H$_2$ overnight. The catalysts were filtered through Celite and the filtrate was concentrated. CH$_2$Cl$_2$ was added and precipitates were filtered, washed with MeOH, CH$_2$Cl$_2$ to afford the title compound as a tan solid. MS m/z: 451.2 (M+1).

EXAMPLE 106

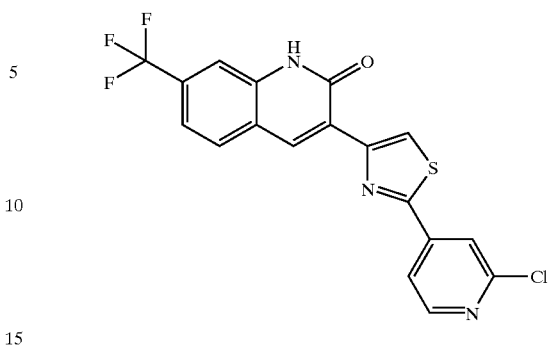

3-[2-(2-Chloro-pyridin-4-yl)-thiazol-4-yl]-7-trifluoromethyl-1H-quinolin-2-one

A solution of 2-chloropyridine-4-carbonitrile (Aldrich) (2.77 g, 20.0 mmol) in 20 mL of pyridine and 8.35 mL of TEA was purged with H$_2$S gas for 1.5 h. Solvents were removed under vacuum. The residue was dissolved in 35 mL of anhydrous MeOH and 7-(α,α,α-trifluoromethyl)-3-(2-bromoacetyl)-1H-quinolin-2-one (Example 102d, 370 mg, 1.1 mmol) was added. The solution was heated at reflux for 3 h. The reaction mixture was cooled to RT. The precipitates were filtered, washed with MeOH, 10% TEA in MeOH, CH$_2$Cl$_2$ to afford the title compound as an off-white solid. MS m/z: 408.1 (M+1).

EXAMPLE 107

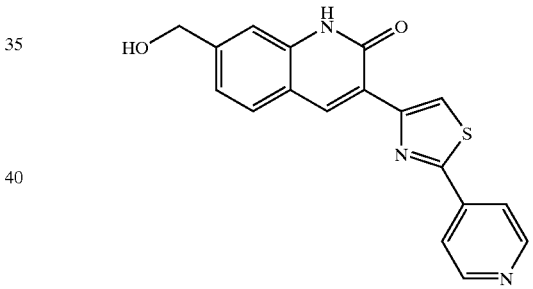

7-Hydroxymethyl-3-(2-pyridin-4-yl-thiazol-4-yl)-1H-quinolin-2-one

Step (a) 1-Methyl 4-tert-butyldimethylsilyloxymethyl-2-nitrobenzoate

A solution of 1-methyl-2-nitroterephthalate (Aldrich, 30.2 g, 134 mmol) in 250 mL of anhydrous THF was treated slowly with 155 mL of BH$_3$ (1.0 M in THF, 155 mmol) over 30 min at RT. Bubbles were generated. The resulting mixture was stirred at RT for 2 days. The reaction was carefully quenched with the addition of 30 mL of anhydrous MeOH and all the solvents were removed under vacuum. The residue was dissolved in 100 mL of MeOH and dried again. This was repeated two more times and the residue thus obtained were used directly in the next step. MS m/z: 212.2 (M+1).

The solid residue was dissolved in 300 mL of CH$_2$Cl$_2$ and 8.3 g of imidazole (150 mmol) was added, followed by addition of 22.3 g of TBS-Cl (Aldrich, 150 mmol). The reaction was stirred for 45 min at RT. 10 mL of anhydrous MeOH was added, followed by dilution with 200 mL of CH$_2$Cl$_2$. The mixture was washed with 400 mL each of H$_2$O and saturated aqueous NaHCO$_3$. The organic layer was dried (Na$_2$SO$_4$) and concentrated to afford the title compound as a light yellow solid upon drying under vacuum. MS m/z: 326.2 (M+1).

Step (b) 2-Amino-4-tert-butyldimethylsilyloxymethylbenzyl alcohol

To a solution of 1-methyl 4-tert-butyldimethylsiloxymethyl-2-nitrobenzoate (33.0 g, 101 mmol) in 350 mL of anhydrous CH$_2$Cl$_2$ was added slowly DIBAL-H (150 mL, 1.5 M in toluene, 225 mmol) over 40 min at −78° C. The reaction mixture was warmed up slowly during the course of 6 h. 20 mL of anhydrous MeOH was added carefully to quench the reaction, followed by 200 mL of saturated aqueous NaHCO$_3$. Gel-like materials formed. The mixture was carefully acidified with 0.3 N HCl until all gel-like materials were gone. The layers were separated, and the aqueous layer was extracted three times with 400 mL of CH$_2$Cl$_2$. The organic layers were combined and washed once with 500 mL of 0.3 N HCl, dried (Na$_2$SO$_4$), and concentrated to give an oily residue which was subjected to reduction without further purification.

The oily residue was dissolved in 500 mL of EtOH and 200 mL of H$_2$O. To this solution, 18.2 g of NH$_4$Cl (202 mmol) and 55.0 g of Fe (980 mmol) were added and the resulting mixture was heated at reflux for 18 h with vigorous stirring. The solids were filtered off through Celite and the filtrate was concentrated to minimal volume. 700 mL of EtOAc was added and the solution was washed with 500 mL of H$_2$O. The organic layer was dried (Na$_2$SO$_4$) and concentrated to afford the title compound as a light yellow solid upon drying under vacuum. MS m/z: 268.3 (M+1).

Step (a) N-[5-(tert-Butyl-dimethyl-silyloxymethyl)-2-hydroxymethyl-phenyl]-2-(2-pyridin-4-yl-thiazol-4-yl)-acetamide The compound was prepared according to the method described in Example 1c by employing (2-pyridin-4-yl-thiazol-4-yl)-acetic acid (Example 1b, 1.97 g, 8.95 mmol) and 2-amino-4-tert-butyldimethylsilyloxymethylbenzyl alcohol (Example 103b, 3.60 g, 13.4 mmol). The reaction was stirred at RT for 2.5 d. Solvents were removed under vacuum. The residue was partitioned between 200 mL of EtOAc and 200 mL of saturated aqueous NaHCO$_3$. The EtOAc layer was separated, dried (Na$_2$SO$_4$), and concentrated. Column chromatography with gradient elution (10%–100% EtOAc in hexanes) afforded the title compound as an oil (3.4 g, 81%). MS m/z: 470.4 (M+1).

Step (d) 7-Hydroxymethyl-3-(2-pyridin-4-yl-thiazol-4-yl)-1H-quinolin-2-one

To a suspension of 10 g of MnO$_2$ in 200 mL of CH$_2$Cl$_2$ was added N-[5-(tert-butyl-dimethyl-silyloxymethyl)-2-hydroxymethyl-phenyl]-2-(2-pyridin-4-yl-thiazol-4-yl)-acetamide (Example 99c, 3.3 g, 7.04 mmol). At three intervals of 1.5 h, an additional 10 g of MnO$_2$ was added each time. The solids were filtered off through Celite. The filtrate was concentrated to dryness and azeotroped twice with toluene to afford the intermediate aldehyde. MS m/z: 468.3 (M+1).

The crude material was dissolved in 150 mL of anhydrous THF and 16 mL of potassium t-butoxide (1.0 M in THF) was added dropwise via a syringe at −38° C. The mixture was warmed slowly to RT over 4 h, upon which time 16 mL of HCl (1.0 M) was added. The solvents were removed under vacuum and the residue was treated with additional 15 mL of HCl (1.0 M) in 150 mL of DMF and 50 mL of H$_2$O at 42° C. for 40 min. All solvents were removed and the solid was washed with 150 mL of H$_2$O. Filtration and washing with copious amount of H$_2$O provided the title compound as a yellow solid. MS m/z: 336.2 (M+1). Anal. Calc'd for C$_{18}$H$_{13}$N$_3$O$_2$S.HCl: C, 58.14; Cl, 9.53; H, 3.79; N, 11.30; O, 8.61; S, 8.62. Found: C, 57.90; Cl, 9.47; H, 3.87; N, 11.36; O, 8.83; S, 8.55.

EXAMPLE 108

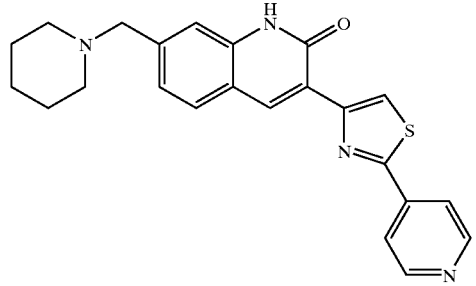

7-Piperidin-1-ylmethyl-3-(2-pyridin-4-yl-thiazol-4-yl)-1H-quinolin-2-one

To a solution of 7-hydroxymethyl-3-(2-pyridin-4-yl-thiazol-4-yl)-1H-quinolin-2-one (Example 103d, 115 mg, 034 mmol) in 30 mL of DMF and 10 mL of DMSO was added 1.1 g of MnO$_2$. The reaction mixture was stirred at RT for 48 h. The solids were filtered off through Celite. The filtrate was concentrated to dryness and 20 mL of anhydrous DMF was added to result in a homogeneous solution.

To 10 mL of the solution described above were added 0.3 mL of piperidine, 0.5 mL of HOAc, and 1.0 mL of trimethyl orthoformate. After stirring at RT for 15 min, 182 mg of NaBH(OAc)$_3$ was added. After 1 h, some gel-like materials formed, and 5 mL of anhydrous CH$_2$Cl$_2$ was added to bring about a homogeneous solution. The reaction was continued for 28 h. The mixture was concentrated to dryness and the residue was purified by Gilson preparative HPLC to afford the title compound as a yellow solid after lyophilization. MS m/z: 403.3 (M+1). HRMS m/z: 403.1581(M+H$^+$, C$_{23}$H$_{22}$N$_4$OS Calc'd 403.1587).

EXAMPLE 109

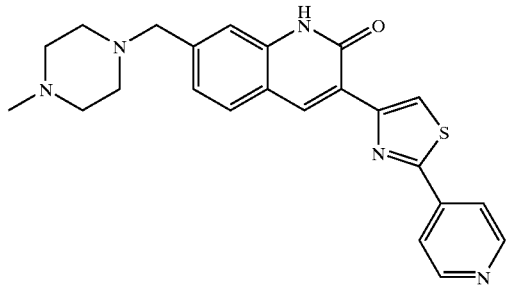

7-(4-Methyl-piperazin-1-ylmethyl)-3-(2-pyridin-4-yl-thiazol-4-yl)-1H-quinolin-2-one This compound was prepared according to the method described in Example 108 by employing 0.3 mL of 1-methylpiperizine. A yellow solid was isolated after lyophilization. MS m/z: 418.4 (M+1). HRMS m/z: 418.1723 (M+H$^+$, C$_{23}$H$_{23}$N$_5$OS Calc'd 418.1696).

EXAMPLE 110

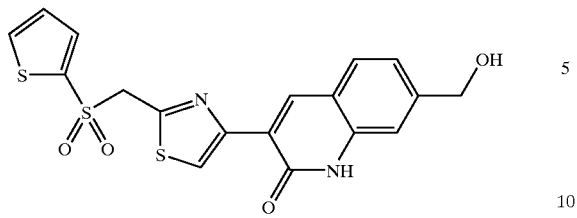

7-Hydroxymethyl-3-[2-(thiophene-2-sulfonylmethyl)-thiazol-4-yl]-1H-quinolin-2-one Step (a) 2-Hydroxymethyl-4-tert-butyldimethylsilyloxy-methylacetoacetanilinamide A solution of 2-amino-4-tert-butyldimethylsilyloxymethylbenzyl alcohol (Example 107b, 24.0 g, 89.8 mmol) and 0.25 g of DMAP in 300 mL of anhydrous $CH_2Cl_2$ was treated slowly with diketene (Aldrich, 17.3 mL, 225 mmol) over 20 min at RT. The reaction mixture was stirred for additional 30 min. After quenching with $H_2O$, the mixture was washed twice with 200 mL of saturated aqueous $NaHCO_3$. The organic layer was separated, dried ($Na_2SO_4$), and concentrated to provide an oily residue that was applied to the next step without further purification. MS m/z: 436.3.

The residue from above was dissolved in 300 mL of THF and 100 mL of MeOH. 200 mL of NaOH (1.0 M) was added and the reaction was stirred vigorously for 6 h at RT. The mixture was acidified with 55 mL of HCl (2.0 M) and concentrated carefully to half of its original volume. The solution was extracted twice with 200 mL of EtOAc. The combined EtOAc layers were dried ($Na_2SO_4$) and concentrated to provide the title compound as a yellow solid. MS m/z: 352.2 (M+1).

Step (b) 4-tert-Butyldimethylsilyloxymethyl-3-acetyl-1H-quinolin-2-one

A solution of 2-hydroxymethyl-4-tert-butyldimethylsiloxymethylacetoacetanilinamide (28.2 g, 80.2 mmol) in 400 mL of anhydrous $CH_2Cl_2$ was treated with 140 g of $MnO_2$ for 3 h with vigorous stirring. Another 70 g of $MnO_2$ was added. After 3 h, a second portion of 70 g of $MnO_2$ was added. The reaction was stirred at RT for 2.5 days. The solids were filtered off through Celite and the filtrate was concentrated to give an oil. This material was dissolved in EtOAc and hexane was added. The precipitate that formed was filtered to provide the title compound as an off-white solid. MS m/z: 322.2 (M+1).

Step (c) 4-tert-Butyldimethylsilyloxymethyl-3-(2-bromoacetyl)-1H-quinolin-2-one

This compound was prepared according to the method described in Example 102d by employing 4-tert-butyldimethylsilyloxymethyl)-3-acetylhydroquinolin-2-one (1.4 g, 4.23 mmol). The solvent was removed under vacuum and the solid was used directly in the next step as a crude compound with 85% purity. MS m/z: 412.2 (M+1).

Step (d) 7-Hydroxymethyl-3-[2-(thiophene-2-sulfonylmethyl)-thiazol-4-yl]-1H-quinolin-2-one This compound was prepared according to the method described in Example 102e by employing 4-tert-butyldimethylsilyloxymethyl-3-(2-bromoacetyl)-1H-quinolin-2-one (4.23 mmol) and 2-(2-thienylsulfonyl)ethanethiocarboxamide (Maybridge, 1.1 g, 4.98 mmol). The reaction mixture was heated at reflux for 5 h. The precipitates were filtered and washed with 5% DIPEA in MeOH, MeOH, and $CH_2Cl_2$ to afford the title compound as an off-white solid. MS m/z: 419.1 (M+1).

EXAMPLE 111

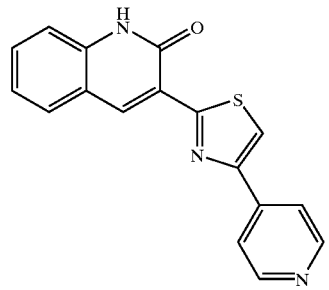

3-(4-Pyridin-4-yl-thiazol-2-yl)-1H-quinolin-2-one

Step (a) 2-Oxohydroquinoline-3-carbonitrile

To a solution of o-aminobenzaldehyde (Sigma) (5.80 g, 48 mmol) in 250 mL of EtOH was added ethyl cyanoacetate (Aldrich) (6.20 mL, 58 mmol) followed by piperidine (Aldrich) (1.4 mL, 14 mmol) at RT. The reaction was heated at 75° C. for 15 h then cooled to RT. The solid was filtered, washed with EtOH and dried in vacuo to give a pale yellow crystalline solid. MS m/z: 171 (M+1); 169 (M−1).

Step (b) 3-(Aminothioxomethyl)hydroquinolin-2-one

To a slurry of 2-oxohydroquinoline-3-carbonitrile (3.17 g, 19 mmol) and TEA (20 mL, 144 mmol) in 200 mL pyridine was bubbled $H_2S$ gas at RT. After 2.5 h the reaction flask was capped with a glass stopper and stirred overnight. $H_2S$ gas was bubbled into the reaction for an additional 6.5 h and the solvent removed in vacuo. The residue was heated in boiling MeOH for 15 min and filtered while hot. The solids were washed with MeOH and dried in vacuo to obtain a yellow amorphous solid. MS m/z: 205 (M+1); 203 (M−1).

Step (c) 3-(4-(4-Pyridyl)-1,3-thiazol-2-yl)hydroquinolin-2-one

To a slurry of 3-(aminothioxomethyl)hydroquinolin-2-one (97 mg, 0.48 mmol) in 5 mL of EtOH was added 4-(bromoacetyl)pyridine hydrobromide (Aust. J. Chem. 1989, 42, 1735; 133 mg, 0.47 mmol) and the reaction mixture was heated to reflux. After 1 h the solids were filtered, washed with EtOH, $H_2O$, and MeOH and dried in vacuo to give an amorphous orange solid. Mp: >300° C. MS m/z: 305 (M+1). Anal. Calc'd for $C_{17}H_{11}N_3OS \cdot 0.5\,HBr \cdot 1.75\,H_2O$: C, 54.11; H, 4.01; N, 11.14; Br, 10.59. Found: C, 53.88; H, 3.62; N, 11.29; Br, 10.72.

EXAMPLE 112

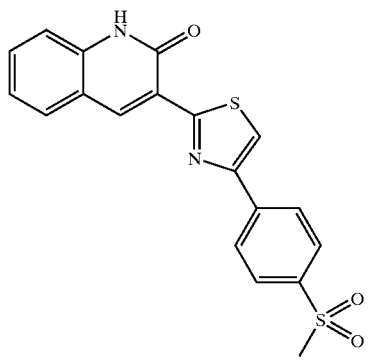

3-{4-[4-(Methylsulfonyl)phenyl]-1,3-thiazol-2-yl}hydroquinolin-2-one

To a slurry of 3-(aminothioxomethyl)hydroquinolin-2-one (Example 111b) (105 mg, 0.51 mmol) in 6 mL MeOH was added 2-bromo-1-[4-(methylsulfonyl)phenyl]-1-ethanone (Maybridge) (144 mg, 0.52 mmol) and the mixture was heated to reflux. After 6.5 h, the reaction was cooled to RT. The solids were filtered, washed with MeOH and dried in vacuo to yield a pale yellow amorphous solid. Mp: >300° C. MS m/z: 383 (M+1); 381 (M−1). Anal. Calc'd for $C_{19}H_{14}N_2O_3S_2 \cdot 0.25H_2O$: C, 58.97; H, 3.78; N, 7.24. Found: C, 59.17; H, 3.67; N, 7.36.

EXAMPLE 113

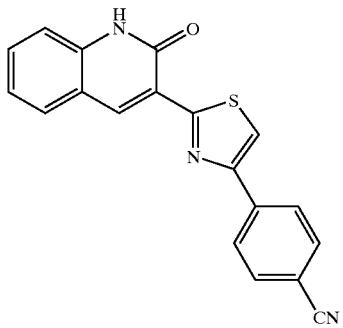

4-[2-(2-Oxo-3-hydroquinolyl)-1,3-thiazol-4-yl]benzenecarbonitrile

To a slurry of 3-(aminothioxomethyl)hydroquinolin-2-one (Example 111b) (134 mg, 0.66 mmol) in 20 mL EtOH was added 4-(2-bromoacetyl)benzonitrile (Maybridge) (158 mg, 0.71 mmol) and the reaction mixture was heated to 65° C. After 4 h, the solids were filtered while hot, washed with MeOH and dried in vacuo to yield a brown amorphous solid. Mp: >300° C. MS m/z: 330 (M+1); 328 (M−1). Anal. Calc'd for $C_{19}H_{11}N_3OS \cdot 0.1\ H_2O$: C, 68.90; H, 3.41; N, 12.69. Found: C, 68.70; H, 3.33; N, 12.67.

EXAMPLE 114

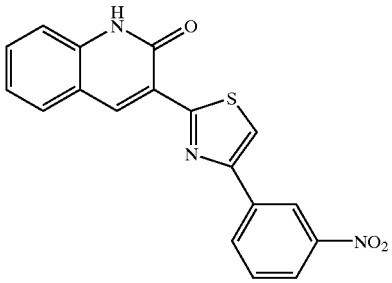

3-[4-(3-Nitrophenyl)-1,3-thiazol-2-yl]hydroquinolin-2-one

To a slurry of 3-(aminothioxomethyl)hydroquinolin-2-one (Example 111b) (158 mg, 0.77 mmol) in 20 mL EtOH was added 2-bromo-1-(3-nitrophenyl)ethan-1-one (Lancaster) (200 mg, 0.82 mmol) and the reaction mixture was heated to 65° C. After 11.5 h, the solids were filtered while hot, washed with EtOH and dried in vacuo to give a pale yellow amorphous solid. Mp: >300 ° C. MS m/z: 350 (M+1); 348 (M−1). Anal. Calc'd for $C_{18}H_{11}N_3O_3S$: C, 61.88; H, 3.17; N, 12.03. Found: C, 61.88; H, 3.15; N, 12.13.

EXAMPLE 115

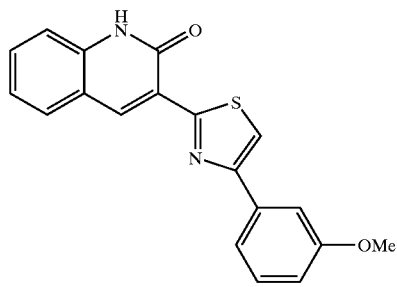

3-[4-(3-Methoxyphenyl)-1,3-thiazol-2-yl]hydroquinolin-2-one

To a slurry of 3-(aminothioxomethyl)hydroquinolin-2-one (151 mg, 0.74 mmol) in 20 mL EtOH was added 2-bromo-1-(3-methoxyphenyl)ethan-1-one (Aldrich) (186 mg, 0.81 mmol) and the reaction mixture was heated to 65° C. After 6.5 h, the solids were filtered while hot, washed with EtOH and dried in vacuo to yield an orange amorphous solid. Mp: 279–282° C. MS m/z: 335 (M+1); 333 (M−1). Anal. Calc'd for $C_{19}H_{14}N_2O_2S \cdot 0.25\ H_2O$: C, 67.34; H, 4.31; N, 8.27. Found: C, 67.10; H, 4.13; N, 8.28.

EXAMPLE 116

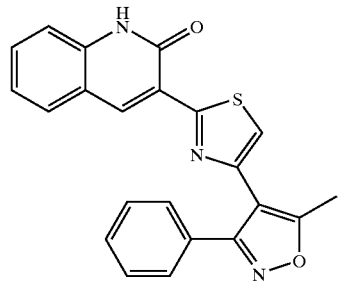

3-[4-(5-Methyl-3-phenylisoxazol-4-yl)-1,3-thiazol-2-yl]hydroquinolin-2-one

To a slurry of 3-(aminothioxomethyl)hydroquinolin-2-one (Example 111b) (101 mg, 0.50 mmol) in 20 mL EtOH was added 2-bromo-1-(5-methyl-3-phenylisoxazol-4-yl)ethan-1-one (Maybridge) (150 mg, 0.53 mmol) and the reaction mixture was heated to 65° C. After 6.5 h, the solids were filtered while hot, washed with EtOH and dried in vacuo to yield an orange crystalline solid. Mp: 242–244° C. MS m/z: 386 (M+1); 384 (M−1). Anal. Calc'd for $C_{22}H_{15}N_3O_2S$: C, 68.55; H, 3.92; N, 10.90. Found: C, 68.34; H, 3.89; N, 11.00.

EXAMPLE 117

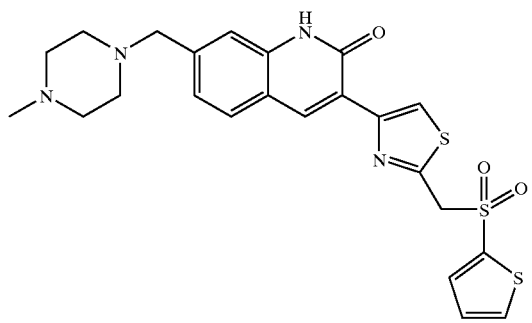

7-(4-Methyl-piperazin-1-ylmethyl)-3-[2-(thiophene-2-sulfonylmethyl)-thiazol-4-yl]-1H-quinolin-2-one To a solution of 7-hydroxymethyl-3-[2-(thiophene-2-sulfonylmethyl)-thiazol-4-yl]-1H-quinolin-2-one (Example 110d, 800 mg, 1.91 mmol) in 100 mL of DMF was added 5 g of $MnO_2$. The reaction mixture was stirred at RT for 72 h. The solids were filtered off through Celite®. The filtrate was concentrated to dryness and 20 mL of anhydrous $CH_2Cl_2$ was added. The precipitates were filtered to afford the intermediate aldehyde as a crude material. MS m/z: 417.2 (M+1).

A solution of the aldehyde (100 mg, 0.24 mmol), 0.1 mL of 1-methylpiperizine, 0.5 mL of HOAc, 1.0 mL of trimethyl orthoformate, and 254 mg of $NaBH(OAc)_3$ in 10 mL of anhydrous DMF and 5 mL of $CH_2Cl_2$ was stirred at RT for 18 h. The mixture was concentrated to dryness and the residue was purified by Gilson preparative HPLC to afford the title compound as a white fluffy solid after lyophilization. MS m/z: 501.2 (M+1).

EXAMPLE 118

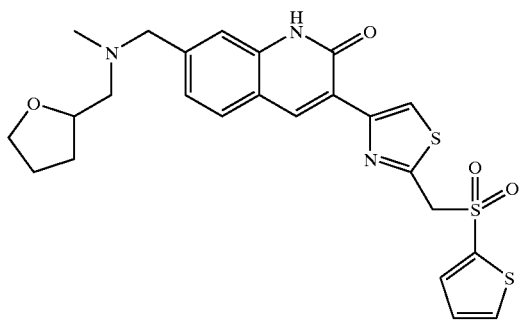

7-{[Methyl-(tetrahydro-furan-2-ylmethyl)-amino]-methyl}-3-[2-(thiophene-2-sulfonylmethyl)-thiazol-4-yl]-1H-quinolin-2-one The compound was prepared according to the method described in Example 117 employing N-methyl-tetrahydrofurylamine (Salor, 0.1 mL). The crude product was purified by Gilson preparative HPLC to afford the compound as a light yellow fluffy solid after lyophilization. MS m/z: 516.3 (M+1).

EXAMPLE 119

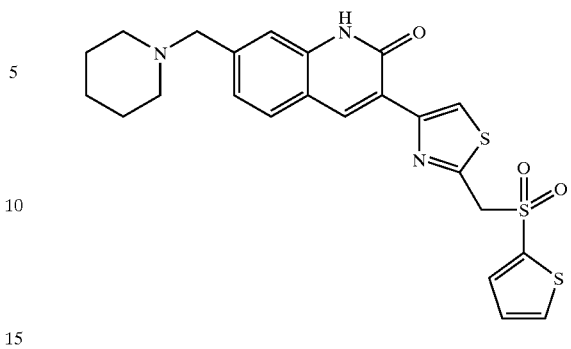

7-Piperidin-1-ylmethyl-3-[2-(thiophene-2-sulfonylmethyl)-thiazol-4-yl]-1H-quinolin-2-one This compound was prepared according to the method described in Example 117 by employing piperidine (Aldrich, 0.1 mL). The crude product was purified by Gilson preparative HPLC to afford the title compound as a yellow fluffy solid after lyophilization. MS m/z: 486.2 (M+1).

EXAMPLE 120

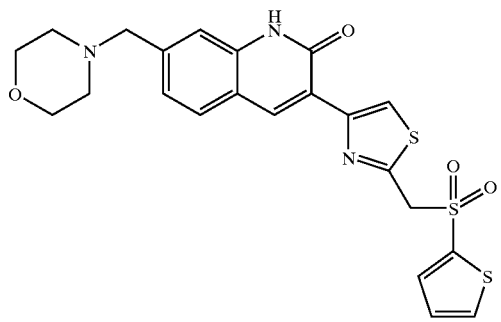

7-Morpholin-4-ylmethyl-3-[2-(thiophene-2-sulfonylmethyl)-thiazol-4-yl]-1H-quinolin-2-one This compound was prepared according to the method described in Example 117 by employing morpholine (Aldrich, 0.1 mL). The crude product was purified by Gilson preparative HPLC to afford the title compound as a yellow fluffy solid after lyophilization. MS m/z: 488.2 (M+1).

The following compounds were prepared by a method similar to that described for Example 117:

a) 3-(2-benzenesulfonylmethyl-thiazol-4-yl)-2-oxo-1,2-dihydro-quinoline-7-carboxylic acid methyl ester;
b) 3-(2-benzenesulfonylmethyl-thiazol-4-yl)-2-oxo-1,2-dihydro-quinoline-7-carboxylic acid; and
c) 7-trifluoromethyl-3-[2-(pyrid-2-ylsulfonylmethyl)-thiazol-4-yl]-1H-quinolin-2-one.

Other compounds included in this invention are set forth in Tables 1–12 below.

TABLE 1

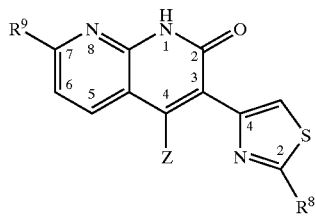

| # | R⁸ | R⁹ | Z |
|---|---|---|---|
| 121. | 4-pyridyl | Cl | H |
| 122. | 4-pyridyl | cyclopropylmethylamino | H |
| 123. | 4-pyridyl | 3-hydroxypropylamino | H |
| 124. | 4-pyridyl | 2-(1-piperidinyl)ethylamino | H |
| 125. | 4-pyridyl | 2-(1-pyrrolidinyl)ethylamino | H |
| 126. | 4-pyridyl | 2-(4-morpholinyl)ethylamino | H |
| 127. | 4-pyridyl | 3-(1-piperidinyl)propylamino | H |
| 128. | 4-pyridyl | 3-(1-pyrrolidinyl)propylamino | H |
| 129. | 4-pyridyl | 3-(4-morpholinyl)propylamino | H |
| 130. | 4-pyridyl | N-methyl-N-(2-piperid-1-ylethyl)amino | H |
| 131. | 4-pyridyl | N-methyl-N-(2-pyrrolidin-1-ylethyl)amino | H |
| 132. | 4-pyridyl | N-methyl-N-(2-morpholin-4-ylethyl)amino | H |
| 133. | 4-pyridyl | ((2S)-2-amino-3-phenylpropyl)amino | H |
| 134. | 4-pyridyl | 4-methylpiperazinylamino | H |
| 135. | 4-pyridyl | 4-methylpiperazinyl | H |
| 136. | 4-pyridyl | 3-aminopyrrolidinyl | H |
| 137. | 4-pyridyl | (diethylamino)ethylamino | H |
| 138. | 4-pyridyl | 3,5-dimethylpiperazin-1-yl | H |
| 139. | 4-pyridyl | (4-piperidylmethyl)amino | H |
| 140. | 4-pyridyl | (2-methylbutyl)amino | H |
| 141. | 4-pyridyl | 2-(dimethylamino)ethoxy | H |
| 142. | 4-pyridyl | 2-(methylamino)ethoxy | H |
| 143. | 4-pyridyl | ((2R)pyrrolidin-2-yl)methoxy | H |
| 144. | 4-pyridyl | ((2R)-1-methylpyrrolidin-2-yl)methoxy | H |
| 145. | 4-pyridyl | 2-(piperid-1-yl)ethoxy | H |
| 146. | 4-pyridyl | 2-(piperazin-1-yl)ethoxy | H |
| 147. | 4-pyridyl | 2-(morpholin-4-yl)ethoxy | H |
| 148. | 4-pyridyl | Cl | NH₂ |
| 149. | 4-pyridyl | cyclopropylmethylamino | NH₂ |
| 150. | 4-pyridyl | 3-hydroxypropylamino | NH₂ |
| 151. | 4-pyridyl | 2-(1-piperidinyl)ethylamino | NH₂ |
| 152. | 4-pyridyl | 2-(1-pyrrolidinyl)ethylamino | NH₂ |
| 153. | 4-pyridyl | 2-(4-morpholinyl)ethylamino | NH₂ |
| 154. | 4-pyridyl | 3-(1-piperidinyl)propylamino | NH₂ |
| 155. | 4-pyridyl | 3-(1-pyrrolidinyl)propylamino | NH₂ |
| 156. | 4-pyridyl | 3-(4-morpholinyl)propylamino | NH₂ |
| 157. | 4-pyridyl | N-methyl-N-(2-piperid-1-ylethyl)amino | NH₂ |
| 158. | 4-pyridyl | N-methyl-N-(2-pyrrolidin-1-ylethyl)amino | NH₂ |
| 159. | 4-pyridyl | N-methyl-N-(2-morpholin-4-ylethyl)amino | NH₂ |
| 160. | 4-pyridyl | ((2S)-2-amino-3-phenylpropyl)amino | NH₂ |
| 161. | 4-pyridyl | 4-methylpiperazinylamino | NH₂ |
| 162. | 4-pyridyl | 4-methylpiperazinyl | NH₂ |
| 163. | 4-pyridyl | 3-aminopyrrolidinyl | NH₂ |
| 164. | 4-pyridyl | (diethylamino)ethylamino | NH₂ |
| 165. | 4-pyridyl | 3,5-dimethylpiperazin-1-yl | NH₂ |
| 166. | 4-pyridyl | (4-piperidylmethyl)amino | NH₂ |
| 167. | 4-pyridyl | (2-methylbutyl)amino | NH₂ |
| 168. | 4-pyridyl | 2-(dimethylamino)ethoxy | NH₂ |
| 169. | 4-pyridyl | 2-(methylamino)ethoxy | NH₂ |
| 170. | 4-pyridyl | ((2R)pyrrolidin-2-yl)methoxy | NH₂ |
| 171. | 4-pyridyl | ((2R)-1-methylpyrrolidin-2-yl)methoxy | NH₂ |
| 172. | 4-pyridyl | 2-(piperid-1-yl)ethoxy | NH₂ |
| 173. | 4-pyridyl | 2-(piperazin-1-yl)ethoxy | NH₂ |
| 174. | 4-pyridyl | 2-(morpholin-4-yl)ethoxy | NH₂ |
| 175. | —(CH₂SO₂)-phenyl | Cl | H |
| 176. | —(CH₂SO₂)-phenyl | cyclopropylmethylamino | H |
| 177. | —(CH₂SO₂)-phenyl | 3-hydroxypropylamino | H |
| 178. | —(CH₂SO₂)-phenyl | 2-(1-piperidinyl)ethylamino | H |
| 179. | —(CH₂SO₂)-phenyl | 2-(1-pyrrolidinyl)ethylamino | H |
| 180. | —(CH₂SO₂)-phenyl | 2-(4-morpholinyl)ethylamino | H |
| 181. | —(CH₂SO₂)-phenyl | 3-(1-piperidinyl)propylamino | H |
| 182. | —(CH₂SO₂)-phenyl | 3-(1-pyrrolidinyl)propylamino | H |
| 183. | —(CH₂SO₂)-phenyl | 3-(4-morpholinyl)propylamino | H |
| 184. | —(CH₂SO₂)-phenyl | N-methyl-N-(2-piperid-1-ylethyl)amino | H |
| 185. | —(CH₂SO₂)-phenyl | N-methyl-N-(2-pyrrolidin-1-ylethyl)amino | H |

TABLE 1-continued

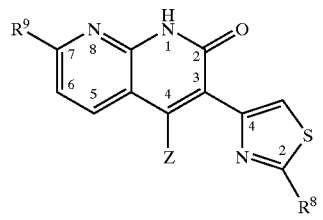

| # | R⁸ | R⁹ | Z |
|---|---|---|---|
| 186. | —(CH₂SO₂)-phenyl | N-methyl-2-N-(2-morpholin-4-ylethyl)amino | H |
| 187. | —(CH₂SO₂)-phenyl | ((2S)-2-amino-3-phenylpropyl)amino | H |
| 188. | —(CH₂SO₂)-phenyl | 4-methylpiperazinylamino | H |
| 189. | —(CH₂SO₂)-phenyl | 4-methylpiperazinyl | H |
| 190. | —(CH₂SO₂)-phenyl | 3-aminopyrrolidinyl | H |
| 191. | —(CH₂SO₂)-phenyl | (diethylamino)ethylamino | H |
| 192. | —(CH₂SO₂)-phenyl | 3,5-dimethylpiperazin-1-yl | H |
| 193. | —(CH₂SO₂)-phenyl | (4-piperidylmethyl)amino | H |
| 194. | —(CH₂SO₂)-phenyl | (2-methylbutyl)amino | H |
| 195. | —(CH₂SO₂)-phenyl | 2-(dimethylamino)ethoxy | H |
| 196. | —(CH₂SO₂)-phenyl | 2-(methylamino)ethoxy | H |
| 197. | —(CH₂SO₂)-phenyl | ((2R)pyrrolidin-2-yl)methoxy | H |
| 198. | —(CH₂SO₂)-phenyl | ((2R)-1-methylpyrrolidin-2-yl)methoxy | H |
| 199. | —(CH₂SO₂)-phenyl | 2-(piperid-1-yl)ethoxy | H |
| 200. | —(CH₂SO₂)-phenyl | 2-(piperazin-1-yl)ethoxy | H |
| 201. | —(CH₂SO₂)-phenyl | 2-(morpholin-4-yl)ethoxy | H |
| 202. | —(CH₂SO₂)-phenyl | Cl | NH₂ |
| 203. | —(CH₂SO₂)-phenyl | cyclopropylmethylamino | NH₂ |
| 204. | —(CH₂SO₂)-phenyl | 3-hydroxypropylamino | NH₂ |
| 205. | —(CH₂SO₂)-phenyl | 2-(1-piperidinyl)ethylamino | NH₂ |
| 206. | —(CH₂SO₂)-phenyl | 2-(1-pyrrolidinyl)ethylamino | NH₂ |
| 207. | —(CH₂SO₂)-phenyl | 2-(4-morpholinyl)ethylamino | NH₂ |
| 208. | —(CH₂SO₂)-phenyl | 3-(1-piperidinyl)propylamino | NH₂ |
| 209. | —(CH₂SO₂)-phenyl | 3-(1-pyrrolidinyl)propylamino | NH₂ |
| 210. | —(CH₂SO₂)-phenyl | 3-(4-morpholinyl)propylamino | NH₂ |
| 211. | —(CH₂SO₂)-phenyl | N-methyl-N-(2-piperid-1-ylethyl)amino | NH₂ |
| 212. | —(CH₂SO₂)-phenyl | N-methyl-N-(2-pyrrolidin-1-ylethyl)amino | NH₂ |
| 213. | —(CH₂SO₂)-phenyl | N-methyl-N-(2-morpholin-4-ylethyl)amino | NH₂ |
| 214. | —(CH₂SO₂)-phenyl | ((2S)-2-amino-3-phenylpropyl)amino | NH₂ |
| 215. | —(CH₂SO₂)-phenyl | 4-methylpiperazinylamino | NH₂ |
| 216. | —(CH₂SO₂)-phenyl | 4-methylpiperazinyl | NH₂ |
| 217. | —(CH₂SO₂)-phenyl | 3-aminopyrrolidinyl | NH₂ |
| 218. | —(CH₂SO₂)-phenyl | (diethylamino)ethylamino | NH₂ |
| 219. | —(CH₂SO₂)-phenyl | 3,5-dimethylpiperazin-1-yl | NH₂ |
| 220. | —(CH₂SO₂)-phenyl | (4-piperidylmethyl)amino | NH₂ |
| 221. | —(CH₂SO₂)-phenyl | (2-methylbutyl)amino | NH₂ |
| 222. | —(CH₂SO₂)-phenyl | 2-(dimethylamino)ethoxy | NH₂ |
| 223. | —(CH₂SO₂)-phenyl | 2-(methylamino)ethoxy | NH₂ |
| 224. | —(CH₂SO₂)-phenyl | ((2R)pyrrolidin-2-yl)methoxy | NH₂ |
| 225. | —(CH₂SO₂)-phenyl | ((2R)-1-methylpyrrolidin-2-yl)methoxy | NH₂ |
| 226. | —(CH₂SO₂)-phenyl | 2-(piperid-1-yl)ethoxy | NH₂ |
| 227. | —(CH₂SO₂)-phenyl | 2-(piperazin-1-yl)ethoxy | NH₂ |
| 228. | —(CH₂SO₂)-phenyl | 2-(morpholin-4-yl)ethoxy | NH₂ |
| 229. | —(CH₂SO₂)-2-thienyl | Cl | H |
| 230. | —(CH₂SO₂)-2-thienyl | cyclopropylmethylamino | H |
| 231. | —(CH₂SO₂)-2-thienyl | 3-hydroxypropylamino | H |
| 232. | —(CH₂SO₂)-2-thienyl | 2-(1-piperidinyl)ethylamino | H |
| 233. | —(CH₂SO₂)-2-thienyl | 2-(1-pyrrolidinyl)ethylamino | H |
| 234. | —(CH₂SO₂)-2-thienyl | 2-(4-morpholinyl)ethylamino | H |
| 235. | —(CH₂SO₂)-2-thienyl | 3-(1-piperidinyl)propylamino | H |
| 236. | —(CH₂SO₂)-2-thienyl | 3-(1-pyrrolidinyl)propylamino | H |
| 237. | —(CH₂SO₂)-2-thienyl | 3-(4-morpholinyl)propylamino | H |
| 238. | —(CH₂SO₂)-2-thienyl | N-methyl-N-(2-piperid-1-ylethyl)amino | H |
| 239. | —(CH₂SO₂)-2-thienyl | N-methyl-N-(2-pyrrolidin-1-ylethyl)amino | H |
| 240. | —(CH₂SO₂)-2-thienyl | N-methyl-N-(2-morpholin-4-ylethyl)amino | H |
| 241. | —(CH₂SO₂)-2-thienyl | ((2S)-2-amino-3-phenylpropyl)amino | H |
| 242. | —(CH₂SO₂)-2-thienyl | 4-methylpiperazinylamino | H |
| 243. | —(CH₂SO₂)-2-thienyl | 4-methylpiperazinyl | H |
| 244. | —(CH₂SO₂)-2-thienyl | 3-aminopyrrolidinyl | H |
| 245. | —(CH₂SO₂)-2-thienyl | (diethylamino)ethylamino | H |
| 246. | —(CH₂SO₂)-2-thienyl | 3,5-dimethylpiperazin-1-yl | H |
| 247. | —(CH₂SO₂)-2-thienyl | (4-piperidylmethyl)amino | H |
| 248. | —(CH₂SO₂)-2-thienyl | (2-methylbutyl)amino | H |
| 249. | —(CH₂SO₂)-2-thienyl | 2-(dimethylamino)ethoxy | H |
| 250. | —(CH₂SO₂)-2-thienyl | 2-(methylamino)ethoxy | H |

TABLE 1-continued

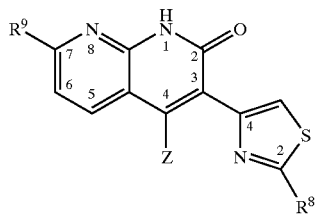

| # | R⁸ | R⁹ | Z |
|---|---|---|---|
| 251. | —(CH₂SO₂)-2-thienyl | ((2R)pyrrolidin-2-yl)methoxy | H |
| 252. | —(CH₂SO₂)-2-thienyl | ((2R)-1-methylpyrrolidin-2-yl)methoxy | H |
| 253. | —(CH₂SO₂)-2-thienyl | 2-(piperid-1-yl)ethoxy | H |
| 254. | —(CH₂SO₂)-2-thienyl | 2-(piperazin-1-yl)ethoxy | H |
| 255. | —(CH₂SO₂)-2-thienyl | 2-(morpholin-4-yl)ethoxy | H |
| 256. | —(CH₂SO₂)-2-thienyl | Cl | NH₂ |
| 257. | —(CH₂SO₂)-2-thienyl | cyclopropylmethylamino | NH₂ |
| 258. | —(CH₂SO₂)-2-thienyl | 3-hydroxypropylamino | NH₂ |
| 259. | —(CH₂SO₂)-2-thienyl | 2-(1-piperidinyl)ethylamino | NH₂ |
| 260. | —(CH₂SO₂)-2-thienyl | 2-(1-pyrrolidinyl)ethylamino | NH₂ |
| 261. | —(CH₂SO₂)-2-thienyl | 2-(4-morpholinyl)ethylamino | NH₂ |
| 262. | —(CH₂SO₂)-2-thienyl | 3-(1-piperidinyl)propylamino | NH₂ |
| 263. | —(CH₂SO₂)-2-thienyl | 3-(1-pyrrolidinyl)propylamino | NH₂ |
| 264. | —(CH₂SO₂)-2-thienyl | 3-(4-morpholinyl)propylamino | NH₂ |
| 265. | —(CH₂SO₂)-2-thienyl | N-methyl-N-(2-piperid-1-ylethyl)amino | NH₂ |
| 266. | —(CH₂SO₂)-2-thienyl | N-methyl-N-(2-pyrrolidin-1-ylethyl)amino | NH₂ |
| 267. | —(CH₂SO₂)-2-thienyl | N-methyl-N-(2-morpholin-4-ylethyl)amino | NH₂ |
| 268. | —(CH₂SO₂)-2-thienyl | ((2S)-2-amino-3-phenylpropyl)amino | NH₂ |
| 269. | —(CH₂SO₂)-2-thienyl | 4-methylpiperazinylamino | NH₂ |
| 270. | —(CH₂SO₂)-2-thienyl | 4-methylpiperazinyl | NH₂ |
| 271. | —(CH₂SO₂)-2-thienyl | 3-aminopyrrolidinyl | NH₂ |
| 272. | —(CH₂SO₂)-2-thienyl | (diethylamino)ethylamino | NH₂ |
| 273. | —(CH₂SO₂)-2-thienyl | 3,5-dimethylpiperazin-1-yl | NH₂ |
| 274. | —(CH₂SO₂)-2-thienyl | (4-piperidylmethyl)amino | NH₂ |
| 275. | —(CH₂SO₂)-2-thienyl | (2-methylbutyl)amino | NH₂ |
| 276. | —(CH₂SO₂)-2-thienyl | 2-(dimethylamino)ethoxy | NH₂ |
| 277. | —(CH₂SO₂)-2-thienyl | 2-(methylamino)ethoxy | NH₂ |
| 278. | —(CH₂SO₂)-2-thienyl | ((2R)pyrrolidin-2-yl)methoxy | NH₂ |
| 279. | —(CH₂SO₂)-2-thienyl | ((2R)-1-methylpyrrolidin-2-yl)methoxy | NH₂ |
| 280. | —(CH₂SO₂)-2-thienyl | 2-(piperid-1-yl)ethoxy | NH₂ |
| 281. | —(CH₂SO₂)-2-thienyl | 2-(piperazin-1-yl)ethoxy | NH₂ |
| 282. | —(CH₂SO₂)-2-thienyl | 2-(morpholin-4-yl)ethoxy | NH₂ |
| 283. | —(CH₂SO₂)-2-pyridyl | Cl | H |
| 284. | —(CH₂SO₂)-2-pyridyl | cyclopropylmethylamino | H |
| 285. | —(CH₂SO₂)-2-pyridyl | 3-hydroxypropylamino | H |
| 286. | —(CH₂SO₂)-2-pyridyl | 2-(1-piperidinyl)ethylamino | H |
| 287. | —(CH₂SO₂)-2-pyridyl | 2-(1-pyrrolidinyl)ethylamino | H |
| 288. | —(CH₂SO₂)-2-pyridyl | 2-(4-morpholinyl)ethylamino | H |
| 289. | —(CH₂SO₂)-2-pyridyl | 3-(1-piperidinyl)propylamino | H |
| 290. | —(CH₂SO₂)-2-pyridyl | 3-(1-pyrrolidinyl)propylamino | H |
| 291. | —(CH₂SO₂)-2-pyridyl | 3-(4-morpholinyl)propylamino | H |
| 292. | —(CH₂SO₂)-2-pyridyl | N-methyl-N-(2-piperid-1-ylethyl)amino | H |
| 293. | —(CH₂SO₂)-2-pyridyl | N-methyl-N-(2-pyrrolidin-1-ylethyl)amino | H |
| 294. | —(CH₂SO₂)-2-pyridyl | N-methyl-N-(2-morpholin-4-ylethyl)amino | H |
| 295. | —(CH₂SO₂)-2-pyridyl | ((2S)-2-amino-3-phenylpropyl)amino | H |
| 296. | —(CH₂SO₂)-2-pyridyl | 4-methylpiperazinylamino | H |
| 297. | —(CH₂SO₂)-2-pyridyl | 4-methylpiperazinyl | H |
| 298. | —(CH₂SO₂)-2-pyridyl | 3-aminopyrrolidinyl | H |
| 299. | —(CH₂SO₂)-2-pyridyl | (diethylamino)ethylamino | H |
| 300. | —(CH₂SO₂)-2-pyridyl | 3,5-dimethylpiperazin-1-yl | H |
| 301. | —(CH₂SO₂)-2-pyridyl | (4-piperidylmethyl)amino | H |
| 302. | —(CH₂SO₂)-2-pyridyl | (2-methylbutyl)amino | H |
| 303. | —(CH₂SO₂)-2-pyridyl | 2-(dimethylamino)ethoxy | H |
| 304. | —(CH₂SO₂)-2-pyridyl | 2-(methylamino)ethoxy | H |
| 305. | —(CH₂SO₂)-2-pyridyl | ((2R)pyrrolidin-2-yl)methoxy | H |
| 306. | —(CH₂SO₂)-2-pyridyl | ((2R)-1-methylpyrrolidin-2-yl)methoxy | H |
| 307. | —(CH₂SO₂)-2-pyridyl | 2-(piperid-1-yl)ethoxy | H |
| 308. | —(CH₂SO₂)-2-pyridyl | 2-(piperazin-1-yl)ethoxy | H |
| 309. | —(CH₂SO₂)-2-pyridyl | 2-(morpholin-4-yl)ethoxy | H |
| 310. | —(CH₂SO₂)-2-pyridyl | Cl | NH₂ |
| 311. | —(CH₂SO₂)-2-pyridyl | cyclopropylmethylamino | NH₂ |
| 312. | —(CH₂SO₂)-2-pyridyl | 3-hydroxypropylamino | NH₂ |
| 313. | —(CH₂SO₂)-2-pyridyl | 2-(1-piperidinyl)ethylamino | NH₂ |
| 314. | —(CH₂SO₂)-2-pyridyl | 2-(1-pyrrolidinyl)ethylamino | NH₂ |
| 315. | —(CH₂SO₂)-2-pyridyl | 2-(4-morpholinyl)ethylamino | NH₂ |

TABLE 1-continued

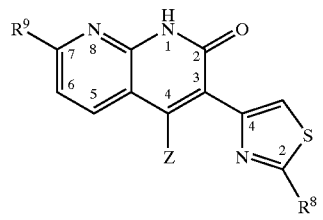

| # | R⁸ | R⁹ | Z |
|---|---|---|---|
| 316. | —(CH₂SO₂)-2-pyridyl | 3-(1-piperidinyl)propylamino | NH₂ |
| 317. | —(CH₂SO₂)-2-pyridyl | 3-(1-pyrrolidinyl)propylamino | NH₂ |
| 318. | —(CH₂SO₂)-2-pyridyl | 3-(4-morpholinyl)propylamino | NH₂ |
| 319. | —(CH₂SO₂)-2-pyridyl | N-methyl-N-(2-piperid-1-ylethyl)amino | NH₂ |
| 320. | —(CH₂SO₂)-2-pyridyl | N-methyl-N-(2-pyrrolidin-1-ylethyl)amino | NH₂ |
| 321. | —(CH₂SO₂)-2-pyridyl | N-methyl-N-(2-morpholin-4-ylethyl)amino | NH₂ |
| 322. | —(CH₂SO₂)-2-pyridyl | ((2S)-2-amino-3-phenylpropyl)amino | NH₂ |
| 323. | —(CH₂SO₂)-2-pyridyl | 4-methylpiperazinylamino | NH₂ |
| 324. | —(CH₂SO₂)-2-pyridyl | 4-methylpiperazinyl | NH₂ |
| 325. | —(CH₂SO₂)-2-pyridyl | 3-aminopyrrolidinyl | NH₂ |
| 326. | —(CH₂SO₂)-2-pyridyl | (diethylamino)ethylamino | NH₂ |
| 327. | —(CH₂SO₂)-2-pyridyl | 3,5-dimethylpiperazin-1-yl | NH₂ |
| 328. | —(CH₂SO₂)-2-pyridyl | (4-piperidylmethyl)amino | NH₂ |
| 329. | —(CH₂SO₂)-2-pyridyl | (2-methylbutyl)amino | NH₂ |
| 330. | —(CH₂SO₂)-2-pyridyl | 2-(dimethylamino)ethoxy | NH₂ |
| 331. | —(CH₂SO₂)-2-pyridyl | 2-(methylamino)ethoxy | NH₂ |
| 332. | —(CH₂SO₂)-2-pyridyl | ((2R)pyrrolidin-2-yl)ethoxy | NH₂ |
| 333. | —(CH₂SO₂)-2-pyridyl | ((2R)-1-methylpyrrolidin-2-yl)methoxy | NH₂ |
| 334. | —(CH₂SO₂)-2-pyridyl | 2-(piperid-1-yl)ethoxy | NH₂ |
| 335. | —(CH₂SO₂)-2-pyridyl | 2-(piperazin-1-yl)ethoxy | NH₂ |
| 336. | —(CH₂SO₂)-2-pyridyl | 2-(morpholin-4-yl)ethoxy | NH₂ |
| 337. | —(CH₂SO₂)-3-pyridyl | Cl | H |
| 338. | —(CH₂SO₂)-3-pyridyl | cyclopropylmethylamino | H |
| 339. | —(CH₂SO₂)-3-pyridyl | 3-hydroxypropylamino | H |
| 340. | —(CH₂SO₂)-3-pyridyl | 2-(1-piperidinyl)ethylamino | H |
| 341. | —(CH₂SO₂)-3-pyridyl | 2-(1-pyrrolidinyl)ethylamino | H |
| 342. | —(CH₂SO₂)-3-pyridyl | 2-(4-morpholinyl)ethylamino | H |
| 343. | —(CH₂SO₂)-3-pyridyl | 3-(1-piperidinyl)propylamino | H |
| 344. | —(CH₂SO₂)-3-pyridyl | 3-(1-pyrrolidinyl)propylamino | H |
| 345. | —(CH₂SO₂)-3-pyridyl | 3-(4-morpholinyl)propylamino | H |
| 346. | —(CH₂SO₂)-3-pyridyl | N-methyl-N-(2-piperid-1-ylethyl)amino | H |
| 347. | —(CH₂SO₂)-3-pyridyl | N-methyl-N-(2-pyrrolidin-1-ylethyl)amino | H |
| 348. | —(CH₂SO₂)-3-pyridyl | N-methyl-N-(2-morpholin-4-ylethyl)amino | H |
| 349. | —(CH₂SO₂)-3-pyridyl | ((2S)-2-amino-3-phenylpropyl)amino | H |
| 350. | —(CH₂SO₂)-3-pyridyl | 4-methylpiperazinylamino | H |
| 351. | —(CH₂SO₂)-3-pyridyl | 4-methylpiperazinyl | H |
| 352. | —(CH₂SO₂)-3-pyridyl | 3-aminopyrrolidinyl | H |
| 353. | —(CH₂SO₂)-3-pyridyl | (diethylamino)ethylamino | H |
| 354. | —(CH₂SO₂)-3-pyridyl | 3,5-dimethylpiperazin-1-yl | H |
| 355. | —(CH₂SO₂)-3-pyridyl | (4-piperidylmethyl)amino | H |
| 356. | —(CH₂SO₂)-3-pyridyl | (2-methylbutyl)amino | H |
| 357. | —(CH₂SO₂)-3-pyridyl | 2-(dimethylamino)ethoxy | H |
| 358. | —(CH₂SO₂)-3-pyridyl | 2-(methylamino)ethoxy | H |
| 359. | —(CH₂SO₂)-3-pyridyl | ((2R)pyrrolidin-2-yl)methoxy | H |
| 360. | —(CH₂SO₂)-3-pyridyl | ((2R)-1-methylpyrrolidin-2-yl)methoxy | H |
| 361. | —(CH₂SO₂)-3-pyridyl | 2-(piperid-1-yl)ethoxy | H |
| 362. | —(CH₂SO₂)-3-pyridyl | 2-(piperazin-1-yl)ethoxy | H |
| 363. | —(CH₂SO₂)-3-pyridyl | 2-(morpholin-4-yl)ethoxy | H |
| 364. | —(CH₂SO₂)-3-pyridyl | Cl | NH₂ |
| 365. | —(CH₂SO₂)-3-pyridyl | cyclopropylmethylamino | NH₂ |
| 366. | —(CH₂SO₂)-3-pyridyl | 3-hydroxypropylamino | NH₂ |
| 367. | —(CH₂SO₂)-3-pyridyl | 2-(1-piperidinyl)ethylamino | NH₂ |
| 368. | —(CH₂SO₂)-3-pyridyl | 2-(1-pyrrolidinyl)ethylamino | NH₂ |
| 369. | —(CH₂SO₂)-3-pyridyl | 2-(4-morpholinyl)ethylamino | NH₂ |
| 370. | —(CH₂SO₂)-3-pyridyl | 3-(1-piperidinyl)propylamino | NH₂ |
| 371. | —(CH₂SO₂)-3-pyridyl | 3-(1-pyrrolidinyl)propylamino | NH₂ |
| 372. | —(CH₂SO₂)-3-pyridyl | 3-(4-morpholinyl)propylamino | NH₂ |
| 373. | —(CH₂SO₂)-3-pyridyl | N-methyl-N-(2-piperid-1-ylethyl)amino | NH₂ |
| 374. | —(CH₂SO₂)-3-pyridyl | N-methyl-N-(2-pyrrolidin-1-ylethyl)amino | NH₂ |
| 375. | —(CH₂SO₂)-3-pyridyl | N-methyl-N-(2-morpholin-4-ylethyl)amino | NH₂ |
| 376. | —(CH₂SO₂)-3-pyridyl | ((2S)-2-amino-3-phenylpropyl)amino | NH₂ |
| 377. | —(CH₂SO₂)-3-pyridyl | 4-methylpiperazinylamino | NH₂ |
| 378. | —(CH₂SO₂)-3-pyridyl | 4-methylpiperazinyl | NH₂ |
| 379. | —(CH₂SO₂)-3-pyridyl | 3-aminopyrrolidinyl | NH₂ |
| 380. | —(CH₂SO₂)-3-pyridyl | (diethylamino)ethylamino | NH₂ |

TABLE 1-continued

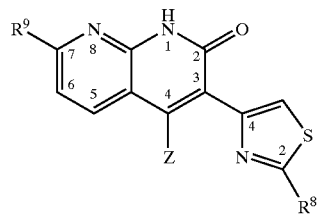

| # | R⁸ | R⁹ | Z |
|---|---|---|---|
| 381. | —(CH₂SO₂)-3-pyridyl | 3,5-dimethylpiperazin-1-yl | NH₂ |
| 382. | —(CH₂SO₂)-3-pyridyl | (4-piperidylmethyl)amino | NH₂ |
| 383. | —(CH₂SO₂)-3-pyridyl | (2-methylbutyl)amino | NH₂ |
| 384. | —(CH₂SO₂)-3-pyridyl | 2-(dimethylamino)ethoxy | NH₂ |
| 385. | —(CH₂SO₂)-3-pyridyl | 2-(methylamino)ethoxy | NH₂ |
| 386. | —(CH₂SO₂)-3-pyridyl | ((2R)pyrrolidin-2-yl)methoxy | NH₂ |
| 387. | —(CH₂SO₂)-3-pyridyl | ((2R)-1-methylpyrrolidin-2-yl)methoxy | NH₂ |
| 388. | —(CH₂SO₂)-3-pyridyl | 2-(piperid-1-yl)ethoxy | NH₂ |
| 389. | —(CH₂SO₂)-3-pyridyl | 2-(piperazin-1-yl)ethoxy | NH₂ |
| 390. | —(CH₂SO₂)-3-pyridyl | 2-(morpholin-4-yl)ethoxy | NH₂ |
| 391. | —(CH₂SO₂)-4-pyridyl | Cl | H |
| 392. | —(CH₂SO₂)-4-pyridyl | cyclopropylmethylamino | H |
| 393. | —(CH₂SO₂)-4-pyridyl | 3-hydroxypropylamino | H |
| 394. | —(CH₂SO₂)-4-pyridyl | 2-(1-piperidinyl)ethylamino | H |
| 395. | —(CH₂SO₂)-4-pyridyl | 2-(1-pyrrolidinyl)ethylamino | H |
| 396. | —(CH₂SO₂)-4-pyridyl | 2-(4-morpholinyl)ethylamino | H |
| 397. | —(CH₂SO₂)-4-pyridyl | 3-(1-piperidinyl)propylamino | H |
| 398. | —(CH₂SO₂)-4-pyridyl | 3-(1-pyrrolidinyl)propylamino | H |
| 399. | —(CH₂SO₂)-4-pyridyl | 3-(4-morpholinyl)propylamino | H |
| 400. | —(CH₂SO₂)-4-pyridyl | N-methyl-N-(2-piperid-1-ylethyl)amino | H |
| 401. | —(CH₂SO₂)-4-pyridyl | N-methyl-N-(2-pyrrolidin-1-ylethyl)amino | H |
| 402. | —(CH₂SO₂)-4-pyridyl | N-methyl-N-(2-morpholin-4-ylethyl)amino | H |
| 403. | —(CH₂SO₂)-4-pyridyl | ((2S)-2-amino-3-phenylpropyl)amino | H |
| 404. | —(CH₂SO₂)-4-pyridyl | 4-methylpiperazinylamino | H |
| 405. | —(CH₂SO₂)-4-pyridyl | 4-methylpiperazinyl | H |
| 406. | —(CH₂SO₂)-4-pyridyl | 3-aminopyrrolidinyl | H |
| 407. | —(CH₂SO₂)-4-pyridyl | (diethylamino)ethylamino | H |
| 408. | —(CH₂SO₂)-4-pyridyl | 3,5-dimethylpiperazin-1-yl | H |
| 409. | —(CH₂SO₂)-4-pyridyl | (4-piperidylmethyl)amino | H |
| 410. | —(CH₂SO₂)-4-pyridyl | (2-methylbutyl)amino | H |
| 411. | —(CH₂SO₂)-4-pyridyl | 2-(dimethylamino)ethoxy | H |
| 412. | —(CH₂SO₂)-4-pyridyl | 2-(methylamino)ethoxy | H |
| 413. | —(CH₂SO₂)-4-pyridyl | ((2R)pyrrolidin-2-yl)methoxy | H |
| 414. | —(CH₂SO₂)-4-pyridyl | ((2R)-1-methylpyrrolidin-2-yl)methoxy | H |
| 415. | —(CH₂SO₂)-4-pyridyl | 2-(piperid-1-yl)ethoxy | H |
| 416. | —(CH₂SO₂)-4-pyridyl | 2-(piperazin-1-yl)ethoxy | H |
| 417. | —(CH₂SO₂)-4-pyridyl | 2-(morpholin-4-yl)ethoxy | H |
| 418. | —(CH₂SO₂)-4-pyridyl | Cl | NH₂ |
| 419. | —(CH₂SO₂)-4-pyridyl | cyclopropylmethylamino | NH₂ |
| 420. | —(CH₂SO₂)-4-pyridyl | 3-hydroxypropylamino | NH₂ |
| 421. | —(CH₂SO₂)-4-pyridyl | 2-(1-piperidinyl)ethylamino | NH₂ |
| 422. | —(CH₂SO₂)-4-pyridyl | 2-(1-pyrrolidinyl)ethylamino | NH₂ |
| 423. | —(CH₂SO₂)-4-pyridyl | 2-(4-morpholinyl)ethylamino | NH₂ |
| 424. | —(CH₂SO₂)-4-pyridyl | 3-(1-piperidinyl)propylamino | NH₂ |
| 425. | —(CH₂SO₂)-4-pyridyl | 3-(1-pyrrolidinyl)propylamino | NH₂ |
| 426. | —(CH₂SO₂)-4-pyridyl | 3-(4-morpholinyl)propylamino | NH₂ |
| 427. | —(CH₂SO₂)-4-pyridyl | N-methyl-N-(2-piperid-1-ylethyl)amino | NH₂ |
| 428. | —(CH₂SO₂)-4-pyridyl | N-methyl-N-(2-pyrrolidin-1-ylethyl)amino | NH₂ |
| 429. | —(CH₂SO₂)-4-pyridyl | N-methyl-N-(2-morpholin-4-ylethyl)amino | NH₂ |
| 430. | —(CH₂SO₂)-4-pyridyl | ((2S)-2-amino-3-phenylpropyl)amino | NH₂ |
| 431. | —(CH₂SO₂)-4-pyridyl | 4-methylpiperazinylamino | NH₂ |
| 432. | —(CH₂SO₂)-4-pyridyl | 4-methylpiperazinyl | NH₂ |
| 433. | —(CH₂SO₂)-4-pyridyl | 3-aminopyrrolidinyl | NH₂ |
| 434. | —(CH₂SO₂)-4-pyridyl | (diethylamino)ethylamino | NH₂ |
| 435. | —(CH₂SO₂)-4-pyridyl | 3,5-dimethylpiperazin-1-yl | NH₂ |
| 436. | —(CH₂SO₂)-4-pyridyl | (4-piperidylmethyl)amino | NH₂ |
| 437. | —(CH₂SO₂)-4-pyridyl | (2-methylbutyl)amino | NH₂ |
| 438. | —(CH₂SO₂)-4-pyridyl | 2-(dimethylamino)ethoxy | NH₂ |
| 439. | —(CH₂SO₂)-4-pyridyl | 2-(methylamino)ethoxy | NH₂ |
| 440. | —(CH₂SO₂)-4-pyridyl | ((2R)pyrrolidin-2-yl)methoxy | NH₂ |
| 441. | —(CH₂SO₂)-4-pyridyl | ((2R)-1-methylpyrrolidin-2-yl)methoxy | NH₂ |
| 442. | —(CH₂SO₂)-4-pyridyl | 2-(piperid-1-yl)ethoxy | NH₂ |
| 443. | —(CH₂SO₂)-4-pyridyl | 2-(piperazin-1-yl)ethoxy | NH₂ |
| 444. | —(CH₂SO₂)-4-pyridyl | 2-(morpholin-4-yl)ethoxy | NH₂ |
| 445. | —(NMeSO₂)-phenyl | Cl | H |

TABLE 1-continued

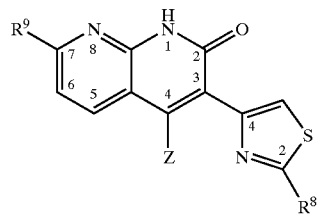

| # | R⁸ | R⁹ | Z |
|---|---|---|---|
| 446. | —(NMeSO₂)-phenyl | cyclopropylmethylamino | H |
| 447. | —(NMeSO₂)-phenyl | 3-hydroxypropylamino | H |
| 448. | —(NMeSO₂)-phenyl | 2-(1-piperidinyl)ethylamino | H |
| 449. | —(NMeSO₂)-phenyl | 2-(1-pyrrolidinyl)ethylamino | H |
| 450. | —(NMeSO₂)-phenyl | 2-(4-morpholinyl)ethylamino | H |
| 451. | —(NMeSO₂)-phenyl | 3-(1-piperidinyl)propylamino | H |
| 452. | —(NMeSO₂)-phenyl | 3-(1-pyrrolidinyl)propylamino | H |
| 453. | —(NMeSO₂)-phenyl | 3-(4-morpholinyl)propylamino | H |
| 454. | —(NMeSO₂)-phenyl | N-methyl-N-(2-piperid-1-ylethyl)amino | H |
| 455. | —(NMeSO₂)-phenyl | N-methyl-N-(2-pyrrolidin-1-ylethyl)amino | H |
| 456. | —(NMeSO₂)-phenyl | N-methyl-N-(2-morpholin-4-ylethyl)amino | H |
| 457. | —(NMeSO₂)-phenyl | ((2S)-2-amino-3-phenylpropyl)amino | H |
| 458. | —(NMeSO₂)-phenyl | 4-methylpiperazinylamino | H |
| 459. | —(NMeSO₂)-phenyl | 4-methylpiperazinyl | H |
| 460. | —(NMeSO₂)-phenyl | 3-aminopyrrolidinyl | H |
| 461. | —(NMeSO₂)-phenyl | (diethylamino)ethylamino | H |
| 462. | —(NMeSO₂)-phenyl | 3,5-dimethylpiperazin-1-yl | H |
| 463. | —(NMeSO₂)-phenyl | (4-piperidylmethyl)amino | H |
| 464. | —(NMeSO₂)-phenyl | (2-methylbutyl)amino | H |
| 465. | —(NMeSO₂)-phenyl | 2-(dimethylamino)ethoxy | H |
| 466. | —(NMeSO₂)-phenyl | 2-(methylamino)ethoxy | H |
| 467. | —(NMeSO₂)-phenyl | ((2R)pyrrolidin-2-yl)methoxy | H |
| 468. | —(NMeSO₂)-phenyl | ((2R)-1-methylpyrrolidin-2-yl)methoxy | H |
| 469. | —(NMeSO₂)-phenyl | 2-(piperid-1-yl)ethoxy | H |
| 470. | —(NMeSO₂)-phenyl | 2-(piperazin-1-yl)ethoxy | H |
| 471. | —(NMeSO₂)-phenyl | 2-(morpholin-4-yl)ethoxy | H |
| 472. | —(NMeSO₂)-phenyl | Cl | NH₂ |
| 473. | —(NMeSO₂)-phenyl | cyclopropylmethylamino | NH₂ |
| 474. | —(NMeSO₂)-phenyl | 3-hydroxypropylamino | NH₂ |
| 475. | —(NMeSO₂)-phenyl | 2-(1-piperidinyl)ethylamino | NH₂ |
| 476. | —(NMeSO₂)-phenyl | 2-(1-pyrrolidinyl)ethylamino | NH₂ |
| 477. | —(NMeSO₂)-phenyl | 2-(4-morpholinyl)ethylamino | NH₂ |
| 478. | —(NMeSO₂)-phenyl | 3-(1-piperidinyl)propylamino | NH₂ |
| 479. | —(NMeSO₂)-phenyl | 3-(1-pyrrolidinyl)propylamino | NH₂ |
| 480. | —(NMeSO₂)-phenyl | 3-(4-morpholinyl)propylamino | NH₂ |
| 481. | —(NMeSO₂)-phenyl | N-methyl-N-(2-piperid-1-ylethyl)amino | NH₂ |
| 482. | —(NMeSO₂)-phenyl | N-methyl-N-(2-pyrrolidin-1-ylethyl)amino | NH₂ |
| 483. | —(NMeSO₂)-phenyl | N-methyl-N-(2-morpholin-4-ylethyl)amino | NH₂ |
| 484. | —(NMeSO₂)-phenyl | ((2S)-2-amino-3-phenylpropyl)amino | NH₂ |
| 485. | —(NMeSO₂)-phenyl | 4-methylpiperazinylamino | NH₂ |
| 486. | —(NMeSO₂)-phenyl | 4-methylpiperazinyl | NH₂ |
| 487. | —(NMeSO₂)-phenyl | 3-aminopyrrolidinyl | NH₂ |
| 488. | —(NMeSO₂)-phenyl | (diethylamino)ethylamino | NH₂ |
| 489. | —(NMeSO₂)-phenyl | 3,5-dimethylpiperazin-1-yl | NH₂ |
| 490. | —(NMeSO₂)-phenyl | (4-piperidylmethyl)amino | NH₂ |
| 491. | —(NMeSO₂)-phenyl | (2-methylbutyl)amino | NH₂ |
| 492. | —(NMeSO₂)-phenyl | 2-(dimethylamino)ethoxy | NH₂ |
| 493. | —(NMeSO₂)-phenyl | 2-(methylamino)ethoxy | NH₂ |
| 494. | —(NMeSO₂)-phenyl | ((2R)pyrrolidin-2-yl)methoxy | NH₂ |
| 495. | —(NMeSO₂)-phenyl | ((2R)-1-methylpyrrolidin-2-yl)methoxy | NH₂ |
| 496. | —(NMeSO₂)-phenyl | 2-(piperid-1-yl)ethoxy | NH₂ |
| 497. | —(NMeSO₂)-phenyl | 2-(piperazin-1-yl)ethoxy | NH₂ |
| 498. | —(NMeSO₂)-phenyl | 2-(morpholin-4-yl)ethoxy | NH₂ |
| 499. | —(NMeSO₂)-2-thienyl | Cl | H |
| 500. | —(NMeSO₂)-2-thienyl | cyclopropylmethylamino | H |
| 501. | —(NMeSO₂)-2-thienyl | 3-hydroxypropylamino | H |
| 502. | —(NMeSO₂)-2-thienyl | 2-(1-piperidinyl)ethylamino | H |
| 503. | —(NMeSO₂)-2-thienyl | 2-(1-pyrrolidinyl)ethylamino | H |
| 504. | —(NMeSO₂)-2-thienyl | 2-(4-morpholinyl)ethylamino | H |
| 505. | —(NMeSO₂)-2-thienyl | 3-(1-piperidinyl)propylamino | H |
| 506. | —(NMeSO₂)-2-thienyl | 3-(1-pyrrolidinyl)propylamino | H |
| 507. | —(NMeSO₂)-2-thienyl | 3-(4-morpholinyl)propylamino | H |
| 508. | —(NMeSO₂)-2-thienyl | N-methyl-N-(2-piperid-1-ylethyl)amino | H |
| 509. | —(NMeSO₂)-2-thienyl | N-methyl-N-(2-pyrrolidin-1-ylethyl)amino | H |
| 510. | —(NMeSO₂)-2-thienyl | N-methyl-N-(2-morpholin-4-ylethyl)amino | H |

TABLE 1-continued

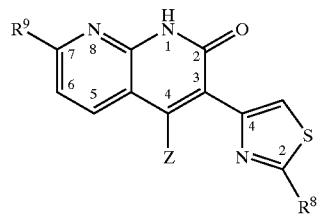

| # | R⁸ | R⁹ | Z |
|---|---|---|---|
| 511. | —(NMeSO₂)-2-thienyl | ((2S)-2-amino-3-phenylpropyl)amino | H |
| 512. | —(NMeSO₂)-2-thienyl | 4-methylpiperazinylamino | H |
| 513. | —(NMeSO₂)-2-thienyl | 4-methylpiperazinyl | H |
| 514. | —(NMeSO₂)-2-thienyl | 3-aminopyrrolidinyl | H |
| 515. | —(NMeSO₂)-2-thienyl | (diethylamino)ethylamino | H |
| 516. | —(NMeSO₂)-2-thienyl | 3,5-dimethylpiperazin-1-yl | H |
| 517. | —(NMeSO₂)-2-thienyl | (4-piperidylmethyl)amino | H |
| 518. | —(NMeSO₂)-2-thienyl | (2-methylbutyl)amino | H |
| 519. | —(NMeSO₂)-2-thienyl | 2-(dimethylamino)ethoxy | H |
| 520. | —(NMeSO₂)-2-thienyl | 2-(methylamino)ethoxy | H |
| 521. | —(NMeSO₂)-2-thienyl | ((2R)pyrrolidin-2-yl)methoxy | H |
| 522. | —(NMeSO₂)-2-thienyl | ((2R)-1-methylpyrrolidin-2-yl)methoxy | H |
| 523. | —(NMeSO₂)-2-thienyl | 2-(piperid-1-yl)ethoxy | H |
| 524. | —(NMeSO₂)-2-thienyl | 2-(piperazin-1-yl)ethoxy | H |
| 525. | —(NMeSO₂)-2-thienyl | 2-(morpholin-4-yl)ethoxy | H |
| 526. | —(NMeSO₂)-2-thienyl | Cl | NH₂ |
| 527. | —(NMeSO₂)-2-thienyl | cyclopropylmethylamino | NH₂ |
| 528. | —(NMeSO₂)-2-thienyl | 3-hydroxypropylamino | NH₂ |
| 529. | —(NMeSO₂)-2-thienyl | 2-(1-piperidinyl)ethylamino | NH₂ |
| 530. | —(NMeSO₂)-2-thienyl | 2-(1-pyrrolidinyl)ethylamino | NH₂ |
| 531. | —(NMeSO₂)-2-thienyl | 2-(4-morpholinyl)ethylamino | NH₂ |
| 532. | —(NMeSO₂)-2-thienyl | 3-(1-piperidinyl)propylamino | NH₂ |
| 533. | —(NMeSO₂)-2-thienyl | 3-(1-pyrrolidinyl)propylamino | NH₂ |
| 534. | —(NMeSO₂)-2-thienyl | 3-(4-morpholinyl)propylamino | NH₂ |
| 535. | —(NMeSO₂)-2-thienyl | N-methyl-N-(2-piperid-1-ylethyl)amino | NH₂ |
| 536. | —(NMeSO₂)-2-thienyl | N-methyl-N-(2-pyrrolidin-1-ylethyl)amino | NH₂ |
| 537. | —(NMeSO₂)-2-thienyl | N-methyl-N-(2-morpholin-4-ylethyl)amino | NH₂ |
| 538. | —(NMeSO₂)-2-thienyl | ((2S)-2-amino-3-phenylpropyl)amino | NH₂ |
| 539. | —(NMeSO₂)-2-thienyl | 4-methylpiperazinylamino | NH₂ |
| 540. | —(NMeSO₂)-2-thienyl | 4-methylpiperazinyl | NH₂ |
| 541. | —(NMeSO₂)-2-thienyl | 3-aminopyrrolidinyl | NH₂ |
| 542. | —(NMeSO₂)-2-thienyl | (diethylamino)ethylamino | NH₂ |
| 543. | —(NMeSO₂)-2-thienyl | 3,5-dimethylpiperazin-1-yl | NH₂ |
| 544. | —(NMeSO₂)-2-thienyl | (4-piperidylmethyl)amino | NH₂ |
| 545. | —(NMeSO₂)-2-thienyl | (2-methylbutyl)amino | NH₂ |
| 546. | —(NMeSO₂)-2-thienyl | 2-(dimethylamino)ethoxy | NH₂ |
| 547. | —(NMeSO₂)-2-thienyl | 2-(methylamino)ethoxy | NH₂ |
| 548. | —(NMeSO₂)-2-thienyl | ((2R)pyrrolidin-2-yl)methoxy | NH₂ |
| 549. | —(NMeSO₂)-2-thienyl | ((2R)-1-methylpyrrolidin-2-yl)methoxy | NH₂ |
| 550. | —(NMeSO₂)-2-thienyl | 2-(piperid-1-yl)ethoxy | NH₂ |
| 551. | —(NMeSO₂)-2-thienyl | 2-(piperazin-1-yl)ethoxy | NH₂ |
| 552. | —(NMeSO₂)-2-thienyl | 2-(morpholin-4-yl)ethoxy | NH₂ |
| 553. | —(NMeSO₂)-2-pyridyl | Cl | H |
| 554. | —(NMeSO₂)-2-pyridyl | cyclopropylmethylamino | H |
| 555. | —(NMeSO₂)-2-pyridyl | 3-hydroxypropylamino | H |
| 556. | —(NMeSO₂)-2-pyridyl | 2-(1-piperidinyl)ethylamino | H |
| 557. | —(NMeSO₂)-2-pyridyl | 2-(1-pyrrolidinyl)ethylamino | H |
| 558. | —(NMeSO₂)-2-pyridyl | 2-(4-morpholinyl)ethylamino | H |
| 559. | —(NMeSO₂)-2-pyridyl | 3-(1-piperidinyl)propylamino | H |
| 560. | —(NMeSO₂)-2-pyridyl | 3-(1-pyrrolidinyl)propylamino | H |
| 561. | —(NMeSO₂)-2-pyridyl | 3-(4-morpholinyl)propylamino | H |
| 562. | —(NMeSO₂)-2-pyridyl | N-methyl-N-(2-piperid-1-ylethyl)amino | H |
| 563. | —(NMeSO₂)-2-pyridyl | N-methyl-N-(2-pyrrolidin-1-ylethyl)amino | H |
| 564. | —(NMeSO₂)-2-pyridyl | N-methyl-N-(2-morpholin-4-ylethyl)amino | H |
| 565. | —(NMeSO₂)-2-pyridyl | ((2S)-2-amino-3-phenylpropyl)amino | H |
| 566. | —(NMeSO₂)-2-pyridyl | 4-methylpiperazinylamino | H |
| 567. | —(NMeSO₂)-2-pyridyl | 4-methylpiperazinyl | H |
| 568. | —(NMeSO₂)-2-pyridyl | 3-aminopyrrolidinyl | H |
| 569. | —(NMeSO₂)-2-pyridyl | (diethylamino)ethylamino | H |
| 570. | —(NMeSO₂)-2-pyridyl | 3,5-dimethylpiperazin-1-yl | H |
| 571. | —(NMeSO₂)-2-pyridyl | (4-piperidylmethyl)amino | H |
| 572. | —(NMeSO₂)-2-pyridyl | (2-methylbutyl)amino | H |
| 573. | —(NMeSO₂)-2-pyridyl | 2-(dimethylamino)ethoxy | H |
| 574. | —(NMeSO₂)-2-pyridyl | 2-(methylamino)ethoxy | H |
| 575. | —(NMeSO₂)-2-pyridyl | ((2R)pyrrolidin-2-yl)methoxy | H |

TABLE 1-continued

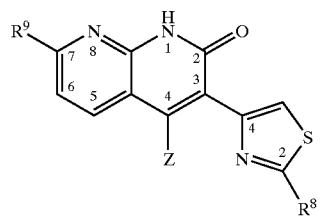

| # | R⁸ | R⁹ | Z |
|---|---|---|---|
| 576. | —(NMeSO₂)-2-pyridyl | ((2R)-1-methylpyrrolidin-2-yl)methoxy | H |
| 577. | —(NMeSO₂)-2-pyridyl | 2-(piperid-1-yl)ethoxy | H |
| 578. | —(NMeSO₂)-2-pyridyl | 2-(piperazin-1-yl)ethoxy | H |
| 579. | —(NMeSO₂)-2-pyridyl | 2-(morpholin-4-yl)ethoxy | H |
| 580. | —(NMeSO₂)-2-pyridyl | Cl | NH₂ |
| 581. | —(NMeSO₂)-2-pyridyl | cyclopropylmethylamino | NH₂ |
| 582. | —(NMeSO₂)-2-pyridyl | 3-hydroxypropylamino | NH₂ |
| 583. | —(NMeSO₂)-2-pyridyl | 2-(1-piperidinyl)ethylamino | NH₂ |
| 584. | —(NMeSO₂)-2-pyridyl | 2-(1-pyrrolidinyl)ethylamino | NH₂ |
| 585. | —(NMeSO₂)-2-pyridyl | 2-(4-morpholinyl)ethylamino | NH₂ |
| 586. | —(NMeSO₂)-2-pyridyl | 3-(1-piperidinyl)propylamino | NH₂ |
| 587. | —(NMeSO₂)-2-pyridyl | 3-(1-pyrrolidinyl)propylamino | NH₂ |
| 588. | —(NMeSO₂)-2-pyridyl | 3-(4-morpholinyl)propylamino | NH₂ |
| 589. | —(NMeSO₂)-2-pyridyl | N-methyl-N-(2-piperid-1-ylethyl)amino | NH₂ |
| 590. | —(NMeSO₂)-2-pyridyl | N-methyl-N-(2-pyrrolidin-1-ylethyl)amino | NH₂ |
| 591. | —(NMeSO₂)-2-pyridyl | N-methyl-N-(2-morpholin-4-ylethyl)amino | NH₂ |
| 592. | —(NMeSO₂)-2-pyridyl | ((2S)-2-amino-3-phenylpropyl)amino | NH₂ |
| 593. | —(NMeSO₂)-2-pyridyl | 4-methylpiperazinylamino | NH₂ |
| 594. | —(NMeSO₂)-2-pyridyl | 4-methylpiperazinyl | NH₂ |
| 595. | —(NMeSO₂)-2-pyridyl | 3-aminopyrrolidinyl | NH₂ |
| 596. | —(NMeSO₂)-2-pyridyl | (diethylamino)ethylamino | NH₂ |
| 597. | —(NMeSO₂)-2-pyridyl | 3,5-dimethylpiperazin-1-yl | NH₂ |
| 598. | —(NMeSO₂)-2-pyridyl | (4-piperidylmethyl)amino | NH₂ |
| 599. | —(NMeSO₂)-2-pyridyl | (2-methylbutyl)amino | NH₂ |
| 600. | —(NMeSO₂)-2-pyridyl | 2-(dimethylamino)ethoxy | NH₂ |
| 601. | —(NMeSO₂)-2-pyridyl | 2-(methylamino)ethoxy | NH₂ |
| 602. | —(NMeSO₂)-2-pyridyl | ((2R)pyrrolidin-2-yl)methoxy | NH₂ |
| 603. | —(NMeSO₂)-2-pyridyl | ((2R)-1-methylpyrrolidin-2-yl)methoxy | NH₂ |
| 604. | —(NMeSO₂)-2-pyridyl | 2-(piperid-1-yl)ethoxy | NH₂ |
| 605. | —(NMeSO₂)-2-pyridyl | 2-(piperazin-1-yl)ethoxy | NH₂ |
| 606. | —(NMeSO₂)-2-pyridyl | 2-(morpholin-4-yl)ethoxy | NH₂ |
| 607. | —(NMeSO₂)-3-pyridyl | Cl | H |
| 608. | —(NMeSO₂)-3-pyridyl | cyclopropylmethylamino | H |
| 609. | —(NMeSO₂)-3-pyridyl | 3-hydroxypropylamino | H |
| 610. | —(NMeSO₂)-3-pyridyl | 2-(1-piperidinyl)ethylamino | H |
| 611. | —(NMeSO₂)-3-pyridyl | 2-(1-pyrrolidinyl)ethylamino | H |
| 612. | —(NMeSO₂)-3-pyridyl | 2-(4-morpholinyl)ethylamino | H |
| 613. | —(NMeSO₂)-3-pyridyl | 3-(1-piperidinyl)propylamino | H |
| 614. | —(NMeSO₂)-3-pyridyl | 3-(1-pyrrolidinyl)propylamino | H |
| 615. | —(NMeSO₂)-3-pyridyl | 3-(4-morpholinyl)propylamino | H |
| 616. | —(NMeSO₂)-3-pyridyl | N-methyl-N-(2-piperid-1-ylethyl)amino | H |
| 617. | —(NHeSO₂)-3-pyridyl | N-methyl-N-(2-pyrrolidin-1-ylethyl)amino | H |
| 618. | —(NMeSO₂)-3-pyridyl | N-methyl-N-(2-morpholin-4-ylethyl)amino | H |
| 619. | —(NMeSO₂)-3-pyridyl | ((2S)-2-amino-3-phenylpropyl)amino | H |
| 620. | —(NMeSO₂)-3-pyridyl | 4-methylpiperazinylamino | H |
| 621. | —(NMeSO₂)-3-pyridyl | 4-methylpiperazinyl | H |
| 622. | —(NMeSO₂)-3-pyridyl | 3-aminopyrrolidinyl | H |
| 623. | —(NMeSO₂)-3-pyridyl | (diethylamino)ethylamino | H |
| 624. | —(NMeSO₂)-3-pyridyl | 3,5-dimethylpiperazin-1-yl | H |
| 625. | —(NMeSO₂)-3-pyridyl | (4-piperidylmethyl)amino | H |
| 626. | —(NMeSO₂)-3-pyridyl | (2-methylbutyl)amino | H |
| 627. | —(NMeSO₂)-3-pyridyl | 2-(dimethylamino)ethoxy | H |
| 628. | —(NMeSO₂)-3-pyridyl | 2-(methylamino)ethoxy | H |
| 629. | —(NMeSO₂)-3-pyridyl | ((2R)pyrrolidin-2-yl)methoxy | H |
| 630. | —(NMeSO₂)-3-pyridyl | ((2R)-1-methylpyrrolidin-2-yl)methoxy | H |
| 631. | —(NMeSO₂)-3-pyridyl | 2-(piperid-1-yl)ethoxy | H |
| 632. | —(NMeSO₂)-3-pyridyl | 2-(piperazin-1-yl)ethoxy | H |
| 633. | —(NMeSO₂)-3-pyridyl | 2-(morpholin-4-yl)ethoxy | H |
| 634. | —(NMeSO₂)-3-pyridyl | Cl | NH₂ |
| 635. | —(NMeSO₂)-3-pyridyl | cyclopropylmethylamino | NH₂ |
| 636. | —(NMeSO₂)-3-pyridyl | 3-hydroxypropylamino | NH₂ |
| 637. | —(NMeSO₂)-3-pyridyl | 2-(1-piperidinyl)ethylamino | NH₂ |
| 638. | —(NMeSO₂)-3-pyridyl | 2-(1-pyrrolidinyl)ethylamino | NH₂ |
| 639. | —(NMeSO₂)-3-pyridyl | 2-(4-morpholinyl)ethylamino | NH₂ |
| 640. | —(NMeSO₂)-3-pyridyl | 3-(1-piperidinyl)propylamino | NH₂ |

TABLE 1-continued

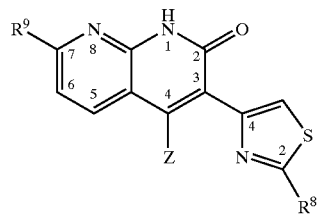

| # | R⁸ | R⁹ | Z |
|---|---|---|---|
| 641. | —(NMeSO₂)-3-pyridyl | 3-(1-pyrrolidinyl)propylamino | NH₂ |
| 642. | —(NMeSO₂)-3-pyridyl | 3-(4-morpholinyl)propylamino | NH₂ |
| 643. | —(NMeSO₂)-3-pyridyl | N-methyl-N-(2-piperid-1-ylethyl)amino | NH₂ |
| 644. | —(NMeSO₂)-3-pyridyl | N-methyl-N-(2-pyrrolidin-1-ylethyl)amino | NH₂ |
| 645. | —(NMeSO₂)-3-pyridyl | N-methyl-N-(2-morpholin-4-ylethyl)amino | NH₂ |
| 646. | —(NMeSO₂)-3-pyridyl | ((2S)-2-amino-3-phenylpropyl)amino | NH₂ |
| 647. | —(NMeSO₂)-3-pyridyl | 4-methylpiperazinylamino | NH₂ |
| 648. | —(NMeSO₂)-3-pyridyl | 4-methylpiperazinyl | NH₂ |
| 649. | —(NMeSO₂)-3-pyridyl | 3-aminopyrrolidinyl | NH₂ |
| 650. | —(NMeSO₂)-3-pyridyl | (diethylamino)ethylamino | NH₂ |
| 651. | —(NMeSO₂)-3-pyridyl | 3,5-dimethylpiperazin-1-yl | NH₂ |
| 652. | —(NMeSO₂)-3-pyridyl | (4-piperidylmethyl)amino | NH₂ |
| 653. | —(NMeSO₂)-3-pyridyl | (2-methylbutyl)amino | NH₂ |
| 654. | —(NMeSO₂)-3-pyridyl | 2-(dimethylamino)ethoxy | NH₂ |
| 655. | —(NMeSO₂)-3-pyridyl | 2-(methylamino)ethoxy | NH₂ |
| 656. | —(NMeSO₂)-3-pyridyl | ((2R)pyrrolidin-2-yl)methoxy | NH₂ |
| 657. | —(NMeSO₂)-3-pyridyl | ((2R)-1-methylpyrrolidin-2-yl)methoxy | NH₂ |
| 658. | —(NMeSO₂)-3-pyridyl | 2-(piperid-1-yl)ethoxy | NH₂ |
| 659. | —(NMeSO₂)-3-pyridyl | 2-(piperazin-1-yl)ethoxy | NH₂ |
| 660. | —(NMeSO₂)-3-pyridyl | 2-(morpholin-4-yl)ethoxy | NH₂ |
| 661. | —(NMeSO₂)-4-pyridyl | Cl | H |
| 662. | —(NMeSO₂)-4-pyridyl | cyclopropylmethylamino | H |
| 663. | —(NMeSO₂)-4-pyridyl | 3-hydroxypropylamino | H |
| 664. | —(NMeSO₂)-4-pyridyl | 2-(1-piperidinyl)ethylamino | H |
| 665. | —(NMeSO₂)-4-pyridyl | 2-(1-pyrrolidinyl)ethylamino | H |
| 666. | —(NMeSO₂)-4-pyridyl | 2-(4-morpholinyl)ethylamino | H |
| 667. | —(NMeSO₂)-4-pyridyl | 3-(1-piperidinyl)propylamino | H |
| 668. | —(NMeSO₂)-4-pyridyl | 3-(1-pyrrolidinyl)propylamino | H |
| 669. | —(NMeSO₂)-4-pyridyl | 3-(4-morpholinyl)propylamino | H |
| 670. | —(NMeSO₂)-4-pyridyl | N-methyl-N-(2-piperid-1-ylethyl)amino | H |
| 671. | —(NMeSO₂)-4-pyridyl | N-methyl-N-(2-pyrrolidin-1-ylethyl)amino | H |
| 672. | —(NMeSO₂)-4-pyridyl | N-methyl-N-(2-morpholin-4-ylethyl)amino | H |
| 673. | —(NMeSO₂)-4-pyridyl | ((2S)-2-amino-3-phenylpropyl)amino | H |
| 674. | —(NMeSO₂)-4-pyridyl | 4-methylpiperazinylamino | H |
| 675. | —(NHeSO₂)-4-pyridyl | 4-methylpiperazinyl | H |
| 676. | —(NMeSO₂)-4-pyridyl | 3-aminopyrrolidinyl | H |
| 677. | —(NMeSO₂)-4-pyridyl | (diethylamino)ethylamino | H |
| 678. | —(NMeSO₂)-4-pyridyl | 3,5-dimethylpiperazin-1-yl | H |
| 679. | —(NMeSO₂)-4-pyridyl | (4-piperidylmethyl)amino | H |
| 680. | —(NMeSO₂)-4-pyridyl | (2-methylbutyl)amino | H |
| 681. | —(NMeSO₂)-4-pyridyl | 2-(dimethylamino)ethoxy | H |
| 682. | —(NMeSO₂)-4-pyridyl | 2-(methylamino)ethoxy | H |
| 683. | —(NMeSO₂)-4-pyridyl | ((2R)pyrrolidin-2-yl)methoxy | H |
| 684. | —(NMeSO₂)-4-pyridyl | ((2R)-1-methylpyrrolidin-2-yl)methoxy | H |
| 685. | —(NMeSO₂)-4-pyridyl | 2-(piperid-1-yl)ethoxy | H |
| 686. | —(NMeSO₂)-4-pyridyl | 2-(piperazin-1-yl)ethoxy | H |
| 687. | —(NMeSO₂)-4-pyridyl | 2-(morpholin-4-yl)ethoxy | H |
| 688. | —(NMeSO₂)-4-pyridyl | Cl | NH₂ |
| 689. | —(NMeSO₂)-4-pyridyl | cyclopropylmethylamino | NH₂ |
| 690. | —(NMeSO₂)-4-pyridyl | 3-hydroxypropylamino | NH₂ |
| 691. | —(NMeSO₂)-4-pyridyl | 2-(1-piperidinyl)ethylamino | NH₂ |
| 692. | —(NMeSO₂)-4-pyridyl | 2-(1-pyrrolidinyl)ethylamino | NH₂ |
| 693. | —(NMeSO₂)-4-pyridyl | 2-(4-morpholinyl)ethylamino | NH₂ |
| 694. | —(NMeSO₂)-4-pyridyl | 3-(1-piperidinyl)propylamino | NH₂ |
| 695. | —(NMeSO₂)-4-pyridyl | 3-(1-pyrrolidinyl)propylamino | NH₂ |
| 696. | —(NMeSO₂)-4-pyridyl | 3-(4-morpholinyl)propylamino | NH₂ |
| 697. | —(NMeSO₂)-4-pyridyl | N-methyl-N-(2-piperid-1-ylethyl)amino | NH₂ |
| 698. | —(NMeSO₂)-4-pyridyl | N-methyl-N-(2-pyrrolidin-1-ylethyl)amino | NH₂ |
| 699. | —(NMeSO₂)-4-pyridyl | N-methyl-N-(2-morpholin-4-ylethyl)amino | NH₂ |
| 700. | —(NMeSO₂)-4-pyridyl | ((2S)-2-amino-3-phenylpropyl)amino | NH₂ |
| 701. | —(NMeSO₂)-4-pyridyl | 4-methylpiperazinylamino | NH₂ |
| 702. | —(NMeSO₂)-4-pyridyl | 4-methylpiperazinyl | NH₂ |
| 703. | —(NMeSO₂)-4-pyridyl | 3-aminopyrrolidinyl | NH₂ |
| 704. | —(NMeSO₂)-4-pyridyl | (diethylamino)ethylamino | NH₂ |
| 705. | —(NMeSO₂)-4-pyridyl | 3,5-dimethylpiperazin-1-yl | NH₂ |

TABLE 1-continued

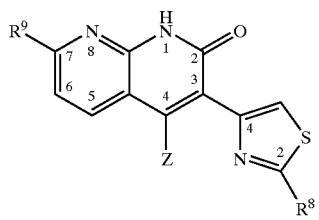

| # | R⁸ | R⁹ | Z |
|---|---|---|---|
| 706. | —(NMeSO₂)-4-pyridyl | (4-piperidylmethyl)amino | NH₂ |
| 707. | —(NMeSO₂)-4-pyridyl | (2-methylbutyl)amino | NH₂ |
| 708. | —(NMeSO₂)-4-pyridyl | 2-(dimethylamino)ethoxy | NH₂ |
| 709. | —(NMeSO₂)-4-pyridyl | 2-(methylamino)ethoxy | NH₂ |
| 710. | —(NMeSO₂)-4-pyridyl | ((2R)pyrrolidin-2-yl)methoxy | NH₂ |
| 711. | —(NMeSO₂)-4-pyridyl | ((2R)-1-methylpyrrolidin-2-yl)methoxy | NH₂ |
| 712. | —(NMeSO₂)-4-pyridyl | 2-(piperid-1-yl)ethoxy | NH₂ |
| 713. | —(NMeSO₂)-4-pyridyl | 2-(piperazin-1-yl)ethoxy | NH₂ |
| 714. | —(NMeSO₂)-4-pyridyl | 2-(morpholin-4-yl)ethoxy | NH₂ |

TABLE 2

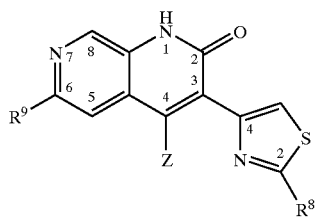

| # | R⁸ | R⁹ | Z |
|---|---|---|---|
| 715. | 4-pyridyl | Cl | H |
| 716. | 4-pyridyl | cyclopropylmethylamino | H |
| 717. | 4-pyridyl | 3-hydroxypropylamino | H |
| 718. | 4-pyridyl | 2-(1-piperidinyl)ethylamino | H |
| 719. | 4-pyridyl | 2-(1-pyrrolidinyl)ethylamino | H |
| 720. | 4-pyridyl | 2-(4-morpholinyl)ethylamino | H |
| 721. | 4-pyridyl | 3-(1-piperidinyl)propylamino | H |
| 722. | 4-pyridyl | 3-(1-pyrrolidinyl)propylamino | H |
| 723. | 4-pyridyl | 3-(4-morpholinyl)propylamino | H |
| 724. | 4-pyridyl | N-methyl-N-(2-piperid-1-ylethyl)amino | H |
| 725. | 4-pyridyl | N-methyl-N-(2-pyrrolidin-1-ylethyl)amino | H |
| 726. | 4-pyridyl | N-methyl-N-(2-morpholin-4-ylethyl)amino | H |
| 727. | 4-pyridyl | ((2S)-2-amino-3-phenylpropyl)amino | H |
| 728. | 4-pyridyl | 4-methylpiperazinylamino | H |
| 729. | 4-pyridyl | 4-methylpiperazinyl | H |
| 730. | 4-pyridyl | 3-aminopyrrolidinyl | H |
| 731. | 4-pyridyl | (diethylamino)ethylamino | H |
| 732. | 4-pyridyl | 3,5-dimethylpiperazin-1-yl | H |
| 733. | 4-pyridyl | (4-piperidylmethyl)amino | H |
| 734. | 4-pyridyl | (2-methylbutyl)amino | H |
| 735. | 4-pyridyl | 2-(dimethylamino)ethoxy | H |
| 736. | 4-pyridyl | 2-(methylamino)ethoxy | H |
| 737. | 4-pyridyl | ((2R)pyrrolidin-2-yl)methoxy | H |
| 738. | 4-pyridyl | ((2R)-1-methylpyrrolidin-2-yl)methoxy | H |
| 739. | 4-pyridyl | 2-(piperid-1-yl)ethoxy | H |
| 740. | 4-pyridyl | 2-(piperazin-1-yl)ethoxy | H |
| 741. | 4-pyridyl | 2-(morpholin-4-yl)ethoxy | H |
| 742. | 4-pyridyl | Cl | NH₂ |
| 743. | 4-pyridyl | cyclopropylmethylamino | NH₂ |
| 744. | 4-pyridyl | 3-hydroxypropylamino | NH₂ |
| 745. | 4-pyridyl | 2-(1-piperidinyl)ethylamino | NH₂ |
| 746. | 4-pyridyl | 2-(1-pyrrolidinyl)ethylamino | NH₂ |
| 747. | 4-pyridyl | 2-(4-morpholinyl)ethylamino | NH₂ |
| 748. | 4-pyridyl | 3-(1-piperidinyl)propylamino | NH₂ |
| 749. | 4-pyridyl | 3-(1-pyrrolidinyl)propylamino | NH₂ |
| 750. | 4-pyridyl | 3-(4-morpholinyl)propylamino | NH₂ |
| 751. | 4-pyridyl | N-methyl-N-(2-piperid-1-ylethyl)amino | NH₂ |
| 752. | 4-pyridyl | N-methyl-N-(2-pyrrolidin-1-ylethyl)amino | NH₂ |

TABLE 2-continued

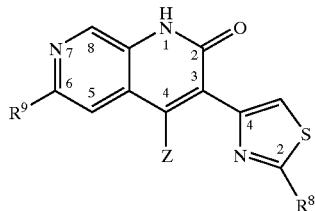

| # | R⁸ | R⁹ | Z |
|---|---|---|---|
| 753. | 4-pyridyl | N-methyl-N-(2-morpholin-4-ylethyl)amino | NH₂ |
| 754. | 4-pyridyl | ((2S)-2-amino-3-phenylpropyl)amino | NH₂ |
| 755. | 4-pyridyl | 4-methylpiperazinylamino | NH₂ |
| 756. | 4-pyridyl | 4-methylpiperazinyl | NH₂ |
| 757. | 4-pyridyl | 3-aminopyrrolidinyl | NH₂ |
| 758. | 4-pyridyl | (diethylamino)ethylamino | NH₂ |
| 759. | 4-pyridyl | 3,5-dimethylpiperazin-1-yl | NH₂ |
| 760. | 4-pyridyl | (4-piperidylmethyl)amino | NH₂ |
| 761. | 4-pyridyl | (2-methylbutyl)amino | NH₂ |
| 762. | 4-pyridyl | 2-(dimethylamino)ethoxy | NH₂ |
| 763. | 4-pyridyl | 2-(methylamino)ethoxy | NH₂ |
| 764. | 4-pyridyl | ((2R)pyrrolidin-2-yl)methoxy | NH₂ |
| 765. | 4-pyridyl | ((2R)-1-methylpyrrolidin-2-yl)methoxy | NH₂ |
| 766. | 4-pyridyl | 2-(piperid-1-yl)ethoxy | NH₂ |
| 767. | 4-pyridyl | 2-(piperazin-1-yl)ethoxy | NH₂ |
| 768. | 4-pyridyl | 2-(morpholin-4-yl)ethoxy | NH₂ |
| 769. | —(CH₂SO₂)-phenyl | Cl | H |
| 770. | —(CH₂SO₂)-phenyl | cyclopropylmethylamino | H |
| 771. | —(CH₂SO₂)-phenyl | 3-hydroxypropylamino | H |
| 772. | —(CH₂SO₂)-phenyl | 2-(1-piperidinyl)ethylamino | H |
| 773. | —(CH₂SO₂)-phenyl | 2-(1-pyrrolidinyl)ethylamino | H |
| 774. | —(CH₂SO₂)-phenyl | 2-(4-morpholinyl)ethylamino | H |
| 775. | —(CH₂SO₂)-phenyl | 3-(1-piperidinyl)propylamino | H |
| 776. | —(CH₂SO₂)-phenyl | 3-(1-pyrrolidinyl)propylamino | H |
| 777. | —(CH₂SO₂)-phenyl | 3-(4-morpholinyl)propylamino | H |
| 778. | —(CH₂SO₂)-phenyl | N-methyl-N-(2-piperid-1-ylethyl)amino | H |
| 779. | —(CH₂SO₂)-phenyl | N-methyl-N-(2-pyrrolidin-1-ylethyl)amino | H |
| 780. | —(CH₂SO₂)-phenyl | N-methyl-N-(2-morpholin-4-ylethyl)amino | H |
| 781. | —(CH₂SO₂)-phenyl | ((2S)-2-amino-3-phenylpropyl)amino | H |
| 782. | —(CH₂SO₂)-phenyl | 4-methylpiperazinylamino | H |
| 783. | —(CH₂SO₂)-phenyl | 4-methylpiperazinyl | H |
| 784. | —(CH₂SO₂)-phenyl | 3-aminopyrrolidinyl | H |
| 785. | —(CH₂SO₂)-phenyl | (diethylamino)ethylamino | H |
| 786. | —(CH₂SO₂)-phenyl | 3,5-dimethylpiperazin-1-yl | H |
| 787. | —(CH₂SO₂)-phenyl | (4-piperidylmethyl)amino | H |
| 788. | —(CH₂SO₂)-phenyl | (2-methylbutyl)amino | H |
| 789. | —(CH₂SO₂)-phenyl | 2-(dimethylamino)ethoxy | H |
| 790. | —(CH₂SO₂)-phenyl | 2-(methylamino)ethoxy | H |
| 791. | —(CH₂SO₂)-phenyl | ((2R)pyrrolidin-2-yl)methoxy | H |
| 792. | —(CH₂SO₂)-phenyl | ((2R)-1-methylpyrrolidin-2-yl)methoxy | H |
| 793. | —(CH₂SO₂)-phenyl | 2-(piperid-1-yl)ethoxy | H |
| 794. | —(CH₂SO₂)-phenyl | 2-(piperazin-1-yl)ethoxy | H |
| 795. | —(CH₂SO₂)-phenyl | 2-(morpholin-4-yl) ethoxy | NH₂ |
| 796. | —(CH₂SO₂)-phenyl | Cl | NH₂ |
| 797. | —(CH₂SO₂)-phenyl | cyclopropylmethylamino | NH₂ |
| 798. | —(CH₂SO₂)-phenyl | 3-hydroxypropylamino | NH₂ |
| 799. | —(CH₂SO₂)-phenyl | 2-(1-piperidinyl)ethylamino | NH₂ |
| 800. | —(CH₂SO₂)-phenyl | 2-(1-pyrrolidinyl)ethylamino | NH₂ |
| 801. | —(CH₂SO₂)-phenyl | 2-(4-morpholinyl)ethylamino | NH₂ |
| 802. | —(CH₂SO₂)-phenyl | 3-(1-piperidinyl)propylamino | NH₂ |
| 803. | —(CH₂SO₂)-phenyl | 3-(1-pyrrolidinyl)propylamino | NH₂ |
| 804. | —(CH₂SO₂) phenyl | 3-(4-morpholinyl)propylamino | NH₂ |
| 805. | —(CH₂SO₂)-phenyl | N-methyl-N-(2-piperid-1-ylethyl)amino | NH₂ |
| 806. | —(CH₂SO₂)-phenyl | N-methyl-N-(2-pyrrolidin-1-ylethyl)amino | NH₂ |
| 807. | —(CH₂SO₂)-phenyl | N-methyl-N-(2-morpholin-4-ylethyl)amino | NH₂ |
| 808. | —(CH₂SO₂)-phenyl | ((2S)-2-amino-3-phenylpropyl)amino | NH₂ |
| 809. | —(CH₂SO₂)-phenyl | 4-methylpiperazinylamino | NH₂ |
| 810. | —(CH₂SO₂)-phenyl | 4-methylpiperazinyl | NH₂ |
| 811. | —(CH₂SO₂)-phenyl | 3-aminopyrrolidinyl | NH₂ |
| 812. | —(CH₂SO₂)-phenyl | (diethylamino)ethylamino | NH₂ |
| 813. | —(CH₂SO₂)-phenyl | 3,5-dimethylpiperazin-1-yl | NH₂ |
| 814. | —(CH₂SO₂)-phenyl | (4-piperidylmethyl)amino | NH₂ |
| 815. | —(CH₂SO₂)-phenyl | (2-methylbutyl)amino | NH₂ |
| 816. | —(CH₂SO₂)-phenyl | 2-(dimethylamino)ethoxy | NH₂ |
| 817. | —(CH₂SO₂) phenyl | 2-(methylamino)ethoxy | NH₂ |

TABLE 2-continued

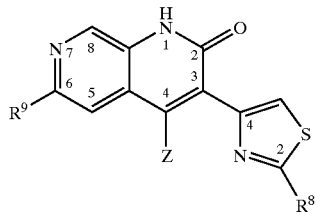

| # | R⁸ | R⁹ | Z |
|---|---|---|---|
| 818. | —(CH₂SO₂)-phenyl | ((2R)pyrrolidin-2-yl)methoxy | NH₂ |
| 819. | —(CH₂SO₂)-phenyl | ((2R)-1-methylpyrrolidin-2-yl)methoxy | NH₂ |
| 820. | —(CH₂SO₂)-phenyl | 2-(piperid-1-yl)ethoxy | NH₂ |
| 821. | —(CH₂SO₂)-phenyl | 2-(piperazin-1-yl)ethoxy | NH₂ |
| 822. | —(CH₂SO₂)-phenyl | 2-(morpholin-4-yl)ethoxy | NH₂ |
| 823. | —(CH₂SO₂)-2-thienyl | Cl | H |
| 824. | —(CH₂SO₂)-2-thienyl | cyclopropylmethylamino | H |
| 825. | —(CH₂SO₂)-2-thienyl | 3-hydroxypropylamino | H |
| 826. | —(CH₂SO₂)-2-thienyl | 2-(1-piperidinyl)ethylamino | H |
| 827. | —(CH₂SO₂)-2-thienyl | 2-(1-pyrrolidinyl)ethylamino | H |
| 828. | —(CH₂SO₂)-2-thienyl | 2-(4-morpholinyl)ethylamino | H |
| 829. | —(CH₂SO₂)-2-thienyl | 3-(1-piperidinyl)propylamino | H |
| 830. | —(CH₂SO₂)-2-thienyl | 3-(1-pyrrolidinyl)propylamino | H |
| 831. | —(CH₂SO₂)-2-thienyl | 3-(4-morpholinyl)propylamino | H |
| 832. | —(CH₂SO₂)-2-thienyl | N-methyl-N-(2-piperid-1-ylethyl)amino | H |
| 833. | —(CH₂SO₂)-2-thienyl | N-methyl-N-(2-pyrrolidin-1-ylethyl)amino | H |
| 834. | —(CH₂SO₂)-2-thienyl | N-methyl-N-(2-morpholin-4-ylethyl)amino | H |
| 835. | —(CH₂SO₂)-2-thienyl | ((2S)-2-amino-3-phenylpropyl)amino | H |
| 836. | —(CH₂SO₂)-2-thienyl | 4-methylpiperazinylamino | H |
| 837. | —(CH₂SO₂)-2-thienyl | 4-methylpiperazinyl | H |
| 838. | —(CH₂SO₂)-2-thienyl | 3-aminopyrrolidinyl | H |
| 839. | —(CH₂SO₂)-2-thienyl | (diethylamino)ethylamino | H |
| 840. | —(CH₂SO₂)-2-thienyl | 3,5-dimethylpiperazin-1-yl | H |
| 841. | —(CH₂SO₂) 2-thienyl | (4-piperidylmethyl)amino | H |
| 842. | —(CH₂SO₂)-2-thienyl | (2-methylbutyl)amino | H |
| 843. | —(CH₂SO₂)-2-thienyl | 2-(dimethylamino)ethoxy | H |
| 844. | —(CH₂SO₂)-2-thienyl | 2-(methylamino)ethoxy | H |
| 845. | —(CH₂SO₂)-2-thienyl | ((2R)pyrrolidin-2-yl)methoxy | H |
| 846. | —(CH₂SO₂)-2-thienyl | ((2R)-1-methylpyrrolidin-2-yl)methoxy | H |
| 847. | —(CH₂SO₂)-2-thienyl | 2-(piperid-1-yl)ethoxy | H |
| 848. | —(CH₂SO₂)-2-thienyl | 2-(piperazin-1-yl)ethoxy | H |
| 849. | —(CH₂SO₂)-2-thienyl | 2-(morpholin-4-yl)ethoxy | H |
| 850. | —(CH₂SO₂)-2-thienyl | Cl | NH₂ |
| 851. | —(CH₂SO₂)-2-thienyl | cyclopropylmethylamino | NH₂ |
| 852. | —(CH₂SO₂)-2-thienyl | 3-hydroxypropylamino | NH₂ |
| 853. | —(CH₂SO₂)-2-thienyl | 2-(1-piperidinyl)ethylamino | NH₂ |
| 854. | —(CH₂SO₂)-2-thienyl | 2-(1-pyrrolidinyl)ethylamino | NH₂ |
| 855. | —(CH₂SO₂)-2-thienyl | 2-(4-morpholinyl)ethylamino | NH₂ |
| 856. | —(CH₂SO₂)-2-thienyl | 3-(1-piperidinyl)propylamino | NH₂ |
| 857. | —(CH₂SO₂)-2-thienyl | 3-(1-pyrrolidinyl)propylamino | NH₂ |
| 858. | —(CH₂SO₂)-2-thienyl | 3-(4-morpholinyl)propylamino | NH₂ |
| 859. | —(CH₂SO₂)-2-thienyl | N-methyl-N-(2-piperid-1-ylethyl)amino | NH₂ |
| 860. | —(CH₂SO₂)-2-thienyl | N-methyl-N-(2-pyrrolidin-1-ylethyl)amino | NH₂ |
| 861. | —(CH₂SO₂)-2-thienyl | N-methyl-N-2-morpholin-4-ylethyl)amino | NH₂ |
| 862. | —(CH₂SO₂)-2-thienyl | ((2S)-2-amino-3-phenylpropyl)amino | NH₂ |
| 863. | —(CH₂SO₂)-2-thienyl | 4-methylpiperazinylamino | NH₂ |
| 864. | —(CH₂SO₂)-2-thienyl | 4-methylpiperazinyl | NH₂ |
| 865. | —(CH₂SO₂)-2-thienyl | 3-aminopyrrolidinyl | NH₂ |
| 866. | —(CH₂SO₂)-2-thienyl | (diethylamino)ethylamino | NH₂ |
| 867. | —(CH₂SO₂)-2-thienyl | 3,5-dimethylpiperazin-1-yl | NH₂ |
| 868. | —(CH₂SO₂)-2-thienyl | (4-piperidylmethyl)amino | NH₂ |
| 869. | —(CH₂SO₂)-2-thienyl | (2-methylbutyl)amino | NH₂ |
| 870. | —(CH₂SO₂)-2-thienyl | 2-(dimethylamino)ethoxy | NH₂ |
| 871. | —(CH₂SO₂) 2-thienyl | 2-(methylamino)ethoxy | NH₂ |
| 872. | —(CH₂SO₂)-2-thienyl | ((2R)pyrrolidin-2-yl)methoxy | NH₂ |
| 873. | —(CH₂SO₂)-2-thienyl | ((2R)-1-methylpyrrolidin-2-yl)methoxy | NH₂ |
| 874. | —(CH₂SO₂)-2-thienyl | 2-piperid-1-yl)ethoxy | NH₂ |
| 875. | —(CH₂SO₂)-2-thienyl | 2-(piperazin-1-yl)ethoxy | NH₂ |
| 876. | —(CH₂SO₂)-2-thienyl | 2-(morpholin-4-yl)ethoxy | NH₂ |
| 877. | —(CH₂SO₂)-2-pyridyl | Cl | H |
| 878. | —(CH₂SO₂)-2-pyridyl | cyclopropylmethylamino | H |
| 879. | —(CH₂SO₂)-2-pyridyl | 3-hydroxypropylamino | H |
| 880. | —(CH₂SO₂)-2-pyridyl | 2-(1-piperidinyl)ethylamino | H |
| 881. | —(CH₂SO₂)-2-pyridyl | 2-(1-pyrrolidinyl)ethylamino | H |
| 882. | —(CH₂SO₂)-2-pyridyl | 2-(4-morpholinyl)ethylamino | H |

TABLE 2-continued

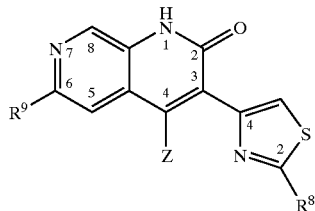

| # | $R^8$ | $R^9$ | Z |
|---|---|---|---|
| 883. | —($CH_2SO_2$)-2-pyridyl | 3-(1-piperidinyl)propylamino | H |
| 884. | —($CH_2SO_2$)-2-pyridyl | 3-(1-pyrrolidinyl)propylamino | H |
| 885. | —($CH_2SO_2$)-2-pyridyl | 3-(4-morpholinyl)propylamino | H |
| 886. | —($CH_2SO_2$)-2-pyridyl | N-methyl-N-(2-piperid-1-ylethyl)amino | H |
| 887. | —($CH_2SO_2$)-2-pyridyl | N-methyl-N-(2-pyrrolidin-1-ylethyl)amino | H |
| 888. | —($CH_2SO_2$)-2-pyridyl | N-methyl-N-(2-morpholin-4-ylethyl)amino | H |
| 889. | —($CH_2SO_2$)-2-pyridyl | ((2S)-2-amino-3-phenylpropyl)amino | H |
| 890. | —($CH_2SO_2$)-2-pyridyl | 4-methylpiperazinylamino | H |
| 891. | —($CH_2SO_2$)-2-pyridyl | 4-methylpiperazinyl | H |
| 892. | —($CH_2SO_2$)-2-pyridyl | 3-aminopyrrolidinyl | H |
| 893. | —($CH_2SO_2$)-2-pyridyl | (diethylamino)ethylamino | H |
| 894. | —($CH_2SO_2$) 2-pyridyl | 3,5-dimethylpiperazin-1-yl | H |
| 895. | —($CH_2SO_2$)-2-pyridyl | (4-piperidylmethyl)amino | H |
| 896. | —($CH_2SO_2$)-2-pyridyl | (2-methylbutyl)amino | H |
| 897. | —($CH_2SO_2$) 2-pyridyl | 2-(dimethylamino)ethoxy | H |
| 898. | —($CH_2SO_2$)-2-pyridyl | 2-(methylamino)ethoxy | H |
| 899. | —($CH_2SO_2$)-2-pyridyl | ((2R)pyrrolidin-2-yl)methoxy | H |
| 900. | —($CH_2SO_2$)-2-pyridyl | ((2R)-1-methylpyrrolidin-2-yl)methoxy | H |
| 901. | —($CH_2SO_2$)-2-pyridyl | 2-(piperid-1-yl)ethoxy | H |
| 902. | —($CH_2SO_2$)-2-pyridyl | 2-(piperazin-1-yl)ethoxy | H |
| 903. | —($CH_2SO_2$)-2-pyridyl | 2-(morpholin-4-yl)ethoxy | H |
| 904. | —($CH_2SO_2$)-2-pyridyl | Cl | $NH_2$ |
| 905. | —($CH_2SO_2$)-2-pyridyl | cyclopropylmethylamino | $NH_2$ |
| 906. | —($CH_2SO_2$)-2-pyridyl | 3-hydroxypropylamino | $NH_2$ |
| 907. | —($CH_2SO_2$)-2-pyridyl | 2-(1-piperidinyl)ethylamino | $NH_2$ |
| 908. | —($CH_2SO_2$)-2-pyridyl | 2-(1-pyrrolidinyl)ethylamino | $NH_2$ |
| 909. | —($CH_2SO_2$)-2-pyridyl | 2-(4-morpholinyl)ethylamino | $NH_2$ |
| 910. | —($CH_2SO_2$)-2-pyridyl | 3-(1-piperidinyl)propylamino | $NH_2$ |
| 911. | —($CH_2SO_2$)-2-pyridyl | 3-(1-pyrrolidinyl)propylamino | $NH_2$ |
| 912. | —($CH_2SO_2$)-2-pyridyl | 3-(4-morpholinyl)propylamino | $NH_2$ |
| 913. | —($CH_2SO_2$)-2-pyridyl | N-methyl-N-(2-piperid-1-ylethyl)amino | $NH_2$ |
| 914. | —($CH_2SO_2$)-2-pyridyl | N-methyl-N-(2-pyrrolidin-1-ylethyl)amino | $NH_2$ |
| 915. | —($CH_2SO_2$)-2-pyridyl | N-methyl-N-(2-morpholin-4-ylethyl)amino | $NH_2$ |
| 916. | —($CH_2SO_2$)-2-pyridyl | ((2S)-2-amino-3-phenylpropyl)amino | $NH_2$ |
| 917. | —($CH_2SO_2$)-2-pyridyl | 4-methylpiperazinylamino | $NH_2$ |
| 918. | —($CH_2SO_2$)-2-pyridyl | 4-methylpiperazinyl | $NH_2$ |
| 919. | —($CH_2SO_2$)-2-pyridyl | 3-aminopyrrolidinyl | $NH_2$ |
| 920. | —($CH_2SO_2$)-2-pyridyl | (diethylamino)ethylamino | $NH_2$ |
| 921. | —($CH_2SO_2$)-2-pyridyl | 3,5-dimethylpiperazin-1-yl | $NH_2$ |
| 922. | —($CH_2SO_2$)-2-pyridyl | (4-piperidylmethyl)amino | $NH_2$ |
| 923. | —($CH_2SO_2$)-2-pyridyl | (2-methylbutyl)amino | $NH_2$ |
| 924. | —($CH_2SO_2$)-2-pyridyl | 2-(dimethylamino)ethoxy | $NH_2$ |
| 925. | —($CH_2SO_2$)-2-pyridyl | 2-(methylamino)ethoxy | $NH_2$ |
| 926. | —($CH_2SO_2$)-2-pyridyl | ((2R)pyrrolidin-2-yl)methoxy | $NH_2$ |
| 927. | —($CH_2SO_2$)-2-pyridyl | ((2R)-1-methylpyrrolidin-2-yl)methoxy | $NH_2$ |
| 928. | —($CH_2SO_2$)-2-pyridyl | 2-(piperid-1-yl)ethoxy | $NH_2$ |
| 929. | —($CH_2SO_2$)-2-pyridyl | 2-(piperazin-1-yl)ethoxy | $NH_2$ |
| 930. | —($CH_2SO_2$)-2-pyridyl | 2-(morpholin-4-yl)ethoxy | $NH_2$ |
| 931. | —($CH_2SO_2$)-3-pyridyl | Cl | H |
| 932. | —($CH_2SO_2$)-3-pyridyl | cyclopropylmethylamino | H |
| 933. | —($CH_2SO_2$)-3-pyridyl | 3-hydroxypropylamino | H |
| 934. | —($CH_2SO_2$)-3-pyridyl | 2-(1-piperidinyl)ethylamino | H |
| 935. | —($CH_2SO_2$)-3-pyridyl | 2-(1-pyrrolidinyl)ethylamino | H |
| 936. | —($CH_2SO_2$)-3-pyridyl | 2-(4-morpholinyl)ethylamino | H |
| 937. | —($CH_2SO_2$)-3-pyridyl | 3-(1-piperidinyl)propylamino | H |
| 938. | —($CH_2SO_2$)-3-pyridyl | 3-(1-pyrrolidinyl)propylamino | H |
| 939. | —($CH_2SO_2$)-3-pyridyl | 3-(4-morpholinyl)propylamino | H |
| 940. | —($CH_2SO_2$)-3-pyridyl | N-methyl-N-(2-piperid-1-ylethyl)amino | H |
| 941. | —($CH_2SO_2$)-3-pyridyl | N-methyl-N-(2-pyrrolidin-1-ylethyl)amino | H |
| 942. | —($CH_2SO_2$)-3-pyridyl | N-methyl-N-(2-morpholin-4-ylethyl)amino | H |
| 943. | —($CH_2SO_2$)-3-pyridyl | ((2S)-2-amino-3-phenylpropyl)amino | H |
| 944. | —($CH_2SO_2$)-3-pyridyl | 4-methylpiperazinylamino | H |
| 945. | —($CH_2SO_2$)-3-pyridyl | 4-methylpiperazinyl | H |
| 946. | —($CH_2SO_2$)-3-pyridyl | 3-aminopyrrolidinyl | H |
| 947. | —($CH_2SO_2$)-3-pyridyl | (diethylamino)ethylamino | H |

TABLE 2-continued

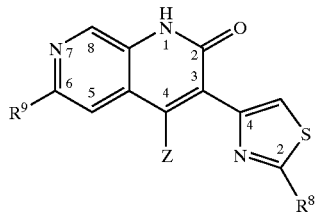

| # | R⁸ | R⁹ | Z |
|---|---|---|---|
| 948. | —(CH$_2$SO$_2$)-3-pyridyl | 3,5-dimethylpiperazin-1-yl | H |
| 949. | —(CH$_2$SO$_2$)-3-pyridyl | (4-piperidylmethyl)amino | H |
| 950. | —(CH$_2$SO$_2$)-3-pyridyl | (2-methylbutyl)amino | H |
| 951. | —(CH$_2$SO$_2$)-3-pyridyl | 2-(dimethylamino)ethoxy | H |
| 952. | —(CH$_2$SO$_2$)-3-pyridyl | 2-(methylamino)ethoxy | H |
| 953. | —(CH$_2$SO$_2$)-3-pyridyl | ((2R)pyrrolidin-2-yl)methoxy | H |
| 954. | —(CH$_2$SO$_2$)-3-pyridyl | ((2R)-1-methylpyrrolidin-2-yl)methoxy | H |
| 955. | —(CH$_2$SO$_2$)-3-pyridyl | 2-(piperid-1-yl)ethoxy | H |
| 956. | —(CH$_2$SO$_2$)-3-pyridyl | 2-(piperazin-1-yl)ethoxy | H |
| 957. | —(CH$_2$SO$_2$)-3-pyridyl | 2-(morpholin-4-yl)ethoxy | H |
| 958. | —(CH$_2$SO$_2$)-3-pyridyl | Cl | NH$_2$ |
| 959. | —(CH$_2$SO$_2$)-3-pyridyl | cyclopropylmethylamino | NH$_2$ |
| 960. | —(CH$_2$SO$_2$)-3-pyridyl | 3-hydroxypropylamino | NH$_2$ |
| 961. | —(CH$_2$SO$_2$)-3-pyridyl | 2-(1-piperidinyl)ethylamino | NH$_2$ |
| 962. | —(CH$_2$SO$_2$)-3-pyridyl | 2-(1-pyrrolidinyl)ethylamino | NH$_2$ |
| 963. | —(CH$_2$SO$_2$)-3-pyridyl | 2-(4-morpholinyl)ethylamino | NH$_2$ |
| 964. | —(CH$_2$SO$_2$)-3-pyridyl | 3-(1-piperidinyl)propylamino | NH$_2$ |
| 965. | —(CH$_2$SO$_2$)-3-pyridyl | 3-(1-pyrrolidinyl)propylamino | NH$_2$ |
| 966. | —(CH$_2$SO$_2$)-3-pyridyl | 3-(4-morpholinyl)propylamino | NH$_2$ |
| 967. | —(CH$_2$SO$_2$)-3-pyridyl | N-methyl-N-(2-piperid-1-ylethyl)amino | NH$_2$ |
| 968. | —(CH$_2$SO$_2$)-3-pyridyl | N-methyl-N-(2-pyrrolidin-1-ylethyl)amino | NH$_2$ |
| 969. | —(CH$_2$SO$_2$)-3-pyridyl | N-methyl-N-(2-morpholin-4-ylethyl)amino | NH$_2$ |
| 970. | —(CH$_2$SO$_2$)-3-pyridyl | ((2S)-2-amino-3-phenylpropyl)amino | NH$_2$ |
| 971. | —(CH$_2$SO$_2$)-3-pyridyl | 4-methylpiperazinylamino | NH$_2$ |
| 972. | —(CH$_2$SO$_2$)-3-pyridyl | 4-methylpiperazinyl | NH$_2$ |
| 973. | —(CH$_2$SO$_2$)-3-pyridyl | 3-aminopyrrolidinyl | NH$_2$ |
| 974. | —(CH$_2$SO$_2$)-3-pyridyl | (diethylamino)ethylamino | NH$_2$ |
| 975. | —(CH$_2$SO$_2$)-3-pyridyl | 3,5-dimethylpiperazin-1-yl | NH$_2$ |
| 976. | —(CH$_2$SO$_2$)-3-pyridyl | (4-piperidylmethyl)amino | NH$_2$ |
| 977. | —(CH$_2$SO$_2$)-3-pyridyl | (2-methylbutyl)amino | NH$_2$ |
| 978. | —(CH$_2$SO$_2$)-3-pyridyl | 2-(dimethylamino)ethoxy | NH$_2$ |
| 979. | —(CH$_2$SO$_2$)-3-pyridyl | 2-(methylamino)ethoxy | NH$_2$ |
| 980. | —(CH$_2$SO$_2$)-3-pyridyl | ((2R)pyrrolidin-2-yl)methoxy | NH$_2$ |
| 981. | —(CH$_2$SO$_2$)-3-pyridyl | ((2R)-1-methylpyrrolidin-2-yl)methoxy | NH$_2$ |
| 982. | —(CH$_2$SO$_2$)-3-pyridyl | 2-(piperid-1-yl)ethoxy | NH$_2$ |
| 983. | —(CH$_2$SO$_2$)-3-pyridyl | 2-(piperazin-1-yl)ethoxy | NH$_2$ |
| 984. | —(CH$_2$SO$_2$)-3-pyridyl | 2-(morpholin-4-yl)ethoxy | NH$_2$ |
| 985. | —(CH$_2$SO$_2$)-4-pyridyl | Cl | H |
| 986. | —(CH$_2$SO$_2$)-4-pyridyl | cyclopropylmethylamino | H |
| 987. | —(CH$_2$SO$_2$)-4-pyridyl | 3-hydroxypropylamino | H |
| 988. | —(CH$_2$SO$_2$)-4-pyridyl | 2-(1-piperidinyl)ethylamino | H |
| 989. | —(CH$_2$SO$_2$)-4-pyridyl | 2-(1-pyrrolidinyl)ethylamino | H |
| 990. | —(CH$_2$SO$_2$)-4-pyridyl | 2-(4-morpholinyl)ethylamino | H |
| 991. | —(CH$_2$SO$_2$)-4-pyridyl | 3-(1-piperidinyl)propylamino | H |
| 992. | —(CH$_2$SO$_2$)-4-pyridyl | 3-(1-pyrrolidinyl)propylamino | H |
| 993. | —(CH$_2$SO$_2$)-4-pyridyl | 3-(4-morpholinyl)propylamino | H |
| 994. | —(CH$_2$SO$_2$)-4-pyridyl | N-methyl-N-(2-piperid-1-ylethyl)amino | H |
| 995. | —(CH$_2$SO$_2$)-4-pyridyl | N-methyl-N-(2-pyrrolidin-1-ylethyl)amino | H |
| 996. | —(CH$_2$SO$_2$)-4-pyridyl | N-methyl-N-(2-morpholin-4-ylethyl)amino | H |
| 997. | —(CH$_2$SO$_2$)-4-pyridyl | ((2S)-2-amino-3-phenylpropyl)amino | H |
| 998. | —(CH$_2$SO$_2$)-4-pyridyl | 4-methylpiperazinylamino | H |
| 999. | —(CH$_2$SO$_2$)-4-pyridyl | 4-methylpiperazinyl | H |
| 1000. | —(CH$_2$SO$_2$)-4-pyridyl | 3-aminopyrrolidinyl | H |
| 1001. | —(CH$_2$SO$_2$)-4-pyridyl | (diethylamino)ethylamino | H |
| 1002. | —(CH$_2$SO$_2$)-4-pyridyl | 3,5-dimethylpiperazin-1-yl | H |
| 1003. | —(CH$_2$SO$_2$)-4-pyridyl | (4-piperidylmethyl)amino | H |
| 1004. | —(CH$_2$SO$_2$)-4-pyridyl | (2-methylbutyl)amino | H |
| 1005. | —(CH$_2$SO$_2$)-4-pyridyl | 2-(dimethylamino)ethoxy | H |
| 1006. | —(CH$_2$SO$_2$)-4-pyridyl | 2-(methylamino)ethoxy | H |
| 1007. | —(CH$_2$SO$_2$)-4-pyridyl | ((2R)pyrrolidin-2-yl)methoxy | H |
| 1008. | —(CH$_2$SO$_2$)-4-pyridyl | ((2R)-1-methylpyrrolidin-2-yl)methoxy | H |
| 1009. | —(CH$_2$SO$_2$)-4-pyridyl | 2-(piperid-1-yl)ethoxy | H |
| 1010. | —(CH$_2$SO$_2$)-4-pyridyl | 2-(piperazin-1-yl)ethoxy | H |
| 1011. | —(CH$_2$SO$_2$)-4-pyridyl | 2-(morpholin-4-yl)ethoxy | H |
| 1012. | —(CH$_2$SO$_2$)-4-pyridyl | Cl | NH$_2$ |

TABLE 2-continued

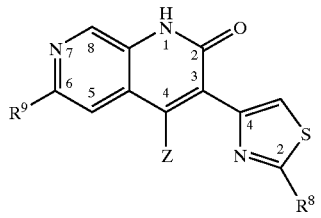

| # | R⁸ | R⁹ | Z |
|---|---|---|---|
| 1013. | —(CH₂SO₂)-4-pyridyl | cyclopropylmethylamino | NH₂ |
| 1014. | —(CH₂SO₂)-4-pyridyl | 3-hydroxypropylamino | NH₂ |
| 1015. | —(CH₂SO₂)-4-pyridyl | 2-(1-piperidinyl)ethylamino | NH₂ |
| 1016. | —(CH₂SO₂)-4-pyridyl | 2-(1-pyrrolidinyl)ethylamino | NH₂ |
| 1017. | —(CH₂SO₂)-4-pyridyl | 2-(4-morpholinyl)ethylamino | NH₂ |
| 1018. | —(CH₂SO₂)-4-pyridyl | 3-(1-piperidinyl)propylamino | NH₂ |
| 1019. | —(CH₂SO₂)-4-pyridyl | 3-(1-pyrrolidinyl)propylamino | NH₂ |
| 1020. | —(CH₂SO₂)-4-pyridyl | 3-(4-morpholinyl)propylamino | NH₂ |
| 1021. | —(CH₂SO₂)-4-pyridyl | N-methyl-N-(2-piperid-1-ylethyl)amino | NH₂ |
| 1022. | —(CH₂SO₂)-4-pyridyl | N-methyl-N-(2-pyrrolidin-1-ylethyl)amino | NH₂ |
| 1023. | —(CH₂SO₂)-4-pyridyl | N-methyl-N-(2-morpholin-4-ylethyl)amino | NH₂ |
| 1024. | —(CH₂SO₂)-4-pyridyl | ((2S)-2-amino-3-phenylpropyl)amino | NH₂ |
| 1025. | —(CH₂SO₂)-4-pyridyl | 4-methylpiperazinylamino | NH₂ |
| 1026. | —(CH₂SO₂)-4-pyridyl | 4-methylpiperazinyl | NH₂ |
| 1027. | —(CH₂SO₂)-4-pyridyl | 3-aminopyrrolidinyl | NH₂ |
| 1028. | —(CH₂SO₂)-4-pyridyl | (diethylamino)ethylamino | NH₂ |
| 1029. | —(CH₂SO₂)-4-pyridyl | 3,5-dimethylpiperazin-1-yl | NH₂ |
| 1030. | —(CH₂SO₂)-4-pyridyl | (4-piperidylmethyl)amino | NH₂ |
| 1031. | —(CH₂SO₂)-4-pyridyl | (2-methylbutyl)amino | NH₂ |
| 1032. | —(CH₂SO₂)-4-pyridyl | 2-(dimethylamino)ethoxy | NH₂ |
| 1033. | —(CH₂SO₂)-4-pyridyl | 2-(methylamino)ethoxy | NH₂ |
| 1034. | —(CH₂SO₂)-4-pyridyl | ((2R)pyrrolidin-2-yl)methoxy | NH₂ |
| 1035. | —(CH₂SO₂)-4-pyridyl | ((2R)-1-methylpyrrolidin-2-yl)methoxy | NH₂ |
| 1036. | —(CH₂SO₂)-4-pyridyl | 2-(piperid-1-yl)ethoxy | NH₂ |
| 1037. | —(CH₂SO₂)-4-pyridyl | 2-(piperazin-1-yl)ethoxy | NH₂ |
| 1038. | —(CH₂SO₂)-4-pyridyl | 2-(morpholin-4-yl)ethoxy | NH₂ |
| 1039. | —(NMeSO₂)-phenyl | Cl | H |
| 1040. | —(NMeSO₂)-phenyl | cyclopropylmethylamino | H |
| 1041. | —(NMeSO₂)-phenyl | 3-hydroxypropylamino | H |
| 1042. | —(NMeSO₂)-phenyl | 2-(1-piperidinyl)ethylamino | H |
| 1043. | —(NMeSO₂)-phenyl | 2-(1-pyrrolidinyl)ethylamino | H |
| 1044. | —(NMeSO₂)-phenyl | 2-(4-morpholinyl)ethylamino | H |
| 1045. | —(NMeSO₂)-phenyl | 3-(1-piperidinyl)propylamino | H |
| 1046. | —(NMeSO₂)-phenyl | 3-(1-pyrrolidinyl)propylamino | H |
| 1047. | —(NMeSO₂)-phenyl | 3-(4-morpholinyl)propylamino | H |
| 1048. | —(NMeSO₂)-phenyl | N-methyl-N-(2-piperid-1-ylethyl)amino | H |
| 1049. | —(NMeSO₂)-phenyl | M-methyl-N-(2-pyrrolidin-1-ylethyl)amino | H |
| 1050. | —(NMeSO₂)-phenyl | N-methyl-N-(2-morpholin-4-ylethyl)amino | H |
| 1051. | —(NMeSO₂) phenyl | ((2S)-2-amino-3-phenylpropyl)amino | H |
| 1052. | —(NMeSO₂)-phenyl | 4-methylpiperazinylamino | H |
| 1053. | —(NMeSO₂)-phenyl | 4-methylpiperazinyl | H |
| 1054. | —(NMeSO₂)-phenyl | 3-aminopyrrolidinyl | H |
| 1055. | —(NMeSO₂)-phenyl | (diethylamino)ethylamino | H |
| 1056. | —(NMeSO₂)-phenyl | 3,5-dimethylpiperazin-1-yl | H |
| 1057. | —(NMeSO₂)-phenyl | (4-piperidylmethyl)amino | H |
| 1058. | —(NMeSO₂)-phenyl | (2-methylbutyl)amino | H |
| 1059. | —(NMeSO₂)-phenyl | 2-(dimethylamino)ethoxy | H |
| 1060. | —(NMeSO₂)-phenyl | 2-(methylamino)ethoxy | H |
| 1061. | —(NMeSO₂)-phenyl | ((2R)pyrrolidin-2-yl)methoxy | H |
| 1062. | —(NMeSO₂)-phenyl | ((2R)-1-methylpyrrolidin-2-yl)methoxy | H |
| 1063. | —(NMeSO₂)-phenyl | 2-(piperid-1-yl)ethoxy | H |
| 1064. | —(NMeSO₂)-phenyl | 2-(piperazin-1-yl)ethoxy | H |
| 1065. | —(NMeSO₂)-phenyl | 2-(morpholin-4-yl)ethoxy | H |
| 1066. | —(NMeSO₂)-phenyl | Cl | NH₂ |
| 1067. | —(NMeSO₂)-phenyl | cyclopropylmethylamino | NH₂ |
| 1068. | —(NMeSO₂)-phenyl | 3-hydroxypropylamino | NH₂ |
| 1069. | —(NMeSO₂)-phenyl | 2-(1-piperidinyl)ethylamino | NH₂ |
| 1070. | —(NMeSO₂) phenyl | 2-(1-pyrrolidinyl)ethylamino | NH₂ |
| 1071. | —(NMeSO₂)-phenyl | 2-(4-morpholinyl)ethylamino | NH₂ |
| 1072. | —(NMeSO₂)-phenyl | 3-(1-piperidinyl)propylamino | NH₂ |
| 1073. | —(NMeSO₂)-phenyl | 3-(1-pyrrolidinyl)propylamino | NH₂ |
| 1074. | —(NMeSO₂)-phenyl | 3-(4-morpholinyl)propylamino | NH₂ |
| 1075. | —(NMeSO₂)-phenyl | N-methyl-N-(2-piperid-1-ylethyl)amino | NH₂ |
| 1076. | —(NMeSO₂)-phenyl | N-methyl-N-(2-pyrrolidin-1-ylethyl)amino | NH₂ |
| 1077. | —(NMeSO₂)-phenyl | N-methyl-N-(2-morpholin-4-ylethyl)amino | NH₂ |

TABLE 2-continued

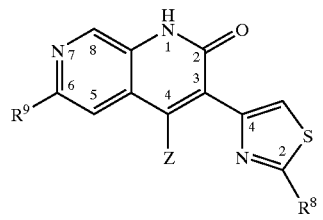

| # | R⁸ | R⁹ | Z |
|---|---|---|---|
| 1078. | —(NMeSO₂)-phenyl | ((2S)-2-amino-3-phenylpropyl)amino | NH₂ |
| 1079. | —(NMeSO₂)-phenyl | 4-methylpiperazinylamino | NH₂ |
| 1080. | —(NMeSO₂)-phenyl | 4-methylpiperazinyl | NH₂ |
| 1081. | —(NMeSO₂)-phenyl | 3-aminopyrrolidinyl | NH₂ |
| 1082. | —(NMeSO₂)-phenyl | (diethylamino)ethylamino | NH₂ |
| 1083. | —(NMeSO₂)-phenyl | 3,5-dimethylpiperazin-1-yl | NH₂ |
| 1084. | —(NMeSO₂)-phenyl | (4-piperidylmethyl)amino | NH₂ |
| 1085. | —(NMeSO₂)-phenyl | (2-methylbutyl)amino | NH₂ |
| 1086. | —(NMeSO₂)-phenyl | 2-(dimethylamino)ethoxy | NH₂ |
| 1087. | —(NMeSO₂)-phenyl | 2-(methylamino)ethoxy | NH₂ |
| 1088. | —(NMeSO₂)-phenyl | ((2R)pyrrolidin-2-yl)methoxy | NH₂ |
| 1089. | —(NMeSO₂)-phenyl | ((2R)-1-methylpyrrolidin-2-yl)methoxy | NH₂ |
| 1090. | —(NMeSO₂)-phenyl | 2-(piperid-1-yl)ethoxy | NH₂ |
| 1091. | —(NMeSO₂)-phenyl | 2-(piperazin-1-yl)ethoxy | NH₂ |
| 1092. | —(NMeSO₂)-phenyl | 2-(morpholin-4-yl)ethoxy | NH₂ |
| 1093. | —(NMeSO₂)-2-thienyl | Cl | H |
| 1094. | —(NMeSO₂)-2-thienyl | cyclopropylmethylamino | H |
| 1095. | —(NMeSO₂)-2-thienyl | 3-hydroxypropylamino | H |
| 1096. | —(NMeSO₂)-2-thienyl | 2-(1-piperidinyl)ethylamino | H |
| 1097. | —(NMeSO₂)-2-thienyl | 2-(1-pyrrolidinyl)ethylamino | H |
| 1098. | —(NMeSO₂) 2-thienyl | 2-(4-morpholinyl)ethylamino | H |
| 1099. | —(NMeSO₂)-2-thienyl | 3-(1-piperidinyl)propylamino | H |
| 1100. | —(NMeSO₂)-2-thienyl | 3-(1-pyrrolidinyl)propylamino | H |
| 1101. | —(NMeSO₂)-2-thienyl | 3-(4-morpholinyl)propylamino | H |
| 1102. | —(NMeSO₂)-2-thienyl | N-methyl-N-(2-piperid-1-ylethyl)amino | H |
| 1103. | —(NMeSO₂)-2-thienyl | N-methyl-N-(2-pyrrolidin-1-ylethyl)amino | H |
| 1104. | —(NMeSO₂)-2-thienyl | N-methyl-N-(2-morpholin-4-ylethyl)amino | H |
| 1105. | —(NMeSO₂)-2-thienyl | ((2S)-2-amino-3-phenylpropyl)amino | H |
| 1106. | —(NMeSO₂)-2-thienyl | 4-methylpiperazinylamino | H |
| 1107. | —(NMeSO₂)-2-thienyl | 4-methylpiperazinyl | H |
| 1108. | —(NMeSO₂)-2-thienyl | 3-aminopyrrolidinyl | H |
| 1109. | —(NMeSO₂)-2-thienyl | (diethylamino)ethylamino | H |
| 1110. | —(NMeSO₂)-2-thienyl | 3,5-dimethylpiperazin-1-yl | H |
| 1111. | —(NMeSO₂)-2-thienyl | (4-piperidylmethyl)amino | H |
| 1112. | —(NMeSO₂)-2-thienyl | (2-methylbutyl)amino | H |
| 1113. | —(NMeSO₂)-2-thienyl | 2-(dimethylamino)ethoxy | H |
| 1114. | —(NMeSO₂)-2-thienyl | 2-(methylamino)ethoxy | H |
| 1115. | —(NMeSO₂)-2-thienyl | ((2R)pyrrolidin-2-yl)methoxy | H |
| 1116. | —(NMeSO₂)-2-thienyl | ((2R)-1-methylpyrrolidin-2-yl)methoxy | H |
| 1117. | —(NMeSO₂)-2-thienyl | 2-(piperid-1-yl)ethoxy | H |
| 1118. | —(NMeSO₂)-2-thienyl | 2-(piperazin-1-yl)ethoxy | H |
| 1119. | —(NMeSO₂)-2-thienyl | 2-(morpholin-4-yl)ethoxy | H |
| 1120. | —(NMeSO₂)-2-thienyl | Cl | NH₂ |
| 1121. | —(NMeSO₂)-2-thienyl | cyclopropylmethylamino | NH₂ |
| 1122. | —(NMeSO₂)-2-thienyl | 3-hydroxypropylamino | NH₂ |
| 1123. | —(NMeSO₂)-2-thienyl | 2-(1-piperidinyl)ethylamino | NH₂ |
| 1124. | —(NMeSO₂)-2-thienyl | 2-(1-pyrrolidinyl)ethylamino | NH₂ |
| 1125. | —(NMeSO₂)-2-thienyl | 2-(4-morpholinyl)ethylamino | NH₂ |
| 1126. | —(NMeSO₂)-2-thienyl | 3-(1-piperidinyl)propylamino | NH₂ |
| 1127. | —(NMeSO₂)-2-thienyl | 3-(1-pyrrolidinyl)propylamino | NH₂ |
| 1128. | —(NMeSO₂)-2-thienyl | 3-(4-morpholinyl)propylamino | NH₂ |
| 1129. | —(NMeSO₂)-2-thienyl | N-methyl-N-(2-piperid-1-ylethyl)amino | NH₂ |
| 1130. | —(NMeSO₂)-2-thienyl | N-methyl-N-(2-pyrrolidin-1-ylethyl)amino | NH₂ |
| 1131. | —(NMeSO₂)-2-thienyl | N-methyl-N-(2-morpholin-4-ylethyl)amino | NH₂ |
| 1132. | —(NMeSO₂)-2-thienyl | ((2S)-2-amino-3-phenylpropyl)amino | NH₂ |
| 1133. | —(NMeSO₂)-2-thienyl | 4-methylpiperazinylamino | NH₂ |
| 1134. | —(NMeSO₂)-2-thienyl | 4-methylpiperazinyl | NH₂ |
| 1135. | —(NMeSO₂)-2-thienyl | 3-aminopyrrolidinyl | NH₂ |
| 1136. | —(NMeSO₂)-2-thienyl | (diethylamino)ethylamino | NH₂ |
| 1137. | —(NMeSO₂)-2-thienyl | 3,5-dimethylpiperazin-1-yl | NH₂ |
| 1138. | —(NMeSO₂)-2-thienyl | (4-piperidylmethyl)amino | NH₂ |
| 1139. | —(NMeSO₂)-2-thienyl | (2-methylbutyl)amino | NH₂ |
| 1140. | —(NMeSO₂)-2-thienyl | 2-(dimethylamino)ethoxy | NH₂ |
| 1141. | —(NMeSO₂)-2-thienyl | 2-(methylamino)ethoxy | NH₂ |
| 1142. | —(NMeSO₂)-2-thienyl | ((2R)pyrrolidin-2-yl)methoxy | NH₂ |

TABLE 2-continued

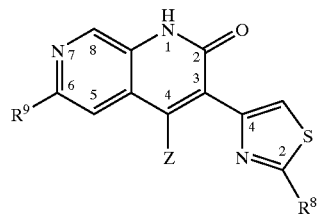

| # | R⁸ | R⁹ | Z |
|---|---|---|---|
| 1143. | —(NMeSO₂)-2-thienyl | ((2R)-1-methylpyrrolidin-2-yl)methoxy | NH₂ |
| 1144. | —(NMeSO₂)-2-thienyl | 2-(piperid-1-yl)ethoxy | NH₂ |
| 1145. | —(NMeSO₂)-2-thienyl | 2-(piperazin-1-yl)ethoxy | NH₂ |
| 1146. | —(NMeSO₂)-2-thienyl | 2-(morpholin-4-yl)ethoxy | NH₂ |
| 1147. | —(NMeSO₂)-2-pyridyl | Cl | H |
| 1148. | —(NMeSO₂)-2-pyridyl | cyclopropylmethylamino | H |
| 1149. | —(NMeSO₂)-2-pyridyl | 3-hydroxypropylamino | H |
| 1150. | —(NMeSO₂)-2-pyridyl | 2-(1-piperidinyl)ethylamino | H |
| 1151. | —(NMeSO₂)-2-pyridyl | 2-(1-pyrrolidinyl)ethylamino | H |
| 1152. | —(NMeSO₂)-2-pyridyl | 2-(4-morpholinyl)ethylamino | H |
| 1153. | —(NMeSO₂)-2-pyridyl | 3-(1-piperidinyl)propylamino | H |
| 1154. | —(NMeSO₂)-2-pyridyl | 3-(1-pyrrolidinyl)propylamino | H |
| 1155. | —(NMeSO₂)-2-pyridyl | 3-(4-morpholinyl)propylamino | H |
| 1156. | —(NMeSO₂)-2-pyridyl | N-methyl-N-(2-piperid-1-ylethyl)amino | H |
| 1157. | —(NMeSO₂)-2-pyridyl | N-methyl-N-(2-pyrrolidin-1-ylethyl)amino | H |
| 1158. | —(NMeSO₂)-2-pyridyl | N-methyl-N-(2-morpholin-4-ylethyl)amino | H |
| 1159. | —(NMeSO₂)-2-pyridyl | ((2S)-2-amino-3-phenylpropyl)amino | H |
| 1160. | —(NMeSO₂)-2-pyridyl | 4-methylpiperazinylamino | H |
| 1161. | —(NMeSO₂)-2-pyridyl | 4-methylpiperazinyl | H |
| 1162. | —(NMeSO₂)-2-pyridyl | 3-aminopyrrolidinyl | H |
| 1163. | —(NMeSO₂)-2-pyridyl | (diethylamino)ethylamino | H |
| 1164. | —(NMeSO₂)-2-pyridyl | 3,5-dimethylpiperazin-1-yl | H |
| 1165. | —(NMeSO₂)-2-pyridyl | (4-piperidylmethyl)amino | H |
| 1166. | —(NMeSO₂)-2-pyridyl | (2-methylbutyl)amino | H |
| 1167. | —(NMeSO₂)-2-pyridyl | 2-(dimethylamino)ethoxy | H |
| 1168. | —(NMeSO₂)-2-pyridyl | 2-(methylamino)ethoxy | H |
| 1169. | —(NMeSO₂)-2-pyridyl | ((2R)pyrrolidin-2-yl)methoxy | H |
| 1170. | —(NMeSO₂)-2-pyridyl | ((2R)-1-methylpyrrolidin-2-yl)methoxy | H |
| 1171. | —(NMeSO₂)-2-pyridyl | 2-(piperid-1-yl)ethoxy | H |
| 1172. | —(NMeSO₂)-2-pyridyl | 2-(piperazin-1-yl)ethoxy | H |
| 1173. | —(NMeSO₂)-2-pyridyl | 2-(morpholin-4-yl)ethoxy | H |
| 1174. | —(NMeSO₂)-2-pyridyl | Cl | NH₂ |
| 1175. | —(NMeSO₂)-2-pyridyl | cyclopropylmethylamino | NH₂ |
| 1176. | —(NMeSO₂)-2-pyridyl | 3-hydroxypropylamino | NH₂ |
| 1177. | —(NMeSO₂)-2-pyridyl | 2-(1-piperidinyl)ethylamino | NH₂ |
| 1178. | —(NMeSO₂)-2-pyridyl | 2-(1-pyrrolidinyl)ethylamino | NH₂ |
| 1179. | —(NMeSO₂)-2-pyridyl | 2-(4-morpholinyl)ethylamino | NH₂ |
| 1180. | —(NMeSO₂)-2-pyridyl | 3-(1-piperidinyl)propylamino | NH₂ |
| 1181. | —(NMeSO₂)-2-pyridyl | 3-(1-pyrrolidinyl)propylamino | NH₂ |
| 1182. | —(NMeSO₂)-2-pyridyl | 3-(4-morpholinyl)propylamino | NH₂ |
| 1183. | —(NMeSO₂)-2-pyridyl | N-methyl-N-(2-piperid-1-ylethyl)amino | NH₂ |
| 1184. | —(NMeSO₂)-2-pyridyl | N-methyl-N-(2-pyrrolidin-1-ylethyl)amino | NH₂ |
| 1185. | —(NMeSO₂)-2-pyridyl | N-methyl-N-(2-morpholin-4-ylethyl)amino | NH₂ |
| 1186. | —(NMeSO₂) 2-pyridyl | ((2S)-2-amino-3-phenylpropyl)amino | NH₂ |
| 1187. | —(NMeSO₂)-2-pyridyl | 4-methylpiperazinylamino | NH₂ |
| 1188. | —(NMeSO₂)-2-pyridyl | 4-methylpiperazinyl | NH₂ |
| 1189. | —(NMeSO₂)-2-pyridyl | 3-aminopyrrolidinyl | NH₂ |
| 1190. | —(NMeSO₂)-2-pyridyl | (diethylamino)ethylamino | NH₂ |
| 1191. | —(NMeSO₂)-2-pyridyl | 3,5-dimethylpiperazin-1-yl | NH₂ |
| 1192. | —(NMeSO₂)-2-pyridyl | (4-piperidylmethyl)amino | NH₂ |
| 1193. | —(NMeSO₂)-2-pyridyl | (2-methylbutyl)amino | NH₂ |
| 1194. | —(NMeSO₂)-2-pyridyl | 2-(dimethylamino)ethoxy | NH₂ |
| 1195. | —(NMeSO₂)-2-pyridyl | 2-(methylamino)ethoxy | NH₂ |
| 1196. | —(NMeSO₂)-2-pyridyl | ((2R)pyrrolidin-2-yl)methoxy | NH₂ |
| 1197. | —(NMeSO₂)-2-pyridyl | ((2R)-1-methylpyrrolidin-2-yl)methoxy | NH₂ |
| 1198. | —(NMeSO₂)-2-pyridyl | 2-(piperid-1-yl)ethoxy | NH₂ |
| 1199. | —(NMeSO₂)-2-pyridyl | 2-(piperazin-1-yl)ethoxy | NH₂ |
| 1200. | —(NMeSO₂)-2-pyridyl | 2-(morpholin-4-yl)ethoxy | NH₂ |
| 1201. | —(NMeSO₂)-3-pyridyl | Cl | H |
| 1202. | —(NMeSO₂)-3-pyridyl | cyclopropylmethylamino | H |
| 1203. | —(NMeSO₂)-3-pyridyl | 3-hydroxypropylamino | H |
| 1204. | —(NMeSO₂)-3-pyridyl | 2-(1-piperidinyl)ethylamino | H |
| 1205. | —(NMeSO₂)-3-pyridyl | 2-(1-pyrrolidinyl)ethylamino | H |
| 1206. | —(NMeSO₂)-3-pyridyl | 2-(4-morpholinyl)ethylamino | H |
| 1207. | —(NMeSO₂)-3-pyridyl | 3-(1-piperidinyl)propylamino | H |

TABLE 2-continued

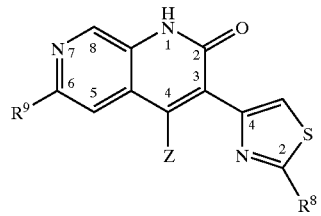

| # | R⁸ | R⁹ | Z |
|---|---|---|---|
| 1208. | —(NMeSO₂)-3-pyridyl | 3-(1-pyrrolidinyl)propylamino | H |
| 1209. | —(NMeSO₂)-3-pyridyl | 3-(4-morpholinyl)propylamino | H |
| 1210. | —(NMeSO₂)-3-pyridyl | N-methyl-N-(2-piperid-1-ylethyl)amino | H |
| 1211. | —(NMeSO₂)-3-pyridyl | N-methyl-N-(2-pyrrolidin-1-ylethyl)amino | H |
| 1212. | —(NMeSO₂)-3-pyridyl | N-methyl-N-(2-morpholin-4-ylethyl)amino | H |
| 1213. | —(NMeSO₂)-3-pyridyl | ((2S)-2-amino-3-phenylpropyl)amino | H |
| 1214. | —(NMeSO₂)-3-pyridyl | 4-methylpiperazinylamino | H |
| 1215. | —(NMeSO₂)-3-pyridyl | 4-methylpiperazinyl | H |
| 1216. | —(NMeSO₂)-3-pyridyl | 3-aminopyrrolidinyl | H |
| 1217. | —(NMeSO₂)-3-pyridyl | (diethylamino)ethylamino | H |
| 1218. | —(NMeSO₂)-3-pyridyl | 3,5-dimethylpiperazin-1-yl | H |
| 1219. | —(NMeSO₂)-3-pyridyl | (4-piperidylmethyl)amino | H |
| 1220. | —(NMeSO₂)-3-pyridyl | (2-methylbutyl)amino | H |
| 1221. | —(NMeSO₂)-3-pyridyl | 2-(dimethylamino)epoxy | H |
| 1222. | —(NMeSO₂)-3-pyridyl | 2-(methylamino)ethoxy | H |
| 1223. | —(NMeSO₂)-3-pyridyl | ((2R)pyrrolidin-2-yl)methoxy | H |
| 1224. | —(NMeSO₂)-3-pyridyl | ((2R)-1-methylpyrrolidin-2-yl)methoxy | H |
| 1225. | —(NMeSO₂)-3-pyridyl | 2-(piperid-1-yl)ethoxy | H |
| 1226. | —(NMeSO₂)-3-pyridyl | 2-(piperazin-1-yl)ethoxy | H |
| 1227. | —(NMeSO₂)-3-pyridyl | 2-(morpholin-4-yl)ethoxy | H |
| 1228. | —(NMeSO₂)-3-pyridyl | Cl | NH₂ |
| 1229. | —(NMeSO₂)-3-pyridyl | cyclopropylmethylamino | NH₂ |
| 1230. | —(NMeSO₂)-3-pyridyl | 3-hydroxypropylamino | NH₂ |
| 1231. | —(NMeSO₂)-3-pyridyl | 2-(1-piperidinyl)ethylamino | NH₂ |
| 1232. | —(NMeSO₂)-3-pyridyl | 2-(1-pyrrolidinyl)ethylamino | NH₂ |
| 1233. | —(NMeSO₂)-3-pyridyl | 2-(4-morpholinyl)ethylamino | NH₂ |
| 1234. | —(NMeSO₂)-3-pyridyl | 3-(1-piperidinyl)propylamino | NH₂ |
| 1235. | —(NMeSO₂)-3-pyridyl | 3-(1-pyrrolidinyl)propylamino | NH₂ |
| 1236. | —(NMeSO₂)-3-pyridyl | 3-(4-morpholinyl)propylamino | NH₂ |
| 1237. | —(NMeSO₂)-3-pyridyl | N-methyl-N-(2-piperid-1-ylethyl)amino | NH₂ |
| 1238. | —(NMeSO₂)-3-pyridyl | N-methyl-N-(2-pyrrolidin-1-ylethyl)amino | NH₂ |
| 1239. | —(NMeSO₂)-3-pyridyl | N-methyl-N-(2-morpholin-4-ylethyl)amino | NH₂ |
| 1240. | —(NMeSO₂)-3-pyridyl | ((2S)-2-amino-3-phenylpropyl)amino | NH₂ |
| 1241. | —(NMeSO₂) 3-pyridyl | 4-methylpiperazinylamino | NH₂ |
| 1242. | —(NMeSO₂)-3-pyridyl | 4-methylpiperazinyl | NH₂ |
| 1243. | —(NMeSO₂)-3-pyridyl | 3-aminopyrrolidinyl | NH₂ |
| 1244. | —(NMeSO₂)-3-pyridyl | (diethylamino)ethylamino | NH₂ |
| 1245. | —(NMeSO₂)-3-pyridyl | 3,5-dimethylpiperazin-1-yl | NH₂ |
| 1246. | —(NMeSO₂)-3-pyridyl | (4-piperidylmethyl)amino | NH₂ |
| 1247. | —(NMeSO₂)-3-pyridyl | (2-methylbutyl)amino | NH₂ |
| 1248. | —(NMeSO₂)-3-pyridyl | 2-(dimethylamino)ethoxy | NH₂ |
| 1249. | —(NMeSO₂)-3-pyridyl | 2-(methylamino)ethoxy | NH₂ |
| 1250. | —(NMeSO₂)-3-pyridyl | ((2R)pyrrolidin-2-yl)methoxy | NH₂ |
| 1251. | —(NMeSO₂)-3-pyridyl | ((2R)-1-methylpyrrolidin-2-yl)methoxy | NH₂ |
| 1252. | —(NMeSO₂)-3-pyridyl | 2-(piperid-1-yl)ethoxy | NH₂ |
| 1253. | —(NMeSO₂)-3-pyridyl | 2-(piperazin-1-yl)ethoxy | NH₂ |
| 1254. | —(NMeSO₂)-3-pyridyl | 2-(morpholin-4-yl)ethoxy | NH₂ |
| 1255. | —(NMeSO₂)-4-pyridyl | Cl | H |
| 1256. | —(NMeSO₂)-4-pyridyl | cyclopropylmethylamino | H |
| 1257. | —(NMeSO₂)-4-pyridyl | 3-hydroxypropylamino | H |
| 1258. | —(NMeSO₂)-4-pyridyl | 2-(1-piperidinyl)ethylamino | H |
| 1259. | —(NMeSO₂)-4-pyridyl | 2-(1-pyrrolidinyl)ethylamino | H |
| 1260. | —(NMeSO₂)-4-pyridyl | 2-(4-morpholinyl)ethylamino | H |
| 1261. | —(NMeSO₂)-4-pyridyl | 3-(1-piperidinyl)propylamimo | H |
| 1262. | —(NMeSO₂)-4-pyridyl | 3-(1-pyrrolidinyl)propylamino | H |
| 1263. | —(NMeSO₂)-4-pyridoyl | 3-(4-morpholinyl)propylamino | H |
| 1264. | —(NMeSO₂)-4-pyridyl | N-methyl-N-(2-piperid-1-ylethyl)amino | H |
| 1265. | —(NMeSO₂)-4-pyridyl | N-methyl-N-(2-pyrrolidin-1-ylethyl)amino | H |
| 1266. | —(NMeSO₂)-4-pyridyl | N-methyl-N-(2-morpholin-4-ylethyl)ainino | H |
| 1267. | —(NMeSO₂)-4-pyridyl | ((2S)-2-amino-3-phenylpropyl)amino | H |
| 1268. | —(NMeSO₂)-4-pyridyl | 4-methylpiperazinylamino | H |
| 1269. | —(NMeSO₂)-4-pyridyl | 4-methylpiperazinyl | H |
| 1270. | —(NMeSO₂)-4-pyridyl | 3-aminopyrrolidinyl | H |
| 1271. | —(NMeSO₂)-4-pyridyl | (diethylamino)ethylamino | H |
| 1272. | —(NMeSO₂)-4-pyridyl | 3,5-dimethylpiperazin-1-yl | H |

TABLE 2-continued

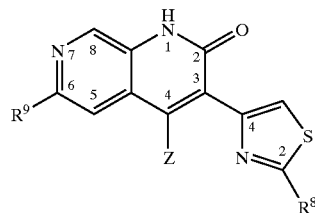

| # | R⁸ | R⁹ | Z |
|---|---|---|---|
| 1273. | —(NMeSO₂)-4-pyridyl | (4-piperidylmethyl)amino | H |
| 1274. | —(NMeSO₂)-4-pyridyl | (2-methylbutyl)amino | H |
| 1275. | —(NMeSO₂)-4-pyridyl | 2-(dimethylamino)ethoxy | H |
| 1276. | —(NMeSO₂)-4-pyridyl | 2-(methylamino)ethoxy | H |
| 1277. | —(NMeSO₂)-4-pyridyl | ((2R)pyrrolidin-2-yl)methoxy | H |
| 1278. | —(NMeSO₂)-4-pyridyl | ((2R)-1-methylpyrrolidin-2-yl)methoxy | H |
| 1279. | —(NMeSO₂)-4-pyridyl | 2-(piperid-1-yl)ethoxy | H |
| 1280. | —(NMeSO₂)-4-pyridyl | 2-(piperazin-1-yl)ethoxy | H |
| 1281. | —(MMeSO₂)-4-pyridyl | 2-(morpholin-4-yl)ethoxy | H |
| 1282. | —(NMeSO₂)-4-pyridyl | Cl | NH₂ |
| 1283. | —(NMeSO₂)-4-pyridyl | cyclopropylmethylamino | NH₂ |
| 1284. | —(NMeSO₂)-4-pyridyl | 3-hydroxypropylamino | NH₂ |
| 1285. | —(NMeSO₂)-4-pyridyl | 2-(1-piperidinyl)ethylamino | NH₂ |
| 1286. | —(NMeSO₂)-4-pyridyl | 2-(1-pyrrolidinyl)ethylamino | NH₂ |
| 1287. | —(NMeSO₂)-4-pyridyl | 2-(4-morpholinyl)ethylamino | NH₂ |
| 1288. | —(NMeSO₂)-4-pyridyl | 3-(1-piperidinyl)propylamino | NH₂ |
| 1289. | —(NMeSO₂)-4-pyridyl | 3-(1-pyrrolidinyl)propylamino | NH₂ |
| 1290. | —(NMeSO₂)-4-pyridyl | 3-(4-morpholinyl)propylamino | NH₂ |
| 1291. | —(NMeSO₂)-4-pyridyl | N-methyl-N-(2-piperid-1-ylethyl)amino | NH₂ |
| 1292. | —(NMeSO₂)-4-pyridyl | N-methyl-N-(2-pyrrolidin-1-ylethyl)amino | NH₂ |
| 1293. | —(NMeSO₂) 4-pyridyl | N-methyl-N-(2-morpholin-4-ylethyl)amino | NH₂ |
| 1294. | —(NMeSO₂)-4-pyridyl | ((2S)-2-amino-3-phenylpropyl)amino | NH₂ |
| 1295. | —(NMeSO₂)-4-pyridyl | 4-methylpiperazinylamino | NH₂ |
| 1296. | —(NMeSO₂)-4-pyridyl | 4-methylpiperazinyl | NH₂ |
| 1297. | —(NMeSO₂)-4-pyridyl | 3-aminopyrrolidinyl | NH₂ |
| 1298. | —(NMeSO₂)-4-pyridyl | (diethylamino)ethylamino | NH₂ |
| 1299. | —(NMeSO₂)-4-pyridyl | 3,5-dimethylpiperazin-1-yl | NH₂ |
| 1300. | —(NMeSO₂)-4-pyridyl | (4-piperidylmethyl)amino | NH₂ |
| 1301. | —(NMeSO₂)-4-pyridyl | (2-methylbutyl)amino | NH₂ |
| 1302. | —(NMeSO₂)-4-pyridyl | 2-(dimethylamino)ethoxy | NH₂ |
| 1303. | —(NMeSO₂)-4-pyridyl | 2-(methylamino)ethoxy | NH₂ |
| 1304. | —(NMeSO₂)-4-pyridyl | ((2R)pyrrolidin-2-yl)methoxy | NH₂ |
| 1305. | —(NMeSO₂)-4-pyridyl | ((2R)-1-methylpyrrolidin-2-yl)methoxy | NH₂ |
| 1306. | —(NMeSO₂)-4-pyridyl | 2-(piperid-1-yl)ethoxy | NH₂ |
| 1307. | —(NMeSO₂)-4-pyridyl | 2-(piperazin-4-yl)ethoxy | NH₂ |
| 1308. | —(NMeSO₂)-4-pyridyl | 2-(morpholin-4-yl)ethoxy | NH₂ |

TABLE 3

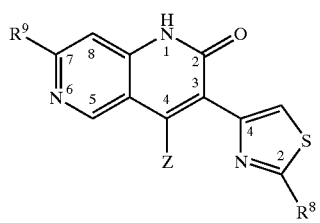

| # | R⁸ | R⁹ | Z |
|---|---|---|---|
| 1309. | 4-pyridyl | Cl | H |
| 1310. | 4-pyridyl | cyclopropylmethylamino | H |
| 1311. | 4-pyridyl | 3-hydroxypropylamino | H |
| 1312. | 4-pyridyl | 2-(1-piperidinyl)ethylamino | H |
| 1313. | 4-pyridyl | 2-(1-pyrrolidinyl)ethylamino | H |
| 1314. | 4-pyridyl | 2-(4-morpholinyl)ethylamino | H |
| 1315. | 4-pyridyl | 3-(1-piperidinyl)propylamino | H |
| 1316. | 4-pyridyl | 3-(1-pyrrolidinyl)propylamino | H |
| 1317. | 4-pyridyl | 3-(4-morpholinyl)propylamino | H |
| 1318. | 4-pyridyl | N-methyl-N-(2-piperid-1-ylethyl)amino | H |
| 1319. | 4-pyridyl | N-methyl-N-(2-pyrrolidin-1-ylethyl)amino | H |

TABLE 3-continued

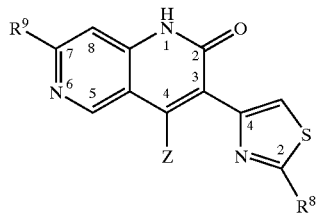

| # | R⁸ | R⁹ | Z |
|---|---|---|---|
| 1320. | 4 pyridyl | N-methyl-N-(2-morpholin-4-ylethyl)amino | H |
| 1321. | 4-pyridyl | ((2S)-2-amino-3-phenylpropyl)amino | H |
| 1322. | 4-pyridyl | 4-methylpiperazinylamino | H |
| 1323. | 4-pyridyl | 4-methylpiperazinyl | H |
| 1324. | 4-pyridyl | 3-aminopyrrolidinyl | H |
| 1325. | 4-pyridyl | (diethylamino)ethylamino | H |
| 1326. | 4-pyridyl | 3,5-dimethylpiperazin-1-yl | H |
| 1327. | 4-pyridyl | (4-piperidylmethyl)amino | H |
| 1328. | 4-pyridyl | (2-methylbutyl)amino | H |
| 1329. | 4-pyridyl | 2-(dimethylamino)ethoxy | H |
| 1330. | 4-pyridyl | 2-(methylamino)ethoxy | H |
| 1331. | 4-pyridyl | ((2R)pyrrolidin-2-yl)methoxy | H |
| 1332. | 4-pyridyl | ((2R)-1-methylpyrrolidin-2-yl)methoxy | H |
| 1333. | 4-pyridyl | 2-(piperid-1-yl)ethoxy | H |
| 1334. | 4-pyridyl | 2-(piperazin-1-yl)ethoxy | H |
| 1335. | 4-pyridyl | 2-(morpholin-4-yl)ethoxy | H |
| 1336. | 4-pyridyl | Cl | $NH_2$ |
| 1337. | 4-pyridyl | cyclopropylmethylamino | $NH_2$ |
| 1338. | 4-pyridyl | 3-hydroxypropylamino | $NH_2$ |
| 1339. | 4-pyridyl | 2-(1-piperidinyl)ethylamino | $NH_2$ |
| 1340. | 4-pyridyl | 2-(1-pyrrolidinyl)ethylamino | $NH_2$ |
| 1341. | 4-pyridyl | 2-(4-morpholinyl)ethylamino | $NH_2$ |
| 1342. | 4-pyridyl | 3-(1-piperidinyl)propylamino | $NH_2$ |
| 1343. | 4-pyridyl | 3-(1-pyrrolidinyl)propylamino | $NH_2$ |
| 1344. | 4-pyridyl | 3-(4-morpholinyl)propylamino | $NH_2$ |
| 1345. | 4-pyridyl | N-methyl-N-(2-piperid-1-ylethyl)amino | $NH_2$ |
| 1346. | 4-pyridyl | N-methyl-N-(2-pyrrolidin-1-ylethyl)amino | $NH_2$ |
| 1347. | 4-pyridyl | N-methyl-N-(2-morpholin-4-ylethyl)amino | $NH_2$ |
| 1348. | 4-pyridyl | ((2S)-2-amino-3-phenylpropyl)amino | $NH_2$ |
| 1349. | 4 pyridyl | 4-methylpiperazinylamino | $NH_2$ |
| 1350. | 4-pyridyl | 4-methylpiperazinyl | $NH_2$ |
| 1351. | 4-pyridyl | 3-aminopyrrolidinyl | $NH_2$ |
| 1352. | 4 pyridyl | (diethylamino)ethylamino | $NH_2$ |
| 1353. | 4-pyridyl | 3,5-dimethylpiperazin-1-yl | $NH_2$ |
| 1354. | 4-pyridyl | (4-piperidylmethyl)amino | $NH_2$ |
| 1355. | 4-pyridyl | (2-methylbutyl)amino | $NH_2$ |
| 1356. | 4-pyridyl | 2-(dimethylamino)ethoxy | $NH_2$ |
| 1357. | 4 pyridyl | 2-(methylamino)ethoxy | $NH_2$ |
| 1358. | 4-pyridyl | ((2R)pyrrolidin-2-yl)methoxy | $NH_2$ |
| 1359. | 4-pyridyl | ((2R)-1-methylpyrrolidin-2-yl)methoxy | $NH_2$ |
| 1360. | 4 pyridyl | 2-(piperid-1-yl)ethoxy | $NH_2$ |
| 1361. | 4 pyridyl | 2-(piperazin-1-yl)ethoxy | $NH_2$ |
| 1362. | 4-pyridyl | 2-(morpholin-4-yl)ethoxy | $NH_2$ |
| 1363. | —($CH_2SO_2$)-phenyl | Cl | H |
| 1364. | —($CH_2SO_2$)-phenyl | cyclopropylmethylamino | H |
| 1365. | —($CH_2SO_2$)-phenyl | 3-hydroxypropylamino | H |
| 1366. | —($CH_2SO_2$)-phenyl | 2-(1-piperidinyl)ethylamino | H |
| 1367. | —($CH_2SO_2$)-phenyl | 2-(1-pyrrolidinyl)ethylamino | H |
| 1368. | —($CH_2SO_2$)-phenyl | 2-(4-morpholinyl)ethylamino | H |
| 1369. | —($CH_2SO_2$)-phenyl | 3-(1-piperidinyl)propylamino | H |
| 1370. | —($CH_2SO_2$)-phenyl | 3-(1-pyrrolidinyl)propylamino | H |
| 1371. | —($CH_2SO_2$)-phenyl | 3-(4-morpholinyl)propylamino | H |
| 1372. | —($CH_2SO_2$)-phenyl | N-methyl-N-(2-piperid-1-ylethyl)amino | H |
| 1373. | —($CH_2SO_2$)-phenyl | N-methyl-N-(2-pyrrolidin-1-ylethyl)amino | H |
| 1374. | —($CH_2SO_2$)-phenyl | N-methyl-N-(2-morpholin-4-ylethyl)amino | H |
| 1375. | —($CH_2SO_2$)-phenyl | ((2S)-2-amino-3-phenylpropyl)amino | H |
| 1376. | —($CH_2SO_2$)-phenyl | 4-methylpiperazinylamino | H |
| 1377. | —($CH_2SO_2$)-phenyl | 4-methylpiperazinyl | H |
| 1378. | —($CH_2SO_2$)-phenyl | 3-aminopyrrolidinyl | H |
| 1379. | —($CH_2SO_2$)-phenyl | (diethylamino)ethylamino | H |
| 1380. | —($CH_2SO_2$)-phenyl | 3,5-dimethylpiperazin-1-yl | H |
| 1381. | —($CH_2SO_2$)-phenyl | (4-piperidylmethyl)amino | H |
| 1382. | —($CH_2SO_2$)-phenyl | (2-methylbutyl)amino | H |
| 1383. | —($CH_2SO_2$)-phenyl | 2-(dimethylamino)ethoxy | H |
| 1384. | —($CH_2SO_2$)-phenyl | 2-(methylamino)ethoxy | H |

TABLE 3-continued

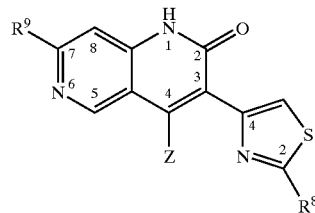

| # | R⁸ | R⁹ | Z |
|---|---|---|---|
| 1385. | —(CH$_2$SO$_2$)-phenyl | ((2R)pyrrolidin-2-yl)methoxy | H |
| 1386. | —(CH$_2$SO$_2$)-phenyl | ((2R)-1-methylpyrrolidin-2-yl)methoxy | H |
| 1387. | —(CH$_2$SO$_2$)-phenyl | 2-(piperid-1-yl)ethoxy | H |
| 1388. | —(CH$_2$SO$_2$)-phenyl | 2-(piperazin-1-yl)ethoxy | H |
| 1389. | —(CH$_2$SO$_2$)-phenyl | 2-(morpholin-4-yl)ethoxy | H |
| 1390. | —(CH$_2$SO$_2$)-phenyl | Cl | NH$_2$ |
| 1391. | —(CH$_2$SO$_2$)-phenyl | cyclopropylmethylamino | NH$_2$ |
| 1392. | —(CH$_2$SO$_2$)-phenyl | 3-hydroxypropylamino | NH$_2$ |
| 1393. | —(CH$_2$SO$_2$)-phenyl | 2-(1-piperidinyl)ethylamino | NH$_2$ |
| 1394. | —(CH$_2$SO$_2$)-phenyl | 2-(1-pyrrolidinyl)ethylamino | NH$_2$ |
| 1395. | —(CH$_2$SO$_2$)-phenyl | 2-(4-morpholinyl)ethylamino | NH$_2$ |
| 1396. | —(CH$_2$SO$_2$)-phenyl | 3-(1-piperidinyl)propylamino | NH$_2$ |
| 1397. | —(CH$_2$SO$_2$)-phenyl | 3-(1-pyrrolidinyl)propylamino | NH$_2$ |
| 1398. | —(CH$_2$SO$_2$)-phenyl | 3-(4-morpholinyl)propylamino | NH$_2$ |
| 1399. | —(CH$_2$SO$_2$)-phenyl | N-methyl-N-(2-piperid-1-ylethyl)amino | NH$_2$ |
| 1400. | —(CH$_2$SO$_2$)-phenyl | N-methyl-N-(2-pyrrolidin-1-ylethyl)amino | NH$_2$ |
| 1401. | —(CH$_2$SO$_2$)-phenyl | N-methyl-N-(2-morpholin-4-ylethyl)amino | NH$_2$ |
| 1402. | —(CH$_2$SO$_2$)-phenyl | ((2S)-2-amino-3-phenylpropyl)amino | NH$_2$ |
| 1403. | —(CH$_2$SO$_2$)-phenyl | 4-methylpiperazinylamino | NH$_2$ |
| 1404. | —(CH$_2$SO$_2$)-phenyl | 4-methylpiperazinyl | NH$_2$ |
| 1405. | —(CH$_2$SO$_2$)-phenyl | 3-aminopyrrolidinyl | NH$_2$ |
| 1406. | —(CH$_2$SO$_2$)-phenyl | (diethylamino)ethylamino | NH$_2$ |
| 1407. | —(CH$_2$SO$_2$)-phenyl | 3,5-dimethylpiperazin-1-yl | NH$_2$ |
| 1408. | —(CH$_2$SO$_2$)-phenyl | (4-piperidylmethyl)amino | NH$_2$ |
| 1409. | —(CH$_2$SO$_2$)-phenyl | (2-methylbutyl)amino | NH$_2$ |
| 1410. | —(CH$_2$SO$_2$)-phenyl | 2-(dimethylamino)ethoxy | NH$_2$ |
| 1411. | —(CH$_2$SO$_2$)-phenyl | 2-(methylamino)ethoxy | NH$_2$ |
| 1412. | —(CH$_2$SO$_2$)-phenyl | ((2R)pyrrolidin-2-yl)methoxy | NH$_2$ |
| 1413. | —(CH$_2$SO$_2$)-phenyl | ((2R)-1-methylpyrrolidin-2-yl)methoxy | NH$_2$ |
| 1414. | —(CH$_2$SO$_2$)-phenyl | 2-(piperid-1-yl)ethoxy | NH$_2$ |
| 1415. | —(CH$_2$SO$_2$)-phenyl | 2-(piperazin-1-yl)ethoxy | NH$_2$ |
| 1416. | —(CH$_2$SO$_2$)-phenyl | 2-(morpholin-4-yl)ethoxy | NH$_2$ |
| 1417. | —(CH$_2$SO$_2$)-2-thienyl | Cl | H |
| 1418. | —(CH$_2$SO$_2$)-2-thienyl | cyclopropylmethylamino | H |
| 1419. | —(CH$_2$SO$_2$)-2-thienyl | 3-hydroxypropylamino | H |
| 1420. | —(CH$_2$SO$_2$)-2-thienyl | 2-(1-piperidinyl)ethylamino | H |
| 1421. | —(CH$_2$SO$_2$)-2-thienyl | 2-(1-pyrrolidinyl)ethylamino | H |
| 1422. | —(CH$_2$SO$_2$)-2-thienyl | 2-(4-morpholinyl)ethylamino | H |
| 1423. | —(CH$_2$SO$_2$)-2-thienyl | 3-(1-piperidinyl)propylamino | H |
| 1424. | —(CH$_2$SO$_2$)-2-thienyl | 3-(1-pyrrolidinyl)propylamino | H |
| 1425. | —(CH$_2$SO$_2$)-2-thienyl | 3-(4-morpholinyl)propylamino | H |
| 1426. | —(CH$_2$SO$_2$)-2-thienyl | N-methyl-N-(2-piperid-1-ylethy)amino | H |
| 1427. | —(CH$_2$SO$_2$)-2-thienyl | N-methyl-N-(2-pyrrolidin-1-ylethyl)amino | H |
| 1428. | —(CH$_2$SO$_2$)-2-thienyl | N-methyl-N-(2-morpholin-4-ylethyl)amino | H |
| 1429. | —(CH$_2$SO$_2$)-2-thienyl | ((2S)-2-amino-3-phenylpropyl)amino | H |
| 1430. | —(CH$_2$SO$_2$)-2-thienyl | 4-methylpiperazinylamino | H |
| 1431. | —(CH$_2$SO$_2$)-2-thienyl | 4-methylpiperazinyl | H |
| 1432. | —(CH$_2$SO$_2$)-2-thienyl | 3-aminopyrrolidinyl | H |
| 1433. | —(CH$_2$SO$_2$)-2-thienyl | (diethylamino)ethylamino | H |
| 1434. | —(CH$_2$SO$_2$)-2-thienyl | 3,5-dimethylpiperazin-1-yl | H |
| 1435. | —(CH$_2$SO$_2$)-2-thienyl | (4-piperidylmethyl)amino | H |
| 1436. | —(CH$_2$SO$_2$)-2-thienyl | (2-methylbutyl)amino | H |
| 1437. | —(CH$_2$SO$_2$)-2-thienyl | 2-(dimethylamino)ethoxy | H |
| 1438. | —(CH$_2$SO$_2$)-2-thienyl | 2-(methylamino)ethoxy | H |
| 1439. | —(CH$_2$SO$_2$)-2-thienyl | ((2R)pyrrolidin-2-yl)methoxy | H |
| 1440. | —(CH$_2$SO$_2$)-2-thienyl | ((2R)-1-methylpyrrolidin-2-yl)methoxy | H |
| 1441. | —(CH$_2$SO$_2$)-2-thienyl | 2-(piperid-1-yl)ethoxy | H |
| 1442. | —(CH$_2$SO$_2$)-2-thienyl | 2-(piperazin-1-yl)ethoxy | H |
| 1443. | —(CH$_2$SO$_2$)-2-thienyl | 2-(morpholin-4-yl)ethoxy | H |
| 1444. | —(CH$_2$SO$_2$)-2-thienyl | Cl | NH$_2$ |
| 1445. | —(CH$_2$SO$_2$)-2-thienyl | cyclopropylmethylamino | NH$_2$ |
| 1446. | —(CH$_2$SO$_2$)-2-thienyl | 3-hydroxypropylamino | NH$_2$ |
| 1447. | —(CH$_2$SO$_2$)-2-thienyl | 2-(1-piperidinyl)ethylamino | NH$_2$ |
| 1448. | —(CH$_2$SO$_2$)-2-thienyl | 2-(1-pyrrolidinyl)ethylamino | NH$_2$ |
| 1449. | —(CH$_2$SO$_2$)-2-thienyl | 2-(4-morpholinyl)ethylamino | NH$_2$ |

TABLE 3-continued

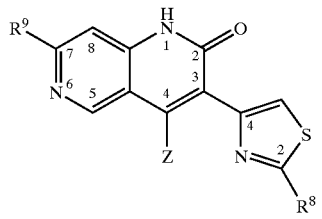

| # | R$^8$ | R$^9$ | Z |
|---|---|---|---|
| 1450. | —(CH$_2$SO$_2$)-2-thienyl | 3-(1-piperidinyl)propylamino | NH$_2$ |
| 1451. | —(CH$_2$SO$_2$)-2-thienyl | 3-(1-pyrrolidinyl)propylamino | NH$_2$ |
| 1452. | —(CH$_2$SO$_2$)-2-thienyl | 3-(4-morpholinyl)propylamino | NH$_2$ |
| 1453. | —(CH$_2$SO$_2$)-2-thienyl | N-methyl-N-(2-piperid-1-ylethyl)amino | NH$_2$ |
| 1454. | —(CH$_2$SO$_2$)-2-thienyl | N-methyl-N-(2-pyrrolidin-1-ylethyl)amino | NH$_2$ |
| 1455. | —(CH$_2$SO$_2$)-2-thienyl | N-methyl-N-(2-morpholin-4-ylethyl)amino | NH$_2$ |
| 1456. | —(CH$_2$SO$_2$)-2-thienyl | ((2S)-2-amino-3-phenylpropyl)amino | NH$_2$ |
| 1457. | —(CH$_2$SO$_2$)-2-thienyl | 4-methylpiperazinylamino | NH$_2$ |
| 1458. | —(CH$_2$SO$_2$)-2-thienyl | 4-methylpiperazinyl | NH$_2$ |
| 1459. | —(CH$_2$SO$_2$)-2-thienyl | 3-aminopyrrolidinyl | NH$_2$ |
| 1460. | —(CH$_2$SO$_2$)-2-thienyl | (diethylamino)ethylamino | NH$_2$ |
| 1461. | —(CH$_2$SO$_2$)-2-thienyl | 3,5-dimethylpiperazin-1-yl | NH$_2$ |
| 1462. | —(CH$_2$SO$_2$)-2-thienyl | (4-piperidylmethyl)amino | NH$_2$ |
| 1463. | —(CH$_2$SO$_2$)-2-thienyl | (2-methylbutyl)amino | NH$_2$ |
| 1464. | —(CH$_2$SO$_2$)-2-thienyl | 2-(dimethylamino)ethoxy | NH$_2$ |
| 1465. | —(CH$_2$SO$_2$)-2-thienyl | 2-(methylamino)ethoxy | NH$_2$ |
| 1466. | —(CH$_2$SO$_2$)-2-thienyl | ((2R)pyrrolidin-2-yl)methoxy | NH$_2$ |
| 1467. | —(CH$_2$SO$_2$)-2-thienyl | ((2R)-1-methylpyrrolidin-2-yl)methoxy | NH$_2$ |
| 1468. | —(CH$_2$SO$_2$)-2-thienyl | 2-(piperid-1-yl)ethoxy | NH$_2$ |
| 1469. | —(CH$_2$SO$_2$)-2-thienyl | 2-(piperazin-1-yl)ethoxy | NH$_2$ |
| 1470. | —(CH$_2$SO$_2$)-2-thienyl | 2-(morpholin-4-yl)ethoxy | NH$_2$ |
| 1471. | —(CH$_2$SO$_2$)-2-pyridyl | Cl | H |
| 1472. | —(CH$_2$SO$_2$)-2-pyridyl | cyclopropylmethylamino | H |
| 1473. | —(CH$_2$SO$_2$)-2-pyridyl | 3-hydroxypropylamino | H |
| 1474. | —(CH$_2$SO$_2$)-2-pyridyl | 2-(1-piperidinyl)ethylamino | H |
| 1475. | —(CH$_2$SO$_2$)-2-pyridyl | 2 (1-pyrrolidinyl)ethylamino | H |
| 1476. | —(CH$_2$SO$_2$)-2-pyridyl | 2-(4-morpholinyl)ethylamino | H |
| 1477. | —(CH$_2$SO$_2$)-2-pyridyl | 3-(1-piperidinyl)propylamino | H |
| 1478. | —(CH$_2$SO$_2$)-2-pyridyl | 3-(1-pyrrolidinyl)propylamino | H |
| 1479. | —(CH$_2$SO$_2$)-2-pyridyl | 3-(4-morpholinyl)propylamino | H |
| 1480. | —(CH$_2$SO$_2$)-2-pyridyl | N-methyl-N-(2-piperid-1-ylethyl)amino | H |
| 1481. | —(CH$_2$SO$_2$)-2-pyridyl | N-methyl-N-(2-pyrrolidin-1-ylethyl)amino | H |
| 1482. | —(CH$_2$SO$_2$)-2-pyridyl | N-methyl-N-(2-morpholin-4-ylethyl)amino | H |
| 1483. | —(CH$_2$SO$_2$)-2-pyridyl | ((2S)-2-amino-3-phenylpropyl)amino | H |
| 1484. | —(CH$_2$SO$_2$)-2-pyridyl | 4-methylpiperazinylamino | H |
| 1485. | —(CH$_2$SO$_2$)-2-pyridyl | 4-methylpiperazinyl | H |
| 1486. | —(CH$_2$SO$_2$)-2-pyridyl | 3-aminopyrrolidinyl | H |
| 1487. | —(CH$_2$SO$_2$)-2-pyridyl | (diethylamino)ethylamino | H |
| 1488. | —(CH$_2$SO$_2$)-2-pyridyl | 3,5-dimethylpiperazin-1-yl | H |
| 1489. | —(CH$_2$SO$_2$)-2-pyridyl | (4-piperidylmethyl)amino | H |
| 1490. | —(CH$_2$SO$_2$)-2-pyridyl | (2-methylbutyl)amino | H |
| 1491. | —(CH$_2$SO$_2$)-2-pyridyl | 2-(dimethylamino)ethoxy | H |
| 1492. | —(CH$_2$SO$_2$)-2-pyridyl | 2-(methylamino)ethoxy | H |
| 1493. | —(CH$_2$SO$_2$)-2-pyridyl | ((2R)pyrrolidin-2-yl)methoxy | H |
| 1494. | —(CH$_2$SO$_2$)-2-pyridyl | ((2R)-1-methylpyrrolidin-2-yl)methoxy | H |
| 1495. | —(CH$_2$SO$_2$)-2-pyridyl | 2-(piperid-1-yl)ethoxy | H |
| 1496. | —(CH$_2$SO$_2$)-2-pyridyl | 2-(piperazin-1-yl)ethoxy | M |
| 1497. | —(CH$_2$SO$_2$)-2-pyridyl | 2-(morpholin-4-yl)ethoxy | H |
| 1498. | —(CH$_2$SO$_2$)-2-pyridyl | Cl | NH$_2$ |
| 1499. | —(CH$_2$SO$_2$)-2-pyridyl | cyclopropylmethylamino | NH$_2$ |
| 1500. | —(CH$_2$SO$_2$)-2-pyridyl | 3-hydroxypropylamino | NH$_2$ |
| 1501. | —(CH$_2$SO$_2$)-2-pyridyl | 2-(1-piperidinyl)ethylamino | NH$_2$ |
| 1502. | —(CH$_2$SO$_2$)-2-pyridyl | 2-(1-pyrrolidinyl)ethylamino | NH$_2$ |
| 1503. | —(CH$_2$SO$_2$)-2-pyridyl | 2-(4-morpholinyl)ethylamino | NH$_2$ |
| 1504. | —(CH$_2$SO$_2$)-2-pyridyl | 3-(1-piperidinyl)propylamino | NH$_2$ |
| 1505. | —(CH$_2$SO$_2$)-2-pyridyl | 3-(1-pyrrolidinyl)propylamino | NH$_2$ |
| 1506. | —(CH$_2$SO$_2$)-2-pyridyl | 3-(4-morpholinyl)propylamino | NH$_2$ |
| 1507. | —(CH$_2$SO$_2$)-2-pyridyl | N-methyl-N-(2-piperid-1-ylethyl)amino | NH$_2$ |
| 1508. | —(CH$_2$SO$_2$)-2-pyridyl | N-methyl-N-(2-pyrrolidin-1-ylethyl)amino | NH$_2$ |
| 1509. | —(CH$_2$SO$_2$)-2-pyridyl | N-methyl-N-(2-morpholin-4-ylethyl)amino | NH$_2$ |
| 1510. | —(CH$_2$SO$_2$)-2-pyridyl | ((2S)-2-amino-3-phenylpropyl)amino | NH$_2$ |
| 1511. | —(CH$_2$SO$_2$)-2-pyridyl | 4-methylpiperazinylamino | NH$_2$ |
| 1512. | —(CH$_2$SO$_2$)-2-pyridyl | 4-methylpiperazinyl | NH$_2$ |
| 1513. | —(CH$_2$SO$_2$)-2-pyridyl | 3-aminopyrrolidinyl | NH$_2$ |
| 1514. | —(CH$_2$SO$_2$)-2-pyridyl | (diethylamino)ethylamino | NH$_2$ |

TABLE 3-continued

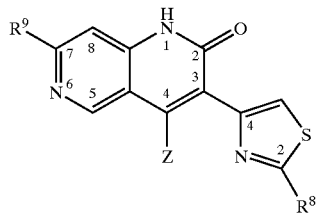

| # | R⁸ | R⁹ | Z |
|---|---|---|---|
| 1515. | —(CH₂SO₂)-2-pyridyl | 3,5-dimethylpiperazin-1-yl | NH₂ |
| 1516. | —(CH₂SO₂)-2-pyridyl | (4-piperidylmethyl)amino | NH₂ |
| 1517. | —(CH₂SO₂)-2-pyridyl | (2-methylbutyl)amino | NH₂ |
| 1518. | —(CH₂SO₂)-2-pyridyl | 2-(dimethylamino)ethoxy | NH₂ |
| 1519. | —(CH₂SO₂)-2-pyridyl | 2-(methylamino)ethoxy | NH₂ |
| 1520. | —(CH₂SO₂)-2-pyridyl | ((2R)pyrrolidin-2-yl)methoxy | NH₂ |
| 1521. | —(CH₂SO₂)-2-pyridyl | ((2R)-1-methylpyrrolidin-2-yl)methoxy | NH₂ |
| 1522. | —(CH₂SO₂)-2-pyridyl | 2-(piperid-1-yl)ethoxy | NH₂ |
| 1523. | —(CH₂SO₂)-2-pyridyl | 2-(piperazin-1-yl)ethoxy | NH₂ |
| 1524. | —(CH₂SO₂)-2-pyridyl | 2-(morpholin-4-yl)ethoxy | NH₂ |
| 1525. | —(CH₂SO₂)-3-pyridyl | Cl | H |
| 1526. | —(CH₂SO₂)-3-pyridyl | cyclopropylmethylamino | H |
| 1527. | —(CH₂SO₂)-3-pyridyl | 3-hydroxypropylamino | H |
| 1528. | —(CH₂SO₂)-3-pyridyl | 2-(1-piperidinyl)ethylamino | H |
| 1529. | —(CH₂SO₂)-3-pyridyl | 2-(1-pyrrolidinyl)ethylamino | H |
| 1530. | —(CH₂SO₂)-3-pyridyl | 2-(4-morpholinyl)ethylamino | H |
| 1531. | —(CH₂SO₂)-3-pyridyl | 3-(1-piperidinyl)propylamino | H |
| 1532. | —(CH₂SO₂)-3-pyridyl | 3-(1-pyrrolidinyl)propylamino | H |
| 1533. | —(CH₂SO₂)-3-pyridyl | 3-(4-morpholinyl)propylamino | H |
| 1534. | —(CH₂SO₂)-3-pyridyl | N-methyl-N-(2-piperid-1-ylethyl)amino | H |
| 1535. | —(CH₂SO₂)-3-pyridyl | N-methyl-N-(2-pyrrolidin-1-ylethyl)amino | H |
| 1536. | —(CH₂SO₂)-3-pyridyl | N-methyl-N-(2-morpholin-4-ylethyl)amino | H |
| 1537. | —(CH₂SO₂)-3-pyridyl | ((2S)-2-amino-3-phenylpropyl)amino | H |
| 1538. | —(CH₂SO₂)-3-pyridyl | 4-methylpiperazinylamino | H |
| 1539. | —(CH₂SO₂)-3 pyridyl | 4-methylpiperazinyl | H |
| 1540. | —(CH₂SO₂)-3-pyridyl | 3-aminopyrrolidinyl | H |
| 1541. | —(CH₂SO₂)-3-pyridyl | (diethylamino)ethylamino | H |
| 1542. | —(CH₂SO₂)-3-pyridyl | 3,5-dimethylpiperazin-1-yl | H |
| 1543. | —(CH₂SO₂)-3-pyridyl | (4-piperidylmethyl)amino | H |
| 1544. | —(CH₂SO₂)-3-pyridyl | (2-methylbutyl)amino | H |
| 1545. | —(CH₂SO₂)-3-pyridyl | 2-(dimethylamino)ethoxy | H |
| 1546. | —(CH₂SO₂)-3-pyridyl | 2-(methylamino)ethoxy | H |
| 1547. | —(CH₂SO₂)-3-pyridyl | ((2R)pyrrolidin-2-yl)methoxy | H |
| 1548. | —(CH₂SO₂)-3-pyridyl | ((2R)-1-methylpyrrolidin-2-yl)methoxy | H |
| 1549. | —(CH₂SO₂)-3-pyridyl | 2-(piperid-1-yl)ethoxy | H |
| 1550. | —(CH₂SO₂)-3-pyridyl | 2-(piperazin-1-yl)ethoxy | H |
| 1551. | —(CH₂SO₂)-3-pyridyl | 2-(morpholin-4-yl)ethoxy | H |
| 1552. | —(CH₂SO₂)-3-pyridyl | Cl | NH₂ |
| 1553. | —(CH₂SO₂)-3-pyridyl | cyclopropylmethylamino | NH₂ |
| 1554. | —(CH₂SO₂)-3-pyridyl | 3-hydroxypropylamino | NH₂ |
| 1555. | —(CH₂SO₂)-3-pyridyl | 2-(1-piperidinyl)ethylamino | NH₂ |
| 1556. | —(CH₂SO₂)-3-pyridyl | 2-(1-pyrrolidinyl)ethylamino | NH₂ |
| 1557. | —(CH₂SO₂)-3-pyridyl | 2-(4-morpholinyl)ethylamino | NH₂ |
| 1558. | —(CH₂SO₂)-3-pyridyl | 3-(1-piperidinyl)propylamino | NH₂ |
| 1559. | —(CH₂SO₂)-3-pyridyl | 3-(1-pyrrolidinyl)propylamino | NH₂ |
| 1560. | —(CH₂SO₂)-3-pyridyl | 3-(4-morpholinyl)propylamino | NH₂ |
| 1561. | —(CH₂SO₂)-3-pyridyl | N-methyl-N-(2-piperid-1-ylethyl)amino | NH₂ |
| 1562. | —(CH₂SO₂)-3-pyridyl | N-methyl-N-(pyrrolidin-1-ylethyl)amino | NH₂ |
| 1563. | —(CH₂SO₂)-3-pyridyl | N-methyl-N-(2-morpholin-4-ylethyl)amino | NH₂ |
| 1564. | —(CH₂SO₂)-3-pyridyl | ((2S)-2-amino-3-phenylpropyl)amino | NH₂ |
| 1565. | —(CH₂SO₂)-3-pyridyl | 4-methylpiperazinylamino | NH₂ |
| 1566. | —(CH₂SO₂)-3-pyridyl | 4-methylpiperazinyl | NH₂ |
| 1567. | —(CH₂SO₂)-3-pyridyl | 3-aminopyrrolidinyl | NH₂ |
| 1568. | —(CH₂SO₂)-3-pyridyl | (diethylamino)ethylamino | NH₂ |
| 1569. | —(CH₂SO₂)-3-pyridyl | 3,5-dimethylpiperazin-1-yl | NH₂ |
| 1570. | —(CH₂SO₂)-3-pyridyl | (4-piperidylmethyl)amino | NH₂ |
| 1571. | —(CH₂SO₂)-3-pyridyl | (2-methylbutyl)amino | NH₂ |
| 1572. | —(CH₂SO₂)-3-pyridyl | 2-(dimethylamino)ethoxy | NH₂ |
| 1573. | —(CH₂SO₂)-3-pyridyl | 2-(methylamino)ethoxy | NH₂ |
| 1574. | —(CH₂SO₂)-3-pyridyl | ((2R)pyrrolidin-2-yl)methoxy | NH₂ |
| 1575. | —(CH₂SO₂)-3-pyridyl | ((2R)-1-methylpyrrolidin-2-yl)methoxy | NH₂ |
| 1576. | —(CH₂SO₂)-3-pyridyl | 2-(piperid-1-yl)ethoxy | NH₂ |
| 1577. | —(CH₂SO₂)-3-pyridyl | 2-(piperazin-1-yl)ethoxy | NH₂ |
| 1578. | —(CH₂SO₂)-3-pyridyl | 2-(morpholin-4-yl)ethoxy | NH₂ |
| 1579. | —(CH₂SO₂)-4-pyridyl | Cl | H |

TABLE 3-continued

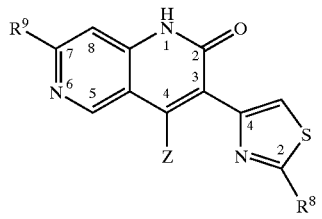

| # | R⁸ | R⁹ | Z |
|---|---|---|---|
| 1580. | —(CH₂SO₂)-4-pyridyl | cyclopropylmethylamino | H |
| 1581. | —(CH₂SO₂)-4-pyridyl | 3-hydroxypropylamino | H |
| 1582. | —(CH₂SO₂)-4-pyridyl | 2-(1-piperidinyl)ethylamino | H |
| 1583. | —(CH₂SO₂)-4-pyridyl | 2-(1-pyrrolidinyl)ethylamino | H |
| 1584. | —(CH₂SO₂)-4-pyridyl | 2-(4-morpholinyl)ethylamino | H |
| 1585. | —(CH₂SO₂)-4-pyridyl | 3-(1-piperidinyl)propylamino | H |
| 1586. | —(CH₂SO₂)-4-pyridyl | 3-(1-pyrrolidinyl)propylamino | H |
| 1587. | —(CH₂SO₂)-4-pyridyl | 3-(4-morpholinyl)propylamino | H |
| 1588. | —(CH₂SO₂)-4-pyridyl | N-methyl-N-(2-piperid-1-ylethyl)amino | H |
| 1589. | —(CH₂SO₂)-4-pyridyl | N-methyl-N-(2-pyrrolidin-1-ylethyl)amino | H |
| 1590. | —(CH₂SO₂)-4-pyridyl | N-methyl-N-(2-morpholin-4-ylethyl)amino | H |
| 1591. | —(CH₂SO₂)-4-pyridyl | ((2S)-2-amino-3-phenylpropyl)amino | H |
| 1592. | —(CH₂SO₂)-4-pyridyl | 4-methylpiperazinylamino | H |
| 1593. | —(CH₂SO₂)-4-pyridyl | 4-methylpiperazinyl | H |
| 1594. | —(CH₂SO₂)-4-pyridyl | 3-aminopyrrolidinyl | H |
| 1595. | —(CH₂SO₂)-4-pyridyl | (diethylamino)ethylamino | H |
| 1596. | —(CH₂SO₂)-4-pyridyl | 3,5-dimethylpiperazin-1-yl | H |
| 1597. | —(CH₂SO₂)-4-pyridyl | (4-piperidylmethyl)amino | H |
| 1598. | —(CH₂SO₂)-4-pyridyl | (2-methylbutyl)amino | H |
| 1599. | —(CH₂SO₂)-4-pyridyl | 2-(dimethylamino)ethoxy | H |
| 1600. | —(CH₂SO₂)-4-pyridyl | 2-(methylamino)ethoxy | H |
| 1601. | —(CH₂SO₂)-4-pyridyl | ((2R)pyrrolidin-2-yl)methoxy | H |
| 1602. | —(CH₂SO₂)-4-pyridyl | ((2R)-1-methylpyrrolidin-2-yl)methoxy | H |
| 1603. | —(CH₂SO₂)-4-pyridyl | 2-(piperid-1-yl)ethoxy | H |
| 1604. | —(CH₂SO₂)-4-pyridyl | 2-(piperazin-1-yl)ethoxy | H |
| 1605. | —(CH₂SO₂)-4-pyridyl | 2-(morpholin-4-yl)ethoxy | H |
| 1606. | —(CH₂SO₂)-4-pyridyl | Cl | NH₂ |
| 1607. | —(CH₂SO₂)-4-pyridyl | cyclopropylmethylamino | NH₂ |
| 1608. | —(CH₂SO₂)-4-pyridyl | 3-hydroxypropylamino | NH₂ |
| 1609. | —(CH₂SO₂)-4-pyridyl | 2-(1-piperidinyl)ethylamino | NH₂ |
| 1610. | —(CH₂SO₂)-4-pyridyl | 2-(1-pyrrolidinyl)ethylamino | NH₂ |
| 1611. | —(CH₂SO₂)-4-pyridyl | 2-(4-morpholinyl)ethylamino | NH₂ |
| 1612. | —(CH₂SO₂)-4-pyridyl | 3-(1-piperidinyl)propylamino | NH₂ |
| 1613. | —(CH₂SO₂)-4-pyridyl | 3-(1-pyrrolidinyl)propylamino | NH₂ |
| 1614. | —(CH₂SO₂)-4-pyridyl | 3-(4-morpholinyl)propylamino | NH₂ |
| 1615. | —(CH₂SO₂)-4-pyridyl | N-methyl-N-(2-piperid-1-ylethyl)amino | NH₂ |
| 1616. | —(CH₂SO₂)-4-pyridyl | N-methyl-N-(2-pyrrolidin-1-ylethyl)amino | NH₂ |
| 1617. | —(CH₂SO₂)-4-pyridyl | N-methyl-N-(2-morpholin-4-ylethyl)amino | NH₂ |
| 1618. | —(CH₂SO₂)-4-pyridyl | ((2S)-2-amino-3-phenylpropyl)amino | NH₂ |
| 1619. | —(CH₂SO₂)-4-pyridyl | 4-methylpiperazinylamino | NH₂ |
| 1620. | —(CH₂SO₂)-4-pyridyl | 4-methylpiperazinyl | NH₂ |
| 1621. | —(CH₂SO₂)-4-pyridyl | 3-aminopyrrolidinyl | NH₂ |
| 1622. | —(CH₂SO₂)-4-pyridyl | (diethylamino)ethylamino | NH₂ |
| 1623. | —(CH₂SO₂)-4-pyridyl | 3,5-dimethylpiperazin-1-yl | NH₂ |
| 1624. | —(CH₂SO₂)-4-pyridyl | (4-piperidylmethyl)amino | NH₂ |
| 1625. | —(CH₂SO₂)-4-pyridyl | (2-methylbutyl)amino | NH₂ |
| 1626. | —(CH₂SO₂)-4-pyridyl | 2-(dimethylamino)ethoxy | NH₂ |
| 1627. | —(CH₂SO₂)-4-pyridyl | 2-(methylamino)ethoxy | NH₂ |
| 1628. | —(CH₂SO₂)-4-pyridyl | ((2R)pyrrolidin-2-yl)methoxy | NH₂ |
| 1629. | —(CH₂SO₂)-4-pyridyl | ((2R)-1-methylpyrrolidin-2-yl)methoxy | NH₂ |
| 1630. | —(CH₂SO₂)-4-pyridyl | 2-(piperid-1-yl)ethoxy | NH₂ |
| 1631. | —(CH₂SO₂)-4-pyridyl | 2-(piperazin-1-yl)ethoxy | NH₂ |
| 1632. | —(CH₂SO₂)-4-pyridyl | 2-(morpholin-4-yl)ethoxy | NH₂ |
| 1633. | —(NMeSO₂)-phenyl | Cl | H |
| 1634. | —(NMeSO₂)-phenyl | cyclopropylmethylamino | H |
| 1635. | —(NMeSO₂)-phenyl | 3-hydroxypropylamino | H |
| 1636. | —(NMeSO₂)-phenyl | 2-(1-piperidinyl)ethylamino | H |
| 1637. | —(NMeSO₂)-phenyl | 2-(1-pyrrolidinyl)ethylamino | H |
| 1638. | —(NMeSO₂)-phenyl | 2-(4-morpholinyl)ethylamino | H |
| 1639. | —(NMeSO₂)-phenyl | 3-(1-piperidinyl)propylamino | H |
| 1640. | —(NMeSO₂)-phenyl | 3-(1-pyrrolidinyl)propylamino | H |
| 1641. | —(NMeSO₂)-phenyl | 3-(4-morpholinyl)propylamino | H |
| 1642. | —(NMeSO₂)-phenyl | N-methyl-N-(2-piperid-1-ylethyl)amino | H |
| 1643. | —(NMeSO₂)-phenyl | N-methyl-N-(2-pyrrolidin-1-ylethyl)amino | H |
| 1644. | —(NMeSO₂)-phenyl | N-methyl-N-(2-morpholin-4-ylethyl)amino | H |

TABLE 3-continued

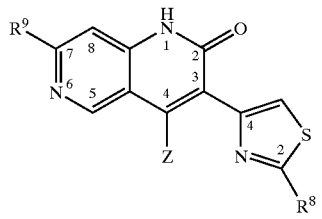

| # | R⁸ | R⁹ | Z |
|---|---|---|---|
| 1645. | —(NMeSO₂)-phenyl | ((2S)-2-amino-3-phenylpropyl)amino | H |
| 1646. | —(NMeSO₂)-phenyl | 4-methylpiperazinylamino | H |
| 1647. | —(NMeSO₂)-phenyl | 4-methylpiperazinyl | H |
| 1648. | —(NMeSO₂)-phenyl | 3-aminopyrrolidinyl | H |
| 1649. | —(NMeSO₂)-phenyl | (diethylamino)ethylamino | H |
| 1650. | —(NMeSO₂)-phenyl | 3,5-dimethylpiperazin-1-yl | H |
| 1651 | —(NMeSO₂)-phenyl | (4-piperidylmethyl)amino | H |
| 1652. | —(NMeSO₂)-phenyl | (2-methylbutyl)amino | H |
| 1653. | —(NMeSO₂)-phenyl | 2-(dimethylamino)ethoxy | H |
| 1654. | —(NMeSO₂)-phenyl | 2-(methylamino)ethoxy | H |
| 1655. | —(NMeSO₂)-phenyl | ((2R)pyrrolidin-2-yl)methoxy | H |
| 1656. | —(NMeSO₂)-phenyl | ((2R)-1-methylpyrrolidin-2-yl)methoxy | H |
| 1657. | —(NMeSO₂)-phenyl | 2-(piperid-1-yl)ethoxy | H |
| 1658. | —(NMeSO₂)-phenyl | 2-(piperazin-1-yl)ethoxy | H |
| 1659. | —(NMeSO₂)-phenyl | 2-(morpholin-4-yl)ethoxy | H |
| 1660. | —(NMeSO₂)-phenyl | Cl | NH₂ |
| 1661. | —(NMeSO₂)-phenyl | cyclopropylmethylamino | NH₂ |
| 1662. | —(NMeSO₂)-phenyl | 3-hydroxypropylamino | NH₂ |
| 1663. | —(NMeSO₂)-phenyl | 2-(1-piperidinyl)ethylamino | NH₂ |
| 1664. | —(NMeSO₂)-phenyl | 2-(1-pyrrolidinyl)ethylamino | NH₂ |
| 1665. | —(NMeSO₂)-phenyl | 2-(4-morpholinyl)ethylamino | NH₂ |
| 1666. | —(NMeSO₂)-phenyl | 3-(1-piperidinyl)propylamino | NH₂ |
| 1667. | —(NMeSO₂)-phenyl | 3-(1-pyrrolidinyl)propylamino | NH₂ |
| 1668. | —(NMeSO₂) | 3-(4-morpholinyl)propylamino | NH₂ |
| 1669. | —(NMeSO₂)-phenyl | N-methyl-N-(2-piperid-1-ylethyl)amino | NH₂ |
| 1670. | —(NMeSO₂)-phenyl | N-methyl-N-(2-pyrrolidin-1-ylethyl)amino | NH₂ |
| 1671. | —(NMeSO₂)-phenyl | N-methyl-N-(2-morpholin-4-ylethyl)amino | NH₂ |
| 1672. | —(NMeSO₂)-phenyl | ((2S)-2-amino-3-phenylpropyl)amino | NH₂ |
| 1673. | —(NMeSO₂)-phenyl | 4-methylpiperazinylamino | NH₂ |
| 1674. | —(NMeSO₂)-phenyl | 4-methylpiperazinyl | NH₂ |
| 1675. | —(NMeSO₂)-phenyl | 3-aminopyrrolidinyl | NH₂ |
| 1676. | —(NMeSO₂)-phenyl | (diethylamino)ethylamino | NH₂ |
| 1677. | —(NMeSO₂)-phenyl | 3,5-dimethylpiperazin-1-yl | NH₂ |
| 1678. | —(NMeSO₂)-phenyl | (4-piperidylmethyl)amino | NH₂ |
| 1679. | —(NMeSO₂)-phenyl | (2-methylbutyl)amino | NH₂ |
| 1680. | —(NMeSO₂)-phenyl | 2-(dimethylamino)ethoxy | NH₂ |
| 1681. | —(NMeSO₂)-phenyl | 2-(methylamino)ethoxy | NH₂ |
| 1682. | —(NMeSO₂)-phenyl | ((2R)pyrrolidin-2-yl)methoxy | NH₂ |
| 1683. | —(NMeSO₂)-phenyl | ((2R)-1-methylpyrrolidin-2-yl)methoxy | NH₂ |
| 1684. | —(NMeSO₂)-phenyl | 2-(piperid-1-yl)ethoxy | NH₂ |
| 1685. | —(NMeSO₂)-phenyl | 2-(piperazin-1-yl)ethoxy | NH₂ |
| 1686. | —(NMeSO₂)-phenyl | 2-(morpholin-4-yl)ethoxy | NH₂ |
| 1687. | —(NMeSO₂)-2-thienyl | Cl | H |
| 1688. | —(NMeSO₂)-2-thienyl | cyclopropylmethylamino | H |
| 1689. | —(NMeSO₂)-2-thienyl | 3-hydroxypropylamino | H |
| 1690. | —(NMeSO₂)-2-thienyl | 2-(1-piperidinyl)ethylamino | H |
| 1691. | —(NMeSO₂)-2-thienyl | 2-(1-pyrrolidinyl)ethylamino | H |
| 1692. | —(NMeSO₂)-2-thienyl | 2-(4-morpholinyl)ethylamino | H |
| 1693. | —(NMeSO₂)-2-thienyl | 3-(1-piperidinyl)propylamino | H |
| 1694. | —(NMeSO₂)-2-thienyl | 3 (1-pyrrolidinyl)propylamino | H |
| 1695. | —(NMeSO₂)-2-thienyl | 3-(4-morpholinyl)propylamino | H |
| 1696. | —(NMeSO₂)-2-thienyl | N-methyl-N-(2-piperid-1-ylethyl)amino | H |
| 1697. | —(NMeSO₂)-2-thienyl | N-methyl-N-(2-pyrrolidin-1-ylethyl)amino | H |
| 1698. | —(NMeSO₂)-2-thienyl | N-methyl-N-(2-morpholin-4-ylethyl)amino | H |
| 1699. | —(NMeSO₂)-2-thienyl | ((2S)-2-amino-3-phenylpropyl)amino | H |
| 1700. | —(NMeSO₂)-2-thienyl | 4-methylpiperazinylamino | H |
| 1701. | —(NMeSO₂)-2-thienyl | 4-methylpiperazinyl | H |
| 1702. | —(NMeSO₂)-2-thienyl | 3-aminopyrrolidinyl | H |
| 1703. | —(NMeSO₂)-2-thienyl | (diethylamino)ethylamino | H |
| 1704. | —(NMeSO₂)-2-thienyl | 3,5-dimethylpiperazin-1-yl | H |
| 1705. | —(NMeSO₂)-2-thienyl | (4-piperidylmethyl)amino | H |
| 1706. | —(NMeSO₂)-2-thienyl | (2-methylbutyl)amino | H |
| 1707. | —(NMeSO₂)-2-thienyl | 2-(dimethylamino)ethoxy | H |
| 1708. | —(NMeSO₂)-2-thienyl | 2-(methylamino)ethoxy | H |
| 1709. | —(NMeSO₂) 2 thienyl | ((2R)pyrrolidin-2-yl)methoxy | H |

TABLE 3-continued

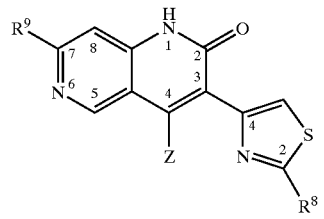

| # | R⁸ | R⁹ | Z |
|---|---|---|---|
| 1710. | —(NMeSO₂)-2-thienyl | ((2R)-1-methylpyrrolidin-2-yl)methoxy | H |
| 1711. | —(NMeSO₂)-2-thienyl | 2-(piperid-1-yl)ethoxy | H |
| 1712. | —(NMeSO₂)-2-thienyl | 2-(piperazin-1-yl)ethoxy | H |
| 1713. | —(NMeSO₂)-2-thienyl | 2-(morpholin-4-yl)ethoxy | H |
| 1714. | —(NMeSO₂)-2-thienyl | Cl | NH₂ |
| 1715. | —(NMeSO₂)-2-thienyl | cyclopropylmethylamino | NH₂ |
| 1716. | —(NMeSO₂)-2-thienyl | 3-hydroxypropylamino | NH₂ |
| 1717. | —(NMeSO₂)-2-thienyl | 2-(1-piperidinyl)ethylamino | NH₂ |
| 1718. | —(NMeSO₂)-2-thienyl | 2-(1-pyrrolidinyl)ethylamino | NH₂ |
| 1719. | —(NMeSO₂)-2-thienyl | 2-(4-morpholinyl)ethylamino | NH₂ |
| 1720. | —(NMeSO₂)-2-thienyl | 3-(1-piperidinyl)propylamino | NH₂ |
| 1721. | —(NMeSO₂)-2-thienyl | 3-(1-pyrrolidinyl)propylamino | NH₂ |
| 1722. | —(NMeSO₂)-2-thienyl | 3-(4-morpholinyl)propylamino | NH₂ |
| 1723. | —(NMeSO₂)-2-thienyl | N-methyl-N-(2-piperid-1-ylethyl)amino | NH₂ |
| 1724. | —(NMeSO₂)-2-thienyl | N-methyl-N-(2-pyrrolidin-1-ylethyl)amino | NH₂ |
| 1725. | —(NMeSO₂)-2-thienyl | N-methyl-N-(2-morpholin-4-ylethyl)amino | NH₂ |
| 1726. | —(NMeSO₂)-2-thienyl | ((2S)-2-amino-3-phenylpropyl)amino | NH₂ |
| 1727. | —(NMeSO₂)-2-thienyl | 4-methylpiperazinylamino | NH₂ |
| 1728. | —(NMeSO₂)-2-thienyl | 4-methylpiperazinyl | NH₂ |
| 1729. | —(NMeSO₂)-2-thienyl | 3-aminopyrrolidinyl | NH₂ |
| 1730. | —(NMeSO₂)-2-thienyl | (diethylamino)ethylamino | NH₂ |
| 1731. | —(NMeSO₂)-2-thienyl | 3,5-dimethylpiperazin-1-yl | NH₂ |
| 1732. | —(NMeSO₂)-2-thienyl | (4-piperidylmethyl)amino | NH₂ |
| 1733. | —(NMeSO₂)-2-thienyl | (2-methylbutyl)amino | NH₂ |
| 1734. | —(NMeSO₂)-2-thienyl | 2-(dimethylamino)ethoxy | NH₂ |
| 1735. | —(NMeSO₂)-2-thienyl | 2-(methylamino)ethoxy | NH₂ |
| 1736. | —(NMeSO₂)-2-thienyl | ((2R)pyrrolidin-2-yl)methoxy | NH₂ |
| 1737. | —(NMeSO₂)-2-thienyl | ((2R)-1-methylpyrrolidin-2-yl)methoxy | NH₂ |
| 1738. | —(NMeSO₂)-2-thienyl | 2-(piperid-1-yl)ethoxy | NH₂ |
| 1739. | —(NMeSO₂)-2-thienyl | 2-(piperazin-1-yl)ethoxy | NH₂ |
| 1740. | —(NMeSO₂)-2-thienyl | 2-(morpholin-4-yl)ethoxy | NH₂ |
| 1741. | —(NMeSO₂)-2-pyridyl | Cl | H |
| 1742. | —(NMeSO₂)-2-pyridyl | cyclopropylmethylamino | H |
| 1743. | —(NMeSO₂)-2-pyridyl | 3-hydroxypropylamino | H |
| 1744. | —(NMeSO₂)-2-pyridyl | 2-(1-piperidinyl)ethylamino | H |
| 1745. | —(NMeSO₂)-2-pyridyl | 2-(1-pyrrolidinyl)ethylamino | H |
| 1746. | —(NMeSO₂)-2-pyridyl | 2-(4-morpholinyl)ethylamino | H |
| 1747. | —(NMeSO₂)-2-pyridyl | 3-(1-piperidinyl)propylamino | H |
| 1748. | —(NMeSO₂)-2-pyridyl | 3-(1-pyrrolidinyl)propylamino | H |
| 1749. | —(NMeSO₂)-2-pyridyl | 3-(4-morpholinyl)propylamino | H |
| 1750. | —(NMeSO₂)-2-pyridyl | N-methyl-N-(2-piperid-1-ylethyl)amino | H |
| 1751. | —(NMeSO₂)-2-pyridyl | N-methyl-N-(2-pyrrolidin-1-ylethyl)amino | H |
| 1752. | —(NMeSO₂)-2-pyridyl | N-methyl-N-(2-morpholin-4-ylethyl)amino | H |
| 1753. | —(NMeSO₂)-2-pyridyl | ((2S)-2-amino-3-phenylpropyl)amino | H |
| 1754. | —(NMeSO₂)-2-pyridyl | 4-methylpiperazinylamino | H |
| 1755. | —(NMeSO₂)-2-pyridyl | 4-methylpiperazinyl | H |
| 1756. | —(NMeSO₂)-2-pyridyl | 3-aminopyrrolidinyl | H |
| 1757. | —(NMeSO₂)-2-pyridyl | (diethylamino)ethylamino | H |
| 1758. | —(NMeSO₂)-2-pyridyl | 3,5-dimethylpiperazin-1-yl | H |
| 1759. | —(NMeSO₂)-2-pyridyl | (4-piperidylmethyl)-amino | H |
| 1760. | —(NMeSO₂)-2-pyridyl | (2-methylbutyl)amino | H |
| 1761. | —(NMeSO₂)-2-pyridyl | 2-(dimethylamino)ethoxy | H |
| 1762. | —(NMeSO₂)-2-pyridyl | 2-(methylamino)-ethoxy | H |
| 1763. | —(NMeSO₂)-2-pyridyl | ((2R)pyrrolidin-2-yl)methoxy | H |
| 1764. | —(NMeSO₂)-2-pyridyl | ((2R)-1-methylpyrrolidin-2-yl)methoxy | H |
| 1765. | —(NMeSO₂)-2-pyridyl | 2-(piperid-1-yl)ethoxy | H |
| 1766. | —(NMeSO₂)-2-pyridyl | 2-(piperazin-1-yl)ethoxy | H |
| 1767. | —(NMeSO₂) 2-pyridyl | 2-(morpholin-4-yl)ethoxy | H |
| 1768. | —(NMeSO₂)-2-pyridyl | Cl | NH₂ |
| 1769. | —(NMeSO₂)-2-pyridyl | cyclopropylmethylamino | NH₂ |
| 1770. | —(NMeSO₂)-2-pyridyl | 3-hydroxypropylamino | NH₂ |
| 1771. | —(NMeSO₂)-2-pyridyl | 2-(1-piperidinyl)ethylamino | NH₂ |
| 1772. | —(NMeSO₂)-2-pyridyl | 2-(1-pyrrolidinyl)ethylamino | NH₂ |
| 1773. | —(NMeSO₂)-2-pyridyl | 2-(4-morpholinyl)ethylamino | NH₂ |
| 1774. | —(NMeSO₂)-2-pyridyl | 3-(1-piperidinyl)propylamino | NH₂ |

TABLE 3-continued

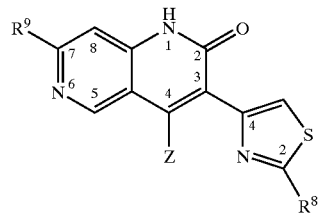

| # | R[8] | R[9] | Z |
|---|---|---|---|
| 1775. | —(NMeSO$_2$)-2-pyridyl | 3-(1-pyrrolidinyl)propylamino | NH$_2$ |
| 1776. | —(NMeSO$_2$)-2-pyridyl | 3-(4-morpholinyl)propylamino | NH$_2$ |
| 1777. | —(NMeSO$_2$)-2-pyridyl | N-methyl-N-(2-piperid-1-ylethyl)amino | NH$_2$ |
| 1778. | —(NMeSO$_2$)-2-pyridyl | N-methyl-N-(2-pyrrolidin-1-ylethyl)amino | NH$_2$ |
| 1779. | —(NMeSO$_2$)-2-pyridyl | N-methyl-N-(2-morpholin-4-ylethyl)amino | NH$_2$ |
| 1780. | —(NMeSO$_2$)-2-pyridyl | ((2S)-2-amino-3-phenylpropyl)amino | NH$_2$ |
| 1781. | —(NMeSO$_2$)-2-pyridyl | 4-methylpiperazinylamino | NH$_2$ |
| 1782. | —(NMeSO$_2$)-2-pyridyl | 4-methylpiperazinyl | NH$_2$ |
| 1783. | —(NMeSO$_2$)-2-pyridyl | 3-aminopyrrolidinyl | NH$_2$ |
| 1784. | —(NMeSO$_2$)-2-pyridyl | (diethylamino)ethylamino | NH$_2$ |
| 1785. | —(NMeSO$_2$)-2-pyridyl | 3,5-dimethylpiperazin-1-yl | NH$_2$ |
| 1786. | —(NMeSO$_2$)-2-pyridyl | (4-piperidylmethyl)amino | NH$_2$ |
| 1787. | —(NMeSO$_2$)-2-pyridyl | (2-methylbutyl)amino | NH$_2$ |
| 1788. | —(NMeSO$_2$)-2-pyridyl | 2-(dimethylamino)ethoxy | NH$_2$ |
| 1789. | —(NMeSO$_2$)-2-pyridyl | 2-(methylamino)ethoxy | NH$_2$ |
| 1790. | —(NMeSO$_2$)-2-pyridyl | ((2R)pyrrolidin-2-yl)methoxy | NH$_2$ |
| 1791. | —(NMeSO$_2$)-2-pyridyl | ((2R)-1-methylpyrrolidin-2-yl)methoxy | NH$_2$ |
| 1792. | —(NMeSO$_2$)-2-pyridyl | 2-(piperid-1-yl)ethoxy | NH$_2$ |
| 1793. | —(NMeSO$_2$)-2-pyridyl | 2-(piperazin-1-yl)ethoxy | NH$_2$ |
| 1794. | —(NMeSO$_2$)-2-pyridyl | 2-(morpholin-4-yl)ethoxy | NH$_2$ |
| 1795. | —(NMeSO$_2$)-3-pyridyl | Cl | H |
| 1796. | —(NMeSO$_2$)-3-pyridyl | cyclopropylmethylamino | H |
| 1797. | —(NMeSO$_2$)-3-pyridyl | 3-hydroxypropylamino | H |
| 1798. | —(NMeSO$_2$)-3-pyridyl | 2-(1-piperidinyl)ethylamino | H |
| 1799. | —(NMeSO$_2$)-3-pyridyl | 2-(1-pyrrolidinyl)ethylamino | H |
| 1800. | —(NMeSO$_2$)-3-pyridyl | 2-(4-morpholinyl)ethylamino | H |
| 1801. | —(NMeSO$_2$)-3-pyridyl | 3-(1-piperidinyl)propylamino | H |
| 1802. | —(NMeSO$_2$)-3-pyridyl | 3-(1-pyrrolidinyl)propylamino | H |
| 1803. | —(NMeSO$_2$)-3-pyridyl | 3-(4-morpholinyl)propylamino | H |
| 1804. | —(NMeSO$_2$)-3-pyridyl | N-methyl-N-(2-piperid-1-ylethyl)amino | H |
| 1805. | —(NMeSO$_2$)-3-pyridyl | N-methyl-N-(2-pyrrolidin-1-ylethyl)amino | H |
| 1806. | —(NMeSO$_2$)-3-pyridyl | N-methyl-N-(2-morpholin-4-ylethyl)amino | H |
| 1807. | —(NMeSO$_2$)-3-pyridyl | ((2S)-2-amino-3-phenylpropyl)amino | H |
| 1808. | —(NMeSO$_2$)-3-pyridyl | 4-methylpiperazinylamino | H |
| 1809. | —(NMeSO$_2$)-3-pyridyl | 4-methylpiperazinyl | H |
| 1810. | —(NMeSO$_2$)-3-pyridyl | 3-aminopyrrolidinyl | H |
| 1811. | —(NMeSO$_2$)-3-pyridyl | (diethylamino)ethylamino | H |
| 1812. | —(NMeSO$_2$)-3-pyridyl | 3,5-dimethylpiperazin-1-yl | H |
| 1813. | —(NMeSO$_2$)-3-pyridyl | (4-piperidylmethyl)amino | H |
| 1814. | —(NMeSO$_2$)-3-pyridyl | (2-methylbutyl)amino | H |
| 1815. | —(NMeSO$_2$)-3-pyridyl | 2-(dimethylamino)ethoxy | H |
| 1816. | —(NMeSO$_2$)-3-pyridyl | 2-(methylamino)ethoxy | H |
| 1817. | —(NMeSO$_2$)-3-pyridyl | ((2R)pyrrolidin-2-yl)methoxy | H |
| 1818. | —(NMeSO$_2$)-3-pyridyl | ((2R)-1-methylpyrrolidin-2-yl)methoxy | H |
| 1819. | —(NMeSO$_2$)-3-pyridyl | 2-(piperid-1-yl)ethoxy | H |
| 1820. | —(NMeSO$_2$)-3-pyridyl | 2-(piperazin-1-yl)ethoxy | H |
| 1821. | —(NMeSO$_2$)-3-pyridyl | 2-(morpholin-4-yl)ethoxy | H |
| 1822. | —(NMeSO$_2$)-3-pyridyl | Cl | NH$_2$ |
| 1823. | —(NMeSO$_2$)-3-pyridyl | cyclopropylmethylamino | NH$_2$ |
| 1824. | —(NMeSO$_2$)-3-pyridyl | 3-hydroxypropylamino | NH$_2$ |
| 1825. | —(NMeSO$_2$)-3-pyridyl | 2-(1-piperidinyl)ethylamino | NH$_2$ |
| 1826. | —(NMeSO$_2$)-3-pyridyl | 2-(1-pyrrolidinyl)ethylamino | NH$_2$ |
| 1827. | —(NMeSO$_2$)-3-pyridyl | 2-(4-morpholinyl)ethylamino | NH$_2$ |
| 1828. | —(NMeSO$_2$)-3-pyridyl | 3-(1-piperidinyl)propylamino | NH$_2$ |
| 1829. | —(NMeSO$_2$)-3-pyridyl | 3-(1-pyrrolidinyl)propylamino | NH$_2$ |
| 1830. | —(NMeSO$_2$)-3-pyridyl | 3-(4-morpholinyl)propylamino | NH$_2$ |
| 1831. | —(NMeSO$_2$)-3-pyridyl | N-methyl-N-(2-piperid-1-ylethyl)amino | NH$_2$ |
| 1832. | —(NMeSO$_2$)-3-pyridyl | N-methyl-N-(2-pyrrolidin-1-ylethyl)amino | NH$_2$ |
| 1833. | —(NMeSO$_2$)-3-pyridyl | N-methyl-N-(2-morpholin-4-ylethyl)amino | NH$_2$ |
| 1834. | —(NMeSO$_2$)-3-pyridyl | ((2S)-2-amino-3-phenylpropyl)amino | NH$_2$ |
| 1835. | —(NMeSO$_2$)-3-pyridyl | 4-methylpiperazinylamino | NH$_2$ |
| 1836. | —(NMeSO$_2$)-3-pyridyl | 4-methylpiperazinyl | NH$_2$ |
| 1837. | —(NMeSO$_2$)-3-pyridyl | 3-aminopyrrolidinyl | NH$_2$ |
| 1838. | —(NMeSO$_2$)-3-pyridyl | (diethylamino)ethylamino | NH$_2$ |
| 1839. | —(NMeSO$_2$)-3-pyridyl | 3,5-dimethylpiperazin-1-yl | NH$_2$ |

TABLE 3-continued

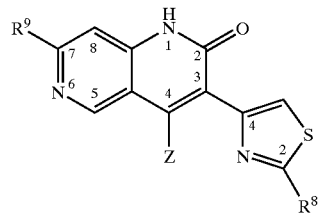

| # | R⁸ | R⁹ | Z |
|---|---|---|---|
| 1840. | —(NMeSO₂)-3-pyridyl | (4-piperidylmethyl)amino | NH₂ |
| 1841. | —(NMeSO₂)-3-pyridyl | (2-methylbutyl)amino | NH₂ |
| 1842. | —(NMeSO₂)-3-pyridyl | 2-(dimethylamino)ethoxy | NH₂ |
| 1843. | —(NMeSO₂)-3-pyridyl | 2-(methylamino)ethoxy | NH₂ |
| 1844. | —(NMeSO₂)-3-pyridyl | ((2R)pyrrolidin-2-yl)methoxy | NH₂ |
| 1845. | —(NMeSO₂)-3-pyridyl | ((2R)-1-methylpyrrolidin-2-yl)methoxy | NH₂ |
| 1846. | —(NMeSO₂)-3-pyridyl | 2-(piperid-1-yl)ethoxy | NH₂ |
| 1847. | —(NMeSO₂)-3-pyridyl | 2-(piperazin-1-yl)ethoxy | NH₂ |
| 1848. | —(NMeSO₂)-3-pyridyl | 2-(morpholin-4-yl)ethoxy | NH₂ |
| 1849. | —(NMeSO₂)-4-pyridyl | Cl | H |
| 1850. | —(NMeSO₂)-4-pyridyl | cyclopropylmethylamino | H |
| 1851. | —(NMeSO₂)-4-pyridyl | 3-hydroxypropylamino | H |
| 1852. | —(NMeSO₂)-4-pyridyl | 2-(1-piperidinyl)ethylamino | H |
| 1853. | —(NMeSO₂)-4-pyridyl | 2-(1-pyrrolidinyl)ethylamino | H |
| 1854. | —(NMeSO₂)-4-pyridyl | 2-(4-morpholinyl)ethylamino | H |
| 1855. | —(NMeSO₂)-4-pyridyl | 3-(1-piperidinyl)propylamino | H |
| 1856. | —(NMeSO₂)-4-pyridyl | 3-(1-pyrrolidinyl)propylamino | H |
| 1857. | —(NMeSO₂)-4-pyridyl | 3-(4-morpholinyl)propylamino | H |
| 1858. | —(NMeSO₂)-4-pyridyl | N-methyl-N-(2-piperid-1-ylethyl)amino | H |
| 1859. | —(NMeSO₂)-4-pyridyl | N-methyl-N-(2-pyrrolidin-1-ylethyl)amino | H |
| 1860. | —(NMeSO₂)-4-pyridyl | N-methyl-H-(2-morpholin-4-ylethyl)amino | H |
| 1861. | —(NMeSO₂)-4-pyridyl | ((2S)-2-amino-3-phenylpropyl)amino | H |
| 1862. | —(NMeSO₂)-4-pyridyl | 4-methylpiperazinylamino | H |
| 1863. | —(NMeSO₂)-4-pyridyl | 4-methylpiperazinyl | H |
| 1864. | —(NMeSO₂)-4-pyridyl | 3-aminopyrrolidinyl | H |
| 1865. | —(NMeSO₂)-4-pyridyl | (diethylamino)ethylamino | H |
| 1866. | —(NMeSO₂)-4-pyridyl | 3,5-dimethylpiperazin-1-yl | H |
| 1867. | —(NMeSO₂)-4-pyridyl | (4-piperidylmethyl)amino | H |
| 1868. | —(NMeSO₂)-4-pyridyl | (2-methylbutyl)amino | H |
| 1869. | —(NMeSO₂)-4-pyridyl | 2-(dimethylamino)ethoxy | H |
| 1870. | —(NMeSO₂)-4-pyridyl | 2-(methylamino)ethoxy | H |
| 1871. | —(NMeSO₂)-4-pyridyl | ((2R)pyrrolidin-2-yl)methoxy | H |
| 1872. | —(NMeSO₂)-4-pyridyl | (2R)-1-methylpyrrolidin-2-yl)methoxy | H |
| 1873. | —(NMeSO₂)-4-pyridyl | 2-(piperid-1-yl)ethoxy | H |
| 1874. | —(NMeSO₂)-4-pyridyl | 2-(piperazin-1-yl)ethoxy | H |
| 1875. | —(NMeSO₂)-4-pyridyl | 2-(morpholin-4-yl)ethoxy | H |
| 1876. | —(NMeSO₂)-4-pyridyl | Cl | NH₂ |
| 1877. | —(NMeSO₂)-4-pyridyl | cyclopropylmethylamino | NH₂ |
| 1878. | —(NMeSO₂)-4-pyridyl | 3-hydroxypropylamino | NH₂ |
| 1879. | —(NMeSO₂)-4-pyridyl | 2-(1-piperidinyl)ethylamino | NH₂ |
| 1880. | —(NMeSO₂)-4-pyridyl | 2-(1-pyrrolidinyl)ethylamino | NH₂ |
| 1881. | —(NMeSO₂)-4-pyridyl | 2-(4-morpholinyl)ethylamino | NH₂ |
| 1882. | —(NMeSO₂)-4-pyridyl | 3-(1-piperidinyl)propylamino | NH₂ |
| 1883. | —(NMeSO₂)-4-pyridyl | 3-(1-pyrrolidinyl)propylamino | NH₂ |
| 1884. | —(NMeSO₂)-4-pyridyl | 3-(4-morpholinyl)propylamino | NH₂ |
| 1885. | —(NMeSO₂)-4-pyridyl | N-methyl-N-(2-piperid-1-ylethyl)amino | NH₂ |
| 1886. | —(NMeSO₂)-4-pyridyl | N-methyl-N-(2-pyrrolidin-1-ylethyl)amino | NH₂ |
| 1887. | —(NMeSO₂)-4-pyridyl | N-methyl-N-(2-morpholin-4-ylethyl)amino | NH₂ |
| 1888. | —(NMeSO₂)-4-pyridyl | ((2S-2-amino-3-phenylpropyl)amino | NH₂ |
| 1889. | —(NMeSO₂)-4-pyridyl | 4-methylpiperazinylamino | NH₂ |
| 1890. | —(NMeSO₂)-4-pyridyl | 4-methylpiperazinyl | NH₂ |
| 1891. | —(NMeSO₂)-4-pyridyl | 3-aminopyrrolidinyl | NH₂ |
| 1892. | —(NMeSO₂)-4-pyridyl | (diethylamino)ethylamino | NH₂ |
| 1893. | —(NMeSO₂)-4-pyridyl | 3,5-dimethylpiperazin-1-yl | NH₂ |
| 1894. | —(NMeSO₂)-4-pyridyl | (4-piperidylmethyl)amino | NH₂ |
| 1895. | —(NMeSO₂)-4-pyridyl | (2-methylbutyl)amino | NH₂ |
| 1896. | —(NMeSO₂)-4-pyridyl | 2-(dimethylamino)ethoxy | NH₂ |
| 1897. | —(NMeSO₂)-4-pyridyl | 2-(methylamino)ethoxy | NH₂ |
| 1898. | —(NMeSO₂)-4-pyridyl | ((2R)pyrrolidin-2-yl)methoxy | NH₂ |
| 1899. | —(NMeSO₂)-4-pyridyl | ((2R)-1-methylpyrrolidin-2-yl)methoxy | NH₂ |
| 1900. | —(NMeSO₂)-4-pyridyl | 2-(piperid-1-yl)ethoxy | NH₂ |
| 1901. | —(NMeSO₂)-4-pyridyl | 2-(piperazin-1-yl)ethoxy | NH₂ |
| 1902. | —(NMeSO₂)-4-pyridyl | 2-(morpholin-4-yl)ethoxy | NH₂ |

TABLE 4

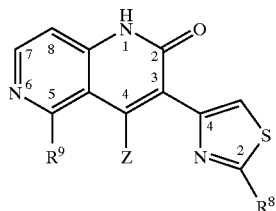

| # | R⁸ | R⁹ | Z |
|---|---|---|---|
| 1903. | 4-pyridyl | Cl | H |
| 1904. | 4-pyridyl | cyclopropylmethylamino | H |
| 1905. | 4-pyridyl | 3-hydroxypropylamino | H |
| 1906. | 4-pyridyl | 2-(1-piperidinyl)ethylamino | H |
| 1907. | 4-pyridyl | 2-(1-pyrrolidinyl)ethylamino | H |
| 1908. | 4-pyridyl | 2-(4-morpholinyl)ethylamino | H |
| 1909. | 4-pyridyl | 3-(1-piperidinyl)propylamino | H |
| 1910. | 4-pyridyl | 3-(1-pyrrolidiny))propylamino | H |
| 1911. | 4-pyridyl | 3-(4-morpholinyl)propylamino | H |
| 1912. | 4-pyridyl | N-methyl-N-(2-piperid-1-ylethyl)amino | H |
| 1913. | 4-pyridyl | N-methyl-N-(2-pyrrolidin-1-ylethyl)amino | H |
| 1914. | 4-pyridyl | N-methyl-N-(2-morpholin-4-ylethyl)amino | H |
| 1915. | 4-pyridyl | ((2S)-2-amino-3-phenylpropyl)amino | H |
| 1916. | 4-pyridyl | 4-methylpiperazinylamino | H |
| 1917. | 4-pyridyl | 4-methylpiperazinyl | H |
| 1918. | 4-pyridyl | 3-aminopyrrolidinyl | H |
| 1919. | 4-pyridyl | (diethylamino)ethylamino | H |
| 1920. | 4-pyridyl | 3,5-dimethylpiperazin-1-yl | H |
| 1921. | 4-pyridyl | (4-piperidylmethyl)amino | H |
| 1922. | 4-pyridyl | (2-methylbutyl)amino | H |
| 1923. | 4-pyridyl | 2-(dimethylamino)ethoxy | H |
| 1924. | 4-pyridyl | 2-(methylamino)ethoxy | H |
| 1925. | 4-pyridyl | ((2R)pyrrolidin-2-yl)methoxy | H |
| 1926. | 4-pyridyl | ((2R)-1-methylpyrrolidin-2-yl)methoxy | H |
| 1927. | 4-pyridyl | 2-(piperid-1-yl)ethoxy | H |
| 1928. | 4-pyridyl | 2-(piperazin-1-yl)ethoxy | H |
| 1929. | 4-pyridyl | 2-(morpholin-4-yl)ethoxy | H |
| 1930. | 4-pyridyl | Cl | $NH_2$ |
| 1931. | 4-pyridyl | cyclopropylmethylamino | $NH_2$ |
| 1932. | 4-pyridyl | 3-hydroxypropylamino | $NH_2$ |
| 1933. | 4-pyridyl | 2-(1-piperidinyl)ethylamino | $NH_2$ |
| 1934. | 4-pyridyl | 2-(1-pyrrolidinyl)ethylamino | $NH_2$ |
| 1935. | 4-pyridyl | 2-(4-morpholinyl)ethylamino | $NH_2$ |
| 1936. | 4-pyridyl | 3-(1-piperidinyl)propylamino | $NH_2$ |
| 1937. | 4-pyridyl | 3-(1-pyrrolidinyl)propylamino | $NH_2$ |
| 1938. | 4-pyridyl | 3-(4-morpholinyl)propylamino | $NH_2$ |
| 1939. | 4-pyridyl | N-methyl-N-(2-piperid-1-ylethyl)amino | $NH_2$ |
| 1940. | 4-pyridyl | N-methyl-N-(2-pyrrolidin-1-ylethyl)amino | $NH_2$ |
| 1941. | 4-pyridyl | N-methyl-N-(2-morpholin-4-ylethyl)amino | $NH_2$ |
| 1942. | 4-pyridyl | ((2S)-2-amino-3-phenylpropyl)amino | $NH_2$ |
| 1943. | 4-pyridyl | 4-methylpiperazinylamino | $NH_2$ |
| 1944. | 4-pyridyl | 4-methylpiperazinyl | $NH_2$ |
| 1945. | 4-pyridyl | 3-aminopyrrolidinyl | $NH_2$ |
| 1946. | 4-pyridyl | (diethylamino)ethylamino | $NH_2$ |
| 1947. | 4-pyridyl | 3,5-dimethylpiperazin-1-yl | $NH_2$ |
| 1948. | 4-pyridyl | (4-piperidylmethyl)amino | $NH_2$ |
| 1949. | 4-pyridyl | (2-methylbutyl)amino | $NH_2$ |
| 1950. | 4-pyridyl | 2-(dimethylamino)ethoxy | $NH_2$ |
| 1951. | 4-pyridyl | 2-(methylamino)ethoxy | $NH_2$ |
| 1952. | 4-pyridyl | ((2R)pyrrolidin-2-yl)methoxy | $NH_2$ |
| 1953. | 4-pyridyl | ((2R)-1-methylpyrrolidin-2-yl)methoxy | $NH_2$ |
| 1954. | 4-pyridyl | 2-(piperid-1-yl)ethoxy | $NH_2$ |
| 1955. | 4-pyridyl | 2-(piperazin-1-yl)ethoxy | $NH_2$ |
| 1956. | 4-pyridyl | 2-(morpholin-4-yl)ethoxy | $NH_2$ |
| 1957. | —($CH_2SO_2$)-phenyl | Cl | H |
| 1958. | —($CH_2SO_2$)-phenyl | cyclopropylmethylamino | H |
| 1959. | —($CH_2SO_2$)-phenyl | 3-hydroxypropylamino | H |
| 1960. | —($CH_2SO_2$)-phenyl | 2-(1-piperidinyl)ethylamino | H |
| 1961. | —($CH_2SO_2$)-phenyl | 2-(1-pyrrolidinyl)ethylamino | H |
| 1962. | —($CH_2SO_2$)-phenyl | 2-(4-morpholinyl)ethylamino | H |
| 1963. | —($CH_2SO_2$) phenyl | 3-(1-piperidinyl)propylamino | H |
| 1964. | —($CH_2SO_2$)-phenyl | 3-(1-pyrrolidinyl)propylamino | H |
| 1965. | —($CH_2SO_2$)-phenyl | 3-(4-morpholinyl)propylamino | H |
| 1966. | —($CH_2SO_2$)-phenyl | N-methyl-N-(2-piperid-1-ylethyl)amino | H |
| 1967. | —($CH_2SO_2$)-phenyl | N-methyl-N-(2-pyrrolidin-1-ylethyl)amino | H |

TABLE 4-continued

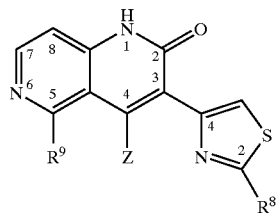

| # | $R^8$ | $R^9$ | Z |
|---|---|---|---|
| 1968. | —(CH$_2$SO$_2$)-phenyl | N-methyl-N-(2-morpholin-4-ylethyl)amino | H |
| 1969. | —(CH$_2$SO$_2$)-phenyl | ((2S)-2-amino-3-phenylpropyl)amino | H |
| 1970. | —(CH$_2$SO$_2$)-phenyl | 4-methylpiperazinylamino | H |
| 1971. | —(CH$_2$SO$_2$)-phenyl | 4-methylpiperazinyl | H |
| 1972. | —(CH$_2$SO$_2$)-phenyl | 3-aminopyrrolidinyl | H |
| 1973. | —(CH$_2$SO$_2$)-phenyl | (diethylamino)ethylamino | H |
| 1974. | —(CH$_2$SO$_2$)-phenyl | 3,5-dimethylpiperazin-1-yl | H |
| 1975. | —(CH$_2$SO$_2$)-phenyl | (4-piperidylmethyl)amino | H |
| 1976. | —(CH$_2$SO$_2$)-phenyl | (2-methylbutyl)amino | H |
| 1977. | —(CH$_2$SO$_2$)-phenyl | 2-(dimethylamino)ethoxy | H |
| 1978. | —(CH$_2$SO$_2$)-phenyl | 2-(methylamino)ethoxy | H |
| 1979. | —(CH$_2$SO$_2$)-phenyl | ((2R)pyrrolidin-2-yl)methoxy | H |
| 1980. | —(CH$_2$SO$_2$)-phenyl | ((2R)-1-methylpyrrolidin-2-yl)methoxy | H |
| 1981. | —(CH$_2$SO$_2$)-phenyl | 2-(piperid-1-yl)ethoxy | H |
| 1982. | —(CH$_2$SO$_2$)-phenyl | 2-(piperazin-1-yl)ethoxy | H |
| 1983. | —(CH$_2$SO$_2$)-phenyl | 2-(morpholin-4-yl)ethoxy | H |
| 1984. | —(CH$_2$SO$_2$)-phenyl | Cl | NH$_2$ |
| 1985. | —(CH$_2$SO$_2$)-phenyl | cyclopropylmethylamino | NH$_2$ |
| 1986. | —(CH$_2$SO$_2$)-phenyl | 3-hydroxypropylamino | NH$_2$ |
| 1987. | —(CH$_2$SO$_2$)-phenyl | 2-(1-piperidinyl)ethylamino | NH$_2$ |
| 1988. | —(CH$_2$SO$_2$)-phenyl | 2-(1-pyrrolidinyl)ethylamino | NH$_2$ |
| 1989. | —(CH$_2$SO$_2$)-phenyl | 2-(4-morpholinyl)ethylamino | NH$_2$ |
| 1990. | —(CH$_2$SO$_2$)-phenyl | 3-(1-piperidinyl)propylamino | NH$_2$ |
| 1991. | —(CH$_2$SO$_2$)-phenyl | 3-(1-pyrrolidinyl)propylamino | NH$_2$ |
| 1992. | —(CH$_2$SO$_2$)-phenyl | 3-(4-morpholinyl)propylamino | NH$_2$ |
| 1993. | —(CH$_2$SO$_2$)-phenyl | N-methyl-N-(2-piperid-1-ylethyl)amino | NH$_2$ |
| 1994. | —(CH$_2$SO$_2$)-phenyl | N-methyl-N-(2-pyrrolidin-1-ylethyl)amino | NH$_2$ |
| 1995. | —(CH$_2$SO$_2$)-phenyl | N-methyl-N-(2-morpholin-4-ylethyl)amino | NH$_2$ |
| 1996. | —(CH$_2$SO$_2$)-phenyl | ((2S)-2-amino-3-phenylpropyl)amino | NH$_2$ |
| 1997. | —(CH$_2$SO$_2$)-phenyl | 4-methylpiperazinylamino | NH$_2$ |
| 1998. | —(CH$_2$SO$_2$)-phenyl | 4-methylpiperazinyl | NH$_2$ |
| 1999. | —(CH$_2$SO$_2$)-phenyl | 3-aminopyrrolidinyl | NH$_2$ |
| 2000. | —(CH$_2$SO$_2$)-phenyl | (diethylamino)ethylamino | NH$_2$ |
| 2001. | —(CH$_2$SO$_2$)-phenyl | 3,5-dimethylpiperazin-1-yl | NH$_2$ |
| 2002. | —(CH$_2$SO$_2$)-phenyl | (4-piperidylmethyl)amino | NH$_2$ |
| 2003. | —(CH$_2$SO$_2$)-phenyl | (2-methylbutyl)amino | NH$_2$ |
| 2004. | —(CH$_2$SO$_2$)-phenyl | 2-(dimethylamino)ethoxy | NH$_2$ |
| 2005. | —(CH$_2$SO$_2$)-phenyl | 2-(methylamino)ethoxy | NH$_2$ |
| 2006. | —(CH$_2$SO$_2$)-phenyl | ((2R)pyrrolidin-2-yl)methoxy | NH$_2$ |
| 2007. | —(CH$_2$SO$_2$)-phenyl | ((2R)-1-methylpyrrolidin-2-yl)methoxy | NH$_2$ |
| 2008. | —(CH$_2$SO$_2$)-phenyl | 2-(piperid-1-yl)ethoxy | NH$_2$ |
| 2009. | —(CH$_2$SO$_2$)-phenyl | 2-(piperazin-1-yl)ethoxy | NH$_2$ |
| 2010. | —(CH$_2$SO$_2$)-phenyl | 2-(morpholin-4-yl)ethoxy | NH$_2$ |
| 2011. | —(CH$_2$SO$_2$)-2-thienyl | Cl | H |
| 2012. | —(CH$_2$SO$_2$)-2-thienyl | cyclopropylmethylamino | H |
| 2013. | —(CH$_2$SO$_2$)-2-thienyl | 3-hydroxypropylamino | H |
| 2014. | —(CH$_2$SO$_2$)-2-thienyl | 2-(1-piperidinyl)ethylamino | H |
| 2015. | —(CH$_2$SO$_2$)-2-thienyl | 2-(1-pyrrolidinyl)ethylamino | H |
| 2016. | —(CH$_2$SO$_2$)-2-thienyl | 2-(4-morpholinyl)ethylamino | H |
| 2017. | —(CH$_2$SO$_2$)-2-thienyl | 3-(1-piperidinyl)propylamino | H |
| 2018. | —(CH$_2$SO$_2$)-2-thienyl | 3-(1-pyrrolidinyl)propylamino | H |
| 2019. | —(CH$_2$SO$_2$)-2-thienyl | 3-(4-morpholinyl)propylamino | H |
| 2020. | —(CH$_2$SO$_2$)-2-thienyl | N-methyl-H-(2-piperid-1-ylethyl)amino | H |
| 2021. | —(CH$_2$SO$_2$)-2-thienyl | N-methyl-N-(2-morpholin-4-ylethyl)amino | H |
| 2022. | —(CH$_2$SO$_2$)-2-thienyl | N-methyl-N-(2-morpholin-4-ylethyl)amino | H |
| 2023. | —(CH$_2$SO$_2$)-2-thienyl | ((2S)-2-amino-3-phenylpropyl)amino | H |
| 2024. | —(CH$_2$SO$_2$)-2-thienyl | 4-methylpiperazinylamino | H |
| 2025. | —(CH$_2$SO$_2$)-2-thienyl | 4-methylpiperazinyl | H |
| 2026. | —(CH$_2$SO$_2$)-2-thienyl | 3-aminopyrrolidinyl | H |
| 2027. | —(CH$_2$SO$_2$)-2-thienyl | (diethylamino)ethylamino | H |
| 2028. | —(CH$_2$SO$_2$)-2-thienyl | 3,5-dimethylpiperazin-1-yl | H |
| 2029. | —(CH$_2$SO$_2$)-2-thienyl | (4-piperidylmethyl)amino | H |
| 2030. | —(CH$_2$SO$_2$)-2-thienyl | (2-methylbutyl)amino | H |
| 2031. | —(CH$_2$SO$_2$)-2-thienyl | 2-(dimethylamino)ethoxy | H |
| 2032. | —(CH$_2$SO$_2$)-2-thienyl | 2-(methylamino)ethoxy | H |

TABLE 4-continued

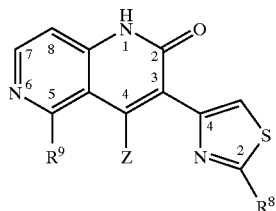

| # | R[8] | R[9] | Z |
|---|---|---|---|
| 2033. | —(CH$_2$SO$_2$)-2-thienyl | ((2R)pyrrolidin-2-yl)methoxy | H |
| 2034. | —(CH$_2$SO$_2$)-2-thienyl | ((2R)-1-methylpyrrolidin-2-yl)methoxy | H |
| 2035. | —(CH$_2$SO$_2$)-2-thienyl | 2-(piperid-1-yl)ethoxy | H |
| 2036. | —(CH$_2$SO$_2$)-2-thienyl | 2-(piperazin-1-yl)ethoxy | H |
| 2037. | —(CH$_2$SO$_2$)-2-thienyl | 2-(morpholin-4-yl)ethoxy | H |
| 2038. | —(CH$_2$SO$_2$)-2-thienyl | Cl | NH$_2$ |
| 2039. | —(CH$_2$SO$_2$)-2-thienyl | cyclopropylmethylamino | NH$_2$ |
| 2040. | —(CH$_2$SO$_2$)-2-thienyl | 3-hydroxypropylamino | NH$_2$ |
| 2041. | —(CH$_2$SO$_2$)-2-thienyl | 2-(1-piperidinyl)ethylamino | NH$_2$ |
| 2042. | —(CH$_2$SO$_2$)-2-thienyl | 2-(1-pyrrolidinyl)ethylamino | NH$_2$ |
| 2043. | —(CH$_2$SO$_2$)-2-thienyl | 2-(4-morpholinyl)ethylamino | NH$_2$ |
| 2044. | —(CH$_2$SO$_2$)-2-thienyl | 3-(1-piperidinyl)propylamino | NH$_2$ |
| 2045. | —(CH$_2$SO$_2$)-2-thienyl | 3-(1-pyrrolidinyl)propylamino | NH$_2$ |
| 2046. | —(CH$_2$SO$_2$)-2-thienyl | 3-(4-morpholinyl)propylamino | NH$_2$ |
| 2047. | —(CH$_2$SO$_2$)-2-thienyl | N-methyl-N-(2-piperid-1-ylethyl)amino | NH$_2$ |
| 2048. | —(CH$_2$SO$_2$)-2-thienyl | N-methyl-N-(2-pyrrolidin-1-ylethyl)amino | NH$_2$ |
| 2049. | —(CH$_2$SO$_2$)-2-thienyl | N-methyl-N-(2-morpholin-4-ylethyl)amino | NH$_2$ |
| 2050. | —(CH$_2$SO$_2$)-2-thienyl | ((2S)-2-amino-3-phenylpropyl)amino | NH$_2$ |
| 2051. | —(CH$_2$SO$_2$)-2-thienyl | 4-methylpiperazinylamino | NH$_2$ |
| 2052. | —(CH$_2$SO$_2$)-2-thienyl | 4-methylpiperazinyl | NH$_2$ |
| 2053. | —(CH$_2$SO$_2$)-2-thienyl | 3-aminopyrrolidinyl | NH$_2$ |
| 2054. | —(CH$_2$SO$_2$)-2-thienyl | (diethylamino)ethylamino | NH$_2$ |
| 2055. | —(CH$_2$SO$_2$)-2-thienyl | 3,5-dimethylpiperazin-1-yl | NH$_2$ |
| 2056. | —(CH$_2$SO$_2$)-2-thienyl | (4-piperidylmethyl)amino | NH$_2$ |
| 2057. | —(CH$_2$SO$_2$)-2-thienyl | (2-methylbutyl)amino | NH$_2$ |
| 2058. | —(CH$_2$SO$_2$)-2-thienyl | 2-(dimethylamino)ethoxy | NH$_2$ |
| 2059. | —(CH$_2$SO$_2$)-2-thienyl | 2-(methylamino)ethoxy | NH$_2$ |
| 2060. | —(CH$_2$SO$_2$)-2-thienyl | ((2R)pyrrolidin-2-yl)methoxy | NH$_2$ |
| 2061. | —(CH$_2$SO$_2$)-2-thienyl | ((2R)-1-methylpyrrolidin-2-yl)methoxy | NH$_2$ |
| 2062. | —(CH$_2$SO$_2$)-2-thienyl | 2-(piperid-1-yl)ethoxy | NH$_2$ |
| 2063. | —(CH$_2$SO$_2$)-2-thienyl | 2-(piperazin-1-yl)ethoxy | NH$_2$ |
| 2064. | —(CH$_2$SO$_2$)-2-thienyl | 2-(morpholin-4-yl)ethoxy | NH$_2$ |
| 2065. | —(CH$_2$SO$_2$)-2-pyridyl | Cl | H |
| 2066. | —(CH$_2$SO$_2$)-2-pyridyl | cyclopropylmethylamino | H |
| 2067. | —(CH$_2$SO$_2$)-2-pyridyl | 3-hydroxypropylamino | H |
| 2068. | —(CH$_2$SO$_2$)-2-pyridyl | 2-(1-piperidinyl)ethylamino | H |
| 2069. | —(CH$_2$SO$_2$)-2-pyridyl | 2-(1-pyrrolidinyl)ethylamino | H |
| 2070. | —(CH$_2$SO$_2$)-2-pyridyl | 2-(4-morpholinyl)ethylamino | H |
| 2071. | —(CH$_2$SO$_2$)-2-pyridyl | 3-(1-piperidinyl)propylamino | H |
| 2072. | —(CH$_2$SO$_2$)-2-pyridyl | 3-(1-pyrrolidinyl)propylamino | H |
| 2073. | —(CH$_2$SO$_2$)-2-pyridyl | 3-(4-morpholinyl)propylamino | H |
| 2074. | —(CH$_2$SO$_2$)-2-pyridyl | N-methyl-N-(2-piperid-1-ylethyl)amino | H |
| 2075. | —(CH$_2$SO$_2$)-2-pyridyl | N-methyl-N-(2-pyrrolidin-1-ylethyl)amino | H |
| 2076. | —(CH$_2$SO$_2$)-2-pyridyl | N-methyl-N-(2-morpholin-4-ylethyl)amino | H |
| 2077. | —(CH$_2$SO$_2$)-2-pyridyl | ((2S)-2-amino-3-phenylpropyl)amino | H |
| 2078. | —(CH$_2$SO$_2$)-2-pyridyl | 4-methylpiperazinylamino | H |
| 2079. | —(CH$_2$SO$_2$)-2-pyridyl | 4-methylpiperazinyl | H |
| 2080. | —(CH$_2$SO$_2$)-2-pyridyl | 3-aminopyrrolidinyl | H |
| 2081. | —(CH$_2$SO$_2$)-2-pyridyl | (diethylamino)ethylamino | H |
| 2082. | —(CH$_2$SO$_2$)-2-pyridyl | 3,5-dimethylpiperazin-1-yl | H |
| 2083. | —(CH$_2$SO$_2$)-2-pyridyl | (4-piperidylmethyl)amino | H |
| 2084. | —(CH$_2$SO$_2$)-2-pyridyl | (2-methylbutyl)amino | H |
| 2085. | —(CH$_2$SO$_2$)-2-pyridyl | 2-(dimethylamino)ethoxy | H |
| 2086. | —(CH$_2$SO$_2$)-2-pyridyl | 2-(methylamino)ethoxy | H |
| 2087. | —(CH$_2$SO$_2$)-2-pyridyl | ((2R)pyrrolidin-2-yl)methoxy | H |
| 2088. | —(CH$_2$SO$_2$)-2-pyridyl | ((2R)-1-methylpyrrolidin-2-yl)methoxy | H |
| 2089. | —(CH$_2$SO$_2$)-2-pyridyl | 2-(piperid-1-yl)ethoxy | H |
| 2090. | —(CH$_2$SO$_2$)-2-pyridyl | 2-(piperazin-1-yl)ethoxy | H |
| 2091. | —(CH$_2$SO$_2$)-2-pyridyl | 2-(morpholin-4-yl)ethoxy | H |
| 2092. | —(CH$_2$SO$_2$)-2-pyridyl | Cl | NH$_2$ |
| 2093. | —(CH$_2$SO$_2$)-2-pyridyl | cyclopropylmethylamino | NH$_2$ |
| 2094. | —(CH$_2$SO$_2$)-2-pyridyl | 3-hydroxypropylamino | NH$_2$ |
| 2095. | —(CH$_2$SO$_2$)-2-pyridyl | 2-(1-piperidinyl)ethylamino | NH$_2$ |
| 2096. | —(CH$_2$SO$_2$) 2-pyridyl | 2-(1-pyrrolidinyl)ethylamino | NH$_2$ |
| 2097. | —(CH$_2$SO$_2$)-2-pyridyl | 2-(4-morpholinyl)ethylamino | NH$_2$ |

TABLE 4-continued

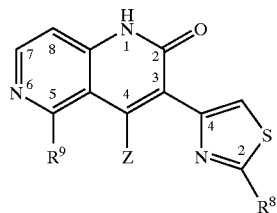

| # | R⁸ | R⁹ | Z |
|---|---|---|---|
| 2098. | —(CH₂SO₂)-2-pyridyl | 3-(1-piperidinyl)propylamino | NH₂ |
| 2099. | —(CH₂SO₂) 2-pyridyl | 3-(1-pyrrolidinyl)propylamino | NH₂ |
| 2100. | —(CH₂SO₂)-2-pyridyl | 3-(4-morpholinyl)propylamino | NH₂ |
| 2101. | —(CH₂SO₂)-2-pyridyl | N-methyl-N-(2-piperid-1-ylethyl)amino | NH₂ |
| 2102. | —(CH₂SO₂)-2-pyridyl | N-methyl-N-(2-pyrrolidin-1-ylethyl)amino | NH₂ |
| 2103. | —(CH₂SO₂)-2-pyridyl | N-methyl-N-(2-morpholin-4-ylethyl)amino | NH₂ |
| 2104. | —(CH₂SO₂)-2-pyridyl | ((2S)-2-amino-3-phenylpropyl)amino | NH₂ |
| 2105. | —(CH₂SO₂)-2-pyridyl | 4-methylpiperazinylamino | NH₂ |
| 2106. | —(CH₂SO₂)-2-pyridyl | 4-methylpiperazinyl | NH₂ |
| 2107. | —(CH₂SO₂)-2-pyridyl | 3-aminopyrrolidinyl | NH₂ |
| 2108. | —(CH₂SO₂)-2-pyridyl | (diethylamino)ethylamino | NH₂ |
| 2109. | —(CH₂SO₂)-2-pyridyl | 3,5-dimethylpiperazin-1-yl | NH₂ |
| 2110. | —(CH₂SO₂)-2-pyridyl | (4-piperidylmethyl)amino | NH₂ |
| 2111. | —(CH₂SO₂)-2-pyridyl | (2-methylbutyl)amino | NH₂ |
| 2112. | —(CH₂SO₂)-2-pyridyl | 2-(dimethylamino)ethoxy | NH₂ |
| 2113. | —(CH₂SO₂)-2-pyridyl | 2-(methylamino)ethoxy | NH₂ |
| 2114. | —(CH₂SO₂)-2-pyridyl | ((2R)pyrrolidin-2-yl)methoxy | NH₂ |
| 2115. | —(CH₂SO₂)-2-pyridyl | ((2R)-1-methylpyrrolidin-2-yl)methoxy | NH₂ |
| 2116. | —(CH₂SO₂)-2-pyridyl | 2-(piperid-1-yl)ethoxy | NH₂ |
| 2117. | —(CH₂SO₂)-2-pyridyl | 2-(piperazin-1-yl)ethoxy | NH₂ |
| 2118. | —(CH₂SO₂)-2-pyridyl | 2-(morpholin-4-yl)ethoxy | NH₂ |
| 2119. | —(CH₂SO₂)-3-pyridyl | Cl | H |
| 2120. | —(CH₂SO₂)-3-pyridyl | cyclopropylmethylamino | H |
| 2121. | —(CH₂SO₂)-3-pyridyl | 3-hydroxypropylamino | H |
| 2122. | —(CH₂SO₂)-3-pyridyl | 2-(1-piperidinyl)ethylamino | H |
| 2123. | —(CH₂SO₂)-3-pyridyl | 2-(1-pyrrolidinyl)ethylamino | H |
| 2124. | —(CH₂SO₂)-3-pyridyl | 2-(4-morpholinyl)ethylamino | H |
| 2125. | —(CH₂SO₂)-3-pyridyl | 3-(1-piperidinyl)propylamino | H |
| 2126. | —(CH₂SO₂)-3-pyridyl | 3-(1-pyrrolidinyl)propylamino | H |
| 2127. | —(CH₂SO₂)-3-pyridyl | 3-(4-morpholinyl)propylamino | H |
| 2128. | —(CH₂SO₂)-3-pyridyl | N-methyl-N-(2-piperid-1-ylethyl)amino | H |
| 2129. | —(CH₂SO₂)-3-pyridyl | N-methyl-N-(2-pyrrolidin-1-ylethyl)amino | H |
| 2130. | —(CH₂SO₂)-3-pyridyl | N-methyl-N-(2-morpholin-4-ylethyl)amino | H |
| 2131. | —(CH₂SO₂)-3-pyridyl | ((2S)-2-amino-3-phenylpropyl)amino | H |
| 2132. | —(CH₂SO₂)-3-pyridyl | 4-methylpiperazinylamino | H |
| 2133. | —(CH₂SO₂)-3-pyridyl | 4-methylpiperazinyl | H |
| 2134. | —(CH₂SO₂)-3-pyridyl | 3-aminopyrrolidinyl | H |
| 2135. | —(CH₂SO₂)-3-pyridyl | (diethylamino)ethylamino | H |
| 2136. | —(CH₂SO₂)-3-pyridyl | 3-5-dimethylpiperazin-1-yl | H |
| 2137. | —(CH₂SO₂)-3-pyridyl | (4-piperidylmethyl)amino | H |
| 2138. | —(CH₂SO₂)-3-pyridyl | (2-methylbutyl)amino | H |
| 2139. | —(CH₂SO₂)-3-pyridyl | 2-(dimethylamino)ethoxy | H |
| 2140. | —(CH₂SO₂)-3-pyridyl | 2-(methylamino)ethoxy | H |
| 2141. | —(CH₂SO₂)-3-pyridyl | ((2R)pyrrolidin-2-yl)methoxy | H |
| 2142. | —(CH₂SO₂)-3-pyridyl | ((2R)-1-methylpyrrolidin-2-yl)methoxy | H |
| 2143. | —(CH₂SO₂)-3-pyridyl | 2-(piperid-1-yl)ethoxy | H |
| 2144. | —(CH₂SO₂)-3-pyridyl | 2-(piperazin-1-yl)ethoxy | H |
| 2145. | —(CH₂SO₂)-3-pyridyl | 2-(morpholin-4-yl)ethoxy | H |
| 2146. | —(CH₂SO₂)-3-pyridyl | Cl | NH₂ |
| 2147. | —(CH₂SO₂)-3-pyridyl | cyclopropylmethylamino | NH₂ |
| 2148. | —(CH₂SO₂)-3-pyridyl | 3-hydroxypropylamino | NH₂ |
| 2149. | —(CH₂SO₂)-3-pyridyl | 2-(1-piperidinyl)ethylamino | NH₂ |
| 2150. | —(CH₂SO₂)-3-pyridyl | 2-(1-pyrrolidinyl)ethylamino | NH₂ |
| 2151. | —(CH₂SO₂)-3-pyridyl | 2-(4-morpholinyl)ethylamino | NH₂ |
| 2152. | —(CH₂SO₂)-3-pyridyl | 3-(1-piperidinyl)propylamino | NH₂ |
| 2153. | —(CH₂SO₂)-3-pyridyl | 3-(1-pyrrolidinyl)propylamino | NH₂ |
| 2154. | —(CH₂SO₂)-3-pyridyl | 3-(4-morpholinyl)propylamino | NH₂ |
| 2155. | —(CH₂SO₂)-3-pyridyl | N-methyl-N-(2-piperid-1-ylethyl)amino | NH₂ |
| 2156. | —(CH₂SO₂)-3-pyridyl | N-methyl-N-(2-pyrrolidin-1-ylethyl)amino | NH₂ |
| 2157. | —(CH₂SO₂)-3-pyridyl | N-methyl-N-(2-morpholin-4-ylethyl)amino | NH₂ |
| 2158. | —(CH₂SO₂)-3-pyridyl | ((2S)-2-amino-3-phenylpropyl)amino | NH₂ |
| 2159. | —(CH₂SO₂)-3-pyridyl | 4-methylpiperazinylamino | NH₂ |
| 2160. | —(CH₂SO₂)-3-pyridyl | 4-methylpiperazinyl | NH₂ |
| 2161. | —(CH₂SO₂)-3-pyridyl | 3-aminopyrrolidinyl | NH₂ |
| 2162. | —(CH₂SO₂)-3-pyridyl | (diethylamino)ethylamino | NH₂ |

TABLE 4-continued

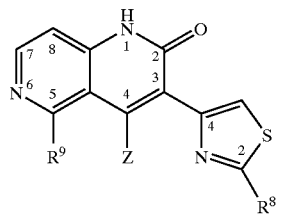

| # | R⁸ | R⁹ | Z |
|---|---|---|---|
| 2163. | —(CH₂SO₂)-3-pyridyl | 3,5-dimethylpiperazin-1-yl | NH₂ |
| 2164. | —(CH₂SO₂)-3-pyridyl | (4-piperidylmethyl)amino | NH₂ |
| 2165. | —(CH₂SO₂)-3-pyridyl | (2-methylbutyl)amino | NH₂ |
| 2166. | —(CH₂SO₂)-3-pyridyl | 2-(dimethylamino)ethoxy | NH₂ |
| 2167. | —(CH₂SO₂)-3-pyridyl | 2-(methylamino)ethoxy | NH₂ |
| 2168. | —(CH₂SO₂)-3-pyridyl | ((2R)pyrrolidin-2-yl)methoxy | NH₂ |
| 2169. | —(CH₂SO₂)-3-pyridyl | ((2R)-1-methylpyrrolidin-2-yl)methoxy | NH₂ |
| 2170. | —(CH₂SO₂)-3-pyridyl | 2-(piperid-1-yl)ethoxy | NH₂ |
| 2171. | —(CH₂SO₂)-3-pyridyl | 2-(piperazin-1-yl)ethoxy | NH₂ |
| 2172. | —(CH₂SO₂)-3-pyridyl | 2-(morpholin-4-yl)ethoxy | NH₂ |
| 2173. | —(CH₂SO₂)-4-pyridyl | Cl | H |
| 2174. | —(CH₂SO₂)-4-pyridyl | cyclopropylmethylamino | H |
| 2175. | —(CH₂SO₂)-4-pyridyl | 3-hydroxypropylamino | H |
| 2176. | —(CH₂SO₂)-4-pyridyl | 2-(1-piperidinyl)ethylamino | H |
| 2177. | —(CH₂SO₂)-4-pyridyl | 2-(1-pyrrolidinyl)ethylamino | H |
| 2178. | —(CH₂SO₂)-4-pyridyl | 2-(4-morpholinyl)ethylamino | H |
| 2179. | —(CH₂SO₂)-4-pyridyl | 3-(1-piperidinyl)propylamino | H |
| 2180. | —(CH₂SO₂)-4-pyridyl | 3-(1-pyrrolidinyl)propylamino | H |
| 2181. | —(CH₂SO₂)-4-pyridyl | 3-(4-morpholinyl)propylamino | H |
| 2182. | —(CH₂SO₂)-4-pyridyl | N-methyl-N-(2-piperid-1-ylethyl)amino | H |
| 2183. | —(CH₂SO₂)-4-pyridyl | N-methyl-N-(2-pyrrolidin-1-ylethyl)amino | H |
| 2184. | —(CH₂SO₂)-4-pyridyl | N-methyl-N-(2-morpholin-4-ylethyl)amino | H |
| 2185. | —(CH₂SO₂)-4-pyridyl | ((2S)-2-amino-3-phenylpropyl)amino | H |
| 2186. | —(CH₂SO₂)-4-pyridyl | 4-methylpiperazinylamino | H |
| 2187. | —(CH₂SO₂)-4-pyridyl | 4-methylpiperazinyl | H |
| 2188. | —(CH₂SO₂)-4-pyridyl | 3-aminopyrrolidinyl | H |
| 2189. | —(CH₂SO₂)-4-pyridyl | (diethylamino)ethylamino | H |
| 2190. | —(CH₂SO₂)-4-pyridyl | 3,5-dimethylpiperazin-1-yl | H |
| 2191. | —(CH₂SO₂)-4-pyridyl | (4-piperidylmethyl)amino | H |
| 2192. | —(CH₂SO₂)-4-pyridyl | (2-methylbutyl)amino | H |
| 2193. | —(CH₂SO₂)-4-pyridyl | 2-(dimethylamino)ethoxy | H |
| 2194. | —(CH₂SO₂)-4-pyridyl | 2-(methylamino)ethoxy | H |
| 2195. | —(CH₂SO₂)-4-pyridyl | ((2R)pyrrolidin-2-yl)methoxy | H |
| 2196. | —(CH₂SO₂)-4-pyridyl | ((2R)1-methylpyrrolidin-2-yl)methoxy | H |
| 2197. | —(CH₂SO₂)-4-pyridyl | 2-(piperid-1-yl)ethoxy | H |
| 2198. | —(CH₂SO₂)-4-pyridyl | 2-(piperazin-1-yl)ethoxy | H |
| 2199. | —(CH₂SO₂)-4-pyridyl | 2-(morpholin-4-yl)ethoxy | H |
| 2200. | —(CH₂SO₂)-4-pyridyl | Cl | NH₂ |
| 2201. | —(CH₂SO₂)-4-pyridyl | cyclopropylmethylamino | NH₂ |
| 2202. | —(CH₂SO₂)-4-pyridyl | 3-hydroxypropylamino | NH₂ |
| 2203. | —(CH₂SO₂)-4-pyridyl | 2-(1-piperidinyl)ethylamino | NH₂ |
| 2204. | —(CH₂SO₂)-4-pyridyl | 2-(1-pyrrolidinyl)ethylamino | NH₂ |
| 2205. | —(CH₂SO₂)-4-pyridyl | 2-(4-morpholinyl)ethylamino | NH₂ |
| 2206. | —(CH₂SO₂)-4-pyridyl | 3-(1-piperidinyl)propylamino | NH₂ |
| 2207. | —(CH₂SO₂)-4-pyridyl | 3-(1-pyrrolidinyl)propylamino | NH₂ |
| 2208. | —(CH₂SO₂)-4-pyridyl | 3-(4-morpholinyl)propylamino | NH₂ |
| 2209. | —(CH₂SO₂)-4-pyridyl | N-methyl-N-(2-piperid-1-ylethyl)amino | NH₂ |
| 2210. | —(CH₂SO₂)-4-pyridyl | N-methyl-N-(2-pyrrolidin-1-ylethyl)amino | NH₂ |
| 2211. | —(CH₂SO₂)-4-pyridyl | N-methyl-N-(2-morpholin-4-ylethyl)amino | NH₂ |
| 2212. | —(CH₂SO₂)-4-pyridyl | ((2S)-2-amino-3-phenylpropyl)amino | NH₂ |
| 2213. | —(CH₂SO₂)-4-pyridyl | 4-methylpiperazinylamino | NH₂ |
| 2214. | —(CH₂SO₂)-4-pyridyl | 4-methylpiperazinyl | NH₂ |
| 2215. | —(CH₂SO₂)-4-pyridyl | 3-aminopyrrolidinyl | NH₂ |
| 2216. | —(CH₂SO₂)-4-pyridyl | (diethylamino)ethylamino | NH₂ |
| 2217. | —(CH₂SO₂)-4-pyridyl | 3,5-dimethylpiperazin-1-yl | NH₂ |
| 2218. | —(CH₂SO₂)-4-pyridyl | (4-piperidylmethyl)amino | NH₂ |
| 2219. | —(CH₂SO₂)-4-pyridyl | (2-methylbutyl)amino | NH₂ |
| 2220. | —(CH₂SO₂)-4-pyridyl | 2-(dimethylamino)ethoxy | NH₂ |
| 2221. | —(CH₂SO₂)-4-pyridyl | 2-(methylamino)ethoxy | NH₂ |
| 2222. | —(CH₂SO₂)-4-pyridyl | ((2R)pyrrolidin-2-yl)methoxy | NH₂ |
| 2223. | —(CH₂SO₂)-4-pyridyl | ((2R)-1-methylpyrrolidin-2-yl)methoxy | NH₂ |
| 2224. | —(CH₂SO₂)-4-pyridyl | 2-(piperid-1-yl)ethoxy | NH₂ |
| 2225. | —(CH₂SO₂)-4-pyridyl | 2-(piperazin-1-yl)ethoxy | NH₂ |
| 2226. | —(CH₂SO₂)-4-pyridyl | 2-(morpholin-4-yl)ethoxy | NH₂ |
| 2227. | —(NMeSO₂)-phenyl | Cl | H |

TABLE 4-continued

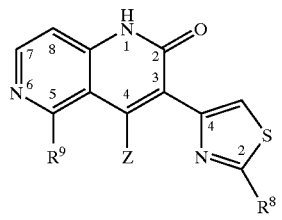

| # | R⁸ | R⁹ | Z |
|---|---|---|---|
| 2228. | —(NMeSO$_2$)-phenyl | cyclopropylmethylamino | H |
| 2229. | —(NMeSO$_2$)-phenyl | 3-hydroxypropylamino | H |
| 2230. | —(NMeSO$_2$)-phenyl | 2-(1-piperidinyl)ethylamino | H |
| 2231. | —(NMeSO$_2$)-phenyl | 2-(1-pyrrolidinyl)ethylamino | H |
| 2232. | —(NMeSO$_2$)-phenyl | 2-(4-morpholinyl)ethylamino | H |
| 2233. | —(NMeSO$_2$)-phenyl | 3-(1-piperidinyl)propylamino | H |
| 2234. | —(NMeSO$_2$)-phenyl | 3-(1-pyrrolidinyl)propylamino | H |
| 2235. | —(NMeSO$_2$)-phenyl | 3-(4-morpholinyl)propylamino | H |
| 2236. | —(NMeSO$_2$)-phenyl | N-methyl-N-(2-piperid-1-ylethyl)amino | H |
| 2237. | —(NMeSO$_2$)-phenyl | N-methyl-N-(2-pyrrolidin-1-ylethyl)amino | H |
| 2238. | —(NMeSO$_2$)-phenyl | N-methyl-N-(2-morpholin-4-ylethyl-amino | H |
| 2239. | —(NMeSO$_2$)-phenyl | ((2S)-2-amino-3-phenylpropyl)amino | H |
| 2240. | —(NMeSO$_2$)-phenyl | 4-methylpiperazinylamino | H |
| 2241. | —(NMeSO$_2$)-phenyl | 4-methylpiperazinyl | H |
| 2242. | —(NMeSO$_2$)-phenyl | 3-aminopyrrolidinyl | H |
| 2243. | —(NMeSO$_2$)-phenyl | (diethylamino)ethylamino | H |
| 2244. | —(NMeSO$_2$)-phenyl | 3,5-dimethylpiperazin-1-yl | H |
| 2245. | —(NMeSO$_2$)-phenyl | (4-piperidylmethyl)amino | H |
| 2246. | —(NMeSO$_2$)-phenyl | (2-methylbutyl)amino | H |
| 2247. | —(NMeSO$_2$)-phenyl | 2-(dimethylamino)ethoxy | H |
| 2248. | —(NMeSO$_2$)-phenyl | 2-(methylamino)ethoxy | H |
| 2249. | —(NMeSO$_2$)-phenyl | ((2R)pyrrolidin-2-yl)methoxy | H |
| 2250. | —(NMeSO$_2$)-phenyl | ((2R)-1-methylpyrrolidin-2-yl)methoxy | H |
| 2251. | —(NMeSO$_2$)-phenyl | 2-(piperid-1-yl)ethoxy | H |
| 2252. | —(NMeSO$_2$)-phenyl | 2-(piperazin-1-yl)ethoxy | H |
| 2253. | —(NMeSO$_2$)-phenyl | 2-(morpholin-4-yl)ethoxy | H |
| 2254. | —(NMeSO$_2$)-phenyl | Cl | NH$_2$ |
| 2255. | —(NMeSO$_2$)-phenyl | cyclopropylmethylamino | NH$_2$ |
| 2256. | —(NMeSO$_2$)-phenyl | 3-hydroxypropylamino | NH$_2$ |
| 2257. | —(NMeSO$_2$)-phenyl | 2-(1-piperidinyl)ethylamino | NH$_2$ |
| 2258. | —(NMeSO$_2$)-phenyl | 2-(1-pyrrolidinyl)ethylamino | NH$_2$ |
| 2259. | —(NMeSO$_2$)-phenyl | 2-(4-morpholinyl)ethylamino | NH$_2$ |
| 2260. | —(NMeSO$_2$)-phenyl | 3-(1-piperidinyl)propylamino | NH$_2$ |
| 2261. | —(NMeSO$_2$)-phenyl | 3-(1-pyrrolidinyl)propylamino | NH$_2$ |
| 2262. | —(NMeSO$_2$)-phenyl | 3-(4-morpholinyl)propylamino | NH$_2$ |
| 2263. | —(NMeSO$_2$)-phenyl | N-methyl-N-(2-piperid-1-ylethyl)amino | NH$_2$ |
| 2264. | —(NMeSO$_2$)-phenyl | N-methyl-N-(2-pyrrolidin-1-ylethyl)amino | NH$_2$ |
| 2265. | —(NMeSO$_2$)-phenyl | N-methyl-N-(2-morpholin-4-ylethyl)amino | NH$_2$ |
| 2266. | —(NMeSO$_2$)-phenyl | ((2S)-2-amino-3-phenylpropyl)amino | NH$_2$ |
| 2267. | —(NMeSO$_2$)-phenyl | 4-methylpiperazinylamino | NH$_2$ |
| 2268. | —(NMeSO$_2$)-phenyl | 4-methylpiperazinyl | NH$_2$ |
| 2269. | —(NMeSO$_2$)-phenyl | 3-aminopyrrolidinyl | NH$_2$ |
| 2270. | —(NMeSO$_2$)-phenyl | (diethylamino)ethylamino | NH$_2$ |
| 2271. | —(NMeSO$_2$)-phenyl | 3,5-dimethylpiperazin-1-yl | NH$_2$ |
| 2272. | —(NMeSO$_2$)-phenyl | (4-piperidylmethyl)amino | NH$_2$ |
| 2273. | —(NMeSO$_2$)-phenyl | (2-methylbutyl)amino | NH$_2$ |
| 2274. | —(NMeSO$_2$)-phenyl | 2-(dimethylamino)ethoxy | NH$_2$ |
| 2275. | —(NMeSO$_2$)-phenyl | 2-(methylamino)ethoxy | NH$_2$ |
| 2276. | —(NMeSO$_2$)-phenyl | ((2R)pyrrolidin-2-yl)methoxy | NH$_2$ |
| 2277. | —(NMeSO$_2$)-phenyl | ((2R)-1-methylpyrrolidin-2-yl)methoxy | NH$_2$ |
| 2278. | —(NMeSO$_2$)-phenyl | 2-(piperid-1-yl)ethoxy | NH$_2$ |
| 2279. | —(NMeSO$_2$)-phenyl | 2-(piperazin-1-yl)ethoxy | NH$_2$ |
| 2280. | —(NMeSO$_2$)-phenyl | 2-(morpholin-4-yl)ethoxy | NH$_2$ |
| 2281. | —(NMeSO$_2$)-2-thienyl | Cl | H |
| 2282. | —(NMeSO$_2$)-2-thienyl | cyclopropylmethylamino | H |
| 2283. | —(NMeSO$_2$)-2-thienyl | 3-hydroxypropylamino | H |
| 2284. | —(NMeSO$_2$)-2-thienyl | 2-(1-piperidinyl)ethylamino | H |
| 2285. | —(NMeSO$_2$)-2-thienyl | 2-(1-pyrrolidinyl)ethylamino | H |
| 2286. | —(NMeSO$_2$)-2-thienyl | 2-(4-morpholinyl)ethylamino | H |
| 2287. | —(NMeSO$_2$)-2-thienyl | 3-(1-piperidinyl)propylamino | H |
| 2288. | —(NMeSO$_2$)-2-thienyl | 3-(1-pyrrolidinyl)propylamino | H |
| 2289. | —(NMeSO$_2$)-2-thienyl | 3-(4-morpholinyl)propylamino | H |
| 2290. | —(NMeSO$_2$)-2-thienyl | N-methyl-N-(2-piperid-1-ylethyl)amino | H |
| 2291. | —(NMeSO$_2$)-2-thienyl | N-methyl-N-(2-pyrrolidin-1-ylethyl)amino | H |
| 2292. | —(NMeSO$_2$)-2-thienyl | N-methyl-N-(2-morpholin-4-ylethyl)amino | H |

TABLE 4-continued

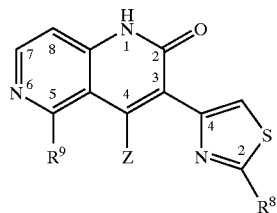

| # | R$^8$ | R$^9$ | Z |
|---|---|---|---|
| 2293. | —(NMeSO$_2$)-2-thienyl | ((2S)-2-amino-3-phenylpropyl)amino | H |
| 2294. | —(NMeSO$_2$)-2-thienyl | 4-methylpiperazinylamino | H |
| 2295. | —(NMeSO$_2$)-2-thienyl | 4-methylpiperazinyl | H |
| 2296. | —(NMeSO$_2$)-2-thienyl | 3-aminopyrrolidinyl | H |
| 2297. | —(NMeSO$_2$)-2-thienyl | (diethylamino)ethylamino | H |
| 2298. | —(NMeSO$_2$)-2-thienyl | 3,5-dimethylpiperazin-1-yl | H |
| 2299. | —(NMeSO$_2$)-2-thienyl | (4-piperidylmethyl)amino | H |
| 2300. | —(NMeSO$_2$)-2-thienyl | (2-methylbutyl)amino | H |
| 2301. | —(NMeSO$_2$)-2-thienyl | 2-(dimethylamino)ethoxy | H |
| 2302. | —(NMeSO$_2$)-2-thienyl | 2-(methylamino)ethoxy | H |
| 2303. | —(NMeSO$_2$)-2-thienyl | ((2R)pyrrolidin-2-yl)methoxy | H |
| 2304. | —(NMeSO$_2$)-2-thienyl | ((2R)-1-methylpyrrolidin-2-yl)methoxy | H |
| 2305. | —(NMeSO$_2$)-2-thienyl | 2-(piperid-1-yl)ethoxy | H |
| 2306. | —(NMeSO$_2$)-2-thienyl | 2-(piperazin-1-yl)ethoxy | H |
| 2307. | —(NMeSO$_2$)-2-thienyl | 2-(morpholin-4-yl)ethoxy | H |
| 2308. | —(NMeSO$_2$)-2-thienyl | Cl | NH$_2$ |
| 2309. | —(NMeSO$_2$)-2-thienyl | cyclopropylmethylamino | NH$_2$ |
| 2310. | —(NMeSO$_2$)-2-thienyl | 3-hydroxypropylamino | NH$_2$ |
| 2311. | —(NMeSO$_2$)-2-thienyl | 2-(1-piperidinyl)ethylamino | NH$_2$ |
| 2312. | —(NMeSO$_2$)-2-thienyl | 2-(1-pyrrolidinyl)ethylamino | NH$_2$ |
| 2313. | —(NMeSO$_2$)-2-thienyl | 2-(4-morpholinyl)ethylamino | NH$_2$ |
| 2314. | —(NMeSO$_2$)-2-thienyl | 3-(1-piperidinyl)propylamino | NH$_2$ |
| 2315. | —(NMeSO$_2$)-2-thienyl | 3-(1-pyrrolidinyl)propylamino | NH$_2$ |
| 2316. | —(NMeSO$_2$)-2-thienyl | 3-(4-morpholinyl)propylamino | NH$_2$ |
| 2317. | —(NMeSO$_2$)-2-thienyl | N-methyl-N-(2-piperid-1-ylethyl)amino | NH$_2$ |
| 2318. | —(NMeSO$_2$)-2-thienyl | N-methyl-N-(2-pyrrolidin-1-ylethyl)amino | NH$_2$ |
| 2319. | —(NMeSO$_2$)-2-thienyl | N-methyl-N-(2-morpholin-4-ylethyl)amino | NH$_2$ |
| 2320. | —(NMeSO$_2$)-2-thienyl | ((2S)-2-amino-3-phenylpropyl)amino | NH$_2$ |
| 2321. | —(NMeSO$_2$)-2-thienyl | 4-methylpiperazinylamino | NH$_2$ |
| 2322. | —(NMeSO$_2$)-2-thienyl | 4-methylpiperazinyl | NH$_2$ |
| 2323. | —(NMeSO$_2$)-2-thienyl | 3-aminopyrrolidinyl | NH$_2$ |
| 2324. | —(NMeSO$_2$)-2-thienyl | (diethylamino)ethylamino | NH$_2$ |
| 2325. | —(NMeSO$_2$)-2-thienyl | 3,5-dimethylpiperazin-1-yl | NH$_2$ |
| 2326. | —(NMeSO$_2$)-2-thienyl | (4-piperidylmethyl)amino | NH$_2$ |
| 2327. | —(NMeSO$_2$)-2-thienyl | (2-methylbutyl)amino | NH$_2$ |
| 2328. | —(NMeSO$_2$)-2-thienyl | 2-(dimethylamino)ethoxy | NH$_2$ |
| 2329. | —(NMeSO$_2$)-2-thienyl | 2-(methylamino)ethoxy | NH$_2$ |
| 2330. | —(NMeSO$_2$)-2-thienyl | ((2R)pyrrolidin-2-yl)methoxy | NH$_2$ |
| 2331. | —(NMeSO$_2$)-2-thienyl | ((2R)-1-methylpyrrolidin-2-yl)methoxy | NH$_2$ |
| 2332. | —(NMeSO$_2$)-2-thienyl | 2-(piperid-1-yl)ethoxy | NH$_2$ |
| 2333. | —(NMeSO$_2$)-2-thienyl | 2-(piperazin-1-yl)ethoxy | NH$_2$ |
| 2334. | —(NMeSO$_2$)-2-thienyl | 2-(morpholin-4-yl)ethoxy | NH$_2$ |
| 2335. | —(NMeSO$_2$)-2-pyridyl | Cl | H |
| 2336. | —(NMeSO$_2$)-2-pyridyl | cyclopropylmethylamino | H |
| 2337. | —(NMeSO$_2$)-2-pyridyl | 3-hydroxypropylamino | H |
| 2338. | —(NMeSO$_2$)-2-pyridyl | 2-(1-piperidinyl)ethylamino | H |
| 2339. | —(NMeSO$_2$)-2-pyridyl | 2-(1-pyrrolidinyl)ethylamino | H |
| 2340. | —(NMeSO$_2$)-2-pyridyl | 2-(4-morpholinyl)ethylamino | H |
| 2341. | —(NMeSO$_2$)-2-pyridyl | 3-(1-piperidinyl)propylamino | H |
| 2342. | —(NMeSO$_2$)-2-pyridyl | 3-(1-pyrrolidinyl)propylamino | H |
| 2343. | —(NMeSO$_2$)-2-pyridyl | 3-(4-morpholinyl)propylamino | H |
| 2344. | —(NMeSO$_2$)-2-pyridyl | N-methyl-N-(2-piperid-1-ylethyl)amino | H |
| 2345. | —(NMeSO$_2$)-2-pyridyl | N-methyl-N-(2-pyrrolidin-1-ylethyl)amino | H |
| 2346. | —(NMeSO$_2$)-2-pyridyl | N-methyl-N-(2-morpholin-4-ylethyl)amino | H |
| 2347. | —(NMeSO$_2$)-2-pyridyl | ((2S)-2-amino-3-phenylpropyl)amino | H |
| 2348. | —(NMeSO$_2$)-2-pyridyl | 4-methylpiperazinylamino | H |
| 2349. | —(NMeSO$_2$)-2-pyridyl | 4-methylpiperazinyl | H |
| 2350. | —(NMeSO$_2$)-2-pyridyl | 3-aminopyrrolidinyl | H |
| 2351. | —(NMeSO$_2$)-2-pyridyl | (diethylamino)ethylamino | H |
| 2352. | —(NMeSO$_2$)-2-pyridyl | 3,5-dimethylpiperazin-1-yl | H |
| 2353. | —(NMeSO$_2$)-2-pyridyl | (4-piperidylmethyl)amino | H |
| 2354. | —(NMeSO$_2$)-2-pyridyl | (2-methylbutyl)amino | H |
| 2355. | —(NMeSO$_2$)-2-pyridyl | 2-(dimethylamino)ethoxy | H |
| 2356. | —(NMeSO$_2$)-2-pyridyl | 2-(methylamino)ethoxy | H |
| 2357. | —(NMeSO$_2$)-2-pyridyl | ((2R)pyrrolidin-2-yl)methoxy | H |

TABLE 4-continued

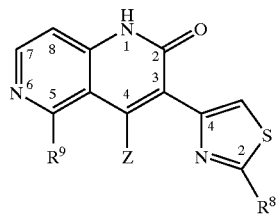

| # | R⁸ | R⁹ | Z |
|---|---|---|---|
| 2358. | —(NMeSO₂)-2-pyridyl | ((2R)-1-methylpyrrolidin-2-yl)methoxy | H |
| 2359. | —(NMeSO₂)-2-pyridyl | 2-(piperid-1-yl)ethoxy | H |
| 2360. | —(NMeSO₂)-2-pyridyl | 2-(piperazin-1-yl)ethoxy | H |
| 2361. | —(NMeSO₂)-2-pyridyl | 2-(morpholin-4-yl)ethoxy | H |
| 2362. | —(NMeSO₂)-2-pyridyl | Cl | NH₂ |
| 2363. | —(NMeSO₂)-2-pyridyl | cyclopropylmethylamino | NH₂ |
| 2364. | —(NMeSO₂)-2-pyridyl | 3-hydroxypropylamino | NH₂ |
| 2365. | —(NMeSO₂)-2-pyridyl | 2-(1-piperidinyl)ethylamino | NH₂ |
| 2366. | —(NMeSO₂)-2-pyridyl | 2-(1-pyrrolidinyl)ethylamino | NH₂ |
| 2367. | —(NMeSO₂)-2-pyridyl | 2-(4-morpholinyl)ethylamino | NH₂ |
| 2368. | —(NMeSO₂)-2-pyridyl | 3-(1-piperidinyl)propylamino | NH₂ |
| 2369. | —(NMeSO₂)-2-pyridyl | 3-(1-pyrrolidinyl)propylamino | NH₂ |
| 2370. | —(NMeSO₂)-2-pyridyl | 3-(4-morpholinyl)propylamino | NH₂ |
| 2371. | —(NMeSO₂)-2-pyridyl | N-methyl-N-(2-piperid-1-ylethyl)amino | NH₂ |
| 2372. | —(NMeSO₂)-2-pyridyl | N-methyl-N-(2-pyrrolidin-1-ylethyl)amino | NH₂ |
| 2373. | —(NMeSO₂)-2-pyridyl | N-methyl-N-(2-morpholin-4-ylethyl)amino | NH₂ |
| 2374. | —(NMeSO₂)-2-pyridyl | ((2S)-2-amino-3-phenylpropyl)amino | NH₂ |
| 2375. | —(NMeSO₂)-2-pyridyl | 4-methylpiperazinylamino | NH₂ |
| 2376. | —(NMeSO₂)-2-pyridyl | 4-methylpiperazinyl | NH₂ |
| 2377. | —(NMeSO₂)-2-pyridyl | 3-aminopyrrolidinyl | NH₂ |
| 2378. | —(NMeSO₂) 2-pyridyl | (diethylamino)ethylamino | NH₂ |
| 2379. | —(NMeSO₂)-2-pyridyl | 3,5-dimethylpiperazin-1-yl | NH₂ |
| 2380. | —(NMeSO₂)-2-pyridyl | (4-piperidylmethyl)amino | NH₂ |
| 2381. | —(NMeSO₂)-2-pyridyl | (2-methylbutyl)amino | NH₂ |
| 2382. | —(NMeSO₂)-2-pyridyl | 2-(dimethylamino)ethoxy | NH₂ |
| 2383. | —(NMeSO₂)-2-pyridyl | 2-(methylamino)ethoxy | NH₂ |
| 2384. | —(NMeSO₂)-2-pyridyl | ((2R)pyrrolidin-2-yl)methoxy | NH₂ |
| 2385. | —(NMeSO₂)-2-pyridyl | ((2R)-1-methylpyrrolidin-2-yl)methoxy | NH₂ |
| 2386. | —(NMeSO₂)-2-pyridyl | 2-(piperid-1-yl)ethoxy | NH₂ |
| 2387. | —(NMeSO₂)-2-pyridyl | 2-(piperazin-1-yl)ethoxy | NH₂ |
| 2388. | —(NMeSO₂)-2-pyridyl | 2-(morpholin-4-yl)ethoxy | NH₂ |
| 2389. | —(NMeSO₂)-3-pyridyl | Cl | H |
| 2390. | —(NMeSO₂)-3-pyridyl | cyclopropylmethylamino | H |
| 2391. | —(NMeSO₂)-3-pyridyl | 3-hydroxypropylamino | H |
| 2392. | —(NMeSO₂)-3-pyridyl | 2-(1-piperidinyl)ethylamino | H |
| 2393. | —(NMeSO₂)-3-pyridyl | 2-(1-pyrrolidinyl)ethylamino | H |
| 2394. | —(NMeSO₂)-3-pyridyl | 2-(4-morpholinyl)ethylamino | H |
| 2395. | —(NMeSO₂)-3-pyridyl | 3-(1-piperidinyl)propylamino | H |
| 2396. | —(NMeSO₂)-3-pyridyl | 3-(1-pyrrolidinyl)propylamino | H |
| 2397. | —(NMeSO₂)-3-pyridyl | 3-(4-morpholinyl)propylamino | H |
| 2398. | —(NMeSO₂)-3-pyridyl | N-methyl-N-(2-piperid-1-ylethyl)amino | H |
| 2399. | —(NMeSO₂)-3-pyridyl | N-methyl-N-(2-pyrrolidin-1-ylethyl)amino | H |
| 2400. | —(NMeSO₂)-3-pyridyl | N-methyl-N-(2-morpholin-4-ylethyl)amino | H |
| 2401. | —(NMeSO₂)-3-pyridyl | ((2S)-2-amino-3-phenylpropyl)amino | H |
| 2402. | —(NMeSO₂)-3-pyridyl | 4-methylpiperazinylamino | H |
| 2403. | —(NMeSO₂)-3-pyridyl | 4-methylpiperazinyl | H |
| 2404. | —(NMeSO₂)-3-pyridyl | 3-aminopyrrolidinyl | H |
| 2405. | —(NMeSO₂)-3-pyridyl | (diethylamino)ethylamino | H |
| 2406. | —(NMeSO₂)-3-pyridyl | 3,5-dimethylpiperazin-1-yl | H |
| 2407. | —(NMeSO₂)-3-pyridyl | (4-piperidylmethyl)amino | H |
| 2408. | —(NMeSO₂)-3-pyridyl | (2-methylbutyl)amino | H |
| 2409. | —(NMeSO₂)-3-pyridyl | 2-(dimethylamino)ethoxy | H |
| 2410. | —(NMeSO₂)-3-pyridyl | 2-(methylamino)ethoxy | H |
| 2411. | —(NMeSO₂)-3-pyridyl | ((2R)pyrrolidin-2-yl)methoxy | H |
| 2412. | —(NMeSO₂)-3-pyridyl | ((2R)-1-methylpyrrolidin-2-yl)methoxy | H |
| 2413. | —(NMeSO₂)-3-pyridyl | 2-(piperid-1-yl)ethoxy | H |
| 2414. | —(NMeSO₂)-3-pyridyl | 2-(piperazin-1-yl)ethoxy | H |
| 2415. | —(NMeSO₂)-3-pyridyl | 2-(morpholin-4-yl)ethoxy | H |
| 2416. | —(NMeSO₂)-3-pyridyl | Cl | NH₂ |
| 2417. | —(NMeSO₂)-3-pyridyl | cyclopropylmethylamino | NH₂ |
| 2418. | —(NMeSO₂)-3-pyridyl | 3-hydroxypropylamino | NH₂ |
| 2419. | —(NMeSO₂)-3-pyridyl | 2-(1-piperidinyl)ethylamino | NH₂ |
| 2420. | —(NMeSO₂)-3-pyridyl | 2-(1-pyrrolidinyl)ethylamino | NH₂ |
| 2421. | —(NMeSO₂)-3-pyridyl | 2-(4-morpholinyl)ethylamino | NH₂ |
| 2422. | —(NMeSO₂)-3-pyridyl | 3-(1-piperidinyl)propylamino | NH₂ |

TABLE 4-continued

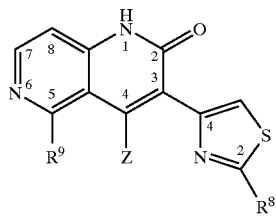

| # | R⁸ | R⁹ | Z |
|---|---|---|---|
| 2423. | —(NMeSO₂)-3-pyridyl | 3-(1-pyrrolidinyl)propylamino | NH₂ |
| 2424. | —(NMeSO₂)-3-pyridyl | 3-(4-morpholinyl)propylamino | NH₂ |
| 2425. | —(NMeSO₂)-3-pyridyl | N-methyl-N-(2-piperid-1-ylethyl)amino | NH₂ |
| 2426. | —(NMeSO₂)-3-pyridyl | N-methyl-N-(2-pyrrolidin-1-ylethyl)amino | NH₂ |
| 2427. | —(NMeSO₂)-3-pyridyl | N-methyl-N-(2-morpholin-4-ylethyl)amino | NH₂ |
| 2428. | —(NMeSO₂)-3-pyridyl | ((2S)-2-amino-3-phenylpropyl)amino | NH₂ |
| 2429. | —(NMeSO₂)-3-pyridyl | 4-methylpiperazinylamino | NH₂ |
| 2430. | —(NMeSO₂)-3-pyridyl | 4-methylpiperazinyl | NH₂ |
| 2431. | —(NMeSO₂)-3-pyridyl | 3-aminopyrrolidinyl | NH₂ |
| 2432. | —(NMeSO₂)-3-pyridyl | (diethylamino)ethylamino | NH₂ |
| 2433. | —(NMeSO₂)-3-pyridyl | 3,5-dimethylpiperazin-1-yl | NH₂ |
| 2434. | —(NMeSO₂)-3-pyridyl | (4-piperidylmethyl)amino | NH₂ |
| 2435. | —(NMeSO₂)-3-pyridyl | (2-methylbutyl)amino | NH₂ |
| 2436. | —(NMeSO₂)-3-pyridyl | 2-(dimethylamino)ethoxy | NH₂ |
| 2437. | —(NMeSO₂)-3-pyridyl | 2-(methylamino)ethoxy | NH₂ |
| 2438. | —(NMeSO₂)-3-pyridyl | ((2R)pyrrolidin-2-yl)methoxy | NH₂ |
| 2439. | —(NMeSO₂)-3-pyridyl | ((2R)-1-methylpyrrolidin-2-yl)methoxy | NH₂ |
| 2440. | —(NMeSO₂)-3-pyridyl | 2-(piperid-1-yl)ethoxy | NH₂ |
| 2441. | —(NMeSO₂)-3-pyridyl | 2-(piperazin-1-yl)ethoxy | NH₂ |
| 2442. | —(NMeSO₂)-3-pyridyl | 2-(morpholin-4-yl)ethoxy | NH₂ |
| 2443. | —(NMeSO₂)-4-pyridyl | Cl | H |
| 2444. | —(NMeSO₂)-4-pyridyl | cyclopropylmethylamino | H |
| 2445. | —(NMeSO₂)-4-pyridyl | 3-hydroxypropylamino | H |
| 2446. | —(NMeSO₂)-4-pyridyl | 2-(1-piperidinyl)ethylamino | H |
| 2447. | —(NMeSO₂)-4-pyridyl | 2-(1-pyrrolidinyl)ethylamino | H |
| 2448. | —(NMeSO₂)-4-pyridyl | 2-(4-morpholinyl)ethylamino | H |
| 2449. | —(NMeSO₂)-4-pyridyl | 3-(1-piperidinyl)propylamino | H |
| 2450. | —(NMeSO₂)-4-pyridyl | 3-(1-pyrrolidinyl)propylamino | H |
| 2451. | —(NMeSO₂)-4-pyridyl | 3-(4-morpholinyl)propylamino | H |
| 2452. | —(NMeSO₂)-4-pyridyl | N-methyl-N-(2-piperid-1-ylethyl)amino | H |
| 2453. | —(NMeSO₂)-4-pyridyl | N-methyl-N-(2-pyrrolidin-1-ylethyl)amino | H |
| 2454. | —(NMeSO₂)-4-pyridyl | N-methyl-N-(2-morpholin-4-ylethyl)amino | H |
| 2455. | —(NMeSO₂)-4-pyridyl | ((2S)-2-amino-3-phenylpropyl)amino | H |
| 2456. | —(NMeSO₂)-4-pyridyl | 4-methylpiperazinylamino | H |
| 2457. | —(NMeSO₂)-4-pyridyl | 4-methylpiperazinyl | H |
| 2458. | —(NMeSO₂)-4-pyridyl | 3-aminopyrrolidinyl | H |
| 2459. | —(NMeSO₂)-4-pyridyl | (diethylamino)ethylamino | H |
| 2460. | —(NMeSO₂)-4-pyridyl | 3,5-dimethylpiperazin-1-yl | H |
| 2461. | —(NMeSO₂)-4-pyridyl | (4-piperidylmethyl)amino | H |
| 2462. | —(NMeSO₂)-4-pyridyl | (2-methylbutyl)amino | H |
| 2463. | —(NMeSO₂)-4-pyridyl | 2-(dimethylamino)ethoxy | H |
| 2464. | —(NMeSO₂)-4-pyridyl | 2-(methylamino)ethoxy | H |
| 2465. | —(NMeSO₂)-4-pyridyl | ((2R)pyrrolidin-2-yl)methoxy | H |
| 2466. | —(NMeSO₂)-4-pyridyl | ((2R)-1-methylpyrrolidin-2-yl)methoxy | H |
| 2467. | —(NMeSO₂)-4-pyridyl | 2-(piperid-1-yl)ethoxy | H |
| 2468. | —(NMeSO₂)-4-pyridyl | 2-(piperazin-1-yl)ethoxy | H |
| 2469. | —(NMeSO₂)-4-pyridyl | 2-(morpholin-4-yl)ethoxy | H |
| 2470. | —(NMeSO₂)-4-pyridyl | Cl | NH₂ |
| 2471. | —(NMeSO₂)-4-pyridyl | cyclopropylmethylamino | NH₂ |
| 2472. | —(NMeSO₂)-4-pyridyl | 3-hydroxypropylamino | NH₂ |
| 2473. | —(NMeSO₂)-4-pyridyl | 2-(1-piperidinyl)ethylamino | NH₂ |
| 2474. | —(NMeSO₂)-4-pyridyl | 2-(1-pyrrolidinyl)ethylamino | NH₂ |
| 2475. | —(NMeSO₂)-4-pyridyl | 2-(4-morpholinyl)ethylamino | NH₂ |
| 2476. | —(NMeSO₂)-4-pyridyl | 3-(1-piperidinyl)propylamino | NH₂ |
| 2477. | —(NMeSO₂)-4-pyridyl | 3-(1-pyrrolidinyl)propylamino | NH₂ |
| 2478. | —(NMeSO₂)-4-pyridyl | 3-(4-morpholinyl)propylamino | NH₂ |
| 2479. | —(NMeSO₂)-4-pyridyl | N-methyl-N-(2-piperid-1-ylethyl)amino | NH₂ |
| 2480. | —(NMeSO₂)-4-pyridyl | N-methyl-N-(2-pyrrolidin-1-ylethyl)amino | NH₂ |
| 2481. | —(NMeSO₂)-4-pyridyl | N-methyl-N-(2-morpholin-4-ylethyl)amino | NH₂ |
| 2482. | —(NMeSO₂)-4-pyridyl | ((2S)-2-amino-3-phenylpropyl)amino | NH₂ |
| 2483. | —(NMeSO₂)-4-pyridyl | 4-methylpiperazinylamino | NH₂ |
| 2484. | —(NMeSO₂)-4-pyridyl | 4-methylpiperazinyl | NH₂ |
| 2485. | —(NMeSO₂)-4-pyridyl | 3-aminopyrrolidinyl | NH₂ |
| 2486. | —(NMeSO₂)-4-pyridyl | (diethylamino)ethylamino | NH₂ |
| 2487. | —(NMeSO₂)-4-pyridyl | 3,5-dimethylpiperazin-1-yl | NH₂ |

TABLE 4-continued

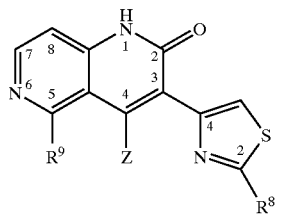

| # | R⁸ | R⁹ | Z |
|---|---|---|---|
| 2488. | —(NMeSO₂)-4-pyridyl | (4-piperidylmethyl)amino | NH₂ |
| 2489. | —(NMeSO₂)-4-pyridyl | (2-methylbutyl)amino | NH₂ |
| 2490. | —(NMeSO₂)-4-pyridyl | 2-(dimethylamino)ethoxy | NH₂ |
| 2491. | —(NMeSO₂)-4-pyridyl | 2-(methylamino)ethoxy | NH₂ |
| 2492. | —(NMeSO₂)-4-pyridyl | ((2R)pyrrolidin-2-yl)methoxy | NH₂ |
| 2493. | —(NMeSO₂)-4-pyridyl | ((2R)-1-methylpyrrolidin-2-yl)methoxy | NH₂ |
| 2494. | —(NMeSO₂)-4-pyridyl | 2-(piperid-1-yl)ethoxy | NH₂ |
| 2495. | —(NMeSO₂)-4-pyridyl | 2-(piperazin-1-yl)ethoxy | NH₂ |
| 2496. | —(NMeSO₂)-4-pyridyl | 2-(morpholin-4-yl)ethoxy | NH₂ |

TABLE 5

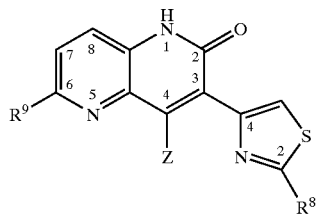

| # | R⁸ | R⁹ | Z |
|---|---|---|---|
| 2497. | 4-pyridyl | Cl | H |
| 2498. | 4-pyridyl | cyclopropylmethylamino | H |
| 2499. | 4-pyridyl | 3-hydroxypropylamino | H |
| 2500. | 4-pyridyl | 2-(1-piperidinyl)ethylamino | H |
| 2501. | 4-pyridyl | 2-(1-pyrrolidinyl)ethylamino | H |
| 2502. | 4-pyridyl | 2-(4-morpholinyl)ethylamino | H |
| 2503. | 4-pyridyl | 3-(1-piperidinyl)propylamino | H |
| 2504. | 4-pyridyl | 3-(1-pyrrolidinyl)propylamino | H |
| 2505. | 4-pyridyl | 3-(4-morpholinyl)propylamino | H |
| 2506. | 4-pyridyl | N-methyl-N-(2-piperid-1-ylethyl)amino | H |
| 2507. | 4-pyridyl | N-methyl-N-(2-pyrrolidin-1-ylethyl)amino | H |
| 2508. | 4-pyridyl | N-methyl-N-(2-morpholin-4-ylethyl)amino | H |
| 2509. | 4-pyridyl | ((2S)-2-amino-3-phenylpropyl)amino | H |
| 2510. | 4-pyridyl | 4-methylpiperazinylamino | H |
| 2511. | 4-pyridyl | 4-methylpiperazinyl | H |
| 2512. | 4-pyridyl | 3-aminopyrrolidinyl | H |
| 2513. | 4-pyridyl | (diethylamino)ethylamino | H |
| 2514. | 4-pyridyl | 3,5-dimethylpiperazin-1-yl | H |
| 2515. | 4-pyridyl | (4-piperidylmethyl)amino | H |
| 2516. | 4-pyridyl | (2-methylbutyl)amino | H |
| 2517. | 4-pyridyl | 2-(dimethylamino)ethoxy | H |
| 2518. | 4-pyridyl | 2-(methylamino)ethoxy | H |
| 2519. | 4-pyridyl | ((2R)pyrrolidin-2-yl)methoxy | H |
| 2520. | 4-pyridyl | ((2R)-1-methylpyrrolidin-2-yl)methoxy | H |
| 2521. | 4-pyridyl | 2-(piperid-1-yl)ethoxy | H |
| 2522. | 4-pyridyl | 2-(piperazin-1-yl)ethoxy | H |
| 2523. | 4-pyridyl | 2-(morpholin-4-yl)ethoxy | H |
| 2524. | 4-pyridyl | Cl | NH₂ |
| 2525. | 4-pyridyi | cyclopropylmethylamino | NH₂ |
| 2526. | 4-pyridyl | 3-hydroxypropylamino | NH₂ |
| 2527. | 4-pyridyl | 2-(1-piperidinyl)ethylamino | NH₂ |
| 2528. | 4-pyridyl | 2-(1-pyrrolidinyl)ethylamino | NH₂ |
| 2529. | 4-pyridyl | 2-(4-morpholinyl)ethylamino | NH₂ |
| 2530. | 4-pyridyl | 3-(1-piperidinyl)propylamino | NH₂ |
| 2531. | 4-pyridyl | 3-(1-pyrrolidinyl)propylamino | NH₂ |
| 2532. | 4-pyridyl | 3-(4-morpholinyl)propylamino | NH₂ |
| 2533. | 4-pyridyl | N-methyl-N-(2-piperid-1-ylethyl)amino | NH₂ |
| 2534. | 4-pyridyl | N-methyl-N-(2-pyrrolidin-1-ylethyl)amino | NH₂ |

TABLE 5-continued

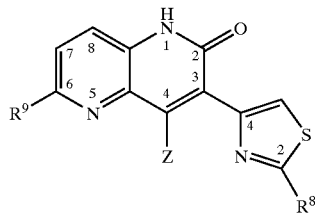

| # | R⁸ | R⁹ | Z |
|---|---|---|---|
| 2535. | 4-pyridyl | N-methyl-N-(2-morpholin-4-ylethyl)amino | $NH_2$ |
| 2536. | 4-pyridyl | ((2S)-2-amino-3-phenylpropyl)amino | $NH_2$ |
| 2537. | 4-pyridyl | 4-methylpiperazinylamino | $NH_2$ |
| 2538. | 4-pyridyl | 4-methylpiperazinyl | $NH_2$ |
| 2539. | 4-pyridyl | 3-aminopyrrolidinyl | $NH_2$ |
| 2540. | 4-pyridyl | (diethylamino)ethylamino | $NH_2$ |
| 2541. | 4-pyridyl | 3,5-dimethylpiperazin-1-yl | $NH_2$ |
| 2542. | 4-pyridyl | (4-piperidylmethyl)amino | $NH_2$ |
| 2543. | 4-pyridyl | (2-methylbutyl)amino | $NH_2$ |
| 2544. | 4-pyridyl | 2-(dimethylamino)ethoxy | $NH_2$ |
| 2545. | 4-pyridyl | 2-(methylamino)ethoxy | $NH_2$ |
| 2546. | 4-pyridyl | ((2R)pyrrolidin-2-yl)methoxy | $NH_2$ |
| 2547. | 4-pyridyl | ((2R)-1-methylpyrrolidin-2-yl)methoxy | $NH_2$ |
| 2548. | 4-pyridyl | 2-(piperid-1-yl)ethoxy | $NH_2$ |
| 2549. | 4-pyridyl | 2-(piperazin-1-yl)ethoxy | $NH_2$ |
| 2550. | 4-pyridyl | 2-(morpholin-4-yl)ethoxy | $NH_2$ |
| 2551. | —($CH_2SO_2$)-phenyl | Cl | H |
| 2552. | —($CH_2SO_2$)-phenyl | cyclopropylmethylamino | H |
| 2553. | —($CH_2SO_2$)-phenyl | 3-hydroxypropylamino | H |
| 2554. | —($CH_2SO_2$)-phenyl | 2-(1-piperidinyl)ethylamino | H |
| 2555. | —($CH_2SO_2$)-phenyl | 2-(1-pyrrolidinyl)ethylamino | H |
| 2556. | —($CH_2SO_2$)-phenyl | 2-(4-morpholinyl)ethylamino | H |
| 2557. | —($CH_2SO_2$)-phenyl | 3-(1-piperidinyl)propylamino | H |
| 2558. | —($CH_2SO_2$)-phenyl | 3-(1-pyrrolidinyl)propylamino | H |
| 2559. | —($CH_2SO_2$)-phenyl | 3-(4-morpholinyl)propylamino | H |
| 2560. | —($CH_2SO_2$) phenyl | N-methyl-N-(2-piperid-1-ylethyl)amino | H |
| 2561. | —($CH_2SO_2$)-phenyl | N-methyl-N-(2-pyrrolidin-1-ylethyl)amino | H |
| 2562. | —($CH_2SO_2$)-phenyl | N-methyl-N-(2-morpholin-4-ylethyl)amino | H |
| 2563. | —($CH_2SO_2$)-phenyl | ((2S)-2-amino-3-phenylpropyl)amino | H |
| 2564. | —($CH_2SO_2$)-phenyl | 4-methylpiperazinylamino | H |
| 2565. | —($CH_2SO_2$)-phenyl | 4-methylpiperazinyl | H |
| 2566. | —($CH_2SO_2$)-phenyl | 3-aminopyrrolidinyl | H |
| 2567. | —($CH_2SO_2$)-phenyl | (diethylamino)ethylamino | H |
| 2568. | —($CH_2SO_2$)-phenyl | 3,5-dimethylpiperazin-1-yl | H |
| 2569. | —($CH_2SO_2$)-phenyl | (4-piperidylmethyl)amino | H |
| 2570. | —($CH_2SO_2$)-phenyl | (2-methylbutyl)amino | H |
| 2571. | —($CH_2SO_2$)-phenyl | 2-(dimethylamino)ethoxy | H |
| 2572. | —($CH_2SO_2$)-phenyl | 2-(methylamino)ethoxy | H |
| 2573. | —($CH_2SO_2$)-phenyl | ((2R)pyrrolidin-2-yl)methoxy | H |
| 2574. | —($CH_2SO_2$)-phenyl | ((2R)-1-methylpyrrolidin-2-yl)methoxy | H |
| 2575. | —($CH_2SO_2$)-phenyl | 2-(piperid-1-yl)ethoxy | H |
| 2576. | —($CH_2SO_2$)-phenyl | 2-(piperazin-1-yl)ethoxy | H |
| 2577. | —($CH_2SO_2$)-phenyl | 2-(morpholin-4-yl)ethoxy | H |
| 2578. | —($CH_2SO_2$)-phenyl | Cl | $NH_2$ |
| 2579. | —($CH_2SO_2$)-phenyl | cyclopropylmethylamino | $NH_2$ |
| 2580. | —($CH_2SO_2$)-phenyl | 3-hydroxypropylamino | $NH_2$ |
| 2581. | —($CH_2SO_2$)-phenyl | 2-(1-piperidinyl)ethylamino | $NH_2$ |
| 2582. | —($CH_2SO_2$)-phenyl | 2-(1-pyrrolidinyl)ethylamino | $NH_2$ |
| 2583. | —($CH_2SO_2$)-phenyl | 2-(4-morpholinyl)ethylamino | $NH_2$ |
| 2584. | —($CH_2SO_2$)-phenyl | 3-(1-piperidinyl)propylamino | $NH_2$ |
| 2585. | —($CH_2SO_2$)-phenyl | 3-(1-pyrrolidinyl)propylamino | $NH_2$ |
| 2586. | —($CH_2SO_2$)-phenyl | 3-(4-morpholinyl)propylamino | $NH_2$ |
| 2587. | —($CH_2SO_2$)-phenyl | N-methyl-N-(2-piperid-1-ylethyl)amino | $NH_2$ |
| 2588. | —($CH_2SO_2$)-phenyl | N-methyl-N-(2-pyrrolidin-1-ylethyl)amino | $NH_2$ |
| 2589. | —($CH_2SO_2$)-phenyl | N-methyl-N-(2-morpholin-4-ylethyl)amino | $NH_2$ |
| 2590. | —($CH_2SO_2$)-phenyl | ((2S)-2-amino-3-phenylpropyl)amino | $NH_2$ |
| 2591. | —($CH_2SO_2$)-phemyl | 4-methylpiperazinylamino | $NH_2$ |
| 2592. | —($CH_2SO_2$)-phenyl | 4-methylpiperazinyl | $NH_2$ |
| 2593. | —($CH_2SO_2$)-phenyl | 3-aminopyrrolidinyl | $NH_2$ |
| 2594. | —($CH_2SO_2$)-phenyl | (diethylamino)ethylamino | $NH_2$ |
| 2595. | —($CH_2SO_2$)-phenyl | 3,5-dimethylpiperazin-1-yl | $NH_2$ |
| 2596. | —($CH_2SO_2$)-phenyl | (4-piperidylmethyl)amino | $NH_2$ |
| 2597. | —($CH_2SO_2$)-phenyl | (2-methylbutyl)amino | $NH_2$ |
| 2598. | —($CH_2SO_2$)-phenyi | 2-(dimethylamino)ethoxy | $NH_2$ |
| 2599. | —($CH_2SO_2$)-phenyl | 2-(methylamino)ethoxy | $NH_2$ |

TABLE 5-continued

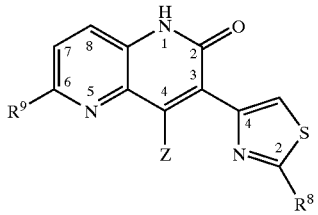

| # | R⁸ | R⁹ | Z |
|---|---|---|---|
| 2600. | —(CH₂SO₂)-phenyl | ((2R)pyrrolidin-2-yl)methoxy | NH₂ |
| 2601. | —(CH₂SO₂)-phenyl | ((2R)-1-methylpyrrolidin-2-yl)methoxy | NH₂ |
| 2602. | —(CH₂SO₂) phenyl | 2-(piperid-1-yl)ethoxy | NH₂ |
| 2603. | —(CH₂SO₂)-phenyl | 2-(piperazin-1-yl)ethoxy | NH₂ |
| 2604. | —(CH₂SO₂)-phenyl | 2-(morpholin-4-yl)ethoxy | NH₂ |
| 2605. | —(CH₂SO₂)-2-thienyl | Cl | H |
| 2606. | —(CH₂SO₂)-2-thienyl | cyclopropylmethylamino | H |
| 2607. | —(CH₂SO₂)-2-thienyl | 3-hydroxypropylamino | H |
| 2608. | —(CH₂SO₂)-2-thienyl | 2-(1-piperidinyl)ethylamino | H |
| 2609. | —(CH₂SO₂)-2-thienyl | 2-(1-pyrrolidinyl)ethylamino | H |
| 2610. | —(CH₂SO₂)-2-thienyl | 2-(4-morpholinyl)ethylamino | H |
| 2611. | —(CH₂SO₂)-2-thienyl | 3-(1-piperidinyl)propylamino | H |
| 2612. | —(CH₂SO₂)-2-thienyl | 3-(1-pyrrolidinyl)propylamino | H |
| 2613. | —(CH₂SO₂)-2-thienyl | 3-(4-morpholinyl)propylamino | H |
| 2614. | —(CH₂SO₂)-2-thienyl | N-methyl-N-(2-piperid-1-ylethyl)amino | H |
| 2615. | —(CH₂SO₂)-2-thienyl | N-methyl-N-(2-pyrrolidin-1-ylethyl)amino | H |
| 2616. | —(CH₂SO₂)-2-thienyl | N-methyl-N-(2-morpholin-4-ylethyl)amino | H |
| 2617. | —(CH₂SO₂)-2-thienyl | ((2S)-2-amino-3-phenylpropyl)amino | H |
| 2618. | —(CH₂SO₂)-2-thienyl | 4-methylpiperazinylamino | H |
| 2619. | —(CH₂SO₂)-2-thienyl | 4-methylpiperazinyl | H |
| 2620. | —(CH₂SO₂)-2-thienyl | 3-aminopyrrolidinyl | H |
| 2621. | —(CH₂SO₂)-2-thienyl | (diethylamino)ethylamino | H |
| 2622. | —(CH₂SO₂)-2-thienyl | 3,5-dimethylpiperazin-1-yl | H |
| 2623. | —(CH₂SO₂)-2-thienyl | (4-piperidylmethyl)amino | H |
| 2624. | —(CH₂SO₂)-2-thienyl | (2-methylbutyl)amino | H |
| 2625. | —(CH₂SO₂)-2-thienyl | 2-(dimethylamino)ethoxy | H |
| 2626. | —(CH₂SO₂)-2-thienyl | 2-(methylamino)ethoxy | H |
| 2627. | —(CH₂SO₂)-2-thienyl | ((2R)pyrrolidin-2-yl)methoxy | H |
| 2628. | —(CH₂SO₂)-2-thienyl | ((2R)-1-methylpyrrolidin-2-yl)methoxy | H |
| 2629. | —(CH₂SO₂)-2-thienyl | 2-(piperid-1-yl)ethoxy | H |
| 2630. | —(CH₂SO₂)-2-thienyl | 2-(piperazin-1-yl)ethoxy | H |
| 2631. | —(CH₂SO₂)-2-thienyl | 2-(morpholin-4-yl)ethoxy | H |
| 2632. | —(CH₂SO₂)-2-thienyl | Cl | NH₂ |
| 2633. | —(CH₂SO₂)-2-thienyl | cyclopropylmethylamino | NH₂ |
| 2634. | —(CH₂SO₂)-2-thienyl | 3-hydroxypropylamino | NH₂ |
| 2635. | —(CH₂SO₂)-2-thienyl | 2-(1-piperidinyl)ethylamino | NH₂ |
| 2636. | —(CH₂SO₂)-2-thienyl | 2-(1-pyrrolidinyl)ethylamino | NH₂ |
| 2637. | —(CH₂SO₂)-2-thienyl | 2-(4-morpholinyl)ethylamino | NH₂ |
| 2638. | —(CH₂SO₂)-2-thienyl | 3-(1-piperidinyl)propylamino | NH₂ |
| 2639. | —(CH₂SO₂)-2-thienyl | 3-(1-pyrrolidinyl)propylamino | NH₂ |
| 2640. | —(CH₂SO₂)-2-thienyl | 3-(4-morpholinyl)propylamino | NH₂ |
| 2641. | —(CH₂SO₂)-2-thienyl | N-methyl-N-(2-piperid-1-ylethyl)amino | NH₂ |
| 2642. | —(CH₂SO₂)-2-thienyl | N-methyl-N-(2-pyrrolidin-1-ylethyl)amino | NH₂ |
| 2643. | —(CH₂SO₂)-2-thienyl | N-methyl-N-(2-morpholin-4-ylethyl)amino | NH₂ |
| 2644. | —(CH₂SO₂)-2-thienyl | ((2S)-2-amino-3-phenylpropyl)amino | NH₂ |
| 2645. | —(CH₂SO₂)-2-thienyl | 4-methylpiperazinylamino | NH₂ |
| 2646. | —(CH₂SO₂)-2-thienyl | 4-methylpiperazinyl | NH₂ |
| 2647. | —(CH₂SO₂) 2-thienyl | 3-aminopyrrolidinyl | NH₂ |
| 2648. | —(CH₂SO₂)-2-thienyl | (diethylamino)ethylamino | NH₂ |
| 2649. | —(CH₂SO₂)-2-thienyl | 3,5-dimethylpiperazin-1-yl | NH₂ |
| 2650. | —(CH₂SO₂)-2-thienyl | (4-piperidylmethyl)amino | NH₂ |
| 2651. | —(CH₂SO₂)-2-thienyl | (2-methylbutyl)amino | NH₂ |
| 2652. | —(CH₂SO₂)-2-thienyl | 2-(dimethylamino)ethoxy | NH₂ |
| 2653. | —(CH₂SO₂)-2-thienyl | 2-(methylamino)ethoxy | NH₂ |
| 2654. | —(CH₂SO₂)-2-thienyl | ((2R)pyrrolidin-2-yl)methoxy | NH₂ |
| 2655. | —(CH₂SO₂)-2-thienyl | ((2R)-1-methylpyrrolidin-2-yl)methoxy | NH₂ |
| 2656. | —(CH₂SO₂)-2-thienyl | 2-(piperid-1-yl)ethoxy | NH₂ |
| 2657. | —(CH₂SO₂)-2-thienyl | 2-(piperazin-1-yl)ethoxy | NH₂ |
| 2658. | —(CH₂SO₂)-2-thienyl | 2-(morpholin-4-yl)ethoxy | NH₂ |
| 2659. | —(CH₂SO₂)-2-pyridyl | Cl | H |
| 2660. | —(CH₂SO₂)-2-pyridyl | cyclopropylmethylamino | H |
| 2661. | —(CH₂SO₂)-2-pyridyl | 3-hydroxypropylamino | H |
| 2662. | —(CH₂SO₂)-2-pyridyl | 2-(1-piperidinyl)ethylamino | H |
| 2663. | —(CH₂SO₂)-2-pyridyl | 2-(1-pyrrolidinyl)ethylamino | H |
| 2664. | —(CH₂SO₂)-2-pyridyl | 2-(4-morpholinyl)ethylamino | H |

TABLE 5-continued

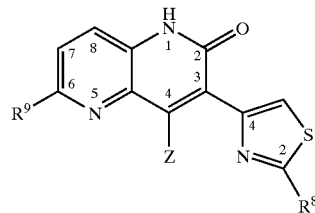

| # | R⁸ | R⁹ | Z |
|---|---|---|---|
| 2665. | —(CH$_2$SO$_2$)-2-pyridyl | 3-(1-piperidinyl)propylamino | H |
| 2666. | —(CH$_2$SO$_2$)-2-pyridyl | 3-(1-pyrrolidinyl)propylamino | H |
| 2667. | —(CH$_2$SO$_2$)-2-pyridyl | 3-(4-morpholinyl)propylamino | H |
| 2668. | —(CH$_2$SO$_2$)-2-pyridyl | N-methyl-N-(2-piperid-1-ylethyl)amino | H |
| 2669. | —(CH$_2$SO$_2$)-2-pyridyl | N-methyl-N-(2-pyrrolidin-1-ylethyl)amino | H |
| 2670. | —(CH$_2$SO$_2$)-2-pyridyl | N-methyl-N-(2-morpholin-4-ylethyl)amino | H |
| 2671. | —(CH$_2$SO$_2$)-2-pyridyl | ((2S)-2-amino-3-phenylpropyl)amino | H |
| 2672. | —(CH$_2$SO$_2$)-2-pyridyl | 4-methylpiperazinylamino | H |
| 2673. | —(CH$_2$SO$_2$)-2-pyridyl | 4-methylpiperazinyl | H |
| 2674. | —(CH$_2$SO$_2$)-2-pyridyl | 3-aminopyrrolidinyl | H |
| 2675. | —(CH$_2$SO$_2$)-2-pyridyl | (diethylamino)ethylamino | H |
| 2676. | —(CH$_2$SO$_2$)-2-pyridyl | 3,5-dimethylpiperazin-1-yl | H |
| 2677. | —(CH$_2$SO$_2$)-2-pyridyl | (4-piperidylmethyl)amino | H |
| 2678. | —(CH$_2$SO$_2$)-2-pyridyl | (2-methylbutyl)amino | H |
| 2679. | —(CH$_2$SO$_2$)-2-pyridyl | 2-(dimethylamino)ethoxy | H |
| 2680. | —(CH$_2$SO$_2$)-2-pyridyl | 2-(methylamino)ethoxy | H |
| 2681. | —(CH$_2$SO$_2$)-2-pyridyl | ((2R)pyrrolidin-2-yl)methoxy | H |
| 2682. | —(CH$_2$SO$_2$)-2-pyridyl | ((2R)-1-methylpyrrolidin-2-yl)methoxy | H |
| 2683. | —(CH$_2$SO$_2$)-2-pyridyl | 2-(piperid-1-yl)ethoxy | H |
| 2684. | —(CH$_2$SO$_2$)-2-pyridyl | 2-(piperazin-1-yl)ethoxy | H |
| 2685. | —(CH$_2$SO$_2$)-2-pyridyl | 2-(morpholin-4-yl)ethoxy | H |
| 2686. | —(CH$_2$SO$_2$)-2-pyridyl | Cl | NH$_2$ |
| 2687. | —(CH$_2$SO$_2$)-2-pyridyl | cyclopropylmethylamino | NH$_2$ |
| 2688. | —(CH$_2$SO$_2$)-2-pyridyl | 3-hydroxypropylamino | NH$_2$ |
| 2689. | —(CH$_2$SO$_2$)-2-pyridyl | 2-(1-piperidinyl)ethylamino | NH$_2$ |
| 2690. | —(CH$_2$SO$_2$)-2-pyridyl | 2-(1-pyrrolidinyl)ethylamino | NH$_2$ |
| 2691. | —(CH$_2$SO$_2$)-2-pyridyl | 2-(4-morpholinyl)ethylamino | NH$_2$ |
| 2692. | —(CH$_2$SO$_2$)-2-pyridyl | 3-(1-piperidinyl)propylamino | NH$_2$ |
| 2693. | —(CH$_2$SO$_2$)-2-pyridyl | 3-(1-pyrrolidinyl)propylamino | NH$_2$ |
| 2694. | —(CH$_2$SO$_2$)-2-pyridyl | 3-(4-morpholinyl)propylamino | NH$_2$ |
| 2695. | —(CH$_2$SO$_2$)-2-pyridyl | N-methyl-N-(2-piperid-1-ylethyl)amino | NH$_2$ |
| 2696. | —(CH$_2$SO$_2$)-2-pyridyl | N-methyl-N-(2-pyrrolidin-1-ylethyl)amino | NH$_2$ |
| 2697. | —(CH$_2$SO$_2$)-2-pyridyl | N-methyl-N-(2-morpholin-4-ylethyl)amino | NH$_2$ |
| 2698. | —(CH$_2$SO$_2$)-2-pyridyl | ((2S)-2-amino-3-phenylpropyl)amino | NH$_2$ |
| 2699. | —(CH$_2$SO$_2$)-2-pyridyl | 4-methylpiperazinylamino | NH$_2$ |
| 2700. | —(CH$_2$SO$_2$)-2-pyridyl | 4-methylpiperazinyl | NH$_2$ |
| 2701. | —(CH$_2$SO$_2$)-2-pyridyl | 3-aminopyrrolidinyl | NH$_2$ |
| 2702. | —(CH$_2$SO$_2$)-2-pyridyl | (diethylamino)ethylamino | NH$_2$ |
| 2703. | —(CH$_2$SO$_2$)-2-pyridyl | 3,5-dimethylpiperazin-1-yl | NH$_2$ |
| 2704. | —(CH$_2$SO$_2$)-2-pyridyl | (4-piperidylmethyl)amino | NH$_2$ |
| 2705. | —(CH$_2$SO$_2$)-2-pyridyl | (2-methylbutyl)amino | NH$_2$ |
| 2706. | —(CH$_2$SO$_2$)-2-pyridyl | 2-(dimethylamino)ethoxy | NH$_2$ |
| 2707. | —(CH$_2$SO$_2$)-2-pyridyl | 2-(methylamino)ethoxy | NH$_2$ |
| 2708. | —(CH$_2$SO$_2$)-2-pyridyl | ((2R)pyrrolidin-2-yl)methoxy | NH$_2$ |
| 2709. | —(CH$_2$SO$_2$)-2-pyridyl | ((2R)-1-methylpyrrolidin-2-yl)methoxy | NH$_2$ |
| 2710. | —(CH$_2$SO$_2$)-2-pyridyl | 2-(piperid-1-yl)ethoxy | NH$_2$ |
| 2711. | —(CH$_2$SO$_2$)-2-pyridyl | 2-(piperazin-1-yl)ethoxy | NH$_2$ |
| 2712. | —(CH$_2$SO$_2$)-2-pyridyl | 2-(morpholin-4-yl)ethoxy | NH$_2$ |
| 2713. | —(CH$_2$SO$_2$)-3-pyridyl | Cl | H |
| 2714. | —(CH$_2$SO$_2$)-3-pyridyl | cyclopropylmethylamino | H |
| 2715. | —(CH$_2$SO$_2$)-3-pyridyl | 3-hydroxypropylamino | H |
| 2716. | —(CH$_2$SO$_2$)-3-pyridyl | 2-(1-piperidinyl)ethylamino | H |
| 2717. | —(CH$_2$SO$_2$)-3-pyridyl | 2-(1-pyrrolidinyl)ethylamino | H |
| 2718. | —(CH$_2$SO$_2$)-3-pyridyl | 2-(4-morpholinyl)ethylamino | H |
| 2719. | —(CH$_2$SO$_2$)-3-pyridyl | 3-(1-piperidinyl)propylamino | H |
| 2720. | —(CH$_2$SO$_2$)-3-pyridyl | 3-(1-pyrrolidinyl)propylamino | H |
| 2721. | —(CH$_2$SO$_2$)-3-pyridyl | 3-(4-morpholinyl)propylamino | H |
| 2722. | —(CH$_2$SO$_2$)-3-pyridyl | N-methyl-N-(2-piperid-1-ylethyl)amino | H |
| 2723. | —(CH$_2$SO$_2$)-3-pyridyl | N-methyl-N-(2-pyrrolidin-1-ylethyl)amino | H |
| 2724. | —(CH$_2$SO$_2$)-3-pyridyl | N-methyl-N-(2-morpholin-4-ylethyl)amino | H |
| 2725. | —(CH$_2$SO$_2$)-3-pyridyl | ((2S)-2-amino-3-phenylpropyl)amino | H |
| 2726. | —(CH$_2$SO$_2$)-3-pyridyl | 4-methylpiperazinylamino | H |
| 2727. | —(CH$_2$SO$_2$)-3-pyridyl | 4-methylpiperazinyl | H |
| 2728. | —(CH$_2$SO$_2$)-3-pyridyl | 3-aminopyrrolidinyl | H |
| 2729. | —(CH$_2$SO$_2$)-3-pyridyl | (diethylamino)ethylamino | H |

TABLE 5-continued

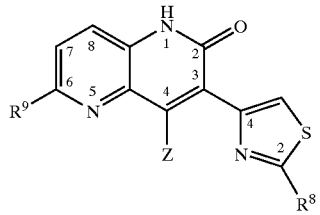

| # | R⁸ | R⁹ | Z |
|---|---|---|---|
| 2730. | —(CH₂SO₂) 3-pyridyl | 3,5-dimethylpiperazin-1-yl | H |
| 2731. | —(CH₂SO₂)-3-pyridyl | (4-piperidylmethyl)amino | H |
| 2732. | —(CH₂SO₂)-3-pyridyl | (2-methylbutyl)amino | H |
| 2733. | —(CH₂SO₂)-3-pyridyl | 2-(dimethylamino)ethoxy | H |
| 2734. | —(CH₂SO₂)-3-pyridyl | 2-(methylamino)ethoxy | H |
| 2735. | —(CH₂SO₂)-3-pyridyl | ((2R)pyrrolidin-2-yl)methoxy | H |
| 2736. | —(CH₂SO₂)-3-pyridyl | ((2R)-1-methylpyrrolidin-2-yl)methoxy | H |
| 2737. | —(CH₂SO₂)-3-pyridyl | 2-(piperid-1-yl)ethoxy | H |
| 2738. | —(CH₂SO₂)-3-pyridyl | 2-(piperazin-1-yl)ethoxy | H |
| 2739. | —(CH₂SO₂)-3-pyridyl | 2-(morpholin-4-yl)ethoxy | H |
| 2740. | —(CH₂SO₂)-3-pyridyl | Cl | NH₂ |
| 2741. | —(CH₂SO₂)-3-pyridyl | cyclopropylmethylamino | NH₂ |
| 2742. | —(CH₂SO₂)-3-pyridyl | 3-hydroxypropylamino | NH₂ |
| 2743. | —(CH₂SO₂)-3-pyridyl | 2-(1-piperidinyl)ethylamino | NH₂ |
| 2744. | —(CH₂SO₂)-3-pyridyl | 2-(1-pyrrolidinyl)ethylamino | NH₂ |
| 2745. | —(CH₂SO₂)-3-pyridyl | 2-(4-morpholinyl)ethylamino | NH₂ |
| 2746. | —(CH₂SO₂)-3-pyridyl | 3-(1-piperidinyl)propylamino | NH₂ |
| 2747. | —(CH₂SO₂)-3-pyridyl | 3-(1-pyrrolidinyl)propylamino | NH₂ |
| 2748. | —(CH₂SO₂)-3-pyridyl | 3-(4-morpholinyl)propylamino | NH₂ |
| 2749. | —(CH₂SO₂)-3-pyridyl | N-methyl-N-(2-piperid-1-ylethyl)amino | NH₂ |
| 2750. | —(CH₂SO₂) 3-pyridyl | N-methyl-N-(2-pyrrolidin-1-ylethyl)amino | NH₂ |
| 2751. | —(CH₂SO₂)-3-pyridyl | N-methyl-N-(2-morpholin-4-ylethyl)amino | NH₂ |
| 2752. | —(CH₂SO₂)-3-pyridyl | ((2S)-2-amino-3-phenylpropyl)amino | NH₂ |
| 2753. | —(CH₂SO₂)-3-pyridyl | 4-methylpiperazinylamino | NH₂ |
| 2754. | —(CH₂SO₂)-3-pyridyl | 4-methylpiperazinyl | NH₂ |
| 2755. | —(CH₂SO₂)-3-pyridyl | 3-aminopyrrolidinyl | NH₂ |
| 2756. | —(CH₂SO₂)-3-pyridyl | (diethylamino)ethylamino | NH₂ |
| 2757. | —(CH₂SO₂)-3-pyridyl | 3,5-dimethylpiperazin-1-yl | NH₂ |
| 2758. | —(CH₂SO₂)-3-pyridyl | (4-piperidylmethyl)amino | NH₂ |
| 2759. | —(CH₂SO₂)-3-pyridyl | (2-methylbutyl)amino | NH₂ |
| 2760. | —(CH₂SO₂)-3-pyridyl | 2-(dimethylamino)ethoxy | NH₂ |
| 2761. | —(CH₂SO₂)-3-pyridyl | 2-(methylamino)ethoxy | NH₂ |
| 2762. | —(CH₂SO₂)-3-pyridyl | ((2R)pyrrolidin-2-yl)methoxy | NH₂ |
| 2763. | —(CH₂SO₂)-3-pyridyl | ((2R)-1-methylpyrrolidin-2-yl)methoxy | NH₂ |
| 2764. | —(CH₂SO₂)-3-pyridyl | 2-(piperid-1-yl)ethoxy | NH₂ |
| 2765. | —(CH₂SO₂)-3-pyridyl | 2-(piperazin-1-yl)ethoxy | NH₂ |
| 2766. | —(CH₂SO₂)-3-pyridyl | 2-(morpholin-4-yl)ethoxy | NH₂ |
| 2767. | —(CH₂SO₂)-4-pyridyl | Cl | H |
| 2768. | —(CH₂SO₂)-4-pyridyl | cyclopropylmethylamino | H |
| 2769. | —(CH₂SO₂)-4-pyridyl | 3-hydroxypropylamino | H |
| 2770. | —(CH₂SO₂)-4-pyridyl | 2-(1-piperidinyl)ethylamino | H |
| 2771. | —(CH₂SO₂)-4-pyridyl | 2-(1-pyrrolidinyl)ethylamino | H |
| 2772. | —(CH₂SO₂)-4-pyridyl | 2-(4-morpholinyl)ethylamino | H |
| 2773. | —(CH₂SO₂)-4-pyridyl | 3-(1-piperidinyl)propylamino | H |
| 2774. | —(CH₂SO₂)-4-pyridyl | 3-(1-pyrrolidinyl)propylamino | H |
| 2775. | —(CH₂SO₂)-4-pyridyl | 3-(4-morpholinyl)propylamino | H |
| 2776. | —(CH₂SO₂)-4-pyridyl | N-methyl-N-(2-piperid-1-ylethyl)amino | H |
| 2777. | —(CH₂SO₂)-4-pyridyl | N-methyl-N-(2-pyrrolidin-1-ylethyl)amino | H |
| 2778. | —(CH₂SO₂)-4-pyridyl | N-methyl-N-(2-morpholin-4-ylethyl)amino | H |
| 2779. | —(CH₂SO₂)-4-pyridyl | ((2S)-2-amino-3-phenylpropyl)amino | H |
| 2780. | —(CH₂SO₂) 4-pyridyl | 4-methylpiperazinylamino | H |
| 2781. | —(CH₂SO₂)-4-pyridyl | 4-methylpiperazinyl | H |
| 2782. | —(CH₂SO₂)-4-pyridyl | 3-aminopyrrolidinyl | H |
| 2783. | —(CH₂SO₂)-4-pyridyl | (diethylamino)ethylamino | H |
| 2784. | —(CH₂SO₂)-4-pyridyl | 3,5-dimethylpiperazin-1-yl | H |
| 2785. | —(CH₂SO₂)-4-pyridyl | (4-piperidylmethyl)amino | H |
| 2786. | —(CH₂SO₂)-4-pyridyl | (2-methylbutyl)amino | H |
| 2787. | —(CH₂SO₂)-4-pyridyl | 2-(dimethylamino)ethoxy | H |
| 2788. | —(CH₂SO₂)-4-pyridyl | 2-(methylamino)ethoxy | H |
| 2789. | —(CH₂SO₂)-4-pyridyl | ((2R)pyrrolidin-2-yl)methoxy | H |
| 2790. | —(CH₂SO₂)-4-pyridyl | ((2R)-1-methylpyrrolidin-2-yl)methoxy | H |
| 2791. | —(CH₂SO₂)-4-pyridyl | 2-(piperid-1-yl)ethoxy | H |
| 2792. | —(CH₂SO₂)-4-pyridyl | 2-(piperazin-1-yl)ethoxy | H |
| 2793. | —(CH₂SO₂)-4-pyridyl | 2-(morpholin-4-yl)ethoxy | H |
| 2794. | —(CH₂SO₂)-4-pyridyl | Cl | NH₂ |

TABLE 5-continued

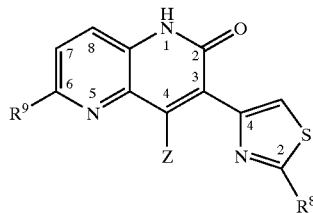

| # | R⁸ | R⁹ | Z |
|---|---|---|---|
| 2795. | —(CH₂SO₂)-4-pyridyl | cyclopropylmethylamino | NH₂ |
| 2796. | —(CH₂SO₂)-4-pyridyl | 3-hydroxypropylamino | NH₂ |
| 2797. | —(CH₂SO₂)-4-pyridyl | 2-(1-piperidinyl)ethylamino | NH₂ |
| 2798. | —(CH₂SO₂)-4-pyridyl | 2-(1-pyrrolidinyl)ethylamino | NH₂ |
| 2799. | —(CH₂SO₂)-4-pyridyl | 2-(4-morpholinyl)ethylamino | NH₂ |
| 2800. | —(CH₂SO₂)-4-pyridyl | 3-(1-piperidinyl)propylamino | NH₂ |
| 2801. | —(CH₂SO₂)-4-pyridyl | 3-(1-pyrrolidinyl)propylamino | NH₂ |
| 2802. | —(CH₂SO₂)-4-pyridyl | 3-(4-morpholinyl)propylamino | NH₂ |
| 2803. | —(CH₂SO₂)-4-pyridyl | N-methyl-N-(2-piperid-1-ylethyl)amino | NH₂ |
| 2804. | —(CH₂SO₂)-4-pyridyl | N-methyl-N-(2-pyrrolidin-1-ylethyl)amino | NH₂ |
| 2805. | —(CH₂SO₂)-4-pyridyl | N-methyl-N-(2-morpholin-4-ylethyl)amino | NH₂ |
| 2806. | —(CH₂SO₂)-4-pyridyl | ((2S)-2-amino-3-phenylpropyl)amino | NH₂ |
| 2807. | —(CH₂SO₂)-4-pyridyl | 4-methylpiperazinylamino | NH₂ |
| 2808. | —(CH₂SO₂)-4-pyridyl | 4-methylpiperazinyl | NH₂ |
| 2809. | —(CH₂SO₂)-4-pyridyl | 3-aminopyrrolidinyl | NH₂ |
| 2810. | —(CH₂SO₂)-4-pyridyl | (diethylamino)ethylamino | NH₂ |
| 2811. | —(CH₂SO₂)-4-pyridyl | 3,5-dimethylpiperazin-1-yl | NH₂ |
| 2812. | —(CH₂SO₂)-4-pyridyl | (4-piperidylmethyl)amino | NH₂ |
| 2813. | —(CH₂SO₂)-4-pyridyl | (2-methylbutyl)amino | NH₂ |
| 2814. | —(CH₂SO₂)-4-pyridyl | 2-(dimethylamino)ethoxy | NH₂ |
| 2815. | —(CH₂SO₂)-4-pyridyl | 2-(methylamino)ethoxy | NH₂ |
| 2816. | —(CH₂SO₂)-4-pyridyl | ((2R)pyrrolidin-2-yl)methoxy | NH₂ |
| 2817. | —(CH₂SO₂)-4-pyridyl | ((2R)-1-methylpyrrolidin-2-yl)methoxy | NH₂ |
| 2818. | —(CH₂SO₂)-4-pyridyl | 2-(piperid-1-yl)ethoxy | NH₂ |
| 2819. | —(CH₂SO₂)-4-pyridyl | 2-(piperazin-1-yl)ethoxy | NH₂ |
| 2820. | —(CH₂SO₂)-4-pyridyl | 2-(morpholin-4-yl)ethoxy | NH₂ |
| 2821. | —(NMeSO₂)-phenyl | Cl | H |
| 2822. | —(NMeSO₂)-phenyl | cyclopropylmethylamino | H |
| 2823. | —(NMeSO₂)-phenyl | 3-hydroxypropylamino | H |
| 2824. | —(NMeSO₂)-phenyl | 2-(1-piperidinyl)ethylamino | H |
| 2825. | —(NMeSO₂)-phenyl | 2-(1-pyrrolidinyl)ethylamino | H |
| 2826. | —(NMeSO₂)-phenyl | 2-(4-morpholinyl)ethylamino | H |
| 2827. | —(NMeSO₂)-phenyl | 3-(1-piperidinyl)propylamino | H |
| 2828. | —(NMeSO₂)-phenyl | 3-(1-pyrrolidinyl)propylamino | H |
| 2829. | —(NMeSO₂)-phenyl | 3-(4-morpholinyl)propylamino | H |
| 2830. | —(NMeSO₂)-phenyl | N-methyl-N-(2-piperid-1-ylethyl)amino | H |
| 2831. | —(NMeSO₂)-phenyl | N-methyl-N-(2-pyrrolidin-1-ylethyl)amino | H |
| 2832. | —(NMeSO₂) phenyl | N-methyl-N-(2-morpholin-4-ylethyl)amino | H |
| 2833. | —(NMeSO₂)-phenyl | ((2S)-2-amino-3-phenylpropyl)amino | H |
| 2834. | —(NMeSO₂)-phenyl | 4-methylpiperazinylamino | H |
| 2835. | —(NMeSO₂)-phenyl | 4-methylpiperazinyl | H |
| 2836. | —(NMeSO₂)-phenyl | 3-aminopyrrolidinyl | H |
| 2837. | —(NMeSO₂)-phenyl | (diethylamino)ethylamino | H |
| 2838. | —(NMeSO₂)-phenyl | 3,5-dimethylpiperazin-1-yl | H |
| 2839. | —(NMeSO₂)-phenyl | (4-piperidylmethyl)amino | H |
| 2840. | —(NMeSO₂)-phenyl | (2-methylbutyl)amino | H |
| 2841. | —(NMeSO₂)-phenyl | 2-(dimethylamino)ethoxy | H |
| 2842. | —(NMeSO₂)-phenyl | 2-(methylamino)ethoxy | H |
| 2643. | —(NMeSO₂)-phenyl | ((2R)pyrrolidin-2-yl)methoxy | H |
| 2844. | —(NMeSO₂)-phenyl | ((2R)-1-methylpyrrolidin-2-yl)methoxy | H |
| 2845. | —(NMeSO₂)-phenyl | 2-(piperid-1-yl)ethoxy | H |
| 2846. | —(NMeSO₂)-phenyl | 2-(piperazin-1-yl)ethoxy | H |
| 2847. | —(NMeSO₂)-phenyl | 2-(morpholin-4-yl)ethoxy | H |
| 2848. | —(NMeSO₂)-phenyl | Cl | NH₂ |
| 2849. | —(NMeSO₂)-phenyl | cyclopropylmethylamino | NH₂ |
| 2850. | —(NMeSO₂)-phenyl | 3-hydroxypropylamino | NH₂ |
| 2851. | —(NMeSO₂)-phenyl | 2-(1-piperidinyl)ethylamino | NH₂ |
| 2852. | —(NMeSO₂)-phenyl | 2-(1-pyrrolidinyl)ethylamino | NH₂ |
| 2853. | —(NMeSO₂)-phenyl | 2-(4-morpholinyl)ethylamino | NH₂ |
| 2854. | —(NMeSO₂)-phenyl | 3-(1-piperidinyl)propylamino | NH₂ |
| 2855. | —(NMeSO₂)-phenyl | 3-(1-pyrrolidinyl)propylamino | NH₂ |
| 2856. | —(NMeSO₂)-phenyl | 3-(4-morpholinyl)propylamino | NH₂ |
| 2857. | —(NMeSO₂)-phenyl | N-methyl-N-(2-piperid-1-ylethyl)amino | NH₂ |
| 2858. | —(NMeSO₂)-phenyl | N-methyl-N-(2-pyrrolidin-1-ylethyl)amino | NH₂ |
| 2859. | —(NMeSO₂)-phenyl | N-methyl-N-(2-morpholin-4-ylethyl)amino | NH₂ |

TABLE 5-continued

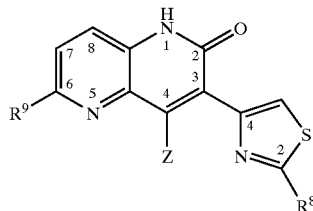

| # | R⁸ | R⁹ | Z |
|---|---|---|---|
| 2860. | —(NMeSO₂)-phenyl | ((2S)-2-amino-3-phenylpropyl)amino | NH₂ |
| 2861. | —(NMeSO₂)-phenyl | 4-methylpiperazinylamino | NH₂ |
| 2862. | —(NMeSO₂)-phenyl | 4-methylpiperazinyl | NH₂ |
| 2863. | —(NMeSO₂)-phenyl | 3-aminopyrrolidinyl | NH₂ |
| 2864. | —(NMeSO₂)-phenyl | (diethylamino)ethylamino | NH₂ |
| 2865. | —(NMeSO₂)-phenyl | 3,5-dimethylpiperazin-1-yl | NH₂ |
| 2866. | —(NMeSO₂)-phenyl | (4-piperidylmethyl)amino | NH₂ |
| 2867. | —(NMeSO₂)-phenyl | (2-methylbutyl)amino | NH₂ |
| 2868. | —(NMeSO₂)-phenyl | 2-(dimethylamino)ethoxy | NH₂ |
| 2869. | —(NMeSO₂)-phenyl | 2-(methylamino)ethoxy | NH₂ |
| 2870. | —(NMeSO₂)-phenyl | ((2R)pyrrolidin-2-yl)methoxy | NH₂ |
| 2871. | —(NMeSO₂)-phenyl | ((2R)-1-methylpyrrolidin-2-yl)methoxy | NH₂ |
| 2872. | —(NMeSO₂)-phenyl | 2-(piperid-1-yl)ethoxy | NH₂ |
| 2873. | —(NMeSO₂)-phenyl | 2-(piperazin-1-yl)ethoxy | NH₂ |
| 2874. | —(NMeSO₂)-phenyl | 2-(morpholin-4-yl)ethoxy | NH₂ |
| 2875. | —(NMeSO₂)-2-thienyl | Cl | H |
| 2876. | —(NMeSO₂)-2-thienyl | cyclopropylmethylamino | H |
| 2877. | —(NMeSO₂)-2-thienyl | 3-hydroxypropylamino | H |
| 2878. | —(NMeSO₂)-2-thienyl | 2-(1-piperidinyl)ethylamino | H |
| 2879. | —(NMeSO₂)-2-thienyl | 2-(1-pyrrolidinyl)ethylamino | H |
| 2880. | —(NMeSO₂)-2-thienyl | 2-(4-morpholinyl)ethylamino | H |
| 2881. | —(NMeSO₂)-2-thienyl | 3-(1-piperidinyl)propylamino | H |
| 2882. | —(NMeSO₂)-2-thienyl | 3-(1-pyrrolidinyl)propylamino | H |
| 2883. | —(NMeSO₂)-2-thienyl | 3-(4-morpholinyl)propylamino | H |
| 2884. | —(NMeSO₂)-2-thienyl | N-methyl-N-(2-piperid-1-ylethyl)amino | H |
| 2885. | —(NMeSO₂)-2-thienyl | N-methyl-N-(2-pyrrolidin-1-ylethyl)amino | H |
| 2886. | —(NMeSO₂)-2-thienyl | N-methyl-N-(2-morpholin-4-ylethyl)amino | H |
| 2887. | —(NMeSO₂)-2-thienyl | ((2S)-2-amino-3-phenylpropyl)amino | H |
| 2888. | —(NMeSO₂)-2-thienyl | 4-methylpiperazinylamino | H |
| 2889. | —(NMeSO₂)-2-thienyl | 4-methylpiperazinyl | H |
| 2890. | —(NMeSO₂)-2-thienyl | 3-aminopyrrolidinyl | H |
| 2891. | —(NMeSO₂)-2-thienyl | (diethylamino)ethylamino | H |
| 2892. | —(NMeSO₂)-2-thienyl | 3,5-dimethylpiperazin-1-yl | H |
| 2893. | —(NMeSO₂)-2-thienyl | (4-piperidylmethyl)amino | H |
| 2894. | —(NMeSO₂)-2-thienyl | (2-methylbutyl)amino | H |
| 2895. | —(NMeSO₂)-2-thienyl | 2-(dimethylamino)ethoxy | H |
| 2896. | —(NMeSO₂)-2-thienyl | 2-(methylamino)ethoxy | H |
| 2897. | —(NMeSO₂)-2-thienyl | ((2R)pyrrolidin-2-yl)methoxy | H |
| 2898. | —(NMeSO₂)-2-thienyl | ((2R)-1-methylpyrrolidin-2-yl)methoxy | H |
| 2899. | —(NMeSO₂)-2-thienyl | 2-(piperid-1-yl)ethoxy | H |
| 2900. | —(NMeSO₂)-2-thienyl | 2-(piperazin-1-yl)ethoxy | H |
| 2901. | —(NMeSO₂)-2-thienyl | 2-(morpholin-4-yl)ethoxy | H |
| 2902. | —(NMeSO₂)-2-thienyl | Cl | NH₂ |
| 2903. | —(NMeSO₂)-2-thienyl | cyclopropylmethylamino | NH₂ |
| 2904. | —(NMeSO₂)-2-thienyl | 3-hydroxypropylamino | NH₂ |
| 2905. | —(NMeSO₂)-2-thienyl | 2-(1-piperidinyl)ethylamino | NH₂ |
| 2906. | —(NMeSO₂)-2-thienyl | 2-(1-pyrrolidinyl)ethylamino | NH₂ |
| 2907. | —(NMeSO₂)-2-thienyl | 2-(4-morpholinyl)ethylamino | NH₂ |
| 2908. | —(NMeSO₂)-2-thienyl | 3-(1-piperidinyl)propylamino | NH₂ |
| 2909. | —(NMeSO₂)-2-thienyl | 3-(1-pyrrolidinyl)propylamino | NH₂ |
| 2910. | —(NMeSO₂)-2-thienyl | 3-(4-morpholinyl)propylamino | NH₂ |
| 2911. | —(NMeSO₂)-2-thienyl | N-methyl-N-(2-piperid-1-ylethyl)amino | NH₂ |
| 2912. | —(NMeSO₂)-2-thienyl | N-methyl-N-(2-pyrrolidin-1-ylethyl)amino | NH₂ |
| 2913. | —(NMeSO₂)-2-thienyl | N-methyl-N-(2-morpholin-4-ylethyl)amino | NH₂ |
| 2914. | —(NMeSO₂)-2-thienyl | ((2S)-2-amino-3-phenylpropyl)amino | NH₂ |
| 2915. | —(NMeSO₂)-2-thienyl | 4-methylpiperazinylamino | NH₂ |
| 2916. | —(NMeSO₂)-2-thienyl | 4-methylpiperazinyl | NH₂ |
| 2917. | —(NMeSO₂)-2-thienyl | 3-aminopyrrolidinyl | NH₂ |
| 2918. | —(NMeSO₂)-2-thienyl | (diethylamino)ethylamino | NH₂ |
| 2919. | —(NMeSO₂)-2-thienyl | 3,5-dimethylpiperazin-1-yl | NH₂ |
| 2920. | —(NMeSO₂)-2-thienyl | (4-piperidylmethyl)amino | NH₂ |
| 2921. | —(NMeSO₂)-2-thienyl | (2-methylbutyl)amino | NH₂ |
| 2922. | —(NMeSO₂)-2-thienyl | 2-(dimethylamino)ethoxy | NH₂ |
| 2923. | —(NMeSO₂)-2-thienyl | 2-(methylamino)ethoxy | NH₂ |
| 2924. | —(NMeSO₂)-2-thienyl | ((2R)pyrrolidin-2-yl)methoxy | NH₂ |

TABLE 5-continued

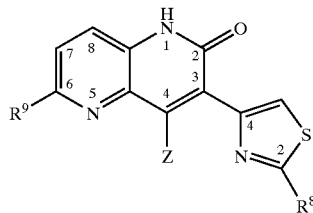

| # | R⁸ | R⁹ | Z |
|---|---|---|---|
| 2925. | —(NMeSO₂)-2-thienyl | ((2R)-1-methylpyrrolidin-2-yl)methoxy | NH₂ |
| 2926. | —(NMeSO₂)-2-thienyl | 2-(piperid-1-yl)ethoxy | NH₂ |
| 2927. | —(NMeSO₂)-2-thienyl | 2-(piperazin-1-yl)ethoxy | NH₂ |
| 2928. | —(NMeSO₂)-2-thienyl | 2-(morpholin-4-yl)ethoxy | NH₂ |
| 2929. | —(NMeSO₂)-2-pyridyl | Cl | H |
| 2930. | —(NMeSO₂)-2-pyridyl | cyclopropylmethylamino | H |
| 2931. | —(NMeSO₂)-2-pyridyl | 3-hydroxypropylamino | H |
| 2932. | —(NMeSO₂)-2-pyridyl | 2-(1-piperidinyl)ethylamino | H |
| 2933. | —(NMeSO₂)-2-pyridyl | 2-(1-pyrrolidinyl)ethylamino | H |
| 2934. | —(NMeSO₂)-2-pyridyl | 2-(4-morpholinyl)ethylamino | H |
| 2935. | —(NMeSO₂)-2-pyridyl | 3-(1-piperidinyl)propylamino | H |
| 2936. | —(NMeSO₂)-2-pyridyl | 3-(1-pyrrolidinyl)propylamino | H |
| 2937. | —(NMeSO₂)-2-pyridyl | 3-(4-morpholinyl)propylamino | H |
| 2938. | —(NMeSO₂)-2-pyridyl | N-methyl-N-(2-piperid-1-ylethyl)amino | H |
| 2939. | —(NMeSO₂)-2-pyridyl | N-methyl-N-(2-pyrrolidin-1-ylethyl)amino | H |
| 2940. | —(NMeSO₂)-2-pyridyl | N-methyl-N-(2-morpholin-4-ylethyl)amino | H |
| 2941. | —(NMeSO₂)-2-pyridyl | ((2S)-2-amino-3-phenylpropyl)amino | H |
| 2942. | —(NMeSO₂)-2-pyridyl | 4-methylpiperazinylamino | H |
| 2943. | —(NMeSO₂)-2-pyridyl | 4-methylpiperazinyl | H |
| 2944. | —(NMeSO₂)-2-pyridyl | 3-aminopyrrolidinyl | H |
| 2945. | —(NMeSO₂)-2-pyridyl | (diethylamino)ethylamino | H |
| 2946. | —(NMeSO₂)-2-pyridyl | 3,5-dimethylpiperazin-1-yl | H |
| 2947. | —(NMeSO₂)-2-pyridyl | (4-piperidylmethyl)amino | H |
| 2948. | —(NMeSO₂)-2-pyridyl | (2-methylbutyl)amino | H |
| 2949. | —(NMeSO₂)-2-pyridyl | 2-(dimethylamino)ethoxy | H |
| 2950. | —(NMeSO₂)-2-pyridyl | 2-(methylamino)ethoxy | H |
| 2951. | —(NMeSO₂)-2-pyridyl | ((2R)pyrrolidin-2-yl)methoxy | H |
| 2952. | —(NMeSO₂)-2-pyridyl | ((2R)-1-methylpyrrolidin-2-yl)methoxy | H |
| 2953. | —(NMeSO₂)-2-pyridyl | 2-(piperid-1-yl)ethoxy | H |
| 2954. | —(NMeSO₂)-2-pyridyl | 2-(piperazin-1-yl)ethoxy | H |
| 2955. | —(NMeSO₂)-2-pyridyl | 2-(morpholin-4-yl)ethoxy | H |
| 2956. | —(NMeSO₂)-2-pyridyl | Cl | NH₂ |
| 2957. | —(NMeSO₂)-2-pyridyl | cyclopropylmethylamino | NH₂ |
| 2958. | —(NMeSO₂)-2-pyridyl | 3-hydroxypropylamino | NH₂ |
| 2959. | —(NMeSO₂)-2-pyridyl | 2-(1-piperidinyl)ethylamino | NH₂ |
| 2960. | —(NMeSO₂)-2-pyridyl | 2-(1-pyrrolidinyl)ethylamino | NH₂ |
| 2961. | —(NMeSO₂)-2-pyridyl | 2-(4-morpholinyl)ethylamino | NH₂ |
| 2962. | —(NMeSO₂)-2-pyridyl | 3-(1-piperidinyl)propylamino | NH₂ |
| 2963. | —(NMeSO₂)-2-pyridyl | 3-(1-pyrrolidinyl)propylamino | NH₂ |
| 2964. | —(NMeSO₂)-2-pyridyl | 3-(4-morpholinyl)propylamino | NH₂ |
| 2965. | —(NMeSO₂)-2-pyridyl | N-methyl-N-(2-piperid-1-ylethyl)amino | NH₂ |
| 2966. | —(NMeSO₂)-2-pyridyl | N-methyl-N-(2-pyrrolidin-1-ylethyl)amino | NH₂ |
| 2967. | —(NMeSO₂)-2-pyridyl | N-methyl-N-(2-morpholin-4-ylethyl)amino | NH₂ |
| 2968. | —(NMeSO₂)-2-pyridyl | ((2S)-2-amino-3-phenylpropyl)amino | NH₂ |
| 2969. | —(NMeSO₂)-2-pyridyl | 4-methylpiperazinylamino | NH₂ |
| 2970. | —(NMeSO₂)-2-pyridyl | 4-methylpiperazinyl | NH₂ |
| 2971. | —(NMeSO₂)-2-pyridyl | 3-aminopyrrolidinyl | NH₂ |
| 2972. | —(NMeSO₂)-2-pyridyl | (diethylamino)ethylamino | NH₂ |
| 2973. | —(NMeSO₂)-2-pyridyl | 3,5-dimethylpiperazin-1-yl | NH₂ |
| 2974. | —(NMeSO₂)-2-pyridyl | (4-piperidylmethyl)amino | NH₂ |
| 2975. | —(NMeSO₂)-2-pyridyl | (2-methylbutyl)amino | NH₂ |
| 2976. | —(NMeSO₂)-2-pyridyl | 2-(dimethylamino)ethoxy | NH₂ |
| 2977. | —(NMeSO₂)-2-pyridyl | 2-(methylamino)ethoxy | NH₂ |
| 2978. | —(NMeSO₂)-2-pyridyl | ((2R)pyrrolidin-2-yl)methoxy | NH₂ |
| 2979. | —(NMeSO₂)-2-pyridyl | ((2R)-1-methylpyrrolidin-2-yl)methoxy | NH₂ |
| 2980. | —(NMeSO₂)-2-pyridyl | 2-(piperid-1-yl)ethoxy | NH₂ |
| 2981. | —(NMeSO₂)-2-pyridyl | 2-(piperazin-1-yl)ethoxy | NH₂ |
| 2982. | —(NMeSO₂)-2-pyridyl | 2-(morpholin-4-yl)ethoxy | NH₂ |
| 2983. | —(NMeSO₂)-3-pyridyl | Cl | H |
| 2984. | —(NMeSO₂)-3-pyridyl | cyclopropylmethylamino | H |
| 2985. | —(NMeSO₂)-3-pyridyl | 3-hydroxypropylamino | H |
| 2986. | —(NMeSO₂)-3-pyridyl | 2-(1-piperidinyl)ethylamino | H |
| 2987. | —(NMeSO₂)-3-pyridyl | 2-(1-pyrrolidinyl)ethylamino | H |
| 2988. | —(NMeSO₂)-3-pyridyl | 2-(4-morpholinyl)ethylamino | H |
| 2989. | —(NMeSO₂)-3-pyridyl | 3-(1-piperidinyl)propylamino | H |

TABLE 5-continued

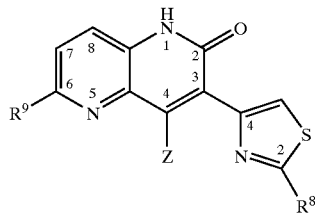

| # | R⁸ | R⁹ | Z |
|---|---|---|---|
| 2990. | —(NMeSO₂)-3-pyridyl | 3-(1-pyrrolidinyl)propylamino | H |
| 2991. | —(NMeSO₂)-3-pyridyl | 3-(4-morpholinyl)propylamino | H |
| 2992. | —(NMeSO₂)-3-pyridyl | N-methyl-N-(2-piperid-1-ylethyl)amino | H |
| 2993. | —(NMeSO₂)-3-pyridyl | N-methyl-N-(2-pyrrolidin-1-ylethyl)amino | H |
| 2994. | —(NMeSO₂)-3-pyridyl | N-methyl-N-(2-morpholin-4-ylethyl)amino | H |
| 2995. | —(NMeSO₂)-3-pyridyl | ((2S)-2-amino-3-phenylpropyl)amino | H |
| 2996. | —(NMeSO₂)-3-pyridyl | 4-methylpiperazinylamino | H |
| 2997. | —(NMeSO₂)-3-pyridyl | 4-methylpiperazinyl | H |
| 2998. | —(NMeSO₂) 3-pyridyl | 3-aminopyrrolidinyl | H |
| 2999. | —(NMeSO₂)-3-pyridyl | (diethylamino)ethylamino | H |
| 3000. | —(NMeSO₂)-3-pyridyl | 3,5-dimethylpiperazin-1-yl | H |
| 3001. | —(NMeSO₂)-3-pyridyl | (4-piperidylmethyl)amino | H |
| 3002. | —(NMeSO₂)-3-pyridyl | (2-methylbutyl)amino | H |
| 3003. | —(NMeSO₂)-3-pyridyl | 2-(dimethylamino)ethoxy | H |
| 3004. | —(NMeSO₂)-3-pyridyl | 2-(methylamino)ethoxy | H |
| 3005. | —(NMeSO₂)-3-pyridyl | ((2R)pyrrolidin-2-yl)methoxy | H |
| 3006. | —(NMeSO₂)-3-pyridyl | ((2R)-1-methylpyrrolidin-2-yl)methoxy | H |
| 3007. | —(NMeSO₂)-3-pyridyl | 2-(piperid-1-yl)ethoxy | H |
| 3008. | —(NMeSO₂)-3-pyridyl | 2-(piperazin-1-yl)ethoxy | H |
| 3009. | —(NMeSO₂)-3-pyridyl | 2-(morpholin-4-yl)ethoxy | H |
| 3010. | —(NMeSO₂)-3-pyridyl | Cl | NH₂ |
| 3011. | —(NMeSO₂)-3-pyridyl | cyclopropylmethylamino | NH₂ |
| 3012. | —(NMeSO₂)-3-pyridyl | 3-hydroxypropylamino | NH₂ |
| 3013. | —(NMeSO₂)-3-pyridyl | 2-(1-piperidinyl)ethylamino | NH₂ |
| 3014. | —(NMeSO₂)-3-pyridyl | 2-(1-pyrrolidinyl)ethylamino | NH₂ |
| 3015. | —(NMeSO₂)-3-pyridyl | 2-(4-morpholinyl)ethylamino | NH₂ |
| 3016. | —(NMeSO₂)-3-pyridyl | 3-(1-piperidinyl)propylamino | NH₂ |
| 3017. | —(NMeSO₂) 3-pyridyl | 3-(1-pyrrolidinyl)propylamino | NH₂ |
| 3018. | —(NMeSO₂)-3-pyridyl | 3-(4-morpholinyl)propylamino | NH₂ |
| 3019. | —(NMeSO₂)-3-pyridyl | N-methyl-N-(2-piperid-1-ylethyl)amino | NH₂ |
| 3020. | —(NMeSO₂)-3-pyridyl | N-methyl-N-(2-pyrrolidin-1-ylethyl)amino | NH₂ |
| 3021. | —(NMeSO₂)-3-pyridyl | N-methyl-N-(2-morpholin-4-ylethyl)amino | NH₂ |
| 3022. | —(NMeSO₂)-3-pyridyl | ((2S)-2-amino-3-phenylpropyl)amino | NH₂ |
| 3023. | —(NMeSo₂)-3-pyridyl | 4-methylpiperazinylamino | NH₂ |
| 3024. | —(NMeSO₂)-3-pyridyl | 4-methylpiperazinyl | NH₂ |
| 3025. | —(NMeSO₂)-3-pyridyl | 3-aminopyrrolidinyl | NH₂ |
| 3026. | —(NMeSO₂) 3-pyridyl | (diethylamino)ethylamino | NH₂ |
| 3027. | —(NMeSO₂)-3-pyridyl | 3,5-dimethylpiperazin-1-yl | NH₂ |
| 3028. | —(NMeSO₂)-3-pyridyl | (4-piperidylmethyl)amino | NH₂ |
| 3029. | —(NMeSO₂)-3-pyridyl | (2-methylbutyl)amino | NH₂ |
| 3030. | —(NMeSO₂)-3-pyridyl | 2-(dimethylamino)ethoxy | NH₂ |
| 3031. | —(HMeSO₂)-3-pyridyl | 2-(methylamino)ethoxy | NH₂ |
| 3032. | —(NMeSO₂)-3-pyridyl | ((2R)pyrrolidin-2-yl)methoxy | NH₂ |
| 3033. | —(NMeSO₂)-3-pyridyl | ((2R)-1-methylpyrrolidin-2-yl)methoxy | NH₂ |
| 3034. | —(NMeSO₂)-3-pyridyl | 2-(piperid-1-yl)ethoxy | NH₂ |
| 3035. | —(NMeSO₂)-3-pyridyl | 2-(piperazin-1-yl)ethoxy | NH₂ |
| 3036. | —(NMeSO₂)-3-pyridyl | 2-(morpholin-4-yl)ethoxy | NH₂ |
| 3037. | —(NMeSO₂)-4-pyridyl | Cl | H |
| 3038. | —(MMeSO₂) 4-pyridyl | cyclopropylmethylamino | H |
| 3039. | —(NMeSO₂)-4-pyridyl | 3-hydroxypropylamino | H |
| 3040. | —(NMeSO₂)-4-pyridyl | 2-(1-piperidinyl)ethylamino | H |
| 3041. | —(NMeSO₂)-4-pyridyl | 2-(1-pyrrolidinyl)ethylamino | H |
| 3042. | —(NMeSO₂)-4-pyridyl | 2-(4-morpholinyl)ethylamino | H |
| 3043. | —(NMeSO₂)-4-pyridyl | 3-(1-piperidinyl)propylamino | H |
| 3044. | —(NMeSO₂)-4-pyridyl | 3-(1-pyrrolidinyl)propylamino | H |
| 3045. | —(NMeSO₂)-4-pyridyl | 3-(4-morpholinyl)propylamino | H |
| 3046. | —(NMeSO₂)-4-pyridyl | N-methyl-N-(2-piperid-1-ylethyl)amino | H |
| 3047. | —(NMeSO₂)-4-pyridyl | N-methyl-N-(2-pyrrolidin-1-ylethyl)amino | H |
| 3048. | —(NMeSO₂)-4-pyridyl | N-methyl-N-(2-morpholin-4-ylethyl)amino | H |
| 3049. | —(NMeSO₂)-4-pyridyl | ((2S)-2-amino-3-phenylpropyl)amino | H |
| 3050. | —(NMeSO₂)-4-pyridyl | 4-methylpiperazinylamino | H |
| 3051. | —(NMeSO₂)-4-pyridyl | 4-methylpiperazinyl | H |
| 3052. | —(NMeSO₂)-4-pyridyl | 3-aminopyrrolidinyl | H |
| 3053. | —(NMeSO₂)-4-pyridyl | (diethylamino)ethylamino | H |
| 3054. | —(NMeSO₂)-4-pyridyl | 3,5-dimethylpiperazin-1-yl | H |

TABLE 5-continued

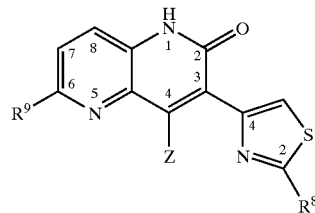

| # | R⁸ | R⁹ | Z |
|---|---|---|---|
| 3055. | —(NMeSO₂)-4-pyridyl | (4-piperidylmethyl)amino | H |
| 3056. | —(NMeSO₂)-4-pyridyl | (2-methylbutyl)amino | H |
| 3057. | —(NMeSO₂)-4-pyridyl | 2-(dimethylamino)ethoxy | H |
| 3058. | —(NMeSO₂)-4-pyridyl | 2-(methylamino)ethoxy | H |
| 3059. | —(NMeSO₂)-4-pyridyl | ((2R)pyrrolidin-2-yl)methoxy | H |
| 3060. | —(NMeSO₂)-4-pyridyl | ((2R)-1-methylpyrrolidin-2-yl)methoxy | H |
| 3061. | —(NMeSO₂)-4-pyridyl | 2-(piperid-1-yl)ethoxy | H |
| 3062. | —(NMeSO₂)-4-pyridyl | 2-(piperazin-1-yl)ethoxy | H |
| 3063. | —(NMeSO₂)-4-pyridyl | 2-(morpholin-4-yl)ethoxy | H |
| 3064. | —(NMeSO₂)-4-pyridyl | Cl | NH₂ |
| 3065. | —(NMeSO₂)-4-pyridyl | cyclopropylmethylamino | NH₂ |
| 3066. | —(NMeSO₂)-4-pyridyl | 3-hydroxypropylamino | NH₂ |
| 3067. | —(NMeSO₂)-4-pyridyl | 2-(1-piperidinyl)ethylamino | NH₂ |
| 3068. | —(NMeSO₂)-4-pyridyl | 2-(1-pyrrolidinyl)ethylamino | NH₂ |
| 3069. | —(NMeSO₂)-4-pyridyl | 2-(4-morpholinyl)ethylamino | NH₂ |
| 3070. | —(NMeSO₂)-4-pyridyl | 3-(1-piperidinyl)propylamino | NH₂ |
| 3071. | —(NMeSO₂)-4-pyridyl | 3-(1-pyrrolidinyl)propylamino | NH₂ |
| 3072. | —(NMeSO₂)-4-pyridyl | 3-(4-morpholinyl)propylamino | NH₂ |
| 3073. | —(NMeSO₂)-4-pyridyl | N-methyl-N-(2-piperid-1-ylethyl)amino | NH₂ |
| 3074. | —(NMeSO₂)-4-pyridyl | N-methyl-N-(2-pyrrolidin-1-ylethyl)amino | NH₂ |
| 3075. | —(NMeSO₂)-4-pyridyl | N-methyl-N-(2-morpholin-4-ylethyl)amino | NH₂ |
| 3076. | —(NMeSO₂)-4-pyridyl | ((2S)-2-amino-3-phenylpropyl)amino | NH₂ |
| 3077. | —(NMeSO₂)-4-pyridyl | 4-methylpiperazinylamino | NH₂ |
| 3078. | —(NMeSO₂)-4-pyridyl | 4-methylpiperazinyl | NH₂ |
| 3079. | —(NMeSO₂)-4-pyridyl | 3-aminopyrrolidinyl | NH₂ |
| 3080. | —(NMeSO₂)-4-pyridyl | (diethylamino)ethylamino | NH₂ |
| 3081. | —(NMeSO₂)-4-pyridyl | 3,5-dimethylpiperazin-1-yl | NH₂ |
| 3082. | —(NMeSO₂)-4-pyridyl | (4-piperidylmethyl)amino | NH₂ |
| 3083. | —(NMeSO₂)-4-pyridyl | (2-methylbutyl)amino | NH₂ |
| 3084. | —(NMeSO₂)-4-pyridyl | 2-(dimethylamino)ethoxy | NH₂ |
| 3085. | —(NMeSO₂)-4-pyridyl | 2-(methylamino)ethoxy | NH₂ |
| 3086. | —(NMeSO₂)-4-pyridyl | ((2R)pyrrolidin-2-yl)methoxy | NH₂ |
| 3087. | —(NMeSO₂)-4-pyridyl | ((2R)-1-methylpyrrolidin-2-yl)methoxy | NH₂ |
| 3088. | —(NMeSO₂)-4-pyridyl | 2-(piperid-1-yl)ethoxy | NH₂ |
| 3089. | —(NMeSO₂)-4-pyridyl | 2-(piperazin-1-yl)ethoxy | NH₂ |
| 3090. | —(NMeSO₂)-4-pyridyl | 2-(morpholin-4-yl)ethoxy | NH₂ |

TABLE 6

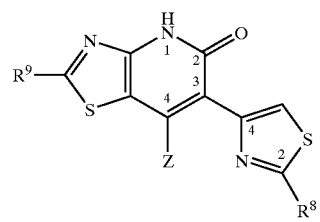

| # | R⁸ | R⁹ | Z |
|---|---|---|---|
| 3091. | 4-pyridyl | 2-methylthio | H |
| 3092. | 4-pyridyl | 2-(methylsulfonyl) | H |
| 3093. | 4-pyridyl | cyclopropylmethylamino | H |
| 3094. | 4-pyridyl | 3-hydroxypropylamino | H |
| 3095. | 4-pyridyl | 2-(1-piperidinyl)ethylamino | H |
| 3096. | 4-pyridyl | 2-(1-pyrrolidinyl)ethylamino | H |
| 3097. | 4-pyridyl | 2-(4-morpholinyl)ethylamino | H |
| 3098. | 4-pyridyl | 3-(1-piperidinyl)propylamino | H |
| 3099. | 4-pyridyl | 3-(1-pyrrolidinyl)propylamino | H |
| 3100. | 4-pyridyl | 3-(4-morpholinyl)propylamino | H |
| 3101. | 4-pyridyl | N-methyl-N-(2-piperid-1-ylethyl)amino | H |

TABLE 6-continued

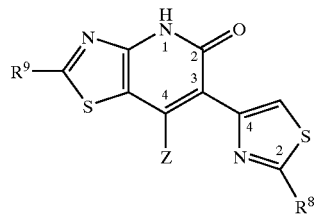

| # | R⁸ | R⁹ | Z |
|---|---|---|---|
| 3102. | 4-pyridyl | N-methyl-N-(2-pyrrolidin-1-ylethyl)amino | H |
| 3103. | 4-pyridyl | N-methyl-N-(2-morpholin-4-ylethyl)amino | H |
| 3104. | 4-pyridyl | ((2S)-2-amino-3-phenylpropyl)amino | H |
| 3105. | 4-pyridyl | 4-methylpiperazinylamino | H |
| 3106. | 4-pyridyl | 4-methylpiperazinyl | H |
| 3107. | 4-pyridyl | 3-aminopyrrolidinyl | H |
| 3108. | 4-pyridyl | (diethylamino)ethylamino | H |
| 3109. | 4-pyridyl | 3,5-dimethylpiperazin-1-yl | H |
| 3110. | 4-pyridyl | (4-piperidylmethyl)amino | H |
| 3111. | 4-pyridyl | (2-methylbutyl)amino | H |
| 3112. | 4-pyridyl | 2-(dimethylamino)ethoxy | H |
| 3113. | 4-pyridyl | 2-(methylamino)ethoxy | H |
| 3114. | 4-pyridyl | ((2R)pyrrolidin-2-yl)methoxy | H |
| 3115. | 4-pyridyl | ((2R)-1-methylpyrrolidin-2-yl)methoxy | H |
| 3116. | 4-pyridyl | 2-(piperid-1-yl)ethoxy | H |
| 3117. | 4-pyridyl | 2-(piperazin-1-yl)ethoxy | H |
| 3118. | 4-pyridyl | 2-(morpholin-4-yl)ethoxy | H |
| 3119. | 4-pyridyl | 2-methylthio | $NH_2$ |
| 3120. | 4-pyridyl | 2-(methylsulfonyl) | $NH_2$ |
| 3121. | 4-pyridyl | cyclopropylmethylamino | $NH_2$ |
| 3122. | 4-pyridyl | 3-hydroxypropylamino | $NH_2$ |
| 3123. | 4-pyridyl | 2-(1-piperidinyl)ethylamino | $NH_2$ |
| 3124. | 4-pyridyl | 2-(1-pyrrolidinyl)ethylamino | $NH_2$ |
| 3125. | 4-pyridyl | 2-(4-morpholinyl)ethylamino | $NH_2$ |
| 3126. | 4-pyridyl | 3-(1-piperidinyl)propylamino | $NH_2$ |
| 3127. | 4-pyridyl | 3-(1-pyrrolidinyl)propylamino | $NH_2$ |
| 3128. | 4-pyridyl | 3-(4-morpholinyl)propylamino | $NH_2$ |
| 3129. | 4-pyridyl | N-methyl-N-(2-piperid-1-ylethyl)amino | $NH_2$ |
| 3130. | 4-pyridyl | N-methyl-N-(2-pyrrolidin-1-ylethyl)amino | $NH_2$ |
| 3131. | 4-pyridyl | N-methyl-N-(2-morpholin-4-ylethyl)amino | $NH_2$ |
| 3132. | 4-pyridyl | ((2S)-2-amino-3-phenylpropyl)amino | $NH_2$ |
| 3133. | 4-pyridyl | 4-methylpiperazinylamino | $NH_2$ |
| 3134. | 4-pyridyl | 4-methylpiperazinyl | $NH_2$ |
| 3135. | 4-pyridyl | 3-aminopyrrolidinyl | $NH_2$ |
| 3136. | 4-pyridyl | (diethylamino)ethylamino | $NH_2$ |
| 3137. | 4-pyridyl | 3,5-dimethylpiperazin-1-yl | $NH_2$ |
| 3138. | 4-pyridyl | (4-piperidylmethyl)amino | $NH_2$ |
| 3139. | 4-pyridyl | (2-methylbutyl)amino | $NH_2$ |
| 3140. | 4-pyridyl | 2-(dimethylamino)ethoxy | $NH_2$ |
| 3141. | 4-pyridyl | 2-(methylamino)ethoxy | $NH_2$ |
| 3142. | 4-pyridyl | ((2R)pyrrolidin-2-yl)methoxy | $NH_2$ |
| 3143. | 4-pyridyl | ((2R)-1-methylpyrrolidin-2-yl)methoxy | $NH_2$ |
| 3144. | 4-pyridyl | 2-(piperid-1-yl)ethoxy | $NH_2$ |
| 3145. | 4-pyridyl | 2-(piperazin-1-yl)ethoxy | $NH_2$ |
| 3146. | 4-pyridyl | 2-(morpholin-4-yl)ethoxy | $NH_2$ |
| 3147. | —($CH_2SO_2$)-phenyl | 2-methylthio | H |
| 3148. | —($CH_2SO_2$)-phenyl | 2-(methylsulfonyl) | H |
| 3149. | —($CH_2SO_2$)-phenyl | cyclopropylmethylamino | H |
| 3150. | —($CH_2SO_2$)-phenyl | 3-hydroxypropylamino | H |
| 3151. | —($CH_2SO_2$)-phenyl | 2-(1-piperidinyl)ethylamino | H |
| 3152. | —($CH_2SO_2$)-phenyl | 2-(1-pyrrolidinyl)ethylamino | H |
| 3153. | —($CH_2SO_2$)-phenyl | 2-(4-morpholinyl)ethylamino | H |
| 3154. | —($CH_2SO_2$)-phenyl | 3-(1-piperidinyl)propylamino | H |
| 3155. | —($CH_2SO_2$)-phenyl | 3-(1-pyrrolidinyl)propylamino | H |
| 3156. | —($CH_2SO_2$)-phenyl | 3-(4-morpholinyl)propylamino | H |
| 3157. | —($CH_2SO_2$)-phenyl | N-methyl-N-(2-piperid-1-ylethyl)amino | H |
| 3158. | —($CH_2SO_2$)-phenyl | N-methyl-N-(2-pyrrolidin-1-ylethyl)amino | H |
| 3159. | —($CH_2SO_2$)-phenyl | N-methyl-N-(2-morpholin-4-ylethyl)amino | H |
| 3160. | —($CH_2SO_2$)-phenyl | ((2S)-2-amino-3-phenylpropyl)amino | H |
| 3161. | —($CH_2SO_2$)-phenyl | 4-methylpiperazinylamino | H |
| 3162. | —($CH_2SO_2$)-phenyl | 4-methylpiperazinyl | H |
| 3163. | —($CH_2SO_2$)-phenyl | 3-aminopyrrolidinyl | H |
| 3164. | —($CH_2SO_2$)-phenyl | (diethylamino)ethylamino | H |
| 3165. | —($CH_2SO_2$)-phenyl | 3,5-dimethylpiperazin-1-yl | H |
| 3166. | —($CH_2SO_2$)-phenyl | (4-piperidylmethyl)amino | H |

TABLE 6-continued

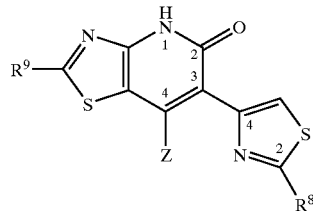

| # | R⁸ | R⁹ | Z |
|---|---|---|---|
| 3167. | —(CH₂SO₂)-phenyl | (2-methylbutyl)amino | H |
| 3168. | —(CH₂SO₂)-phenyl | 2-(dimethylamino)ethoxy | H |
| 3169. | —(CH₂SO₂)-phenyl | 2-(methylamino)ethoxy | H |
| 3170. | —(CH₂SO₂)-phenyl | ((2R)pyrrolidin-2-yl)methoxy | H |
| 3171. | —(CH₂SO₂)-phenyl | ((2R)-1-methylpyrrolidin-2-yl)methoxy | H |
| 3172. | —(CH₂SO₂)-phenyl | 2-(piperid-1-yl)ethoxy | H |
| 3173. | —(CH₂SO₂)-phenyl | 2-(piperazin-1-yl)ethoxy | H |
| 3174. | —(CH₂SO₂)-phenyl | 2-(morpholin-4-yl)ethoxy | H |
| 3175. | —(CH₂SO₂)-phenyl | 2-methylthio | NH₂ |
| 3176. | —(CH₂SO₂)-phenyl | 2-(methylsulfonyl) | NH₂ |
| 3177. | —(CH₂SO₂) phenyl | cyclopropylmethylamino | NH₂ |
| 3178. | —(CH₂SO₂)-phenyl | 3-hydroxypropylamino | NH₂ |
| 3179. | —(CH₂SO₂)-phenyl | 2-(1-piperidinyl)ethylamino | NH₂ |
| 3180. | —(CH₂SO₂)-phenyl | 2-(1-pyrrolidinyl)ethylamino | NH₂ |
| 3181. | —(CH₂SO₂)-phenyl | 2-(4-morpholinyl)ethylamino | NH₂ |
| 3182. | —(CH₂SO₂)-phenyl | 3-(1-piperidinyl)propylamino | NH₂ |
| 3183. | —(CH₂SO₂)-phenyl | 3-(1-pyrrolidinyl)propylamino | NH₂ |
| 3184. | —(CH₂SO₂)-phenyl | 3-(4-morpholinyl)propylamino | NH₂ |
| 3185. | —(CH₂SO₂)-phenyl | N-methyl-N-(2-piperid-1-ylethyl)amino | NH₂ |
| 3186. | —(CH₂SO₂)-phenyl | N-methyl-N-(2-pyrrolidin-1-ylethyl)amino | NH₂ |
| 3187. | —(CH₂SO₂)-phenyl | N-methyl-N-(2-morpholin-4-ylethyl)amino | NH₂ |
| 3188. | —(CH₂SO₂)-phenyl | ((2S)-2-amino-3-phenylpropyl)amino | NH₂ |
| 3189. | —(CH₂SO₂)-phenyl | 4-methylpiperazinylamino | NH₂ |
| 3190. | —(CH₂SO₂)-phenyl | 4-methylpiperazinyl | NH₂ |
| 3191. | —(CH₂SO₂)-phenyl | 3-aminopyrrolidinyl | NH₂ |
| 3192. | —(CH₂SO₂)-phenyl | (diethylamino)ethylamino | NH₂ |
| 3193. | —(CH₂SO₂)-phenyl | 3,5-dimethylpiperazin-1-yl | NH₂ |
| 3194. | —(CH₂SO₂)-phenyl | (4-piperidylmethyl)amino | NH₂ |
| 3195. | —(CH₂SO₂)-phenyl | (2-methylbutyl)amino | NH₂ |
| 3196. | —(CH₂SO₂)-phenyl | 2-(dimethylamino)ethoxy | NH₂ |
| 3197. | —(CH₂SO₂)-phenyl | 2-(methylamino)ethoxy | NH₂ |
| 3198. | —(CH₂SO₂)-phenyl | ((2R)pyrrolidin-2-yl)methoxy | NH₂ |
| 3199. | —(CH₂SO₂)-phenyl | ((2R)-1-methylpyrrolidin-2-yl)methoxy | NH₂ |
| 3200. | —(CH₂SO₂)-phenyl | 2-(piperid-1-yl)ethoxy | NH₂ |
| 3201. | —(CH₂SO₂)-phenyl | 2-(piperazin-1-yl)ethoxy | NH₂ |
| 3202. | —(CH₂SO₂)-phenyl | 2-(morpholin-4-yl)ethoxy | NH₂ |
| 3203. | —(CH₂SO₂)-2-thienyl | 2-methylthio | H |
| 3204. | —(CH₂SO₂)-2-thienyl | 2-(methylsulfonyl) | H |
| 3205. | —(CH₂SO₂)-2-thienyl | cyclopropylmethylamino | H |
| 3206. | —(CH₂SO₂)-2-thienyl | 3-hydroxypropylamino | H |
| 3207. | —(CH₂SO₂)-2-thienyl | 2-(1-piperidinyl)ethylamino | H |
| 3208. | —(CH₂SO₂)-2-thienyl | 2-(1-pyrrolidinyl)ethylamino | H |
| 3209. | —(CH₂SO₂)-2-thienyl | 2-(4-morpholinyl)ethylamino | H |
| 3210. | —(CH₂SO₂)-2-thienyl | 3-(1-piperidinyl)propylamino | H |
| 3211. | —(CH₂SO₂)-2-thienyl | 3-(1-pyrrolidinyl)propylamino | H |
| 3212. | —(CH₂SO₂)-2-thienyl | 3-(4-morpholinyl)propylamino | H |
| 3213. | —(CH₂SO₂)-2-thienyl | N-methyl-N-(2-piperid-1-ylethyl)amino | H |
| 3214. | —(CH₂SO₂)-2-thienyl | N-methyl-N-(2-pyrrolidin-1-ylethyl)amino | H |
| 3215. | —(CH₂SO₂) 2-thienyl | N-methyl-N-(2-morpholin-4-ylethyl)amino | H |
| 3216. | —(CH₂SO₂)-2-thienyl | ((2S)-2-amino-3-phenylpropyl)amino | H |
| 3217. | —(CH₂SO₂)-2-thienyl | 4-methylpiperazinylamino | H |
| 3218. | —(CH₂SO₂)-2-thienyl | 4-methylpiperazinyl | H |
| 3219. | —(CH₂SO₂)-2-thienyl | 3-aminopyrrolidinyl | H |
| 3220. | —(CH₂SO₂)-2-thienyl | (diethylamino)ethylamino | H |
| 3221. | —(CH₂SO₂)-2-thienyl | 3,5-dimethylpiperazin-1-yl | H |
| 3222. | —(CH₂SO₂)-2-thienyl | (4-piperidylmethyl)amino | H |
| 3223. | —(CH₂SO₂)-2-thienyl | (2-methylbutyl)amino | H |
| 3224. | —(CH₂SO₂)-2-thienyl | 2-(dimethylamino)ethoxy | H |
| 3225. | —(CH₂SO₂)-2-thienyl | 2-(methylamino)ethoxy | H |
| 3226. | —(CH₂SO₂)-2-thienyl | ((2R)pyrrolidin-2-yl)methoxy | H |
| 3227. | —(CH₂SO₂)-2-thienyl | ((2R)-1-methylpyrrolidin-2-yl)methoxy | H |
| 3228. | —(CH₂SO₂)-2-thienyl | 2-(piperid-1-yl)ethoxy | H |
| 3229. | —(CH₂SO₂)-2-thienyl | 2-(piperazin-1-yl)ethoxy | H |
| 3230. | —(CH₂SO₂)-2-thienyl | 2-(morpholin-4-yl)ethoxy | H |
| 3231. | —(CH₂SO₂)-2-thienyl | 2-methylthio | NH₂ |

TABLE 6-continued

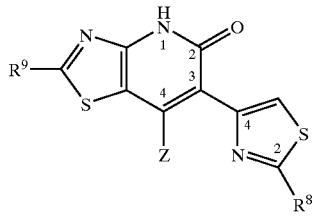

| # | R⁸ | R⁹ | Z |
|---|---|---|---|
| 3232. | —(CH₂SO₂)-2-thienyl | 2-(methylsulfonyl) | NH₂ |
| 3233. | —(CH₂SO₂)-2-thienyl | cyclopropylmethylamino | NH₂ |
| 3234. | —(CH₂SO₂)-2-thienyl | 3-hydroxypropylamino | NH₂ |
| 3235. | —(CH₂SO₂)-2-thienyl | 2-(1-piperidinyl)ethylamino | NH₂ |
| 3236. | —(CH₂SO₂)-2-thienyl | 2-(1-pyrrolidinyl)ethylamino | NH₂ |
| 3237. | —(CH₂SO₂)-2-thienyl | 2-(4-morpholinyl)ethylamino | NH₂ |
| 3238. | —(CH₂SO₂)-2-thienyl | 3-(1-piperidinyl)propylamino | NH₂ |
| 3239. | —(CH₂SO₂)-2-thienyl | 3-(1-pyrrolidinyl)propylamino | NH₂ |
| 3240. | —(CH₂SO₂)-2-thienyl | 3-(4-morpholinyl)propylamino | NH₂ |
| 3241. | —(CH₂SO₂)-2-thienyl | N-methyl-N-(2-piperid-1-ylethyl)amino | NH₂ |
| 3242. | —(CH₂SO₂)-2-thienyl | N-methyl-N-(2-pyrrolidin-1-ylethyl)amino | NH₂ |
| 3243. | —(CH₂SO₂)-2-thienyl | N-methyl-N-(2-morpholin-4-ylethyl)amino | NH₂ |
| 3244. | —(CH₂SO₂)-2-thienyl | ((2S)-2-amino-3-phenylpropyl)amino | NH₂ |
| 3245. | —(CH₂SO₂)-2-thienyl | 4-methylpiperazinylamino | NH₂ |
| 3246. | —(CH₂SO₂)-2-thienyl | 4-methylpiperazinyl | NH₂ |
| 3247. | —(CH₂SO₂)-2-thienyl | 3-aminopyrrolidinyl | NH₂ |
| 3248. | —(CH₂SO₂)-2-thienyl | (diethylamino)ethylamino | NH₂ |
| 3249. | —(CH₂SO₂)-2-thienyl | 3,5-dimethylpiperazin-1-yl | NH₂ |
| 3250. | —(CH₂SO₂)-2-thienyl | (4-piperidylmethyl)amino | NH₂ |
| 3251. | —(CH₂SO₂)-2-thienyl | (2-methylbutyl)amino | NH₂ |
| 3252. | —(CH₂SO₂)-2-thienyl | 2-(dimethylamino)ethoxy | NH₂ |
| 3253. | —(CH₂SO₂)-2-thienyl | 2-(methylamino)ethoxy | NH₂ |
| 3254. | —(CH₂SO₂)-2-thienyl | ((2R)pyrrolidin-2-yl)methoxy | NH₂ |
| 3255. | —(CH₂SO₂)-2-thienyl | ((2R)-1-methylpyrrolidin-2-yl)methoxy | NH₂ |
| 3256. | —(CH₂SO₂)-2-thienyl | 2-(piperid-1-yl)ethoxy | NH₂ |
| 3257. | —(CH₂SO₂)-2-thienyl | 2-(piperazin-1-yl)ethoxy | NH₂ |
| 3258. | —(CH₂SO₂)-2-thienyl | 2-(morpholin-4-yl)ethoxy | NH₂ |
| 3259. | —(CH₂SO₂)-2-pyridyl | 2-methylthio | H |
| 3260. | —(CH₂SO₂)-2-pyridyl | 2-(methylsulfonyl) | H |
| 3261. | —(CH₂SO₂)-2-pyridyl | cyclopropylmethylamino | H |
| 3262. | —(CH₂SO₂)-2-pyridyl | 3-hydroxypropylamino | H |
| 3263. | —(CH₂SO₂)-2-pyridyl | 2-(1-piperidinyl)ethylamino | H |
| 3264. | —(CH₂SO₂)-2-pyridyl | 2-(1-pyrrolidinyl)ethylamino | H |
| 3265. | —(CH₂SO₂)-2-pyridyl | 2-(4-morpholinyl)ethylamino | H |
| 3266. | —(CH₂SO₂)-2-pyridyl | 3-(1-piperidinyl)propylamino | H |
| 3267. | —(CH₂SO₂)-2-pyridyl | 3-(1-pyrrolidinyl)propylamino | H |
| 3268. | —(CH₂SO₂)-2-pyridyl | 3-(4-morpholinyl)propylamino | H |
| 3269. | —(CH₂SO₂)-2-pyridyl | N-methyl-N-(2-piperid-1-ylethyl)amino | H |
| 3270. | —(CH₂SO₂)-2-pyridyl | N-methyl-N-(2-pyrrolidin-1-ylethyl)amino | H |
| 3271. | —(CH₂SO₂)-2-pyridyl | N-methyl-N-(2-morpholin-4-ylethyl)amino | H |
| 3272. | —(CH₂SO₂)-2-pyridyl | ((2S)-2-amino-3-phenylpropyl)amino | H |
| 3273. | —(CH₂SO₂)-2-pyridyl | 4-methylpiperazinylamino | H |
| 3274. | —(CH₂SO₂)-2-pyridyl | 4-methylpiperazinyl | H |
| 3275. | —(CH₂SO₂)-2-pyridyl | 3-aminopyrrolidinyl | H |
| 3276. | —(CH₂SO₂)-2-pyridyl | (diethylamino)ethylamino | H |
| 3277. | —(CH₂SO₂)-2-pyridyl | 3,5-dimethylpiperazin-1-yl | H |
| 3278. | —(CH₂SO₂)-2-pyridyl | (4-piperidylmethyl)amino | H |
| 3279. | —(CH₂SO₂)-2-pyridyl | (2-methylbutyl)amino | H |
| 3280. | —(CH₂SO₂)-2-pyridyl | 2-(dimethylamino)ethoxy | H |
| 3281. | —(CH₂SO₂)-2-pyridyl | 2-(methylamino)ethoxy | H |
| 3282. | —(CH₂SO₂)-2-pyridyl | ((2R)pyrrolidin-2-yl)methoxy | H |
| 3283. | —(CH₂SO₂)-2-pyridyl | ((2R)-1-methylpyrrolidin-2-yl)methoxy | H |
| 3284. | —(CH₂SO₂)-2-pyridyl | 2-(piperid-1-yl)ethoxy | H |
| 3285. | —(CH₂SO₂)-2-pyridyl | 2-(piperazin-1-yl)ethoxy | H |
| 3286. | —(CH₂SO₂)-2-pyridyl | 2-(morpholin-4-yl)ethoxy | H |
| 3287. | —(CH₂SO₂)-2-pyridyl | 2-methylthio | NH₂ |
| 3288. | —(CH₂SO₂)-2-pyridyl | 2-(methylsulfonyl) | NH₂ |
| 3289. | —(CH₂SO₂)-2-pyridyl | cyclopropylmethylamino | NH₂ |
| 3290. | —(CH₂SO₂)-2-pyridyl | 3-hydroxypropylamino | NH₂ |
| 3291. | —(CH₂SO₂)-2-pyridyl | 2-(1-piperidinyl)ethylamino | NH₂ |
| 3292. | —(CH₂SO₂) 2-pyridyl | 2-(1-pyrrolidinyl)ethylamino | NH₂ |
| 3293. | —(CH₂SO₂)-2-pyridyl | 2-(4-morpholinyl)ethylamino | NH₂ |
| 3294. | —(CH₂SO₂)-2-pyridyl | 3-(1-piperidinyl)propylamino | NH₂ |
| 3295. | —(CH₂SO₂)-2-pyridyl | 3-(1-pyrrolidinyl)propylamino | NH₂ |
| 3296. | —(CH₂SO₂)-2-pyridyl | 3-(4-morpholinyl)propylamino | NH₂ |

TABLE 6-continued

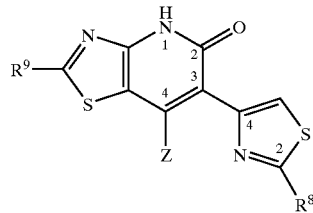

| # | R⁸ | R⁹ | Z |
|---|---|---|---|
| 3297. | —(CH₂SO₂)-2-pyridyl | N-methyl-N-(2-piperid-1-ylethyl)amino | NH₂ |
| 3298. | —(CH₂SO₂)-2-pyridyl | N-methyl-N-(2-pyrrolidin-1-ylethyl)amino | NH₂ |
| 3299. | —(CH₂SO₂)-2-pyridyl | N-methyl-N-(2-morpholin-4-ylethyl)amino | NH₂ |
| 3300. | —(CH₂SO₂)-2-pyridyl | ((2S)-2-amino-3-phenylpropyl)amino | NH₂ |
| 3301. | —(CH₂SO₂)-2-pyridyl | 4-methylpiperazinylamino | NH₂ |
| 3302. | —(CH₂SO₂)-2-pyridyl | 4-methylpiperazinyl | NH₂ |
| 3303. | —(CH₂SO₂)-2-pyridyl | 3-aminopyrrolidinyl | NH₂ |
| 3304. | —(CH₂SO₂)-2-pyridyl | (diethylamino)ethylamino | NH₂ |
| 3305. | —(CH₂SO₂)-2-pyridyl | 3,5-dimethylpiperazin-1-yl | NH₂ |
| 3306. | —(CH₂SO₂)-2-pyridyl | (4-piperidylmethyl)amino | NH₂ |
| 3307. | —(CH₂SO₂)-2-pyridyl | (2-methylbutyl)amino | NH₂ |
| 3308. | —(CH₂SO₂)-2-pyridyl | 2-(dimethylamino)ethoxy | NH₂ |
| 3309. | —(CH₂SO₂)-2-pyridyl | 2-(methylamino)ethoxy | NH₂ |
| 3310. | —(CH₂SO₂)-2-pyridyl | ((2R)pyrrolidin-2-yl)methoxy | NH₂ |
| 3311. | —(CH₂SO₂)-2-pyridyl | ((2R)-1-methylpyrrolidin-2-yl)methoxy | NH₂ |
| 3312. | —(CH₂SO₂)-2-pyridyl | 2-(piperid-1-yl)ethoxy | NH₂ |
| 3313. | —(CH₂SO₂)-2-pyridyl | 2-(piperazin-1-yl)ethoxy | NH₂ |
| 3314. | —(CH₂SO₂)-2-pyridyl | 2-(morpholin-4-yl)ethoxy | NH₂ |
| 3315. | —(CH₂SO₂)-3-pyridyl | 2-methylthio | H |
| 3316. | —(CH₂SO₂)-3-pyridyl | 2-(methylsulfonyl) | H |
| 3317. | —(CH₂SO₂)-3-pyridyl | cyclopropylmethylamino | H |
| 3318. | —(CH₂SO₂)-3-pyridyl | 3-hydroxypropylamino | H |
| 3319. | —(CH₂SO₂)-3-pyridyl | 2-(1-piperidinyl)ethylamino | H |
| 3320. | —(CH₂SO₂)-3-pyridyl | 2-(1-pyrrolidinyl)ethylamino | H |
| 3321. | —(CH₂SO₂)-3-pyridyl | 2-(4-morpholinyl)ethylamino | H |
| 3322. | —(CH₂SO₂)-3-pyridyl | 3-(1-piperidinyl)propylamino | H |
| 3323. | —(CH₂SO₂)-3-pyridyl | 3-(1-pyrrolidinyl)propylamino | H |
| 3324. | —(CH₂SO₂)-3-pyridyl | 3-(4-morpholinyl)propylamino | H |
| 3325. | —(CH₂SO₂)-3-pyridyl | N-methyl-N-(2-piperid-1-ylethyl)amino | H |
| 3326. | —(CH₂SO₂)-3-pyridyl | N-methyl-N-(2-pyrrolidin-1-ylethyl)amino | H |
| 3327. | —(CH₂SO₂)-3-pyridyl | N-methyl-N-(2-morpholin-4-ylethyl)amino | H |
| 3328. | —(CH₂SO₂)-3-pyridyl | ((2S)-2-amino-3-phenylpropyl)amino | H |
| 3329. | —(CH₂SO₂)-3-pyridyl | 4-methylpiperazinylamino | H |
| 3330. | —(CH₂SO₂)-3-pyridyl | 4-methylpiperazinyl | H |
| 3331. | —(CH₂SO₂)-3-pyridyl | 3-aminopyrrolidinyl | H |
| 3332. | —(CH₂SO₂)-3-pyridyl | (diethylamino)ethylamino | H |
| 3333. | —(CH₂SO₂)-3-pyridyl | 3,5-dimethylpiperazin-1-yl | H |
| 3334. | —(CH₂SO₂) 3-pyridyl | (4-piperidylmethyl)amino | H |
| 3335. | —(CH₂SO₂)-3-pyridyl | (2-methylbutyl)amino | H |
| 3336. | —(CH₂SO₂)-3-pyridyl | 2-(dimethylamino)ethoxy | H |
| 3337. | —(CH₂SO₂)-3-pyridyl | 2-(methylamino)ethoxy | H |
| 3338. | —(CH₂SO₂)-3-pyridyl | ((2R)pyrrolidin-2-yl)methoxy | H |
| 3339. | —(CH₂SO₂)-3-pyridyl | ((2R)-1-methylpyrrolidin-2-yl)methoxy | H |
| 3340. | —(CH₂SO₂)-3-pyridyi | 2-(piperid-1-yl)ethoxy | H |
| 3341. | —(CH₂SO₂)-3-pyridyl | 2-(piperazin-1-yl)ethoxy | H |
| 3342. | —(CH₂SO₂)-3-pyridyl | 2-(morpholin-4-yl)ethoxy | H |
| 3343. | —(CH₂SO₂)-3-pyridyl | 2-methylthio | NH₂ |
| 3344. | —(CH₂SO₂)-3-pyridyl | 2-(methylsulfonyl) | NH₂ |
| 3345. | —(CH₂SO₂)-3-pyridyl | cyclopropylmethylamino | NH₂ |
| 3346. | —(CH₂SO₂)-3-pyridyl | 3-hydroxypropylamino | NH₂ |
| 3347. | —(CH₂SO₂)-3-pyridyl | 2-(1-piperidinyl)ethylamino | NH₂ |
| 3348. | —(CH₂SO₂)-3-pyridyl | 2-(1-pyrrolidinyl)ethylamino | NH₂ |
| 3349. | —(CH₂SO₂)-3-pyridyl | 2-(4-morpholinyl)ethylamino | NH₂ |
| 3350. | —(CH₂SO₂)-3-pyridyl | 3-(1-piperidinyl)propylamino | NH₂ |
| 3351. | —(CH₂SO₂)-3-pyridyl | 3-(1-pyrrolidinyl)propylamino | NH₂ |
| 3352. | —(CH₂SO₂)-3-pyridyl | 3-(4-morpholinyl)propylamino | NH₂ |
| 3353. | —(CH₂SO₂)-3-pyridyl | N-methyl-N-(2-piperid-1-ylethyl)amino | NH₂ |
| 3354. | —(CH₂SO₂)-3-pyridyl | N-methyl-N-(2-pyrrolidin-1-ylethyl)amino | NH₂ |
| 3355. | —(CH₂SO₂)-3-pyridyl | N-methyl-N-(2-morpholin-4-ylethyl)amino | NH₂ |
| 3356. | —(CH₂SO₂)-3-pyridyl | ((2S)-2-amino-3-phenylpropyl)amino | NH₂ |
| 3357. | —(CH₂SO₂)-3-pyridyl | 4-methylpiperazinylamino | NH₂ |
| 3358. | —(CH₂SO₂)-3-pyridyl | 4-methylpiperazinyl | NH₂ |
| 3359. | —(CH₂SO₂)-3-pyridyl | 3-aminopyrrolidinyl | NH₂ |
| 3360. | —(CH₂SO₂)-3-pyridyl | (diethylamino)ethylamino | NH₂ |
| 3361. | —(CH₂SO₂)-3-pyridyl | 3,5-dimethylpiperazin-1-yl | NH₂ |

TABLE 6-continued

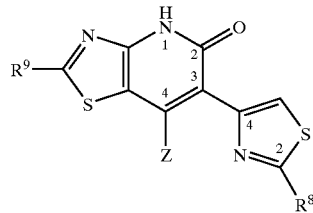

| # | R⁸ | R⁹ | Z |
|---|---|---|---|
| 3362. | —(CH₂SO₂)-3-pyridyl | (4-piperidylmethyl)amino | NH₂ |
| 3363. | —(CH₂SO₂)-3-pyridyl | (2-methylbutyl)amino | NH₂ |
| 3364. | —(CH₂SO₂)-3-pyridyl | 2-(dimethylamino)ethoxy | NH₂ |
| 3365. | —(CH₂SO₂)-3-pyridyl | 2-(methylamino)ethoxy | NH₂ |
| 3366. | —(CH₂SO₂)-3-pyridyl | ((2R)pyrrolidin-2-yl)methoxy | NH₂ |
| 3367. | —(CH₂SO₂)-3-pyridyl | ((2R)-1-methylpyrrolidin-2-yl)methoxy | NH₂ |
| 3368. | —(CH₂SO₂)-3-pyridyl | 2-(piperid-1-yl)ethoxy | NH₂ |
| 3369. | —(CH₂SO₂)-3-pyridyl | 2-(piperazin-1-yl)ethoxy | NH₂ |
| 3370. | —(CH₂SO₂)-3-pyridyl | 2-(morpholin-4-yl)ethoxy | NH₂ |
| 3371. | —(CH₂SO₂)-4-pyridyl | 2-methylthio | H |
| 3372. | —(CH₂SO₂)-4-pyridyl | 2-(methylsulfonyl) | H |
| 3373. | —(CH₂SO₂)-4-pyridyl | cyclopropylmethylamino | H |
| 3374. | —(CH₂SO₂)-4-pyridyl | 3-hydroxypropylamino | H |
| 3375. | —(CH₂SO₂)-4-pyridyl | 2-(1-piperidinyl)ethylamino | H |
| 3376. | —(CH₂SO₂) 4-pyridyl | 2-(1-pyrrolidinyl)ethylamino | H |
| 3377. | —(CH₂SO₂)-4-pyridyl | 2-(4-morpholinyl)ethylamino | H |
| 3378. | —(CH₂SO₂)-4-pyridyl | 3-(1-piperidinyl)propylamino | H |
| 3379. | —(CH₂SO₂)-4-pyridyl | 3-(1-pyrrolidinyl)propylamino | H |
| 3380. | —(CH₂SO₂)-4-pyridyl | 3-(4-morpholinyl)propylamino | H |
| 3381. | —(CH₂SO₂)-4-pyridyl | N-methyl-N-(2-piperid-1-ylethyl)amino | H |
| 3382. | —(CH₂SO₂)-4-pyridyl | N-methyl-N-(2-pyrrolidin-1-ylethyl)amino | H |
| 3383. | —(CH₂SO₂)-4-pyridyl | N-methyl-N-(2-morpholin-4-ylethyl)amino | H |
| 3384. | —(CH₂SO₂)-4-pyridyl | ((2S)-2-amino-3-phenylpropyl)amino | H |
| 3385. | —(CH₂SO₂)-4-pyridyl | 4-methylpiperazinylamino | H |
| 3386. | —(CH₂SO₂)-4-pyridyl | 4-methylpiperazinyl | H |
| 3387. | —(CH₂SO₂)-4-pyridyl | 3-aminopyrrolidinyl | H |
| 3388. | —(CH₂SO₂)-4-pyridyl | (diethylamino)ethylamino | H |
| 3389. | —(CH₂SO₂)-4-pyridyl | 3,5-dimethylpiperazin-1-yl | H |
| 3390. | —(CH₂SO₂)-4-pyridyl | (4-piperidylmethyl)amino | H |
| 3391. | —(CH₂SO₂)-4-pyridyl | (2-methylbutyl)amino | H |
| 3392. | —(CH₂SO₂)-4-pyridyl | 2-(dimethylamino)ethoxy | H |
| 3393. | —(CH₂SO₂)-4-pyridyl | 2-(methylamino)ethoxy | H |
| 3394. | —(CH₂SO₂)-4-pyridyl | ((2R)pyrrolidin-2-yl)methoxy | H |
| 3395. | —(CH₂SO₂)-4-pyridyl | ((2R)-1-methylpyrrolidin-2-yl)methoxy | H |
| 3396. | —(CH₂SO₂)-4-pyridyl | 2-(piperid-1-yl)ethoxy | H |
| 3397. | —(CH₂SO₂)-4-pyridyl | 2-(piperazin-1-yl)ethoxy | H |
| 3398. | —(CH₂SO₂)-4-pyridyl | 2-(morpholin-4-yl)ethoxy | H |
| 3399. | —(CH₂SO₂)-4-pyridyl | 2-methylthio | NH₂ |
| 3400. | —(CH₂SO₂)-4-pyridyl | 2-(methylsulfonyl) | NH₂ |
| 3401. | —(CH₂SO₂)-4-pyridyl | cyclopropylmethylamino | NH₂ |
| 3402. | —(CH₂SO₂)-4-pyridyl | 3-hydroxypropylamino | NH₂ |
| 3403. | —(CH₂SO₂)-4-pyridyl | 2-(1-piperidinyl)ethylamino | NH₂ |
| 3404. | —(CH₂SO₂)-4-pyridyl | 2-(1-pyrrolidinyl)ethylamino | NH₂ |
| 3405. | —(CH₂SO₂)-4-pyridyl | 2-(4-morpholinyl)ethylamino | NH₂ |
| 3406. | —(CH₂SO₂)-4-pyridyl | 3-(1-piperidinyl)propylamino | NH₂ |
| 3407. | —(CH₂SO₂)-4-pyridyl | 3-(1-pyrrolidinyl)propylamino | NH₂ |
| 3408. | —(CH₂SO₂)-4-pyridyl | 3-(4-morpholinyl)propylamino | NH₂ |
| 3409. | —(CH₂SO₂)-4-pyridyl | N-methyl-N-(2-piperid-1-ylethyl)amino | NH₂ |
| 3410. | —(CH₂SO₂)-4-pyridyl | N-methyl-N-(2-pyrrolidin-1-ylethyl)amino | NH₂ |
| 3411. | —(CH₂SO₂)-4-pyridyl | N-methyl-N-(2-morpholin-4-ylethyl)amino | NH₂ |
| 3412. | —(CH₂SO₂)-4-pyridyl | ((2S)-2-amino-3-phenylpropyl)amino | NH₂ |
| 3413. | —(CH₂SO₂)-4-pyridyl | 4-methylpiperazinylamino | NH₂ |
| 3414. | —(CH₂SO₂)-4-pyridyl | 4-methylpiperazinyl | NH₂ |
| 3415. | —(CH₂SO₂)-4-pyridyl | 3-aminopyrrolidinyl | NH₂ |
| 3416. | —(CH₂SO₂)-4-pyridyl | (diethylamino)ethylamino | NH₂ |
| 3417. | —(CH₂SO₂)-4-pyridyl | 3,5-dimethylpiperazin-1-yl | NH₂ |
| 3418. | —(CH₂SO₂)-4-pyridyl | (4-piperidylmethyl)amino | NH₂ |
| 3419. | —(CH₂SO₂)-4-pyridyl | (2-methylbutyl)amino | NH₂ |
| 3420. | —(CH₂SO₂)-4-pyridyl | 2-(dimethylamino)ethoxy | NH₂ |
| 3421. | —(CH₂SO₂)-4-pyridyl | 2-(methylamino)ethoxy | NH₂ |
| 3422. | —(CH₂SO₂)-4-pyridyl | ((2R)pyrrolidin-2-yl)methoxy | NH₂ |
| 3423. | —(CH₂SO₂)-4-pyridyl | ((2R)-1-methylpyrrolidin-2-yl)methoxy | NH₂ |
| 3424. | —(CH₂SO₂)-4-pyridyl | 2-(piperid-1-yl)ethoxy | NH₂ |
| 3425. | —(CH₂SO₂)-4-pyridyl | 2-(piperazin-1-yl)ethoxy | NH₂ |
| 3426. | —(CH₂SO₂)-4-pyridyl | 2-(morpholin-4-yl)ethoxy | NH₂ |

TABLE 6-continued

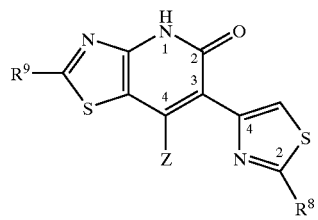

| # | R⁸ | R⁹ | Z |
|---|---|---|---|
| 3427. | —(NMeSO₂)-phenyl | 2-methylthio | H |
| 3428. | —(NMeSO₂)-phenyl | 2-(methylsulfonyl) | H |
| 3429. | —(NMeSO₂)-phenyl | cyclopropylmethylamino | H |
| 3430. | —(NMeSO₂)-phenyl | 3-hydroxypropylamino | H |
| 3431. | —(NMeSO₂)-phenyl | 2-(1-piperidinyl)ethylamino | H |
| 3432. | —(NMeSO₂)-phenyl | 2-(1-pyrrolidinyl)ethylamino | H |
| 3433. | —(NMeSO₂)-phenyl | 2-(4-morpholinyl)ethylamino | H |
| 3434. | —(NMeSO₂)-phenyl | 3-(1-piperidinyl)propylamino | H |
| 3435. | —(NMeSO₂)-phenyl | 3-(1-pyrrolidinyl)propylamino | H |
| 3436. | —(NMeSO₂)-phenyl | 3-(4-morpholinyl)propylamino | H |
| 3437. | —(NMeSO₂)-phenyl | N-methyl-N-(2-piperid-1-ylethyl)amino | H |
| 3438. | —(NMeSO₂)-phenyl | N-methyl-N-(2-pyrrolidin-1-ylethyl)amino | H |
| 3439. | —(NMeSO₂)-phenyl | N-methyl-N-(2-morpholin-4-ylethyl)amino | H |
| 3440. | —(NMeSO₂)-phenyl | ((2S)-2-amino-3-phenylpropyl)amino | H |
| 3441. | —(NMeSO₂)-phenyl | 4-methylpiperazinylamino | H |
| 3442. | —(NMeSO₂)-phenyl | 4-methylpiperazinyl | H |
| 3443. | —(NMeSO₂)-phenyl | 3-aminopyrrolidinyl | H |
| 3444. | —(NMeSO₂)-phenyl | (diethylamino)ethylamino | H |
| 3445. | —(NMeSO₂)-phenyl | 3,5-dimethylpiperazin-1-yl | H |
| 3446. | —(NMeSO₂)-phenyl | (4-piperidylmethyl)amino | H |
| 3447. | —(NMeSO₂)-phenyl | (2-methylbutyl)amino | H |
| 3448. | —(NMeSO₂)-phenyl | 2-(dimethylamino)ethoxy | H |
| 3449. | —(NMeSO₂)-phenyl | 2-(methylamino)ethoxy | H |
| 3450. | —(NMeSO₂)-phenyl | ((2R)pyrrolidin-2-yl)methoxy | H |
| 3451. | —(NMeSO₂)-phenyl | ((2R)-1-methylpyrrolidin-2-yl)methoxy | H |
| 3452. | —(NMeSO₂)-phenyl | 2-(piperid-1-yl)ethoxy | H |
| 3453. | —(MMeSO₂)-phenyl | 2-(piperazin-1-yl)ethoxy | H |
| 3454. | —(NMeSO₂)-phenyl | 2-(morpholin-4-yl)ethoxy | H |
| 3455. | —(NMeSO₂)-phenyl | 2-methylthio | NH₂ |
| 3456. | —(NMeSO₂)-phenyl | 2-(methylsulfonyl) | NH₂ |
| 3457. | —(NMeSO₂)-phenyl | cyclopropylmethylamino | NH₂ |
| 3458. | —(NMeSO₂)-phenyl | 3-hydroxypropylamino | NH₂ |
| 3459. | —(NMeSO₂)-phenyl | 2-(1-piperidinyl)ethylamino | NH₂ |
| 3460. | —(NMeSO₂)-phenyl | 2-(1-pyrrolidinyl)ethylamino | NH₂ |
| 3461. | —(NMeSO₂)-phenyl | 2-(4-morpholinyl)ethylamino | NH₂ |
| 3462. | —(NMeSO₂)-phenyl | 3-(1-piperidinyl)propylamino | NH₂ |
| 3463. | —(NMeSO₂)-phenyl | 3-(1-pyrrolidinyl)propylamino | NH₂ |
| 3464. | —(NMeSO₂)-phenyl | 3-(4-morpholinyl)propylamino | NH₂ |
| 3465. | —(NMeSO₂)-phenyl | N-methyl-N-(2-piperid-1-ylethyl)amino | NH₂ |
| 3466. | —(NMeSO₂)-phenyl | N-methyl-N-(2-pyrrolidin-1-ylethyl)amino | NH₂ |
| 3467. | —(NMeSO₂)-phenyl | N-methyl-N-(2-morpholin-4-ylethyl)amino | NH₂ |
| 3468. | —(NMeSO₂)-phenyl | ((2S)-2-amino-3-phenylpropyl)amino | NH₂ |
| 3469. | —(NMeSO₂)-phenyl | 4-methylpiperazinylamino | NH₂ |
| 3470. | —(NMeSO₂)-phenyl | 4-methylpiperazinyl | NH₂ |
| 3471. | —(NMeSO₂)-phenyl | 3-aminopyrrolidinyl | NH₂ |
| 3472. | —(NMeSO₂)-phenyl | (diethylamino)ethylamino | NH₂ |
| 3473. | —(NMeSO₂)-phenyl | 3,5-dimethylpiperazin-1-yl | NH₂ |
| 3474. | —(NMeSO₂)-phenyl | (4-piperidylmethyl)amino | NH₂ |
| 3475. | —(NMeSO₂)-phenyl | (2-methylbutyl)amino | NH₂ |
| 3476. | —(NMeSO₂)-phenyl | 2-(dimethylamino)ethoxy | NH₂ |
| 3477. | —(NMeSO₂)-phenyl | 2-(methylamino)ethoxy | NH₂ |
| 3478. | —(NMeSO₂)-phenyl | ((2R)pyrrolidin-2-yl)methoxy | NH₂ |
| 3479. | —(NMeSO₂)-phenyl | ((2R)-1-methylpyrrolidin-2-yl)methoxy | NH₂ |
| 3480. | —(NMeSO₂)-phenyl | 2-(piperid-1-yl)ethoxy | NH₂ |
| 3481. | —(NMeSO₂)-phenyl | 2-(piperazin-1-yl)ethoxy | NH₂ |
| 3482. | —(NMeSO₂)-phenyl | 2-(morpholin-4-yl)ethoxy | NH₂ |
| 3483. | —(NMeSO₂)-2-thienyl | 2-methylthio | H |
| 3484. | —(NMeSO₂)-2-thienyl | 2-(methylsulfonyl) | H |
| 3485. | —(NMeSO₂)-2-thienyl | cyclopropylmethylamino | H |
| 3486. | —(NMeSO₂)-2-thienyl | 3-hydroxypropylamino | H |
| 3487. | —(NMeSO₂)-2-thienyl | 2-(1-piperidinyl)ethylamino | H |
| 3488. | —(NMeSO₂)-2-thienyl | 2-(1-pyrrolidinyl)ethylamino | H |
| 3489. | —(NMeSO₂)-2-thienyl | 2-(4-morpholinyl)ethylamino | H |
| 3490. | —(NMeSO₂)-2-thienyl | 3-(1-piperidinyl)propylamino | H |
| 3491. | —(NMeSO₂)-2-thienyl | 3-(1-pyrrolidinyl)propylamino | H |

TABLE 6-continued

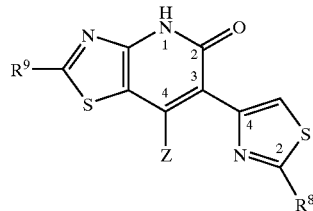

| # | R⁸ | R⁹ | Z |
|---|---|---|---|
| 3492. | —(NMeSO₂)-2-thienyl | 3-(4-morpholinyl)propylamino | H |
| 3493. | —(NMeSO₂)-2-thienyl | N-methyl-N-(2-piperid-1-ylethyl)amino | H |
| 3494. | —(NMeSO₂)-2-thienyl | N-methyl-N-(2-pyrrolidin-1-ylethyl)amino | H |
| 3495. | —(NMeSO₂)-2-thienyl | N-methyl-N-(2-morpholin-4-ylethyl)amino | H |
| 3496. | —(NMeSO₂)-2-thienyl | ((2S)-2-amino-3-phenylpropyl)amino | H |
| 3497. | —(NMeSO₂)-2-thienyl | 4-methylpiperazinylamino | H |
| 3498. | —(NMeSO₂)-2-thienyl | 4-methylpiperazinyl | H |
| 3499. | —(NMeSO₂)-2-thienyl | 3-aminopyrrolidinyl | H |
| 3500. | —(NMeSO₂)-2-thienyl | (diethylamino)ethylamino | H |
| 3501. | —(NMeSO₂)-2-thienyl | 3,5-dimethylpiperazin-1-yl | H |
| 3502. | —(NMeSO₂)-2-thienyl | (4-piperidylmethyl)amino | H |
| 3503. | —(NMeSO₂)-2-thienyl | (2-methylbutyl)amino | H |
| 3504. | —(NMeSO₂)-2-thienyl | 2-(dimethylamino)ethoxy | H |
| 3505. | —(NMeSO₂)-2-thienyl | 2-(methylamino)ethoxy | H |
| 3506. | —(NMeSO₂)-2-thienyl | ((2R)pyrrolidin-2-yl)methoxy | H |
| 3507. | —(NMeSO₂)-2-thienyl | ((2R)-1-methylpyrrolidin-2-yl)methoxy | H |
| 3508. | —(NMeSO₂)-2-thienyl | 2-(piperid-1-yl)ethoxy | H |
| 3509. | —(NMeSO₂)-2-thienyl | 2-(piperazin-1-yl)ethoxy | H |
| 3510. | —(NMeSO₂)-2-thienyl | 2-(morpholin-4-yl)ethoxy | H |
| 3511. | —(NMeSO₂)-2-thienyl | 2-methylthio | NH₂ |
| 3512. | —(NMeSO₂)-2-thienyl | 2-(methylsulfonyl) | NH₂ |
| 3513. | —(NMeSO₂)-2-thienyl | cyclopropylmethylamino | NH₂ |
| 3514. | —(NMeSO₂)-2-thienyl | 3-hydroxypropylamino | NH₂ |
| 3515. | —(NMeSO₂)-2-thienyl | 2-(1-piperidinyl)ethylamino | NH₂ |
| 3516. | —(NMeSO₂)-2-thienyl | 2-(1-pyrrolidinyl)ethylamino | NH₂ |
| 3517. | —(NMeSO₂)-2-thienyl | 2-(4-morpholinyl)ethylamino | NH₂ |
| 3518. | —(NMeSO₂)-2-thienyl | 3-(1-piperidinyl)propylamino | NH₂ |
| 3519. | —(NMeSO₂)-2-thienyl | 3-(1-pyrrolidinyl)propylamino | NH₂ |
| 3520. | —(NMeSO₂)-2-thienyl | 3-(4-morpholinyl)propylamino | NH₂ |
| 3521. | —(NMeSO₂)-2-thienyl | N-methyl-N-(2-piperid-1-ylethyl)amino | NH₂ |
| 3522. | —(NMeSO₂)-2-thienyl | N-methyl-N-(2-pyrrolidin-1-ylethyl)amino | NH₂ |
| 3523. | —(NMeSO₂)-2-thienyl | N-methyl-N-(2-morpholin-4-ylethyl)amino | NH₂ |
| 3524. | —(NMeSO₂)-2-thienyl | ((2S)-2-amino-3-phenylpropyl)amino | NH₂ |
| 3525. | —(NMeSO₂)-2-thienyl | 4-methylpiperazinylamino | NH₂ |
| 3526. | —(NMeSO₂)-2-thienyl | 4-methylpiperazinyl | NH₂ |
| 3527. | —(NMeSO₂)-2-thienyl | 3-aminopyrrolidinyl | NH₂ |
| 3528. | —(NMeSO₂)-2-thienyl | (diethylamino)ethylamino | NH₂ |
| 3529. | —(NMeSO₂)-2-thienyl | 3,5-dimethylpiperazin-1-yl | NH₂ |
| 3530. | —(NMeSO₂)-2-thienyl | (4-piperidylmethyl)amino | NH₂ |
| 3531. | —(NMeSO₂)-2-thienyl | (2-methylbutyl)amino | NH₂ |
| 3532. | —(NMeSO₂)-2-thienyl | 2-(dimethylamino)ethoxy | NH₂ |
| 3533. | —(NMeSO₂)-2-thienyl | 2-(methylamino)ethoxy | NH₂ |
| 3534. | —(NMeSO₂)-2-thienyl | ((2R)pyrrolidin-2-yl)methoxy | NH₂ |
| 3535. | —(NMeSO₂)-2-thienyl | ((2R)-1-methylpyrrolidin-2-yl)methoxy | NH₂ |
| 3536. | —(NMeSO₂)-2-thienyl | 2-(piperid-1-yl)ethoxy | NH₂ |
| 3537. | —(NMeSO₂)-2-thienyl | 2-(piperazin-1-yl)ethoxy | NH₂ |
| 3538. | —(NMeSO₂)-2-thienyl | 2-(morpholin-4-yl)ethoxy | NH₂ |
| 3539. | —(NMeSO₂)-2-pyridyl | 2-methylthio | H |
| 3540. | —(NMeSO₂)-2-pyridyl | 2-(methylsulfonyl) | H |
| 3541. | —(NMeSO₂)-2-pyridyl | cyclopropylmethylamino | H |
| 3542. | —(NMeSO₂)-2-pyridyl | 3-hydroxypropylamino | H |
| 3543. | —(NMeSO₂)-2-pyridyl | 2-(1-piperidinyl)ethylamino | H |
| 3544. | —(NMeSO₂)-2-pyridyl | 2-(1-pyrrolidinyl)ethylamino | H |
| 3545. | —(NMeSO₂)-2-pyridyl | 2-(4-morpholinyl)ethylamino | H |
| 3546. | —(NMeSO₂)-2-pyridyl | 3-(1-piperidinyl)propylamino | H |
| 3547. | —(NMeSO₂)-2-pyridyl | 3-(1-pyrrolidinyl)propylamino | H |
| 3548. | —(NMeSO₂)-2-pyridyl | 3-(4-morpholinyl)propylamino | H |
| 3549. | —(NMeSO₂)-2-pyridyl | N-methyl-N-(2-piperid-1-ylethyl)amino | H |
| 3550. | —(NMeSO₂)-2-pyridyl | N-methyl-N-(2-pyrrolidin-1-ylethyl)amino | H |
| 3551. | —(NMeSO₂)-2-pyridyl | N-methyl-N-(2-morpholin-4-ylethyl)amino | H |
| 3552. | —(NMeSO₂)-2-pyridyl | ((2S)-2-amino-3-phenylpropyl)amino | H |
| 3553. | —(NMeSO₂)-2-pyridyl | 4-methylpiperazinylamino | H |
| 3554. | —(NMeSO₂)-2-pyridyl | 4-methylpiperazinyl | H |
| 3555. | —(NMeSO₂)-2-pyridyl | 3-aminopyrrolidinyl | H |
| 3556. | —(NMeSO₂)-2-pyridyl | (diethylamino)ethylamino | H |

TABLE 6-continued

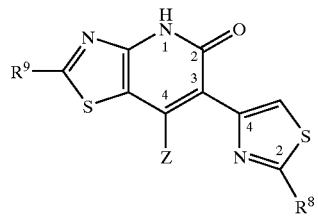

| # | R⁸ | R⁹ | Z |
|---|---|---|---|
| 3557. | —(NMeSO₂)-2-pyridyl | 3,5-dimethylpiperazin-1-yl | H |
| 3558. | —(NMeSO₂)-2-pyridyl | (4-piperidylmethyl)amino | H |
| 3559. | —(NMeSO₂)-2-pyridyl | (2-methylbutyl)amino | H |
| 3560. | —(NMeSO₂)-2-pyridyl | 2-(dimethylamino)ethoxy | H |
| 3561. | —(NMeSO₂)-2-pyridyl | 2-(methylamino)ethoxy | H |
| 3562. | —(NMeSO₂)-2-pyridyl | ((2R)pyrrolidin-2-yl)methoxy | H |
| 3563. | —(NMeSO₂)-2-pyridyl | ((2R)-1-methylpyrrolidin-2-yl)methoxy | H |
| 3564. | —(NMeSO₂)-2-pyridyl | 2-(piperid-1-yl)ethoxy | H |
| 3565. | —(NMeSO₂)-2-pyridyl | 2-(piperazin-1-yl)ethoxy | H |
| 3566. | —(NMeSO₂)-2-pyridyl | 2-(morpholin-4-yl)ethoxy | H |
| 3567. | —(NMeSO₂)-2-pyridyl | 2-methylthio | NH₂ |
| 3568. | —(NMeSO₂)-2-pyridyl | 2-(methylsulfonyl) | NH₂ |
| 3569. | —(NMeSO₂)-2-pyridyl | cyclopropylmethylamino | NH₂ |
| 3570. | —(NMeSO₂)-2-pyridyl | 3-hydroxypropylamino | NH₂ |
| 3571. | —(NMeSO₂)-2-pyridyl | 2-(1-piperidinyl)ethylamino | NH₂ |
| 3572. | —(NMeSO₂)-2-pyridyl | 2-(1-pyrrolidinyl)ethylamino | NH₂ |
| 3573. | —(NMeSO₂)-2-pyridyl | 2-(4-morpholinyl)ethylamino | NH₂ |
| 3574. | —(NMeSO₂)-2-pyridyl | 3-(1-piperidinyl)propylamino | NH₂ |
| 3575. | —(NMeSO₂)-2-pyridyl | 3-(1-pyrrolidinyl)propylamino | NH₂ |
| 3576. | —(NMeSO₂)-2-pyridyl | 3-(4-morpholinyl)propylamino | NH₂ |
| 3577. | —(NMeSO₂)-2-pyridyl | N-methyl-N-(2-piperid-1-ylethyl)amino | NH₂ |
| 3578. | —(NMeSO₂)-2-pyridyl | N-methyl-N-(2-pyrrolidin-1-ylethyl)amino | NH₂ |
| 3579. | —(NMeSO₂)-2-pyridyl | N-methyl-N-(2-morpholin-4-ylethyl)amino | NH₂ |
| 3580. | —(NMeSO₂)-2-pyridyl | ((2S)-2-amino-3-phenylpropyl)amino | NH₂ |
| 3581. | —(NMeSO₂)-2-pyridyl | 4-methylpiperazinylamino | NH₂ |
| 3582. | —(NMeSO₂)-2-pyridyl | 4-methylpiperazinyl | NH₂ |
| 3583. | —(NMeSO₂)-2-pyridyl | 3-aminopyrrolidinyl | NH₂ |
| 3584. | —(NMeSO₂)-2-pyridyl | (diethylamino)ethylamino | NH₂ |
| 3585. | —(NMeSO₂)-2-pyridyl | 3,5-dimethylpiperazin-1-yl | NH₂ |
| 3566. | —(NMeSO₂)-2-pyridyl | (4-piperidylmethyl)amino | NH₂ |
| 3587. | —(NMeSO₂)-2-pyridyl | (2-methylbutyl)amino | NH₂ |
| 3588. | —(NMeSO₂)-2-pyridyl | 2-(dimethylamino)ethoxy | NH₂ |
| 3589. | —(NMeSO₂)-2-pyridyl | 2-(methylamino)ethoxy | NH₂ |
| 3590. | —(NMeSO₂)-2-pyridyl | ((2R)pyrrolidin-2-yl)methoxy | NH₂ |
| 3591. | —(NMeSO₂)-2-pyridyl | ((2R)-1-methylpyrrolidin-2-yl)methoxy | NH₂ |
| 3592. | —(NMeSO₂)-2-pyridyl | 2-(piperid-1-yl)ethoxy | NH₂ |
| 3593. | —(NMeSO₂)-2-pyridyl | 2-(piperazin-1-yl)ethoxy | NH₂ |
| 3594. | —(NMeSO₂)-2-pyridyl | 2-(morpholin-4-yl)ethoxy | NH₂ |
| 3595. | —(NMeSO₂)-3-pyridyl | 2-methylthio | H |
| 3596. | —(NMeSO₂)-3-pyridyl | 2-(methylsulfonyl) | H |
| 3597. | —(NMeSO₂)-3-pyridyl | cyclopropylmethylamino | H |
| 3598. | —(NMeSO₂)-3-pyridyl | 3-hydroxypropylamino | H |
| 3599. | —(NMeSO₂)-3-pyridyl | 2-(1-piperidinyl)ethylamino | H |
| 3600. | —(NMeSO₂)-3-pyridyl | 2-(1-pyrrolidinyl)ethylamino | H |
| 3601. | —(NMeSO₂)-3-pyridyl | 2-(4-morpholinyl)ethylamino | H |
| 3602. | —(NMeSO₂)-3-pyridyl | 3-(1-piperidinyl)propylamino | H |
| 3603. | —(NMeSO₂)-3-pyridyl | 3-(1-pyrrolidinyl)propylamino | H |
| 3604. | —(NMeSO₂)-3-pyridyl | 3-(4-morpholinyl)propylamino | H |
| 3605. | —(NMeSO₂)-3-pyridyl | N-methyl-N-(2-piperid-1-ylethyl)amino | H |
| 3606. | —(NMeSO₂)-3-pyridyl | N-methyl-N-(2-pyrrolidin-1-ylethyl)amino | H |
| 3607. | —(NMeSO₂)-3-pyridyl | N-methyl-N-(2-morpholin-4-ylethyl)amino | H |
| 3608. | —(NMeSO₂)-3-pyridyl | ((2S)-2-amino-3-phenylpropyl)amino | H |
| 3609. | —(NMeSO₂)-3-pyridyl | 4-methylpiperazinylamino | H |
| 3610. | —(NMeSO₂)-3-pyridyl | 4-methylpiperazinyl | H |
| 3611. | —(NMeSO₂)-3-pyridyl | 3-aminopyrrolidinyl | H |
| 3612. | —(NMeSO₂)-3-pyridyl | (diethylamino)ethylamino | H |
| 3613. | —(NMeSO₂)-3-pyridyl | 3,5-dimethylpiperazin-1-yl | H |
| 3614. | —(NMeSO₂)-3-pyridyl | (4-piperidylmethyl)amino | H |
| 3615. | —(NMeSO₂)-3-pyridyl | (2-methylbutyl)amino | H |
| 3616. | —(NMeSO₂)-3-pyridyl | 2-(dimethylamino)ethoxy | H |
| 3617. | —(NMeSO₂)-3-pyridyl | 2-(methylamino)ethoxy | H |
| 3618. | —(NMeSO₂)-3-pyridyl | ((2R)pyrrolidin-2-yl)methoxy | H |
| 3619. | —(NMeSO₂)-3-pyridyl | ((2R)-1-methylpyrrolidin-2-yl)methoxy | H |
| 3620. | —(NMeSO₂)-3-pyridyl | 2-(piperid-1-yl)ethoxy | H |
| 3621. | —(NMeSO₂)-3-pyridyl | 2-(piperazin-1-yl)ethoxy | H |

TABLE 6-continued

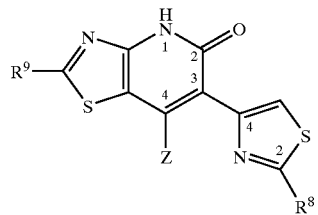

| # | R8 | R9 | Z |
|---|----|----|---|
| 3622. | —(NMeSO₂)-3-pyridyl | 2-(morpholin-4-yl)ethoxy | H |
| 3623. | —(NMeSO₂)-3-pyridyl | 2-methylthio | NH₂ |
| 3624. | —(NMeSO₂)-3-pyridyl | 2-(methylsulfonyl) | NH₂ |
| 3625. | —(NMeSO₂)-3-pyridyl | cyclopropylmethylamino | NH₂ |
| 3626. | —(NMeSO₂)-3-pyridyl | 3-hydroxypropylamino | NH₂ |
| 3627. | —(NMeSO₂)-3-pyridyl | 2-(1-piperidinyl)ethylamino | NH₂ |
| 3628. | —(NMeSO₂)-3-pyridyl | 2-(1-pyrrolidinyl)ethylamino | NH₂ |
| 3629. | —(NMeSO₂)-3-pyridyl | 2-(4-morpholinyl)ethylamino | NH₂ |
| 3630. | —(NMeSO₂)-3-pyridyl | 3-(1-piperidinyl)propylamino | NH₂ |
| 3631. | —(NMeSO₂)-3-pyridyl | 3-(1-pyrrolidinyl)propylamino | NH₂ |
| 3632. | —(NMeSO₂)-3-pyridyl | 3-(4-morpholinyl)propylamino | NH₂ |
| 3633. | —(NMeSO₂)-3-pyridyl | N-methyl-N-(2-piperid-1-ylethyl)amino | NH₂ |
| 3634. | —(NMeSO₂)-3-pyridyl | N-methyl-N-(2-pyrrolidin-1-ylethyl)amino | NH₂ |
| 3635 | —(NMeSO₂)-3-pyridyl | N-methyl-N-(2-morpholin-4-ylethyl)amino | NH₂ |
| 3636. | —(NMeSO₂)-3-pyridyl | ((2S)-2-amino-3-phenylpropyl)amino | NH₂ |
| 3637. | —(NMeSO₂)-3-pyridyl | 4-methylpiperazinylamino | NH₂ |
| 3638. | —(NMeSO₂)-3-pyridyl | 4-methylpiperazinyl | NH₂ |
| 3639. | —(NMeSO₂)-3-pyridyl | 3-aminopyrrolidinyl | NH₂ |
| 3640. | —(NMeSO₂)-3-pyridyl | (diethylamino)ethylamino | NH₂ |
| 3641. | —(NMeSO₂)-3-pyridyl | 3,5-dimethylpiperazin-1-yl | NH₂ |
| 3642. | —(NMeSO₂)-3-pyridyl | (4-piperidylmethyl)amino | NH₂ |
| 3643. | —(NMeSO₂)-3-pyridyl | (2-methylbutyl)amino | NH₂ |
| 3644. | —(NMeSO₂)-3-pyridyl | 2-(dimethylamino)ethoxy | NH₂ |
| 3645. | —(NMeSO₂)-3-pyridyl | 2-(methylamino)ethoxy | NH₂ |
| 3646. | —(NMeSO₂)-3-pyridyl | ((2R)pyrrolidin-2-yl)methoxy | NH₂ |
| 3647. | —(NMeSO₂)-3-pyridyl | ((2R)-1-methylpyrrolidin-2-yl)methoxy | NH₂ |
| 3648. | —(NMeSO₂)-3-pyridyl | 2-(piperid-1-yl)ethoxy | NH₂ |
| 3649. | —(NMeSO₂)-3-pyridyl | 2-(piperazin-1-yl)ethoxy | NH₂ |
| 3650. | —(NMeSO₂)-3-pyridyl | 2-(morpholin-4-yl)ethoxy | NH₂ |
| 3651. | —(NMeSO₂)-4-pyridyl | 2-methylthio | H |
| 3652. | —(NMeSO₂)-4-pyridyl | 2-(methylsulfonyl) | H |
| 3653. | —(NMeSO₂)-4-pyridyl | cyclopropylmethylamino | H |
| 3654. | —(NMeSO₂)-4-pyridyl | 3-hydroxypropylamino | H |
| 3655. | —(NMeSO₂)-4-pyridyl | 2-(1-piperidinyl)ethylamino | H |
| 3656. | —(NMeSO₂)-4-pyridyl | 2-(1-pyrrolidinyl)ethylamino | H |
| 3657. | —(NMeSO₂)-4-pyridyl | 2-(4-morpholinyl)ethylamino | H |
| 3658. | —(NMeSO₂)-4-pyridyl | 3-(1-piperidinyl)propylamino | H |
| 3659. | —(NMeSO₂)-4-pyridyl | 3-(1-pyrrolidinyl)propylamino | H |
| 3660. | —(NMeSO₂)-4-pyridyl | 3-(4-morpholinyl)propylamino | H |
| 3661. | —(NMeSO₂)-4-pyridyl | N-methyl-N-(2-piperid-1-ylethyl)amino | H |
| 3662. | —(NMeSO₂)-4-pyridyl | N-methyl-N-(2-pyrrolidin-1-ylethyl)amino | H |
| 3663. | —(NMeSO₂)-4-pyridyl | N-methyl-N-(2-morpholin-4-ylethyl)amino | H |
| 3664. | —(NMeSO₂)-4-pyridyl | ((2S)-2-amino-3-phenylpropyl)amino | H |
| 3665. | —(NMeSO₂)-4-pyridyl | 4-methylpiperazinylamino | H |
| 3666. | —(NMeSO₂)-4-pyridyl | 4-methylpiperazinyl | H |
| 3667. | —(NMeSO₂)-4-pyridyl | 3-aminopyrrolidinyl | H |
| 3668. | —(NMeSO₂)-4-pyridyl | (diethylamino)ethylamino | H |
| 3669. | —(NMeSO₂)-4-pyridyl | 3,5-dimethylpiperazin-1-yl | H |
| 3670. | —(NMeSO₂)-4-pyridyl | (4-piperidylmethyl)amino | H |
| 3671. | —(NMeSO₂)-4-pyrioyl | (2-methylbutyl)amino | H |
| 3672. | —(NMeSO₂)-4-pyridyl | 2-(dimethylamino)ethoxy | H |
| 3673. | —(NMeSO₂)-4-pyridyl | 2-(methylamino)ethoxy | H |
| 3674. | —(NMeSO₂)-4-pyridyl | ((2R)pyrrolidin-2-yl)methoxy | H |
| 3675. | —(NMeSO₂)-4-pyridyl | ((2R)-1-methylpyrrolidin-2-yl)methoxy | H |
| 3676. | —(NMeSO₂)-4-pyridyl | 2-(piperid-1-yl)ethoxy | H |
| 3677. | —(NMeSO₂)-4-pyridyl | 2-(piperazin-1-yl)ethoxy | H |
| 3678. | —(NMeSO₂)-4-pyridyl | 2-(morpholin-4-yl)ethoxy | H |
| 3679. | —(NMeSO₂)-4-pyridyl | 2-methylthio | NH₂ |
| 3680. | —(NMeSO₂)-4-pyridyl | 2-(methylsulfonyl) | NH₂ |
| 3681. | —(NMeSO₂)-4-pyridyl | cyclopropylmethylamino | NH₂ |
| 3682. | —(NMeSO₂)-4-pyridyl | 3-hydroxypropylamino | NH₂ |
| 3683. | —(NMeSO₂)-4-pyridyl | 2-(1-piperidinyl)ethylamino | NH₂ |
| 3684. | —(NMeSO₂)-4-pyridyl | 2-(1-pyrrolidinyl)ethylamino | NH₂ |
| 3685. | —(NMeSO₂)-4-pyridyl | 2-(4-morpholinyl)ethylamino | NH₂ |
| 3686. | —(NMeSO₂)-4-pyridyl | 3-(1-piperidinyl)propylamino | NH₂ |

TABLE 6-continued

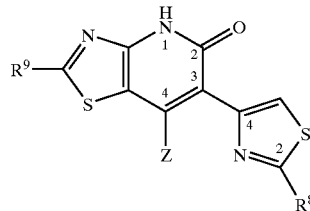

| # | R⁸ | R⁹ | Z |
|---|---|---|---|
| 3687. | —(NMeSO₂)-4-pyridyl | 3-(1-pyrrolidinyl)propylamino | NH₂ |
| 3688. | —(NMeSO₂)-4-pyridyl | 3-(4-morpholinyl)propylamino | NH₂ |
| 3689. | —(NMeSO₂)-4-pyridyl | N-methyl-N-(2-piperid-1-ylethyl)amino | NH₂ |
| 3690. | —(NMeSO₂)-4-pyridyl | N-methyl-N-(2-pyrrolidin-1-ylethyl)amino | NH₂ |
| 3691. | —(NMeSO₂)-4-pyridyl | N-methyl-N-(2-morpholin-4-ylethyl)amino | NH₂ |
| 3692. | —(NMeSO₂)-4-pyridyl | ((2S)-2-amino-3-phenylpropyl)amino | NH₂ |
| 3693. | —(NMeSO₂)-4-pyridyl | 4-methylpiperazinylamino | NH₂ |
| 3694. | —(NMeSO₂)-4-pyridyl | 4-methylpiperazinyl | NH₂ |
| 3695. | —(NMeSO₂)-4-pyridyl | 3-aminopyrrolidinyl | NH₂ |
| 3696. | —(NMeSO₂)-4-pyridyl | (diethylamino)ethylamino | NH₂ |
| 3697. | —(NMeSO₂)-4-pyridyl | 3,5-dimethylpiperazin-1-yl | NH₂ |
| 3698. | —(HMeSO₂) | (4-piperidylmethyl)amino | NH₂ |
| 3699. | —(NMeSO₂)-4-pyridyl | (2-methylbutyl)amino | NH₂ |
| 3700. | —(NMeSO₂)-4-pyridyl | 2-(dimethylamino)ethoxy | NH₂ |
| 3701. | —(NMeSO₂)-4-pyridyl | 2-(methylamino)ethoxy | NH₂ |
| 3702. | —(NMeSO₂)-4-pyridyl | ((2R)pyrrolidin-2-yl)methoxy | NH₂ |
| 3703. | —(NMeSO₂)-4-pyridyl | ((2R)-1-methylpyrrolidin-2-yl)methoxy | NH₂ |
| 3704. | —(NMeSO₂)-4-pyridyl | 2-(piperid-1-yl)ethoxy | NH₂ |
| 3705. | —(NMeSO₂)-4-pyridyl | 2-(piperazin-1-yl)ethoxy | NH₂ |
| 3706. | —(NMeSO₂)-4-pyridyl | 2-(morpholin-4-yl)ethoxy | NH₂ |

TABLE 7

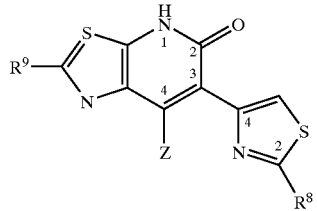

| # | R⁸ | R⁹ | Z |
|---|---|---|---|
| 3707. | 4-pyridyl | 2-methylthio | H |
| 3708. | 4-pyridyl | 2-(methylsulfonyl) | H |
| 3709. | 4-pyridyl | cyclopropylmethylamino | H |
| 3710. | 4-pyridyl | 3-hydroxypropylamino | H |
| 3711. | 4-pyridyl | 2-(1-piperidinyl)ethylamino | H |
| 3712. | 4-pyridyl | 2-(1-pyrrolidinyl)ethylamino | H |
| 3713. | 4-pyridyl | 2-(4-morpholinyl)ethylamino | H |
| 3714. | 4-pyridyl | 3-(1-piperidinyl)propylamino | H |
| 3715. | 4-pyridyl | 3-(1-pyrrolidinyl)propylamino | H |
| 3716. | 4-pyridyl | 3-(4-morpholinyl)propylamino | H |
| 3717. | 4-pyridyl | N-methyl-N-(2-piperid-1-ylethyl)amino | H |
| 3718. | 4-pyridyl | N-methyl-N-(2-pyrrolidin-1-ylethyl)amino | H |
| 3719. | 4-pyridyl | N-methyl-N-(2-morpholin-4-ylethyl)amino | H |
| 3720. | 4-pyridyl | ((2S)-2-amino-3-phenylpropyl)amino | H |
| 3721. | 4-pyridyl | 4-methylpiperazinylamino | H |
| 3722. | 4-pyridyl | 4-methylpiperazinyl | H |
| 3723. | 4-pyridyl | 3-aminopyrrolidinyl | H |
| 3724. | 4-pyridyl | (diethylamino)ethylamino | H |
| 3725. | 4-pyridyl | 3,5-dimethylpiperazin-1-yl | H |
| 3726. | 4-pyridyl | (4-piperidylmethyl)amino | H |
| 3727. | 4-pyridyl | (2-methylbutyl)amino | H |
| 3728. | 4-pyridyl | 2-(dimethylamino)ethoxy | N |

TABLE 7-continued

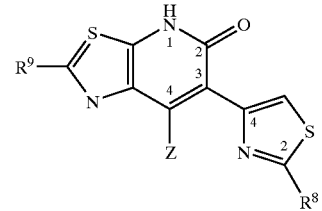

| # | R⁸ | R⁹ | Z |
|---|---|---|---|
| 3729. | 4-pyridyl | 2-(methylamino)ethoxy | H |
| 3730. | 4-pyridyl | ((2R)pyrrolidin-2-yl)methoxy | H |
| 3731. | 4-pyridyl | ((2R)-1-methylpyrrolidin-2-yl)methoxy | H |
| 3732. | 4-pyridyl | 2-(piperid-1-yl)ethoxy | H |
| 3733. | 4-pyridyl | 2-(piperazin-1-yl)ethoxy | H |
| 3734. | 4-pyridyl | 2-(morpholin-4-yl)ethoxy | H |
| 3735. | 4-pyridyl | 2-methylthio | NH₂ |
| 3736. | 4-pyridyl | 2-(methylsulfonyl) | NH₂ |
| 3737. | 4-pyridyl | cyclopropylmethylamino | NH₂ |
| 3738. | 4-pyridyl | 3-hydroxypropylamino | NH₂ |
| 3739. | 4-pyridyl | 2-(1-piperidinyl)ethylamino | NH₂ |
| 3740. | 4-pyridyl | 2-(1-pyrrolidinyl)ethylamino | NH₂ |
| 3741. | 4-pyridyl | 2-(4-morpholinyl)ethylamino | NH₂ |
| 3742. | 4-pyridyl | 3-(1-piperidinyl)propylamino | NH₂ |
| 3743. | 4-pyridyl | 3-(1-pyrrolidinyl)propylamino | NH₂ |
| 3744. | 4-pyridyl | 3-(4-morpholinyl)propylamino | NH₂ |
| 3745. | 4-pyridyl | N-methyl-N-(2-piperid-1-ylethyl)amino | NH₂ |
| 3746. | 4-pyridyl | N-methyl-N-(2-pyrrolidin-1-ylethyl)amino | NH₂ |
| 3747. | 4-pyridyl | N-methyl-N-(2-morpholin-4-ylethyl)amino | NH₂ |
| 3748. | 4-pyridyl | ((2S)-2-amino-3-phenylpropyl)amino | NH₂ |
| 3749. | 4-pyridyl | 4-methylpiperazinylamino | NH₂ |

TABLE 7-continued

| # | R⁸ | R⁹ | Z |
|---|---|---|---|
| 3750. | 4-pyridyl | 4-methylpiperazinyl | NH₂ |
| 3751. | 4-pyridyl | 3-aminopyrrolidinyl | NH₂ |
| 3752. | 4-pyridyl | (diethylamino)ethylamino | NH₂ |
| 3753. | 4-pyridyl | 3-5-dimethylpiperazin-1-yl | NH₂ |
| 3754. | 4-pyridyl | (4-piperidylmethyl)amino | NH₂ |
| 3755. | 4-pyridyl | (2-methylbutyl)amino | NH₂ |
| 3756. | 4-pyridyl | 2-(dimethylamino)ethoxy | NH₂ |
| 3757. | 4-pyridyl | 2-(methylamino)ethoxy | NH₂ |
| 3758. | 4-pyridyl | ((2R)-pyrrolidin-2-yl)methoxy | NH₂ |
| 3759. | 4-pyridyl | ((2R)-1-methylpyrrolidin-2-yl)methoxy | NH₂ |
| 3760. | 4-pyridyl | 2-(piperid-1-yl)ethoxy | NH₂ |
| 3761. | 4-pyridyl | 2-(piperazin-1-yl)ethoxy | NH₂ |
| 3762. | 4-pyridyl | 2-(morpholin-4-yl)ethoxy | NH₂ |
| 3763. | —(CH₂SO₂)-phenyl | 2-methylthio | H |
| 3764. | —(CH₂SO₂)-phenyl | 2-(methylsulfonyl) | H |
| 3765. | —(CH₂SO₂)-phenyl | cyclopropylmethylamino | H |
| 3766. | —(CH₂SO₂)-phenyl | 3-hydroxypropylamino | H |
| 3767. | —(CH₂SO₂)-phenyl | 2-(1-piperidinyl)ethylamino | H |
| 3768. | —(CH₂SO₂)-phenyl | 2-(1-pyrrolidinyl)ethylamino | H |
| 3769. | —(CH₂SO₂)-phenyl | 2-(4-morpholinyl)ethylamino | H |
| 3770. | —(CH₂SO₂)-phenyl | 3-(1-piperidinyl)propylamino | H |
| 3771. | —(CH₂SO₂)-phenyl | 3-(1-pyrrolidinyl)propylamino | H |
| 3772. | —(CH₂SO₂)-phenyl | 3-(4-morpholinyl)propylamino | H |
| 3773. | —(CH₂SO₂)-phenyl | N-methyl-N-(2-piperid-1-ylethyl)amino | H |
| 3774. | —(CH₂SO₂)-phenyl | N-methyl-N-(2-pyrrolidin-1-ylethyl)amino | H |
| 3775. | —(CH₂SO₂)-phenyl | N-methyl-N-(2-morpholin-4-ylethyl)amino | H |
| 3776. | —(CH₂SO₂)-phenyl | ((2S)-2-amino-3-phenylpropyl)amino | H |
| 3777. | —(CH₂SO₂)-phenyl | 4-methylpiperazinylamino | H |
| 3778. | —(CH₂SO₂)-phenyl | 4-methylpiperazinyl | H |
| 3779. | —(CH₂SO₂)-phenyl | 3-aminopyrrolidinyl | H |
| 3780. | —(CH₂SO₂)-phenyl | (diethylamino)ethylamino | H |
| 3781. | —(CH₂SO₂)-phenyl | 3-5-dimethylpiperazin-1-yl | H |
| 3782. | —(CH₂SO₂)-phenyl | (4-piperidylmethyl)amino | H |
| 3783. | —(CH₂SO₂)-phenyl | (2-methylbutyl)amino | H |
| 3784. | —(CH₂SO₂)-phenyl | 2-(dimethylamino)ethoxy | H |
| 3785. | —(CH₂SO₂)-phenyl | 2-(methylamino)ethoxy | H |
| 3786. | —(CH₂SO₂)-phenyl | ((2R)pyrrolidin-2-yl)methoxy | H |
| 3787. | —(CH₂SO₂)-phenyl | ((2R)-1-methylpyrrolidin-2-yl)methoxy | H |
| 3788. | —(CH₂SO₂) phenyl | 2-(piperid-1-yl)ethoxy | H |
| 3789. | —(CH₂SO₂)-phenyl | 2-(piperazin-1-yl)ethoxy | H |
| 3790. | —(CH₂SO₂)-phenyl | 2-(morpholin-4-yl)ethoxy | H |
| 3791. | —(CH₂SO₂)-phenyl | 2-methylthio | NH₂ |
| 3792. | —(CH₂SO₂)-phenyl | 2-(methylsulfonyl) | NH₂ |
| 3793. | —(CH₂SO₂)-phenyl | cyclopropylmethylamino | NH₂ |
| 3794. | —(CH₂SO₂)-phenyl | 3-hydroxypropylamino | NH₂ |
| 3795. | —(CH₂SO₂)-phenyl | 2-(1-piperidinyl)ethylamino | NH₂ |
| 3796. | —(CH₂SO₂)-phenyl | 2-(1-pyrrolidinyl)ethylamino | NH₂ |
| 3797. | —(CH₂SO₂)-phenyl | 2-(4-morpholinyl)ethylamino | NH₂ |
| 3798. | —(CH₂SO₂)-phenyl | 3-(1-piperidinyl)propylamino | NH₂ |
| 3799. | —(CH₂SO₂)-phenyl | 3-(1-pyrrolidinyl)propylamino | NH₂ |
| 3800. | —(CH₂SO₂)-phenyl | 3-(4-morpholinyl)propylamino | NH₂ |
| 3801. | —(CH₂SO₂)-phenyl | N-methyl-N-(2-piperid-1-ylethyl)amino | NH₂ |
| 3802. | —(CH₂SO₂)-phenyl | N-methyl-N-(2-pyrrolidin-1-ylethyl)amino | NH₂ |
| 3803. | —(CH₂SO₂)-phenyl | N-methyl-N-(2-morpholin-4-ylethyl)amino | NH₂ |
| 3804. | —(CH₂SO₂)-phenyl | ((2S)-2-amino-3-phenylpropyl)amino | NH₂ |
| 3805. | —(CH₂SO₂)-phenyl | 4-methylpiperazinylamino | NH₂ |
| 3806. | —(CH₂SO₂)-phenyl | 4-methylpiperazinyl | NH₂ |
| 3807. | —(CH₂SO₂)-phenyl | 3-aminopyrrolidinyl | NH₂ |
| 3808. | —(CH₂SO₂)-phenyl | (diethylamino)ethylamino | NH₂ |
| 3809. | —(CH₂SO₂)-phenyl | 3,5-dimethylpiperazinyl-1-yl | NH₂ |
| 3810. | —(CH₂SO₂) phenyl | (4-piperidylmethyl)amino | NH₂ |
| 3811. | —(CH₂SO₂)-phenyl | (2-methylbutyl)amino | NH₂ |
| 3812. | —(CH₂SO₂)-phenyl | 2-(dimethylamino)ethoxy | NH₂ |
| 3813. | —(CH₂SO₂)-phenyl | 2-(methylamino)ethoxy | NH₂ |
| 3814. | —(CH₂SO₂)-phenyl | ((2R)pyrrolidin-2-yl)methoxy | NH₂ |
| 3815. | —(CH₂SO₂)-phenyl | ((2R)-1-methylpyrrolidin-2-yl)methoxy | NH₂ |
| 3816. | —(CH₂SO₂)-phenyl | 2-(piperid-1-yl)ethoxy | NH₂ |
| 3817. | —(CH₂SO₂)-phenyl | 2-(piperazin-1-yl)ethoxy | NH₂ |
| 3818. | —(CH₂SO₂)-phenyl | 2-(morpholin-4-yl)ethoxy | NH₂ |
| 3819. | —(CH₂SO₂)-2-thienyl | 2-methylthio | H |
| 3820. | —(CH₂SO₂)-2-thienyl | 2-(methylsulfonyl) | H |
| 3821. | —(CH₂SO₂)-2-thienyl | cyclopropylmethylamino | H |
| 3822. | —(CH₂SO₂)-2-thienyl | 3-hydroxypropylamino | H |
| 3823. | —(CH₂SO₂)-2-thienyl | 2-(1-piperidinyl)ethylamino | H |
| 3824. | —(CH₂SO₂)-2-thienyl | 2-(1-pyrrolidinyl)ethylamino | H |
| 3825. | —(CH₂SO₂)-2-thienyl | 2-(4-morpholinyl)ethylamino | H |
| 3826. | —(CH₂SO₂)-2-thienyl | 3-(1-piperidinyl)propylamino | H |
| 3827. | —(CH₂SO₂)-2-thienyl | 3-(1-pyrrolidinyl)propylamino | H |
| 3828. | —(CH₂SO₂)-2-thienyl | 3-(4-morpholinyl)propylamino | H |
| 3829. | —(CH₂SO₂)-2-thienyl | N-methyl-N-(2-piperid-1-ylethyl)amino | H |
| 3830. | —(CH₂SO₂)-2-thienyl | N-methyl-N-(2-pyrrolidin-1-ylethyl)amino | H |
| 3831. | —(CH₂SO₂) 2-thienyl | N-methyl-N-(2-morpholin-4-ylethyl)amino | H |
| 3832. | —(CH₂SO₂)-2-thienyl | ((2S)-2-amino-3-phenylpropyl)amino | H |
| 3833. | —(CH₂SO₂)-2-thienyl | 4-methylpiperazinylamino | H |
| 3834. | —(CH₂SO₂)-2-thienyl | 4-methylpiperazinyl | H |
| 3835. | —(CH₂SO₂)-2-thienyl | 3-aminopyrrolidinyl | H |
| 3836. | —(CH₂SO₂)-2-thienyl | (diethylamino)ethylamino | H |
| 3837. | —(CH₂SO₂)-2-thienyl | 3,5-dimethylpiperazinyl-1-yl | H |
| 3838. | —(CH₂SO₂)-2-thienyl | (4-piperidylmethyl)-amino | H |
| 3839. | —(CH₂SO₂)-2-thienyl | (2-methylbutyl)amino | H |
| 3840. | —(CH₂SO₂)-2-thienyl | 2-(dimethylamino)ethoxy | H |
| 3841. | —(CH₂SO₂)-2-thienyl | 2-(methylamino)ethoxy | H |
| 3842. | —(CH₂SO₂)-2-thienyl | ((2R)pyrrolidin-2-yl)methoxy | H |
| 3843. | —(CH₂SO₂)-2-thienyl | ((2R)-1-methylpyrrolidin-2-yl)methoxy | H |
| 3844. | —(CH₂SO₂)-2-thienyl | 2-(piperid-1-yl)ethoxy | H |
| 3845. | —(CH₂SO₂)-2-thienyl | 2-(piperazin-1-yl)ethoxy | H |
| 3846. | —(CH₂SO₂)-2-thienyl | 2-(morpholin-4-yl)ethoxy | H |
| 3847. | —(CH₂SO₂)-2-thienyl | 2-methylthio | NH₂ |
| 3848. | —(CH₂SO₂)-2-thienyl | 2-(methylsulfonyl) | NH₂ |
| 3849. | —(CH₂SO₂)-2-thienyl | cyclopropylmethylamino | NH₂ |
| 3850. | —(CH₂SO₂)-2-thienyl | 3-hydroxypropylamino | NH₂ |
| 3851. | —(CH₂SO₂)-2-thienyl | 2-(1-piperidinyl)ethylamino | NH₂ |
| 3852. | —(CH₂SO₂)-2-thienyl | 2-(1-pyrrolidinyl)ethylamino | NH₂ |
| 3853. | —(CH₂SO₂)-2-thienyl | 2-(4-morpholinyl)ethylamino | NH₂ |
| 3854. | —(CH₂SO₂)-2-thienyl | 3-(1-piperidinyl)propylamino | NH₂ |
| 3855. | —(CH₂SO₂)-2-thienyl | 3-(1-pyrrolidinyl)propylamino | NH₂ |
| 3856. | —(CH₂SO₂)-2-thienyl | 3-(4-morpholinyl)propylamino | NH₂ |
| 3857. | —(CH₂SO₂)-2-thienyl | N-methyl-N-(2-piperid-1-ylethyl)amino | NH₂ |
| 3858. | —(CH₂SO₂)-2-thienyl | N-methyl-N-(2-pyrrolidin-1-ylethyl)amino | NH₂ |
| 3859. | —(CH₂SO₂)-2-thienyl | N-methyl-N-(2-morpholin-4-ylethyl)amino | NH₂ |

TABLE 7-continued

| # | R⁸ | R⁹ | Z |
|---|---|---|---|
| 3860. | —(CH₂SO₂)-2-thienyl | ((2S)-2-amino-3-phenylpropyl)amino | NH₂ |
| 3861. | —(CH₂SO₂)-2-thienyl | 4-methylpiperazinylamino | NH₂ |
| 3862. | —(CH₂SO₂)-2-thienyl | 4-methylpiperazinyl | NH₂ |
| 3863. | —(CH₂SO₂)-2-thienyl | 3-aminopyrrolidinyl | NH₂ |
| 3864. | —(CH₂SO₂)-2-thienyl | (diethylamino)ethylamino | NH₂ |
| 3865. | —(CH₂SO₂)-2-thienyl | 3,5-dimethylpiperazin-1-yl | NH₂ |
| 3866. | —(CH₂SO₂)-2-thienyl | (4-piperidylmethyl)-amino | NH₂ |
| 3867. | —(CH₂SO₂)-2-thienyl | (2-methylbutyl)amino | NH₂ |
| 3868. | —(CH₂SO₂)-2-thienyl | 2-(dimethylamino)ethoxy | NH₂ |
| 3869. | —(CH₂SO₂)-2-thienyl | 2-(methylamino)ethoxy | NH₂ |
| 3870. | —(CH₂SO₂)-2-thienyl | ((2R)pyrrolidin-2-yl)methoxy | NH₂ |
| 3871. | —(CH₂SO₂)-2-thienyl | ((2R)-1-methylpyrrolidin-2-yl)methoxy | NH₂ |
| 3872. | —(CH₂SO₂)-2-thienyl | 2-(piperid-1-yl)ethoxy | NH₂ |
| 3873. | —(CH₂SO₂)-2-thienyl | 2-(piperazin-1-yl)ethoxy | NH₂ |
| 3874. | —(CH₂SO₂)-2-thienyl | 2-(morpholin-4-yl)ethoxy | NH₂ |
| 3875. | —(CH₂SO₂)-2-pyridyl | 2-methylthio | H |
| 3876. | —(CH₂SO₂)-2-pyridyl | 2-(methylsulfonyl) | H |
| 3877. | —(CH₂SO₂)-2-pyridyl | cyclopropylmethylamino | H |
| 3878. | —(CH₂SO₂)-2-pyridyl | 3-hydroxypropylamino | H |
| 3879. | —(CH₂SO₂)-2-pyridyl | 2-(1-piperidinyl)ethylamino | H |
| 3880. | —(CH₂SO₂)-2-pyridyl | 2-(1-pyrrolidinyl)ethylamino | H |
| 3881. | —(CH₂SO₂)-2-pyridyl | 2-(4-morpholinyl)ethylamino | H |
| 3882. | —(CH₂SO₂)-2-pyridyl | 3-(1-piperidinyl)propylamino | H |
| 3883. | —(CH₂SO₂)-2-pyridyl | 3-(1-pyrrolidinyl)propylamino | H |
| 3884. | —(CH₂SO₂)-2-pyridyl | 3-(4-morpholinyl)propylamino | H |
| 3885. | —(CH₂SO₂)-2-pyridyl | N-methyl-N-(2-piperid-1-ylethyl)amino | H |
| 3886. | —(CH₂SO₂)-2-pyridyl | N-methyl-N-(2-pyrrolidin-1-ylethyl)amino | H |
| 3887. | —(CH₂SO₂)-2-pyridyl | N-methyl-N-(2-morpholin-4-ylethyl)amino | H |
| 3888. | —(CH₂SO₂)-2-pyridyl | ((2S)-2-amino-3-phenylpropyl)amino | H |
| 3889. | —(CH₂SO₂)-2-pyridyl | 4-methylpiperazinylamino | H |
| 3890. | —(CH₂SO₂)-2-pyridyl | 4-methylpiperazinyl | H |
| 3891. | —(CH₂SO₂)-2-pyridyl | 3-aminopyrrolidinyl | H |
| 3892. | —(CH₂SO₂)-2-pyridyl | (diethylamino)ethylamino | H |
| 3893. | —(CH₂SO₂)-2-pyridyl | 3,5-dimethylpiperazin-1-yl | H |
| 3894. | —(CH₂SO₂)-2-pyridyl | (4-piperidylmethyl)-amino | H |
| 3895. | —(CH₂SO₂)-2-pyridyl | (2-methylbutyl)amino | H |
| 3896. | —(CH₂SO₂)-2-pyridyl | 2-(dimethylamino)ethoxy | H |
| 3897. | —(CH₂SO₂)-2-pyridyl | 2-(methylamino)ethoxy | H |
| 3898. | —(CH₂SO₂)-2-pyridyl | ((2R)pyrrolidin-2-yl)methoxy | H |
| 3899. | —(CH₂SO₂)-2-pyridyl | ((2R)-1-methylpyrrolidin-2-yl)methoxy | H |
| 3900. | —(CH₂SO₂)-2-pyridyl | 2-(piperid-1-yl)ethoxy | H |
| 3901. | —(CH₂SO₂)-2-pyridyl | 2-(piperazin-1-yl)ethoxy | H |
| 3902. | —(CH₂SO₂)-2-pyridyl | 2-(morpholin-4-yl)ethoxy | H |
| 3903. | —(CH₂SO₂)-2-pyridyl | 2-methylthio | NH₂ |
| 3904. | —(CH₂SO₂)-2-pyridyl | 2-(methylsulfonyl) | NH₂ |
| 3905. | —(CH₂SO₂)-2-pyridyl | cyclopropylmethylamino | NH₂ |
| 3906. | —(CH₂SO₂)-2-pyridyl | 3-hydroxypropylamino | NH₂ |
| 3907. | —(CH₂SO₂)-2-pyridyl | 2-(1-piperidinyl)ethylamino | NH₂ |
| 3908. | —(CH₂SO₂)-2-pyridyl | 2-(1-pyrrolidinyl)ethylamino | NH₂ |
| 3909. | —(CH₂SO₂)-2-pyridyl | 2-(4-morpholinyl)ethylamino | NH₂ |
| 3910. | —(CH₂SO₂)-2-pyridyl | 3-(1-piperidinyl)propylamino | NH₂ |
| 3911. | —(CH₂SO₂)-2-pyridyl | 3-(1-pyrrolidinyl)propylamino | NH₂ |
| 3912. | —(CH₂SO₂)-2-pyridyl | 3-(4-morpholinyl)propylamino | NH₂ |
| 3913. | —(CH₂SO₂)-2-pyridyl | N-methyl-N-(2-piperid-1-ylethyl)amino | NH₂ |
| 3914. | —(CH₂SO₂)-2-pyridyl | N-methyl-N-(2-pyrrolidin-1-ylethyl)amino | NH₂ |
| 3915. | —(CH₂SO₂)-2-pyridyl | N-methyl-N-(2-morpholin-4-ylethyl)amino | NH₂ |
| 3916. | —(CH₂SO₂)-2-pyridyl | ((2S)-2-amino-3-phenylpropyl)amino | NH₂ |
| 3917. | —(CH₂SO₂)-2-pyridyl | 4-methylpiperazinylamino | NH₂ |
| 3918. | —(CH₂SO₂)-2-pyridyl | 4-methylpiperazinyl | NH₂ |
| 3919. | —(CH₂SO₂)-2-pyridyl | 3-aminopyrrolidinyl | NH₂ |
| 3920. | —(CH₂SO₂)-2-pyridyl | (diethylamino)ethylamino | NH₂ |
| 3921. | —(CH₂SO₂)-2-pyridyl | 3,5-dimethylpiperazin-1-yl | NH₂ |
| 3922. | —(CH₂SO₂)-2-pyridyl | (4-piperidylmethyl)-amino | NH₂ |
| 3923. | —(CH₂SO₂)-2-pyridyl | (2-methylbutyl)amino | NH₂ |
| 3924. | —(CH₂SO₂)-2-pyridyl | 2-(dimethylamino)ethoxy | NH₂ |
| 3925. | —(CH₂SO₂)-2-pyridyl | 2-(methylamino)ethoxy | NH₂ |
| 3926. | —(CH₂SO₂)-2-pyridyl | ((2R)pyrrolidin-2-yl)methoxy | NH₂ |
| 3927. | —(CH₂SO₂)-2-pyridyl | ((2R)-1-methylpyrrolidin-2-yl)methoxy | NH₂ |
| 3928. | —(CH₂SO₂)-2-pyridyl | 2-(piperid-1-yl)ethoxy | NH₂ |
| 3929. | —(CH₂SO₂)-2-pyridyl | 2-(piperazin-1-yl)ethoxy | NH₂ |
| 3930. | —(CH₂SO₂)-2-pyridyl | 2-(morpholin-4-yl)ethoxy | NH₂ |
| 3931. | —(CH₂SO₂)-3-pyridyl | 2-methylthio | H |
| 3932. | —(CH₂SO₂)-3-pyridyl | 2-(methylsulfonyl) | H |
| 3933. | —(CH₂SO₂)-3-pyridyl | cyclopropylmethylamino | H |
| 3934. | —(CH₂SO₂)-3-pyridyl | 3-hydroxypropylamino | H |
| 3935. | —(CH₂SO₂)-3-pyridyl | 2-(1-piperidinyl)ethylamino | H |
| 3936. | —(CH₂SO₂)-3-pyridyl | 2-(1-pyrrolidinyl)ethylamino | H |
| 3937. | —(CH₂SO₂)-3-pyridyl | 2-(4-morpholinyl)ethylamino | H |
| 3938. | —(CH₂SO₂)-3-pyridyl | 3-(1-piperidinyl)propylamino | H |
| 3939. | —(CH₂SO₂)-3-pyridyl | 3-(1-pyrrolidinyl)propylamino | H |
| 3940. | —(CH₂SO₂)-3-pyridyl | 3-(4-morpholinyl)propylamino | H |
| 3941. | —(CH₂SO₂)-3-pyridyl | N-methyl-N-(2-piperid-1-ylethyl)amino | H |
| 3942. | —(CH₂SO₂)-3-pyridyl | N-methyl-N-(2-pyrrolidin-1-ylethyl)amino | H |
| 3943. | —(CH₂SO₂)-3-pyridyl | N-methyl-N-(2-morpholin-4-ylethyl)amino | H |
| 3944. | —(CH₂SO₂)-3-pyridyl | ((2S)-2-amino-3-phenylpropyl)amino | H |
| 3945. | —(CH₂SO₂)-3-pyridyl | 4-methylpiperazinylamino | H |
| 3946. | —(CH₂SO₂)-3-pyridyl | 4-methylpiperazinyl | H |
| 3947. | —(CH₂SO₂)-3-pyridyl | 3-aminopyrrolidinyl | H |
| 3948. | —(CH₂SO₂)-3-pyridyl | (diethylamino)ethylamino | H |
| 3949. | —(CH₂SO₂)-3-pyridyl | 3,5-dimethylpiperazin-1-yl | H |
| 3950. | —(CH₂SO₂)-3-pyridyl | (4-piperidylmethyl)-amino | H |
| 3951. | —(CH₂SO₂)-3-pyridyl | (2-methylbutyl)amino | H |
| 3952. | —(CH₂SO₂)-3-pyridyl | 2-(dimethylamino)ethoxy | H |
| 3953. | —(CH₂SO₂)-3-pyridyl | 2-(methylamino)ethoxy | H |
| 3954. | —(CH₂SO₂)-3-pyridyl | ((2R)pyrrolidin-2-yl)methoxy | H |
| 3955. | —(CH₂SO₂)-3-pyridyl | ((2R)-1-methylpyrrolidin-2-yl)methoxy | H |
| 3956. | —(CH₂SO₂)-3-pyridyl | 2-(piperid-1-yl)ethoxy | H |
| 3957. | —(CH₂SO₂)-3-pyridyl | 2-(piperazin-1-yl)ethoxy | H |
| 3958. | —(CH₂SO₂)-3-pyridyl | 2-(morpholin-4-yl)ethoxy | H |
| 3959. | —(CH₂SO₂)-3-pyridyl | 2-methylthio | NH₂ |
| 3960. | —(CH₂SO₂)-3-pyridyl | 2-(methylsulfonyl) | NH₂ |
| 3961. | —(CH₂SO₂)-3-pyridyl | cyclopropylmethylamino | NH₂ |
| 3962. | —(CH₂SO₂)-3-pyridyl | 3-hydroxypropylamino | NH₂ |
| 3963. | —(CH₂SO₂)-3-pyridyl | 2-(1-piperidinyl)ethylamino | NH₂ |
| 3964. | —(CH₂SO₂)-3-pyridyl | 2-(1-pyrrolidinyl)ethylamino | NH₂ |
| 3965. | —(CH₂SO₂)-3-pyridyl | 2-(4-morpholinyl)ethylamino | NH₂ |
| 3966. | —(CH₂SO₂)-3-pyridyl | 3-(1-piperidinyl)propylamino | NH₂ |
| 3967. | —(CH₂SO₂)-3-pyridyl | 3-(1-pyrrolidinyl)propylamino | NH₂ |
| 3968. | —(CH₂SO₂)-3-pyridyl | 3-(4-morpholinyl)propylamino | NH₂ |
| 3969. | —(CH₂SO₂)-3-pyridyl | N-methyl-N-(2-piperid-1-ylethyl)amino | NH₂ |

TABLE 7-continued

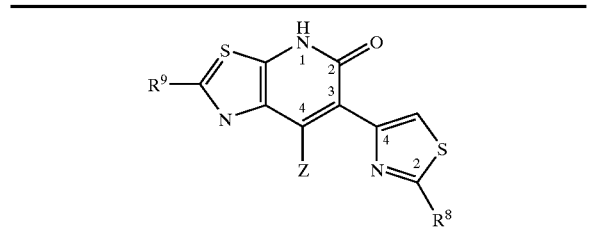

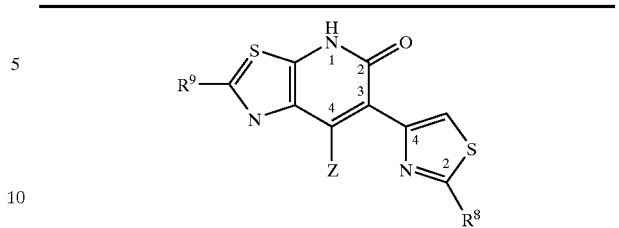

| # | R⁸ | R⁹ | Z |
|---|---|---|---|
| 3970. | —(CH₂SO₂)-3-pyridyl | N-methyl-N-(2-pyrrolidin-1-ylethyl)amino | NH₂ |
| 3971. | —(CH₂SO₂)-3-pyridyl | N-methyl-N-(2-morpholin-4-ylethyl)amino | NH₂ |
| 3972. | —(CH₂SO₂)-3-pyridyl | ((2S)-2-amino-3-phenylpropyl)amino | NH₂ |
| 3973. | —(CH₂SO₂)-3-pyridyl | 4-methylpiperazinylamino | NH₂ |
| 3974. | —(CH₂SO₂)-3-pyridyl | 4-methylpiperazinyl | NH₂ |
| 3975. | —(CH₂SO₂)-3-pyridyl | 3-aminopyrrolidinyl | NH₂ |
| 3976. | —(CH₂SO₂)-3-pyridyl | (diethylamino)ethylamino | NH₂ |
| 3977. | —(CH₂SO₂)-3-pyridyl | 3,5-dimethylpiperazin-1-yl | NH₂ |
| 3978. | —(CH₂SO₂)-3-pyridyl | (4-piperidylmethyl)-amino | NH₂ |
| 3979. | —(CH₂SO₂)-3-pyridyl | (2-methylbutyl)amino | NH₂ |
| 3980. | —(CH₂SO₂)-3-pyridyl | 2-(dimethylamino)ethoxy | NH₂ |
| 3981. | —(CH₂SO₂)-3-pyridyl | 2-(methylamino)ethoxy | NH₂ |
| 3982. | —(CH₂SO₂)-3-pyridyl | ((2R)pyrrolidin-2-yl)methoxy | NH₂ |
| 3983. | —(CH₂SO₂)-3-pyridyl | ((2R)-1-methylpyrrolidin-2-yl)methoxy | NH₂ |
| 3984. | —(CH₂SO₂)-3-pyridyl | 2-(piperid-1-yl)ethoxy | NH₂ |
| 3985. | —(CH₂SO₂)-3-pyridyl | 2-(piperazin-1-yl)ethoxy | NH₂ |
| 3986. | —(CH₂SO₂)-3-pyridyl | 2-(morpholin-4-yl)ethoxy | NH₂ |
| 3987. | —(CH₂SO₂)-4-pyridyl | 2-methylthio | H |
| 3988. | —(CH₂SO₂)-4-pyridyl | 2-(methylsulfonyl) | H |
| 3989. | —(CH₂SO₂)-4-pyridyl | cyclopropylmethylamino | H |
| 3990. | —(CH₂SO₂)-4-pyridyl | 3-hydroxypropylamino | H |
| 3991. | —(CH₂SO₂)-4-pyridyl | 2-(1-piperidinyl)ethylamino | H |
| 3992. | —(CH₂SO₂)-4-pyridyl | 2-(1-pyrrolidinyl)ethylamino | H |
| 3993. | —(CH₂SO₂)-4-pyridyl | 2-(4-morpholinyl)ethylamino | H |
| 3994. | —(CH₂SO₂)-4-pyridyl | 3-(1-piperidinyl)propylamino | H |
| 3995. | —(CH₂SO₂)-4-pyridyl | 3-(1-pyrrolidinyl)propylamino | H |
| 3996. | —(CH₂SO₂)-4-pyridyl | 3-(4-morpholinyl)propylamino | H |
| 3997. | —(CH₂SO₂)-4-pyridyl | N-methyl-N-(2-piperid-1-ylethyl)amino | H |
| 3998. | —(CH₂SO₂)-4-pyridyl | N-methyl-N-(2-pyrrolidin-1-ylethyl)amino | H |
| 3999. | —(CH₂SO₂)-4-pyridyl | N-methyl-N-(2-morpholin-4-ylethyl)amino | H |
| 4000. | —(CH₂SO₂)-4-pyridyl | ((2S)-2-amino-3-phenylpropyl)amino | H |
| 4001. | —(CH₂SO₂)-4-pyridyl | 4-methylpiperazinylamino | H |
| 4002. | —(CH₂SO₂)-4-pyridyl | 4-methylpiperazinyl | H |
| 4003. | —(CH₂SO₂)-4-pyridyl | 3-aminopyrrolidinyl | H |
| 4004. | —(CH₂SO₂)-4-pyridyl | (diethylamino)ethylamino | H |
| 4005. | —(CH₂SO₂)-4-pyridyl | 3,5-dimethylpiperazin-1-yl | H |
| 4006. | —(CH₂SO₂)-4-pyridyl | (4-piperidylmethyl)amino | H |
| 4007. | —(CH₂SO₂)-4-pyridyl | (2-methylbutyl)amino | H |
| 4008. | —(CH₂SO₂)-4-pyridyl | 2-(dimethylamino)ethoxy | H |
| 4009. | —(CH₂SO₂)-4-pyridyl | 2-(methylamino)ethoxy | H |
| 4010. | —(CH₂SO₂)-4-pyridyl | ((2R)pyrrolidin-2-yl)methoxy | H |
| 4011. | —(CH₂SO₂)-4-pyridyl | ((2R)-1-methylpyrrolidin-2-yl)methoxy | H |
| 4012. | —(CH₂SO₂)-4-pyridyl | 2-(piperid-1-yl)ethoxy | H |
| 4013. | —(CH₂SO₂)-4-pyridyl | 2-(piperazin-1-yl)ethoxy | H |
| 4014. | —(CH₂SO₂)-4-pyridyl | 2-(morpholin-4-yl)ethoxy | H |
| 4015. | —(CH₂SO₂)-4-pyridyl | 2-methylthio | NH₂ |
| 4016. | —(CH₂SO₂(-4-pyridyl | 2-(methylsulfonyl) | NH₂ |
| 4017. | —(CH₂SO₂)-4-pyridyl | cyclopropylmethylamino | NH₂ |
| 4018. | —(CH₂SO₂)-4-pyridyl | 3-hydroxypropylamino | NH₂ |
| 4019. | —(CH₂SO₂)-4-pyridyl | 2-(1-piperidinyl)ethylamino | NH₂ |
| 4020. | —(CH₂SO₂)-4-pyridyl | 2-(1-pyrrolidinyl)ethylamino | NH₂ |
| 4021. | —(CH₂SO₂)-4-pyridyl | 2-(4-morpholinyl)ethylamino | NH₂ |
| 4022. | —(CH₂SO₂)-4-pyridyl | 3-(1-piperidinyl)propylamino | NH₂ |
| 4023. | —(CH₂SO₂)-4-pyridyl | 3-(1-pyrrolidinyl)propylamino | NH₂ |
| 4024. | —(CH₂SO₂)-4-pyridyl | 3-(4-morpholinyl)propylamino | NH₂ |
| 4025. | —(CH₂SO₂)-4-pyridyl | N-methyl-N-(2-piperid-1-ylethyl)amino | NH₂ |
| 4026. | —(CH₂SO₂)-4-pyridyl | N-methyl-N-(2-pyrrolidin-1-ylethyl)amino | NH₂ |
| 4027. | —(CH₂SO₂)-4-pyridyl | N-methyl-N-(2-morpholin-4-ylethyl)amino | NH₂ |
| 4028. | —(CH₂SO₂)-4-pyridyl | ((2S)-2-amino-3-phenylpropyl)amino | NH₂ |
| 4029. | —(CH₂SO₂)-4-pyridyl | 4-methylpiperazinylamino | NH₂ |
| 4030. | —(CH₂SO₂)-4-pyridyl | 4-methylpiperazinyl | NH₂ |
| 4031. | —(CH₂SO₂)-4-pyridyl | 3-aminopyrrolidinyl | NH₂ |
| 4032. | —(CH₂SO₂)-4-pyridyl | (diethylamino)ethylamino | NH₂ |
| 4033. | —(CH₂SO₂)-4-pyridyl | 3,5-dimethylpiperazin-1-yl | NH₂ |
| 4034. | —(CH₂s02)-4-pyridyl | (4-piperidylmethyl)amino | NH₂ |
| 4035. | —(CH₂SO₂)-4-pyridyl | (2-methylbutyl)amino | NH₂ |
| 4036. | —(CH₂SO₂)-4-pyridyl | 2-(dimethylamino)ethoxy | NH₂ |
| 4037. | —(CH₂SO₂)-4-pyridyl | 2-(methylamino)ethoxy | NH₂ |
| 4038. | —(CH₂SO₂)-4-pyridyl | ((2R)pyrrolidin-2-yl)methoxy | NH₂ |
| 4039. | —(CH₂SO₂)-4-pyridyl | ((2R)-1-methylpyrrolidin-2-yl)methoxy | NH₂ |
| 4040. | —(CH₂SO₂)-4-pyridyl | 2-(piperid-1-yl)ethoxy | NH₂ |
| 4041. | —(CH₂SO₂)-4-pyridyl | 2-(piperazin-1-yl)ethoxy | NH₂ |
| 4042. | —(CH₂SO₂)-4-pyridyl | 2-(morpholin-4-yl)ethoxy | NH₂ |
| 4043. | —(NMeSO₂)-phenyl | 2-methylthio | H |
| 4044. | —(NMeSO₂)-phenyl | 2-(methylsulfonyl) | H |
| 4045. | —(NMeSO₂)-phenyl | cyclopropylmethylamino | H |
| 4046. | —(NMeSO₂)-phenyl | 3-hydroxypropylamino | H |
| 4047. | —(NMeSO₂)-phenyl | 2-(1-piperidinyl)ethylamino | H |
| 4048. | —(NMeSO₂)-phenyl | 2-(1-pyrrolidinyl)ethylamino | H |
| 4049. | —(NMeSO₂)-phenyl | 2-(4-morpholinyl)ethylamino | H |
| 4050. | —(NMeSO₂)-phenyl | 3-(1-piperidinyl)propylamino | H |
| 4051. | —(NMeSO₂)-phenyl | 3-(1-pyrrolidinyl)propylamino | H |
| 4052. | —(NMeSO₂)-phenyl | 3-(4-morpholinyl)propylamino | H |
| 4053. | —(NMeSO₂)-phenyl | N-methyl-N-(2-piperid-1-ylethyl)amino | H |
| 4054. | —(NMeSO₂)-phenyl | N-methyl-N-(2-pyrrolidin-1-ylethyl)amino | H |
| 4055. | —(NMeSO₂)-phenyl | N-methyl-N-(2-morpholin-4-ylethyl)amino | H |
| 4056. | —(NMeSO₂)-phenyl | ((2S)-2-amino-3-phenylpropyl)amino | H |
| 4057. | —(NMeSO₂)-phenyl | 4-methylpiperazinylamino | H |
| 4058. | —(NMeSO₂)-phenyl | 4-methylpiperazinyl | H |
| 4059. | —(NMeSO₂)-phenyl | 3-aminopyrrolidinyl | H |
| 4060. | —(NMeSO₂)-phenyl | (diethylamino)ethylamino | H |
| 4061. | —(NMeSO₂)-phenyl | 3,5-dimethylpiperazin-1-yl | H |
| 4062. | —(NMeSO₂)-phenyl | (4-piperidylmethyl)amino | H |
| 4063. | —(NMeSO₂)-phenyl | (2-methylbutyl)amino | H |
| 4064. | —(NMeSO₂)-phenyl | 2-(dimethylamino)ethoxy | H |
| 4065. | —(NMeSO₂)-phenyl | 2-(methylamino)ethoxy | H |
| 4066. | —(NMeSO₂)-phenyl | ((2R)pyrrolidin-2-yl)methoxy | H |
| 4067. | —(NMeSO₂)-phenyl | ((2R)-1-methylpyrrolidin-2-yl)methoxy | H |
| 4068. | —(NMeSO₂)-phenyl | 2-(piperid-1-yl)ethoxy | H |
| 4069. | —(NMeSO₂)-phenyl | 2-(piperazin-1-yl)ethoxy | H |
| 4070. | —(NMeSO₂)-phenyl | 2-(morpholin-4-yl)ethoxy | H |
| 4071. | —(NMeSO₂)-phenyl | 2-methylthio | NH₂ |
| 4072. | —(NMeSO₂)-phenyl | 2-(methylsulfonyl) | NH₂ |
| 4073. | —(NMeSO₂)-phenyl | cyclopropylmethylamino | NH₂ |
| 4074. | —(NMeSO₂)-phenyl | 3-hydroxypropylamino | NH₂ |
| 4075. | —(NMeSO₂)-phenyl | 2-(1-piperidinyl)ethylamino | NH₂ |
| 4076. | —(NMeSO₂)-phenyl | 2-(1-pyrrolidinyl)ethylamino | NH₂ |
| 4077. | —(NMeSO₂)-phenyl | 2-(4-morpholinyl)ethylamino | NH₂ |
| 4078. | —(NMeSO₂)-phenyl | 3-(1-piperidinyl)propylamino | NH₂ |
| 4079. | —(NMeSO₂)-phenyl | 3-(1-pyrrolidinyl)propylamino | NH₂ |

TABLE 7-continued

[Structure: thiazolo-pyridinone core with R⁹ at 2-position, Z at 7-position, and 4-thiazolyl substituent at 3-position bearing R⁸ at 2-position of thiazole]

| # | R⁸ | R⁹ | Z |
|---|---|---|---|
| 4080. | —(NMeSO₂)-phenyl | 3-(4-morpholinyl)propylamino | NH₂ |
| 4081. | —(NMeSO₂)-phenyl | N-methyl-N-(2-piperid-1-ylethyl)amino | NH₂ |
| 4082. | —(NMeSO₂)-phenyl | N-methyl-N-(2-pyrrolidin-1-ylethyl)amino | NH₂ |
| 4083. | —(NMeSO₂)-phenyl | N-methyl-N-(2-morpholin-4-ylethyl)amino | NH₂ |
| 4084. | —(NMeSO₂)-phenyl | ((2S)-2-amino-3-phenylpropyl)amino | NH₂ |
| 4085. | —(NMeSO₂)-phenyl | 4-methylpiperazinylamino | NH₂ |
| 4086. | —(NMeSO₂)-phenyl | 4-methylpiperazinyl | NH₂ |
| 4087. | —(NMeSO₂)-phenyl | 3-aminopyrrolidinyl | NH₂ |
| 4088. | —(NMeSO₂)-phenyl | (diethylamino)ethylamino | NH₂ |
| 4089. | —(NMeSO₂)-phenyl | 3,5-dimethylpiperazin-1-yl | NH₂ |
| 4090. | —(NMeSO₂)-phenyl | (4-piperidylmethyl)amino | NH₂ |
| 4091. | —(NMeSO₂)-phenyl | (2-methylbutyl)amino | NH₂ |
| 4092. | —(NMeSO₂)-phenyl | 2-(dimethylamino)ethoxy | NH₂ |
| 4093. | —(NMeSO₂)-phenyl | 2-(methylamino-ethoxy | NH₂ |
| 4094. | —(NMeSO₂)-phenyl | ((2R)pyrrolidin-2-yl)methoxy | NH₂ |
| 4095. | —(NMeSO₂)-phenyl | ((2R)-1-methylpyrrolidin-2-yl)methoxy | NH₂ |
| 4096. | —(NMeSO₂)-phenyl | 2-(piperid-1-yl)ethoxy | NH₂ |
| 4097. | —(NMeSO₂)-phenyl | 2-(piperazin-1-yl)ethoxy | NH₂ |
| 4098. | —(NMeSO₂)-phenyl | 2-(morpholin-4-yl)ethoxy | NH₂ |
| 4099. | —(NMeSO₂)-2-thienyl | 2-methylthio | H |
| 4100. | —(NMeSO₂)-2-thienyl | 2-(methylsulfonyl) | H |
| 4101. | —(NMeSO₂)-2-thienyl | cyclopropylmethylamino | H |
| 4102. | —(NMeSO₂)-2-thienyl | 3-hydroxypropylamino | H |
| 4103. | —(NMeSO₂)-2-thienyl | 2-(1-piperidinyl)ethylamino | H |
| 4104. | —(NMeSO₂)-2-thienyl | 2-(1-pyrrolidinyl)ethylamino | H |
| 4105. | —(NMeSO₂)-2-thienyl | 2-(4-morpholinyl)ethylamino | H |
| 4106. | —(NMeSO₂)-2-thienyl | 3-(1-piperidinyl)propylamino | H |
| 4107. | —(NMeSO₂)-2-thienyl | 3-(1-pyrrolidinyl)propylamino | H |
| 4108. | —(NMeSO₂)-2-thienyl | 3-(4-morpholinyl)propylamino | H |
| 4109. | —(NMeSO₂)-2-thienyl | N-methyl-N-(2-piperid-1-ylethyl)amino | H |
| 4110. | —(NMeSO₂)-2-thienyl | N-methyl-N-(2-pyrrolidin-1-ylethyl)amino | H |
| 4111. | —(NMeSO₂)-2-thienyl | N-methyl-N-(2-morpholin-4-ylethyl)amino | H |
| 4112. | —(NMeSO₂)-2-thienyl | ((2S)-2-amino-3-phenylpropyl)amino | H |
| 4113. | —(NMeSO₂)-2-thienyl | 4-methylpiperazinylamino | H |
| 4114. | —(NMeSO₂)-2-thienyl | 4-methylpiperazinyl | H |
| 4115. | —(NMeSO₂)-2-thienyl | 3-aminopyrrolidinyl | H |
| 4116. | —(NMeSO₂)-2-thienyl | (diethylamino)ethylamino | H |
| 4117. | —(NMeSO₂)-2-thienyl | 3,5-dimethylpiperazin-1-yl | H |
| 4118. | —(NMeSO₂)-2-thienyl | (4-piperidylmethyl)amino | H |
| 4119. | —(NMeSO₂)-2-thienyl | (2-methylbutyl)amino | H |
| 4120. | —(NMeSO₂)-2-thienyl | 2-(dimethylamino)ethoxy | H |
| 4121. | —(NMeSO₂)-2-thienyl | 2-(methylamino)ethoxy | H |
| 4122. | —(NMeSO₂)-2-thienyl | ((2R)pyrrolidin-2-yl)methoxy | H |
| 4123. | —(NMeSO₂)-2-thienyl | ((2R)-1-methylpyrrolidin-2-yl)methoxy | H |
| 4124. | —(NMeSO₂)-2-thienyl | 2-(piperid-1-yl)ethoxy | H |
| 4125. | —(NMeSO₂)-2-thienyl | 2-(piperazin-1-yl)ethoxy | H |
| 4126. | —(NMeSO₂)-2-thienyl | 2-(morpholin-4-yl)ethoxy | H |
| 4127. | —(NMeSO₂)-2-thienyl | 2-methylthio | NH₂ |
| 4128. | —(NMeSO₂)-2-thienyl | 2-(methylsulfonyl) | NH₂ |
| 4129. | —(NMeSO₂)-2-thienyl | cyclopropylmethylamino | NH₂ |
| 4130. | —(NMeSO₂)-2-thienyl | 3-hydroxypropylamino | NH₂ |
| 4131. | —(NMeSO₂)-2-thienyl | 2-(1-piperidinyl)ethylamino | NH₂ |
| 4132. | —(NMeSO₂)-2-thienyl | 2-(1-pyrrolidinyl)ethylamino | NH₂ |
| 4133. | —(NMeSO₂)-2-thienyl | 2-(4-morpholinyl)ethylamino | NH₂ |
| 4134. | —(NMeSO₂)-2-thienyl | 3-(1-piperidinyl)propylamino | NH₂ |
| 4135. | —(NMeSO₂)-2-thienyl | 3-(1-pyrrolidinyl)propylamino | NH₂ |
| 4136. | —(NMeSO₂)-2-thienyl | 3-(4-morpholinyl)propylamino | NH₂ |
| 4137. | —(NMeSO₂)-2-thienyl | N-methyl-N-(2-piperid-1-ylethyl)amino | NH₂ |
| 4138. | —(NMeSO₂)-2-thienyl | N-methyl-N-(2-pyrrolidin-1-ylethyl)amino | NH₂ |
| 4139. | —(NMeSO₂)-2-thienyl | N-methyl-N-(2-morpholin-4-ylethyl)amino | NH₂ |
| 4140. | —(NMeSO₂)-2-thienyl | ((2S)-2-amino-3-phenylpropyl)amino | NH₂ |
| 4141. | —(NMeSO₂)-2-thienyl | 4-methylpiperazinylamino | NH₂ |
| 4142. | —(NMeSO₂)-2-thienyl | 4-methylpiperazinyl | NH₂ |
| 4143. | —(NMeSO₂)-2-thienyl | 3-aminopyrrolidinyl | NH₂ |
| 4144. | —(NMeSO₂)-2-thienyl | (diethylamino)ethylamino | NH₂ |
| 4145. | —(NMeSO₂)-2-thienyl | 3,5-dimethylpiperazin-1-yl | NH₂ |
| 4146. | —(NMeSO₂)-2-thienyl | (4-piperidylmethyl)amino | NH₂ |
| 4147. | —(NMeSO₂)-2-thienyl | (2-methylbutyl)amino | NH₂ |
| 4148. | —(NMeSO₂)-2-thienyl | 2-(dimethylamino)ethoxy | NH₂ |
| 4149. | —(NMeSO₂)-2-thienyl | 2-(methylamino)ethoxy | NH₂ |
| 4150. | —(NMeSO₂)-2-thienyl | ((2R)pyrrolidin-2-yl)methoxy | NH₂ |
| 4151. | —(NMeSO₂)-2-thienyl | ((2R)-1-methylpyrrolidin-2-yl)methoxy | NH₂ |
| 4152. | —(NMeSO₂)-2-thienyl | 2-(piperid-1-yl)ethoxy | NH₂ |
| 4153. | —(NMeSO₂)-2-thienyl | 2-(piperazin-1-yl)ethoxy | NH₂ |
| 4154. | —(NMeSO₂)-2-thienyl | 2-(morpholin-4-yl)ethoxy | NH₂ |
| 4155. | —(NMeSO₂)-2-pyridyl | 2-methylthio | H |
| 4156. | —(NMeSO₂)-2-pyridyl | 2-(methylsulfonyl) | H |
| 4157. | —(NMeSO₂)-2-pyridyl | cyclopropylmethylamino | H |
| 4158. | —(NMeSO₂)-2-pyridyl | 3-hydroxypropylamino | H |
| 4159. | —(NMeSO₂)-2-pyridyl | 2-(1-piperidinyl)ethylamino | H |
| 4160. | —(NMeSO₂)-2-pyridyl | 2-(1-pyrrolidinyl)ethylamino | H |
| 4161. | —(NMeSO₂)-2-pyridyl | 2-(4-morpholinyl)ethylamino | H |
| 4162. | —(NMeSO₂)-2-pyridyl | 3-(1-piperidinyl)propylamino | H |
| 4163. | —(NMeSO₂)-2-pyridyl | 3-(1-pyrrolidinyl)propylamino | H |
| 4164. | —(NMeSO₂)-2-pyridyl | 3-(4-morpholinyl)propylamino | H |
| 4165. | —(NMeSO₂)-2-pyridyl | N-methyl-N-(2-piperid-1-ylethyl)amino | H |
| 4166. | —(NMeSO₂)-2-pyridyl | N-methyl-N-(2-pyrrolidin-1-ylethyl)amino | H |
| 4167. | —(NMeSO₂)-2-pyridyl | N-methyl-N-(2-morpholin-4-ylethyl)amino | H |
| 4168. | —(NMeSO₂)-2-pyridyl | ((2S)-2-amino-3-phenylpropyl)amino | H |
| 4169. | —(NMeSO₂)-2-pyridyl | 4-methylpiperazinylamino | H |
| 4170. | —(NMeSO₂)-2-pyridyl | 4-methylpiperazinyl | H |
| 4171. | —(NMeSO₂)-2-pyridyl | 3-aminopyrrolidinyl | H |
| 4172. | —(NMeSO₂)-2-pyridyl | (diethylamino)ethylamino | H |
| 4173. | —(NMeSO₂)-2-pyridyl | 3,5-dimethylpiperazin-1-yl | H |
| 4174. | —(NMeSO₂)-2-pyridyl | (4-piperidylmethyl)amino | H |
| 4175. | —(NMeSO₂)-2-pyridyl | (2-methylbutyl)amino | H |
| 4176. | —(NMeSO₂)-2-pyridyl | 2-(dimethylamino)ethoxy | H |
| 4177. | —(NMeSO₂)-2-pyridyl | 2-(methylamino)ethoxy | H |
| 4178. | —(NMeSO₂)-2-pyridyl | ((2R)pyrrolidin-2-yl)methoxy | H |
| 4179. | —(NMeSO₂)-2-pyridyl | ((2R)-1-methylpyrrolidin-2-yl)methoxy | H |
| 4180. | —(NMeSO₂)-2-pyridyl | 2-(piperid-1-yl)ethoxy | H |
| 4181. | —(NMeSO₂)-2-pyridyl | 2-(piperazin-1-yl)ethoxy | H |
| 4182. | —(NMeSO₂)-2-pyridyl | 2-(morpholin-4-yl)ethoxy | H |
| 4183. | —(NMeSO₂)-2-pyridyl | 2-methylthio | NH₂ |
| 4184. | —(NMeSO₂)-2-pyridyl | 2-(methylsulfonyl) | NH₂ |
| 4185. | —(NMeSO₂)-2-pyridyl | cyclopropylmethylamino | NH₂ |
| 4186. | —(NMeSO₂)-2-pyridyl | 3-hydroxypropylamino | NH₂ |
| 4187. | —(NMeSO₂)-2-pyridyl | 2-(1-piperidinyl)ethylamino | NH₂ |
| 4198. | —(NMeSO₂)-2-pyridyl | 2-(1-pyrrolidinyl)ethylamino | NH₂ |
| 4189. | —(NMeSO₂)-2-pyridyl | 2-(4-morpholinyl(ethylamino | NH₂ |

TABLE 7-continued

| # | R⁸ | R⁹ | Z |
|---|---|---|---|
| 4190. | —(NMeSO₂)-2-pyridyl | 3-(1-piperidinyl)propylamino | NH₂ |
| 4191. | —(NMeSO₂)-2-pyridyl | 3-(1-pyrrolidinyl)propylamino | NH₂ |
| 4192. | —(NMeSO₂)-2-pyridyl | 3-(4-morpholinyl)propylamino | NH₂ |
| 4193. | —(NMeSO₂)-2-pyridyl | N-methyl-N-(2-piperid-1-ylethyl)amino | NH₂ |
| 4194. | —(NMeSO₂)-2-pyridyl | N-methyl-N-(2-pyrrolidin-1-ylethyl)amino | NH₂ |
| 4195. | —(NMeSO₂)-2-pyridyl | N-methyl-N-(2-morpholin-4-ylethyl)amino | NH₂ |
| 4196. | —(NMeSO₂)-2-pyridyl | ((2S)-2-amino-3-phenylpropyl)amino | NH₂ |
| 4197. | —(NMeSO₂)-2-pyridyl | 4-methylpiperazinylamino | NH₂ |
| 4198. | —(NMeSO₂)-2-pyridyl | 4-methylpiperazinyl | NH₂ |
| 4199. | —(NMeSO₂)-2-pyridyl | 3-aminopyrrolidinyl | NH₂ |
| 4200. | —(NMeSO₂)-2-pyridyl | (diethylamino)ethylamino | NH₂ |
| 4201. | —(NMeSO₂)-2-pyridyl | 3,5-dimethylpiperazin-1-yl | NH₂ |
| 4202. | —(NMeSO₂)-2-pyridyl | (4-piperidylmethyl)amino | NH₂ |
| 4203. | —(NMeSO₂)-2-pyridyl | (2-methylbutyl)amino | NH₂ |
| 4204. | —(NMeSO₂)-2-pyridyl | 2-(dimethylamino)ethoxy | NH₂ |
| 4205. | —(NMeSO₂)-2-pyridyl | 2-(methylamino)ethoxy | NH₂ |
| 4206. | —(NMeSO₂)-2-pyridyl | ((2R)pyrrolidin-2-yl)methoxy | NH₂ |
| 4207. | —(NMeSO₂)-2-pyridyl | ((2R)-1-methylpyrrolidin-2-yl)methoxy | NH₂ |
| 4208. | —(NMeSO₂)-2-pyridyl | 2-(piperid-1-yl)ethoxy | NH₂ |
| 4209. | —(NMeSO₂)-2-pyridyl | 2-(piperazin-1-yl)ethoxy | NH₂ |
| 4210. | —(NMeSO₂)-2-pyridyl | 2-(morpholin-4-yl)ethoxy | NH₂ |
| 4211. | —(NMeSO₂)-3-pyridyl | 2-methylthio | H |
| 4212. | —(NMeSO₂)-3-pyridyl | 2-(methylsulfonyl) | H |
| 4213. | —(NMeSO₂)-3-pyridyl | cyclopropylmethylamino | H |
| 4214. | —(NMeSO₂)-3-pyridyl | 3-hydroxypropylamino | H |
| 4215. | —(NMeSO₂)-3-pyridyl | 2-(1-piperidinyl)ethylamino | H |
| 4216. | —(NMeSO₂)-3-pyridyl | 2-(1-pyrrolidinyl)ethylamino | H |
| 4217. | —(NMeSO₂)-3-pyridyl | 2-(4-morpholinyl)ethylamino | H |
| 4218. | —(NMeSO₂)-3-pyridyl | 3-(1-piperidinyl)propylamino | H |
| 4219. | —(NMeSO₂)-3-pyridyl | 3-(1-pyrrolidinyl)propylamino | H |
| 4220. | —(NMeSO₂)-3-pyridyl | 3-(4-morpholinyl)propylamino | H |
| 4221. | —(NMeSO₂)-3-pyridyl | N-methyl-N-(2-piperid-1-ylethyl)amino | H |
| 4222. | —(NMeSO₂)-3-pyridyl | N-methyl-N-(2-pyrrolidin-1-ylethyl)amino | H |
| 4223. | —(NMeSO₂)-3-pyridyl | N-methyl-N-(2-morpholin-4-ylethyl)amino | H |
| 4224. | —(NMeSO₂)-3-pyridyl | ((2S)-2-amino-3-phenylpropyl)amino | H |
| 4225. | —(NMeSO₂)-3-pyridyl | 4-methylpiperazinylamino | H |
| 4226. | —(NMeSO₂)-3-pyridyl | 4-methylpiperazinyl | H |
| 4227. | —(NMeSO₂)-3-pyridyl | 3-aminopyrrolidinyl | H |
| 4228. | —(NMeSO₂) 3-pyridyl | (diethylamino)ethylamino | H |
| 4229. | —(NMeSO₂) 3-pyridyl | 3,5-dimethylpiperazin-1-yl | H |
| 4230. | —(NMeSO₂)-3-pyridyl | (4-piperidylmethyl)amino | H |
| 4231. | —(NMeSO₂)-3-pyridyl | (2-methylbutyl)amino | H |
| 4232. | —(NMeSO₂)-3-pyridyl | 2-(dimethylamino)ethoxy | H |
| 4233. | —(NMeSO₂)-3-pyridyl | 2-(methylamino-ethoxy | H |
| 4234. | —(NMeSO₂)-3-pyridyl | ((2R)pyrrolidin-2-yl)methoxy | H |
| 4235. | —(NMeSO₂)-3-pyridyl | ((2R)-1-methylpyrrolidin-2-yl)methoxy | H |
| 4236. | —(NMeSO₂)-3-pyridyl | 2-(piperid-1-yl)ethoxy | H |
| 4237. | —(NMeSO₂)-3-pyridyl | 2-(piperazin-1-yl)ethoxy | H |
| 4238. | —(NMeSO₂)-3-pyridyl | 2-(morpholin-4-yl)ethoxy | H |
| 4239. | —(NMeSO₂)-3-pyridyl | 2-methylthio | NH₂ |
| 4240. | —(NMeSO₂)-3-pyridyl | 2-(methylsulfonyl) | NH₂ |
| 4241. | —(NMeSO₂)-3-pyridyl | cyclopropylmethylamino | NH₂ |
| 4242. | —(NHeSO₂)-3-pyridyl | 3-hydroxypropylamino | NH₂ |
| 4243. | —(NMeSO₂)-3-pyridyl | 2-(1-piperidinyl)ethylamino | NH₂ |
| 4244. | —(NMeSO₂)-3-pyridyl | 2-(1-pyrrolidinyl)ethylamino | NH₂ |
| 4245. | —(NMeSO₂)-3-pyridyl | 2-(4-morpholinyl)ethylamino | NH₂ |
| 4246. | —(NMeSO₂)-3-pyridyl | 3-(1-piperidinyl)propylamino | NH₂ |
| 4247. | —(NMeSO₂)-3-pyridyl | 3-(1-pyrrolidinyl)propylamino | NH₂ |
| 4248. | —(NMeSO₂)-3-pyridyl | 3-(4-morpholinyl)propylamino | NH₂ |
| 4249. | —(NMeSO₂)-3-pyridyl | N-methyl-N-(2-piperid-1-ylethyl)amino | NH₂ |
| 4250. | —(NMeSO₂)-3-pyridyl | N-methyl-N-(2-pyrrolidin-1-ylethyl)amino | NH₂ |
| 4251. | —(NMeSO₂)-3-pyridyl | N-methyl-N-(2-morpholin-4-ylethyl)amino | NH₂ |
| 4252. | —(NMeSO₂)-3-pyridyl | ((2S)-2-amino-3-phenylpropyl)amino | NH₂ |
| 4253. | —(NMeSO₂)-3-pyridyl | 4-methylpiperazinylamino | NH₂ |
| 4254. | —(NMeSO₂)-3-pyridyl | 4-methylpiperazinyl | NH₂ |
| 4255. | —(NMeSO₂)-3-pyridyl | 3-aminopyrrolidinyl | NH₂ |
| 4256. | —(NHeSO₂)-3-pyridyl | (diethylamino)ethylamino | NH₂ |
| 4257. | —(NMeSO₂)-3-pyridyl | 3,5-dimethylpiperazin-1-yl | NH₂ |
| 4258. | —(NMeSO₂)-3-pyridyl | (4-piperidylmethyl)amino | NH₂ |
| 4259. | —(NMeSO₂)-3-pyridyl | (2-methylbutyl)amino | NH₂ |
| 4260. | —(NMeSO₂)-3-pyridyl | 2-(dimethylamino)ethoxy | NH₂ |
| 4261. | —(NMeSO₂)-3-pyridyl | 2-(methylamino)ethoxy | NH₂ |
| 4262. | —(NMeSO₂)-3-pyridyl | ((2R)pyrrolidin-2-yl)methoxy | NH₂ |
| 4263. | —(NMeSO₂) 3-pyridyl | ((2R)-1-methylpyrrolidin-2-yl)methoxy | NH₂ |
| 4264. | —(NMeSO₂)-3-pyridyl | 2-(piperid-1-yl)ethoxy | NH₂ |
| 4265. | —(NMeSO₂)-3-pyridyl | 2-(piperazin-1-yl)ethoxy | NH₂ |
| 4266. | —(NMeSO₂)-3-pyridyl | 2-(morpholin-4-yl)ethoxy | NH₂ |
| 4267. | —(NMeSO₂)-4-pyridyl | 2-methylthio | H |
| 4268. | —(NNeSO₂)-4-pyridyl | 2-(methylsulfonyl) | H |
| 4269. | —(NMeSO₂)-4-pyridyl | cyclopropylmethylamino | H |
| 4270. | —(NMeSO₂)-4-pyridyl | 3-hydroxypropylamino | H |
| 4271. | —(NMeSO₂)-4-pyridyl | 2-(1-piperidinyl)ethylamino | H |
| 4272. | —(NMeSO₂)-4-pyridyl | 2-(1-pyrrolidinyl)ethylamino | H |
| 4273. | —(NMeSO₂)-4-pyridyl | 2-(4-morpholinyl)ethylamino | H |
| 4274. | —(NMeSO₂)-4-pyridyl | 3-(1-piperidinyl)propylamino | H |
| 4275. | —(NMeSO₂)-4-pyridyl | 3-(1-pyrrolidinyl)propylamino | H |
| 4276. | —(NMeSO₂)-4-pyridyl | 3-(4-morpholinyl)propylamino | H |
| 4277. | —(NMeSO₂)-4-pyridyl | N-methyl-N-(2-piperid-1-ylethyl)amino | H |
| 4278. | —(NMeSO₂)-4-pyridyl | N-methyl-N-(2-pyrrolidin-1-ylethyl)amino | H |
| 4279. | —(NMeSO₂)-4-pyridyl | N-methyl-N-(2-morpholin-4-ylethyl)amino | H |
| 4280. | —(NMeSO₂)-4-pyridyl | ((2S)-2-amino-3-phenylpropyl)amino | H |
| 4281. | —(NMeSO₂)-4-pyridyl | 4-methylpiperazinylamino | H |
| 4282. | —(NMeSO₂)-4-pyridyl | 4-methylpiperazinyl | H |
| 4283. | —(NMeSO₂)-4-pyridyl | 3-aminopyrrolidinyl | H |
| 4284. | —(NMeSO₂)-4-pyridyl | (diethylamino)ethylamino | H |
| 4285. | —(NMeSO₂)-4-pyridyl | 3,5-dimethylpiperazin-1-yl | H |
| 4286. | —(NMeSO₂)-4-pyridyl | (4-piperidylmethyl)amino | H |
| 4287. | —(NMeSO₂)-4-pyridyl | (2-methylbutyl)amino | H |
| 4288. | —(NMeSO₂)-4-pyridyl | 2-(dimethylamino)ethoxy | H |
| 4289. | —(NMeSO₂)-4-pyridyl | 2-(methylamino)ethoxy | H |
| 4290. | —(NMeSO₂)-4-pyridyl | ((2R)pyrrolidin-2-yl)methoxy | H |
| 4291. | —(NMeSO₂)-4-pyridyl | ((2R)-1-methylpyrrolidin-2-yl)methoxy | H |
| 4292. | —(NMeSO₂)-4-pyridyl | 2-(piperid-1-yl)ethoxy | H |
| 4293. | —(NMeSO₂)-4-pyridyl | 2-(piperazin-1-yl)ethoxy | H |
| 4294. | —(NMeSO₂)-4-pyridyl | 2-(morpholin-4-yl)ethoxy | H |
| 4295. | —(NMeSO₂)-4-pyridyl | 2-methylthio | NH₂ |
| 4296. | —(NMeSO₂)-4-pyridyl | 2-(methylsulfonyl) | NH₂ |
| 4297. | —(NMeSO₂)-4-pyridyl | cyclopropylmethylamino | NH₂ |
| 4298. | —(MMeSO₂)-4-pyridyl | 3-hydroxypropylamino | NH₂ |
| 4299. | —(NMeSO₂)-4-pyridyl | 2-(1-piperidinyl)ethylamino | NH₂ |

TABLE 7-continued

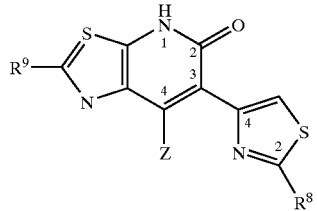

| # | R⁸ | R⁹ | Z |
|---|---|---|---|
| 4300. | —(NMeSO₂)-4-pyridyl | 2-(1-pyrrolidinyl)ethylamino | NH₂ |
| 4301. | —(NMeSO₂)-4-pyridyl | 2-(4-morpholinyl)ethylamino | NH₂ |
| 4302. | —(NMeSO₂)-4-pyridyl | 3-(1-piperidinyl)propylamino | NH₂ |
| 4303. | —(NMeSO₂)-4-pyridyl | 3-(1-pyrrolidinyl)propylamino | NH₂ |
| 4304. | —(NMeSO₂)-4-pyridyl | 3-(4-morpholinyl)propylamino | NH₂ |
| 4305. | —(NMeSO₂)-4-pyridyl | N-methyl-N-(2-piperid-1-ylethyl)amino | NH₂ |
| 4306. | —(NMeSO₂)-4-pyridyl | N-methyl-N-(2-pyrrolidin-1-ylethyl)amino | NH₂ |
| 4307. | —(NMeSO₂)-4-pyridyl | N-methyl-N-(2-morpholin-4-ylethyl)amino | NH₂ |
| 4308. | —(NMeSO₂)-4-pyridyl | ((2S)-2-amino-3-phenylpropyl)amino | NH₂ |
| 4309. | —(NMeSO₂)-4-pyridyl | 4-methylpiperazinylamino | NH₂ |
| 4310. | —(NMeSO₂)-4-pyridyl | 4-methylpiperazinyl | NH₂ |
| 4311. | —(NMeSO₂)-4-pyridyl | 3-aminopyrrolidinyl | NH₂ |
| 4312. | —(NMeSO₂)-4-pyridyl | (diethylamino)ethylamino | NH₂ |
| 4313. | —(NMeSO₂)-4-pyridyl | 3,5-dimethylpiperazin-1-yl | NH₂ |
| 4314. | —(NMeSO₂)-4-pyridyl | (4-piperidylmethyl)amino | NH₂ |
| 4315. | —(NMeSO₂)-4-pyridyl | (2-methylbutyl)amino | NH₂ |
| 4316. | —(NMeSO₂)-4-pyridyl | 2-(dimethylamino)ethoxy | NH₂ |
| 4317. | —(NMeSO₂)-4-pyridyl | 2-(methylamino)ethoxy | NH₂ |
| 4318. | —(NMeSO₂)-4-pyridyl | ((2R)pyrrolidin-2-yl)methoxy | NH₂ |
| 4319. | —(NMeSO₂)-4-pyridyl | ((2R)-1-methylpyrrolidin-2-yl)methoxy | NH₂ |
| 4320. | —(NMeSO₂)-4-pyridyl | 2-(piperid-1-yl)ethoxy | NH₂ |
| 4321. | —(NMeSO₂)-4-pyridyl | 2-(piperazin-1-yl)ethoxy | NH₂ |
| 4322. | —(NMeSO₂)-4-pyridyl | 2-(morpholin-4-yl)ethoxy | NH₂ |

TABLE 8

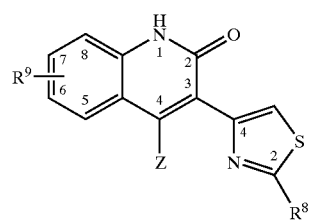

| # | R⁸ | R⁹ | Z |
|---|---|---|---|
| 4323. | 4-pyridyl | 7-(morpholin-4-yl-CH₂—) | H |
| 4324. | 4-pyridyl | 7-(diethylamino-CH₂—) | H |
| 4325. | 4-pyridyl | 7-(1-pyrrolidinyl-CH₂—) | H |
| 4326. | 4-pyridyl | 7-(azaperhydroepinyl-CH₂—) | H |
| 4327. | 4-pyridyl | 7-[(3,5-dimethylpiperid-1-yl)-CH₂—] | H |
| 4328. | 4-pyridyl | 7-[(4-methylpiperid-1-yl-CH₂—] | H |
| 4329. | 4-pyridyl | 7-[(3-methylpiperid-1-yl-CH₂—] | H |
| 4330. | 4-pyridyl | 7-[(2-methylpiperid-1-yl-CH₂—] | H |
| 4331. | 4-pyridyl | 7-(piperid-1-yl-CH₂CH₂—) | H |
| 4332. | 4-pyridyl | 7-(1-CH₃-piperazin-4-yl-CH₂CH₂—) | H |
| 4333. | 4-pyridyl | 7-(morpholin-4-yl-CH₂CH₂—) | H |
| 4334. | 4-pyridyl | 7-(diethylamino-CH₂CH₂—) | H |
| 4335. | 4-pyridyl | 7-(1-pyrrolidinyl-CH₂CH₂—) | H |
| 4336. | 4-pyridyl | 7-(azaperhydroepinyl-CH₂CH₂—) | H |
| 4337. | 4-pyridyl | 7-[(3,5-dimethylpiperid-1-yl)-CH₂CH₂—] | H |

TABLE 8-continued

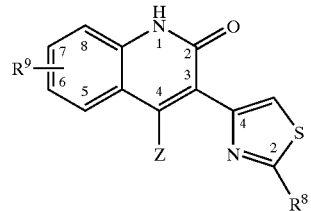

| # | R⁸ | R⁹ | Z |
|---|---|---|---|
| 4338. | 4-pyridyl | 7-[(4-methylpiperid-1-yl-CH₂CH₂—) | H |
| 4339. | 4-pyridyl | 7-[(3-methylpiperid-1-yl-CH₂CH₂—)] | H |
| 4340. | 4-pyridyl | 7-[(2-methylpiperid-1-yl-CH₂CH₂—)—] | H |
| 4341. | 4-pyridyl | 7-(1-piperidylcarbonyl) | H |
| 4342. | 4-pyridyl | 7-[(4-methylpiperazin-1-yl)carbonyl] | H |
| 4343. | 4-pyridyl | 7-(morpholin-4-ylcarbonyl) | H |
| 4344. | 4-pyridyl | 7-(diethylaminocarbonyl) | H |
| 4345. | 4-pyridyl | 7-(1-pyrrolidinylcarbonyl) | H |
| 4346. | 4-pyridyl | 7-(azaperhydroepinylcarbonyl) | H |
| 4347. | 4-pyridyl | 7-[(3,5-dimethylpiperid-1-yl)carbonyl] | H |
| 4348. | 4-pyridyl | 7-[(4-methylpiperid-1-ylcarbonyl) | H |
| 4349. | 4-pyridyl | 7-[(3-methylpiperid-1-ylcarbonyl) | H |
| 4350. | 4-pyridyl | 7-[(2-methylpiperid-1-ylcarbonyl) | H |
| 4351. | 4-pyridyl | 7-[2-(dimethylamino)ethoxy] | H |
| 4352. | 4-pyridyl | 7-[2-(methylamino)ethoxy] | H |
| 4353. | 4-pyridyl | 7-[((2R)pyrrolidin-2-yl)methoxy] | H |
| 4354. | 4-pyridyl | 7-(((2R)-1-methylpyrrolidin-2-yl)methoxy] | H |
| 4355. | 4-pyridyl | 7-[2-(piperid-1-yl)ethoxy] | H |
| 4356. | 4-pyridyl | 7-[2-(piperazin-1-yl)ethoxy] | H |
| 4357. | 4-pyridyl | 7-[2-(morpholin-4-yl)ethoxy] | H |
| 4358. | 4-pyridyl | 7-[2-(1-methyl(4-piperidyl))ethoxy] | H |
| 4359. | 4-pyridyl | 7-[2-(1-methyl(4-piperidyl))methoxy] | H |
| 4360. | 4-pyridyl | 7-(1-methyl(4-piperidyloxy)) | H |
| 4361. | 4-pyridyl | 7-(piperid-1-yl-CH₂—) | NH₂ |
| 4362. | 4-pyridyl | 7-(1-CH₃-piperazin-4-yl-CH₂—) | NH₂ |
| 4363. | 4-pyridyl | 7-(morpholin-4-yl-CH₂—) | NH₂ |
| 4364. | 4-pyridyl | 7-(diethylamino-CH₂—) | NH₂ |
| 4365. | 4-pyridyl | 7-(1-pyrrolidinyl-CH₂—) | NH₂ |
| 4366. | 4-pyridyl | 7-(azaperhydroepinyl-CH₂—) | NH₂ |
| 4367. | 4-pyridyl | 7-[(3,5-dimethylpiperid-1-yl)-CH₂—] | NH₂ |
| 4368. | 4-pyridyl | 7-[(4-methylpiperid-1-yl-CH₂—] | NH₂ |
| 4369. | 4-pyridyl | 7-[(3-methylpiperid-1-yl-CH₂—] | NH₂ |
| 4370. | 4-pyridyl | 7-[(2-methylpiperid-1-yl-CH₂—] | NH₂ |
| 4371. | 4-pyridyl | 7-(piperid-1-yl-CH₂CH₂—) | NH₂ |
| 4372. | 4-pyridyl | 7-(1-CH₃-piperazin-4-yl-CH₂CH₂—) | NH₂ |
| 4373. | 4-pyridyl | 7-(morpholin-4-yl-CH₂CH₂—) | NH₂ |
| 4374. | 4-pyridyl | 7-(diethylamino-CH₂CH₂—) | NH₂ |
| 4375. | 4-pyridyl | 7-(1-pyrrolidinyl-CH₂CH₂—) | NH₂ |
| 4376. | 4-pyridyl | 7-(azaperhydroepinyl-CH₂CH₂—) | NH₂ |
| 4377. | 4-pyridyl | 7-[(3,5-dimethylpiperid-1-yl)-CH₂CH₂—] | NH₂ |
| 4378. | 4-pyridyl | 7-[(4-methylpiperid-1-yl-CH₂CH₂—) | NH₂ |
| 4379. | 4-pyridyl | 7-[(3-methylpiperid-1-yl-CH₂CH₂—)] | NH₂ |
| 4380. | 4-pyridyl | 7-[(2-methylpiperid-1-yl-CH₂CH₂—)—] | NH₂ |
| 4381. | 4-pyridyl | 7-(1-piperidylcarbonyl) | NH₂ |
| 4382. | 4-pyridyl | 7-[(4-methylpiperazin-1-yl)carbonyl] | NH₂ |

TABLE 8-continued

| # | R⁸ | R⁹ | Z |
|---|---|---|---|
| 4383. | 4-pyridyl | 7-(morpholin-4-ylcarbonyl) | NH₂ |
| 4384. | 4-pyridyl | 7-(diethylaminocarbonyl) | NH₂ |
| 4385. | 4-pyridyl | 7-(1-pyrrolidinylcarbonyl) | NH₂ |
| 4386. | 4-pyridyl | 7-(azaperhydroepinylcarbonyl) | NH₂ |
| 4387. | 4-pyridyl | 7-[(3,5-dimethylpiperid-1-yl)carbonyl] | NH₂ |
| 4388. | 4-pyridyl | 7-[(4-methylpiperid-1-ylcarbonyl) | NH₂ |
| 4389. | 4-pyridyl | 7-[(3-methylpiperid-1-ylcarbonyl) | NH₂ |
| 4390. | 4-pyridyl | 7-[(2-methylpiperid-1-ylcarbonyl) | NH₂ |
| 4391. | 4-pyridyl | 7-[2-(dimethylamino)ethoxy] | NH₂ |
| 4392. | 4-pyridyl | 7-[2-(methylamino)ethoxy] | NH₂ |
| 4393. | 4-pyridyl | 7-[((2R)pyrrolidin-2-yl)methoxy] | NH₂ |
| 4394. | 4-pyridyl | 7-[((2R)-1-methylpyrrolidin-2-yl)methoxy] | NH₂ |
| 4395. | 4-pyridyl | 7-[2-(piperid-1-yl)ethoxy] | NH₂ |
| 4396. | 4-pyridyl | 7-[2-(piperazin-1-yl)ethoxy] | NH₂ |
| 4397. | 4-pyridyl | 7-[2-(morpholin-4-yl)ethoxy] | NH₂ |
| 4398. | 4-pyridyl | 7-[2-(1-methyl(4-piperidyl))ethoxy] | NH₂ |
| 4399. | 4-pyridyl | 7-[2-(1-methyl(4-piperidyl))methoxy] | NH₂ |
| 4400. | 4-pyridyl | 7-(1-methyl(4-piperidyloxy)) | NH₂ |
| 4401. | —(CH₂SO₂)-phenyl | 7-(piperid-1-yl-CH₂—) | H |
| 4402. | —(CH₂SO₂)-phenyl | 7-(1-CH₃-piperazin-4-yl-CH₂—) | H |
| 4403. | —(CH₂SO₂)-phenyl | 7-(morpholin-4-yl-CH₂—) | H |
| 4404. | —(CH₂SO₂)-phenyl | 7-(diethylamino-CH₂—) | H |
| 4405. | —(CH₂SO₂)-phenyl | 7-(1-pyrrolidinyl-CH₂—) | H |
| 4406. | —(CH₂SO₂)-phenyl | 7-(azaperhydroepinyl-CH₂—) | H |
| 4407. | —(CH₂SO₂)-phenyl | 7-[(3,5-dimethylpiperid-1-yl)-CH₂—] | H |
| 4408. | —(CH₂SO₂)-phenyl | 7-[(4-methylpiperid-1-yl-CH₂—] | H |
| 4409. | —(CH₂SO₂)-phenyl | 7-[(3-methylpiperid-1-yl-CH₂—] | H |
| 4410. | —(CH₂SO₂)-phenyl | 7-[(2-methylpiperid-1-yl-CH₂—] | H |
| 4411. | —(CH₂SO₂)-phenyl | 7-(piperid-1-yl-CH₂CH₂—) | H |
| 4412. | —(CH₂SO₂)-phenyl | 7-(1-CH₃-piperazin-4-yl-CH₂CH₂—) | H |
| 4413. | —(CH₂SO₂)-phenyl | 7-(morpholin-4-yl-CH₂CH₂—) | H |
| 4414. | —(CH₂SO₂)-phenyl | 7-(diethylamino-CH₂CH₂—) | H |
| 4415. | —(CH₂SO₂)-phenyl | 7-(1-pyrrolidinyl-CH₂CH₂—) | H |
| 4416. | —(CH₂SO₂)-phenyl | 7-(azaperhydroepinyl-CH₂CH₂—) | H |
| 4417. | —(CH₂SO₂)-phenyl | 7-[(3,5-dimethylpiperid-1-yl)-CH₂CH₂—] | H |
| 4418. | —(CH₂SO₂)-phenyl | 7-[(4-methylpiperid-1-yl-CH₂CH₂—) | H |
| 4419. | —(CH₂SO₂)-phenyl | 7-[(3-methylpiperid-1-yl-CH₂CH₂—)—] | H |
| 4420. | —(CH₂SO₂)-phenyl | 7-[(2-methylpiperid-1-yl-CH₂CH₂—)—] | H |
| 4421. | —(CH₂SO₂)-phenyl | 7-(1-piperidylcarbonyl) | H |
| 4422. | —(CH₂SO₂)-phenyl | 7-[(4-methylpiperazin-1-yl)carbonyl] | H |
| 4423. | —(CH₂SO₂)-phenyl | 7-(morpholin-4-ylcarbonyl) | H |
| 4424. | —(CH₂SO₂)-phenyl | 7-(diethylaminocarbonyl) | H |
| 4425. | —(CH₂SO₂)-phenyl | 7-(1-pyrrolidinylcarbonyl) | H |
| 4426. | —(CH₂SO₂)-phenyl | 7-(azaperhydroepinylcarbonyl) | H |
| 4427. | —(CH₂SO₂)-phenyl | 7-[(3,5-dimethylpiperid-1-yl)carbonyl] | H |
| 4428. | —(CH₂SO₂)-phenyl | 7-[(4-methylpiperid-1-ylcarbonyl) | H |
| 4429. | —(CH₂SO₂)-phenyl | 7-[(3-methylpiperid-1-ylcarbonyl) | H |
| 4430. | —(CH₂SO₂)-phenyl | 7-[(2-methylpiperid-1-ylcarbonyl) | H |
| 4431. | —(CH₂SO₂)-phenyl | 7-[2-(dimethylamino)ethoxy] | H |
| 4432. | —(CH₂SO₂)-phenyl | 7-[2-(methylamino)ethoxy] | H |
| 4433. | —(CH₂SO₂)-phenyl | 7-[((2R)pyrrolidin-2-yl)methoxy] | H |
| 4434. | —(CH₂SO₂)-phenyl | 7-[((2R)-1-methylpyrrolidin-2-yl)methoxy] | H |
| 4435. | —(CH₂SO₂)-phenyl | 7-[2-(piperid-1-yl)ethoxy] | H |
| 4436. | —(CH₂SO₂)-phenyl | 7-[2-(piperazin-1-yl)ethoxy] | H |
| 4437. | —(CH₂SO₂)-phenyl | 7-[2-(morpholin-4-yl)ethoxy] | H |
| 4438. | —(CH₂SO₂)-phenyl | 7-[2-(1-methyl(4-piperidyl))ethoxy] | H |
| 4439. | —(CH₂SO₂)-phenyl | 7-[2-(1-methyl(4-piperidyl))methoxy] | H |
| 4440. | —(CH₂SO₂)-phenyl | 7-(1-methyl(4-piperidyloxy)) | H |
| 4441. | —(CH₂SO₂)-phenyl | 7-(piperid-1-yl-CH₂—) | NH₂ |
| 4442. | —(CH₂SO₂)-phenyl | 7-(1-CH₃-piperazin-4-yl-CH₂—) | NH₂ |
| 4443. | —(CH₂SO₂)-phenyl | 7-(morpholin-4-yl-CH₂—) | NH₂ |
| 4444. | —(CH₂SO₂)-phenyl | 7-(diethylamino-CH₂—) | NH₂ |
| 4445. | —(CH₂SO₂)-phenyl | 7-(1-pyrrolidinyl-CH₂—) | NH₂ |
| 4446. | —(CH₂SO₂)-phenyl | 7-(azaperhydroepinyl-CH₂—) | NH₂ |
| 4447. | —(CH₂SO₂)-phenyl | 7-[(3,5-dimethylpiperid-1-yl)-CH₂—] | NH₂ |
| 4448. | —(CH₂SO₂)-phenyl | 7-[(4-methylpiperid-1-yl-CH₂—] | NH₂ |
| 4449. | —(CH₂SO₂)-phenyl | 7-[(3-methylpiperid-1-yl-CH₂—] | NH₂ |
| 4450. | —(CH₂SO₂)-phenyl | 7-[(2-methylpiperid-1-yl-CH₂—] | NH₂ |
| 4451. | —(CH₂SO₂)-phenyl | 7-(piperid-1-yl-CH₂CH₂—) | NH₂ |
| 4452. | —(CH₂SO₂)-phenyl | 7-(1-CH₃-piperazin-4-yl-CH₂CH₂—) | NH₂ |
| 4453. | —(CH₂SO₂)-phenyl | 7-(morpholin-4-yl-CH₂CH₂—) | NH₂ |
| 4454. | —(CH₂SO₂)-phenyl | 7-(diethylamino-CH₂CH₂—) | NH₂ |
| 4455. | —(CH₂SO₂)-phenyl | 7-(1-pyrrolidinyl-CH₂CH₂—) | NH₂ |
| 4456. | —(CH₂SO₂)-phenyl | 7-(azaperhydroepinyl-CH₂CH₂—) | NH₂ |
| 4457. | —(CH₂SO₂)-phenyl | 7-[(3,5-dimethylpiperid-1-yl)-CH₂CH₂—] | NH₂ |
| 4458. | —(CH₂SO₂)-phenyl | 7-[(4-methylpiperid-1-yl-CH₂CH₂—) | NH₂ |
| 4459. | —(CH₂SO₂)-phenyl | 7-[(3-methylpiperid-1-yl-CH₂CH₂—)—] | NH₂ |
| 4460. | —(CH₂SO₂)-phenyl | 7-[(2-methylpiperid-1-yl-CH₂CH₂—)—] | NH₂ |
| 4461. | —(CH₂SO₂)-phenyl | 7-(1-piperidylcarbonyl) | NH₂ |
| 4462. | —(CH₂SO₂)-phenyl | 7-[(4-methylpiperazin-1-yl)carbonyl] | NH₂ |
| 4463. | —(CH₂SO₂)-phenyl | 7-(morpholin-4-ylcarbonyl) | NH₂ |
| 4464. | —(CH₂SO₂)-phenyl | 7-(diethylaminocarbonyl) | NH₂ |
| 4465. | —(CH₂SO₂)-phenyl | 7-(1-pyrrolidinylcarbonyl) | NH₂ |
| 4466. | —(CH₂SO₂)-phenyl | 7-(azaperhydroepinylcarbonyl) | NH₂ |
| 4467. | —(CH₂SO₂)-phenyl | 7-[(3,5-dimethylpiperid-1-yl)carbonyl] | NH₂ |
| 4468. | —(CH₂SO₂)-phenyl | 7-[(4-methylpiperid-1-ylcarbonyl) | NH₂ |
| 4469. | —(CH₂SO₂)-phenyl | 7-[(3-methylpiperid-1-ylcarbonyl) | NH₂ |
| 4470. | —(CH₂SO₂)-phenyl | 7-[(2-methylpiperid-1-ylcarbonyl) | NH₂ |
| 4471. | —(CH₂SO₂)-phenyl | 7-[2-(dimethylamino)ethoxy] | NH₂ |
| 4472. | —(CH₂SO₂)-phenyl | 7-[2-(methylamino)ethoxy] | NH₂ |
| 4473. | —(CH₂SO₂)-phenyl | 7-[((2R)pyrrolidin-2-yl)methoxy] | NH₂ |

TABLE 8-continued

| # | R⁸ | R⁹ | Z |
|---|---|---|---|
| 4474. | —(CH₂SO₂)-phenyl | 7-[((2R)-1-methylpyrrolidin-2-yl)methoxy] | NH₂ |
| 4475. | —(CH₂SO₂)-phenyl | 7-[2-(piperid-1-yl)ethoxy] | NH₂ |
| 4476. | —(CH₂SO₂)-phenyl | 7-[2-(piperazin-1-yl)ethoxy] | NH₂ |
| 4477. | —(CH₂SO₂)-phenyl | 7-[2-(morpholin-4-yl)ethoxy] | NH₂ |
| 4478. | —(CH₂SO₂)-phenyl | 7-[2-(1-methyl(4-piperidyl))ethoxy] | NH₂ |
| 4479. | —(CH₂SO₂)-phenyl | 7-[2-(1-methyl(4-piperidyl))methoxy] | NH₂ |
| 4480. | —(CH₂SO₂)-phenyl | 7-(1-methyl(4-piperidyloxy)) | NH₂ |
| 4481. | —(CH₂SO₂)-2-thienyl | 7-(diethylamino-CH₂—) | H |
| 4482. | —(CH₂SO₂)-2-thienyl | 7-(1-pyrrolidinyl-CH₂—) | H |
| 4483. | —(CH₂SO₂)-2-thienyl | 7-(azaperhydroepinyl-CH₂—) | H |
| 4484. | —(CH₂SO₂)-2-thienyl | 7-[(3,5-dimethylpiperid-1-yl)-CH₂—] | H |
| 4485. | —(CH₂SO₂)-2-thienyl | 7-[(4-methylpiperid-1-yl-CH₂—] | H |
| 4486. | —(CH₂SO₂)-2-thienyl | 7-[(3-methylpiperid-1-yl-CH₂—] | H |
| 4487. | —(CH₂SO₂)-2-thienyl | 7-[(2-methylpiperid-1-yl-CH₂—] | H |
| 4488. | —(CH₂SO₂)-2-thienyl | 7-(piperid-1-yl-CH₂CH₂—) | H |
| 4489. | —(CH₂SO₂)-2-thienyl | 7-(1-CH₃-piperazin-4-yl-CH₂CH₂—) | H |
| 4490. | —(CH₂SO₂)-2-thienyl | 7-(morpholin-4-yl-CH₂CH₂—) | H |
| 4491. | —(CH₂SO₂)-2-thienyl | 7-(diethylamino-CH₂CH₂—) | H |
| 4492. | —(CH₂SO₂)-2-thienyl | 7-(1-pyrrolidinyl-CH₂CH₂—) | H |
| 4493. | —(CH₂SO₂)-2-thienyl | 7-(azaperhydroepinyl-CH₂CH₂—) | H |
| 4494. | —(CH₂SO₂)-2-thienyl | 7-[(3,5-dimethylpiperid-1-yl)-CH₂CH₂—] | H |
| 4495. | —(CH₂SO₂)-2-thienyl | 7-[(4-methylpiperid-1-yl-CH₂CH₂—) | H |
| 4496. | —(CH₂SO₂)-2-thienyl | 7-[(3-methylpiperid-1-yl-CH₂CH₂—)—] | H |
| 4497. | —(CH₂SO₂)-2-thienyl | 7-[(2-methylpiperid-1-yl-CH₂CH₂—)—] | H |
| 4498. | —(CH₂SO₂)-2-thienyl | 7-(1-piperidylcarbonyl) | H |
| 4499. | —(CH₂SO₂)-2-thienyl | 7-[(4-methylpiperazin-1-yl)carbonyl] | H |
| 4500. | —(CH₂SO₂)-2-thienyl | 7-(morpholin-4-ylcarbonyl) | H |
| 4501. | —(CH₂SO₂)-2-thienyl | 7-(diethylaminocarbonyl) | H |
| 4502. | —(CH₂SO₂)-2-thienyl | 7-(1-pyrrolidinylcarbonyl) | H |
| 4503. | —(CH₂SO₂)-2-thienyl | 7-(azaperhydroepinylcarbonyl) | H |
| 4504. | —(CH₂SO₂)-2-thienyl | 7-[(3,5-dimethylpiperid-1-yl)carbonyl] | H |
| 4505. | —(CH₂SO₂)-2-thienyl | 7-[(4-methylpiperid-1-ylcarbonyl) | H |
| 4506. | —(CH₂SO₂)-2-thienyl | 7-[(3-methylpiperid-1-ylcarbonyl) | H |
| 4507. | —(CH₂SO₂)-2-thienyl | 7-[(2-methylpiperid-1-ylcarbonyl) | H |
| 4508. | —(CH₂SO₂)-2-thienyl | 7-[2-(dimethylamino)ethoxy] | H |
| 4509. | —(CH₂SO₂)-2-thienyl | 7-[2-(methylamino)ethoxy] | H |
| 4510. | —(CH₂SO₂)-2-thienyl | 7-[((2R)pyrrolidin-2-yl)methoxy] | H |
| 4511. | —(CH₂SO₂)-2-thienyl | 7-[((2R)-1-methylpyrrolidin-2-yl)methoxy] | H |
| 4512. | —(CH₂SO₂)-2-thienyl | 7-[2-(piperid-1-yl)ethoxy] | H |
| 4513. | —(CH₂SO₂)-2-thienyl | 7-[2-(piperazin-1-yl)ethoxy] | H |
| 4514. | —(CH₂SO₂)-2-thienyl | 7-[2-(morpholin-4-yl)ethoxy] | H |
| 4515. | —(CH₂SO₂)-2-thienyl | 7-[2-(1-methyl(4-piperidyl))ethoxy] | H |
| 4516. | —(CH₂SO₂)-2-thienyl | 7-[2-(1-methyl(4-piperidyl))methoxy] | H |
| 4517. | —(CH₂SO₂)-2-thienyl | 7-(1-methyl(4-piperidyloxy)) | H |
| 4518. | —(CH₂SO₂)-2-thienyl | 7-(piperid-1-yl-CH₂—) | NH₂ |
| 4519. | —(CH₂SO₂)-2-thienyl | 7-(1-CH₃-piperazin-4-yl-CH₂—) | NH₂ |
| 4520. | —(CH₂SO₂)-2-thienyl | 7-(morpholin-4-yl-CH₂—) | NH₂ |
| 4521. | —(CH₂SO₂)-2-thienyl | 7-(diethylamino-CH₂—) | NH₂ |
| 4522. | —(CH₂SO₂)-2-thienyl | 7-(1-pyrrolidinyl-CH₂—) | NH₂ |
| 4523. | —(CH₂SO₂)-2-thienyl | 7-(azaperhydroepinyl-CH₂—) | NH₂ |
| 4524. | —(CH₂SO₂)-2-thienyl | 7-[(3,5-dimethylpiperid-1-yl)-CH₂—] | NH₂ |
| 4525. | —(CH₂SO₂)-2-thienyl | 7-[(4-methylpiperid-1-yl-CH₂—] | NH₂ |
| 4526. | —(CH₂SO₂)-2-thienyl | 7-[(3-methylpiperid-1-yl-CH₂—] | NH₂ |
| 4527. | —(CH₂SO₂)-2-thienyl | 7-[(2-methylpiperid-1-yl-CH₂—] | NH₂ |
| 4528. | —(CH₂SO₂)-2-thienyl | 7-(piperid-1-yl-CH₂CH₂—) | NH₂ |
| 4529. | —(CH₂SO₂)-2-thienyl | 7-(1-CH₃-piperazin-4-yl-CH₂CH₂—) | NH₂ |
| 4530. | —(CH₂SO₂)-2-thienyl | 7-(morpholin-4-yl-CH₂CH₂—) | NH₂ |
| 4531. | —(CH₂SO₂)-2-thienyl | 7-(diethylamino-CH₂CH₂—) | NH₂ |
| 4532. | —(CH₂SO₂)-2-thienyl | 7-(1-pyrrolidinyl-CH₂CH₂—) | NH₂ |
| 4533. | —(CH₂SO₂)-2-thienyl | 7-(azaperhydroepinyl-CH₂CH₂—) | NH₂ |
| 4534. | —(CH₂SO₂)-2-thienyl | 7-[(3,5-dimethylpiperid-1-yl)-CH₂CH₂—] | NH₂ |
| 4535. | —(CH₂SO₂)-2-thienyl | 7-[(4-methylpiperid-1-yl-CH₂CH₂—) | NH₂ |
| 4536. | —(CH₂SO₂)-2-thienyl | 7-[(3-methylpiperid(-1-yl-CH₂CH₂—)—] | NH₂ |
| 4537. | —(CH₂SO₂)-2-thienyl | 7-[(2-methylpiperid-1-yl-CH₂CH₂—)—] | NH₂ |
| 4538. | —(CH₂SO₂)-2-thienyl | 7-(1-piperidylcarbonyl) | NH₂ |
| 4539. | —(CH₂SO₂)-2-thienyl | 7-[(4-methylpiperazin-1-yl)carbonyl] | NH₂ |
| 4540. | —(CH₂SO₂)-2-thienyl | 7-(morpholin-4-ylcarbonyl) | NH₂ |
| 4541. | —(CH₂SO₂)-2-thienyl | 7-(diethylaminocarbonyl) | NH₂ |
| 4542. | —(CH₂SO₂)-2-thienyl | 7-(1-pyrrolidinylcarbonyl) | NH₂ |
| 4543. | —(CH₂SO₂)-2-thienyl | 7-(azaperhydroepinylcarbonyl) | NH₂ |
| 4544. | —(CH₂SO₂)-2-thienyl | 7-[(3,5-dimethylpiperid-1-yl)carbonyl] | NH₂ |
| 4545. | —(CH₂SO₂)-2-thienyl | 7-[(4-methylpiperid-1-ylcarbonyl) | NH₂ |
| 4546. | —(CH₂SO₂)-2-thienyl | 7-[(3-methylpiperid-1-ylcarbonyl) | NH₂ |
| 4547. | —(CH₂SO₂)-2-thienyl | 7-[(2-methylpiperid-1-ylcarbonyl) | NH₂ |
| 4548. | —(CH₂SO₂)-2-thienyl | 7-[2-(dimethylamino)ethoxy] | NH₂ |
| 4549. | —(CH₂SO₂)-2-thienyl | 7-[2-(methylamino)ethoxy] | NH₂ |
| 4550. | —(CH₂SO₂)-2-thienyl | 7-[((2R)pyrrolidin-2-yl)methoxy] | NH₂ |
| 4551. | —(CH₂SO₂)-2-thienyl | 7-[((2R)-1-methylpyrrolidin-2-yl)methoxy] | NH₂ |
| 4552. | —(CH₂SO₂)-2-thienyl | 7-[2-(piperid-1-yl)ethoxy] | NH₂ |
| 4553. | —(CH₂SO₂)-2-thienyl | 7-[2-(piperazin-1-yl)ethoxy] | NH₂ |
| 4554. | —(CH₂SO₂)-2-thienyl | 7-[2-(morpholin-4-yl)ethoxy] | NH₂ |
| 4555. | —(CH₂SO₂)-2-thienyl | 7-[2-(1-methyl(4-piperidyl))ethoxy] | NH₂ |
| 4556. | —(CH₂SO₂)-2-thienyl | 7-[2-(1-methyl(4-piperidyl))methoxy] | NH₂ |
| 4557. | —(CH₂SO₂)-2-thienyl | 7-(1-methyl(4-piperidyloxy)) | NH₂ |
| 4558. | —(CH₂SO₂)-2-pyridyl | 7-(piperid-1-yl-CH₂—) | H |
| 4559. | —(CH₂SO₂)-2-pyridyl | 7-(1-CH₃-piperazin-4-yl-CH₂—) | H |
| 4560. | —(CH₂SO₂)-2-pyridyl | 7-(morpholin-4-yl-CH₂—) | H |
| 4561. | —(CH₂SO₂)-2-pyridyl | 7-(diethylamino-CH₂—) | H |
| 4562. | —(CH₂SO₂)-2-pyridyl | 7-(1-pyrrolidinyl-CH₂—) | H |
| 4563. | —(CH₂SO₂)-2-pyridyl | 7-(azaperhydroepinyl-CH₂—) | H |
| 4564. | —(CH₂SO₂)-2-pyridyl | 7-[(3,5-dimethylpiperid-1-yl)-CH₂—] | H |
| 4565. | —(CH₂SO₂)-2-pyridyl | 7-[(4-methylpiperid-1-yl-CH₂—] | H |
| 4566. | —(CH₂SO₂)-2-pyridyl | 7-[(3-methylpiperid-1-yl-CH₂—] | H |
| 4567. | —(CH₂SO₂)-2-pyridyl | 7-[(2-methylpiperid-1-yl-CH₂—] | H |

TABLE 8-continued

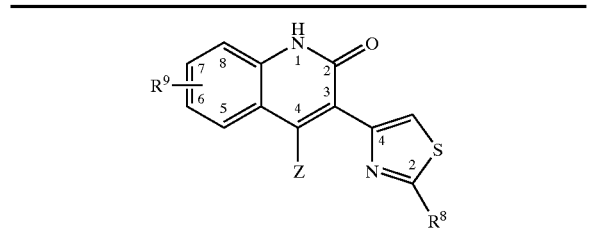

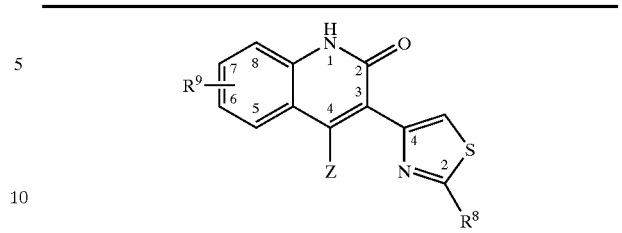

| # | R8 | R9 | Z |
|---|---|---|---|
| 4568. | —(CH2SO2)-2-pyridyl | 7-(piperid-1-yl-CH2CH2—) | H |
| 4569. | —(CH2SO2)-2-pyridyl | 7-(1-CH3-piperazin-4-yl-CH2CH2—) | H |
| 4570. | —(CH2SO2)-2-pyridyl | 7-(morpholin-4-yl-CH2CH2—) | H |
| 4571. | —(CH2SO2)-2-pyridyl | 7-(diethylamino-CH2CH2—) | H |
| 4572. | —(CH2SO2)-2-pyridyl | 7-(1-pyrrolidinyl-CH2CH2—) | H |
| 4573. | —(CH2SO2)-2-pyridyl | 7-(azaperhydroepinyl-CH2CH2—) | H |
| 4574. | —(CH2SO2)-2-pyridyl | 7-[(3,5-dimethylpiperid-1-yl)-CH2CH2—] | H |
| 4575. | —(CH2SO2)-2-pyridyl | 7-[(4-methylpiperid-1-yl-CH2CH2—) | H |
| 4576. | —(CH2SO2)-2-pyridyl | 7-[(3-methylpiperid(-1-yl-CH2CH2—)—] | H |
| 4577. | —(CH2SO2)-2-pyridyl | 7-[(2-methylpiperid-1-yl-CH2CH2—)—] | H |
| 4578. | —(CH2SO2)-2-pyridyl | 7-(1-piperidylcarbonyl) | H |
| 4579. | —(CH2SO2)-2-pyridyl | 7-[(4-methylpiperazin-1-yl)carbonyl] | H |
| 4580. | —(CH2SO2)-2-pyridyl | 7-(morpholin-4-ylcarbonyl) | H |
| 4581. | —(CH2SO2)-2-pyridyl | 7-(diethylaminocarbonyl) | H |
| 4582. | —(CH2SO2)-2-pyridyl | 7-(1-pyrrolidinylcarbonyl) | H |
| 4583. | —(CH2SO2)-2-pyridyl | 7-(azaperhydroepinylcarbonyl) | H |
| 4584. | —(CH2SO2)-2-pyridyl | 7-[(3,5-dimethylpiperid-1-yl)carbonyl] | H |
| 4585. | —(CH2SO2)-2-pyridyl | 7-[(4-methylpiperid-1-ylcarbonyl) | H |
| 4586. | —(CH2SO2)-2-pyridyl | 7-[(3-methylpiperid-1-ylcarbonyl) | H |
| 4587. | —(CH2SO2)-2-pyridyl | 7-[(2-methylpiperid-1-ylcarbonyl) | H |
| 4588. | —(CH2SO2)-2-pyridyl | 7-[2-(dimethylamino)ethoxy] | H |
| 4589. | —(CH2SO2)-2-pyridyl | 7-[2-(methylamino)ethoxy] | H |
| 4590. | —(CH2SO2)-2-pyridyl | 7-[((2R)pyrrolidin-2-yl)methoxy] | H |
| 4591. | —(CH2SO2)-2-pyridyl | 7-[((2R)-1-methylpyrrolidin-2-yl)methoxy] | H |
| 4592. | —(CH2SO2)-2-pyridyl | 7-[2-(piperid-1-yl)ethoxy] | H |
| 4593. | —(CH2SO2)-2-pyridyl | 7-[2-(piperazin-1-yl)ethoxy] | H |
| 4594. | —(CH2SO2)-2-pyridyl | 7-[2-(morpholin-4-yl)ethoxy] | H |
| 4595. | —(CH2SO2)-2-pyridyl | 7-[2-(1-methyl(4-piperidyl))ethoxy] | H |
| 4596. | —(CH2SO2)-2-pyridyl | 7-[2-(1-methyl(4-piperidyl))methoxy] | H |
| 4597. | —(CH2SO2)-2-pyridyl | 7-(1-methyl(4-piperidyloxy)) | H |
| 4598. | —(CH2SO2)-2-pyridyl | 7-(piperid-1-yl-CH2—) | NH2 |
| 4599. | —(CH2SO2)-2-pyridyl | 7-(1-CH3-piperazin-4-yl-CH2—) | NH2 |
| 4600. | —(CH2SO2)-2-pyridyl | 7-(morpholin-4-yl-CH2—) | NH2 |
| 4601. | —(CH2SO2)-2-pyridyl | 7-(diethylamino-CH2—) | NH2 |
| 4602. | —(CH2SO2)-2-pyridyl | 7-(1-pyrrolidinyl-CH2—) | NH2 |
| 4603. | —(CH2SO2)-2-pyridyl | 7-(azaperhydroepinyl-CH2—) | NH2 |
| 4604. | —(CH2SO2)-2-pyridyl | 7-[(3,5-dimethylpiperid-1-yl)-CH2—] | NH2 |
| 4605. | —(CH2SO2)-2-pyridyl | 7-[(4-methylpiperid-1-yl-CH2—] | NH2 |
| 4606. | —(CH2SO2)-2-pyridyl | 7-[(3-methylpiperid-1-yl-CH2—] | NH2 |
| 4607. | —(CH2SO2)-2-pyridyl | 7-[(2-methylpiperid-1-yl-CH2—] | NH2 |
| 4608. | —(CH2SO2)-2-pyridyl | 7-(piperid-1-yl-CH2CH2—) | NH2 |
| 4609. | —(CH2SO2)-2-pyridyl | 7-(1-CH3-piperazin-4-yl-CH2CH2—) | NH2 |
| 4610. | —(CH2SO2)-2-pyridyl | 7-(morpholin-4-yl-CH2CH2—) | NH2 |
| 4611. | —(CH2SO2)-2-pyridyl | 7-(diethylamino-CH2CH2—) | NH2 |
| 4612. | —(CH2SO2)-2-pyridyl | 7-(1-pyrrolidinyl-CH2CH2—) | NH2 |
| 4613. | —(CH2SO2)-2-pyridyl | 7-(azaperhydroepinyl-CH2CH2—) | NH2 |
| 4614. | —(CH2SO2)-2-pyridyl | 7-[(3,5-dimethylpiperid-1-yl)-CH2CH2—] | NH2 |
| 4615. | —(CH2SO2)-2-pyridyl | 7-[(4-methylpiperid-1-yl-CH2CH2—) | NH2 |
| 4616. | —(CH2SO2)-2-pyridyl | 7-[(3-methylpiperid(-1-yl-CH2CH2—)—] | NH2 |
| 4617. | —(CH2SO2)-2-pyridyl | 7-[(2-methylpiperid-1-yl-CH2CH2—)—] | NH2 |
| 4618. | —(CH2SO2)-2-pyridyl | 7-(1-piperidylcarbonyl) | NH2 |
| 4619. | —(CH2SO2)-2-pyridyl | 7-[(4-methylpiperazin-1-yl)carbonyl] | NH2 |
| 4620. | —(CH2SO2)-2-pyridyl | 7-(morpholin-4-ylcarbonyl) | NH2 |
| 4621. | —(CH2SO2)-2-pyridyl | 7-(diethylaminocarbonyl) | NH2 |
| 4622. | —(CH2SO2)-2-pyridyl | 7-(1-pyrrolidinylcarbonyl) | NH2 |
| 4623. | —(CH2SO2)-2-pyridyl | 7-(azaperhydroepinylcarbonyl) | NH2 |
| 4624. | —(CH2SO2)-2-pyridyl | 7-[(3,5-dimethylpiperid-1-yl)carbonyl] | NH2 |
| 4625. | —(CH2SO2)-2-pyridyl | 7-[(4-methylpiperid-1-ylcarbonyl) | NH2 |
| 4626. | —(CH2SO2)-2-pyridyl | 7-[(3-methylpiperid-1-ylcarbonyl) | NH2 |
| 4627. | —(CH2SO2)-2-pyridyl | 7-[(2-methylpiperid-1-ylcarbonyl) | NH2 |
| 4628. | —(CH2SO2)-2-pyridyl | 7-[2-(dimethylamino)ethoxy] | NH2 |
| 4629. | —(CH2SO2)-2-pyridyl | 7-[2-(methylamino)ethoxy] | NH2 |
| 4630. | —(CH2SO2)-2-pyridyl | 7-[((2R)pyrrolidin-2-yl)methoxy] | NH2 |
| 4631. | —(CH2SO2)-2-pyridyl | 7-[((2R)-1-methylpyrrolidin-2-yl)methoxy] | NH2 |
| 4632. | —(CH2SO2)-2-pyridyl | 7-[2-(piperid-1-yl)ethoxy] | NH2 |
| 4633. | —(CH2SO2)-2-pyridyl | 7-[2-(piperazin-1-yl)ethoxy] | NH2 |
| 4634. | —(CH2SO2)-2-pyridyl | 7-[2-(morpholin-4-yl)ethoxy] | NH2 |
| 4635. | —(CH2SO2)-2-pyridyl | 7-[2-(1-methyl(4-piperidyl))ethoxy] | NH2 |
| 4636. | —(CH2SO2)-2-pyridyl | 7-[2-(1-methyl(4-piperidyl))methoxy] | NH2 |
| 4637. | —(CH2SO2)-2-pyridyl | 7-(1-methyl(4-piperidyloxy)) | NH2 |
| 4638. | —(CH2SO2)-3-pyridyl | 7-(piperid-1-yl-CH2—) | H |
| 4639. | —(CH2SO2)-3-pyridyl | 7-(1-CH3-piperazin-4-yl-CH2—) | H |
| 4640. | —(CH2SO2)-3-pyridyl | 7-(morpholin-4-yl-CH2—) | H |
| 4641. | —(CH2SO2)-3-pyridyl | 7-(diethylamino-CH2—) | H |
| 4642. | —(CH2SO2)-3-pyridyl | 7-(1-pyrrolidinyl-CH2—) | H |
| 4643. | —(CH2SO2)-3-pyridyl | 7-(azaperhydroepinyl-CH2—) | H |
| 4644. | —(CH2SO2)-3-pyridyl | 7-[(3,5-dimethylpiperid-1-yl)-CH2—] | H |
| 4645. | —(CH2SO2)-3-pyridyl | 7-[(4-methylpiperid-1-yl-CH2—] | H |
| 4646. | —(CH2SO2)-3-pyridyl | 7-[(3-methylpiperid-1-yl-CH2—] | H |
| 4647. | —(CH2SO2)-3-pyridyl | 7-[(2-methylpiperid-1-yl-CH2—] | H |
| 4648. | —(CH2SO2)-3-pyridyl | 7-(piperid-1-yl-CH2CH2—) | H |
| 4649. | —(CH2SO2)-3-pyridyl | 7-(1-CH3-piperazin-4-yl-CH2CH2—) | H |
| 4650. | —(CH2SO2)-3-pyridyl | 7-(morpholin-4-yl-CH2CH2—) | H |
| 4651. | —(CH2SO2)-3-pyridyl | 7-(diethylamino-CH2CH2—) | H |
| 4652. | —(CH2SO2)-3-pyridyl | 7-(1-pyrrolidinyl-CH2CH2—) | H |
| 4653. | —(CH2SO2)-3-pyridyl | 7-(azaperhydroepinyl-CH2CH2—) | H |
| 4654. | —(CH2SO2)-3-pyridyl | 7-[(3,5-dimethylpiperid-1-yl)-CH2CH2—] | H |
| 4655. | —(CH2SO2)-3-pyridyl | 7-[(4-methylpiperid-1-yl-CH2CH2—) | H |
| 4656. | —(CH2SO2)-3-pyridyl | 7-[(3-methylpiperid(-1-yl-CH2CH2—)—] | H |
| 4657. | —(CH2SO2)-3-pyridyl | 7-[(2-methylpiperid-1-yl-CH2CH2—)—] | H |
| 4658. | —(CH2SO2)-3-pyridyl | 7-(1-piperidylcarbonyl) | H |

TABLE 8-continued

| # | R⁸ | R⁹ | Z |
|---|---|---|---|
| 4659. | —(CH₂SO₂)-3-pyridyl | 7-[(4-methylpiperazin-1-yl)carbonyl] | H |
| 4660. | —(CH₂SO₂)-3-pyridyl | 7-(morpholin-4-ylcarbonyl) | H |
| 4661. | —(CH₂SO₂)-3-pyridyl | 7-(diethylaminocarbonyl) | H |
| 4662. | —(CH₂SO₂)-3-pyridyl | 7-(1-pyrrolidinylcarbonyl) | H |
| 4663. | —(CH₂SO₂)-3-pyridyl | 7-(azaperhydroepinylcarbonyl) | H |
| 4664. | —(CH₂SO₂)-3-pyridyl | 7-[(3,5-dimethylpiperid-1-yl)carbonyl] | H |
| 4665. | —(CH₂SO₂)-3-pyridyl | 7-[(4-methylpiperid-1-ylcarbonyl) | H |
| 4666. | —(CH₂SO₂)-3-pyridyl | 7-[(3-methylpiperid-1-ylcarbonyl) | H |
| 4667. | —(CH₂SO₂)-3-pyridyl | 7-[(2-methylpiperid-1-ylcarbonyl) | H |
| 4668. | —(CH₂SO₂)-3-pyridyl | 7-[2-(dimethylamino)ethoxy] | H |
| 4669. | —(CH₂SO₂)-3-pyridyl | 7-[2-(methylamino)ethoxy] | H |
| 4670. | —(CH₂SO₂)-3-pyridyl | 7-[((2R)pyrrolidin-2-yl)methoxy] | H |
| 4671. | —(CH₂SO₂)-3-pyridyl | 7-[((2R)-1-methylpyrrolidin-2-yl)methoxy] | H |
| 4672. | —(CH₂SO₂)-3-pyridyl | 7-[2-(piperid-1-yl)ethoxy] | H |
| 4673. | —(CH₂SO₂)-3-pyridyl | 7-[2-(piperazin-1-yl)ethoxy] | H |
| 4674. | —(CH₂SO₂)-3-pyridyl | 7-[2-(morpholin-4-yl)ethoxy] | H |
| 4675. | —(CH₂SO₂)-3-pyridyl | 7-[2-(1-methyl(4-piperidyl))ethoxy] | H |
| 4676. | —(CH₂SO₂)-3-pyridyl | 7-[2-(1-methyl(4-piperidyl))methoxy] | H |
| 4677. | —(CH₂SO₂)-3-pyridyl | 7-(1-methyl(4-piperidyloxy)) | H |
| 4678. | —(CH₂SO₂)-3-pyridyl | 7-(piperid-1-yl-CH₂—) | NH₂ |
| 4679. | —(CH₂SO₂)-3-pyridyl | 7-(1-CH₃-piperazin-4-yl-CH₂—) | NH₂ |
| 4680. | —(CH₂SO₂)-3-pyridyl | 7-(morpholin-4-yl-CH₂—) | NH₂ |
| 4681. | —(CH₂SO₂)-3-pyridyl | 7-(diethylamino-CH₂—) | NH₂ |
| 4682. | —(CH₂SO₂)-3-pyridyl | 7-(1-pyrrolidinyl-CH₂—) | NH₂ |
| 4683. | —(CH₂SO₂)-3-pyridyl | 7-(azaperhydroepinyl-CH₂—) | NH₂ |
| 4684. | —(CH₂SO₂)-3-pyridyl | 7-[(3,5-dimethylpiperid-1-yl)-CH₂—] | NH₂ |
| 4685. | —(CH₂SO₂)-3-pyridyl | 7-[(4-methylpiperid-1-yl-CH₂—] | NH₂ |
| 4686. | —(CH₂SO₂)-3-pyridyl | 7-[(3-methylpiperid-1-yl-CH₂—] | NH₂ |
| 4687. | —(CH₂SO₂)-3-pyridyl | 7-[(2-methylpiperid-1-yl-CH₂—] | NH₂ |
| 4688. | —(CH₂SO₂)-3-pyridyl | 7-(piperid-1-yl-CH₂CH₂—) | NH₂ |
| 4689. | —(CH₂SO₂)-3-pyridyl | 7-(1-CH₃-piperazin-4-yl-CH₂CH₂—) | NH₂ |
| 4690. | —(CH₂SO₂)-3-pyridyl | 7-(morpholin-4-yl-CH₂CH₂—) | NH₂ |
| 4691. | —(CH₂SO₂)-3-pyridyl | 7-(diethylamino-CH₂CH₂—) | NH₂ |
| 4692. | —(CH₂SO₂)-3-pyridyl | 7-(1-pyrrolidinyl-CH₂CH₂—) | NH₂ |
| 4693. | —(CH₂SO₂)-3-pyridyl | 7-(azaperhydroepinyl-CH₂CH₂—) | NH₂ |
| 4694. | —(CH₂SO₂)-3-pyridyl | 7-[(3,5-dimethylpiperid-1-yl)-CH₂CH₂—] | NH₂ |
| 4695. | —(CH₂SO₂)-3-pyridyl | 7-[(4-methylpiperid-1-yl-CH₂CH₂—) | NH₂ |
| 4696. | —(CH₂SO₂)-3-pyridyl | 7-[(3-methylpiperid(-1-yl-CH₂CH₂—)—] | NH₂ |
| 4697. | —(CH₂SO₂)-3-pyridyl | 7-[(2-methylpiperid-1-yl-CH₂CH₂—)—] | NH₂ |
| 4698. | —(CH₂SO₂)-3-pyridyl | 7-(1-piperidylcarbonyl) | NH₂ |
| 4699. | —(CH₂SO₂)-3-pyridyl | 7-(4-methylpiperazin-1-yl)carbonyl] | NH₂ |
| 4700. | —(CH₂SO₂)-3-pyridyl | 7-(morpholin-4-ylcarbonyl) | NH₂ |
| 4701. | —(CH₂SO₂)-3-pyridyl | 7-(diethylaminocarbonyl) | NH₂ |
| 4702. | —(CH₂SO₂)-3-pyridyl | 7-(1-pyrrolidinylcarbonyl) | NH₂ |
| 4703. | —(CH₂SO₂)-3-pyridyl | 7-(azaperhydroepinylcarbonyl) | NH₂ |
| 4704. | —(CH₂SO₂)-3-pyridyl | 7-[(3,5-dimethylpiperid-1-yl)carbonyl] | NH₂ |
| 4705. | —(CH₂SO₂)-3-pyridyl | 7-[(4-methylpiperid-1-ylcarbonyl) | NH₂ |
| 4706. | —(CH₂SO₂)-3-pyridyl | 7-[(3-methylpiperid-1-ylcarbonyl) | NH₂ |
| 4707. | —(CH₂SO₂)-3-pyridyl | 7-[(2-methylpiperid-1-ylcarbonyl) | NH₂ |
| 4708. | —(CH₂SO₂)-3-pyridyl | 7-[2-(dimethylamino)ethoxy] | NH₂ |
| 4709. | —(CH₂SO₂)-3-pyridyl | 7-[2-(methylamino)ethoxy] | NH₂ |
| 4710. | —(CH₂SO₂)-3-pyridyl | 7-[((2R)pyrrolidin-2-yl)methoxy] | NH₂ |
| 4711. | —(CH₂SO₂)-3-pyridyl | 7-[((2R)-1-methylpyrrolidin-2-yl)methoxy] | NH₂ |
| 4712. | —(CH₂SO₂)-3-pyridyl | 7-[2-(piperid-1-yl)ethoxy] | NH₂ |
| 4713. | —(CH₂SO₂)-3-pyridyl | 7-[2-(piperazin-1-yl)ethoxy] | NH₂ |
| 4714. | —(CH₂SO₂)-3-pyridyl | 7-[2-(morpholin-4-yl)ethoxy] | NH₂ |
| 4715. | —(CH₂SO₂)-3-pyridyl | 7-[2-(1-methyl(4-piperidyl))ethoxy] | NH₂ |
| 4716. | —(CH₂SO₂)-3-pyridyl | 7-[2-(1-methyl(4-piperidyl))methoxy] | NH₂ |
| 4717. | —(CH₂SO₂)-3-pyridyl | 7-(1-methyl(4-piperidyloxy)) | NH₂ |
| 4718. | —(CH₂SO₂)-4-pyridyl | 7-(piperid-1-yl-CH₂—) | H |
| 4719. | —(CH₂SO₂)-4-pyridyl | 7-(1-CH₃-piperazin-4-yl-CH₂—) | H |
| 4720. | —(CH₂SO₂)-4-pyridyl | 7-(morpholin-4-yl-CH₂—) | H |
| 4721. | —(CH₂SO₂)-4-pyridyl | 7-(diethylamino-CH₂—) | H |
| 4722. | —(CH₂SO₂)-4-pyridyl | 7-(1-pyrrolidinyl-CH₂—) | H |
| 4723. | —(CH₂SO₂)-4-pyridyl | 7-(azaperhydroepinyl-CH₂—) | H |
| 4724. | —(CH₂SO₂)-4-pyridyl | 7-[(3,5-dimethylpiperid-1-yl)-CH₂—] | H |
| 4725. | —(CH₂SO₂)-4-pyridyl | 7-[(4-methylpiperid-1-yl-CH₂—] | H |
| 4726. | —(CH₂SO₂)-4-pyridyl | 7-[(3-methylpiperid-1-yl-CH₂—] | H |
| 4727. | —(CH₂SO₂)-4-pyridyl | 7-[(2-methylpiperid-1-yl-CH₂—] | H |
| 4728. | —(CH₂SO₂)-4-pyridyl | 7-(piperid-1-yl-CH₂CH₂—) | H |
| 4729. | —(CH₂SO₂)-4-pyridyl | 7-(1-CH₃-piperazin-4-yl-CH₂CH₂—) | H |
| 4730. | —(CH₂SO₂)-4-pyridyl | 7-(morpholin-4-yl-CH₂CH₂—) | H |
| 4731. | —(CH₂SO₂)-4-pyridyl | 7-(diethylamino-CH₂CH₂—) | H |
| 4732. | —(CH₂SO₂)-4-pyridyl | 7-(1-pyrrolidinyl-CH₂CH₂—) | H |
| 4733. | —(CH₂SO₂)-4-pyridyl | 7-(azaperhydroepinyl-CH₂CH₂—) | H |
| 4734. | —(CH₂SO₂)-4-pyridyl | 7-[(3,5-dimethylpiperid-1-yl)-CH₂CH₂—) | H |
| 4735. | —(CH₂SO₂)-4-pyridyl | 7-[(4-methylpiperid-1-yl-CH₂CH₂—) | H |
| 4736. | —(CH₂SO₂)-4-pyridyl | 7-[(3-methylpiperid(-1-yl-CH₂CH₂—)—] | H |
| 4737. | —(CH₂SO₂)-4-pyridyl | 7-[(2-methylpiperid-1-yl-CH₂CH₂—)—] | H |
| 4738. | —(CH₂SO₂)-4-pyridyl | 7-(1-piperidylcarbonyl) | H |
| 4739. | —(CH₂SO₂)-4-pyridyl | 7-[(4-methylpiperazin-1-yl)carbonyl] | H |
| 4740. | —(CH₂SO₂)-4-pyridyl | 7-(morpholin-4-ylcarbonyl) | H |
| 4741. | —(CH₂SO₂)-4-pyridyl | 7-(diethylaminocarbonyl) | H |
| 4742. | —(CH₂SO₂)-4-pyridyl | 7-(1-pyrrolidinylcarbonyl) | H |
| 4743. | —(CH₂SO₂)-4-pyridyl | 7-(azaperhydroepinylcarbonyl) | H |
| 4744. | —(CH₂SO₂)-4-pyridyl | 7-[(3,5-dimethylpiperid-1-yl)carbonyl] | H |
| 4745. | —(CH₂SO₂)-4-pyridyl | 7-[(4-methylpiperid-1-ylcarbonyl) | H |
| 4746. | —(CH₂SO₂)-4-pyridyl | 7-[(3-methylpiperid-1-ylcarbonyl) | H |
| 4747. | —(CH₂SO₂)-4-pyridyl | 7-[(2-methylpiperid-1-ylcarbonyl) | H |
| 4748. | —(CH₂SO₂)-4-pyridyl | 7-[2-(dimethylamino)ethoxy] | H |
| 4749. | —(CH₂SO₂)-4-pyridyl | 7-[2-(methylamino)ethoxy] | H |

TABLE 8-continued

[Structure: quinolin-2(1H)-one with R9 at position 6/7, Z at position 4, and thiazole at position 3 bearing R8 at thiazole position 2]

| # | R8 | R9 | Z |
|---|---|---|---|
| 4750. | —(CH₂SO₂)-4-pyridyl | 7-[((2R)pyrrolidin-2-yl)methoxy] | H |
| 4751. | —(CH₂SO₂)-4-pyridyl | 7-[((2R)-1-methylpyrrolidin-2-yl)methoxy] | H |
| 4752. | —(CH₂SO₂)-4-pyridyl | 7-[2-(piperid-1-yl)ethoxy] | H |
| 4753. | —(CH₂SO₂)-4-pyridyl | 7-[2-(piperazin-1-yl)ethoxy] | H |
| 4754. | —(CH₂SO₂)-4-pyridyl | 7-[2-(morpholin-4-yl)ethoxy] | H |
| 4755. | —(CH₂SO₂)-4-pyridyl | 7-[2-(1-methyl(4-piperidyl))ethoxy] | H |
| 4756. | —(CH₂SO₂)-4-pyridyl | 7-[2-(1-methyl(4-piperidyl))methoxy] | H |
| 4757. | —(CH₂SO₂)-4-pyridyl | 7-(1-methyl(4-piperidyloxy)) | H |
| 4758. | —(CH₂SO₂)-4-pyridyl | 7-(piperid-1-yl-CH₂—) | NH₂ |
| 4759. | —(CH₂SO₂)-4-pyridyl | 7-(1-CH₃-piperazin-4-yl-CH₂—) | NH₂ |
| 4760. | —(CH₂SO₂)-4-pyridyl | 7-(morpholin-4-yl-CH₂—) | NH₂ |
| 4761. | —(CH₂SO₂)-4-pyridyl | 7-(diethylamino-CH₂—) | NH₂ |
| 4762. | —(CH₂SO₂)-4-pyridyl | 7-(1-pyrrolidinyl-CH₂—) | NH₂ |
| 4763. | —(CH₂SO₂)-4-pyridyl | 7-(azaperhydroepinyl-CH₂—) | NH₂ |
| 4764. | —(CH₂SO₂)-4-pyridyl | 7-[(3,5-dimethylpiperid-1-yl)-CH₂—] | NH₂ |
| 4765. | —(CH₂SO₂)-4-pyridyl | 7-[(4-methylpiperid-1-yl-CH₂—] | NH₂ |
| 4766. | —(CH₂SO₂)-4-pyridyl | 7-[(3-methylpiperid-1-yl-CH₂—] | NH₂ |
| 4767. | —(CH₂SO₂)-4-pyridyl | 7-[(2-methylpiperid-1-yl-CH₂—] | NH₂ |
| 4768. | —(CH₂SO₂)-4-pyridyl | 7-(piperid-1-yl-CH₂CH₂—) | NH₂ |
| 4769. | —(CH₂SO₂)-4-pyridyl | 7-(1-CH₃-piperazin-4-yl-CH₂CH₂—) | NH₂ |
| 4770. | —(CH₂SO₂)-4-pyridyl | 7-(morpholin-4-yl-CH₂CH₂—) | NH₂ |
| 4771. | —(CH₂SO₂)-4-pyridyl | 7-(diethylamino-CH₂CH₂—) | NH₂ |
| 4772. | —(CH₂SO₂)-4-pyridyl | 7-(1-pyrrolidinyl-CH₂CH₂—) | NH₂ |
| 4773. | —(CH₂SO₂)-4-pyridyl | 7-(azaperhydroepinyl-CH₂CH₂—) | NH₂ |
| 4774. | —(CH₂SO₂)-4-pyridyl | 7-[(3,5-dimethylpiperid-1-yl)-CH₂CH₂—] | NH₂ |
| 4775. | —(CH₂SO₂)-4-pyridyl | 7-[(4-methylpiperid-1-yl-CH₂CH₂—) | NH₂ |
| 4776. | —(CH₂SO₂)-4-pyridyl | 7-[(3-methylpiperid(-1-yl-CH₂CH₂—)—] | NH₂ |
| 4777. | —(CH₂SO₂)-4-pyridyl | 7-[(2-methylpiperid-1-yl-CH₂CH₂—)—] | NH₂ |
| 4778. | —(CH₂SO₂)-4-pyridyl | 7-(1-piperidylcarbonyl) | NH₂ |
| 4779. | —(CH₂SO₂)-4-pyridyl | 7-(4-methylpiperazin-1-yl)carbonyl] | NH₂ |
| 4780. | —(CH₂SO₂)-4-pyridyl | 7-(morpholin-4-ylcarbonyl) | NH₂ |
| 4781. | —(CH₂SO₂)-4-pyridyl | 7-(diethylaminocarbonyl) | NH₂ |
| 4782. | —(CH₂SO₂)-4-pyridyl | 7-(1-pyrrolidinylcarbonyl) | NH₂ |
| 4783. | —(CH₂SO₂)-4-pyridyl | 7-(azaperhydroepinylcarbonyl) | NH₂ |
| 4784. | —(CH₂SO₂)-4-pyridyl | 7-[(3,5-dimethylpiperid-1-yl)carbonyl] | NH₂ |
| 4785. | —(CH₂SO₂)-4-pyridyl | 7-[(4-methylpiperid-1-ylcarbonyl) | NH₂ |
| 4786. | —(CH₂SO₂)-4-pyridyl | 7-[(3-methylpiperid-1-ylcarbonyl) | NH₂ |
| 4787. | —(CH₂SO₂)-4-pyridyl | 7-[(2-methylpiperid-1-ylcarbonyl) | NH₂ |
| 4788. | —(CH₂SO₂)-4-pyridyl | 7-[2-(dimethylamino)ethoxy] | NH₂ |
| 4789. | —(CH₂SO₂)-4-pyridyl | 7-[2-(methylamino)ethoxy] | NH₂ |
| 4790. | —(CH₂SO₂)-4-pyridyl | 7-[((2R)pyrrolidin-2-yl)methoxy] | NH₂ |
| 4791. | —(CH₂SO₂)-4-pyridyl | 7-[((2R)-1-methylpyrrolidin-2-yl)methoxy] | NH₂ |
| 4792. | —(CH₂SO₂)-4-pyridyl | 7-[2-(piperid-1-yl)ethoxy] | NH₂ |
| 4793. | —(CH₂SO₂)-4-pyridyl | 7-[2-(piperazin-1-yl)ethoxy] | NH₂ |
| 4794. | —(CH₂SO₂)-4-pyridyl | 7-[2-(morpholin-4-yl)ethoxy] | NH₂ |
| 4795. | —(CH₂SO₂)-4-pyridyl | 7-[2-(1-methyl(4-piperidyl))ethoxy] | NH₂ |
| 4796. | —(CH₂SO₂)-4-pyridyl | 7-[2-(1-methyl(4-piperidyl))methoxy] | NH₂ |
| 4797. | —(CH₂SO₂)-4-pyridyl | 7-(1-methyl(4-piperidyloxy)) | NH₂ |
| 4798. | —(NMeSO₂)-phenyl | 7-(piperid-1-yl-CH₂—) | H |
| 4799. | —(NMeSO₂)-phenyl | 7-(1-CH₃-piperazin-4-yl-CH₂—) | H |
| 4800. | —(NMeSO₂)-phenyl | 7-(morpholin-4-yl-CH₂—) | H |
| 4801. | —(NMeSO₂)-phenyl | 7-(diethylamino-CH₂—) | H |
| 4802. | —(NMeSO₂)-phenyl | 7-(1-pyrrolidinyl-CH₂—) | H |
| 4803. | —(NMeSO₂)-phenyl | 7-(azaperhydroepinyl-CH₂—) | H |
| 4804. | —(NMeSO₂)-phenyl | 7-[(3,5-dimethylpiperid-1-yl)-CH₂—] | H |
| 4805. | —(NMeSO₂)-phenyl | 7-[(4-methylpiperid-1-yl-CH₂—] | H |
| 4806. | —(NMeSO₂)-phenyl | 7-[(3-methylpiperid-1-yl-CH₂—] | H |
| 4807. | —(NMeSO₂)-phenyl | 7-[(2-methylpiperid-1-yl-CH₂—] | H |
| 4808. | —(NMeSO₂)-phenyl | 7-(piperid-1-yl-CH₂CH₂—) | H |
| 4809. | —(NMeSO₂)-phenyl | 7-(1-CH₃-piperazin-4-yl-CH₂CH₂—) | H |
| 4810. | —(NMeSO₂)-phenyl | 7-(morpholin-4-yl-CH₂CH₂—) | H |
| 4811. | —(NMeSO₂)-phenyl | 7-(diethylamino-CH₂CH₂—) | H |
| 4812. | —(NMeSO₂)-phenyl | 7-(1-pyrrolidinyl-CH₂CH₂—) | H |
| 4813. | —(NMeSO₂)-phenyl | 7-(azaperhydroepinyl-CH₂CH₂—) | H |
| 4814. | —(NMeSO₂)-phenyl | 7-[(3,5-dimethylpiperid-1-yl)-CH₂CH₂—] | H |
| 4815. | —(NMeSO₂)-phenyl | 7-[(4-methylpiperid-1-yl-CH₂CH₂—) | H |
| 4816. | —(NMeSO₂)-phenyl | 7-[(3-methylpiperid(-1-yl-CH₂CH₂—)—] | H |
| 4817. | —(NMeSO₂)-phenyl | 7-[(2-methylpiperid-1-yl-CH₂CH₂—)—] | H |
| 4818. | —(NMeSO₂)-phenyl | 7-(1-piperidylcarbonyl) | H |
| 4819. | —(NMeSO₂)-phenyl | 7-[(4-methylpiperazin-1-yl)carbonyl] | H |
| 4820. | —(NMeSO₂)-phenyl | 7-(morpholin-4-ylcarbonyl) | H |
| 4821. | —(NMeSO₂)-phenyl | 7-(diethylaminocarbonyl) | H |
| 4822. | —(NMeSO₂)-phenyl | 7-(1-pyrrolidinylcarbonyl) | H |
| 4823. | —(NMeSO₂)-phenyl | 7-(azaperhydroepinylcarbonyl) | H |
| 4824. | —(NMeSO₂)-phenyl | 7-[(3,5-dimethylpiperid-1-yl)carbonyl] | H |
| 4825. | —(NMeSO₂)-phenyl | 7-[(4-methylpiperid-1-ylcarbonyl) | H |
| 4826. | —(NMeSO₂)-phenyl | 7-[(3-methylpiperid-1-ylcarbonyl) | H |
| 4827. | —(NMeSO₂)-phenyl | 7-[(2-methylpiperid-1-ylcarbonyl) | H |
| 4828. | —(NMeSO₂)-phenyl | 7-[2-(dimethylamino)ethoxy] | H |
| 4829. | —(NMeSO₂)-phenyl | 7-[2-(methylamino)ethoxy] | H |
| 4830. | —(NMeSO₂)-phenyl | 7-[((2R)pyrrolidin-2-yl)methoxy] | H |
| 4831. | —(NMeSO₂)-phenyl | 7-[((2R)-1-methylpyrrolidin-2-yl)methoxy] | H |
| 4832. | —(NMeSO₂)-phenyl | 7-[2-(piperid-1-yl)ethoxy] | H |
| 4833. | —(NMeSO₂)-phenyl | 7-[2-(piperazin-1-yl)ethoxy] | H |
| 4834. | —(NMeSO₂)-phenyl | 7-[2-(morpholin-4-yl)ethoxy] | H |
| 4835. | —(NMeSO₂)-phenyl | 7-[2-(1-methyl(4-piperidyl))ethoxy] | H |
| 4836. | —(NMeSO₂)-phenyl | 7-[2-(1-methyl(4-piperidyl))methoxy] | H |
| 4837. | —(NMeSO₂)-phenyl | 7-(1-methyl(4-piperidyloxy)) | H |
| 4838. | —(NMeSO₂)-phenyl | 7-(piperid-1-yl-CH₂—) | NH₂ |
| 4839. | —(NMeSO₂)-phenyl | 7-(1-CH₃-piperazin-4-yl-CH₂—) | NH₂ |
| 4840. | —(NMeSO₂)-phenyl | 7-(morpholin-4-yl-CH₂—) | NH₂ |
| 4841. | —(NMeSO₂)-phenyl | 7-(diethylamino-CH₂—) | NH₂ |
| 4842. | —(NMeSO₂)-phenyl | 7-(1-pyrrolidinyl-CH₂—) | NH₂ |
| 4843. | —(NMeSO₂)-phenyl | 7-(azaperhydroepinyl-CH₂—) | NH₂ |

TABLE 8-continued

| # | R⁸ | R⁹ | Z |
|---|---|---|---|
| 4844. | —(NMeSO₂)-phenyl | 7-[(3,5-dimethylpiperid-1-yl)-CH₂—] | NH₂ |
| 4845. | —(NMeSO₂)-phenyl | 7-[(4-methylpiperid-1-yl-CH₂—] | NH₂ |
| 4846. | —(NMeSO₂)-phenyl | 7-[(3-methylpiperid-1-yl-CH₂—] | NH₂ |
| 4847. | —(NMeSO₂)-phenyl | 7-[(2-methylpiperid-1-yl-CH₂—] | NH₂ |
| 4848. | —(NMeSO₂)-phenyl | 7-(piperid-1-yl-CH₂CH₂—) | NH₂ |
| 4849. | —(NMeSO₂)-phenyl | 7-(1-CH₃-piperazin-4-yl-CH₂CH₂—) | NH₂ |
| 4850. | —(NMeSO₂)-phenyl | 7-(morpholin-4-yl-CH₂CH₂—) | NH₂ |
| 4851. | —(NMeSO₂)-phenyl | 7-(diethylamino-CH₂CH₂—) | NH₂ |
| 4852. | —(NMeSO₂)-phenyl | 7-(1-pyrrolidinyl-CH₂CH₂—) | NH₂ |
| 4853. | —(NMeSO₂)-phenyl | 7-(azaperhydroepinyl-CH₂CH₂—) | NH₂ |
| 4854. | —(NMeSO₂)-phenyl | 7-[(3,5-dimethylpiperid-1-yl)-CH₂CH₂—] | NH₂ |
| 4855. | —(NMeSO₂)-phenyl | 7-[(4-methylpiperid-1-yl-CH₂CH₂—) | NH₂ |
| 4856. | —(NMeSO₂)-phenyl | 7-[(3-methylpiperid(-1-yl-CH₂CH₂—)—] | NH₂ |
| 4857. | —(NMeSO₂)-phenyl | 7-[(2-methylpiperid-1-yl-CH₂CH₂—)—] | NH₂ |
| 4858. | —(NMeSO₂)-phenyl | 7-(1-piperidylcarbonyl) | NH₂ |
| 4859. | —(NMeSO₂)-phenyl | 7-[4-methylpiperazin-1-yl)carbonyl] | NH₂ |
| 4860. | —(NMeSO₂)-phenyl | 7-(morpholin-4-ylcarbonyl) | NH₂ |
| 4861. | —(NMeSO₂)-phenyl | 7-(diethylaminocarbonyl) | NH₂ |
| 4862. | —(NMeSO₂)-phenyl | 7-(1-pyrrolidinylcarbonyl) | NH₂ |
| 4863. | —(NMeSO₂)-phenyl | 7-(azaperhydroepinylcarbonyl) | NH₂ |
| 4864. | —(NMeSO₂)-phenyl | 7-[(3,5-dimethylpiperid-1-yl)carbonyl] | NH₂ |
| 4865. | —(NMeSO₂)-phenyl | 7-[(4-methylpiperid-1-ylcarbonyl] | NH₂ |
| 4866. | —(NMeSO₂)-phenyl | 7-[(3-methylpiperid-1-ylcarbonyl] | NH₂ |
| 4867. | —(NMeSO₂)-phenyl | 7-[(2-methylpiperid-1-ylcarbonyl) | NH₂ |
| 4868. | —(NMeSO₂)-phenyl | 7-[2-(dimethylamino)ethoxy] | NH₂ |
| 4869. | —(NMeSO₂)-phenyl | 7-[2-(methylamino)ethoxy] | NH₂ |
| 4870. | —(NMeSO₂)-phenyl | 7-[((2R)pyrrolidin-2-yl)methoxy] | NH₂ |
| 4871. | —(NMeSO₂)-phenyl | 7-[((2R)-1-methylpyrrolidin-2-yl)methoxy] | NH₂ |
| 4872. | —(NMeSO₂)-phenyl | 7-[2-(piperid-1-yl)ethoxy] | NH₂ |
| 4873. | —(NMeSO₂)-phenyl | 7-[2-(piperazin-1-yl)ethoxy] | NH₂ |
| 4874. | —(NMeSO₂)-phenyl | 7-[2-(morpholin-4-yl)ethoxy] | NH₂ |
| 4875. | —(NMeSO₂)-phenyl | 7-[2-(1-methyl(4-piperidyl))ethoxy] | NH₂ |
| 4876. | —(NMeSO₂)-phenyl | 7-[2-(1-methyl(4-piperidyl))methoxy] | NH₂ |
| 4877. | —(NMeSO₂)-phenyl | 7-(1-methyl(4-piperidyloxy)) | NH₂ |
| 4878. | —(NMeSO₂)-2-thienyl | 7-(piperid-1-yl-CH₂—) | H |
| 4879. | —(NMeSO₂)-2-thienyl | 7-(1-CH₃-piperazin-4-yl-CH₂—) | H |
| 4880. | —(NMeSO₂)-2-thienyl | 7-(morpholin-4-yl-CH₂—) | H |
| 4881. | —(NMeSO₂)-2-thienyl | 7-(diethylamino-CH₂—) | H |
| 4882. | —(NMeSO₂)-2-thienyl | 7-(1-pyrrolidinyl-CH₂—) | H |
| 4883. | —(NMeSO₂)-2-thienyl | 7-(azaperhydroepinyl-CH₂—) | H |
| 4884. | —(NMeSO₂)-2-thienyl | 7-[(3,5-dimethylpiperid-1-yl)-CH₂—] | H |
| 4885. | —(NMeSO₂)-2-thienyl | 7-[(4-methylpiperid-1-yl-CH₂—] | H |
| 4886. | —(NMeSO₂)-2-thienyl | 7-[(3-methylpiperid-1-yl-CH₂—] | H |
| 4887. | —(NMeSO₂)-2-thienyl | 7-[(2-methylpiperid-1-yl-CH₂—] | H |
| 4888. | —(NMeSO₂)-2-thienyl | 7-(piperid-1-yl-CH₂CH₂—) | H |
| 4889. | —(NMeSO₂)-2-thienyl | 7-(1-CH₃-piperazin-4-yl-CH₂CH₂—) | H |
| 4890. | —(NMeSO₂)-2-thienyl | 7-(morpholin-4-yl-CH₂CH₂—) | H |
| 4891. | —(NMeSO₂)-2-thienyl | 7-(diethylamino-CH₂CH₂—) | H |
| 4892. | —(NMeSO₂)-2-thienyl | 7-(1-pyrrolidinyl-CH₂CH₂—) | H |
| 4893. | —(NMeSO₂)-2-thienyl | 7-(azaperhydroepinyl-CH₂CH₂—) | H |
| 4894. | —(NMeSO₂)-2-thienyl | 7-[(3,5-dimethylpiperid-1-yl)-CH₂CH₂—] | H |
| 4895. | —(NMeSO₂)-2-thienyl | 7-(4-methylpiperid-1-yl-CH₂CH₂—) | H |
| 4896. | —(NMeSO₂)-2-thienyl | 7-[(3-methylpiperid(-1-yl-CH₂CH₂—)—] | H |
| 4897. | —(NMeSO₂)-2-thienyl | 7-[(2-methylpiperid-1-yl-CH₂CH₂—)—] | H |
| 4898. | —(NMeSO₂)-2-thienyl | 7-(1-piperidylcarbonyl) | H |
| 4899. | —(NMeSO₂)-2-thienyl | 7-[(4-methylpiperazin-1-yl)carbonyl] | H |
| 4900. | —(NMeSO₂)-2-thienyl | 7-(morpholin-4-ylcarbonyl) | H |
| 4901. | —(NMeSO₂)-2-thienyl | 7-(diethylaminocarbonyl) | H |
| 4902. | —(NMeSO₂)-2-thienyl | 7-(1-pyrrolidinylcarbonyl) | H |
| 4903. | —(NMeSO₂)-2-thienyl | 7-(azaperhydroepinylcarbonyl) | H |
| 4904. | —(NMeSO₂)-2-thienyl | 7-[(3,5-dimethylpiperid-1-yl)carbonyl] | H |
| 4905. | —(NMeSO₂)-2-thienyl | 7-[(4-methylpiperid-1-ylcarbonyl) | H |
| 4906. | —(NMeSO₂)-2-thienyl | 7-[(3-methylpiperid-1-ylcarbonyl) | H |
| 4907. | —(NMeSO₂)-2-thienyl | 7-[(2-methylpiperid-1-ylcarbonyl) | H |
| 4908. | —(NMeSO₂)-2-thienyl | 7-[2-(dimethylamino)ethoxy] | H |
| 4909. | —(NMeSO₂)-2-thienyl | 7-[2-(methylamino)ethoxy] | H |
| 4910. | —(NMeSO₂)-2-thienyl | 7-[((2R)pyrrolidin-2-yl)methoxy] | H |
| 4911. | —(NMeSO₂)-2-thienyl | 7-[((2R)-1-methylpyrrolidin-2-yl)methoxy] | H |
| 4912. | —(NMeSO₂)-2-thienyl | 7-[2-(piperid-1-yl)ethoxy] | H |
| 4913. | —(NMeSO₂)-2-thienyl | 7-[2-(piperazin-1-yl)ethoxy] | H |
| 4914. | —(NMeSO₂)-2-thienyl | 7-[2-(morpholin-4-yl)ethoxy] | H |
| 4915. | —(NMeSO₂)-2-thienyl | 7-[2-(1-methyl(4-piperidyl))ethoxy] | H |
| 4916. | —(NMeSO₂)-2-thienyl | 7-[2-(1-methyl(4-piperidyl))methoxy] | H |
| 4917. | —(NMeSO₂)-2-thienyl | 7-(1-methyl(4-piperidyloxy)) | H |
| 4918. | —(NMeSO₂)-2-thienyl | 7-(piperid-1-yl-CH₂—) | NH₂ |
| 4919. | —(NMeSO₂)-2-thienyl | 7-(1-CH₃-piperazin-4-yl-CH₂—) | NH₂ |
| 4920. | —(NMeSO₂)-2-thienyl | 7-(morpholin-4-yl-CH₂—) | NH₂ |
| 4921. | —(NMeSO₂)-2-thienyl | 7-(diethylamino-CH₂—) | NH₂ |
| 4922. | —(NMeSO₂)-2-thienyl | 7-(1-pyrrolidinyl-CH₂—) | NH₂ |
| 4923. | —(NMeSO₂)-2-thienyl | 7-(azaperhydroepinyl-CH₂—) | NH₂ |
| 4924. | —(NMeSO₂)-2-thienyl | 7-[(3,5-dimethylpiperid-1-yl)-CH₂—] | NH₂ |
| 4925. | —(NMeSO₂)-2-thienyl | 7-[(4-methylpiperid-1-yl-CH₂—] | NH₂ |
| 4926. | —(NMeSO₂)-2-thienyl | 7-[(3-methylpiperid-1-yl-CH₂—] | NH₂ |
| 4927. | —(NMeSO₂)-2-thienyl | 7-[(2-methylpiperid-1-yl-CH₂—] | NH₂ |
| 4928. | —(NMeSO₂)-2-thienyl | 7-(piperid-1-yl-CH₂CH₂—) | NH₂ |
| 4929. | —(NMeSO₂)-2-thienyl | 7-(1-CH₃-piperazin-4-yl-CH₂CH₂—) | NH₂ |
| 4930. | —(NMeSO₂)-2-thienyl | 7-(morpholin-4-yl-CH₂CH₂—) | NH₂ |
| 4931. | —(NMeSO₂)-2-thienyl | 7-(diethylamino-CH₂CH₂—) | NH₂ |
| 4932. | —(NMeSO₂)-2-thienyl | 7-(1-pyrrolidinyl-CH₂CH₂—) | NH₂ |
| 4933. | —(NMeSO₂)-2-thienyl | 7-(azaperhydroepinyl-CH₂CH₂—) | NH₂ |
| 4934. | —(NMeSO₂)-2-thienyl | 7-[(3,5-dimethylpiperid-1-yl)-CH₂CH₂—] | NH₂ |
| 4935. | —(NMeSO₂)-2-thienyl | 7-[(4-methylpiperid-1-yl-CH₂CH₂—] | NH₂ |

TABLE 8-continued

| # | R⁸ | R⁹ | Z |
|---|---|---|---|
| 4936. | —(NMeSO₂)-2-thienyl | 7-[(3-methylpiperid(-1-yl-CH₂CH₂—)—] | NH₂ |
| 4937. | —(NMeSO₂)-2-thienyl | 7-[(2-methylpiperid-1-yl-CH₂CH₂—)—] | NH₂ |
| 4938. | —(NMeSO₂)-2-thienyl | 7-(1-piperidylcarbonyl) | NH₂ |
| 4939. | —(NMeSO₂)-2-thienyl | 7-[(4-methylpiperazin-1-yl)carbonyl] | NH₂ |
| 4940. | —(NMeSO₂)-2-thienyl | 7-(morpholin-4-ylcarbonyl) | NH₂ |
| 4941. | —(NMeSO₂)-2-thienyl | 7-(diethylaminocarbonyl) | NH₂ |
| 4942. | —(NMeSO₂)-2-thienyl | 7-(1-pyrrolidinylcarbonyl) | NH₂ |
| 4943. | —(NMeSO₂)-2-thienyl | 7-(azaperhydroepinylcarbonyl) | NH₂ |
| 4944. | —(NMeSO₂)-2-thienyl | 7-[(3,5-dimethylpiperid-1-yl)carbonyl] | NH₂ |
| 4945. | —(NMeSO₂)-2-thienyl | 7-[(4-methylpiperid-1-ylcarbonyl) | NH₂ |
| 4946. | —(NMeSO₂)-2-thienyl | 7-[(3-methylpiperid-1-ylcarbonyl) | NH₂ |
| 4947. | —(NMeSO₂)-2-thienyl | 7-[(2-methylpiperid-1-ylcarbonyl) | NH₂ |
| 4948. | —(NMeSO₂)-2-thienyl | 7-[2-(dimethylamino)ethoxy] | NH₂ |
| 4949. | —(NMeSO₂)-2-thienyl | 7-[2-(methylamino)ethoxy] | NH₂ |
| 4950. | —(NMeSO₂)-2-thienyl | 7-[((2R)pyrrolidin-2-yl)methoxy] | NH₂ |
| 4951. | —(NMeSO₂)-2-thienyl | 7-[((2R)-1-methylpyrrolidin-2-yl)methoxy] | NH₂ |
| 4952. | —(NMeSO₂)-2-thienyl | 7-[2-(piperid-1-yl)ethoxy] | NH₂ |
| 4953. | —(NMeSO₂)-2-thienyl | 7-[2-(piperazin-1-yl)ethoxy] | NH₂ |
| 4954. | —(NMeSO₂)-2-thienyl | 7-[2-(morpholin-4-yl)ethoxy] | NH₂ |
| 4955. | —(NMeSO₂)-2-thienyl | 7-[2-(1-methyl(4-piperidyl))ethoxy] | NH₂ |
| 4956. | —(NMeSO₂)-2-thienyl | 7-[2-(1-methyl(4-piperidyl))methoxy] | NH₂ |
| 4957. | —(NMeSO₂)-2-thienyl | 7-(1-methyl(4-piperidyloxy)) | NH₂ |
| 4958. | —(NMeSO₂)-2-pyridyl | 7-(piperid-1-yl-CH₂—) | H |
| 4959. | —(NMeSO₂)-2-pyridyl | 7-(1-CH₃-piperazin-4-yl-CH₂—) | H |
| 4960. | —(NMeSO₂)-2-pyridyl | 7-(morpholin-4-yl-CH₂—) | H |
| 4961. | —(NMeSO₂)-2-pyridyl | 7-(diethylamino-CH₂—) | H |
| 4962. | —(NMeSO₂)-2-pyridyl | 7-(1-pyrrolidinyl-CH₂—) | H |
| 4963. | —(NMeSO₂)-2-pyridyl | 7-(azaperhydroepinyl-CH₂—) | H |
| 4964. | —(NMeSO₂)-2-pyridyl | 7-[(3,5-dimethylpiperid-1-yl)-CH₂—] | H |
| 4965. | —(NMeSO₂)-2-pyridyl | 7-[(4-methylpiperid-1-yl-CH₂—] | H |
| 4966. | —(NMeSO₂)-2-pyridyl | 7-[(3-methylpiperid-1-yl-CH₂—] | H |
| 4967. | —(NMeSO₂)-2-pyridyl | 7-[(2-methylpiperid-1-yl-CH₂—] | H |
| 4968. | —(NMeSO₂)-2-pyridyl | 7-(piperid-1-yl-CH₂CH₂—) | H |
| 4969. | —(NMeSO₂)-2-pyridyl | 7-(1-CH₃-piperazin-4-yl-CH₂CH₂—) | H |
| 4970. | —(NMeSO₂)-2-pyridyl | 7-(morpholin-4-yl-CH₂CH₂—) | H |
| 4971. | —(NMeSO₂)-2-pyridyl | 7-(diethylamino-CH₂CH₂—) | H |
| 4972. | —(NMeSO₂)-2-pyridyl | 7-(1-pyrrolidinyl-CH₂CH₂—) | H |
| 4973. | —(NMeSO₂)-2-pyridyl | 7-(azaperhydroepinyl-CH₂CH₂—) | H |
| 4974. | —(NMeSO₂)-2-pyridyl | 7-[(3,5-dimethylpiperid-1-yl)-CH₂CH₂—] | H |
| 4975. | —(NMeSO₂)-2-pyridyl | 7-[(4-methylpiperid-1-yl-CH₂CH₂—) | H |
| 4976. | —(NMeSO₂)-2-pyridyl | 7-[(3-methylpiperid(-1-yl-CH₂CH₂—)—] | H |
| 4977. | —(NMeSO₂)-2-pyridyl | 7-[(2-methylpiperid-1-yl-CH₂CH₂—)—] | H |
| 4978. | —(NMeSO₂)-2-pyridyl | 7-(1-piperidylcarbonyl) | H |
| 4979. | —(NMeSO₂)-2-pyridyl | 7-[4-methylpiperazin-1-yl)carbonyl] | H |
| 4980. | —(NMeSO₂)-2-pyridyl | 7-(morpholin-4-ylcarbonyl) | H |
| 4981. | —(NMeSO₂)-2-pyridyl | 7-(diethylaminocarbonyl) | H |
| 4982. | —(NMeSO₂)-2-pyridyl | 7-(1-pyrrolidinylcarbonyl) | H |
| 4983. | —(NMeSO₂)-2-pyridyl | 7-(azaperhydroepinylcarbonyl) | H |
| 4984. | —(NMeSO₂)-2-pyridyl | 7-[(3,5-dimethylpiperid-1-yl)carbonyl] | H |
| 4985. | —(NMeSO₂)-2-pyridyl | 7-[(4-methylpiperid-1-ylcarbonyl) | H |
| 4986. | —(NMeSO₂)-2-pyridyl | 7-[(3-methylpiperid-1-ylcarbonyl) | H |
| 4987. | —(NMeSO₂)-2-pyridyl | 7-[(2-methylpiperid-1-ylcarbonyl) | H |
| 4988. | —(NMeSO₂)-2-pyridyl | 7-[2-(dimethylamino)ethoxy] | H |
| 4989. | —(NMeSO₂)-2-pyridyl | 7-[2-(methylamino)ethoxy] | H |
| 4990. | —(NMeSO₂)-2-pyridyl | 7-[((2R)pyrrolidin-2-yl)methoxy] | H |
| 4991. | —(NMeSO₂)-2-pyridyl | 7-[((2R)-1-methylpyrrolidin-2-yl)methoxy] | H |
| 4992. | —(NMeSO₂)-2-pyridyl | 7-[2-(piperid-1-yl)ethoxy] | H |
| 4993. | —(NMeSO₂)-2-pyridyl | 7-[2-(piperazin-1-yl)ethoxy] | H |
| 4994. | —(NMeSO₂)-2-pyridyl | 7-[2-(morpholin-4-yl)ethoxy] | H |
| 4995. | —(NMeSO₂)-2-pyridyl | 7-[2-(1-methyl(4-piperidyl))ethoxy] | H |
| 4996. | —(NMeSO₂)-2-pyridyl | 7-[2-(1-methyl(4-piperidyl))methoxy] | H |
| 4997. | —(NMeSO₂)-2-pyridyl | 7-(1-methyl(4-piperidyloxy)) | H |
| 4998. | —(NMeSO₂)-2-pyridyl | 7-(piperid-1-yl-CH₂—) | NH₂ |
| 4999. | —(NMeSO₂)-2-pyridyl | 7-(1-CH₃-piperazin-4-yl-CH₂—) | NH₂ |
| 5000. | —(NMeSO₂)-2-pyridyl | 7-(morpholin-4-yl-CH₂—) | NH₂ |
| 5001. | —(NMeSO₂)-2-pyridyl | 7-(diethylamino-CH₂—) | NH₂ |
| 5002. | —(NMeSO₂)-2-pyridyl | 7-(1-pyrrolidinyl-CH₂—) | NH₂ |
| 5003. | —(NMeSO₂)-2-pyridyl | 7-(azaperhydroepinyl-CH₂—) | NH₂ |
| 5004. | —(NMeSO₂)-2-pyridyl | 7-[(3,5-dimethylpiperid-1-yl)-CH₂—] | NH₂ |
| 5005. | —(NMeSO₂)-2-pyridyl | 7-[(4-methylpiperid-1-yl-CH₂—] | NH₂ |
| 5006. | —(NMeSO₂)-2-pyridyl | 7-[(3-methylpiperid-1-yl-CH₂—] | NH₂ |
| 5007. | —(NMeSO₂)-2-pyridyl | 7-[(2-methylpiperid-1-yl-CH₂—] | NH₂ |
| 5008. | —(NMeSO₂)-2-pyridyl | 7-(piperid-1-yl-CH₂CH₂—) | NH₂ |
| 5009. | —(NMeSO₂)-2-pyridyl | 7-(1-CH₃-piperazin-4-yl-CH₂CH₂—) | NH₂ |
| 5010. | —(NMeSO₂)-2-pyridyl | 7-(morpholin-4-yl-CH₂CH₂—) | NH₂ |
| 5011. | —(NMeSO₂)-2-pyridyl | 7-(diethylamino-CH₂CH₂—) | NH₂ |
| 5012. | —(NMeSO₂)-2-pyridyl | 7-(1-pyrrolidinyl-CH₂CH₂—) | NH₂ |
| 5013. | —(NMeSO₂)-2-pyridyl | 7-(azaperhydroepinyl-CH₂CH₂—) | NH₂ |
| 5014. | —(NMeSO₂)-2-pyridyl | 7-[(3,5-dimethylpiperid-1-yl)-CH₂CH₂—] | NH₂ |
| 5015. | —(NMeSO₂)-2-pyridyl | 7-[(4-methylpiperid-1-yl-CH₂CH₂—) | NH₂ |
| 5016. | —(NMeSO₂)-2-pyridyl | 7-[(3-methylpiperid(-1-yl-CH₂CH₂—)—] | NH₂ |
| 5017. | —(NMeSO₂)-2-pyridyl | 7-[(2-methylpiperid-1-yl-CH₂CH₂—)—] | NH₂ |
| 5018. | —(NMeSO₂)-2-pyridyl | 7-(1-piperidylcarbonyl) | NH₂ |
| 5019. | —(NMeSO₂)-2-pyridyl | 7-[(4-methylpiperazin-1-yl)carbonyl] | NH₂ |
| 5020. | —(NMeSO₂)-2-pyridyl | 7-(morpholin-4-ylcarbonyl) | NH₂ |
| 5021. | —(NMeSO₂)-2-pyridyl | 7-(diethylaminocarbonyl) | NH₂ |
| 5022. | —(NMeSO₂)-2-pyridyl | 7-(1-pyrrolidinylcarbonyl) | NH₂ |
| 5023. | —(NMeSO₂)-2-pyridyl | 7-(azaperhydroepinylcarbonyl) | NH₂ |
| 5024. | —(NMeSO₂)-2-pyridyl | 7-[(3,5-dimethylpiperid-1-yl)carbonyl] | NH₂ |
| 5025. | —(NMeSO₂)-2-pyridyl | 7-[(4-methylpiperid-1-ylcarbonyl) | NH₂ |
| 5026. | —(NMeSO₂)-2-pyridyl | 7-[(3-methylpiperid-1-ylcarbonyl) | NH₂ |

TABLE 8-continued

[Structure: quinolin-2(1H)-one with R⁹ at position 7, Z at position 4, and a thiazole at position 3 with R⁸ at position 2 of thiazole]

| # | R⁸ | R⁹ | Z |
|---|---|---|---|
| 5027. | —(NMeSO₂)-2-pyridyl | 7-[2-methylpiperid-1-ylcarbonyl) | NH₂ |
| 5028. | —(NMeSO₂)-2-pyridyl | 7-[2-(dimethylamino)ethoxy] | NH₂ |
| 5029. | —(NMeSO₂)-2-pyridyl | 7-[2-(methylamino)ethoxy] | NH₂ |
| 5030. | —(NMeSO₂)-2-pyridyl | 7-[((2R)pyrrolidin-2-yl)methoxy] | NH₂ |
| 5031. | —(NMeSO₂)-2-pyridyl | 7-[((2R)-1-methylpyrrolidin-2-yl)methoxy] | NH₂ |
| 5032. | —(NMeSO₂)-2-pyridyl | 7-[2-(piperid-1-yl)ethoxy] | NH₂ |
| 5033. | —(NMeSO₂)-2-pyridyl | 7-[2-(piperazin-1-yl)ethoxy] | NH₂ |
| 5034. | —(NMeSO₂)-2-pyridyl | 7-[2-(morpholin-4-yl)ethoxy] | NH₂ |
| 5035. | —(NMeSO₂)-2-pyridyl | 7-[2-(1-methyl(4-piperidyl))ethoxy] | NH₂ |
| 5036. | —(NMeSO₂)-2-pyridyl | 7-[2-(1-methyl(4-piperidyl))methoxy] | NH₂ |
| 5037. | —(NMeSO₂)-2-pyridyl | 7-(1-methyl(4-piperidyloxy)) | NH₂ |
| 5038. | —(NMeSO₂)-3-pyridyl | 7-(piperid-1-yl-CH₂—) | H |
| 5039. | —(NMeSO₂)-3-pyridyl | 7-(1-CH₃-piperazin-4-yl-CH₂—) | H |
| 5040. | —(NMeSO₂)-3-pyridyl | 7-(morpholin-4-yl-CH₂—) | H |
| 5041. | —(NMeSO₂)-3-pyridyl | 7-(diethylamino-CH₂—) | H |
| 5042. | —(NMeSO₂)-3-pyridyl | 7-(1-pyrrolidinyl-CH₂—) | H |
| 5043. | —(NMeSO₂)-3-pyridyl | 7-(azaperhydroepinyl-CH₂—) | H |
| 5044. | —(NMeSO₂)-3-pyridyl | 7-[(3,5-dimethylpiperid-1-yl)-CH₂—] | H |
| 5045. | —(NMeSO₂)-3-pyridyl | 7-[(4-methylpiperid-1-yl-CH₂—] | H |
| 5050. | —(NMeSO₂)-3-pyridyl | 7-[(3-methylpiperid-1-yl-CH₂—] | H |
| 5047. | —(NMeSO₂)-3-pyridyl | 7-[(2-methylpiperid-1-yl-CH₂—] | H |
| 5048. | —(NMeSO₂)-3-pyridyl | 7-(piperid-1-yl-CH₂CH₂—) | H |
| 5049. | —(NMeSO₂)-3-pyridyl | 7-(1-CH₃-piperazin-4-yl-CH₂CH₂—) | H |
| 5050. | —(NMeSO₂)-3-pyridyl | 7-(morpholin-4-yl-CH₂CH₂—) | H |
| 5051. | —(NMeSO₂)-3-pyridyl | 7-(diethylamino-CH₂CH₂—) | H |
| 5052. | —(NMeSO₂)-3-pyridyl | 7-(1-pyrrolidinyl-CH₂CH₂—) | H |
| 5053. | —(NMeSO₂)-3-pyridyl | 7-(azaperhydroepinyl-CH₂CH₂—) | H |
| 5054. | —(NMeSO₂)-3-pyridyl | 7-[(3,5-dimethylpiperid-1-yl)-CH₂CH₂—] | H |
| 5055. | —(NMeSO₂)-3-pyridyl | 7-[(4-methylpiperid-1-yl-CH₂CH₂—) | H |
| 5056. | —(NMeSO₂)-3-pyridyl | 7-[(3-methylpiperid(-1-yl-CH₂CH₂—)—] | H |
| 5057. | —(NMeSO₂)-3-pyridyl | 7-[(2-methylpiperid-1-yl-CH₂CH₂—)—] | H |
| 5058. | —(NMeSO₂)-3-pyridyl | 7-(1-piperidylcarbonyl) | H |
| 5059. | —(NMeSO₂)-3-pyridyl | 7-[(4-methylpiperazin-1-yl)carbonyl] | H |
| 5060. | —(NMeSO₂)-3-pyridyl | 7-(morpholin-4-ylcarbonyl) | H |
| 5061. | —(NMeSO₂)-3-pyridyl | 7-(diethylaminocarbonyl) | H |
| 5062. | —(NMeSO₂)-3-pyridyl | 7-(1-pyrrolidinylcarbonyl) | H |
| 5063. | —(NMeSO₂)-3-pyridyl | 7-(azaperhydroepinylcarbonyl) | H |
| 5064. | —(NMeSO₂)-3-pyridyl | 7-[(3,5-dimethylpiperid-1-yl)carbonyl] | H |
| 5065. | —(NMeSO₂)-3-pyridyl | 7-[(4-methylpiperid-1-ylcarbonyl] | H |
| 5066. | —(NMeSO₂)-3-pyridyl | 7-[(3-methylpiperid-1-ylcarbonyl] | H |
| 5067. | —(NMeSO₂)-3-pyridyl | 7-[(2-methylpiperid-1-ylcarbonyl] | H |
| 5068. | —(NMeSO₂)-3-pyridyl | 7-[2-(dimethylamino)ethoxy] | H |
| 5069. | —(NMeSO₂)-3-pyridyl | 7-[2-(methylamino)ethoxy] | H |
| 5070. | —(NMeSO₂)-3-pyridyl | 7-[((2R)pyrrolidin-2-yl)methoxy] | H |
| 5071. | —(NMeSO₂)-3-pyridyl | 7-[((2R)-1-methylpyrrolidin-2-yl)methoxy] | H |
| 5072. | —(NMeSO₂)-3-pyridyl | 7-[2-(piperid-1-yl)ethoxy] | H |
| 5073. | —(NMeSO₂)-3-pyridyl | 7-[2-(piperazin-1-yl)ethoxy] | H |
| 5074. | —(NMeSO₂)-3-pyridyl | 7-[2-(morpholin-4-yl)ethoxy] | H |
| 5075. | —(NMeSO₂)-3-pyridyl | 7-[2-(1-methyl(4-piperidyl))ethoxy] | H |
| 5076. | —(NMeSO₂)-3-pyridyl | 7-[2-(1-methyl(4-piperidyl))methoxy] | H |
| 5077. | —(NMeSO₂)-3-pyridyl | 7-(1-methyl(4-piperidyloxy)) | H |
| 5078. | —(NMeSO₂)-3-pyridyl | 7-(piperid-1-yl-CH₂—) | NH₂ |
| 5079. | —(NMeSO₂)-3-pyridyl | 7-(1-CH₃-piperazin-4-yl-CH₂—) | NH₂ |
| 5080. | —(NMeSO₂)-3-pyridyl | 7-(morpholin-4-yl-CH₂—) | NH₂ |
| 5081. | —(NMeSO₂)-3-pyridyl | 7-(diethylamino-CH₂—) | NH₂ |
| 5082. | —(NMeSO₂)-3-pyridyl | 7-(1-pyrrolidinyl-CH₂—) | NH₂ |
| 5083. | —(NMeSO₂)-3-pyridyl | 7-(azaperhydroepinyl-CH₂—) | NH₂ |
| 5084. | —(NMeSO₂)-3-pyridyl | 7-[(3,5-dimethylpiperid-1-yl)-CH₂—] | NH₂ |
| 5085. | —(NMeSO₂)-3-pyridyl | 7-[(4-methylpiperid-1-yl-CH₂—] | NH₂ |
| 5086. | —(NMeSO₂)-3-pyridyl | 7-[(3-methylpiperid-1-yl-CH₂—] | NH₂ |
| 5087. | —(NMeSO₂)-3-pyridyl | 7-[(2-methylpiperid-1-yl-CH₂—] | NH₂ |
| 5088. | —(NMeSO₂)-3-pyridyl | 7-(piperid-1-yl-CH₂CH₂—) | NH₂ |
| 5089. | —(NMeSO₂)-3-pyridyl | 7-(1-CH₃-piperazin-4-yl-CH₂CH₂—) | NH₂ |
| 5090. | —(NMeSO₂)-3-pyridyl | 7-(morpholin-4-yl-CH₂CH₂—) | NH₂ |
| 5091. | —(NMeSO₂)-3-pyridyl | 7-(diethylamino-CH₂CH₂—) | NH₂ |
| 5092. | —(NMeSO₂)-3-pyridyl | 7-(1-pyrrolidinyl-CH₂CH₂—) | NH₂ |
| 5093. | —(NMeSO₂)-3-pyridyl | 7-(azaperhydroepinyl-CH₂CH₂—) | NH₂ |
| 5094. | —(NMeSO₂)-3-pyridyl | 7-[(3,5-dimethylpiperid-1-yl)-CH₂CH₂—] | NH₂ |
| 5095. | —(NMeSO₂)-3-pyridyl | 7-[(4-methylpiperid-1-yl-CH₂CH₂—) | NH₂ |
| 5096. | —(NMeSO₂)-3-pyridyl | 7-[(3-methylpiperid(-1-yl-CH₂CH₂—)—] | NH₂ |
| 5097. | —(NMeSO₂)-3-pyridyl | 7-[(2-methylpiperid-1-yl-CH₂CH₂—)—] | NH₂ |
| 5098. | —(NMeSO₂)-3-pyridyl | 7-(1-piperidylcarbonyl) | NH₂ |
| 5099. | —(NMeSO₂)-3-pyridyl | 7-[(4-methylpiperazin-1-yl)carbonyl] | NH₂ |
| 5100. | —(NMeSO₂)-3-pyridyl | 7-(morpholin-4-ylcarbonyl) | NH₂ |
| 5101. | —(NMeSO₂)-3-pyridyl | 7-(diethylaminocarbonyl) | NH₂ |
| 5102. | —(NMeSO₂)-3-pyridyl | 7-(1-pyrrolidinylcarbonyl) | NH₂ |
| 5103. | —(NMeSO₂)-3-pyridyl | 7-(azaperhydroepinylcarbonyl) | NH₂ |
| 5104. | —(NMeSO₂)-3-pyridyl | 7-[(3,5-dimethylpiperid-1-yl)carbonyl] | NH₂ |
| 5105. | —(NMeSO₂)-3-pyridyl | 7-[(4-methylpiperid-1-ylcarbonyl] | NH₂ |
| 5106. | —(NMeSO₂)-3-pyridyl | 7-[(3-methylpiperid-1-ylcarbonyl] | NH₂ |
| 5107. | —(NMeSO₂)-3-pyridyl | 7-[(2-methylpiperid-1-ylcarbonyl] | NH₂ |
| 5108. | —(NMeSO₂)-3-pyridyl | 7-[2-(dimethylamino)ethoxy] | NH₂ |
| 5109. | —(NMeSO₂)-3-pyridyl | 7-[2-(methylamino)ethoxy] | NH₂ |
| 5110. | —(NMeSO₂)-3-pyridyl | 7-[((2R)pyrrolidin-2-yl)methoxy] | NH₂ |
| 5111. | —(NMeSO₂)-3-pyridyl | 7-[((2R)-1-methylpyrrolidin-2-yl)methoxy] | NH₂ |
| 5112. | —(NMeSO₂)-3-pyridyl | 7-[2-(piperid-1-yl)ethoxy] | NH₂ |
| 5113. | —(NMeSO₂)-3-pyridyl | 7-[2-(piperazin-1-yl)ethoxy] | NH₂ |
| 5114. | —(NMeSO₂)-3-pyridyl | 7-[2-(morpholin-4-yl)ethoxy] | NH₂ |
| 5115. | —(NMeSO₂)-3-pyridyl | 7-[2-(1-methyl(4-piperidyl))ethoxy] | NH₂ |
| 5116. | —(NMeSO₂)-3-pyridyl | 7-[2-(1-methyl(4-piperidyl))methoxy] | NH₂ |
| 5117. | —(NMeSO₂)-3-pyridyl | 7-(1-methyl(4-piperidyloxy)) | NH₂ |
| 5118. | —(NMeSO₂)-4-pyridyl | 7-(piperid-1-yl-CH₂—) | H |
| 5119. | —(NMeSO₂)-4-pyridyl | 7-(1-CH₃-piperazin-4-yl-CH₂—) | H |

TABLE 8-continued

| # | R⁸ | R⁹ | Z |
|---|---|---|---|
| 5120. | —(NMeSO₂)-4-pyridyl | 7-(morpholin-4-yl-CH₂—) | H |
| 5121. | —(NMeSO₂)-4-pyridyl | 7-(diethylamino-CH₂—) | H |
| 5122. | —(NMeSO₂)-4-pyridyl | 7-(1-pyrrolidinyl-CH₂—) | H |
| 5123. | —(NMeSO₂)-4-pyridyl | 7-(azaperhydroepinyl-CH₂—) | H |
| 5124. | —(NMeSO₂)-4-pyridyl | 7-[(3,5-dimethylpiperid-1-yl)-CH₂—] | H |
| 5125. | —(NMeSO₂)-4-pyridyl | 7-[(4-methylpiperid-1-yl-CH₂—] | H |
| 5126. | —(NMeSO₂)-4-pyridyl | 7-[(3-methylpiperid-1-yl-CH₂—] | H |
| 5127. | —(NMeSO₂)-4-pyridyl | 7-[(2-methylpiperid-1-yl-CH₂—] | H |
| 5128. | —(NMeSO₂)-4-pyridyl | 7-(piperid-1-yl-CH₂CH₂—) | H |
| 5129. | —(NMeSO₂)-4-pyridyl | 7-(1-CH₃-piperazin-4-yl-CH₂CH₂—) | H |
| 5130. | —(NMeSO₂)-4-pyridyl | 7-(morpholin-4-yl-CH₂CH₂—) | H |
| 5131. | —(NMeSO₂)-4-pyridyl | 7-(diethylamino-CH₂CH₂—) | H |
| 5132. | —(NMeSO₂)-4-pyridyl | 7-(1-pyrrolidinyl-CH₂CH₂—) | H |
| 5133. | —(NMeSO₂)-4-pyridyl | 7-(azaperhydroepinyl-CH₂CH₂—) | H |
| 5134. | —(NMeSO₂)-4-pyridyl | 7-[(3,5-dimethylpiperid-1-yl)-CH₂CH₂—] | H |
| 5135. | —(NMeSO₂)-4-pyridyl | 7-[(4-methylpiperid-1-yl-CH₂CH₂—) | H |
| 5136. | —(NMeSO₂)-4-pyridyl | 7-[(3-methylpiperid(-1-yl-CH₂CH₂—)—] | H |
| 5137. | —(NMeSO₂)-4-pyridyl | 7-[(2-methylpiperid-1-yl-CH₂CH₂—)—] | H |
| 5138. | —(NMeSO₂)-4-pyridyl | 7-(1-piperidylcarbonyl) | H |
| 5139. | —(NMeSO₂)-4-pyridyl | 7-[(4-methylpiperazin-1-yl)carbonyl] | H |
| 5140. | —(NMeSO₂)-4-pyridyl | 7-(morpholin-4-ylcarbonyl) | H |
| 5141. | —(NMeSO₂)-4-pyridyl | 7-(diethylaminocarbonyl) | H |
| 5142. | —(NMeSO₂)-4-pyridyl | 7-(1-pyrrolidinylcarbonyl) | H |
| 5143. | —(NMeSO₂)-4-pyridyl | 7-(azaperhydroepinylcarbonyl) | H |
| 5144. | —(NMeSO₂)-4-pyridyl | 7-[(3,5-dimethylpiperid-1-yl)carbonyl] | H |
| 5145. | —(NMeSO₂)-4-pyridyl | 7-[(4-methylpiperid-1-ylcarbonyl) | H |
| 5146. | —(NMeSO₂)-4-pyridyl | 7-[(3-methylpiperid-1-ylcarbonyl) | H |
| 5147. | —(NMeSO₂)-4-pyridyl | 7-[(2-methylpiperid-1-ylcarbonyl) | H |
| 5148. | —(NMeSO₂)-4-pyridyl | 7-[2-(dimethylamino)ethoxy] | H |
| 5149. | —(NMeSO₂)-4-pyridyl | 7-[2-(methylamino)ethoxy] | H |
| 5150. | —(NMeSO₂)-4-pyridyl | 7-[((2R)pyrrolidin-2-yl)methoxy] | H |
| 5151. | —(NMeSO₂)-4-pyridyl | 7-[((2R)-1-methylpyrrolidin-2-yl)methoxy] | H |
| 5152. | —(NMeSO₂)-4-pyridyl | 7-[2-(piperid-1-yl)ethoxy] | H |
| 5153. | —(NMeSO₂)-4-pyridyl | 7-[2-(piperazin-1-yl)ethoxy] | H |
| 5154. | —(NMeSO₂)-4-pyridyl | 7-[2-(morpholin-4-yl)ethoxy] | H |
| 5155. | —(NMeSO₂)-4-pyridyl | 7-[2-(1-methyl(4-piperidyl))ethoxy] | H |
| 5156. | —(NMeSO₂)-4-pyridyl | 7-[2-(1-methyl(4-piperidyl))methoxy] | H |
| 5157. | —(NMeSO₂)-4-pyridyl | 7-(1-methyl(4-piperidyloxy)) | H |
| 5158. | —(NMeSO₂)-4-pyridyl | 7-(piperid-1-yl-CH₂—) | NH₂ |
| 5159. | —(NMeSO₂)-4-pyridyl | 7-(1-CH₃-piperazin-4-yl-CH₂—) | NH₂ |
| 5160. | —(NMeSO₂)-4-pyridyl | 7-(morpholin-4-yl-CH₂—) | NH₂ |
| 5161. | —(NMeSO₂)-4-pyridyl | 7-(diethylamino-CH₂—) | NH₂ |
| 5162. | —(NMeSO₂)-4-pyridyl | 7-(1-pyrrolidinyl-CH₂—) | NH₂ |
| 5163. | —(NMeSO₂)-4-pyridyl | 7-(azaperhydroepinyl-CH₂—) | NH₂ |
| 5164. | —(NMeSO₂)-4-pyridyl | 7-[(3,5-dimethylpiperid-1-yl)-CH₂—] | NH₂ |
| 5165. | —(NMeSO₂)-4-pyridyl | 7-[(4-methylpiperid-1-yl-CH₂—] | NH₂ |
| 5166. | —(NMeSO₂)-4-pyridyl | 7-[(3-methylpiperid-1-yl-CH₂—] | NH₂ |
| 5167. | —(NMeSO₂)-4-pyridyl | 7-[(2-methylpiperid-1-yl-CH₂—] | NH₂ |
| 5168. | —(NMeSO₂)-4-pyridyl | 7-(piperid-1-yl-CH₂CH₂—) | NH₂ |
| 5169. | —(NMeSO₂)-4-pyridyl | 7-(1-CH₃-piperazin-4-yl-CH₂CH₂—) | NH₂ |
| 5170. | —(NMeSO₂)-4-pyridyl | 7-(morpholin-4-yl-CH₂CH₂—) | NH₂ |
| 5171. | —(NMeSO₂)-4-pyridyl | 7-(diethylamino-CH₂CH₂—) | NH₂ |
| 5172. | —(NMeSO₂)-4-pyridyl | 7-(1-pyrrolidinyl-CH₂CH₂—) | NH₂ |
| 5173. | —(NMeSO₂)-4-pyridyl | 7-(azaperhydroepinyl-CH₂CH₂—) | NH₂ |
| 5174. | —(NMeSO₂)-4-pyridyl | 7-[(3,5-dimethylpiperid-1-yl)-CH₂CH₂—] | NH₂ |
| 5175. | —(NMeSO₂)-4-pyridyl | 7-[(4-methylpiperid-1-yl-CH₂CH₂—) | NH₂ |
| 5176. | —(NMeSO₂)-4-pyridyl | 7-[(3-methylpiperid(-1-yl-CH₂CH₂—)—] | NH₂ |
| 5177. | —(NMeSO₂)-4-pyridyl | 7-[(2-methylpiperid-1-yl-CH₂CH₂—)—] | NH₂ |
| 5178. | —(NMeSO₂)-4-pyridyl | 7-(1-piperidylcarbonyl) | NH₂ |
| 5179. | —(NMeSO₂)-4-pyridyl | 7-[(4-methylpiperazin-1-yl)carbonyl] | NH₂ |
| 5180. | —(NMeSO₂)-4-pyridyl | 7-(morpholin-4-ylcarbonyl) | NH₂ |
| 5181. | —(NMeSO₂)-4-pyridyl | 7-(diethylaminocarbonyl) | NH₂ |
| 5182. | —(NMeSO₂)-4-pyridyl | 7-(1-pyrrolidinylcarbonyl) | NH₂ |
| 5183. | —(NMeSO₂)-4-pyridyl | 7-(azaperhydroepinylcarbonyl) | NH₂ |
| 5184. | —(NMeSO₂)-4-pyridyl | 7-[(3,5-dimethylpiperid-1-yl)carbonyl] | NH₂ |
| 5185. | —(NMeSO₂)-4-pyridyl | 7-[(4-methylpiperid-1-ylcarbonyl) | NH₂ |
| 5186. | —(NMeSO₂)-4-pyridyl | 7-[(3-methylpiperid-1-ylcarbonyl) | NH₂ |
| 5187. | —(NMeSO₂)-4-pyridyl | 7-[(2-methylpiperid-1-ylcarbonyl) | NH₂ |
| 5188. | —(NMeSO₂)-4-pyridyl | 7-[2-(dimethylamino)ethoxy] | NH₂ |
| 5189. | —(NMeSO₂)-4-pyridyl | 7-[2-(methylamino)ethoxy] | NH₂ |
| 5190. | —(NMeSO₂)-4-pyridyl | 7-[((2R)pyrrolidin-2-yl)methoxy] | NH₂ |
| 5191. | —(NMeSO₂)-4-pyridyl | 7-[((2R)-1-methylpyrrolidin-2-yl)methoxy] | NH₂ |
| 5192. | —(NMeSO₂)-4-pyridyl | 7-[2-(piperid-1-yl)ethoxy] | NH₂ |
| 5193. | —(NMeSO₂)-4-pyridyl | 7-[2-(piperazin-1-yl)ethoxy] | NH₂ |
| 5194. | —(NMeSO₂)-4-pyridyl | 7-[2-(morpholin-4-yl)ethoxy] | NH₂ |
| 5195. | —(NMeSO₂)-4-pyridyl | 7-[2-(1-methyl(4-piperidyl))ethoxy] | NH₂ |
| 5196. | —(NMeSO₂)-4-pyridyl | 7-[2-(1-methyl(4-piperidyl))methoxy] | NH₂ |
| 5197. | —(NMeSO₂)-4-pyridyl | 7-(1-methyl(4-piperidyloxy)) | NH₂ |
| 5198. | —(CH₂S)-phenyl | H | H |
| 5199. | —(CH₂SO)-phenyl | H | H |

TABLE 9

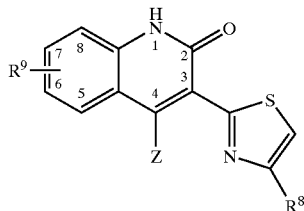

| # | R⁸ | R⁹ | Z |
|---|---|---|---|
| 5200. | 4-pyridyl | 7-(piperid-1-yl-CH$_2$—) | H |
| 5201. | 4-pyridyl | 7-(1-CH$_3$-piperazin-4-yl-CH$_2$—) | H |
| 5202. | 4-pyridyl | 7-(morpholin-4-yl-CH$_2$—) | H |
| 5203. | 4-pyridyl | 7-(diethylamino-CH$_2$—) | H |
| 5204. | 4-pyridyl | 7-(1-pyrrolidinyl-CH$_2$—) | H |
| 5205. | 4-pyridyl | 7-(azaperhydroepinyl-CH$_2$—) | H |
| 5206. | 4-pyridyl | 7-[(3,5-dimethylpiperid-1-yl)-CH$_2$—] | H |
| 5207. | 4-pyridyl | 7-[(4-methylpiperid-1-yl-CH$_2$—] | H |
| 5208. | 4-pyridyl | 7-[(3-methylpiperid-1-yl-CH$_2$—] | H |
| 5209. | 4-pyridyl | 7-[(2-methylpiperid-1-yl-CH$_2$—] | H |
| 5210. | 4-pyridyl | 7-(piperid-1-yl-CH$_2$CH$_2$—) | H |
| 5211. | 4-pyridyl | 7-(1-CH$_3$-piperazin-4-yl-CH$_2$CH$_2$—) | H |
| 5212. | 4-pyridyl | 7-(morpholin-4-yl-CH$_2$CH$_2$—) | H |
| 5213. | 4-pyridyl | 7-(diethylamino-CH$_2$CH$_2$—) | H |
| 5214. | 4-pyridyl | 7-(1-pyrrolidinyl-CH$_2$CH$_2$—) | H |
| 5215. | 4-pyridyl | 7-(azaperhydroepinyl-CH$_2$CH$_2$—) | H |
| 5216. | 4-pyridyl | 7-[(3,5-dimethylpiperid-1-yl)-CH$_2$CH$_2$—) | H |
| 5217. | 4-pyridyl | 7-[(4-methylpiperid-1-yl-CH$_2$CH$_2$—) | H |
| 5218. | 4-pyridyl | 7-[(3-methylpiperid-1-yl-CH$_2$CH$_2$—)—] | H |
| 5219. | 4-pyridyl | 7-[(2-methylpiperid-1-yl-CH$_2$CH$_2$—)—] | H |
| 5220. | 4-pyridyl | 7-(1-piperidylcarbonyl) | H |
| 5221. | 4-pyridyl | 7-[(4-methylpiperazin-1-yl)carbonyl] | H |
| 5222. | 4-pyridyl | 7-(morpholin-4-ylcarbonyl) | H |
| 5223. | 4-pyridyl | 7-(diethylaminocarbonyl) | H |
| 5224. | 4-pyridyl | 7-(1-pyrrolidinylcarbonyl) | H |
| 5225. | 4-pyridyl | 7-(azaperhydroepinylcarbonyl) | H |
| 5226. | 4-pyridyl | 7-[(3,5-dimethylpiperid-1-yl)carbonyl) | H |
| 5227. | 4-pyridyl | 7-[(4-methylpiperid-1-ylcarbonyl) | H |
| 5228. | 4-pyridyl | 7-[(3-methylpiperid-1-ylcarbonyl) | H |
| 5229. | 4-pyridyl | 7-[(2-methylpiperid-1-ylcarbonyl) | H |
| 5230. | 4-pyridyl | 7-[2-(dimethylamino)ethoxy] | H |
| 5231. | 4-pyridyl | 7-[2-(methylamino)ethoxy] | H |
| 5232. | 4-pyridyl | 7-[((2R)pyrrolidin-2-yl)methoxy] | H |
| 5233. | 4-pyridyl | 7-[((2R)-1-methylpyrrolidin-2-yl)methoxy] | H |
| 5234. | 4-pyridyl | 7-[2-(piperid-1-yl)ethoxy] | H |
| 5235. | 4-pyridyl | 7-[2-(piperazin-1-yl)ethoxy] | H |
| 5236. | 4-pyridyl | 7-[2-(morpholin-4-yl)ethoxy] | H |
| 5237. | 4-pyridyl | 7-[2-(1-methyl(4-piperidyl))ethoxy] | H |
| 5238. | 4-pyridyl | 7-[2-(1-methyl(4-piperidyl))methoxy] | H |
| 5239. | 4-pyridyl | 7-(1-methyl(4-piperidyloxy)) | H |
| 5240. | 4-pyridyl | 7-(piperid-1-yl-CH$_2$—) | NH$_2$ |
| 5241. | 4-pyridyl | 7-(1-CH$_3$-piperazin-4-yl-CH$_2$—) | NH$_2$ |
| 5242. | 4-pyridyl | 7-(morpholin-4-yl-CH$_2$—) | NH$_2$ |
| 5243. | 4-pyridyl | 7-(diethylamino-CH$_2$—) | NH$_2$ |
| 5244. | 4-pyridyl | 7-(1-pyrrolidinyl-CH$_2$—) | NH$_2$ |
| 5245. | 4-pyridyl | 7-(azaperhydroepinyl-CH$_2$—) | NH$_2$ |
| 5246. | 4-pyridyl | 7-[(3,5-dimethylpiperid-1-yl)-CH$_2$—] | NH$_2$ |
| 5247. | 4-pyridyl | 7-[(4-methylpiperid-1-yl-CH$_2$—] | NH$_2$ |
| 5248. | 4-pyridyl | 7-[(3-methylpiperid-1-yl-CH$_2$—] | NH$_2$ |
| 5249. | 4-pyridyl | 7-[(2-methylpiperid-1-yl-CH$_2$—] | NH$_2$ |
| 5250. | 4-pyridyl | 7-(piperid-1-yl-CH$_2$CH$_2$—) | NH$_2$ |
| 5251. | 4-pyridyl | 7-(1-CH$_3$-piperazin-4-yl-CH$_2$CH$_2$—) | NH$_2$ |
| 5252. | 4-pyridyl | 7-(morpholin-4-yl-CH$_2$CH$_2$—) | NH$_2$ |
| 5253. | 4-pyridyl | 7-(diethylamino-CH$_2$CH$_2$—) | NH$_2$ |
| 5254. | 4-pyridyl | 7-(1-pyrrolidinyl-CH$_2$CH$_2$—) | NH$_2$ |
| 5255. | 4-pyridyl | 7-(azaperhydroepinyl-CH$_2$CH$_2$—) | NH$_2$ |
| 5256. | 4-pyridyl | 7-[(3,5-dimethylpiperid-1-yl)-CH$_2$CH$_2$—) | NH$_2$ |
| 5257. | 4-pyridyl | 7-[(4-methylpiperid-1-yl-CH$_2$CH$_2$—) | NH$_2$ |
| 5258. | 4-pyridyl | 7-[(3-methylpiperid-1-yl-CH$_2$CH$_2$—)—] | NH$_2$ |
| 5259. | 4-pyridyl | 7-[(2-methylpiperid-1-yl-CH$_2$CH$_2$—)—] | NH$_2$ |
| 5260. | 4-pyridyl | 7-(1-piperidylcarbonyl) | NH$_2$ |
| 5261. | 4-pyridyl | 7-[(4-methylpiperazin-1-yl)carbonyl] | NH$_2$ |
| 5262. | 4-pyridyl | 7-(morpholin-4-ylcarbonyl) | NH$_2$ |
| 5263. | 4-pyridyl | 7-(diethylaminocarbonyl) | NH$_2$ |
| 5264. | 4-pyridyl | 7-(1-pyrrolidinylcarbonyl) | NH$_2$ |

TABLE 9-continued

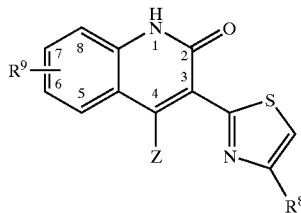

| # | R[8] | R[9] | Z |
|---|---|---|---|
| 5265. | 4-pyridyl | 7-(azaperhydroepinylcarbonyl) | $NH_2$ |
| 5266. | 4-pyridyl | 7-[(3,5-dimethylpiperid-1-yl)carbonyl] | $NH_2$ |
| 5267. | 4-pyridyl | 7-[(4-methylpiperid-1-ylcarbonyl] | $NH_2$ |
| 5268. | 4-pyridyl | 7-[(3-methylpiperid-1-ylcarbonyl] | $NH_2$ |
| 5269. | 4-pyridyl | 7-[(2-methylpiperid-1-ylcarbonyl] | $NH_2$ |
| 5270. | 4-pyridyl | 7-[2-(dimethylamino)ethoxy] | $NH_2$ |
| 5271. | 4-pyridyl | 7-[2-(methylamino)ethoxy] | $NH_2$ |
| 5272. | 4-pyridyl | 7-[((2R)pyrrolidin-2-yl)methoxy] | $NH_2$ |
| 5273. | 4-pyridyl | 7-[((2R)-1-methylpyrrolidin-2-yl)methoxy] | $NH_2$ |
| 5274. | 4-pyridyl | 7-[2-(piperid-1-yl)ethoxy] | $NH_2$ |
| 5275. | 4-pyridyl | 7-[2-(piperazin-1-yl)ethoxy] | $NH_2$ |
| 5276. | 4-pyridyl | 7-[2-(morpholin-4-yl)ethoxy] | $NH_2$ |
| 5277. | 4-pyridyl | 7-[2-(1-methyl(4-piperidyl))ethoxy] | $NH_2$ |
| 5278. | 4-pyridyl | 7-[2-(1-methyl(4-piperidyl))methoxy] | $NH_2$ |
| 5279. | 4-pyridyl | 7-(1-methyl(4-piperidyloxy)) | $NH_2$ |
| 5280. | —($CH_2SO_2$)-phenyl | 7-(piperid-1-yl-$CH_2$—) | H |
| 5281. | —($CH_2SO_2$)-phenyl | 7-(1-$CH_3$-piperazin-4-yl-$CH_2$—) | H |
| 5282. | —($CH_2SO_2$)-phenyl | 7-(morpholin-4-yl-$CH_2$—) | H |
| 5283. | —($CH_2SO_2$)-phenyl | 7-(diethylamino-$CH_2$—) | H |
| 5284. | —($CH_2SO_2$)-phenyl | 7-(1-pyrrolidinyl-$CH_2$—) | H |
| 5285. | —($CH_2SO_2$)-phenyl | 7-(azaperhydroepinyl-$CH_2$—) | H |
| 5286. | —($CH_2SO_2$)-phenyl | 7-[(3,5-dimethylpiperid-1-yl)-$CH_2$—] | H |
| 5287. | —($CH_2SO_2$)-phenyl | 7-[(4-methylpiperid-1-yl-$CH_2$—] | H |
| 5288. | —($CH_2SO_2$)-phenyl | 7-[(3-methylpiperid-1-yl-$CH_2$—] | H |
| 5289. | —($CH_2SO_2$)-phenyl | 7-[(2-methylpiperid-1-yl-$CH_2$—] | H |
| 5290. | —($CH_2SO_2$)-phenyl | 7-(piperid-1-yl-$CH_2CH_2$—) | H |
| 5291. | —($CH_2SO_2$)-phenyl | 7-(1-$CH_3$-piperazin-4-yl-$CH_2CH_2$—) | H |
| 5292. | —($CH_2SO_2$)-phenyl | 7-(morpholin-4-yl-$CH_2CH_2$—) | H |
| 5293. | —($CH_2SO_2$)-phenyl | 7-(diethylamino-$CH_2CH_2$—) | H |
| 5294. | —($CH_2SO_2$)-phenyl | 7-(1-pyrrolidinyl-$CH_2CH_2$—) | H |
| 5295. | —($CH_2SO_2$)-phenyl | 7-(azaperhydroepinyl-$CH_2CH_2$—) | H |
| 5296. | —($CH_2SO_2$)-phenyl | 7-[(3,5-dimethylpiperid-1-yl)-$CH_2CH_2$—) | H |
| 5297. | —($CH_2SO_2$)-phenyl | 7-[(4-methylpiperid-1-yl-$CH_2CH_2$—] | H |
| 5298. | —($CH_2SO_2$)-phenyl | 7-[(3-methylpiperid-1-yl-$CH_2CH_2$—)—] | H |
| 5299. | —($CH_2SO_2$)-phenyl | 7-[(2-methylpiperid-1-yl-$CH_2CH_2$—)—] | H |
| 5300. | —($CH_2SO_2$)-phenyl | 7-(1-piperidylcarbonyl) | H |
| 5301. | —($CH_2SO_2$)-phenyl | 7-[(4-methylpiperazin-1-yl)carbonyl] | H |
| 5302. | —($CH_2SO_2$)-phenyl | 7-(morpholin-4-ylcarbonyl) | H |
| 5303. | —($CH_2SO_2$)-phenyl | 7-(diethylaminocarbonyl) | H |
| 5304. | —($CH_2SO_2$)-phenyl | 7-(1-pyrrolidinylcarbonyl) | H |
| 5305. | —($CH_2SO_2$)-phenyl | 7-(azaperhydroepinylcarbonyl) | H |
| 5306. | —($CH_2SO_2$)-phenyl | 7-[(3,5-dimethylpiperid-1-yl)carbonyl] | H |
| 5307. | —($CH_2SO_2$)-phenyl | 7-[(4-methylpiperid-1-yl-carbonyl) | H |
| 5308. | —($CH_2SO_2$)-phenyl | 7-[(3-methylpiperid-1-yl-carbonyl) | H |
| 5309. | —($CH_2SO_2$)-phenyl | 7-[(2-methylpiperid-1-yl-carbonyl) | H |
| 5310. | —($CH_2SO_2$)-phenyl | 7-[2-(dimethylamino)ethoxy] | H |
| 5311. | —($CH_2SO_2$)-phenyl | 7-[2-(methylamnino)ethoxy] | H |
| 5312. | —($CH_2SO_2$)-phenyl | 7-[((2R)pyrrolidin-2-yl)methoxy] | H |
| 5313. | —($CH_2SO_2$)-phenyl | 7-[((2R)-1-methylpyrrolidin-2-yl)methoxy] | H |
| 5314. | —($CH_2SO_2$)-phenyl | 7-[2-(piperid-1-yl)ethoxy] | H |
| 5315. | —($CH_2SO_2$)-phenyl | 7-[2-(piperazin-1-yl)ethoxy] | H |
| 5316. | —($CH_2SO_2$)-phenyl | 7-[2-(morpholin-4-yl)ethoxy] | H |
| 5317. | —($CH_2SO_2$)-phenyl | 7-[2-(1-methyl(4-piperidyl))ethoxy] | H |
| 5318. | —($CH_2SO_2$)-phenyl | 7-[2-(1-methyl(4-piperidyl))methoxy] | H |
| 5319. | —($CH_2SO_2$)-phenyl | 7-(1-methyl(4-piperidyloxy)) | H |
| 5320. | —($CH_2SO_2$)-phenyl | 7-(piperid-1-yl-$CH_2$—) | $NH_2$ |
| 5321. | —($CH_2SO_2$)-phenyl | 7-(1-$CH_3$-piperazin-4-yl-$CH_2$—) | $NH_2$ |
| 5322. | —($CH_2SO_2$)-phenyl | 7-(morpholin-4-yl-$CH_2$—) | $NH_2$ |
| 5323. | —($CH_2SO_2$)-phenyl | 7-(diethylamino-$CH_2$—) | $NH_2$ |
| 5324. | —($CH_2SO_2$)-phenyl | 7-(1-pyrrolidinyl-$CH_2$—) | $NH_2$ |
| 5325. | —($CH_2SO_2$)-phenyl | 7-(azaperhydroepinyl-$CH_2$—) | $NH_2$ |
| 5326. | —($CH_2SO_2$)-phenyl | 7-[(3,5-dimethylpiperid-1-yl)-$CH_2$—] | $NH_2$ |
| 5327. | —($CH_2SO_2$)-phenyl | 7-[(4-methylpiperid-1-yl-$CH_2$—] | $NH_2$ |
| 5328. | —($CH_2SO_2$)-phenyl | 7-[(3-methylpiperid-1-yl-$CH_2$—] | $NH_2$ |
| 5329. | —($CH_2SO_2$)-phenyl | 7-[(2-methylpiperid-1-yl-$CH_2$—] | $NH_2$ |

TABLE 9-continued

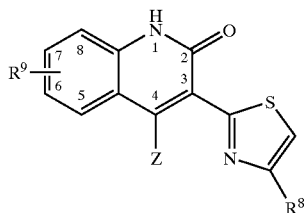

| # | R⁸ | R⁹ | Z |
|---|---|---|---|
| 5330. | —(CH₂SO₂)-phenyl | 7-(piperid-1-yl-CH₂CH₂—) | NH₂ |
| 5331. | —(CH₂SO₂)-phenyl | 7-(1-CH₃-piperazin-4-yl-CH₂CH₂—) | NH₂ |
| 5332. | —(CH₂SO₂)-phenyl | 7-(morpholin-4-yl-CH₂CH₂—) | NH₂ |
| 5333. | —(CH₂SO₂)-phenyl | 7-(diethylamino-CH₂CH₂—) | NH₂ |
| 5334. | —(CH₂SO₂)-phenyl | 7-(1-pyrrolidinyl-CH₂CH₂—) | NH₂ |
| 5335. | —(CH₂SO₂)-phenyl | 7-(azeperhydroepinyl-CH₂CH₂—) | NH₂ |
| 5336. | —(CH₂SO₂)-phenyl | 7-[(3,5-dimethylpiperid-1-yl)-CH₂CH₂—) | NH₂ |
| 5337. | —(CH₂SO₂)-phenyl | 7-[(4-methylpiperid-1-yl-CH₂CH₂—) | NH₂ |
| 5338. | —(CH₂SO₂)-phenyl | 7-[(3-methylpiperid-1-yl-CH₂CH₂—)—] | NH₂ |
| 5339. | —(CH₂SO₂)-phenyl | 7-[(2-methylpiperid-1-yl-CH₂CH₂—)—] | NH₂ |
| 5340. | —(CH₂SO₂)-phenyl | 7-(1-piperidylcarbonyl) | NH₂ |
| 5341. | —(CH₂SO₂)-phenyl | 7-[(4-methylpiperazin-1-yl)carbonyl] | NH₂ |
| 5342. | —(CH₂SO₂)-phenyl | 7-(morpholin-4-ylcarbonyl) | NH₂ |
| 5343. | —(CH₂SO₂)-phenyl | 7-(diethylaminocarbonyl) | NH₂ |
| 5344. | —(CH₂SO₂)-phenyl | 7-(1-pyrrolidinylcarbonyl) | NH₂ |
| 5345. | —(CH₂SO₂)-phenyl | 7-(azaperhydroepinylcarbonyl) | NH₂ |
| 5346. | —(CH₂SO₂)-phenyl | 7-[(3,5-dimethylpiperid-1-yl)carbonyl] | NH₂ |
| 5347. | —(CH₂SO₂)-phenyl | 7-[(4-methylpiperid-1-ylcarbonyl) | NH₂ |
| 5348. | —(CH₂SO₂)-phenyl | 7-[(3-methylpiperid-1-ylcarbonyl) | NH₂ |
| 5349. | —(CH₂SO₂)-phenyl | 7-[(2-methylpiperid-1-ylcarbonyl) | NH₂ |
| 5350. | —(CH₂SO₂)-phenyl | 7-[2-(dimethylamino)ethoxy] | NH₂ |
| 5351. | —(CH₂SO₂)-phenyl | 7-[2-(methylamino)ethoxy] | NH₂ |
| 5352. | —(CH₂SO₂)-phenyl | 7-[((2R)pyrrolidin-2-yl)methoxy] | NH₂ |
| 5353. | —(CH₂SO₂)-phenyl | 7-[((2R)-1-methylpyrrolidin-2-yl)methoxy] | NH₂ |
| 5354. | —(CH₂SO₂)-phenyl | 7-[2-(piperid-1-yl)ethoxy] | NH₂ |
| 5355. | —(CH₂SO₂)-phenyl | 7-[2-(piperazin-1-yl)ethoxy] | NH₂ |
| 5356. | —(CH₂SO₂)-phenyl | 7-[2-(morpholin-4-yl)ethoxy] | NH₂ |
| 5357. | —(CH₂SO₂)-phenyl | 7-[2-(1-methyl(4-piperidyl)ethoxy] | NH₂ |
| 5358. | —(CH₂SO₂)-phenyl | 7-[2-(1-methyl(4-piperidyl))methoxy] | NH₂ |
| 5359. | —(CH₂SO₂)-phenyl | 7-(1-methyl(4-piperidyloxy)) | NH₂ |
| 5360. | —(CH₂SO₂)-2-thienyl | 7-(piperid-1-yl-CH₂—) | H |
| 5361. | —(CH₂SO₂)-2-thienyl | 7-(1-CH₃-piperazin-4-yl-CH₂—) | H |
| 5362. | —(CH₂SO₂)-2-thienyl | 7-(morpholin-4-yl-CH₂—) | H |
| 5363. | —(CH₂SO₂)-2-thienyl | 7-(diethylamino-CH₂—) | H |
| 5364. | —(CH₂SO₂)-2-thienyl | 7-(1-pyrrolidinyl-CH₂—) | H |
| 5365. | —(CH₂SO₂)-2-thienyl | 7-(azaperhydroepinyl-CH₂—) | H |
| 5366. | —(CH₂SO₂)-2-thienyl | 7-[(3,5-dimethylpiperid-1-yl)-CH₂—] | H |
| 5367. | —(CH₂SO₂)-2-thienyl | 7-[(4-methylpiperid-1-yl-CH₂—] | H |
| 5368. | —(CH₂SO₂)-2-thienyl | 7-[(3-methylpiperid-1-yl-CH₂—] | H |
| 5369. | —(CH₂SO₂)-2-thienyl | 7-[(2-methylpiperid-1-yl-CH₂—] | H |
| 5370. | —(CH₂SO₂)-2-thienyl | 7-(piperid-1-yl-CH₂CH₂—) | H |
| 5371. | —(CH₂SO₂)-2-thienyl | 7-(1-CH₃-piperazin-4-yl-CH₂CH₂—) | H |
| 5372. | —(CH₂SO₂)-2-thienyl | 7-(morpholin-4-yl-CH₂CH₂—) | H |
| 5373. | —(CH₂SO₂)-2-thienyl | 7-(diethylamino-CH₂CH₂—) | H |
| 5374. | —(CH₂SO₂)-2-thienyl | 7-(1-pyrrolidinyl-CH₂CH₂—) | H |
| 5375. | —(CH₂SO₂)-2-thienyl | 7-(azaperhydroepinyl-CH₂CH₂—) | H |
| 5376. | —(CH₂SO₂)-2-thienyl | 7-[(3,5-dimethylpiperid-1-yl)-CH₂CH₂—) | H |
| 5377. | —(CH₂SO₂)-2-thienyl | 7-[(4-methylpiperid-1-yl-CH₂CH₂—) | H |
| 5378. | —(CH₂SO₂)-2-thienyl | 7-[(3-methylpiperid-1-yl-CH₂CH₂—)—] | H |
| 5379. | —(CH₂SO₂)-2-thienyl | 7-[(2-methylpiperid-1-yl-CH₂CH₂—)—] | H |
| 5380. | —(CH₂SO₂)-2-thienyl | 7-(1-piperidylcarbonyl) | H |
| 5381. | —(CH₂SO₂)-2-thienyl | 7-[(4-methylpiperazin-1-yl)carbonyl] | H |
| 5382. | —(CH₂SO₂)-2-thienyl | 7-(morpholin-4-ylcarbonyl) | H |
| 5383. | —(CH₂SO₂)-2-thienyl | 7-(diethylaminocarbonyl) | H |
| 5384. | —(CH₂SO₂)-2-thienyl | 7-(1-pyrrolidinylcarbonyl) | H |
| 5385. | —(CH₂SO₂)-2-thienyl | 7-(azaperhydroepinylcarbonyl) | H |
| 5386. | —(CH₂SO₂)-2-thienyl | 7-[(3,5-dimethylpiperid-1-yl)carbonyl] | H |
| 5387. | —(CH₂SO₂)-2-thienyl | 7-[(4-methylpiperid-1-ylcarbonyl) | H |
| 5388. | —(CH₂SO₂)-2-thienyl | 7-[(3-methylpiperid-1-ylcarbonyl) | H |
| 5389. | —(CH₂SO₂)-2-thienyl | 7-[(2-methylpiperid-1-ylcarbonyl) | H |
| 5390. | —(CH₂SO₂)-2-thienyl | 7-[2-(dimethylamino)ethoxy] | H |
| 5391. | —(CH₂SO₂)-2-thienyl | 7-[2-(methylamino)ethoxy] | H |
| 5392. | —(CH₂SO₂)-2-thienyl | 7-[((2R)pyrrolidin-2-yl)methoxy] | H |
| 5393. | —(CH₂SO₂)-2-thienyl | 7-[((2R)-1-methylpyrrolidin-2-yl)methoxy] | H |
| 5394. | —(CH₂SO₂)-2-thienyl | 7-[2-(piperid-1-yl)ethoxy] | H |

TABLE 9-continued

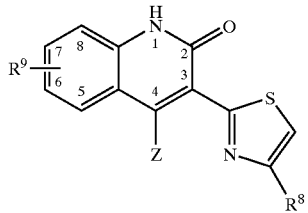

| # | R⁸ | R⁹ | Z |
|---|---|---|---|
| 5395. | —(CH₂SO₂)-2-thienyl | 7-[2-(piperazin-1-yl)ethoxy] | H |
| 5396. | —(CH₂SO₂)-2-thienyl | 7-[2-(morpholin-4-yl)ethoxy] | H |
| 5397. | —(CH₂SO₂)-2-thienyl | 7-[2-(1-methyl(4-piperidyl))ethoxy] | H |
| 5398. | —(CH₂SO₂)-2-thienyl | 7-[2-(1-methyl(4-piperidyl))methoxy] | H |
| 5399. | —(CH₂SO₂)-2-thienyl | 7-(1-methyl(4-piperidyloxy)) | H |
| 5400. | —(CH₂SO₂)-2-thienyl | 7-(piperid-1-yl-CH₂—) | NH₂ |
| 5401. | —(CH₂SO₂)-2-thienyl | 7-(1-CH₃—piperazin-4-yl-CH₂—) | NH₂ |
| 5402. | —(CH₂SO₂)-2-thienyl | 7-(morpholin-4-yl-CH₂—) | NH₂ |
| 5403. | —(CH₂SO₂)-2-thienyl | 7-(diethylamino-CH₂—) | NH₂ |
| 5404. | —(CH₂SO₂)-2-thienyl | 7-(1-pyrrolidinyl-CH₂—) | NH₂ |
| 5405. | —(CH₂SO₂)-2-thienyl | 7-(azaperhydroepinyl-CH₂—) | NH₂ |
| 5406. | —(CH₂SO₂)-2-thienyl | 7-[(3,5-dimethylpiperid-1-yl)-CH₂—] | NH₂ |
| 5407. | —(CH₂SO₂)-2-thienyl | 7-[(4-methylpiperid-1-yl-CH₂—] | NH₂ |
| 5408. | —(CH₂SO₂)-2-thienyl | 7-[(3-methylpiperid-1-yl-CH₂—] | NH₂ |
| 5409. | —(CH₂SO₂)-2-thienyl | 7-[(2-methylpiperid-1-yl-CH₂—] | NH₂ |
| 5410. | —(CH₂SO₂)-2-thienyl | 7-(piperid-1-yl-CH₂CH₂—) | NH₂ |
| 5411. | —(CH₂SO₂)-2-thienyl | 7-(1-CH₃-piperazin-4-yl-CH₂CH₂—) | NH₂ |
| 5412. | —(CH₂SO₂)-2-thienyl | 7-(morpholin-4-yl-CH₂CH₂—) | NH₂ |
| 5413. | —(CH₂SO₂)-2-thienyl | 7-(diethylamino-CH₂CH₂—) | NH₂ |
| 5414. | —(CH₂SO₂)-2-thienyl | 7-(1-pyrrolidinyl-CH₂CH₂—) | NH₂ |
| 5415. | —(CH₂SO₂)-2-thienyl | 7-(azaperhydroepinyl-CH₂CH₂—) | NH₂ |
| 5416. | —(CH₂SO₂)-2-thienyl | 7-[(3,5-dimethylpiperid-1-yl)-CH₂CH₂—] | NH₂ |
| 5417. | —(CH₂SO₂)-2-thienyl | 7-[(4-methylpiperid-1-yl-CH₂CH₂—] | NH₂ |
| 5418. | —(CH₂SO₂)-2-thienyl | 7-[(3-methylpiperid-1-yl-CH₂CH₂—)—] | NH₂ |
| 5419. | —(CH₂SO₂)-2-thienyl | 7-[(2-methylpiperid-1-yl-CH₂CH₂—)—] | NH₂ |
| 5420. | —(CH₂SO₂)-2-thienyl | 7-(1-piperidylcarbonyl) | NH₂ |
| 5421. | —(CH₂SO₂)-2-thienyl | 7-[(4-methylpiperazin-1-yl)carbonyl] | NH₂ |
| 5422. | —(CH₂SO₂) 2-thienyl | 7-(morpholin-4-ylcarbonyl) | NH₂ |
| 5423. | —(CH₂SO₂)-2-thienyl | 7-(diethylaminocarbonyl) | NH₂ |
| 5424. | —(CH₂SO₂)-2-thienyl | 7-(1-pyrrolidinylcarbonyl) | NH₂ |
| 5425. | —(CH₂SO₂)-2-thienyl | 7-(azaperhydroepinylcarbonyl) | NH₂ |
| 5426. | —(CH₂SO₂)-2-thienyl | 7-[(3,5-dimethylpiperid-1-yl)carbonyl) | NH₂ |
| 5427. | —(CH₂SO₂)-2-thienyl | 7-[(4-methylpiperid-1-ylcarbonyl) | NH₂ |
| 5428. | —(CH₂SO₂)-2-thienyl | 7-[(3-methylpiperid-1-ylcarbonyl) | NH₂ |
| 5429. | —(CH₂SO₂)-2-thienyl | 7-[(2-methylpiperid-1-ylcarbonyl) | NH₂ |
| 5430. | —(CH₂SO₂)-2-thienyl | 7-[2-(dimethylamino)ethoxy] | NH₂ |
| 5431. | —(CH₂SO₂)-2-thienyl | 7-[2-(methylamino)ethoxy] | NH₂ |
| 5432. | —(CH₂SO₂)-2-thienyl | 7-[((2R)pyrrolidin-2-yl)methoxy] | NH₂ |
| 5433. | —(CH₂SO₂)-2-thienyl | 7-[((2R)-1-methylpyrrolidin-2-yl)methoxy] | NH₂ |
| 5434. | —(CH₂SO₂)-2-thienyl | 7-[2-(piperid-1-yl)ethoxy] | NH₂ |
| 5435. | —(CH₂SO₂)-2-thienyl | 7-[2-(piperazin-1-yl)ethoxy] | NH₂ |
| 5436. | —(CH₂SO₂)-2-thienyl | 7-[2-(morpholin-4-yl)ethoxy] | NH₂ |
| 5437. | —(CH₂SO₂)-2-thienyl | 7-[2-(1-methyl(4-piperidyl))ethoxy] | NH₂ |
| 5438. | —(CH₂SO₂)-2-thienyl | 7-[2-(1-methyl(4-piperidyl))methoxy] | NH₂ |
| 5439. | —(CH₂SO₂)-2-thienyl | 7-(1-methyl(4-piperidyloxy)) | NH₂ |
| 5440. | —(CH₂SO₂)-2-pyridyl | 7-(piperid-1-yl-CH₂—) | H |
| 5441. | —(CH₂SO₂)-2-pyridyl | 7-(1-CH₃-piperazin-4-yl-CH₂—) | H |
| 5442. | —(CH₂SO₂)-2-pyridyl | 7-(morpholin-4-yl-CH₂—) | H |
| 5443. | —(CH₂SO₂)-2-pyridyl | 7-(diethylamino-CH₂—) | H |
| 5444. | —(CH₂SO₂)-2-pyridyl | 7-(1-pyrrolidinyl-CH₂—) | H |
| 5445. | —(CH₂SO₂)-2-pyridyl | 7-(azaperhydroepinyl-CH₂—) | H |
| 5446. | —(CH₂SO₂)-2-pyridyl | 7-[(3,5-dimethylpiperid-1-yl)-CH₂—] | H |
| 5447. | —(CH₂SO₂)-2-pyridyl | 7-[(4-methylpiperid-1-yl-CH₂—] | H |
| 5448. | —(CH₂SO₂)-2-pyridyl | 7-[(3-methylpiperid-1-yl-CH₂—] | H |
| 5449. | —(CH₂SO₂)-2-pyridyl | 7-[(2-methylpiperid-1-yl-CH₂—] | H |
| 5450. | —(CH₂SO₂)-2-pyridyl | 7-(piperid-1-yl-CH₂CH₂—) | H |
| 5451. | —(CH₂SO₂)-2-pyridyl | 7-(1-CH₃-piperazin-4-yl-CH₂CH₂—) | H |
| 5452. | —(CH₂SO₂)-2-pyridyl | 7-(morpholin-4-yl-CH₂CH₂—) | H |
| 5453. | —(CH₂SO₂)-2-pyridyl | 7-(diethylamino-CH₂CH₂—) | H |
| 5454. | —(CH₂SO₂)-2-pyridyl | 7-(1-pyrrolidinyl-CH₂CH₂—) | H |
| 5455. | —(CH₂SO₂)-2-pyridyl | 7-(azaperhydroepinyl-CH₂CH₂—) | H |
| 5456. | —(CH₂SO₂) 2-pyridyl | 7-[(3,5-dimethylpiperid-1-yl)-CH₂CH₂—) | H |
| 5457. | —(CH₂SO₂)-2-pyridyl | 7-[(4-methylpiperid-1-yl-CH₂CH₂—) | H |
| 5458. | —(CH₂SO₂)-2-pyridyl | 7-[(3-methylpiperid-1-yl-CH₂CH₂—)—] | H |
| 5459. | —(CH₂SO₂)-2-pyridyl | 7-[(2-methylpiperid-1-yl-CH₂CH₂—)—] | H |

TABLE 9-continued

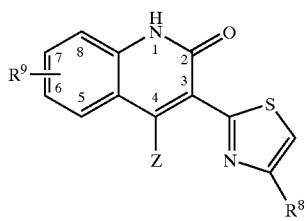

| # | R[8] | R[9] | Z |
|---|---|---|---|
| 5460. | —(CH$_2$SO$_2$) 2-pyridyl | 7-(1-piperidylcarbonyl) | H |
| 5461. | —(CH$_2$SO$_2$)-2-pyridyl | 7-[(4-methylpiperazin-1-yl)carbonyl] | H |
| 5462. | —(CH$_2$SO$_2$)-2-pyridyl | 7-(morpholin-4-ylcarbonyl) | H |
| 5463. | —(CH$_2$SO$_2$)-2-pyridyl | 7-(diethylaminocarbonyl) | H |
| 5464. | —(CH$_2$SO$_2$)-2-pyridyl | 7-(1-pyrrolidinylcarbonyl) | H |
| 5465. | —(CH$_2$SO$_2$)-2-pyridyl | 7-(azaperhydroepinylcarbonyl) | H |
| 5466. | —(CH$_2$SO$_2$)-2-pyridyl | 7-[(3,5-dimethylpiperid-1-yl)carbonyl) | H |
| 5467. | —(CH$_2$SO$_2$)-2-pyridyl | 7-[(4-methylpiperid-1-ylcarbonyl] | H |
| 5468. | —(CH$_2$SO$_2$)-2-pyridyl | 7-[(3-dimethylpiperid-1-ylcarbonyl) | H |
| 5469. | —(CH$_2$SO$_2$)-2-pyridyl | 7-[(2-methylpiperid-1-ylcarbonyl) | H |
| 5470. | —(CH$_2$SO$_2$)-2-pyridyl | 7-[2-(dimethylamino)ethoxy] | H |
| 5471. | —(CH$_2$SO$_2$)-2-pyridyl | 7-[2-(methylamino)ethoxy] | H |
| 5472. | —(CH$_2$SO$_2$)-2-pyridyl | 7-[((2R)pyrrolidin-2-yl)methoxy] | H |
| 5473. | —(CH$_2$SO$_2$)-2-pyridyl | 7-[((2R)-1-methylpyrrolidin-2-yl)methoxy] | H |
| 5474. | —(CH$_2$SO$_2$)-2-pyridyl | 7-[2-(piperid-1-yl)ethoxy] | H |
| 5475. | —(CH$_2$SO$_2$)-2-pyridyl | 7-[2-(piperazin-1-yl)ethoxy] | H |
| 5476. | —(CH$_2$SO$_2$)-2-pyridyl | 7-[2-(morpholin-4-yl)ethoxy] | H |
| 5477. | —(CH$_2$SO$_2$)-2-pyridyl | 7-[2-(1-methyl(4-piperidyl))ethoxy] | H |
| 5478. | —(CH$_2$SO$_2$)-2-pyridyl | 7-[2-(1-methyl(4-piperidyl))methoxy] | H |
| 5479. | —(CH$_2$SO$_2$)-2-pyridyl | 7-(1-methyl(4-piperidyloxy)) | H |
| 5480. | —(CH$_2$SO$_2$)-2-pyridyl | 7-(piperid-1-yl-CH$_2$—) | NH$_2$ |
| 5481. | —(CH$_2$SO$_2$)-2-pyridyl | 7-(1-CH$_3$-piperazin-4-yl-CH$_2$—) | NH$_2$ |
| 5482. | —(CH$_2$SO$_2$)-2-pyridyl | 7-(morpholin-4-yl-CH$_2$—) | NH$_2$ |
| 5483. | —(CH$_2$SO$_2$)-2-pyridyl | 7-(diethylamino-CH$_2$—) | NH$_2$ |
| 5484. | —(CH$_2$SO$_2$)-2-pyridyl | 7-(1-pyrrolidinyl-CH$_2$—) | NH$_2$ |
| 5485. | —(CH$_2$SO$_2$)-2-pyridyl | 7-(azaperhydroepinyl-CH$_2$—) | NH$_2$ |
| 5486. | —(CH$_2$SO$_2$)-2-pyridyl | 7-[(3,5-dimethylpiperid-1-yl)-CH$_2$—] | NH$_2$ |
| 5487. | —(CH$_2$SO$_2$)-2-pyridyl | 7-[(4-methylpiperid-1-yl-CH$_2$—] | NH$_2$ |
| 5488. | —(CH$_2$SO$_2$)-2-pyridyl | 7-[(3-methylpiperid-1-yl-CH$_2$—] | NH$_2$ |
| 5489. | —(CH$_2$SO$_2$)-2-pyridyl | 7-[(2-methylpiperid-1-yl-CH$_2$—] | NH$_2$ |
| 5490. | —(CH$_2$SO$_2$)-2-pyridyl | 7-(piperid-1-yl-CH$_2$CH$_2$—) | NH$_2$ |
| 5491. | —(CH$_2$SO$_2$)-2-pyridyl | 7-(1-CH$_3$-piperazin-4-yl-CH$_2$CH$_2$—) | NH$_2$ |
| 5492. | —(CH$_2$SO$_2$)-2-pyridyl | 7-(morpholin-4-yl-CH$_2$CH$_2$—) | NH$_2$ |
| 5493. | —(CH$_2$SO$_2$)-2-pyridyl | 7-(diethylamino-CH$_2$CH$_2$—) | NH$_2$ |
| 5494. | —(CH$_2$SO$_2$)-2-pyridyl | 7-(1-pyrrolidinyl-CH$_2$CH$_2$—) | NH$_2$ |
| 5495. | —(CH$_2$SO$_2$)-2-pyridyl | 7-(azaperhydroepinyl-CH$_2$CH$_2$—) | NH$_2$ |
| 5496. | —(CH$_2$SO$_2$)-2-pyridyl | 7-[(3,5-dimethylpiperid-2-yl)-CH$_2$CH$_2$—) | NH$_2$ |
| 5497. | —(CH$_2$SO$_2$)-2-pyridyl | 7-[(4-methylpiperid-1-yl-CH$_2$CH$_2$—) | NH$_2$ |
| 5498. | —(CH$_2$SO$_2$)-2-pyridyl | 7-[(3-methylpiperid-1-yl-CH$_2$CH$_2$—)—] | NH$_2$ |
| 5499. | —(CH$_2$SO$_2$)-2-pyridyl | 7-[(2-methylpiperid-1-yl-CH$_2$CH$_2$—)—] | NH$_2$ |
| 5500. | —(CH$_2$SO$_2$)-2-pyridyl | 7-(1-piperidylcarbonyl) | NH$_2$ |
| 5501. | —(CH$_2$SO$_2$)-2-pyridyl | 7-[(4-methylpiperazin-1-yl)carbonyl] | NH$_2$ |
| 5502. | —(CH$_2$SO$_2$)-2-pyridyl | 7-(morpholin-4-ylcarbonyl) | NH$_2$ |
| 5503. | —(CH$_2$SO$_2$)-2-pyridyl | 7-(diethylaminocarbonyl) | NH$_2$ |
| 5504. | —(CH$_2$SO$_2$)-2-pyridyl | 7-(1-pyrrolidinylcarbonyl) | NH$_2$ |
| 5505. | —(CH$_2$SO$_2$)-2-pyridyl | 7-(azaperhydroepinylcarbonyl) | NH$_2$ |
| 5506. | —(CH$_2$SO$_2$)-2-pyridyl | 7-[(3,5-dimethylpiperid-1-yl)carbonyl) | NH$_2$ |
| 5507. | —(CH$_2$SO$_2$)-2-pyridyl | 7-[(4-methylpiperid-1-ylcarbonyl) | NH$_2$ |
| 5508. | —(CH$_2$SO$_2$)-2-pyridyl | 7-[(3-methylpiperid-1-ylcarbonyl) | NH$_2$ |
| 5509. | —(CH$_2$SO$_2$)-2-pyridyl | 7-[(2-methylpiperid-1-ylcarbonyl) | NH$_2$ |
| 5510. | —(CH$_2$SO$_2$)-2-pyridyl | 7-[2-(dimethylamino)ethoxy] | NH$_2$ |
| 5511. | —(CH$_2$SO$_2$)-2-pyridyl | 7-[2-(methylamino)ethoxy] | NH$_2$ |
| 5512. | —(CH$_2$SO$_2$)-2-pyridyl | 7-[((2R)pyrrolidin-2-yl)methoxy] | NH$_2$ |
| 5513. | —(CH$_2$SO$_2$)-2-pyridyl | 7-[((2R)-1-methylpyrrolidin-2-yl)methoxy] | NH$_2$ |
| 5514. | —(CH$_2$SO$_2$)-2-pyridyl | 7-[2-(piperid-1-yl)ethoxy] | NH$_2$ |
| 5515. | —(CH$_2$SO$_2$)-2-pyridyl | 7-[2-(piperazin-1-yl)ethoxy] | NH$_2$ |
| 5516. | —(CH$_2$SO$_2$)-2-pyridyl | 7-[2-(morpholin-4-yl)ethoxy] | NH$_2$ |
| 5517. | —(CH$_2$SO$_2$)-2-pyridyl | 7-[2-(1-methyl(4-piperidyl))ethoxy] | NH$_2$ |
| 5518. | —(CH$_2$SO$_2$)-2-pyridyl | 7-[2-(1-methyl(4-piperidyl))methoxy] | NH$_2$ |
| 5519. | —(CH$_2$SO$_2$)-2-pyridyl | 7-(1-methyl(4-piperidyloxy)) | NH$_2$ |
| 5520. | —(CH$_2$SO$_2$)-3-pyridyl | 7-(piperid-1-yl-CH$_2$—) | H |
| 5521. | —(CH$_2$SO$_2$)-3-pyridyl | 7-(1-CH$_3$-piperazin-4-yl-CH$_2$—) | H |
| 5522. | —(CH$_2$SO$_2$)-3-pyridyl | 7-(morpholin-4-yl-CH$_2$—) | H |
| 5523. | —(CH$_2$SO$_2$)-3-pyridyl | 7-(diethylamino-CH$_2$—) | H |
| 5524. | —(CH$_2$SO$_2$)-3-pyridyl | 7-(1-pyrrolidinyl-CH$_2$—) | H |

TABLE 9-continued

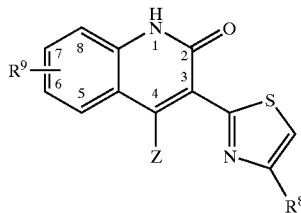

| # | R⁸ | R⁹ | Z |
|---|---|---|---|
| 5525. | —(CH₂SO₂)-3-pyridyl | 7-(azaperhydroepinyl-CH₂—) | H |
| 5526. | —(CH₂SO₂)-3-pyridyl | 7-[(3,5-dimethylpiperid-1-yl)-CH₂—] | H |
| 5527. | —(CH₂SO₂)-3-pyridyl | 7-[(4-methylpiperid-1-yl-CH₂—] | H |
| 5528. | —(CH₂SO₂)-3-pyridyl | 7-[(3-methylpiperid-1-yl-CH₂—] | H |
| 5529. | —(CH₂SO₂)-3-pyridyl | 7-[(2-methylpiperid-1-yl-CH₂—] | H |
| 5530. | —(CH₂SO₂) 3-pyridyl | 7-(piperid-1-yl-CH₂CH₂—) | H |
| 5531. | —(CH₂SO₂)-3-pyridyl | 7-(1-CH₃-piperazin-4-yl-CH₂CH₂—) | H |
| 5532. | —(CH₂SO₂)-3-pyridyl | 7-(morpholin-4-yl-CH₂CH₂—) | H |
| 5533. | —(CH₂SO₂)-3-pyridyl | 7-(diethylamino-CH₂CH₂—) | H |
| 5534. | —(CH₂SO₂)-3-pyridyl | 7-(1-pyrrolidinyl-CH₂CH₂—) | H |
| 5535. | —(CH₂SO₂)-3-pyridyl | 7-(azeperhydroepinyl-CH₂CH₂—) | H |
| 5536. | —(CH₂SO₂)-3-pyridyl | 7-[(3,5-dimethylpiperid-1-yl)-CH₂CH₂—) | H |
| 5537. | —(CH₂SO₂)-3-pyridyl | 7-[(4-methylpiperid-1-yl-CH₂CH₂—) | H |
| 5538. | —(CH₂SO₂)-3-pyridyl | 7-[(3-methylpiperid-1-yl-CH₂CH₂—)—] | H |
| 5539. | —(CH₂SO₂)-3-pyridyl | 7-[(2-methylpiperid-1-yl-CH₂CH₂—)—] | H |
| 5540. | —(CH₂SO₂)-3-pyridyl | 7-(1-piperidylcarbonyl) | H |
| 5541. | —(CH₂SO₂)-3-pyridyl | 7-[(4-methylpiperazin-1-yl)carbonyl] | H |
| 5542. | —(CH₂SO₂)-3-pyridyl | 7-(morpholin-4-ylcarbonyl) | H |
| 5543. | —(CH₂SO₂)-3-pyridyl | 7-(diethylaminocarbonyl) | H |
| 5544. | —(CH₂SO₂)-3-pyridyl | 7-(1-pyrrolidinylcarbonyl) | H |
| 5545. | —(CH₂SO₂)-3-pyridyl | 7-(azaperhydroepinylcarbonyl) | H |
| 5546. | —(CH₂SO₂)-3-pyridyl | 7-[(3,5-dimethylpiperid-1-yl)carbonyl] | H |
| 5547. | —(CH₂SO₂)-3-pyridyl | 7-[(4-methylpiperid-1-ylcarbonyl) | H |
| 5548. | —(CH₂SO₂)-3-pyridyl | 7-[(3-methylpiperid-1-ylcarbonyl) | H |
| 5549. | —(CH₂SO₂)-3-pyridyl | 7-[(2-methylpiperid-1-ylcarbonyl) | H |
| 5550. | —(CH₂SO₂)-3-pyridyl | 7-[2-(dimethylamino)ethoxy] | H |
| 5551. | —(CH₂SO₂)-3-pyridyl | 7-[2-(methylamino)ethoxy] | H |
| 5552. | —(CH₂SO₂)-3-pyridyl | 7-[((2R)pyrrolidin-2-yl)methoxy] | H |
| 5553. | —(CH₂SO₂)-3-pyridyl | 7-[((2R)-1-methylpyrrolidin-2-yl)methoxy] | H |
| 5554. | —(CH₂SO₂)-3-pyridyl | 7-[2-(piperid-1-yl)ethoxy] | H |
| 5555. | —(CH₂SO₂)-3-pyridyl | 7-[2-(piperazin-1-yl)ethoxy] | H |
| 5556. | —(CH₂SO₂)-3-pyridyl | 7-[2-(morpholin-4-yl)ethoxy] | H |
| 5557. | —(CH₂SO₂)-3-pyridyl | 7-[2-(1-methyl(4-piperidyl))ethoxy] | H |
| 5558. | —(CH₂SO₂)-3-pyridyl | 7-[2-(1-methyl(4-piperidyl))methoxy] | H |
| 5559. | —(CH₂SO₂)-3-pyridyl | 7-(1-methyl(4-piperidyloxy)) | H |
| 5560. | —(CH₂SO₂)-3-pyridyl | 7-(piperid-1-yl-CH₂—) | NH₂ |
| 5561. | —(CH₂SO₂)-3-pyridyl | 7-(1-CH₃-piperazin-4-yl-CH₂—) | NH₂ |
| 5562. | —(CH₂SO₂)-3-pyridyl | 7-(morpholin-4-yl-CH₂—) | NH₂ |
| 5563. | —(CH₂SO₂)-3-pyridyl | 7-(diethylamino-CH₂—) | NH₂ |
| 5564. | —(CH₂SO₂)-3-pyridyl | 7-(1-pyrrolidinyl-CH₂—) | NH₂ |
| 5565. | —(CH₂SO₂)-3-pyridyl | 7-(azaperhydroepinyl-CH₂—) | NH₂ |
| 5566. | —(CH₂SO₂)-3-pyridyl | 7-[(3,5-dimethylpiperid-1-yl)-CH₂—] | NH₂ |
| 5567. | —(CH₂SO₂)-3-pyridyl | 7-[(4-methylpiperid-1-yl-CH₂—] | NH₂ |
| 5568. | —(CH₂SO₂)-3-pyridyl | 7-[(3-methylpiperid-1-yl-CH₂—] | NH₂ |
| 5569. | —(CH₂SO₂)-3-pyridyl | 7-[(2-methylpiperid-1-yl-CH₂—] | NH₂ |
| 5570. | —(CH₂SO₂)-3-pyridyl | 7-(piperid-1-yl-CH₂CH₂—) | NH₂ |
| 5571. | —(CH₂SO₂)-3-pyridyl | 7-(1-CH₃-piperazin-4-yl-CH₂CH₂—) | NH₂ |
| 5572. | —(CH₂SO₂)-3-pyridyl | 7-(morpholin-4-yl-CH₂CH₂—) | NH₂ |
| 5573. | —(CH₂SO₂)-3-pyridyl | 7-(diethylamino-CH₂CH₂—) | NH₂ |
| 5574. | —(CH₂SO₂)-3-pyridyl | 7-(1-pyrrolidinyl-CH₂CH₂—) | NH₂ |
| 5575. | —(CH₂SO₂)-3-pyridyl | 7-(azaperhydroepinyl-CH₂CH₂—) | NH₂ |
| 5576. | —(CH₂SO₂)-3-pyridyl | 7-[(3,5-dimethylpiperid-1-yl)-CH₂CH₂—) | NH₂ |
| 5577. | —(CH₂SO₂)-3-pyridyl | 7-[(4-methylpiperid-1-yl-CH₂CH₂—) | NH₂ |
| 5578. | —(CH₂SO₂)-3-pyridyl | 7-[(3-methylpiperid-1-yl-CH₂CH₂—)—] | NH₂ |
| 5579. | —(CH₂SO₂)-3-pyridyl | 7-[(2-methylpiperid-1-yl-CH₂CH₂—)—] | NH₂ |
| 5580. | —(CH₂SO₂)-3-pyridyl | 7-(1-piperidylcarbonyl) | NH₂ |
| 5581. | —(CH₂SO₂)-3-pyridyl | 7-[(4-methylpiperazin-1-yl)carbonyl] | NH₂ |
| 5582. | —(CH₂SO₂)-3-pyridyl | 7-(morpholin-4-ylcarbonyl) | NH₂ |
| 5583. | —(CH₂SO₂)-3-pyridyl | 7-(diethylaminocarbonyl) | NH₂ |
| 5584. | —(CH₂SO₂)-3-pyridyl | 7-(1-pyrrolidinylcarbonyl) | NH₂ |
| 5585. | —(CH₂SO₂)-3-pyridyl | 7-(azaperhydroepinylcarbonyl) | NH₂ |
| 5586. | —(CH₂SO₂)-3-pyridyl | 7-[(3,5-dimethylpiperid-1-yl)carbonyl] | NH₂ |
| 5587. | —(CH₂SO₂)-3-pyridyl | 7-[(4-methylpiperid-1-ylcarbonyl) | NH₂ |
| 5588. | —(CH₂SO₂)-3-pyridyl | 7-[(3-methylpiperid-1-ylcarbonyl) | NH₂ |
| 5589. | —(CH₂SO₂)-3-pyridyl | 7-[(2-methylpiperid-1-ylcarbonyl) | NH₂ |

TABLE 9-continued

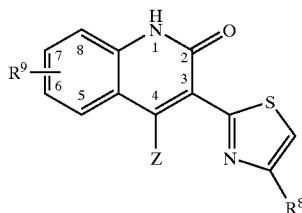

| # | R⁸ | R⁹ | Z |
|---|---|---|---|
| 5590. | —(CH₂SO₂)-3-pyridyl | 7-[2-(dimethylamino)ethoxy] | NH₂ |
| 5591. | —(CH₂SO₂)-3-pyridyl | 7-[2-(methylamino)ethoxy] | NH₂ |
| 5592. | —(CH₂SO₂)-3-pyridyl | 7-[((2R)pyrrolidin-2-yl)methoxy] | NH₂ |
| 5593. | —(CH₂SO₂)-3-pyridyl | 7-[((2R)-1-methylpyrrolidin-2-yl)methoxyl] | NH₂ |
| 5594. | —(CH₂SO₂)-3-pyridyl | 7-[2-(piperid-1-yl)ethoxy] | NH₂ |
| 5595. | —(CH₂SO₂)-3-pyridyl | 7-[2-(piperazin-1-yl)ethoxy] | NH₂ |
| 5596. | —(CH₂SO₂)-3-pyridyl | 7-[2-(morpholin-4-yl)ethoxy) | NH₂ |
| 5597. | —(CH₂SO₂)-3-pyridyl | 7-[2-(1-methyl(4-piperidyl))ethoxy] | NH₂ |
| 5598. | —(CH₂SO₂)-3-pyridyl | 7-[2-(1-methyl(4-piperidyl))methoxy] | NH₂ |
| 5599. | —(CH₂SO₂)-3-pyridyl | 7-(1-methyl(4-piperidyloxy)) | NH₂ |
| 5600. | —(CH₂SO₂)-4-pyridyl | 7-(piperid-1-yl-CH₂—) | H |
| 5601. | —(CH₂SO₂)-4-pyridyl | 7-(1-CH₃-piperazin-4-yl-CH₂—) | H |
| 5602. | —(CH₂SO₂)-4-pyridyl | 7-(morpholin-4-yl-CH₂—) | H |
| 5603. | —(CH₂SO₂)-4-pyridyl | 7-(diethylamino-CH₂—) | H |
| 5604. | —(CH₂SO₂)-4-pyridyl | 7-(1-pyrrolidinyl-CH₂—) | H |
| 5605. | —(CH₂SO₂)-4-pyridyl | 7-(azaperhydroepinyl-CH₂—) | H |
| 5606. | —(CH₂SO₂)-4-pyridyl | 7-[(3,5-dimethylpiperid-1-yl)-CH₂—) | H |
| 5607. | —(CH₂SO₂)-4-pyridyl | 7-[(4-methylpiperid-1-yl-CH₂—] | H |
| 5608. | —(CH₂SO₂)-4-pyridyl | 7-[(3-methylpiperid-1-yl-CH₂—] | H |
| 5609. | —(CH₂SO₂)-4-pyridyl | 7-[(2-methylpiperid-1-yl-CH₂—] | H |
| 5610. | —(CH₂SO₂) 4-pyridyl | 7-(piperid-1-yl-CH₂CH₂—) | H |
| 5611. | —(CH₂SO₂)-4-pyridyl | 7-(1-CH₃-piperazin-4-yl-CH₂CH₂—) | H |
| 5612. | —(CH₂SO₂)-4-pyridyl | 7-(morpholin-4-yl-CH₂CH₂—) | H |
| 5613. | —(CH₂SO₂)-4-pyridyl | 7-(diethylamino-CH₂CH₂—) | H |
| 5614. | —(CH₂SO₂)-4-pyridyl | 7-(1-pyrrolidinyl-CH₂CH₂—) | H |
| 5615. | —(CH₂SO₂)-4-pyridyl | 7-(azaperhydroepinyl-CH₂CH₂—) | H |
| 5616. | —(CH₂SO₂)-4-pyridyl | 7-[(3,5-dimethylpiperid-1-yl)-CH₂CH₂—) | H |
| 5617. | —(CH₂SO₂)-4-pyridyl | 7-[(4-methylpiperid-1-yl-CH₂CH₂—) | H |
| 5618. | —(CH₂SO₂)-4-pyridyl | 7-[(3-methylpiperid-1-yl-CH₂CH₂—)—] | H |
| 5619. | —(CH₂SO₂)-4-pyridyl | 7-[(2-methylpiperid-1-yl-CH₂CH₂—)—] | H |
| 5620. | —(CH₂SO₂)-4-pyridyl | 7-(1-piperidylcarbonyl) | H |
| 5621. | —(CH₂SO₂)-4-pyridyl | 7-[(4-methylpiperazin-1-yl)carbonyl] | H |
| 5622. | —(CH₂SO₂)-4-pyridyl | 7-(morpholin-4-ylcarbonyl) | H |
| 5623. | —(CH₂SO₂)-4-pyridyl | 7-(diethylaminocarbonyl) | H |
| 5624. | —(CH₂SO₂)-4-pyridyl | 7-(1-pyrrolidinylcarbonyl) | H |
| 5625. | —(CH₂SO₂)-4-pyridyl | 7-(azaperhydroepinylcarbonyl) | H |
| 5626. | —(CH₂SO₂)-4-pyridyl | 7-[(3,5-dimethylpiperid-1-yl)carbonyl] | H |
| 5627. | —(CH₂SO₂)-4-pyridyl | 7-[(4-methylpiperid-1-ylcarbonyl) | H |
| 5628. | —(CH₂SO₂)-4-pyridyl | 7-[(3-methylpiperid-1-ylcarbonyl) | H |
| 5629. | —(CH₂SO₂)-4-pyridyl | 7-[(2-methylpiperid-1-ylcarbonyl) | H |
| 5630. | —(CH₂SO₂)-4-pyridyl | 7-[2-(dimethylamino)ethoxy] | H |
| 5631. | —(CH₂SO₂)-4-pyridyl | 7-[2-(methylamino)ethoxy] | H |
| 5632. | —(CH₂SO₂)-4-pyridyl | 7-[((2R)pyrrolidin-2-yl)methoxy] | H |
| 5633. | —(CH₂SO₂)-4-pyridyl | 7-[((2R)-1-methylpyrrolidin-2-yl)methoxy] | H |
| 5634. | —(CH₂SO₂)-4-pyridyl | 7-[2-(piperid-1-yl)ethoxy] | H |
| 5635. | —(CH₂SO₂)-4-pyridyl | 7-[2-(piperazin-1-yl)ethoxy] | H |
| 5636. | —(CH₂SO₂)-4-pyridyl | 7-[2-(morpholin-4-yl)ethoxy] | H |
| 5637. | —(CH₂SO₂)-4-pyridyl | 7-[2-(1-methyl(4-piperidyl))ethoxy] | H |
| 5638. | —(CH₂SO₂)-4-pyridyl | 7-[2-(1-methyl(4-piperidyl))methoxy] | H |
| 5639. | —(CH₂SO₂)-4-pyridyl | 7-(1-methyl(4-piperidyloxy)) | H |
| 5640. | —(CH₂SO₂)-4-pyridyl | 7-(piperid-1-yl-CH₂—) | NH₂ |
| 5641. | —(CH₂SO₂)-4-pyridyl | 7-(1-CH₃—piperazin-4-yl-CH₂—) | NH₂ |
| 5642. | —(CH₂SO₂)-4-pyridyl | 7-(morpholin-4-yl-CH₂—) | NH₂ |
| 5643. | —(CH₂SO₂)-4-pyridyl | 7-(diethylamino-CH₂—) | NH₂ |
| 5644. | —(CH₂SO₂)-4-pyridyl | 7-(1-pyrrolidinyl-CH₂—) | NH₂ |
| 5645. | —(CH₂SO₂)-4-pyridyl | 7-(azaperhydroepinyl-CH₂—) | NH₂ |
| 5646. | —(CH₂SO₂)-4-pyridyl | 7-[(3,5-dimethylpiperid-1-yl)-CH₂—] | NH₂ |
| 5647. | —(CH₂SO₂)-4-pyridyl | 7-[(4-methylpiperid-1-yl-CH₂—1 | NH₂ |
| 5648. | —(CH₂SO₂)-4-pyridyl | 7-[(3-methylpiperid-1-yl-CH₂—] | NH₂ |
| 5649. | —(CH₂SO₂)-4-pyridyl | 7-[(2-methylpiperid-1-yl-CH₂—] | NH₂ |
| 5650. | —(CH₂SO₂)-4-pyridyl | 7-(piperid-1-yl-CH₂CH₂—) | NH₂ |
| 5651. | —(CH₂SO₂)-4-pyridyl | 7-(1-CH₃-piperazin-4-yl-CH₂CH₂—) | NH₂ |
| 5652. | —(CH₂SO₂)-4-pyridyl | 7-(morpholin-4-yl-CH₂CH₂—) | NH₂ |
| 5653. | —(CH₂SO₂)-4-pyridyl | 7-(diethylamino-CH₂CH₂—) | NH₂ |
| 5654. | —(CH₂SO₂)-4-pyridyl | 7-(1-pyrrolidinyl-CH₂CH₂—) | NH₂ |

TABLE 9-continued

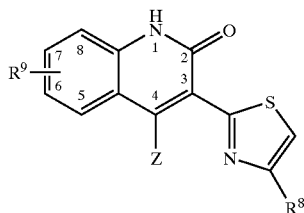

| # | R⁸ | R⁹ | Z |
|---|---|---|---|
| 5655. | —(CH₂SO₂)-4-pyridyl | 7-(azaperhydroepinyl-CH₂CH₂—) | NH₂ |
| 5656. | —(CH₂SO₂)-4-pyridyl | 7-[(3,5-dimethylpiperid-1-yl)-CH₂CH₂—) | NH₂ |
| 5657. | —(CH₂SO₂)-4-pyridyl | 7-[(4-methylpiperid-1-yl-CH₂CH₂—) | NH₂ |
| 5658. | —(CH₂SO₂)-4-pyridyl | 7-[(3-methylpiperid-1-yl-CH₂CH₂—)—] | NH₂ |
| 5659. | —(CH₂SO₂)-4-pyridyl | 7-[(2-methylpiperid-1-yl-CH₂CH₂—)—] | NH₂ |
| 5660. | —(CH₂SO₂)-4-pyridyl | 7-(1-piperidylcarbonyl) | NH₂ |
| 5661. | —(CH₂SO₂)-4-pyridyl | 7-[(4-methylpiperazin-1-yl)carbonyl] | NH₂ |
| 5662. | —(CH₂SO₂)-4-pyridyl | 7-(morpholin-4-ylcarbonyl) | NH₂ |
| 5663. | —(CH₂SO₂)-4-pyridyl | 7-(diethylaminocarbonyl) | NH₂ |
| 5664. | —(CH₂SO₂)-4-pyridyl | 7-(1-pyrrolidinylcarbonyl) | NH₂ |
| 5665. | —(CH₂SO₂)-4-pyridyl | 7-(azaperhydroepinylcarbonyl) | NH₂ |
| 5666. | —(CH₂SO₂)-4-pyridyl | 7-[(3,5-dimethylpiperid-1-yl)carbonyl] | NH₂ |
| 5667. | —(CH₂SO₂)-4-pyridyl | 7-[(4-methylpiperid-1-ylcarbonyl) | NH₂ |
| 5668. | —(CH₂SO₂)-4-pyridyl | 7-[(3-methylpiperid-1-ylcarbonyl) | NH₂ |
| 5669. | —(CH₂SO₂)-4-pyridyl | 7-[(2-methylpiperid-1-ylcarbonyl) | NH₂ |
| 5670. | —(CH₂SO₂)-4-pyridyl | 7-[2-(dimethylamino)ethoxy] | NH₂ |
| 5671. | —(CH₂SO₂)-4-pyridyl | 7-[2-(methylamino)ethoxy] | NH₂ |
| 5672. | —(CH₂SO₂)-4-pyridyl | 7-[((2R)pyrrolidin-2-yl)methoxy] | NH₂ |
| 5673. | —(CH₂SO₂)-4-pyridyl | 7-[((2R)-1-methylpyrrolidin-2-yl)methoxy] | NH₂ |
| 5674. | —(CH₂SO₂)-4-pyridyl | 7-[2-(piperid-1-yl)ethoxy] | NH₂ |
| 5675. | —(CH₂SO₂)-4-pyridyl | 7-[2-(piperazin-1-yl)ethoxy] | NH₂ |
| 5676. | —(CH₂SO₂)-4-pyridyl | 7-[2-(morpholin-4-yl)ethoxy] | NH₂ |
| 5677. | —(CH₂SO₂)-4-pyridyl | 7-[2-(1-methyl(4-piperidyl))ethoxy] | NH₂ |
| 5678. | —(CH₂SO₂)-4-pyridyl | 7-[2-(1-methyl(4-piperidyl))methoxy] | NH₂ |
| 5679. | —(CH₂SO₂)-4-pyridyl | 7-(1-methyl(4-piperidyloxy)) | NH₂ |
| 5680. | —(NMeSO₂)-phenyl | 7-(piperid-1-yl-CH₂—) | H |
| 5681. | —(NMeSO₂)-phenyl | 7-(1-CH₃—piperazin-4-yl-CH₂—) | H |
| 5682. | —(NMeSO₂)-phenyl | 7-(morpholin-4-yl-CH₂—) | H |
| 5683. | —(NMeSO₂)-phenyl | 7-(diethylamino-CH₂—) | H |
| 5684. | —(NMeSO₂)-phenyl | 7-(1-pyrrolidinyl-CH₂—) | H |
| 5685. | —(NMeSO₂)-phenyl | 7-(azaperhydroepinyl-CH₂—) | H |
| 5686. | —(NMeSO₂)-phenyl | 7-[(3,5-dimethylpiperid-1-yl)-CH₂—] | H |
| 5687. | —(NMeSO₂)-phenyl | 7-[(4-methylpiperid-1-yl-CH₂—] | H |
| 5688. | —(NMeSO₂)-phenyl | 7-[(3-methylpiperid-1-yl-CH₂—] | H |
| 5689. | —(NMeSO₂)-phenyl | 7-[(2-methylpiperid-1-yl-CH₂—] | H |
| 5690. | —(NMeSO₂)-phenyl | 7-(piperid-1-yl-CH₂CH₂—) | H |
| 5691. | —(NMeSO₂)-phenyl | 7-(1-CH₃-piperazin-4-yl-CH₂CH₂—) | H |
| 5692. | —(NMeSO₂)-phenyl | 7-(morpholin-4-yl-CH₂CH₂—) | H |
| 5693. | —(NMeSO₂)-phenyl | 7-(diethylamino-CH₂CH₂—) | H |
| 5694. | —(NMeSO₂)-phenyl | 7-(1-pyrrolidinyl-CH₂CH₂—) | H |
| 5695. | —(NMeSO₂)-phenyl | 7-(azaperhydroepinyl-CH₂CH₂—) | H |
| 5696. | —(NMeSO₂)-phenyl | 7-[(3,5-dimethylpiperid-1-yl)-CH₂CH₂—) | H |
| 5697. | —(NMeSO₂)-phenyl | 7-[(4-methylpiperid-1-yl-CH₂CH₂—) | H |
| 5698. | —(NMeSO₂)-phenyl | 7-[(3-methylpiperid-1-yl-CH₂CH₂—)—] | H |
| 5699. | —(NMeSO₂)-phenyl | 7-[(2-methylpiperid-1-yl-CH₂CH₂—)—] | H |
| 5700. | —(NMeSO₂)-phenyl | 7-(1-piperidylcarbonyl) | H |
| 5701. | —(NMeSO₂)-phenyl | 7-[(4-methylpiperazin-1-yl)carbonyl] | H |
| 5702. | —(NMeSO₂) phenyl | 7-(morpholin-4-ylcarbonyl) | H |
| 5703. | —(NMeSO₂)-phenyl | 7-(diethylaminocarbonyl) | H |
| 5704. | —(NMeSO₂)-phenyl | 7-(1-pyrrolidinylcarbonyl) | H |
| 5705. | —(NMeSO₂)-phenyl | 7-(azaperhydroepinylcarbonyl) | H |
| 5706. | —(NMeSO₂)-phenyl | 7-[(3,5-dimethylpiperid-1-yl)carbonyl] | H |
| 5707. | —(NMeSO₂)-phenyl | 7-[(4-methylpiperid-1-ylcarbonyl) | H |
| 5708. | —(NMeSO₂)-phenyl | 7-[(3-methylpiperid-1-ylcarbonyl) | H |
| 5709. | —(NMeSO₂)-phenyl | 7-[(2-methylpiperid-1-ylcarbonyl) | H |
| 5710. | —(NMeSO₂)-phenyl | 7-[2-(dimethylamino)ethoxy] | H |
| 5711. | —(NMeSO₂)-phenyl | 7-[2-(methylamino)ethoxy] | H |
| 5712. | —(NMeSO₂)-phenyl | 7-[((2R)pyrrolidin-2-yl)-methoxy] | H |
| 5713. | —(NMeSO₂)-phenyl | 7-[((2R)-1-methylpyrrolidin-2-yl)methoxy] | H |
| 5714. | —(NMeSO₂)-phenyl | 7-[2-(piperid-1-yl)ethoxy] | H |
| 5715. | —(NMeSO₂)-phenyl | 7-[2-(piperazin-1-yl)ethoxy] | H |
| 5716. | —(NMeSO₂)-phenyl | 7-[2-(morpholin-4-yl)ethoxy] | H |
| 5717. | —(NMeSO₂)-phenyl | 7-[2-(1-methyl(4-piperidyl))ethoxy] | H |
| 5718. | —(NMeSO₂)-phenyl | 7-[2-(1-methyl(4-piperidyl))methoxy] | H |
| 5719. | —(NMeSO₂)-phenyl | 7-(1-methyl(4-piperidyloxy)) | H |

TABLE 9-continued

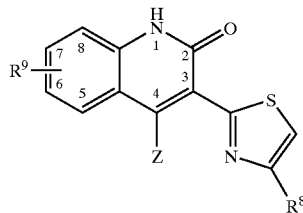

| # | R⁸ | R⁹ | Z |
|---|---|---|---|
| 5720. | —(NMeSO₂)-phenyl | 7-(piperid-1-yl-CH₂—) | NH₂ |
| 5721. | —(NMeSO₂)-phenyl | 7-(1-CH₃-piperazin-4-yl-CH₂—) | NH₂ |
| 5722. | —(NMeSO₂)-phenyl | 7-(morpholin-4-yl-CH₂—) | NH₂ |
| 5723. | —(NMeSO₂)-phenyl | 7-(diethylamino-CH₂—) | NH₂ |
| 5724. | —(NMeSO₂)-phenyl | 7-(1-pyrrolidinyl-CH₂—) | NH₂ |
| 5725. | —(NMeSO₂)-phenyl | 7-(azaperhydroepinyl-CH₂—) | NH₂ |
| 5726. | —(NMeSO₂)-phenyl | 7-[(3,5-dimethylpiperid-1-yl)-CH₂—) | NH₂ |
| 5727. | —(NMeSO₂)-phenyl | 7-[(4-methylpiperid-1-yl-CH₂—] | NH₂ |
| 5728. | —(NMeSO₂)-phenyl | 7-[(3-methylpiperid-1-yl-CH₂—] | NH₂ |
| 5729. | —(NMeSO₂)-phenyl | 7-[(2-methylpiperid-1-yl-CH₂—] | NH₂ |
| 5730. | —(NMeSO₂)-phenyl | 7-(piperid-1-yl-CH₂CH₂—) | NH₂ |
| 5731. | —(NMeSO₂)-phenyl | 7-(1-CH₃-piperazin-4-yl-CH₂CH₂—) | NH₂ |
| 5732. | —(NMeSO₂)-phenyl | 7-(morpholin-4-yl-CH₂CH₂—) | NH₂ |
| 5733. | —(NMeSO₂)-phenyl | 7-(diethylamino-CH₂CH₂—) | NH₂ |
| 5734. | —(NMeSO₂)-phenyl | 7-(1-pyrrolidinyl-CH₂CH₂—) | NH₂ |
| 5735. | —(NMeSO₂)-phenyl | 7-(azaperhydroepinyl-CH₂CH₂—) | NH₂ |
| 5736. | —(NMeSO₂)-phenyl | 7-[(3,5-dimethylpiperid-1-yl)-CH₂CH₂—) | NH₂ |
| 5737. | —(NMeSO₂)-phenyl | 7-[(4-methylpiperid-1-yl-CH₂CH₂—) | NH₂ |
| 5738. | —(NMeSO₂)-phenyl | 7-[(3-methylpiperid-1-yl-CH₂CH₂—)—] | NH₂ |
| 5739. | —(NMeSO₂)-phenyl | 7-[(2-methylpiperid-1-yl-CH₂CH₂—)—] | NH₂ |
| 5740. | —(NMeSO₂)-phenyl | 7-(1-piperidylcarbonyl) | NH₂ |
| 5741. | —(NMeSO₂)-phenyl | 7-[(4-methylpiperazin-1-yl)carbonyl] | NH₂ |
| 5742. | —(NMeSO₂)-phenyl | 7-(morpholin-4-ylcarbonyl) | NH₂ |
| 5743. | —(NMeSO₂)-phenyl | 7-(diethylaminocarbonyl) | NH₂ |
| 5744. | —(NMeSO₂)-phenyl | 7-(1-pyrrolidinylcarbonyl) | NH₂ |
| 5745. | —(NMeSO₂)-phenyl | 7-(azaperhydroepinylcarbonyl) | NH₂ |
| 5746. | —(NMeSO₂)-phenyl | 7-[(3,5-dimethylpiperid-1-yl)carbonyl) | NH₂ |
| 5747. | —(NMeSO₂)-phenyl | 7-[(4-methylpiperid-1-ylcarbonyl) | NH₂ |
| 5748. | —(NMeSO₂)-phenyl | 7-[(3-methylpiperid-1-ylcarbonyl) | NH₂ |
| 5749. | —(NMeSO₂)-phenyl | 7-[(2-methylpiperid-1-ylcarbonyl) | NH₂ |
| 5750. | —(NMeSO₂)-phenyl | 7-[2-(dimethylamino)ethoxy] | NH₂ |
| 5751. | —(NMeSO₂)-phenyl | 7-[2-(methylamino)ethoxy] | NH₂ |
| 5752. | —(NMeSO₂)-phenyl | 7-[((2R)pyrrolidin-2-yl)methoxy] | NH₂ |
| 5753. | —(NMeSO₂)-phenyl | 7-[((2R)-1-methylpyrrolidin-2-yl)methoxy] | NH₂ |
| 5754. | —(NMeSO₂)-phenyl | 7-[2-(piperid-1-yl)ethoxy] | NH₂ |
| 5755. | —(NMeSO₂)-phenyl | 7-[2-(piperazin-1-yl)ethoxy] | NH₂ |
| 5756. | —(NMeSO₂)-phenyl | 7-[2-(morpholin-4-yl)ethoxy] | NH₂ |
| 5757. | —(NMeSO₂)-phenyl | 7-[2-(1-methyl(4-piperidyl))ethoxy] | NH₂ |
| 5758. | —(NMeSO₂)-phenyl | 7-[2-(1-methyl(4-piperidyl))methoxy] | NH₂ |
| 5759. | —(NMeSO₂)-phenyl | 7-(1-methyl(4-piperidyloxy)) | NH₂ |
| 5760. | —(NMeSO₂)-2-thienyl | 7-(piperid-1-yl-CH₂—) | H |
| 5761. | —(NMeSO₂)-2-thienyl | 7-(1-CH₃-piperazin-4-yl-CH₂—) | H |
| 5762. | —(NMeSO₂)-2-thienyl | 7-(morpholin-4-yl-CH₂—) | H |
| 5763. | —(NMeSO₂)-2-thienyl | 7-(diethylamino-CH₂—) | H |
| 5764. | —(NMeSO₂)-2-thienyl | 7-(1-pyrrolidinyl-CH₂—) | H |
| 5765. | —(NMeSO₂)-2-thienyl | 7-(azaperhydroepinyl-CH₂—) | H |
| 5766. | —(NMeSO₂)-2-thienyl | 7-[(3,5-dimethylpiperid-1-yl)-CH₂—] | H |
| 5767. | —(NMeSO₂)-2-thienyl | 7-[(4-methylpiperid-1-yl-CH₂—] | H |
| 5768. | —(NMeSO₂)-2-thienyl | 7-[(3-methylpiperid-1-yl-CH₂—] | H |
| 5769. | —(NMeSO₂)-2-thienyl | 7-[(2-methylpiperid-1-yl-CH₂—] | H |
| 5770. | —(NMeSO₂)-2-thienyl | 7-(piperid-1-yl-CH₂CH₂—] | H |
| 5771. | —(NMeSO₂)-2-thienyl | 7-(1-CH₃-piperazin-4-yl-CH₂CH₂—) | H |
| 5772. | —(NMeSO₂)-2-thienyl | 7-(morpholin-4-yl-CH₂CH₂—) | H |
| 5773. | —(NMeSO₂)-2-thienyl | 7-(diethylamino-CH₂CH₂—) | H |
| 5774. | —(NMeSO₂)-2-thienyl | 7-(1-pyrrolidinyl-CH₂CH₂—) | H |
| 5775. | —(NMeSO₂)-2-thienyl | 7-(azaperhydroepinyl-CH₂CH₂—) | H |
| 5776. | —(NMeSO₂)-2-thienyl | 7-[(3,5-dimethylpiperid-1-yl)-CH₂CH₂—) | H |
| 5777. | —(NMeSO₂)-2-thienyl | 7-[(4-methylpiperid-1-yl-CH₂CH₂—) | H |
| 5778. | —(NMeSO₂)-2-thienyl | 7-[(3-methylpiperid-1-yl-CH₂CH₂—)—] | H |
| 5779. | —(NMeSO₂)-2-thienyl | 7-[(2-methylpiperid-1-yl-CH₂CH₂—)—] | H |
| 5780. | —(NMeSO₂)-2-thienyl | 7-(1-piperidylcarbonyl) | H |
| 5781. | —(NMeSO₂)-2-thienyl | 7-[(4-methylpiperazin-1-yl)carbonyl] | H |
| 5782. | —(NMeSO₂)-2-thienyl | 7-(morpholin-4-ylcarbonyl) | H |
| 5783. | —(NMeSO₂)-2-thienyl | 7-(diethylaminocarbonyl) | H |
| 5784. | —(NMeSO₂)-2-thienyl | 7-(1-pyrrolidinylcarbonyl) | H |

TABLE 9-continued

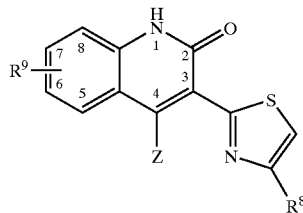

| # | R⁸ | R⁹ | Z |
|---|---|---|---|
| 5785. | —(NMeSO₂)-2-thienyl | 7-(azaperhydroepinylcarbonyl) | H |
| 5786. | —(NMeSO₂)-2-thienyl | 7-[(3,5-dimethylpiperid-1-yl)carbonyl] | H |
| 5787. | —(NMeSO₂)-2-thienyl | 7-[(4-methylpiperid-1-ylcarbonyl) | H |
| 5788. | —(NMeSO₂)-2-thienyl | 7-[(3-methylpiperid-1-ylcarbonyl) | H |
| 5789. | —(NMeSO₂)-2-thienyl | 7-[(2-methylpiperid-1-ylcarbonyl) | H |
| 5790. | —(NMeSO₂)-2-thienyl | 7-[2-(dimethylamino)ethoxy] | H |
| 5791. | —(NMeSO₂)-2-thienyl | 7-[2-(methylamino)ethoxy] | H |
| 5792. | —(NMeSO₂)-2-thienyl | 7-[((2R)pyrrolidin-2-yl)methoxy] | H |
| 5793. | —(NMeSO₂)-2-thienyl | 7-[((2R)-1-methylpyrrolidin-2-yl)methoxy] | H |
| 5794. | —(NMeSO₂)-2-thienyl | 7-[2-(piperid-1-yl)ethoxy] | H |
| 5795. | —(NMeSO₂)-2-thienyl | 7-[2-(piperazin-1-yl)ethoxy] | H |
| 5796. | —(NMeSO₂)-2-thienyl | 7-[2-(morpholin-4-yl)ethoxy] | H |
| 5797. | —(NMeSO₂)-2-thienyl | 7-[2-(1-methyl(4-piperidyl))ethoxy] | H |
| 5798. | —(NMeSO₂)-2-thienyl | 7-[2-(1-methyl(4-piperidyl))methoxy] | H |
| 5799. | —(NMeSO₂)-2-thienyl | 7-(1-methyl(4-piperidyloxy)) | H |
| 5800. | —(NMeSO₂)-2-thienyl | 7-(piperid-1-yl-CH₂—) | NH₂ |
| 5801. | —(NMeSO₂)-2-thienyl | 7-(1-CH₃-piperazin-4-yl-CH₂—) | NH₂ |
| 5802. | —(NMeSO₂)-2-thienyl | 7-(morpholin-4-yl-CH₂—) | NH₂ |
| 5803. | —(NMeSO₂)-2-thienyl | 7-(diethylamino-CH₂—) | NH₂ |
| 5804. | —(NMeSO₂)-2-thienyl | 7-(1-pyrrolidinyl-CH₂—) | NH₂ |
| 5805. | —(NMeSO₂)-2-thienyl | 7-(azaperhydroepinyl-CH₂—) | NH₂ |
| 5806. | —(NMeSO₂)-2-thienyl | 7-[(3,5-dimethylpiperid-1-yl)-CH₂—] | NH₂ |
| 5807. | —(NMeSO₂)-2-thienyl | 7-[(4-methylpiperid-1-yl-CH₂—] | NH₂ |
| 5808. | —(NMeSO₂)-2-thienyl | 7-[(3-methylpiperid-1-yl-CH₂—] | NH₂ |
| 5809. | —(NMeSO₂)-2-thienyl | 7-[(2-methylpiperid-1-yl-CH₂—] | NH₂ |
| 5810. | —(NMeSO₂)-2-thienyl | 7-(piperid-1-yl-CH₂CH₂—) | NH₂ |
| 5811. | —(NMeSO₂)-2-thienyl | 7-(1-CH₃-piperazin-4-yl-CH₂CH₂—) | NH₂ |
| 5812. | —(NMeSO₂)-2-thienyl | 7-(morpholin-4-yl-CH₂CH₂—) | NH₂ |
| 5813. | —(NMeSO₂)-2-thienyl | 7-(diethylamino-CH₂CH₂—) | NH₂ |
| 5814. | —(NMeSO₂)-2-thienyl | 7-(1-pyrrolidinyl-CH₂CH₂—) | NH₂ |
| 5815. | —(NMeSO₂)-2-thienyl | 7-(azaperhydroepinyl-CH₂CH₂—) | NH₂ |
| 5816. | —(NMeSO₂)-2-thienyl | 7-[(3,5-dimethylpiperid-1-yl)-CH₂—] | NH₂ |
| 5817. | —(NMeSO₂)-2-thienyl | 7-[(4-methylpiperid-1-yl-CH₂CH₂—) | NH₂ |
| 5818. | —(NMeSO₂)-2-thienyl | 7-[(3-methylpiperid-1-yl-CH₂CH₂—)—] | NH₂ |
| 5819. | —(NMeSO₂)-2-thienyl | 7-[(2-methylpiperid-1-yl-CH₂CH₂—)—] | NH₂ |
| 5820. | —(NMeSO₂)-2-thienyl | 7-(1-piperidylcarbonyl) | NH₂ |
| 5821. | —(NMeSO₂)-2-thienyl | 7-[(4-methylpiperazin-1-yl)carbonyl] | NH₂ |
| 5822. | —(NMeSO₂) 2-thienyl | 7-(morpholin-4-ylcarbonyl) | NH₂ |
| 5823. | —(NMeSO₂)-2-thienyl | 7-(diethylaminocarbonyl) | NH₂ |
| 5824. | —(NMeSO₂)-2-thienyl | 7-(1-pyrrolidinylcarbonyl) | NH₂ |
| 5825. | —(NMeSO₂)-2-thienyl | 7-(azaperhydroepinylcarbonyl) | NH₂ |
| 5826. | —(NMeSO₂)-2-thienyl | 7-[(3,5-dimethylpiperid-1-yl)carbonyl] | NH₂ |
| 5827. | —(NMeSO₂)-2-thienyl | 7-[(4-methylpiperid-1-ylcarbonyl) | NH₂ |
| 5828. | —(NMeSO₂)-2-thienyl | 7-[(3-methylpiperid-1-ylcarbonyl) | NH₂ |
| 5829. | —(NMeSO₂)-2-thienyl | 7-[(2-methylpiperid-1-ylcarbonyl) | NH₂ |
| 5830. | —(NMeSO₂)-2-thienyl | 7-[2-(dimethylamino)ethoxy] | NH₂ |
| 5831. | —(NMeSO₂)-2-thienyl | 7-[2-(methylamino)ethoxy] | NH₂ |
| 5832. | —(NMeSO₂)-2-thienyl | 7-[((2R)pyrrolidin-2-yl)methoxy] | NH₂ |
| 5833. | —(NMeSO₂)-2-thienyl | 7-[((2R)-1-methylpyrrolidin-2-yl)methoxy] | NH₂ |
| 5834. | —(NMeSO₂)-2-thienyl | 7-[2-(piperid-1-yl)ethoxy] | NH₂ |
| 5835. | —(NMeSO₂)-2-thienyl | 7-[2-(piperazin-1-yl)ethoxy] | NH₂ |
| 5836. | —(NMeSO₂)-2-thienyl | 7-[2-(morpholin-4-yl)ethoxy] | NH₂ |
| 5837. | —(NMeSO₂)-2-thienyl | 7-[2-(1-methyl(4-piperidyl))ethoxy] | NH₂ |
| 5838. | —(NMeSO₂)-2-thienyl | 7-[2-(1-methyl(4-piperidyl))methoxy] | NH₂ |
| 5839. | —(NMeSO₂)-2-thienyl | 7-(1-methyl(4-piperidyloxy)) | NH₂ |
| 5840. | —(NMeSO₂)-2-pyridyl | 7-(piperid-1-yl-CH₂—) | H |
| 5841. | —(NMeSO₂)-2-pyridyl | 7-(1-CH₃-piperazin-4-yl-CH₂—) | H |
| 5842. | —(NMeSO₂)-2-pyridyl | 7-(morpholin-4-yl-CH₂—) | H |
| 5843. | —(NMeSO₂) 2-pyridyl | 7-(diethylamino-CH₂—) | H |
| 5844. | —(NMeSO₂)-2-pyridyl | 7-(1-pyrrolidinyl-CH₂—) | H |
| 5845. | —(NMeSO₂)-2-pyridyl | 7-(azaperhydroepinyl-CH₂—) | H |
| 5846. | —(NMeSO₂)-2-pyridyl | 7-[(3,5-dimethylpiperid-1-yl)-CH₂—] | H |
| 5847. | —(NMeSO₂)-2-pyridyl | 7-[(4-methylpiperid-1-yl-CH₂—] | H |
| 5848. | —(NMeSO₂)-2-pyridyl | 7-[(3-methylpiperid-1-yl-CH₂—] | H |
| 5849. | —(NMeSO₂)-2-pyridyl | 7-[(2-methylpiperid-1-yl-CH₂—] | H |

TABLE 9-continued

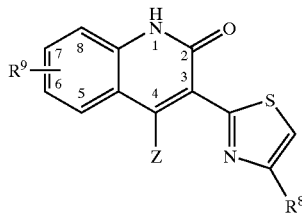

| # | R⁸ | R⁹ | Z |
|---|---|---|---|
| 5850. | —(NMeSO$_2$)-2-pyridyl | 7-(piperid-1-yl-CH$_2$CH$_2$—) | H |
| 5851. | —(NMeSO$_2$)-2-pyridyl | 7-(1-CH$_3$-piperazin-4-yl-CH$_2$CH$_2$—) | H |
| 5852. | —(NMeSO$_2$)-2-pyridyl | 7-(morpholin-4-yl-CH$_2$CH$_2$—) | H |
| 5853. | —(NMeSO$_2$)-2-pyridyl | 7-(diethylamino-CH$_2$CH$_2$—) | H |
| 5854. | —(NMeSO$_2$)-2-pyridyl | 7-(1-pyrrolidinyl-CH$_2$CH$_2$—) | H |
| 5855. | —(NMeSO$_2$)-2-pyridyl | 7-(azaperhydroepinyl-CH$_2$CH$_2$—) | H |
| 5856. | —(NMeSO$_2$)-2-pyridyl | 7-[(3,5-dimethylpiperid-1-yl)-CH$_2$CH$_2$—) | H |
| 5857. | —(NMeSO$_2$)-2-pyridyl | 7-[(4-methylpiperid-1-yl-CH$_2$—) | H |
| 5858. | —(NMeSO$_2$) 2-pyridyl | 7-[(3-methylpiperid-1-yl-CH$_2$CH$_2$—)—] | H |
| 5859. | —(NMeSO$_2$)-2-pyridyl | 7-[(2-methylpiperid-1-yl-CH-CH$_2$—)—] | H |
| 5860. | —(NMeSO$_2$)-2-pyridyl | 7-(1-piperidylcarbonyl) | H |
| 5861. | —(NMeSO$_2$)-2-pyridyl | 7-[(4-methylpiperazin-1-yl)carbonyl] | H |
| 5862. | —(NMeSO$_2$)-2-pyridyl | 7-(morpholin-4-ylcarbonyl) | H |
| 5863. | —(NMeSO$_2$)-2-pyridyl | 7-(diethylaminocarbonyl) | H |
| 5864. | —(NMeSO$_2$)-2-pyridyl | 7-(1-pyrrolidinylcarbonyl) | H |
| 5865. | —(NMeSO$_2$)-2-pyridyl | 7-(azaperhydroepinylcarbonyl) | H |
| 5866. | —(NMeSO$_2$)-2-pyridyl | 7-[(3,5-dimethylpiperid-1-yl)carbonyl] | H |
| 5867. | —(NMeSO$_2$)-2-pyridyl | 7-[(4-methylpiperid-1-ylcarbonyl) | H |
| 5868. | —(NMeSO$_2$)-2-pyridyl | 7-[(3-methylpiperid-1-ylcarbonyl) | H |
| 5869. | —(NMeSO$_2$)-2-pyridyl | 7-[(2-methylpiperid-1-ylcarbonyl) | H |
| 5870. | —(NMeSO$_2$)-2-pyridyl | 7-[2-(dimethylamino)ethoxy] | H |
| 5871. | —(NMeSO$_2$)-2-pyridyl | 7-[2-(methylamino)ethoxy] | H |
| 5872. | —(NMeSO$_2$)-2-pyridyl | 7-[((2R)pyrrolidin-2-yl)methoxy] | H |
| 5873. | —(NMeO$_2$)-2-pyridyl | 7-[((2R)-1-methylpyrrolidin-2-yl)methoxy] | H |
| 5874. | —(NMeSO$_2$)-2-pyridyl | 7-[2-(piperid-1-yl)ethoxy] | H |
| 5875. | —(NMeSO$_2$)-2-pyridyl | 7-[2-(piperazin-1-yl)ethoxy] | H |
| 5876. | —(NMeSO$_2$)-2-pyridyl | 7-[2-(morpholin-4-yl)ethoxy] | H |
| 5877. | —(NMeSO$_2$)-2-pyridyl | 7-[2-(1-methyl(4-piperidyl))ethoxy] | H |
| 5878. | —(NMeSO$_2$)-2-pyridyl | 7-[2-(1-methyl(4-piperidyl))methoxy] | H |
| 5879. | —(NMeSO$_2$)-2-pyridyl | 7-(1-methyl(4-piperidyloxy)) | H |
| 5880. | —(NMeSO$_2$)-2-pyridyl | 7-(piperid-1-yl-CH$_2$—) | NH$_2$ |
| 5881. | —(NMeSO$_2$)-2-pyridyl | 7-(1-CH$_3$-piperazin-4-yl-CH$_2$—) | NH$_2$ |
| 5882. | —(NMeSO$_2$)-2-pyridyl | 7-(morpholin-4-yl-CH$_2$—) | NH$_2$ |
| 5883. | —(NMeSO$_2$) 2-pyridyl | 7-(diethylamino-CH$_2$—) | NH$_2$ |
| 5884. | —(NMeSO$_2$)-2-pyridyl | 7-(1-pyrrolidinyl-CH$_2$—) | NH$_2$ |
| 5885. | —(NMeSO$_2$)-2-pyridyl | 7-(azaperhydroepinyl-CH$_2$—) | NH$_2$ |
| 5886. | —(NMeSO$_2$)-2-pyridyl | 7-[(3,5-dimethylpiperid-1-yl)-CH$_2$—] | NH$_2$ |
| 5887. | —(NMeSO$_2$)-2-pyridyl | 7-[(4-methylpiperid-1-yl-CH$_2$—] | NH$_2$ |
| 5888. | —(NMeSO$_2$)-2-pyridyl | 7-[(3-methylpiperid-1-yl-CH$_2$—] | NH$_2$ |
| 5889. | —(NMeSO$_2$)-2-pyridyl | 7-[(2-methylpiperid-1-yl-CH$_2$—] | NH$_2$ |
| 5890. | —(NMeSO$_2$) 2-pyridyl | 7-(piperid-1-yl-CH$_2$CH$_2$—) | NH$_2$ |
| 5891. | —(NMeSO$_2$)-2-pyridyl | 7-(1-CH$_3$-piperazin-4-yl-CH$_2$CH$_2$—) | NH$_2$ |
| 5892. | —(NMeSO$_2$)-2-pyridyl | 7-(morpholin-4-yl-CH$_2$CH$_2$—) | NH$_2$ |
| 5893. | —(NMeSO$_2$)-2-pyridyl | 7-(diethylamino-CH$_2$CH$_2$—) | NH$_2$ |
| 5894. | —(NMeSO$_2$)-2-pyridyl | 7-(1-pyrrolidinyl-CH$_2$CH$_2$—) | NH$_2$ |
| 5895. | —(NMeSO$_2$)-2-pyridyl | 7-(azaperhydroepinyl-CH$_2$CH$_2$—) | NH$_2$ |
| 5896. | —(NMeSO$_2$)-2-pyridyl | 7-[(3,5-dimethylpiperid-1-yl)-CH$_2$CH$_2$—) | NH$_2$ |
| 5897. | —(NMeSO$_2$)-2-pyridyl | 7-[(4-methylpiperid-1-yl-CH$_2$CH$_2$—) | NH$_2$ |
| 5898. | —(NMeSO$_2$)-2-pyridyl | 7-[(3-methylpiperid-1-yl-CH$_2$CH$_2$—)—] | NH$_2$ |
| 5899. | —(NMeSO$_2$)-2-pyridyl | 7-[(2-methylpiperid-1-yl-CH$_2$CH$_2$—)—] | NH$_2$ |
| 5900. | —(NMeSO$_2$)-2-pyridyl | 7-(1-piperidylcarbonyl) | NH$_2$ |
| 5901. | —(NMeSO$_2$)-2-pyridyl | 7-[(4-methylpiperazin-1-yl)carbonyl] | NH$_2$ |
| 5902. | —(NMeSO$_2$)-2-pyridyl | 7-(morpholin-4-ylcarbonyl) | NH$_2$ |
| 5903. | —(NMeSO$_2$)-2-pyridyl | 7-(diethylaminocarbonyl) | NH$_2$ |
| 5904. | —(NMeSO$_2$)-2-pyridyl | 7-(1-pyrrolidinylcarbonyl) | NH$_2$ |
| 5905. | —(NMeSO$_2$)-2-pyridyl | 7-(azaperhydroepinylcarbonyl) | NH$_2$ |
| 5906. | —(NMeSO$_2$)-2-pyridyl | 7-[(3,5-dimethylpiperid-1-yl)carbonyl) | NH$_2$ |
| 5907. | —(NMeSO$_2$)-2-pyridyl | 7-[(4-methylpiperid-1-ylcarbonyl) | NH$_2$ |
| 5908. | —(NMeSO$_2$)-2-pyridyl | 7-[(3-methylpiperid-1-ylcarbonyl) | NH$_2$ |
| 5909. | —(NMeSO$_2$)-2-pyridyl | 7-[2-methylpiperid-1-ylcarbonyl) | NH$_2$ |
| 5910. | —(NMeSO$_2$)-2-pyridyl | 7-[2-(dimethylamino)ethoxy] | NH$_2$ |
| 5911. | —(NMeSO$_2$)-2-pyridyl | 7-[2-(methylamino)ethoxy] | NH$_2$ |
| 5912. | —(NMeSO$_2$)-2-pyridyl | 7-[((2R)pyrrolidin-2-yl)methoxy] | NH$_2$ |
| 5913. | —(NMeSO$_2$)-2-pyridyl | 7-[((2R)-1-methylpyrrolidin-2-yl)methoxy] | NH$_2$ |
| 5914. | —(NMeSO$_2$)-2-pyridyl | 7-[2-(piperid-1-yl)ethoxy] | NH$_2$ |

TABLE 9-continued

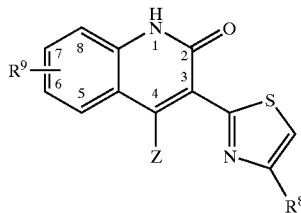

| # | R⁸ | R⁹ | Z |
|---|---|---|---|
| 5915. | —(NMeSO₂)-2-pyridyl | 7-[2-(piperazin-1-yl)ethoxy] | NH₂ |
| 5916. | —(NMeSO₂)-2-pyridyl | 7-[2-(morpholin-4-yl)ethoxy] | NH₂ |
| 5917. | —(NMeSO₂)-2-pyridyl | 7-[2-(1-methyl(4-piperidyl))ethoxy] | NH₂ |
| 5918. | —(NMeSO₂)-2-pyridyl | 7-[2-(1-methyl(4-piperidyl))methoxy] | NH₂ |
| 5919. | —(NMeSO₂)-2-pyridyl | 7-(1-methyl(4-piperidyloxy)) | NH₂ |
| 5920. | —(NMeSO₂)-3-pyridyl | 7-(piperid-1-yl-CH₂—) | H |
| 5921. | —(NMeSO₂)-3-pyridyl | 7-(1-CH₃-piperazin-4-yl-CH₂—) | H |
| 5922. | —(NMeSO₂)-3-pyridyl | 7-(morpholin-4-yl-CH₂—) | H |
| 5923. | —(NMeSO₂)-3-pyridyl | 7-(diethylamino-CH₂—) | H |
| 5924. | —(NMeSO₂)-3-pyridyl | 7-(1-pyrrolidinyl-CH₂—) | H |
| 5925. | —(NMeSO₂)-3-pyridyl | 7-(azaperhydroepinyl-CH₂—) | H |
| 5926. | —(NMeSO₂)-3-pyridyl | 7-[(3,5-dimethylpiperid-1-yl)-CH₂—] | H |
| 5927. | —(NMeSO₂)-3-pyridyl | 7-[(4-methylpiperid-1-yl-CH₂—] | H |
| 5928. | —(NMeSO₂)-3-pyridyl | 7-[(3-methylpiperid-1-yl-CH₂—] | H |
| 5929. | —(NMeSO₂)-3-pyridyl | 7-[(2-methylpiperid-1-yl-CH₂—] | H |
| 5930. | —(NMeSO₂)-3-pyridyl | 7-(piperid-1-yl-CH₂CH₂—) | H |
| 5931. | —(NMeSO₂)-3-pyridyl | 7-(1-CH₃-piperazin-4-yl-CH₂CH₂—) | H |
| 5932. | —(NMeSO₂)-3-pyridyl | 7-(morpholin-4-yl-CH₂CH₂—) | H |
| 5933. | —(NMeSO₂)-3-pyridyl | 7-(diethylamino-CH₂CH₂—) | H |
| 5934. | —(NMeSO₂)-3-pyridyl | 7-(1-pyrrolidinyl-CH₂CH₂—) | H |
| 5935. | —(NMeSO₂)-3-pyridyl | 7-(azaperhydroepinyl-CH₂CH₂—) | H |
| 5936. | —(NMeSO₂)-3-pyridyl | 7-[(3,5-dimethylpiperid-1-yl)-CH₂CH₂—) | H |
| 5937. | —(NMeSO₂)-3-pyridyl | 7-[(4-methylpiperid-1-yl-CH₂CH₂—) | H |
| 5938. | —(NMeSO₂)-3-pyridyl | 7-[(3-methylpiperid-1-yl-CH₂CH₂—)—] | H |
| 5939. | —(NMeSO₂)-3-pyridyl | 7-[(2-methylpiperid-1-yl-CH₂CH₂—)—] | H |
| 5940. | —(NMeSO₂)-3-pyridyl | 7-(1-piperidylcarbonyl) | H |
| 5941. | —(NMeSO₂)-3-pyridyl | 7-[(4-methylpiperazin-1-yl)carbonyl] | H |
| 5942. | —(NMeSO₂)-3-pyridyl | 7-(morpholin-4-ylcarbonyl) | H |
| 5943. | —(NMeSO₂)-3-pyridyl | 7-(diethylaminocarbonyl) | H |
| 5944. | —(NMeSO₂)-3-pyridyl | 7-(1-pyrrolidinylcarbonyl) | H |
| 5945. | —(NMeSO₂)-3-pyridyl | 7-(azaperhydroepinylcarbopyl) | H |
| 5946. | —(NMeSO₂)-3-pyridyl | 7-[(3,5-dimethylpiperid-1-yl)carbonyl) | H |
| 5947. | —(NMeSO₂)-3-pyridyl | 7-[(4-methylpiperid-1-ylcarbonyl) | H |
| 5948. | —(NMeSO₂)-3-pyridyl | 7-[(3-methylpiperid-1-ylcarbonyl) | H |
| 5949. | —(NMeSO₂)-3-pyridyl | 7-[(2-methylpiperid-1-ylcarbonyl) | H |
| 5950. | —(NMeSO₂)-3-pyridyl | 7-[2-(dimethylamino)ethoxy] | H |
| 5951. | —(NMeSO₂)-3-pyridyl | 7-[2-(methylamimo)ethoxy] | H |
| 5952. | —(NMeSO₂)-3-pyridyl | 7-[((2R)pyrrolidin-2-yl)methoxy] | H |
| 5953. | —(NMeSO₂)-3-pyridyl | 7-[((2R)-1-methylpyrrolidin-2-yl)methoxy] | H |
| 5954. | —(NMeSO₂)-3-pyridyl | 7-[2-(piperid-1-yl)ethoxy] | H |
| 5955. | —(NMeSO₂)-3-pyridyl | 7-[2-(piperazin-1-yl)ethoxy] | H |
| 5956. | —(NMeSO₂)-3-pyridyl | 7-[2-(morpholin-4-yl)ethoxy] | H |
| 5957. | —(NMeSO₂)-3-pyridyl | 7-[2-(1-methyl(4-piperidyl))ethoxy] | H |
| 5958. | —(NMeSO₂)-3-pyridyl | 7-[2-(1-methyl(4-piperidyl))methoxy] | H |
| 5959. | —(NMeSO₂)-3-pyridyl | 7-(1-methyl(4-piperidyloxy)) | H |
| 5960. | —(NMeSO₂)-3-pyridyl | 7-(piperid-1-yl-CH₂—) | NH₂ |
| 5961. | —(NMeSO₂)-3-pyridyl | 7-(1-CH₃-piperazin-4-yl-CH₂—] | NH₂ |
| 5962. | —(NMeSO₂)-3-pyridyl | 7-(morpholin-4-yl-CH₂—) | NH₂ |
| 5963. | —(NMeSO₂)-3-pyridyl | 7-(diethylamino-CH₂—) | NH₂ |
| 5964. | —(NMeSO₂)-3-pyridyl | 7-(1-pyrrolidinyl-CH₂—) | NH₂ |
| 5965. | —(NMeSO₂)-3-pyridyl | 7-(azaperhydroepinyl-CH₂—) | NH₂ |
| 5966. | —(NMeSO₂)-3-pyridyl | 7-[(3,5-dimethylpiperid-1-yl)-CH₂—) | NH₂ |
| 5967. | —(NMeSO₂)-3-pyridyl | 7-[(4-methylpiperid-1-yl-CH₂—] | NH₂ |
| 5968. | —(NMeSO₂)-3-pyridyl | 7-[(3-methylpiperid-1-yl-CH₂—] | NH₂ |
| 5969. | —(NMeSO₂)-3-pyridyl | 7-[(2-methylpiperid-1-yl-CH₂—] | NH₂ |
| 5970. | —(NMeSO₂)-3-pyridyl | 7-(piperid-1-yl-CH₂CH₂—) | NH₂ |
| 5971. | —(NMeSO₂)-3-pyridyl | 7-(1-CH₃-piperazin-4-yl-CH₂CH₂—) | NH₂ |
| 5972. | —(NMeSO₂)-3-pyridyl | 7-(morpholin-4-yl-CH₂CH₂—) | NH₂ |
| 5973. | —(NMeSO₂)-3-pyridyl | 7-(diethylamino-CH₂CH₂—) | NH₂ |
| 5974. | —(NMeSO₂)-3-pyridyl | 7-(1-pyrrolidinyl-CH₂CH₂—) | NH₂ |
| 5975. | —(NMeSO₂)-3-pyridyl | 7-(azaperhydroepinyl-CH₂CH₂—) | NH₂ |
| 5976. | —(NMeSO₂)-3-pyridyl | 7-[(3,5-dimethylpiperid-1-yl)-CH₂CH₂—) | NH₂ |
| 5977. | —(NMeSO₂)-3-pyridyl | 7-[(4-methylpiperid-1-yl-CH₂CH₂—) | NH₂ |
| 5978. | —(NMeSO₂)-3-pyridyl | 7-[(3-methylpiperid(-1-yl-CH₂CH₂—)—] | NH₂ |
| 5979. | —(NMeSO₂)-3-pyridyl | 7-[(2-methylpiperid-1-yl-CH₂CH₂—)—] | NH₂ |

TABLE 9-continued

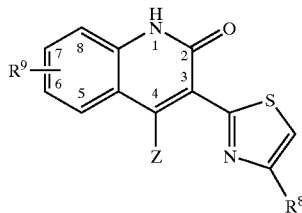

| # | R⁸ | R⁹ | Z |
|---|----|----|---|
| 5980. | —(NMeSO₂)-3-pyridyl | 7-(1-piperidylcarbonyl) | NH₂ |
| 5981. | —(NMeSO₂)-3-pyridyl | 7-[(4-methylpiperazin-1-yl)carbonyl] | NH₂ |
| 5982. | —(NMeSO₂)-3-pyridyl | 7-(morpholin-4-ylcarbonyl) | NH₂ |
| 5983. | —(NMeSO₂)-3-pyridyl | 7-(diethylaminocarbonyl) | NH₂ |
| 5984. | —(NMeSO₂)-3-pyridyl | 7-(1-pyrrolidinylcarbonyl) | NH₂ |
| 5985. | —(NMeSO₂)-3-pyridyl | 7-(azaperhydroepinylcarbonyl) | NH₂ |
| 5986. | —(NMeSO₂)-3-pyridyl | 7-[(3,5-dimethylpiperid-1-yl)carbonyl) | NH₂ |
| 5987. | —(NMeSO₂)-3-pyridyl | 7-[(4-methylpiperid-1-ylcarbonyl) | NH₂ |
| 5988. | —(NMeSO₂)-3-pyridyl | 7-[(3-methylpiperid-1-ylcarbonyl) | NH₂ |
| 5989. | —(NMeSO₂)-3-pyridyl | 7-[(2-methylpiperid-1-ylcarbonyl) | NH₂ |
| 5990. | —(NMeSO₂)-3-pyridyl | 7-[2-(dimethylamino)ethoxy] | NH₂ |
| 5991. | —(NMeSO₂)-3-pyridyl | 7-[2-(methylamino)ethoxy] | NH₂ |
| 5992. | —(NMeSO₂)-3-pyridyl | 7-[((2R)pyrrolidin-2-yl)methoxy) | NH₂ |
| 5993. | —(NMeSO₂)-3-pyridyl | 7-[((2R)-1-methylpyrrolidin-2-yl)methoxy] | NH₂ |
| 5994. | —(NMeSO₂)-3-pyridyl | 7-[2-(piperid-1-yl)ethoxy] | NH₂ |
| 5995. | —(NMeSO₂)-3-pyridyl | 7-[2-(piperazin-1-yl)ethoxy] | NH₂ |
| 5996. | —(NMeSO₂)-3-pyridyl | 7-[2-(morpholin-4-yl)ethoxy] | NH₂ |
| 5997. | —(NMeSO₂)-3-pyridyl | 7-[2-(1-methyl(4-piperidyl))ethoxy] | NH₂ |
| 5998. | —(NMeSO₂)-3-pyridyl | 7-[2-(1-methyl(4-piperidyl))methoxy] | NH₂ |
| 5999. | —(NMeSO₂)-3-pyridyl | 7-(1-methyl(4-piperidyloxy)) | NH₂ |
| 6000. | —(NMeSO₂)-4-pyridyl | 7-(piperid-1-yl-CH₂—) | H |
| 6001. | —(NMeSO₂)-4-pyridyl | 7-(1-CH₃-piperazin-4-yl-CH₂—) | H |
| 6002. | —(NMeSO₂)-4-pyridyl | 7-(morpholin-4-yl-CH₂—) | H |
| 6003. | —(NMeSO₂)-4-pyridyl | 7-(diethylamino-CH₂—) | H |
| 6004. | —(NMeSO₂)-4-pyridyl | 7-(1-pyrrolidinyl-CH₂—) | H |
| 6005. | —(NMeSO₂)-4-pyridyl | 7-(azaperhydroepinyl-CH₂—) | H |
| 6006. | —(NMeSO₂)-4-pyridyl | 7-[(3,5-dimethylpiperid-1-yl)-CH₂—) | H |
| 6007. | —(NMeSO₂)-4-pyridyl | 7-[(4-methylpiperid-1-yl-CH₂—] | H |
| 6008. | —(NMeSO₂)-4-pyridyl | 7-[(3-methylpiperid-1-yl-CH₂—] | H |
| 6009. | —(NMeSO₂)-4-pyridyl | 7-[(2-methylpiperid-1-yl-CH₂—] | H |
| 6010. | —(NMeSO₂)-4-pyridyl | 7-(piperid-1-yl-CH₂CH₂—) | H |
| 6011. | —(NMeSO₂)-4-pyridyl | 7-(1-CH₃-piperazin-4-yl-CH₂CH₂—) | H |
| 6012. | —(NMeSO₂)-4-pyridyl | 7-(morpholin-4-yl-CH₂CH₂—) | H |
| 6013. | —(NMeSO₂)-4-pyridyl | 7-(diethylamino-CH₂CH₂—) | H |
| 6014. | —(NMeSO₂)-4-pyridyl | 7-(1-pyrrolidinyl-CH₂CH₂—) | H |
| 6015. | —(NMeSO₂)-4-pyridyl | 7-(azaperhydroepinyl-CH₂CH₂—) | H |
| 6016. | —(NMeSO₂)-4-pyridyl | 7-[(3,5-dimethylpiperid-1-yl)-CH₂CH₂—) | H |
| 6017. | —(NMeSO₂)-4-pyridyl | 7-[(4-methylpiperid-1-yl-CH₂CH₂—) | H |
| 6018. | —(NMeSO₂)-4-pyridyl | 7-[(3-methylpiperid(-1-yl-CH₂CH₂—)—] | H |
| 6019. | —(NMeSO₂)-4-pyridyl | 7-[(2-methylpiperid-1-yl-CH₂CH₂—)—] | H |
| 6020. | —(NMeSO₂)-4-pyridyl | 7-(1-piperidylcarbonyl) | H |
| 6021. | —(NMeSO₂)-4-pyridyl | 7-[(4-methylpiperazin-1-yl)carbonyl] | H |
| 6022. | —(NMeSO₂)-4-pyridyl | 7-(morpholin-4-ylcarbonyl) | H |
| 6023. | —(NMeSO₂)-4-pyridyl | 7-(diethylaminocarbonyl) | H |
| 6024. | —(NMeSO₂)-4-pyridyl | 7-(1-pyrrolidinylcarbonyl) | H |
| 6025. | —(NMeSO₂)-4-pyridyl | 7-(azaperhydroepinylcarbonyl) | H |
| 6026. | —(NMeSO₂)-4-pyridyl | 7-[(3,5-dimethylpiperid-1-yl)carbonyl) | H |
| 6027. | —(NMeSO₂)-4-pyridyl | 7-[(4-methylpiperid-1-ylcarbonyl) | H |
| 6028. | —(NMeSO₂)-4-pyridyl | 7-[(3-methylpiperid-1-ylcarbonyl) | H |
| 6029. | —(NMeSO₂)-4-pyridyl | 7-[(2-methylpiperid-1-ylcarbonyl) | H |
| 6030. | —(NMeSO₂)-4-pyridyl | 7-[2-(dimethylamino)ethoxy] | H |
| 6031. | —(NMeSO₂)-4-pyridyl | 7-[2-(methylamino)ethoxy] | H |
| 6032. | —(NMeSO₂)-4-pyridyl | 7-[((2R)pyrrolidin-2-yl)methoxy) | H |
| 6033. | —(NMeSO₂)-4-pyridyl | 7-[((2R)-1-methylpyrrolidin-2-yl)methoxy] | H |
| 6034. | —(NMeSO₂)-4-pyridyl | 7-[2-(piperid-1-yl)ethoxy] | H |
| 6035. | —(NMeSO₂)-4-pyridyl | 7-[2-(piperazin-1-yl)ethoxy] | H |
| 6036. | —(NMeSO₂)-4-pyridyl | 7-[2-(morpholin-4-yl)ethoxy] | H |
| 6037. | —(NMeSO₂)-4-pyridyl | 7-[2-(1-methyl(4-piperidyl))ethoxy] | H |
| 6038. | —(NMeSO₂)-4-pyridyl | 7-(2-(1-methyl(4-piperidyl))methoxy] | H |
| 6039. | —(NMeSO₂)-4-pyridyl | 7-(1-methyl(4-piperidyloxy)) | H |
| 6040. | —(NMeSO₂)-4-pyridyl | 7-(piperid-1-yl-CH₂—) | NH₂ |
| 6041. | —(NMeSO₂)-4-pyridyl | 7-(1-CH₃-piperazin-4-yl-CH₂—) | NH₂ |
| 6042. | —(NMeSO₂)-4-pyridyl | 7-(morpholin-4-yl-CH₂—) | NH₂ |
| 6043. | —(NMeSO₂)-4-pyridyl | 7-(diethylamino-CH₂—) | NH₂ |
| 6044. | —(NMeSO₂)-4-pyridyl | 7-(1-pyrrolidinyl-CH₂—) | NH₂ |

TABLE 9-continued

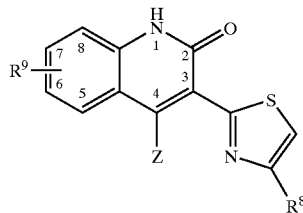

| # | R$^8$ | R$^9$ | Z |
|---|---|---|---|
| 6045. | —(NMeSO$_2$)-4-pyridyl | 7-(azaperhydroepinyl-CH$_2$—) | NH$_2$ |
| 6046. | —(NMeSO$_2$)-4-pyridyl | 7-[(3,5-dimethylpiperid-1-yl)-CH$_2$—) | NH$_2$ |
| 6047. | —(NMeSO$_2$)-4-pyridyl | 7-[(4-methylpiperid-1-yl)-CH$_2$—) | NH$_2$ |
| 6048. | —(NMeSO$_2$)-4-pyridyl | 7-[(3-methylpiperid-1-yl)-CH$_2$—) | NH$_2$ |
| 6049. | —(NMeSO$_2$)-4-pyridyl | 7-[(2-methylpiperid-1-yl)-CH$_2$—) | NH$_2$ |
| 6050. | —(NMeSO$_2$)-4-pyridyl | 7-(piperid-1-yl-CH$_2$CH$_2$—) | NH$_2$ |
| 6051. | —(NMeSO$_2$) | 7-(1-CH$_3$-piperazin-4-yl-CH$_2$CH$_2$—) | NH$_2$ |
| 6052. | —(NMeSO$_2$)-4-pyridyl | 7-(morpholin-4-yl-CH$_2$CH$_2$—) | NH$_2$ |
| 6053. | —(NMeSO$_2$)-4-pyridyl | 7-(diethylamino-CH$_2$CH$_2$—) | NH$_2$ |
| 6054. | —(NMeSO$_2$)-4-pyridyl | 7-(1-pyrrolidinyl-CH$_2$CH$_2$—) | NH$_2$ |
| 6055. | —(NMeSO$_2$)-4-pyridyl | 7-(azaperhydroepinyl-CH$_2$CH$_2$—) | NH$_2$ |
| 6056. | —(NMeSO$_2$)-4-pyridyl | 7-[(3,5-dimethylpiperid-1-yl)-CH$_2$CH$_2$—) | NH$_2$ |
| 6057. | —(NMeSO$_2$)-4-pyridyl | 7-[(4-methylpiperid-1-yl)-CH$_2$CH$_2$—) | NH$_2$ |
| 6058. | —(NMeSO$_2$)-4-pyridyl | 7-[(3-methylpiperid-1-yl)-CH$_2$CH$_2$—)—] | NH$_2$ |
| 6059. | —(NMeSO$_2$)-4-pyridyl | 7-[(2-methylpiperid-1-yl)-CH$_2$CH$_2$—)—] | NH$_2$ |
| 6060. | —(NMeSO$_2$)-4-pyridyl | 7-(1-piperidylcarbonyl) | NH$_2$ |
| 6061. | —(NMeSO$_2$)-4-pyridyl | 7-[(4-methylpiperazin-1-yl)carbonyl] | NH$_2$ |
| 6062. | —(NMeSO$_2$)-4-pyridyl | 7-(morpholin-4-ylcarbonyl) | NH$_2$ |
| 6063. | —(NMeSO$_2$)-4-pyridyl | 7-(diethylaminocarbonyl) | NH$_2$ |
| 6064. | —(NMeSO$_2$)-4-pyridyl | 7-(1-pyrrolidinylcarbonyl) | NH$_2$ |
| 6065. | —(NMeSO$_2$)-4-pyridyl | 7-(azaperhydroepinylcarbonyl) | NH$_2$ |
| 6066. | —(NMeSO$_2$)-4-pyridyl | 7-[(3,5-dimethylpiperid-1-yl)carbonyl) | NH$_2$ |
| 6067. | —(NMeSO$_2$)-4-pyridyl | 7-[(4-methylpiperid-1-ylcarbonyl) | NH$_2$ |
| 6068. | —(NMeSO$_2$)-4-pyridyl | 7-[(3-methylpiperid-1-ylcarbonyl) | NH$_2$ |
| 6069. | —(NMeSO$_2$)-4-pyridyl | 7-[(2-methylpiperid-1-ylcarbonyl) | NH$_2$ |
| 6070. | —(NMeSO$_2$)-4-pyridyl | 7-[2-(dimethylamino)ethoxy] | NH$_2$ |
| 6071. | —(NMeSO$_2$)-4-pyridyl | 7-[2-(methylamino)ethoxy] | NH$_2$ |
| 6072. | —(NMeSO$_2$)-4-pyridyl | 7-[((2R)pyrrolidin-2-yl)methoxy] | NH$_2$ |
| 6073. | —(NMeSO$_2$)-4-pyridyl | 7-[((2R)-1-methylpyrrolidin-2-yl)mehtoxy] | NH$_2$ |
| 6074. | —(NMeSO$_2$)-4-pyridyl | 7-(2-(piperid-1-yl)ethoxy] | NH$_2$ |
| 6675. | —(NMeSO$_2$)-4-pyridyl | 7-[2-(piperazin-1-yl)ethoxy] | NH$_2$ |
| 6076. | —(NMeSO$_2$)-4-pyridyl | 7-(2-(morpholin-4-yl)ethoxyl | NH$_2$ |
| 6077. | —(NMeSO$_2$)-4-pyridyl | 7-[2-(1-methyl(4-piperidyl))ethoxy] | NH$_2$ |
| 6078. | —(NMeSO$_2$)-4-pyridyl | 7-(2-(1-methyl(4-piperidyl))methoxy] | NH$_2$ |
| 6079. | —(NMeSO$_2$)-4-pyridyl | 7-(1-methyl(4-piperidyloxy)) | NH$_2$ |

TABLE 10

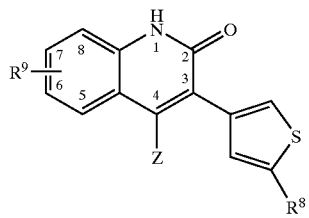

| # | R$^8$ | R$^9$ | Z |
|---|---|---|---|
| 6080. | 4-pyridyl | 7-(piperid-1-yl-CH$_2$—) | H |
| 6081. | 4-pyridyl | 7-(1-CH$_3$-piperazin-4-yl-CH$_2$—) | H |
| 6082. | 4-pyridyl | 7-(morpholin-4-yl-CH$_2$—) | H |
| 6083. | 4-pyridyl | 7-(diethylamino-CH$_2$—) | H |
| 6084. | 4-pyridyl | 7-(1-pyrrolidinyl-CH$_2$—) | H |
| 6085. | 4-pyridyl | 7-(azaperhydroepinyl-CH$_2$—) | H |
| 6086. | 4-pyridyl | 7-[(3,5-dimethylpiperid-1-yl)-CH$_2$—] | H |
| 6087. | 4-pyridyl | 7-[(4-methylpiperid-1-yl)-CH$_2$—] | H |
| 6088. | 4-pyridyl | 7-[(3-methylpiperid-1-yl)-CH$_2$—] | H |
| 6089. | 4-pyridyl | 7-[(2-methylpiperid-1-yl)-CH$_2$—] | H |
| 6090. | 4-pyridyl | 7-(piperid-1-yl-CH$_2$CH$_2$—) | H |
| 6091. | 4-pyridyl | 7-(1-CH$_3$-piperezin-4-yl-CH$_2$CH$_2$—) | H |

TABLE 10-continued

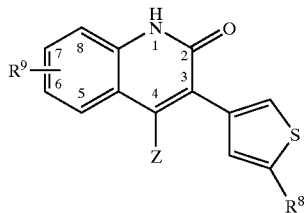

| # | R⁸ | R⁹ | Z |
|---|---|---|---|
| 6092. | 4-pyridyl | 7-(morpholin-4-yl-CH₂CH₂—) | H |
| 6093. | 4-pyridyl | 7-(diethylamino-CH₂CH₂—) | H |
| 6094. | 4-pyridyl | 7-(1-pyrrolidinyl-CH₂CH₂—) | H |
| 6095. | 4-pyridyl | 7-(azaperhydroepinyl-CH₂CH₂—) | H |
| 6096. | 4-pyridyl | 7-[(3,5-dimethylpiperid-1-yl)-CH₂CH₂—) | H |
| 6097. | 4-pyridyl | 7-[(4-methylpiperid-1-yl-CH₂CH₂—] | H |
| 6098. | 4-pyridyl | 7-[(3-methylpiperid-1-yl-CH₂CH₂—)—] | H |
| 6099. | 4-pyridyl | 7-[(2-methylpiperid-1-yl-CH₂CH₂—)—] | H |
| 6100. | 4-pyridyl | 7-(1-piperidylcarbonyl) | H |
| 6101. | 4-pyridyl | 7-[(4-methylpiperazin-1-yl)carbonyl) | H |
| 6102. | 4-pyridyl | 7-(morpholin-4-ylcarbonyl) | H |
| 6103. | 4-pyridyl | 7-(diethylaminocarbonyl) | H |
| 6104. | 4-pyridyl | 7-(1-pyrrolidinylcarbonyl) | H |
| 6105. | 4-pyridyl | 7-(azaperhydroepinylcarbonyl) | H |
| 6106. | 4-pyridyl | 7-((3,5-dimethylpiperid-1-yl)carbonyl) | H |
| 6107. | 4-pyridyl | 7-[(4-methylpiperid-1-ylcarbonyl) | H |
| 6108. | 4-pyridyl | 7-[(3-methylpiperid-1-ylcarbonyl) | H |
| 6109. | 4-pyridyl | 7-[(2-methylpiperid-1-ylcarbonyl) | H |
| 6110. | 4-pyridyl | 7-[2-(dimethylamino)ethoxy] | H |
| 6111. | 4-pyridyl | 7-[2-(methylamino)ethoxy] | H |
| 6112. | 4-pyridyl | 7-[((2R)pyrrolidin-2-yl)methoxy] | H |
| 6113. | 4-pyridyl | 7-[((2R)-1-methylpyrrolidin-2-yl)methoxy] | H |
| 6114. | 4-pyridyl | 7-[2-(piperid-1-yl)ethoxy] | H |
| 6115. | 4-pyridyl | 7-[2-(piperazin-1-yl)ethoxy] | H |
| 6116. | 4-pyridyl | 7-[2-(morpholin-4-yl)ethoxy] | H |
| 6117. | 4-pyridyl | 7-[2-(1-methyl(4-piperidyl))ethoxy] | H |
| 6118. | 4-pyridyl | 7-[2-(1-methyl(4-piperidyl))methoxy] | H |
| 6119. | 4-pyridyl | 7-(1-methyl(4-piperidyloxy)) | H |
| 6120. | 4-pyridyl | 7-(piperid-1-yl-CH₂—) | NH₂ |
| 6121. | 4-pyridyl | 7-(1-CH₃-piperazin-4-yl-CH₂—) | NH₂ |
| 6122. | 4-pyridyl | 7-(morpholin-4-yl-CH₂—] | NH₂ |
| 6123. | 4-pyridyl | 7-(diethylamino-CH₂—) | NH₂ |
| 6124. | 4-pyridyl | 7-(1-pyrrolidinyl-CH₂—) | NH₂ |
| 6125. | 4-pyridyl | 7-(azaperhydroepinyl-CH₂—) | NH₂ |
| 6126. | 4-pyridyl | 7-[(3,5-dimethylpiperid-1-yl)-CH₂—] | NH₂ |
| 6127. | 4-pyridyl | 7-[(4-methylpiperid-1-yl-CH₂—] | NH₂ |
| 6128. | 4-pyridyl | 7-[(3-methylpiperid-1-yl-CH₂—] | NH₂ |
| 6129. | 4-pyridyl | 7-[(2-methylpiperid-1-yl-CH₂—] | NH₂ |
| 6130. | 4-pyridyl | 7-(piperid-1-yl-CH₂CH₂—) | |
| 6131. | 4-pyridyl | 7-(1-CH₃-piperazin-4-yl-CH₂CH₂—) | NH₂ |
| 6132. | 4-pyridyl | 7-(morpholin-4-yl-CH₂CH₂—) | NH₂ |
| 6133. | 4-pyridyl | 7-(diethylamino-CH₂CH₂—) | NH₂ |
| 6134. | 4-pyridyl | 7-(1-pyrrolidinyl-CH₂CH₂—) | NH₂ |
| 6135. | 4-pyridyl | 7-(azaperhydroepinyl-CH₂CH₂—) | NH₂ |
| 6136. | 4-pyridyl | 7-[(3,5-dimethylpiperid-1-yl)-CH₂CH₂—) | NH₂ |
| 6137. | 4-pyridyl | 7-[(4-methylpiperid-1-yl-CH₂CH₂—) | NH₂ |
| 6138. | 4-pyridyl | 7-[(3-methylpiperid-1-yl-CH₂CH₂—)—] | NH₂ |
| 6139. | 4-pyridyl | 7-[(2-methylpiperid-1-yl-CH₂CH₂—)—] | NH₂ |
| 6140. | 4-pyridyl | 7-(1-piperidylcarbonyl) | NH₂ |
| 6141. | 4-pyridyl | 7-[(4-methylpiperazin-1-yl)carbonyl] | NH₂ |
| 6142. | 4-pyridyl | 7-(morpholin-4-ylcarbonyl) | NH₂ |
| 6143. | 4-pyridyl | 7-(diethylaminocarbonyl) | NH₂ |
| 6144. | 4-pyridyl | 7-(1-pyrrolidinylcarbonyl) | NH₂ |
| 6145. | 4-pyridyl | 7-(azaperhydroepinylcarbonyl) | NH₂ |
| 6146. | 4-pyridyl | 7-[(3,5-dimethylpiperid-1-yl)carbonyl) | NH₂ |
| 6147. | 4-pyridyl | 7-[(4-methylpiperid-1-ylcarbonyl) | NH₂ |
| 6148. | 4-pyridyl | 7-[(3-methylpiperid-1-ylcarbonyl) | NH₂ |
| 6149. | 4-pyridyl | 7-[(2-methylpiperid-1-ylcarbonyl) | NH₂ |
| 6150. | 4-pyridyl | 7-[2-(dimethylamino)ethoxy] | NH₂ |
| 6151. | 4-pyridyl | 7-[2-(methylamino)ethoxy] | NH₂ |
| 6152. | 4-pyridyl | 7-[((2R)pyrrolidin-2-yl)methoxy] | HH2 |
| 6153. | 4-pyridyl | 7-[((2R)-1-methylpyrrolidin-2-yl)methoxy] | NH₂ |
| 6154. | 4-pyridyl | 7-[2-(piperid-1-yl)ethoxy] | NH₂ |
| 6155. | 4-pyridyl | 7-[2-(piperazin-1-yl)ethoxy] | NH₂ |
| 6156. | 4-pyridyl | 7-[2-(morpholin-4-yl)ethoxy] | NH₂ |

TABLE 10-continued

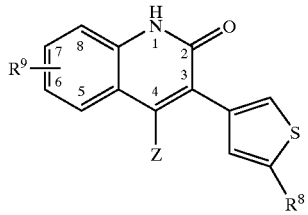

| # | R⁸ | R⁹ | Z |
|---|---|---|---|
| 6157. | 4-pyridyl | 7-[2-(1-methyl(4-piperidyl))ethoxy] | $NH_2$ |
| 6158. | 4-pyridyl | 7-[2-(1-methyl(4-piperidyl))methoxy] | $NH_2$ |
| 6159. | 4-pyridyl | 7-(1-methyl(4-piperidyloxy)) | $NH_2$ |
| 6160. | —($CH_2SO_2$)-phenyl | 7-(piperid-1-yl-$CH_2$—) | H |
| 6161. | —($CH_2SO_2$)-phenyl | 7-(1-$CH_3$-piperazin-4-yl-$CH_2$—) | H |
| 6162. | —($CH_2SO_2$)-phenyl | 7-(morpholin-4-yl-$CH_2$—) | H |
| 6163. | —($CH_2SO_2$)-phenyl | 7-(diethylamino-$CH_2$—) | H |
| 6164. | —($CH_2SO_2$)-phenyl | 7-(1-pyrrolidinyl-$CH_2$—) | H |
| 6165. | —($CH_2SO_2$)-phenyl | 7-(azaperhydroepinyl-$CH_2$—) | H |
| 6166. | —($CH_2SO_2$)-phenyl | 7-[(3-5-dimethylpiperid-1-yl)-$CH_2$—] | H |
| 6167. | —($CH_2SO_2$)-Phenyl | 7-[(4-methylpiperid-1-yl-$CH_2$—] | H |
| 6168. | —($CH_2SO_2$)-phenyl | 7-[(3-methylpiperid-1-yl-$CH_2$—] | H |
| 6169. | —($CH_2SO_2$)-phenyl | 7-[(2-methylpiperid-1-yl-$CH_2$—] | H |
| 6170. | —($CM_2SO_2$)-phenyl | 7-(piperid-1-yl-$CH_2CH_2$—) | H |
| 6171. | —($CH_2SO_2$)-phenyl | 7-(1-$CH_3$-piperazin-4-yl-$CH_2CH_2$—) | H |
| 6172. | —($CH_2SO_2$)-phenyl | 7-(morpholin-4-yl-$CH_2CH_2$—) | H |
| 6173. | —($CH_2SO_2$)-phenyl | 7-(diethylamino-$CH_2CH_2$—) | H |
| 6174. | —($CH_2SO_2$)-phenyl | 7-(1-pyrrolidinyl-$CH_2CH_2$—) | H |
| 6175. | —($CH_2SO_2$)-phenyl | 7-(azaperhydroepinyl-$CH_2CH_2$—) | H |
| 6176. | —($CH_2SO_2$)-phenyl | 7-[(3,5-dimethylpiperid-1-yl)-$CH_2CH_2$—) | H |
| 6177. | —($CH_2SO_2$)-phenyl | 7-[(4-methylpiperid-1-yl-$CH_2CH_2$—] | H |
| 6178. | —($CH_2SO_2$)-phenyl | 7-[(3-methylpiperid-1-yl-$CH_2CH_2$—)—] | H |
| 6179. | —($CH_2SO_2$)-phenyl | 7-[(2-methylpiperid-1-yl-$CH_2CH_2$—)—] | H |
| 6180. | —($CH_2SO_2$)-phenyl | 7-(1-piperidylcarbonyl) | H |
| 6181. | —($CH_2SO_2$)-phenyl | 7-[(4-methylpiperazin-1-yl)carbonyl] | H |
| 6182. | —($CH_2SO_2$)-phenyl | 7-(morpholin-4-ylcarbonyl) | H |
| 6183. | —($CH_2SO_2$)-phenyl | 7-(diethylaminocarbonyl) | H |
| 6184. | —($CH_2SO_2$)-phenyl | 7-(1-pyrrolidinylcarbonyl) | H |
| 6185. | —($CH_2SO_2$)-phenyl | 7-(azaperhydroepinylcarbonyl) | H |
| 6186. | —($CH_2SO_2$)-phenyl | 7-[(3,5-dimethylpiperid-1-yl)carbonyl] | H |
| 6187. | —($CH_2SO_2$)-phenyl | 7-[(4-methylpiperid-1-ylcarbonyl) | H |
| 6188. | —($CH_2SO_2$)-phenyl | 7-[3-methylpiperid-1-ylcarbonyl) | H |
| 6199. | —($CH_2SO_2$)-phenyl | 7-[2-(methylpiperid-1-ylcarbonyl) | H |
| 6190. | —($CH_2SO_2$)-phenyl | 7-[2-(dimethylamino)ethoxy] | H |
| 6191. | —($CH_2SO_2$)-phenyl | 7-[2-(methylamino)ethoxy] | H |
| 6192. | —($CH_2SO_2$)-phenyl | 7-[((2R)pyrrolidin-2-yl)methoxy] | H |
| 6193. | —($CH_2SO_2$)-phenyl | 7-[((2R)-1-methylpyrrolidin-2-yl)methoxy] | H |
| 6194. | —($CH_2SO_2$)-phenyl | 7-[2-(piperid-1-yl)ethoxy] | H |
| 6195. | —($CH_2SO_2$)-phenyl | 7-[2-(piperazin-1-yl)ethoxy] | H |
| 6196. | —($CH_2SO_2$)-phenyl | 7-[2-(morpholin-4-yl)ethoxy] | H |
| 6197. | —($CH_2SO_2$)-phenyl | 7-[2-(1-methyl(4-piperidyl))ethoxy] | H |
| 6198. | —($CH_2SO_2$)-phenyl | 7-[2-(1-methyl(4-piperidyl))methoxy) | H |
| 6199. | —($CH_2SO_2$)-phenyl | 7-(1-methyl(4-piperidyloxy)) | H |
| 6200. | —($CH_2SO_2$)-phenyl | 7-(piperid-1-yl-$CH_2$—) | $NH_2$ |
| 6201. | —($CH_2SO_2$)-phenyl | 7-(1-$CH_3$-piperazin-4-yl-$CH_2$—) | $NH_2$ |
| 6202. | —($CH_2SO_2$)-phenyl | 7-(morpholin-4-yl-$CH_2$—) | $NH_2$ |
| 6203. | —($CH_2SO_2$)-phenyl | 7-(diethylamino-$CH_2$—) | $NH_2$ |
| 6204. | —($CH_2SO_2$)-phenyl | 7-(1-pyrrolidinyl-$CH_2$—) | $NH_2$ |
| 6205. | —($CH_2SO_2$)-phenyl | 7-(azaperhydroepinyl-$CH_2$—) | $NH_2$ |
| 6206. | —($CH_2SO_2$)-phenyl | 7-[(3,5-dimethylpiperid-1-yl)-$CH_2$—] | $NH_2$ |
| 6207. | —($CH_2SO_2$)-phenyl | 7-[(4-methylpiperid-1-yl-$CH_2$—) | $NH_2$ |
| 6208. | —($CH_2SO_2$)-phenyl | 7-[(3-methylpiperid-1-yl-$CH_2$—) | $NH_2$ |
| 6209. | —($CH_2SO_2$)-phenyl | 7-[(2-methylpiperid-1-yl-$CH_2$—) | $NH_2$ |
| 6210. | —($CH_2SO_2$)-phenyl | 7-(piperid-1-yl-$CH_2CH_2$—) | $NH_2$ |
| 6211. | —($CH_2SO_2$)-phenyl | 7-(1-$CH_3$-piperazin-4-yl-$CH_2CH_2$—) | $NH_2$ |
| 6212. | —($CH_2SO_2$)-phenyl | 7-(morpholin-4-yl-$CH_2CH_2$—) | $NH_2$ |
| 6213. | —($CH_2SO_2$)-phenyl | 7-(diethylamino-$CH_2CH_2$—) | $NH_2$ |
| 6214. | —($CH_2SO_2$)-phenyl | 7-(1-pyrrolidinyl-$CH_2CH_2$—) | $NH_2$ |
| 6215. | —($CH_2SO_2$)-phenyl | 7-(azaperhydroepinyl-$CH_2CH_2$—) | $NH_2$ |
| 6216. | —($CH_2SO_2$)-phenyl | 7-[(3,5-dimethylpiperid-1-yl)-$CH_2CH_2$—) | $NH_2$ |
| 6217. | —($CH_2SO_2$)-phenyl | 7-[(4-methylpiperid-1-yl-$CH_2CH_2$—) | $NH_2$ |
| 6218. | —($CH_2SO_2$)-phenyl | 7-[(3-methylpiperid-1-yl-$CH_2CH_2$—)—] | $NH_2$ |
| 6219. | —($CH_2SO_2$)-phenyl | 7-[(2-methylpiperid-1-yl-$CH_2CH_2$—)—] | $NH_2$ |
| 6220. | —($CH_2SO_2$)-phenyl | 7-(1-piperidylcarbonyl) | $NH_2$ |
| 6221. | —($CH_2SO_2$)-phenyl | 7-[(4-methylpiperazin-1-yl)carbonyl] | $NH_2$ |

TABLE 10-continued

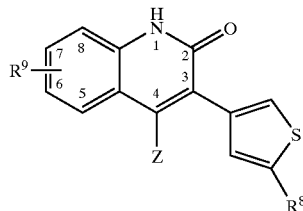

| # | R⁸ | R⁹ | Z |
|---|---|---|---|
| 6222. | —(CH₂SO₂)-phenyl | 7-(morpholin-4-ylcarbonyl) | NH₂ |
| 6223. | —(CH₂SO₂)-phenyl | 7-(diethylaminocarbonyl) | NH₂ |
| 6224. | —(CH₂SO₂)-phenyl | 7-(1-pyrrolidinylcarbonyl) | NH₂ |
| 6225. | —(CH₂SO₂)-phenyl | 7-(azaperhydroepinylcarbonyl) | NH₂ |
| 6226. | —(CH₂SO₂)-phenyl | 7-[(3,5-dimethylpiperid-1-yl)carbonyl) | NH₂ |
| 6227. | —(CH₂SO₂)-phenyl | 7-[(4-methylpiperid-1-ylcarhonyl) | NH₂ |
| 6228. | —(CH₂SO₂)-phenyl | 7-[(3-methylpiperid-1-ylcarbonyl) | NH₂ |
| 6229. | —(CH₂SO₂)-phenyl | 7-[(2-methylpiperid-1-ylcarbonyl) | NH₂ |
| 6230. | —(CH₂SO₂)-phenyl | 7-[2-(dimethylamino)ethoxy) | NH₂ |
| 6231. | —(CH₂SO₂)-phenyl | 7-[2-(methylamino)ethoxy) | NH₂ |
| 6232. | —(CH₂SO₂)-phenyl | 7-[((2R)pyrrolidin-2-yl)methoxy) | NH₂ |
| 6233. | —(CH₂SO₂)-phenyl | 7-[((2R)-1-methylpyrrolidin-2-yl)methoxy] | NH₂ |
| 6234. | —(CH₂SO₂)-phenyl | 7-[2-(piperid-1-yl)ethoxy] | NH₂ |
| 6235. | —(CH₂SO₂)-phenyl | 7-[2-(piperazin-1-yl)ethoxy] | NH₂ |
| 6236. | —(CH₂SO₂)-phenyl | 7-[2-(morpholin-4-yl)ethoxy] | NH₂ |
| 6237. | —(CH₂SO₂)-phenyl | 7-[2-(1-methyl(4-piperidyl))ethoxy] | NH₂ |
| 6238. | —(CH₂SO₂)-phenyl | 7-[2-(1-methyl(4-piperidyl))methoxy] | NH₂ |
| 6239. | —(CH₂SO₂)-phenyl | 7-(1-methyl(4-piperidyloxy)) | NH₂ |
| 6240. | —(CH₂SO₂)-2-thienyl | 7-(piperid-1-yl-CH₂—) | H |
| 6241. | —(CH₂SO₂)-2-thienyl | 7-(1-CH₃-piperazin-4-yl-CH₂—) | H |
| 6242. | —(CH₂SO₂)-2-thienyl | 7-(morpholin-4-yl-CH₂—) | H |
| 6243. | —(CH₂SO₂)-2-thienyl | 7-(diethylamino-CH₂—) | H |
| 6244. | —(CH₂SO₂)-2-thienyl | 7-(1-pyrrolidinyl-CH₂—) | H |
| 6245. | —(CH₂SO₂)-2-thienyl | 7-(azaperhydroepinyl-CH₂—) | H |
| 6246. | —(CH₂SO₂)-2-thienyl | 7-[(3,5-dimethylpiperid-1-yl)-CH₂—) | H |
| 6247. | —(CH₂SO₂)-2-thienyl | 7-[(4-methylpiperid-1-yl)-CH₂—] | H |
| 6248. | —(CH₂SO₂)-2-thienyl | 7-[(3-methylpiperid-1-yl)-CH₂—] | H |
| 6249. | —(CH₂SO₂)-2-thienyl | 7-[(2-methylpiperid-1-yl)-CH₂—] | H |
| 6250. | —(CH₂SO₂)-2-thienyl | 7-(piperid-1-yl-CH₂CH₂—) | H |
| 6251. | —(CH₂SO₂)-2-thienyl | 7-(1-CH₃-piperazin-4-yl-CH₂CH₂—) | H |
| 6252. | —(CH₂SO₂)-2-thienyl | 7-(morpholin-4-yl-CH₂CH₂—) | H |
| 6253. | —(CH₂SO₂)-2-thienyl | 7-(diethylamino-CH₂CH₂—) | H |
| 6254. | —(CH₂SO₂)-2-thienyl | 7-(1-pyrrolidinyl-CH₂CH₂—) | H |
| 6255. | —(CH₂SO₂)-2-thienyl | 7-(azaperhydroepinyl-CH₂CH₂—) | H |
| 6256. | —(CH₂SO₂)-2-thienyl | 7-[(3,5-dimethylpiperid-1-yl)-CH₂CH₂—) | H |
| 6257. | —(CH₂SO₂)-2-thienyl | 7-(4-methylpiperid-1-yl-CH₂CH₂—) | H |
| 6258. | —(CH₂SO₂)-2-thienyl | 7-[(3-methylpiperid-1-yl-CH₂CH₂—)—] | H |
| 6259. | —(CH₂SO₂)-2-thienyl | 7-[(2-methylpiperid-1-yl-CH₂CH₂—)—] | H |
| 6260. | —(CH₂SO₂)-2-thienyl | 7-(1-piperidylcarbonyl) | H |
| 6261. | —(CH₂SO₂)-2-thienyl | 7-[(4-methylpiperazin-1-yl)carbonyl] | H |
| 6262. | —(CH₂SO₂)-2-thienyl | 7-(morpholin-4-ylcarbonyl) | H |
| 6263. | —(CH₂SO₂)-2-thienyl | 7-(diethylaminocarbonyl) | H |
| 6264. | —(CH₂SO₂)-2-thienyl | 7-(1-pyrrolidinylcarbonyl) | H |
| 6265. | —(CH₂SO₂)-2-thienyl | 7-(azaperhydroepinylcarbonyl) | H |
| 6266. | —(CH₂SO₂)-2-thienyl | 7-[(3,5-dimethylpiperid-1-yl)carbonyl) | H |
| 6267. | —(CH₂SO₂)-2-thienyl | 7-[(4-methylpiperid-1-ylcarbonyl) | H |
| 6268. | —(CH₂SO₂)-2-thienyl | 7-[(3-methylpiperid-1-ylcarbonyl) | H |
| 6269. | —(CH₂SO₂)-2-thienyl | 7-[(2-methylpiperid-1-ylcarbonyl) | H |
| 6270. | —(CH₂SO₂)-2-thienyl | 7-[2-(dimethylamino)ethoxy] | H |
| 6271. | —(CH₂SO₂)-2-thienyl | 7-[2-(methylamino)ethoxy] | H |
| 6272. | —(CH₂SO₂)-2-thienyl | 7-[((2R)pyrrolidin-2-yl)methoxy] | H |
| 6273. | —(CH₂SO₂)-2-thienyl | 7-[((2R)-1-methylpyrrolidin-2-yl)methoxy] | H |
| 6274. | —(CH₂SO₂)-2-thienyl | 7-[2-(piperid-1-yl)ethoxy] | H |
| 6275. | —(CH₂SO₂)-2-thienyl | 7-[2-(piperazin-1-yl)ethoxy] | H |
| 6276. | —(CH₂SO₂)-2-thienyl | 7-[2-(morpholin-4-yl)ethoxy] | H |
| 6277. | —(CH₂SO₂)-2-thienyl | 7-[2-(1-methyl(4-piperidyl))ethoxy] | H |
| 6278. | —(CH₂SO₂)-2-thienyl | 7-[2-(1-methyl(4-piperidyl))methoxy] | H |
| 6279. | —(CH₂SO₂)-2-thienyl | 7-(1-methyl(4-piperidyloxy)) | H |
| 6280. | —(CH₂SO₂)-2-thienyl | 7-(piperid-1-yl-CH₂—) | NH₂ |
| 6281. | —(CH₂SO₂)-2-thienyl | 7-(1-CH₃-piperazin-4-yl-CH₂—) | NH₂ |
| 6282. | —(CH₂SO₂)-2-thienyl | 7-(morpholin-4-yl-CH₂—) | NH₂ |
| 6283. | —(CH₂SO₂)-2-thienyl | 7-(diethylamino-CH₂—) | NH₂ |
| 6284. | —(CH₂SO₂)-2-thienyl | 7-(1-pyrrolidinyl-CH₂—) | NH₂ |
| 6285. | —(CH₂SO₂)-2-thienyl | 7-(azaperhydroepinyl-CH₂—) | NH₂ |
| 6286. | —(CH₂SO₂)-2-thienyl | 7-[(3,5-dimethylpiperid-1-yl)-CH₂—] | NH₂ |

TABLE 10-continued

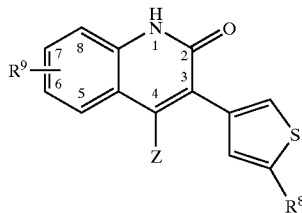

| # | R⁸ | R⁹ | Z |
|---|---|---|---|
| 6287. | —(CH$_2$SO$_2$)-2-thienyl | 7-[(4-methylpiperid-1-yl-CH$_2$—] | NH$_2$ |
| 6288. | —(CH$_2$SO$_2$)-2-thienyl | 7-[(3-methylpiperid-1-yl-CH$_2$—] | NH$_2$ |
| 6289. | —(CH$_2$SO$_2$)-2-thienyl | 7-[(2-methylpiperid-1-yl-CH$_2$—] | NH$_2$ |
| 6290. | —(CH$_2$SO$_2$)-2-thienyl | 7-(piperid-1-yl-CH$_2$CH$_2$—) | NH$_2$ |
| 6291. | —(CH$_2$SO$_2$)-2-thienyl | 7-(1-CH$_3$-piperazin-4-yl-CH$_2$CH$_2$—) | NH$_2$ |
| 6292. | —(CH$_2$SO$_2$)-2-thienyl | 7-(morpholin-4-yl-CH$_2$CH$_2$—) | NH$_2$ |
| 6293. | —(CH$_2$SO$_2$)-2-thienyl | 7-(diethylamino-CH$_2$CH$_2$—) | NH$_2$ |
| 6294. | —(CH$_2$SO$_2$)-2-thienyl | 7-(1-pyrrodinyl-CH$_2$CH$_2$—) | NH$_2$ |
| 6295. | —(CH$_2$SO$_2$)-2-thienyl | 7-(azaperhydroepinyl-CH$_2$CH$_2$—) | NH$_2$ |
| 6296. | —(CH$_2$SO$_2$)-2-thienyl | 7-[(3,5-dimethylpiperid-1-yl)-CH$_2$CH$_2$—) | NH$_2$ |
| 6297. | —(CH$_2$SO$_2$)-2-thienyl | 7-[(4-methylpiperid-1-yl-CH$_2$CH$_2$—) | NH$_2$ |
| 6298. | —(CH$_2$SO$_2$)-2-thienyl | 7-[(3-methylpiperid-1-yl-CH$_2$CH$_2$—)—] | NH$_2$ |
| 6299. | —(CH$_2$SO$_2$)-2-thienyl | 7-[(2-methylpiperid-1-yl-CH$_2$CH$_2$—)—] | NH$_2$ |
| 6300. | —(CH$_2$SO$_2$)-2-thienyl | 7-(1-piperidylcarbonyl) | NH$_2$ |
| 6301. | —(CH$_2$SO$_2$)-2-thienyl | 7-[(4-methylpiperazin-1-yl)carbonyl] | NH$_2$ |
| 6302. | —(CH$_2$SO$_2$)-2-thienyl | 7-(morpholin-4-ylcarbonyl) | NH$_2$ |
| 6303. | —(CH$_2$SO$_2$)-2-thienyl | 7-(diethylaminocarbonyl) | NH$_2$ |
| 6304. | —(CH$_2$SO$_2$)-2-thienyl | 7-(1-pyrrolidinylcarbonyl) | NH$_2$ |
| 6305. | —(CH$_2$SO$_2$)-2-thienyl | 7-(azaperhydroepinylcarbonyl) | NH$_2$ |
| 6306. | —(CH$_2$SO$_2$)-2-thienyl | 7-[(3,5-dimethylpiperid-1-yl)carbonyl) | NH$_2$ |
| 6307. | —(CH$_2$SO$_2$)-2-thienyl | 7-[(4-methylpiperid-1-ylcarbonyl) | NH$_2$ |
| 6308. | —(CH$_2$SO$_2$)-2-thienyl | 7-[(3-methylpiperid-1-ylcarbonyl) | NH$_2$ |
| 6309. | —(CH$_2$SO$_2$)-2-thienyl | 7-[(2-methylpiperid-1-ylcarbonyl) | NH$_2$ |
| 6310. | —(CH$_2$SO$_2$)-2-thienyl | 7-[2-(dimethylamino)ethoxy] | NH$_2$ |
| 6311. | —(CH$_2$SO$_2$)-2-thienyl | 7-[2-(methylamino)ethoxy] | NH$_2$ |
| 6312. | —(CH$_2$SO$_2$)-2-thienyl | 7-[((2R)pyrrolidin-2-yl)methoxy] | NH$_2$ |
| 6313. | —(CH$_2$SO$_2$)-2-thienyl | 7-[((2R)-1-methylpyrrolidin-2-yl)methoxy] | NH$_2$ |
| 6314. | —(CH$_2$SO$_2$)-2-thienyl | 7-[2-(piperid-1-yl)ethoxy] | NH$_2$ |
| 6315. | —(CH$_2$SO$_2$)-2-thienyl | 7-[2-(piperazin-1-yl)ethoxy] | NH$_2$ |
| 6316. | —(CH$_2$SO$_2$)-2-thienyl | 7-[2-(morpholin-4-yl)ethoxy] | NH$_2$ |
| 6317. | —(CH$_2$SO$_2$)-2-thienyl | 7-[2-(1-methyl(4-piperidyl))ethoxy] | NH$_2$ |
| 6318. | —(CH$_2$SO$_2$)-2-thienyl | 7-[2-(1-methyl(4-piperidyl))methoxy] | NH$_2$ |
| 6319. | —(CH$_2$SO$_2$)-2-thienyl | 7-(1-methyl(4-piperidyloxy)) | NH$_2$ |
| 6320. | —(CH$_2$SO$_2$)-2-pyridyl | 7-(piperid-1-yl-CH$_2$—) | H |
| 6321. | —(CH$_2$SO$_2$)-2-pyridyl | 7-(1-CH$_3$-piperezin-4-yl-CH$_2$—) | H |
| 6322. | —(CH$_2$SO$_2$)-2-pyridyl | 7-(morpholin-4-yl-CH$_2$—) | H |
| 6323. | —(CH$_2$SO$_2$)-2-pyridyl | 7-(diethylamino-CH$_2$—) | H |
| 6324. | —(CH$_2$SO$_2$)-2-pyridyl | 7-(1-pyrrolidinyl-CH$_2$—) | H |
| 6325. | —(CH$_2$SO$_2$)-2-pyridyl | 7-(azaperhydroepinyl-CH$_2$—) | H |
| 6326. | —(CH$_2$SO$_2$)-2-pyridyl | 7-[(3,5-dimethylpiperid-1-yl)-CH$_2$—] | H |
| 6327. | —(CH$_2$SO$_2$)-2-pyridyl | 7-[(4-methylpiperid-1-yl-CH$_2$—] | H |
| 6328. | —(CH$_2$SO$_2$)-2-pyridyl | 7-[(3-methylpiperid-1-yl-CH$_2$—] | H |
| 6329. | —(CH$_2$SO$_2$)-2-pyridyl | 7-[(2-methylpiperid-1-yl-CH$_2$—] | H |
| 6330. | —(CH$_2$SO$_2$)-2-pyridyl | 7-(piperid-1-yl-CH$_2$CH$_2$—) | H |
| 6331. | —(CH$_2$SO$_2$)-2-pyridyl | 7-(1-CH$_3$-piperazin-4-yl-CH$_2$CH$_2$—) | H |
| 6332. | —(CH$_2$SO$_2$)-2-pyridyl | 7-(morpholin-4-yl-CH$_2$CH$_2$—) | H |
| 6333. | —(CH$_2$SO$_2$)-2-pyridyl | 7-(diethylamino-CH$_2$CH$_2$—) | H |
| 6334. | —(CH$_2$SO$_2$)-2-pyridyl | 7-(1-pyrrolidinyl-CH$_2$CH$_2$—) | H |
| 6335. | —(CH$_2$SO$_2$)-2-pyridyl | 7-(azaperhydroepinyl-CH$_2$CH$_2$—) | H |
| 6336. | —(CH$_2$SO$_2$)-2-pyridyl | 7-[(3,5-dimethylpiperid-1-yl)-CH$_2$CH$_2$—) | H |
| 6337. | —(CH$_2$SO$_2$)-2-pyridyl | 7-[(4-methylpiperid-1-yl-CH$_2$CH$_2$—) | H |
| 6338. | —(CH$_2$SO$_2$)-2-pyridyl | 7-[(3-methylpiperid-1-yl-CH$_2$CH$_2$—)—] | H |
| 6339. | —(CH$_2$SO$_2$)-2-pyridyl | 7-[(2-methylpiperid-1-yl-CH$_2$CH$_2$—)—] | H |
| 6340. | —(CH$_2$SO$_2$)-2-pyridyl | 7-(1-piperidylcarbonyl) | H |
| 6341. | —(CH$_2$SO$_2$)-2-pyridyl | 7-[(4-methylpiperazin-1-yl)carbonyl) | H |
| 6342. | —(CH$_2$SO$_2$)-2-pyridyl | 7-(morpholin-4-ylcarbonyl) | H |
| 6343. | —(CH$_2$SO$_2$)-2-pyridyl | 7-(diethylaminocarbonyl) | H |
| 6344. | —(CH$_2$SO$_2$)-2-pyridyl | 7-(1-pyrrolidinylcarbonyl) | H |
| 6345. | —(CH$_2$SO$_2$)-2-pyridyl | 7-(azaperhydroepinylcarbonyl) | H |
| 6346. | —(CH$_2$SO$_2$)-2-pyridyl | 7-[(3,5-dimethylpiperid-1-yl)carbonyl) | H |
| 6347. | —(CH$_2$SO$_2$)-2-pyridyl | 7-[(4-methylpiperid-1-ylcarbonyl) | H |
| 6348. | —(CH$_2$SO$_2$)-2-pyridyl | 7-[(3-methylpiperid-1-ylcarbonyl) | H |
| 6349. | —(CH$_2$SO$_2$)-2-pyridyl | 7-[(2-methylpiperid-1-ylcarbonyl) | H |
| 6350. | —(CH$_2$SO$_2$)-2-pyridyl | 7-[2-(dimethylamino)ethoxy] | H |
| 6351. | —(CH$_2$SO$_2$)-2-pyridyl | 7-[2-(methylamino)ethoxy] | H |

TABLE 10-continued

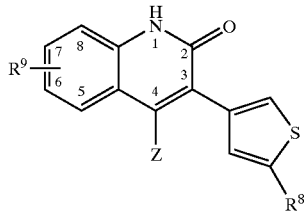

| # | R⁸ | R⁹ | Z |
|---|---|---|---|
| 6352. | —(CH₂SO₂)-2-pyridyl | 7-[((2R)pyrrolidin-2-yl)methoxy] | H |
| 6353. | —(CH₂SO₂)-2-pyridyl | 7-[((2R)-1-methylpyrrolidin-2-yl)methoxy] | H |
| 6354. | —(CH₂SO₂)-2-pyridyl | 7-[2-(piperid-1-yl)ethoxy] | H |
| 6355. | —(CH₂SO₂)-2-pyridyl | 7-[2-(piperazin-1-yl)ethoxy) | H |
| 6356. | —(CH₂SO₂)-2-pyridyl | 7-[2-(morpholin-4-yl)ethoxy] | H |
| 6357. | —(CH₂SO₂)-2-pyridyl | 7-[2-(1-methyl(4-piperidyl))ethoxy] | H |
| 6358. | —(CH₂SO₂)-2-pyridyl | 7-[2-(1-methyl(4-piperidyl))methoxy] | H |
| 6359. | —(CH₂SO₂)-2-pyridyl | 7-(1-methyl(4-piperidyloxy)) | H |
| 6360. | —(CH₂SO₂)-2-pyridyl | 7-(piperid-1-yl-CH₂—) | NH₂ |
| 6361. | —(CH₂SO₂)-2-pyridyl | 7-(1-CH₃-piperazin-4-yl-CH₂—) | NH₂ |
| 6362. | —(CH₂SO₂)-2-pyridyl | 7-(morpholin-4-yl-CH₂—) | NH₂ |
| 6363. | —(CH₂SO₂)-2-pyridyl | 7-(diethylamino-CH₂—) | NH₂ |
| 6364. | —(CH₂SO₂)-2-pyridyl | 7-(1-pyrrolidinyl-CH₂—) | NH₂ |
| 6365. | —(CH₂SO₂)-2-pyridyl | 7-(azaperhydroepinyl-CH₂—) | NH₂ |
| 6366. | —(CH₂SO₂)-2-pyridyl | 7-[(3,5-dimethylpiperid-1-yl)-CH₂—] | NH₂ |
| 6367. | —(CH₂SO₂)-2-pyridyl | 7-[(4-methylpiperid-1-yl-CH₂—] | NH₂ |
| 6368. | —(CH₂SO₂)-2-pyridyl | 7-[(3-methylpiperid-1-yl-CH₂—] | NH₂ |
| 6369. | —(CH₂SO₂)-2-pyridyl | 7-[(2-methylpiperid-1-yl-CH₂—) | NH₂ |
| 6370. | —(CH₂SO₂)-2-pyridyl | 7-(piperid-1-yl-CH₂CH₂—) | NH₂ |
| 6371. | —(CH₂SO₂)-2-pyridyl | 7-(1-CH₃-piperazin-4-yl-CH₂CH₂—) | NH₂ |
| 6372. | —(CH₂SO₂)-2-pyridyl | 7-(morpholin-4-yl-CH₂CH₂—) | NH₂ |
| 6373. | —(CH₂SO₂)-2-pyridyl | 7-(diethylamino-CH₂CH₂—) | NH₂ |
| 6374. | —(CH₂SO₂)-2-pyridyl | 7-(1-pyrrolidinyl-CH₂CH₂—) | NH₂ |
| 6375. | —(CH₂SO₂)-2-pyridyl | 7-(azeperhydroepinyl-CH₂CH₂—) | NH₂ |
| 6376. | —(CH₂SO₂)-2-pyridyl | 7-[(3,5-dimethylpiperid-1-yl)-CH₂CH₂—) | NH₂ |
| 6377. | —(CH₂SO₂)-2-pyridyl | 7-[(4-methylpiperid-1-yl-CH₂CH₂—) | NH₂ |
| 6378. | —(CH₂SO₂)-2-pyridyl | 7-[(3-methylpiperid-1-yl-CH₂CH₂—)—] | NH₂ |
| 6379. | —(CH₂SO₂)-2-pyridyl | 7-[(2-methylpiperid-1-yl-CH₂CH₂—)—] | NH₂ |
| 6380. | —(CH₂SO₂)-2-pyridyl | 7-(1-piperidylcarbonyl) | NH₂ |
| 6381. | —(CH₂SO₂)-2-pyridyl | 7-[(4-methylpiperazin-1-yl)carbonyl] | NH₂ |
| 6382. | —(CH₂SO₂)-2-pyridyl | 7-(morpholin-4-ylcarbonyl) | NH₂ |
| 6383. | —(CH₂SO₂)-2-pyridyl | 7-(diethylaminocarbonyl) | NH₂ |
| 6384. | —(CH₂SO₂)-2-pyridyl | 7-(1-pyrrolidinylcarbonyl) | NH₂ |
| 6385. | —(CH₂SO₂)-2-pyridyl | 7-(azaperhydroepinylcarbonyl) | NH₂ |
| 6386. | —(CH₂SO₂)-2-pyridyl | 7-[(3,5-dimethylpiperid-1-yl)carbonyl) | NH₂ |
| 6387. | —(CH₂SO₂)-2-pyridyl | 7-[(4-methylpiperid-1-ylcarbonyl) | NH₂ |
| 6388. | —(CH₂SO₂)-2-pyridyl | 7-[(3-methylpiperid-1-ylcarbonyl) | NH₂ |
| 6389. | —(CH₂SO₂)-2-pyridyl | 7-[(2-methylpiperid-1-ylcarbonyl) | NH₂ |
| 6390. | —(CH₂SO₂)-2-pyridyl | 7-[2-(dimethylamino)ethoxy] | NH₂ |
| 6391. | —(CH₂SO₂)-2-pyridyl | 7-[2-(methylamino)ethoxy] | NH₂ |
| 6392. | —(CH₂SO₂)-2-pyridyl | 7-[((2R)pyrrolidin-2-yl)methoxy] | NH₂ |
| 6393. | —(CH₂SO₂)-2-pyridyl | 7-[((2R)-1-methylpyrrolidin-2-yl)methoxy] | NH₂ |
| 6394. | —(CH₂SO₂)-2-pyridyl | 7-[2-(piperid-1-yl)ethoxy] | NH₂ |
| 6395. | —(CH₂SO₂)-2-pyridyl | 7-[2-(piperazin-1-yl)ethoxy] | NH₂ |
| 6396. | —(CH₂SO₂)-2-pyridyl | 7-[2-(morpholin-4-yl)ethoxy] | NH₂ |
| 6397. | —(CH₂SO₂)-2-pyridyl | 7-[2-(1-methyl(4-piperidyl))ethoxy] | NH₂ |
| 6398. | —(CH₂SO₂)-2-pyridyl | 7-[2-(1-methyl(4-piperidyl))methoxy] | NH₂ |
| 6399. | —(CH₂SO₂)-2-pyridyl | 7-(1-methyl(4-piperidyloxy)) | NH₂ |
| 6400. | —(CH₂SO₂)-3-pyridyl | 7-(piperid-1-yl-CH₂—) | H |
| 6401. | —(CH₂SO₂)-3-pyridyl | 7-(1-CH₃-piperazin-4-yl-CH₂—) | H |
| 6402. | —(CH₂SO₂)-3-pyridyl | 7-(morpholin-4-yl-CH₂—) | H |
| 6403. | —(CH₂SO₂)-3-pyridyl | 7-(diethylamino-CH₂—) | H |
| 6404. | —(CH₂SO₂)-3-pyridyl | 7-(1-pyrrolidinyl-CH₂—) | H |
| 6405. | —(CH₂SO₂)-3-pyridyl | 7-(azaperhydroepinyl-CH₂—) | H |
| 6406. | —(CH₂SO₂)-3-pyridyl | 7-[(3,5-dimethylpiperid-1-yl)-CH₂—] | H |
| 6407. | —(CH₂SO₂)-3-pyridyl | 7-[(4-methylpiperid-1-yl-CH₂—] | H |
| 6408. | —(CH₂SO₂)-3-pyridyl | 7-[(3-methylpiperid-1-yl-CH₂—) | H |
| 6409. | —(CH₂SO₂)-3-pyridyl | 7-[(2-methylpiperid-1-yl-CH₂—] | H |
| 6410. | —(CH₂SO₂)-3-pyridyl | 7-(piperid-1-yl-CH₂CH₂—) | H |
| 6411. | —(CH₂SO₂)-3-pyridyl | 7-(1-CH₃-piperazin-4-yl-CH₂CH₂—) | H |
| 6412. | —(CH₂SO₂)-3-pyridyl | 7-(morpholin-4-yl-CH₂CH₂—) | H |
| 6413. | —(CH₂SO₂)-3-pyridyl | 7-(diethylamino-CH₂CH₂—) | H |
| 6414. | —(CH₂SO₂)-3-pyridyl | 7-(1-pyrrolidinyl-CH₂CH₂—) | H |
| 6415. | —(CH₂SO₂)-3-pyridyl | 7-(azaperhydroepinyl-CH₂CH₂—) | H |
| 6416. | —(CH₂SO₂)-3-pyridyl | 7-[(3,5-dimethylpiperid-1-yl)-CH₂CH₂—) | H |

TABLE 10-continued

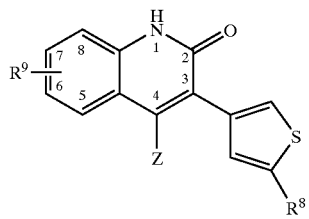

| # | R⁸ | R⁹ | Z |
|---|---|---|---|
| 6417. | —(CH₂SO₂)-3-pyridyl | 7-[(4-methylpiperid-1-yl-CH₂CH₂—)] | H |
| 6418. | —(CH₂SO₂)-3-pyridyl | 7-[(3-methylpiperid-1-yl-CH₂CH₂—)—] | H |
| 6419. | —(CH₂SO₂)-3-pyridyl | 7-[(2-methylpiperid-1-yl-CH₂CH₂—)—] | H |
| 6420. | —(CH₂SO₂)-3-pyridyl | 7-(1-piperidylcarbonyl) | H |
| 6421. | —(CH₂SO₂)-3-pyridyl | 7-[(4-methylpiperazin-1-yl)carbonyl] | H |
| 6422. | —(CH₂SO₂)-3-pyridyl | 7-(morpholin-4-ylcarbonyl) | H |
| 6423. | —(CH₂SO₂)-3-pyridyl | 7-(diethylaminocarbonyl) | H |
| 6424. | —(CH₂SO₂)-3-pyridyl | 7-(1-pyrrolidinylcarbonyl) | H |
| 6425. | —(CH₂SO₂)-3-pyridyl | 7-(azaperhydroepinylcarbonyl) | H |
| 6426. | —(CH₂SO₂)-3-pyridyl | 7-[(3,5-dimethylpiperid-1-yl)carbonyl] | H |
| 6427. | —(CH₂SO₂)-3-pyridyl | 7-[4-methylpiperid-1-ylcarbonyl] | H |
| 6428. | —(CH₂SO₂)-3-pyridyl | 7-[(3-methylpiperid-1-ylcarbonyl)] | H |
| 6429. | —(CH₂SO₂)-3-pyridyl | 7-[(2-methylpiperid-1-ylcarbonyl)] | H |
| 6430. | —(CH₂SO₂)-3-pyridyl | 7-[2-(dimethylamino)ethoxy] | H |
| 6431. | —(CH₂SO₂)-3-pyridyl | 7-[2-(methylamino)ethoxy] | H |
| 6432. | —(CH₂SO₂)-3-pyridyl | 7-[((2R)pyrrolidin-2-yl)methoxy] | H |
| 6433. | —(CH₂SO₂)-3-pyridyl | 7-[((2R)-1-methylpyrrolidin-2-yl)methoxy] | H |
| 6434. | —(CH₂SO₂)-3-pyridyl | 7-[2-(piperid-1-yl)ethoxy] | H |
| 6435. | —(CH₂SO₂)-3-pyridyl | 7-[2-(piperazin-1-yl)ethoxy] | H |
| 6436. | —(CH₂SO₂)-3-pyridyl | 7-[2-(morpholin-4-yl)ethoxy] | H |
| 6437. | —(CH₂SO₂)-3-pyridyl | 7-[2-(1-methyl(4-piperidyl))ethoxy] | H |
| 6438. | —(CH₂SO₂)-3-pyridyl | 7-[2-(1-methyl(4-piperidyl))methoxy] | H |
| 6439. | —(CH₂SO₂)-3-pyridyl | 7-(1-methyl(4-piperidyloxy)) | H |
| 6440. | —(CH₂SO₂)-3-pyridyl | 7-(piperid-1-yl-CH₂—] | NH₂ |
| 6441. | —(CH₂SO₂)-3-pyridyl | 7-(1-CH₃-piperazin-4-yl-CH₂—) | NH₂ |
| 6442. | —(CH₂SO₂)-3-pyridyl | 7-(morpholin-4-yl-CH₂—) | NH₂ |
| 6443. | —(CH₂SO₂)-3-pyridyl | 7-(diethylamino-CH₂—) | NH₂ |
| 6444. | —(CH₂SO₂)-3-pyridyl | 7-(1-pyrrolidinyl-CH₂—) | NH₂ |
| 6445. | —(CH₂SO₂)-3-pyridyl | 7-(azaperhydroepinyl-CH₂—) | NH₂ |
| 6446. | —(CH₂SO₂)-3-pyridyl | 7-[(3,5-dimethylpiperid-1-yl)-CH₂—] | NH₂ |
| 6447. | —(CH₂SO₂)-3-pyridyl | 7-[(4-methylpiperid-1-yl-CH₂—] | NH₂ |
| 6448. | —(CH₂SO₂)-3-pyridyl | 7-[(3-methylpiperid-1-yl-CH₂—] | NH₂ |
| 6449. | —(CH₂SO₂)-3-pyridyl | 7-[(2-methylpiperid-1-yl-CH₂—] | NH₂ |
| 6450. | —(CH₂SO₂)-3-pyridyl | 7-(piperid-1-yl-CH₂CH₂—) | NH₂ |
| 6451. | —(CH₂SO₂)-3-pyridyl | 7-(1-CH₃-piperazin-4-yl-CH₂CH₂—) | NH₂ |
| 6452. | —(CH₂SO₂)-3-pyridyl | 7-(morpholin-4-yl-CH₂CH₂—) | NH₂ |
| 6453. | —(CH₂SO₂)-3-pyridyl | 7-(diethylamino-CH₂CH₂—) | NH₂ |
| 6454. | —(CH₂SO₂)-3-pyridyl | 7-(1-pyrrolidinyl-CH₂CH₂—) | NH₂ |
| 6455. | —(CH₂SO₂)-3-pyridyl | 7-(azaperhydroepinyl-CH₂CH₂—) | NH₂ |
| 6456. | —(CH₂SO₂)-3-pyridyl | 7-[(3,5-dimethylpiperid-1-yl)-CH₂CH₂—) | NH₂ |
| 6457. | —(CH₂SO₂)-3-pyridyl | 7-[(4-methylpiperid-1-yl-CH₂CH₂—) | NH₂ |
| 6458. | —(CH₂SO₂)-3-pyridyl | 7-[(3-methylpiperid-1-yl-CH₂CH₂—)—] | NH₂ |
| 6459. | —(CH₂SO₂)-3-pyridyl | 7-[(2-methylpiperid-1-yl-CH₂CH₂—)—] | NH₂ |
| 6460. | —(CH₂SO₂)-3-pyridyl | 7-(1-piperidylcarbonyl) | NH₂ |
| 6461. | —(CH₂SO₂)-3-pyridyl | 7-[(4-methylpiperazin-1-yl)carbonyl] | NH₂ |
| 6462. | —(CH₂SO₂)-3-pyridyl | 7-(morpholin-4-ylcarbonyl) | NH₂ |
| 6463. | —(CH₂SO₂)-3-pyridyl | 7-(diethylaminocarbonyl) | NH₂ |
| 6464. | —(CH₂SO₂)-3-pyridyl | 7-(1-pyrrolidinylcarbonyl) | NH₂ |
| 6465. | —(CH₂SO₂)-3-pyridyl | 7-(azaperhydroepinylcarbonyl) | NH₂ |
| 6466. | —(CH₂SO₂)-3-pyridyl | 7-[(3,5-dimethylpiperid-1-yl)carbonyl] | NH₂ |
| 6467. | —(CH₂SO₂)-3-pyridyl | 7-[(4-methylpiperid-1-ylcarbonyl)] | NH₂ |
| 6468. | —(CH₂SO₂)-3-pyridyl | 7-[(3-methylpiperid-1-ylcarbonyl)] | NH₂ |
| 6469. | —(CH₂SO₂)-3-pyridyl | 7-[(2-methylpiperid-1-ylcarbonyl)] | NH₂ |
| 6470. | —(CH₂SO₂)-3-pyridyl | 7-[2-(dimethylamino)ethoxy] | NH₂ |
| 6471. | —(CH₂SO₂)-3-pyridyl | 7-[2-(methylamino)ethoxy] | NH₂ |
| 6472. | —(CH₂SO₂)-3-pyridyl | 7-[((2R)pyrrolidin-2-yl)methoxy] | NH₂ |
| 6473. | —(CH₂SO₂)-3-pyridyl | 7-[((2R)-1-methylpyrrolidin-2-yl)methoxy] | NH₂ |
| 6474. | —(CH₂SO₂)-3-pyridyl | 7-[2-(piperid-1-yl)ethoxy] | NH₂ |
| 6475. | —(CH₂SO₂)-3-pyridyl | 7-[2-(piperazin-1-yl)ethoxy] | NH₂ |
| 6476. | —(CH₂SO₂)-3-pyridyl | 7-[2-(morpholin-4-yl)ethoxy] | NH₂ |
| 6477. | —(CH₂SO₂)-3-pyridyl | 7-[2-(1-methyl(4-piperidyl))ethoxy] | NH₂ |
| 6478. | —(CH₂SO₂)-3-pyridyl | 7-[2-(1-methyl(4-piperidyl))methoxy] | NH₂ |
| 6479. | —(CH₂SO₂)-3-pyridyl | 7-(1-methyl(4-piperidyloxy)) | NH₂ |
| 6480. | —(CH₂SO₂)-4-pyridyl | 7-(piperid-1-yl-CH₂—) | H |
| 6481. | —(CH₂SO₂)-4-pyridyl | 7-(1-CH₃-piperazin-4-yl-CH₂—) | H |

TABLE 10-continued

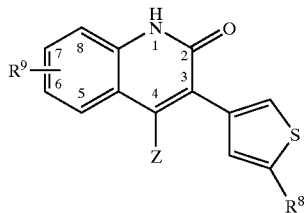

| # | R⁸ | R⁹ | Z |
|---|---|---|---|
| 6482. | —(CH₂SO₂)-4-pyridyl | 7-(morpholin-4-yl-CH₂—) | H |
| 6483. | —(CH₂SO₂)-4-pyridyl | 7-(diethylamino-CH₂—) | H |
| 6484. | —(CH₂SO₂)-4-pyridyl | 7-(1-pyrrolidinyl-CH₂—) | H |
| 6485. | —(CH₂SO₂)-4-pyridyl | 7-(azaperhydroepinyl-CH₂—) | H |
| 6486. | —(CH₂SO₂)-4-pyridyl | 7-[(3,5-dimethylpiperid-1-yl)-CH₂—] | H |
| 6487. | —(CH₂SO₂)-4-pyridyl | 7-[(4-methylpiperid-1-yl-CH₂—] | H |
| 6488. | —(CH₂SO₂)-4-pyridyl | 7-[(3-methylpiperid-1-yl-CH₂—] | H |
| 6489. | —(CH₂SO₂)-4-pyridyl | 7-[(2-methylpiperid-1-yl-CH₂—] | H |
| 6490. | —(CH₂SO₂)-4-pyridyl | 7-(piperid-1-yl-CH₂CH₂—) | H |
| 6491. | —(CH₂SO₂)-4-pyridyl | 7-(1-CH₃-piperazin-4-yl-CH₂CH₂—) | H |
| 6492. | —(CH₂SO₂)-4-pyridyl | 7-(morpholin-4-yl-CH₂CH₂—) | H |
| 6493. | —(CH₂SO₂)-4-pyridyl | 7-(diethylamino-CH₂CH₂—) | H |
| 6494. | —(CH₂SO₂)-4-pyridyl | 7-(1-pyrrolidinyl-CH₂CH₂—) | H |
| 6495. | —(CH₂SO₂)-4-pyridyl | 7-(azaperhydroepinyl-CH₂CH₂—) | H |
| 6496. | —(CH₂SO₂)-4-pyridyl | 7-[(3,5-dimethylpiperid-1-yl)-CH₂CH₂—) | H |
| 6497. | —(CH₂SO₂)-4-pyridyl | 7-[(4-methylpiperid-1-yl-CH₂CH₂—) | H |
| 6498. | —(CH₂SO₂)-4-pyridyl | 7-[(3-methylpiperid-1-yl-CH₂CH₂—)—] | H |
| 6499. | —(CH₂SO₂)-4-pyridyl | 7-[(2-methylpiperid-1-yl-CH₂CH₂—)—] | H |
| 6500. | —(CH₂SO₂)-4-pyridyl | 7-(1-piperidylcarbonyl) | H |
| 6501. | —(CH₂SO₂)-4-pyridyl | 7-[(4-methylpiperazin-1-yl)carbonyl] | H |
| 6502. | —(CH₂SO₂)-4-pyridyl | 7-(morpholin-4-ylcarbonyl) | H |
| 6503. | —(CH₂SO₂)-4-pyridyl | 7-(diethylaminocarbonyl) | H |
| 6504. | —(CH₂SO₂)-4-pyridyl | 7-(1-pyrrolidinylcarbonyl) | H |
| 6505. | —(CH₂SO₂)-4-pyridyl | 7-(azaperhydroepinylcarbonyl) | H |
| 6506. | —(CH₂SO₂)-4-pyridyl | 7-[(3,5-dimethylpiperid-1-yl)carbonyl] | H |
| 6507. | —(CH₂SO₂)-4-pyridyl | 7-[(4-methylpiperid-1-ylcarbonyl) | H |
| 6508. | —(CH₂SO₂)-4-pyridyl | 7-[(3-methylpiperid-1-ylcarbonyl) | H |
| 6509. | —(CH₂SO₂)-4-pyridyl | 7-[(2-methylpiperid-1-ylcarbonyl) | H |
| 6510. | —(CH₂SO₂)-4-pyridyl | 7-[2-(dimethylamino)ethoxy] | H |
| 6511. | —(CH₂SO₂)-4-pyridyl | 7-[2-(methylamino)ethoxy] | H |
| 6512. | —(CH₂SO₂)-4-pyridyl | 7-[((2R)pyrrolidin-2-yl)methoxy] | H |
| 6513. | —(CH₂SO₂)-4-pyridyl | 7-[((2R)-1-methylpyrrolidin-2-yl)methoxy] | H |
| 6514. | —(CH₂SO₂)-4-pyridyl | 7-[2-(piperid-1-yl)ethoxy] | H |
| 6515. | —(CH₂SO₂)-4-pyridyl | 7-[2-(piperazin-1-yl)ethoxy] | H |
| 6516. | —(CH₂SO₂)-4-pyridyl | 7-[2-(morpholin-4-yl)ethoxy] | H |
| 6517. | —(CH₂SO₂)-4-pyridyl | 7-[2-(1-methyl(4-piperidyl))ethoxy] | H |
| 6518. | —(CH₂SO₂)-4-pyridyl | 7-[2-(1-methyl(4-piperidyl))methoxy] | H |
| 6519. | —(CH₂SO₂)-4-pyridyl | 7-(1-methyl(4-piperidyloxy)) | H |
| 6520. | —(CH₂SO₂)-4-pyridyl | 7-(piperid-1-yl-CH₂—) | NH₂ |
| 6521. | —(CH₂SO₂)-4-pyridyl | 7-(1-CH₃-piperazin-4-yl-CH₂—) | NH₂ |
| 6522. | —(CH₂SO₂)-4-pyridyl | 7-(morpholin-4-yl-CH₂— | NH₂ |
| 6523. | —(CH₂SO₂)-4-pyridyl | 7-(diethylamino-CH₂—) | NH₂ |
| 6524. | —(CH₂SO₂)-4-pyridyl | 7-(1-pyrrolidinyl-CH₂—) | NH₂ |
| 6525. | —(CH₂SO₂)-4-pyridyl | 7-(azaperhydroepinyl-CH₂—) | NH₂ |
| 6526. | —(CH₂SO₂)-4-pyridyl | 7-[(3,5-dimethylpiperid-1-yl)-CH₂—] | NH₂ |
| 6527. | —(CH₂SO₂)-4-pyridyl | 7-[(4-methylpiperid-1-yl-CH₂—] | NH₂ |
| 6528. | —(CH₂SO₂)-4-pyridyl | 7-[(3-methylpiperid-1-yl-CH₂—] | NH₂ |
| 6529. | —(CH₂SO₂)-4-pyridyl | 7-[(2-methylpiperid-1-yl-CH₂—] | NH₂ |
| 6530. | —(CH₂SO₂)-4-pyridyl | 7-(piperid-1-yl-CH₂CH₂—) | NH₂ |
| 6531. | —(CH₂SO₂)-4-pyridyl | 7-(1-CH₃-piperazin-4-yl-CH₂CH₂—) | NH₂ |
| 6532. | —(CH₂SO₂)-4-pyridyl | 7-(morpholin-4-yl-CH₂CH₂—) | NH₂ |
| 6533. | —(CH₂SO₂)-4-pyridyl | 7-(diethylamino-CH₂CH₂—) | NH₂ |
| 6534. | —(CH₂SO₂)-4-pyridyl | 7-(1-pyrrolidinyl-CH₂CH₂—) | NH₂ |
| 6535. | —(CH₂SO₂)-4-pyridyl | 7-(azaperhydroepinyl-CH₂CH₂—) | NH₂ |
| 6536. | —(CH₂SO₂)-4-pyridyl | 7-[(3,5-dimethylpiperid-1-yl)-CH₂CH₂—) | NH₂ |
| 6537. | —(CH₂SO₂)-4-pyridyl | 7-[(4-methylpiperid-1-yl-CH₂CH₂—) | NH₂ |
| 6538. | —(CH₂SO₂)-4-pyridyl | 7-[(3-methylpiperid-1-yl-CH₂CH₂—)—] | NH₂ |
| 6539. | —(CH₂SO₂)-4-pyridyl | 7-[(2-methylpiperid-1-yl-CH₂CH₂—)—] | NH₂ |
| 6540. | —(CH₂SO₂)-4-pyridyl | 7-(1-piperidylcarbonyl) | NH₂ |
| 6541. | —(CH₂SO₂)-4-pyridyl | 7-[(4-methylpiperazin-1-yl)carbonyl] | NH₂ |
| 6542. | —(CH₂SO₂)-4-pyridyl | 7-(morpholin-4-ylcarbonyl) | NH₂ |
| 6543. | —(CH₂SO₂)-4-pyridyl | 7-(diethylaminocarbonyl) | NH₂ |
| 6544. | —(CH₂SO₂)-4-pyridyl | 7-(1-pyrrolidinylcarbonyl) | NH₂ |
| 6545. | —(CH₂SO₂)-4-pyridyl | 7-(azaperhydroepinylcarbonyl) | NH₂ |
| 6546. | —(CH₂SO₂)-4-pyridyl | 7-[(3 5-dimethylpiperid-1-yl)carbonyl) | NH₂ |

TABLE 10-continued

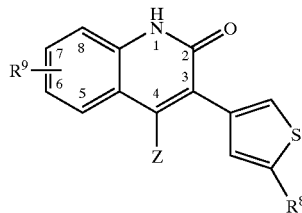

| # | R⁸ | R⁹ | Z |
|---|---|---|---|
| 6547. | —(CH₂SO₂)-4-pyridyl | 7-[(4-methylpiperid-1-yl)carbonyl] | NH₂ |
| 6548. | —(CH₂SO₂)-4-pyridyl | 7-[(3-methylpiperid-1-yl)carbonyl] | NH₂ |
| 6549. | —(CH₂SO₂)-4-pyridyl | 7-[(2-methylpiperid-1-yl)carbonyl] | NH₂ |
| 6550. | —(CH₂SO₂)-4-pyridyl | 7-[2-(dimethylamino)ethoxy] | NH₂ |
| 6551. | —(CH₂SO₂)-4-pyridyl | 7-[2-(methylamino)ethoxy] | NH₂ |
| 6552. | —(CH₂SO₂)-4-pyridyl | 7-[((2R)pyrrolidin-2-yl)methoxy] | NH₂ |
| 6553. | —(CH₂SO₂)-4-pyridyl | 7-[((2R)-1-methylpyrrolidin-2-yl)methoxy] | NH₂ |
| 6554. | —(CH₂SO₂)-4-pyridyl | 7-[2-(piperid-1-yl)ethoxy] | NH₂ |
| 6555. | —(CH₂SO₂)-4-pyridyl | 7-[2-(piperazin-1-yl)ethoxy] | NH₂ |
| 6556. | —(CH₂SO₂)-4-pyridyl | 7-[2-(morpholin-4-yl)ethoxy] | NH₂ |
| 6557. | —(CH₂SO₂)-4-pyridyl | 7-[2-(1-methyl(4-piperidyl))ethoxy] | NH₂ |
| 6558. | —(CH₂SO₂)-4-pyridyl | 7-[2-(1-methyl(4-piperidyl))methoxy] | NH₂ |
| 6559. | —(CH₂SO₂)-4-pyridyl | 7-(1-methyl(4-piperidyloxy)) | NH₂ |
| 6560. | —(NMeSO₂)-phenyl | 7-(piperid-1-yl-CH₂—) | H |
| 6561. | —(NMeSO₂)-phenyl | 7-(1-CH₃-piperazin-4-yl-CH₂—) | H |
| 6562. | —(NMeSO₂)-phenyl | 7-(morpholin-4-yl-CH₂—) | H |
| 6563. | —(NMeSO₂)-phenyl | 7-(diethylamino-CH₂—) | H |
| 6564. | —(NMeSO₂)-phenyl | 7-(1-pyrrolidinyl-CH₂—) | H |
| 6565. | —(NMeSO₂)-phenyl | 7-(azaperhydroepinyl-CH₂—) | H |
| 6566. | —(NMeSO₂)-phenyl | 7-[(3,5-dimethylpiperid-1-yl)-CH₂—] | H |
| 6567. | —(NMeSO₂)-phenyl | 7-[(4-methylpiperid-1-yl)-CH₂—] | H |
| 6568. | —(NMeSO₂)-phenyl | 7-[(3-methylpiperid-1-yl)-CH₂—] | H |
| 6569. | —(NMeSO₂)-phenyl | 7-[(2-methylpiperid-1-yl)-CH₂—] | H |
| 6570. | —(NMeSO₂)-phenyl | 7-(piperid-1-yl-CH₂CH₂—) | H |
| 6571. | —(NMeSO₂)-phenyl | 7-(1-CH₃-piperazin-4-yl-CH₂CH₂—) | H |
| 6572. | —(NMeSO₂)-phenyl | 7-(morpholin-4-yl-CH₂CH₂—) | H |
| 6573. | —(NMeSO₂)-phenyl | 7-(diethylamino-CH₂CH₂—) | H |
| 6574. | —(NMeSO₂)-phenyl | 7-(1-pyrrolidinyl-CH₂CH₂—) | H |
| 6575. | —(NMeSO₂)-phenyl | 7-(azaperhydroepinyl-CH₂CH₂—) | H |
| 6576. | —(NMeSO₂)-phenyl | 7-[(3,5-dimethylpiperid-1-yl)-CH₂CH₂—) | H |
| 6577. | —(NMeSO₂)-phenyl | 7-[(4-methylpiperid-1-yl)-CH₂CH₂—) | H |
| 6578. | —(NMeSO₂)-phenyl | 7-[(3-methylpiperid-1-yl-CH₂CH₂—)—] | H |
| 6579. | —(NMeSO₂)-phenyl | 7-[(2-methylpiperid-1-yl-CH₂CH₂—)—] | H |
| 6580. | —(NMeSO₂)-phenyl | 7-(1-piperidylcarbonyl) | H |
| 6581. | —(NMeSO₂)-phenyl | 7-[(4-methylpiperazin-1-yl)carbonyl] | H |
| 6582. | —(NMeSO₂)-phenyl | 7-(morpholin-4-ylcarbonyl) | H |
| 6583. | —(NMeSO₂)-phenyl | 7-(diethylaminocarbonyl) | H |
| 6584. | —(NMeSO₂)-phenyl | 7-(1-pyrrolidinylcarbonyl) | H |
| 6585. | —(NMeSO₂)-phenyl | 7-(azaperhydroepinylcarbonyl) | H |
| 6586. | —(NMeSO₂)-phenyl | 7-[(3,5-dimethylpiperid-1-yl)carbonyl] | H |
| 6587. | —(NMeSO₂)-phenyl | 7-[(4-methylpiperid-1-yl)carbonyl] | H |
| 6588. | —(NMeSO₂)-phenyl | 7-[(3-methylpiperid-1-yl)carbonyl] | H |
| 6589. | —(NMeSO₂)-phenyl | 7-[(2-methylpiperid-1-yl)carbonyl] | H |
| 6590. | —(NMeSO₂)-phenyl | 7-[2-(dimethylamino)ethoxy] | H |
| 6591. | —(NMeSO₂)-phenyl | 7-[2-(methylamino)ethoxy] | H |
| 6592. | —(NMeSO₂)-phenyl | 7-[((2R)pyrrolidin-2-yl)methoxy] | H |
| 6593. | —(NMeSO₂)-phenyl | 7-[((2R)-1-methylpyrrolidin-2-yl)methoxy] | H |
| 6594. | —(NMeSO₂)-phenyl | 7-[2-(piperid-1-yl)ethoxy] | H |
| 6595. | —(NMeSO₂)-phenyl | 7-[2-(piperazin-1-yl)ethoxy] | H |
| 6596. | —(NMeSO₂)-phenyl | 7-[2-(morpholin-4-yl)ethoxy] | H |
| 6597. | —(NMeSO₂)-phenyl | 7-[2-(1-methyl(4-piperidyl))ethoxy] | H |
| 6598. | —(NMeSO₂)-phenyl | 7-[2-(1-methyl(4-piperidyl))methoxy] | H |
| 6599. | —(NMeSO₂)-phenyl | 7-(1-methyl(4-piperidyloxy)) | H |
| 6600. | —(NMeSO₂)-phenyl | 7-(piperid-1-yl-CH₂—) | NH₂ |
| 6601. | —(NMeSO₂)-phenyl | 7-(1-CH₃-piperazin-4-yl-CH₂—) | NH₂ |
| 6602. | —(NMeSO₂)-phenyl | 7-(morpholin-4-yl-CH₂—) | NH₂ |
| 6603. | —(NMeSO₂)-phenyl | 7-(diethylamino-CH₂—) | NH₂ |
| 6604. | —(NMeSO₂)-phenyl | 7-(1-pyrrolidinyl-CH₂—) | NH₂ |
| 6605. | —(NMeSO₂)-phenyl | 7-(azaperhydroepinyl-CH₂—) | NH₂ |
| 6606. | —(NMeSO₂)-phenyl | 7-[(3,5-dimethylpiperid-1-yl)-CH₂CH₂—] | NH₂ |
| 6607. | —(NMeSO₂)-pnenyl | 7-[(4-methylpiperid-1-yl)-CH₂—] | NH₂ |
| 6608. | —(NMeSO₂)-phenyl | 7-[(3-methylpiperid-1-yl)-CH₂—] | NH₂ |
| 6609. | —(NMeSO₂)-phenyl | 7-[(2-methylpiperid-1-yl)-CH₂—] | NH₂ |
| 6610. | —(NMeSO₂)-phenyl | 7-(piperid-1-yl-CH₂CH₂—) | NH₂ |
| 6611. | —(NMeSO₂)-phenyl | 7-(1-CH₃-piperazin-4-yl-CH₂CH₂—) | NH₂ |

TABLE 10-continued

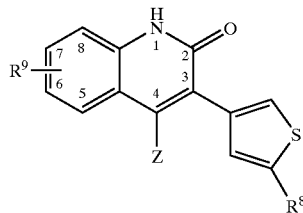

| # | R⁸ | R⁹ | Z |
|---|---|---|---|
| 6612. | —(NMeSO₂)-phenyl | 7-(morpholin-4-yl-CH₂CH₂—) | NH₂ |
| 6613. | —(NMeSO₂)-phenyl | 7-(diethylamino-CH₂CH₂—) | NH₂ |
| 6614. | —(NMeSO₂)-phenyl | 7-(1-pyrrolidinyl-CH₂CH₂—) | NH₂ |
| 6615. | —(NMeSO₂)-phenyl | 7-(azaperhydroepinyl-CH₂CH₂—) | NH₂ |
| 6616. | —(NMeSO₂)-phenyl | 7-[(3,5-dimethylpiperid-1-yl)-CH₂CH₂—) | NH₂ |
| 6617. | —(NMeSO₂)-phenyl | 7-[(4-methylpiperid-1-yl-CH₂CH₂—] | NH₂ |
| 6618. | —(NMeSO₂)-phenyl | 7-[(3-methylpiperid-1-yl-CH₂CH₂—)—] | NH₂ |
| 6619. | —(NMeSO₂)-phenyl | 7-[(2-methylpiperid-1-yl-CH₂CH₂—)—] | NH₂ |
| 6620. | —(NMeSO₂)-phenyl | 7-(1-piperidylcarbonyl) | NH₂ |
| 6621. | —(NMeSO₂)-phenyl | 7-[(4-methylpiperazin-1-yl)carbonyl] | NH₂ |
| 6622. | —(NMeSO₂)-phenyl | 7-(morpholin-4-ylcarbonyl) | NH₂ |
| 6623. | —(NMeSO₂)-phenyl | 7-(diethylaminocarbonyl) | NH₂ |
| 6624. | —(NMeSO₂)-phenyl | 7-(1-pyrrolidinylcarbonyl) | NH₂ |
| 6625. | —(NMeSO₂)-phenyl | 7-(azaperhydroepinylcarbonyl) | NH₂ |
| 6626. | —(NMeSO₂)-phenyl | 7-[(3,5-dimethylpiperid-1-yl)carbonyl) | NH₂ |
| 6627. | —(NMeSO₂)-phenyl | 7-[(4-methylpiperid-1-ylcarbonyl) | NH₂ |
| 6628. | —(NMeSO₂)-phenyl | 7-[(3-methylpiperid-1-ylcarbonyl) | NH₂ |
| 6629. | —(NMeSO₂)-phenyl | 7-[(2-methylpiperid-1-ylcarbonyl) | NH₂ |
| 6630. | —(NMeSO₂)-phenyl | 7-[2-(dimethylamino)ethoxy] | NH₂ |
| 6631. | —(NMeSO₂)-phenyl | 7-[2-(methylamino)ethoxy] | NH₂ |
| 6632. | —(NMeSO₂)-phenyl | 7-[((2R)pyrrolidin-2-yl)methoxy] | NH₂ |
| 6633. | —(NMeSO₂)-phenyl | 7-[((2R)-1-methylpyrrolidin-2-yl)methoxy] | NH₂ |
| 6634. | —(NMeSO₂)-phenyl | 7-[2-(piperid-1-yl)ethoxy] | NH₂ |
| 6635. | —(NMeSO₂)-phenyl | 7-[2-(piperazin-1-yl)ethoxy] | NH₂ |
| 6636. | —(NMeSO₂)-phenyl | 7-[2-(morpholin-4-yl)ethoxy] | NH₂ |
| 6637. | —(NMeSO₂)-phenyl | 7-[2-(1-methyl(4-piperidyl))ethoxy] | NH₂ |
| 6638. | —(NMeSO₂)-phenyl | 7-[2-(1-methyl(4-piperidyl))methoxy) | NH₂ |
| 6639. | —(NMeSO₂)-phenyl | 7-(1-methyl(4-piperidyloxy)) | NH₂ |
| 6640. | —(NMeSO₂)-2-thienyl | 7-(piperid-1-yl-CH₂—) | H |
| 6641. | —(NMeSO₂)-2-thienyl | 7-(1-CH₃-piperazin-4-yl-CH₂—) | H |
| 6642. | —(NMeSO₂)-2-thienyl | 7-(morpholin-4-yl-CH₂—) | H |
| 6643. | —(NMeSO₂)-2-thienyl | 7-(diethylamino-CH₂—) | H |
| 6644. | —(NMeSO₂)-2-thienyl | 7-(1-pyrrolidinyl-CH₂—) | H |
| 6645. | —(NMeSO₂)-2-thienyl | 7-(azaperhydroepinyl-CH₂—) | H |
| 6646. | —(NMeSO₂)-2-thienyl | 7-[(3,5-dimethylpiperid-1-yl)-CH₂—] | H |
| 6647. | —(NMeSO₂)-2-thienyl | 7-[(4-methylpiperid-1-yl-CH₂—] | H |
| 6648. | —(NMeSO₂)-2-thienyl | 7-[(3-methylpiperid-1-yl-CH₂—) | H |
| 6649. | —(NMeSO₂)-2-thienyl | 7-[(2-methylpiperid-1-yl-CH₂—) | H |
| 6650. | —(NMeSO₂)-2-thienyl | 7-(piperid-1-yl-CH₂CH₂—) | H |
| 6651. | —(NMeSO₂)-2-thienyl | 7-(1-CH₃-piperazin-4-yl-CH₂—) | H |
| 6652. | —(NMeSO₂)-2-thienyl | 7-(morpholin-4-yl-CH₂CH₂—) | H |
| 6653. | —(NMeSO₂)-2-thienyl | 7-(diethylamino-CH₂CH₂—) | H |
| 6654. | —(NMeSO₂)-2-thienyl | 7-(1-pyrrolidinyl-CH₂CH₂—) | H |
| 6655. | —(NMeSO₂)-2-thienyl | 7-(azaperhydroepinyl-CH₂CH₂—) | H |
| 6656. | —(NMeSO₂)-2-thienyl | 7-[(3,5-dimethylpiperid-1-yl)-CH₂CH₂—) | H |
| 6657. | —(NMeSO₂)-2-thienyl | 7-[(4-methylpiperid-1-yl-CH₂CH₂—) | H |
| 6658. | —(NMeSO₂)-2-thienyl | 7-[(3-methylpiperid-1-yl-CH₂CH₂—)—] | H |
| 6659. | —(NMeSO₂)-2-thienyl | 7-[(2-methylpiperid-1-yl-CH₂CH₂—)—] | H |
| 6660. | —(NMeSO₂)-2-thienyl | 7-(1-piperidylcarbonyl) | H |
| 6661. | —(NMeSO₂)-2-thienyl | 7-[(4-methylpiperazin-1-yl)carbonyl] | H |
| 6662. | —(NMeSO₂)-2-thienyl | 7-(morpholin-4-ylcarbonyl) | H |
| 6663. | —(NMeSO₂)-2-thienyl | 7-(diethylaminocarbonyl) | H |
| 6664. | —(NMeSO₂)-2-thienyl | 7-(1-pyrrolidinylcarbonyl) | H |
| 6665. | —(NMeSO₂)-2-thienyl | 7-(azaperhydroepinylcarbonyl) | H |
| 6666. | —(NMeSO₂)-2-thienyl | 7-[(3,5-dimethylpiperid-1-yl)carbonyl) | H |
| 6667. | —(NMeSO₂)-2-thienyl | 7-[(4-methylpiperid-1-ylcarbonyl) | H |
| 6668. | —(NMeSO₂)-2-thienyl | 7-[(3-methylpiperid-1-ylcarbonyl) | H |
| 6669. | —(NMeSO₂)-2-thienyl | 7-[(2-methylpiperid-1-ylcarbonyl) | H |
| 6670. | —(NMeSO₂)-2-thienyl | 7-[2-(dimethylamino)ethoxy] | H |
| 6671. | —(NMeSO₂)-2-thienyl | 7-[2-(methylamino)ethoxy] | H |
| 6672. | —(NMeSO₂)-2-thienyl | 7-[((2R)pyrrolidin-2-yl)methoxy] | H |
| 6673. | —(NMeSO₂)-2-thienyl | 7-[((2R)-1-methylpyrrolidin-2-yl)methoxy] | H |
| 6674. | —(NMeSO₂)-2-thienyl | 7-[2-(piperid-1-yl)ethoxy] | H |
| 6675. | —(NMeSO₂)-2-thienyl | 7-[2-(piperazin-1-yl)ethoxy] | H |
| 6676. | —(NMeSO₂)-2-thienyl | 7-[2-(morpholin-4-yl)ethoxy] | H |

TABLE 10-continued

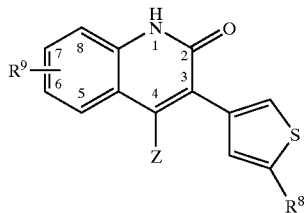

| # | R⁸ | R⁹ | Z |
|---|---|---|---|
| 6677. | —(NMeSO₂)-2-thienyl | 7-[2-(1-methyl(4-piperidyl))ethoxy] | H |
| 6678. | —(NMeSO₂)-2-thienyl | 7-[2-(1-methyl(4-piperidyl))methoxy] | H |
| 6679. | —(NMeSO₂)-2-thienyl | 7-(1-methyl(4-piperidyloxy)) | H |
| 6680. | —(NMeSO₂)-2-thienyl | 7-(piperid-1-yl-CH₂—) | NH₂ |
| 6681. | —(NMeSO₂)-2-thienyl | 7-(1-CH₃-piperazin-4-yl-CH₂—) | NH₂ |
| 6682. | —(NMeSO₂)-2-thienyl | 7-(morpholin-4-yl-CH₂—) | NH₂ |
| 6683. | —(NMeSO₂)-2-thienyl | 7-(diethylamino-CH₂—) | NH₂ |
| 6684. | —(NMeSO₂)-2-thienyl | 7-(1-pyrrolidinyl-CH₂—) | NH₂ |
| 6685. | —(NMeSO₂)-2-thienyl | 7-(azaperhydroepinyl-CH₂—) | NH₂ |
| 6686. | —(NMeSO₂)-2-thienyl | 7-[(3,5-dimethylpiperid-1-yl)-CH₂—] | NH₂ |
| 6687. | —(NMeSO₂)-2-thienyl | 7-[(4-methylpiperid-1-yl-CH₂—1 | NH₂ |
| 6688. | —(NMeSO₂)-2-thienyl | 7-[(3-methylpiperid-1-yl-CH₂—] | NH₂ |
| 6689. | —(NMeSO₂)-2-thienyl | 7-[(2-methylpiperid-1-yl-CH₂—] | NH₂ |
| 6690. | —(NMeSO₂)-2-thienyl | 7-(piperid-1-yl-CH₂CH₂—) | NH₂ |
| 6691. | —(NMeSO₂)-2-thienyl | 7-(1-CH₃-piperazin-4-yl-CH₂CH₂—] | NH₂ |
| 6692. | —(NMeSO₂)-2-thienyl | 7-(morpholin-4-yl-CH₂CH₂—) | NH₂ |
| 6693. | —(NMeSO₂)-2-thienyl | 7-(diethylamino-CH₂CH₂—] | NH₂ |
| 6694. | —(NMeSO₂)-2-thienyl | 7-(1-pyrrolidinyl-CH₂CH₂—) | NH₂ |
| 6695. | —(NMeSO₂)-2-thienyl | 7-(azaperhydroep4nyl-CH₂CH₂—) | NH₂ |
| 6696. | —(NMeSO₂)-2-thienyl | 7-[(3,5-dimethylpiperid-1-yl)-CH₂CH₂—) | NH₂ |
| 6697. | —(NMeSO₂)-2-thienyl | 7-[(4-methylpiperid-1-yl-CH₂CH₂—) | NH₂ |
| 6698. | —(NMeSO₂)-2-thienyl | 7-[(3-methylpiperid-1-yl-CH₂CH₂—)—] | NH₂ |
| 6699. | —(NMeSO₂)-2-thienyl | 7-[(2-methylpiperid-1-yl-CH₂CH₂—)—] | NH₂ |
| 6700. | —(NMeSO₂)-2-thienyl | 7-(1-piperidylcarbonyl) | NH₂ |
| 6701. | —(NMeSO₂)-2-thienyl | 7-[(4-methylpiperazin-1-yl)carbonyl] | NH₂ |
| 6702. | —(NMeSO₂)-2-thienyl | 7-(morpholin-4-ylcarbonyl) | NH₂ |
| 6703. | —(NMeSO₂)-2-thienyl | 7-(diethylaminocarbonyl) | NH₂ |
| 6704. | —(NMeSO₂)-2-thienyl | 7-(1-pyrrolidinylcarbonyl) | NH₂ |
| 6705. | —(NMeSO₂)-2-thienyl | 7-(azaperhydroepinylcarbonyl) | NH₂ |
| 6706. | —(NMeSO₂)-2-thienyl | 7-[(3,5-dimethylpiperid-1-yl)carbonyl] | NH₂ |
| 6707. | —(NMeSO₂)-2-thienyl | 7-[(4-methylpiperid-1-ylcarbonyl) | NH₂ |
| 6708. | —(NMeSO₂)-2-thienyl | 7-[(3-methylpiperid-1-ylcarbonyl) | NH₂ |
| 6709. | —(NMeSO₂)-2-thienyl | 7-[(2-methylpiperid-1-ylcarbonyl) | NH₂ |
| 6710. | —(NMeSO₂)-2-thienyl | 7-[2-(dimethylamino)ethoxy] | NH₂ |
| 6711. | —(NMeSO₂)-2-thienyl | 7-[2-(methylamino)ethoxy] | NH₂ |
| 6712. | —(NMeSO₂)-2-thienyl | 7-[((2R)pyrrolidin-2-yl)methoxy) | NH₂ |
| 6713. | —(NMeSO₂)-2-thienyl | 7-[((2R)-1-methylpyrrolidin-2-yl)methoxy] | NH₂ |
| 6714. | —(NMeSO₂)-2-thienyl | 7-[2-(piperid-1-yl)ethoxy] | NH₂ |
| 6715. | —(NMeSO₂)-2-thienyl | 7-[2-(piperazin-1-yl)ethoxy] | NH₂ |
| 6716. | —(NMeSO₂)-2-thienyl | 7-[2-(morpholin-4-yl)ethoxy] | NH₂ |
| 6717. | —(NMeSO₂)-2-thienyl | 7-[2-(1-methyl(4-piperidyl))ethoxy] | NH₂ |
| 6718. | —(NMeSO₂)-2-thienyl | 7-[2-(1-methyl(4-piperidyl))methoxy] | NH₂ |
| 6719. | —(NMeSO₂)-2-thienyl | 7-(1-methyl(4-piperidyloxy)) | NH₂ |
| 6720. | —(NMeSO₂)-2-pyridyl | 7-(piperid-1-yl-CH₂—) | H |
| 6721. | —(NMeSO₂)-2-pyridyl | 7-(1-CH₃—piperazin-4-yl-CH₂—) | H |
| 6722. | —(NMeSO₂)-2-pyridyl | 7-(morpholin-4-yl-CH₂—) | H |
| 6723. | —(NMeSO₂)-2-pyridyl | 7-(diethylamino-CH₂—) | H |
| 6724. | —(NMeSO₂)-2-pyridyl | 7-(1-pyrrolidinyl-CH₂—) | H |
| 6725. | —(NMeSO₂)-2-pyridyl | 7-(azaperhydroepinyl-CH₂—) | H |
| 6726. | —(NMeSO₂)-2-pyridyl | 7-[(3-5-dimethylpiperid-1-yl)-CH₂—) | H |
| 6727. | —(NMeSO₂)-2-pyridyl | 7-[(4-methylpiperid-1-yl-CH₂—] | H |
| 6728. | —(NMeSO₂)-2-pyridyl | 7-[(3-methylpiperid-1-yl-CH₂—] | H |
| 6729. | —(NMeSO₂)-2-pyridyl | 7-[(2-methylpiperid-1-yl-CH₂—] | H |
| 6730. | —(NMeSO₂)-2-pyridyl | 7-(piperid-1-yl-CH₂CH₂—) | H |
| 6731. | —(NMeSO₂)-2-pyridyl | 7-(1-CH₃-piperazin-4-yl-CH₂CH₂—) | H |
| 6732. | —(NMeSO₂)-2-pyridyl | 7-(morpholin-4-yl-CH₂CH₂—) | H |
| 6733. | —(NMeSO₂)-2-pyridyl | 7-(diethylamino-CH₂CH₂—) | H |
| 6734. | —(NMeSO₂)-2-pyridyl | 7-(1-pyrrolidinyl-CH₂CH₂—) | H |
| 6735. | —(NMeSO₂)-2-pyridyl | 7-(azaperhydroepinyl-CH₂CH₂—) | H |
| 6736. | —(NMeSO₂)-2-pyridyl | 7-[(3,5-dimethylpiperid-1-yl)-CH₂CH₂—) | H |
| 6737. | —(NMeSO₂)-2-pyridyl | 7-[(4-methylpiperid-1-yl-CH₂CH₂—) | H |
| 6738. | —(NMeSO₂)-2-pyridyl | 7-[(3-methylpiperid-1-yl-CH₂CH₂—)—] | H |
| 6739. | —(NMeSO₂)-2-pyridyl | 7-[(2-methylpiperid-1-yl-CH₂CH₂—)—] | H |
| 6740. | —(NMeSO₂)-2-pyridyl | 7-(1-piperidylcarbonyl) | H |
| 6741. | —(NMeSO₂)-2-pyridyl | 7-[(4-methylpiperazim-1-yl)carbonyl] | H |

TABLE 10-continued

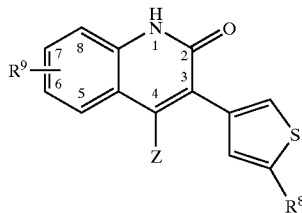

| # | R⁸ | R⁹ | Z |
|---|---|---|---|
| 6742. | —(NMeSO₂)-2-pyridyl | 7-(morpholin-4-ylcarbonyl) | H |
| 6743. | —(NMeSO₂)-2-pyridyl | 7-(diethylaminocarbonyl) | H |
| 6744. | —(NMeSO₂)-2-pyridyl | 7-(1-pyrrolidinylcarbonyl) | H |
| 6745. | —(NMeSO₂)-2-pyridyl | 7-(azaperhydroepinylcarbonyl) | H |
| 6746. | —(NMeSO₂)-2-pyridyl | 7-[(3,5-dimethylpiperid-1-yl)carbonyl] | H |
| 6747. | —(NMeSO₂)-2-pyridyl | 7-[(4-methylpiperid-1-ylcarbonyl) | H |
| 6748. | —(NMeSO₂)-2-pyridyl | 7-[(3-methylpiperid-1-ylcarbonyl) | H |
| 6749. | —(NMeSO₂)-2-pyridyl | 7-[(2-methylpiperid-1-ylcarbonyl) | H |
| 6750. | —(NMeSO₂)-2-pyridyl | 7-[2-(dimethylamino)ethoxy] | H |
| 6751. | —(NMeSO₂)-2-pyridyl | 7-[2-(methylamino)ethoxy] | H |
| 6752. | —(NMeSO₂)-2-pyridyl | 7-[((2R)pyrrolidin-2-yl)methoxy] | H |
| 6753. | —(NMeSO₂)-2-pyridyl | 7-[((2R)-1-methylpyrrolidin-2-yl)methoxy] | H |
| 6754. | —(NMeSO₂)-2-pyridyl | 7-[2-(piperid-1-yl)ethoxy] | H |
| 6755. | —(NMeSO₂)-2-pyridyl | 7-[2-(piperazin-1-yl)ethoxy] | H |
| 6756. | —(NMeSO₂)-2-pyridyl | 7-[2-(morpholin-4-yl)ethoxy] | H |
| 6757. | —(NMeSO₂)-2-pyridyl | 7-[2-(1-methyl(4-piperidyl))ethoxy] | H |
| 6758. | —(NMeSO₂)-2-pyridyl | 7-[2-(1-methyl(4-piperidyl))methoxy] | H |
| 6759. | —(NMeSO₂)-2-pyridyl | 7-(1-methyl(4-piperidyloxy)) | H |
| 6760. | —(NMeSO₂)-2-pyridyl | 7-(piperid-1-yl-CH₂—) | NH₂ |
| 6761. | —(NMeSO₂)-2-pyridyl | 7-(1-CH₃-piperazin-4-yl-CH₂—) | NH₂ |
| 6762. | —(NMeSO₂)-2-pyridyl | 7-(morpholin-4-yl-CH₂—) | NH₂ |
| 6763. | —(NMeSO₂)-2-pyridyl | 7-(diethylamino-CH₂—) | NH₂ |
| 6764. | —(NMeSO₂)-2-pyridyl | 7-(1-pyrrolidinyl-CH₂—) | NH₂ |
| 6765. | —(NMeSO₂)-2-pyridyl | 7-(azaperhydroepinyl-CH₂—) | NH₂ |
| 6766. | —(NMeSO₂)-2-pyridyl | 7-[(3,5-dimethylpiperid-1-yl)-CH₂—] | NH₂ |
| 6767. | —(NMeSO₂)-2-pyridyl | 7-[(4-methylpiperid-1-yl-CH₂—] | NH₂ |
| 6768. | —(NMeSO₂)-2-pyridyl | 7-[(3-methylpiperid-1-yl-CH₂—] | NH₂ |
| 6769. | —(NMeSO₂)-2-pyridyl | 7-[(2-methylpiperid-1-yl-CH₂—) | NH₂ |
| 6770. | —(NMeSO₂)-2-pyridyl | 7-(piperid-1-yl-CH₂CH₂—) | NH₂ |
| 6771. | —(NMeSO₂)-2-pyridyl | 7-(1-CH₃-piperazin-4-yl-CH₂CH₂—) | NH₂ |
| 6772. | —(NMeSO₂)-2-pyridyl | 7-(morpholin-4-yl-CH₂CH₂—) | NH₂ |
| 6773. | —(NMeSO₂)-2-pyridyl | 7-(diethylamino-CH₂—) | NH₂ |
| 6774. | —(NMeSO₂)-2-pyridyl | 7-(1-pyrrolidinyl-CH₂CH₂—) | NH₂ |
| 6775. | —(NMeSO₂)-2-pyridyl | 7-(azaperhydroepinyl-CH₂CH₂—) | NH₂ |
| 6776. | —(NMeSO₂)-2-pyridyl | 7-[(3,5-dimethylpiperid-1-yl)-CH₂CH₂—) | NH₂ |
| 6777. | —(NMeSO₂)-2-pyridyl | 7-[(4-methylpiperid-1-yl-CH₂—] | NH₂ |
| 6778. | —(NMeSO₂)-2-pyridyl | 7-[(3-methylpiperid-1-yl-CH₂CH₂—)—] | NH₂ |
| 6779. | —(NMeSO₂)-2-pyridyl | 7-[(2-methylpiperid-1-yl-CH₂CH₂—)—] | NH₂ |
| 6780. | —(NMeSO₂)-2-pyridyl | 7-(1-piperidylcarbonyl) | NH₂ |
| 6781. | —(NMeSO₂)-2-pyridyl | 7-[(4-methylpiperazin-1-yl)carbonyl] | NH₂ |
| 6782. | —(NMeSO₂)-2-pyridyl | 7-(morpholin-4-ylcarbonyl) | NH₂ |
| 6783. | —(NMeSO₂)-2-pyridyl | 7-(diethylaminocarbonyl) | NH₂ |
| 6784. | —(NMeSO₂)-2-pyridyl | 7-(1-pyrrolidinylcarbonyl) | NH₂ |
| 6785. | —(NMeSO₂)-2-pyridyl | 7-(azaperhydroepinylcarbonyl) | NH₂ |
| 6786. | —(NMeSO₂)-2-pyridyl | 7-[(3,5-dimethylpiperid-1-yl)carbonyl] | NH₂ |
| 6787. | —(NMeSO₂)-2-pyridyl | 7-[(4-methylpiperid-1-ylcarbonyl) | NH₂ |
| 6788. | —(NMeSO₂)-2-pyridyl | 7-[(3-methylpiperid-1-ylcarbonyl) | NH₂ |
| 6789. | —(NMeSO₂)-2-pyridyl | 7-[(2-methylpiperid-1-ylcarbonyl) | NH₂ |
| 6790. | —(NMeSO₂)-2-pyridyl | 7-[2-(dimethylamino)ethoxy] | NH₂ |
| 6791. | —(NMeSO₂)-2-pyridyl | 7-[2-(methylamino)ethoxy] | NH₂ |
| 6792. | —(NMeSO₂)-2-pyridyl | 7-[((2R)pyrrolidin-2-yl)methoxy] | NH₂ |
| 6793. | —(NMeSO₂)-2-pyridyl | 7-[((2R)-1-methylpyrrolidin-2-yl)methoxy] | NH₂ |
| 6794. | —(NMeSO₂)-2-pyridyl | 7-[2-(piperid-1-yl)ethoxy] | NH₂ |
| 6795. | —(NMeSO₂)-2-pyridyl | 7-[2-(piperazin-1-yl)ethoxy] | NH₂ |
| 6796. | —(NMeSO₂)-2-pyridyl | 7-[2-(morpholin-4-yl)ethoxy] | NH₂ |
| 6797. | —(NMeSO₂)-2-pyridyl | 7-[2-(1-methyl(4-piperidyl))ethoxy] | NH₂ |
| 6798. | —(NMeSO₂)-2-pyridyl | 7-[2-(1-methyl(4-piperidyl))methoxy] | NH₂ |
| 6799. | —(NMeSO₂)-2-pyridyl | 7-(1-methyl(4-piperidyloxy)) | NH₂ |
| 6800. | —(NMeSO₂)-3-pyridyl | 7-(piperid-1-yl-CH₂—) | H |
| 6801. | —(NMeSO₂)-3-pyridyl | 7-(1-CH₃-piperazin-4-yl-CH₂—) | H |
| 6802. | —(NMeSO₂)-3-pyridyl | 7-(morpholin-4-yl-CH₂—) | H |
| 6803. | —(NMeSO₂)-3-pyridyl | 7-(diethylamino-CH₂—) | H |
| 6804. | —(NMeSO₂)-3-pyridyl | 7-(2-pyrrolidinyl-CH₂—) | H |
| 6805. | —(NMeSO₂)-3-pyridyl | 7-(azaperhydroepinyl-CH₂—) | H |
| 6806. | —(NMeSO₂)-3-pyridyl | 7-[(3,5-dimethylpiperid-1-yl)-CH₂—] | H |

TABLE 10-continued

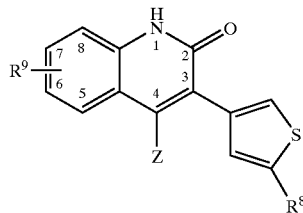

| # | R⁸ | R⁹ | Z |
|---|---|---|---|
| 6807. | —(NMeSO$_2$)-3-pyridyl | 7-[(4-methylpiperid-1-yl-CH$_2$—] | H |
| 6808. | —(NMeSO$_2$)-3-pyridyl | 7-[(3-methylpiperid-1-yl-CH$_2$—] | H |
| 6809. | —(NMeSO$_2$)-3-pyridyl | 7-[(2-methylpiperid-1-yl-CH$_2$—] | H |
| 6810. | —(NMeSO$_2$)-3-pyridyl | 7-(piperid-1-yl-CH$_2$CH$_2$—) | H |
| 6811. | —(NMeSO$_2$)-3-pyridyl | 7-(1-CH$_3$-piperazin-4-yl-CH$_2$CH$_2$—) | H |
| 6812. | —(NMeSO$_2$)-3-pyridyl | 7-(morpholin-4-yl-CH$_2$CH$_2$—) | H |
| 6813. | —(NMeSO$_2$)-3-pyridyl | 7-(diethylamino-CH$_2$CH$_2$—) | H |
| 6814. | —(NMeSO$_2$)-3-pyridyl | 7-(1-pyrrolidinyl-CH$_2$CH$_2$—) | H |
| 6815. | —(NMeSO$_2$)-3-pyridyl | 7-(azaperhydroepinyl-CH$_2$CH$_2$—) | H |
| 6816. | —(NMeSO$_2$)-3-pyridyl | 7-[(3,5-dimethylpiperid-1-yl)-CH$_2$CH$_2$—) | H |
| 6817. | —(NMeSO$_2$)-3-pyridyl | 7-[(4-methylpiperid-1-yl-CH$_2$CH$_2$—) | H |
| 6818. | —(NMeSO$_2$)-3-pyridyl | 7-[(3-methylpiperid-1-yl-CH$_2$CH$_2$—)—] | H |
| 6819. | —(NMeSO$_2$)-3-pyridyl | 7-[(2-methylpiperid-1-yl-CH$_2$CH$_2$—)—] | H |
| 6820. | —(NMeSO$_2$)-3-pyridyl | 7-(1-piperidylcarbonyl) | H |
| 6821. | —(NMeSO$_2$)-3-pyridyl | 7-[(4-methylpiperazin-1-yl)carbonyl] | H |
| 6822. | —(NMeSO$_2$)-3-pyridyl | 7-(morpholin-4-ylcarbonyl) | H |
| 6823. | —(NMeSO$_2$)-3-pyridyl | 7-(diethylaminocarbonyl) | H |
| 6824. | —(NMeSO$_2$)-3-pyridyl | 7-(1-pyrrolidinylcarbonyl) | H |
| 6825. | —(NMeSO$_2$)-3-pyridyl | 7-(azaperhydroepinylcarbonyl) | H |
| 6826. | —(NMeSO$_2$)-3-pyridyl | 7-[(3,5-dimethylpiperid-1-yl)carbonyl) | H |
| 6827. | —(NMeSO$_2$)-3-pyridyl | 7-[(4-methylpiperid-1-ylcarbonyl) | H |
| 6828. | —(NMeSO$_2$)-3-pyridyl | 7-[(3-methylpiperid-1-ylcarbonyl) | H |
| 6829. | —(NMeSO$_2$)-3-pyridyl | 7-[(2-methylpiperid-1-ylcarbonyl) | H |
| 6830. | —(NMeSO$_2$)-3-pyridyl | 7-[2-(dimethylamino)ethoxy] | H |
| 6831. | —(NMeSO$_2$)-3-pyridyl | 7-[2-(methylamino)ethoxy] | H |
| 6832. | —(NMeSO$_2$)-3-pyridyl | 7-[((2R)pyrrolidin-2-yl)methoxy] | H |
| 6833. | —(NMeSO$_2$)-3-pyridyl | 7-[((2R)-1-methylpyrrolidin-2-yl)methoxy] | H |
| 6834. | —(NMeSO$_2$)-3-pyridyl | 7-[2-(piperid-1-yl)ethoxy] | H |
| 6835. | —(NMeSO$_2$)-3-pyridyl | 7-[2-(piperazin-1-yl)ethoxy] | H |
| 6836. | —(NMeSO$_2$)-3-pyridyl | 7-[2-(morpholin-4-yl)ethoxy] | H |
| 6837. | —(NMeSO$_2$)-3-pyridyl | 7-[2-(1-methyl(4-piperidyl))ethoxy] | H |
| 6838. | —(NMeSO$_2$)-3-pyridyl | 7-[2-(1-methyl(4-piperidyl))methoxy] | H |
| 6839. | —(NMeSO$_2$)-3-pyridyl | 7-(1-methyl(4-piperidyloxy)) | H |
| 6840. | —(NMeSO$_2$)-3-pyridyl | 7-(piperid-1-yl-CH$_2$—) | NH$_2$ |
| 6841. | —(NMeSO$_2$)-3-pyridyl | 7-(1-CH$_3$-piperazin-4-yl-CH$_2$—) | NH$_2$ |
| 6842. | —(NMeSO$_2$)-3-pyridyl | 7-(morpholin-4-yl-CH$_2$—) | NH$_2$ |
| 6843. | —(NMeSO$_2$)-3-pyridyl | 7-(diethylamino-CH$_2$—) | NH$_2$ |
| 6844. | —(NMeSO$_2$)-3-pyridyl | 7-(1-pyrrolidinyl-CH$_2$—) | NH$_2$ |
| 6845. | —(NMeSO$_2$)-3-pyridyl | 7-(azaperhydroepinyl-CH$_2$—) | NH$_2$ |
| 6846. | —(NMeSO$_2$)-3-pyridyl | 7-[(3,5-dimethylpiperid-1-yl)-CH$_2$—) | NH$_2$ |
| 6847. | —(NMeSO$_2$)-3-pyridyl | 7-[(4-methylpiperid-1-yl-CH$_2$—] | NH$_2$ |
| 6848. | —(NMeSO$_2$)-3-pyridyl | 7-[(3-methylpiperid-1-yl-CH$_2$—] | NH$_2$ |
| 6849. | —(NMeSO$_2$)-3-pyridyl | 7-[(2-methylpiperid-1-yl-CH$_2$—] | NH$_2$ |
| 6850. | —(NMeSO$_2$)-3-pyridyl | 7-(piperid-1-yl-CH$_2$CH$_2$—) | NH$_2$ |
| 6851. | —(NMeSO$_2$)-3-pyridyl | 7-(1-CH$_3$-piperazin-4-yl-CH$_2$CH$_2$—) | NH$_2$ |
| 6852. | —(NMeSO$_2$)-3-pyridyl | 7-(morpholin-4-yl-CH$_2$CH$_2$—) | NH$_2$ |
| 6853. | —(NMeSO$_2$)-3-pyridyl | 7-(diethylamino-CH$_2$CH$_2$—) | NH$_2$ |
| 6854. | —(NMeSO$_2$)-3-pyridyl | 7-(1-pyrrolidinyl-CH$_2$CH$_2$—) | NH$_2$ |
| 6855. | —(NMeSO$_2$)-3-pyridyl | 7-(azaperhydroepinyl-CH$_2$CH$_2$—) | NH$_2$ |
| 6856. | —(NMeSO$_2$)-3-pyridyl | 7-[(3,5-dimethylpiperid-1-yl)-CH$_2$CH$_2$—) | NH$_2$ |
| 6857. | —(NMeSO$_2$)-3-pyridyl | 7-[(4-methylpiperid-1-yl-CH$_2$CH$_2$—) | NH$_2$ |
| 6858. | —(NMeSO$_2$)-3-pyridyl | 7-[(3-methylpiperid-1-yl-CH$_2$CH$_2$—)—] | NH$_2$ |
| 6859. | —(NMeSO$_2$)-3-pylidyl | 7-[(2-methylpiperid-1-yl-CH$_2$CH$_2$—)—] | NH$_2$ |
| 6860. | —(NMeSO$_2$)-3-pyridyl | 7-(1-piperidylcarbonyl) | NH$_2$ |
| 6861. | —(NMeSO$_2$)-3-pyridyl | 7-[(4-methylpiperazin-1-yl)carbonyl] | NH$_2$ |
| 6862. | —(NMeSO$_2$)-3-pyridyl | 7-(morpholin-4-ylcarbonyl) | NH$_2$ |
| 6863. | —(NMeSO$_2$)-3-pyridyl | 7-(diethyleminocarbonyl) | NH$_2$ |
| 6864. | —(NMeSO$_2$)-3-pyridyl | 7-(1-pyrrolidinylcarbonyl) | NH$_2$ |
| 6865. | —(NMeSO$_2$)-3-pyridyl | 7-(azaperhydroepinylcarbonyl) | NH$_2$ |
| 6866. | —(NMeSO$_2$)-3-pyridyl | 7-[(3,5-dimethylpiperid-1-yl)carbonyl) | NH$_2$ |
| 6867. | —(NMeSO$_2$)-3-pyridyl | 7-[(4-methylpiperid-1-ylcarbonyl) | NH$_2$ |
| 6868. | —(NMeSO$_2$)-3-pyridyl | 7-[(3-methylpiperid-1-ylcarbonyl) | NH$_2$ |
| 6869. | —(NMeSO$_2$)-3-pyridyl | 7-[(2-methylpiperid-1-ylcarbonyl) | NH$_2$ |
| 6870. | —(NMeSO$_2$)-3-pyridyl | 7-[2-(dimethylamino)ethoxy] | NH$_2$ |
| 6871. | —(NMeSO$_2$)-3-pyridyl | 7-[2-(methylamino)ethoxy] | NH$_2$ |

TABLE 10-continued

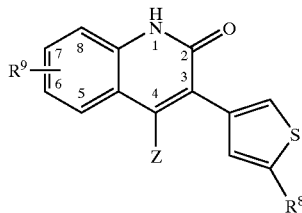

| # | R⁸ | R⁹ | Z |
|---|---|---|---|
| 6872. | —(NMeSO₂)-3-pyridyl | 7-[((2R)pyrrolidin-2-yl)methoxy] | NH₂ |
| 6873. | —(NMeSO₂)-3-pyridyl | 7-[((2R)-1-methylpyrrolidin-2-yl)methoxy] | NH₂ |
| 6874. | —(NMeSO₂)-3-pyridyl | 7-[2-(piperid-1-yl)ethoxy] | NH₂ |
| 6875. | —(NMeSO₂)-3-pyridyl | 7-[2-(piperazin-1-yl)ethoxy] | NH₂ |
| 6876. | —(NMeSO₂)-3-pyridyl | 7-[2-(morpholin-4-yl)ethoxy] | NH₂ |
| 6877. | —(NMeSO₂)-3-pyridyl | 7-[2-(1-methyl(4-piperidyl))ethoxy] | NH₂ |
| 6878. | —(NMeSO₂)-3-pyridyl | 7-[2-(1-methyl(4-piperidyl))methoxy] | NH₂ |
| 6879. | —(NMeSO₂)-3-pyridyl | 7-(1-methyl(4-piperidyloxy)) | NH₂ |
| 6880. | —(NMeSO₂)-4-pyridyl | 7-(piperid-1-yl-CH₂—) | H |
| 6881. | —(NMeSO₂)-4-pyridyl | 7-(1-CH₃-piperazin-4-yl-CH₂—) | H |
| 6882. | —(NMeSO₂)-4-pyridyl | 7-(morpholin-4-yl-CH₂—) | H |
| 6883. | —(NMeSO₂)-4-pyridyl | 7-(diethylamino-CH₂—) | H |
| 6884. | —(NMeSO₂)-4-pyridyl | 7-(1-pyrrolidinyl-CH₂—) | H |
| 6885. | —(NMeSO₂)-4-pyridyl | 7-(azaperhydroepinyl-CH₂—) | H |
| 6886. | —(NMeSO₂)-4-pyridyl | 7-[(3,5-dimethylpiperid-1-yl)-CH₂—] | H |
| 6887. | —(NMeSO₂)-4-pyridyl | 7-[(4-methylpiperid-1-yl-CH₂—] | H |
| 6888. | —(NMeSO₂)-4-pyridyl | 7-[(3-methylpiperid-1-yl-CH₂—] | H |
| 6889. | —(NMeSO₂)-4-pyridyl | 7-[(2-methylpiperid-1-yl-CH₂—] | H |
| 6890. | —(NMeSO₂)-4-pyridyl | 7-(piperid-1-yl-CH₂CH₂—) | H |
| 6891. | —(NMeSO₂)-4-pyridyl | 7-(1-CH₃-piperazin-4-yl-CH₂CH₂—) | H |
| 6892. | —(NMeSO₂)-4-pyridyl | 7-(morpholin-4-yl-CH₂CH₂—) | H |
| 6893. | —(NMeSO₂)-4-pyridyl | 7-(diethylamino-CH₂CH₂—) | H |
| 6894. | —(NMeSO₂)-4-pyridyl | 7-(1-pyrrolidinyl-CH₂CH₂—) | H |
| 6895. | —(NMeSO₂)-4-pyridyl | 7-(azaperhydroepinyl-CH₂CH₂—) | H |
| 6896. | —(NMeSO₂)-4-pyridyl | 7-[(3,5-dimethylpiperid-1-yl)-CH₂CH₂—) | H |
| 6897. | —(NMeSO₂)-4-pyridyl | 7-[(4-methylpiperid-1-yl-CH₂CH₂—) | H |
| 6898. | —(NMeSO₂)-4-pyridyl | 7-[(3-methylpiperid-1-yl-CH₂CH₂—)—] | H |
| 6899. | —(NMeSO₂)-4-pyridyl | 7-[(2-methylpiperid-1-yl-CH₂CH₂—)—] | H |
| 6900. | —(NMeSO₂)-4-pyridyl | 7-(1-piperidylcarbonyl) | H |
| 6901. | —(NMeSO₂)-4-pyridyl | 7-[(4-methylpiperazin-1-yl)carbonyl] | H |
| 6902. | —(NMeSO₂)-4-pyridyl | 7-(morpholin-4-ylcarbonyl) | H |
| 6903. | —(NMeSO₂)-4-pyridyl | 7-(diethylaminocarbonyl) | H |
| 6904. | —(NMeSO₂)-4-pyridyl | 7-(1-pyrrolidinylcarbonyl) | H |
| 6905. | —(NMeSO₂)-4-pyridyl | 7-(azaperhydroepinylcarbonyl) | H |
| 6906. | —(NMeSO₂)-4-pyridyl | 7-[(3,5-dimethylpiperid-1-yl)carbonyl) | H |
| 6907. | —(NMeSO₂)-4-pyridyl | 7-[(4-methylpiperid-1-ylcarbonyl) | H |
| 6908. | —(NMeSO₂)-4-pyridyl | 7-[(3-methylpiperid-1-ylcarbonyl) | H |
| 6909. | —(NMeSO₂)-4-pyridyl | 7-[(2-methylpiperid-1-ylcarbonyl) | H |
| 6910. | —(NMeSO₂)-4-pyridyl | 7-[2-(dimethylamino)ethoxy] | H |
| 6911. | —(NMeSO₂)-4-pyridyl | 7-[2-(methylamino)ethoxy] | H |
| 5912. | —(NMeSO₂)-4-pyridyl | 7-[((2R)pyrrolidin-2-yl)methoxy] | H |
| 6913. | —(NMeSO₂)-4-pyridyl | 7-[((2R)-1-methylpyrrolidin-2-yl)methoxy] | H |
| 6914. | —(NMeSO₂)-4-pyridyl | 7-[2-(piperid-1-yl)ethoxy] | H |
| 6915. | —(NMeSO₂)-4-pyridyl | 7-[2-(piperazin-1-yl)ethoxy] | H |
| 6916. | —(NMeSO₂)-4-pyridyl | 7-[2-(morpholin-4-yl)ethoxy] | H |
| 6917. | —(NMeSO₂)-4-pyridyl | 7-[2-(1-methyl(4-piperidyl))ethoxy] | H |
| 6918. | —(NMeSO₂)-4-pyridyl | 7-[2-(1-methyl(4-piperidyl))methoxy] | H |
| 6919. | —(NMeSO₂)-4-pyridyl | 7-(1-methyl(4-piperidyloxy)) | H |
| 6920. | —(NMeSO₂)-4-pyridyl | 7-(piperid-1-yl-CH₂—) | NH₂ |
| 6921. | —(NMeSO₂)-4-pyridyl | 7-(1-CH₃-piperazin-4-yl-CH₂—) | NH₂ |
| 6922. | —(NMeSO₂)-4-pyridyl | 7-(morpholin-4-yl-CH₂—) | NH₂ |
| 6923. | —(NMeSO₂)-4-pyridyl | 7-(diethylamino-CH₂—) | NH₂ |
| 6924. | —(NMeSO₂)-4-pyridyl | 7-(1-pyrrolidinyl-CH₂—) | NH₂ |
| 6925. | —(NMeSO₂)-4-pyridyl | 7-(azaperhydroepinyl-CH₂—) | NH₂ |
| 6926. | —(NMeSO₂)-4-pyridyl | 7-[(3,5-dimethylpiperid-1-yl)-CH₂—] | NH₂ |
| 6927. | —(NMeSO₂)-4-pyridyl | 7-[(4-methylpiperid-1-yl-CH₂—] | NH₂ |
| 6928. | —(NMeSO₂)-4-pyridyl | 7-[(3-methylpiperid-1-yl-CH₂—] | NH₂ |
| 6929. | —(NMeSO₂)-4-pyridyl | 7-[(2-methylpiperid-1-yl-CH₂—] | NH₂ |
| 6930. | —(NMeSO₂)-4-pyridyl | 7-(piperid-1-yl-CH₂CH₂—) | NH₂ |
| 6931. | —(NMeSO₂)-4-pyridyl | 7-(1-CH₃-piperazin-4-yl-CH₂CH₂—) | NH₂ |
| 6932. | —(NMeSO₂)-4-pyridyl | 7-(morpholin-4-yl-CH₂CH₂—) | NH₂ |
| 6933. | —(NMeSO₂)-4-pyridyl | 7-(diethylamino-CH₂CH₂—) | NH₂ |
| 6934. | —(NMeSO₂)-4-pyridyl | 7-(1-pyrrolidinyl-CH₂CH₂—) | NH₂ |
| 6935. | —(NMeSO₂)-4-pyridyl | 7-(azaperhydroepinyl-CH₂CH₂—) | NH₂ |
| 6936. | —(NMeSO₂)-4-pyridyl | 7-[(3,5-dimethylpiperid-1-yl)-CH₂CH₂—) | NH₂ |

TABLE 10-continued

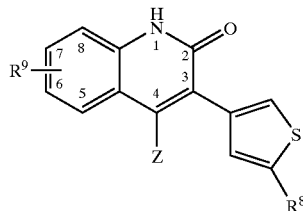

| # | R⁸ | R⁹ | Z |
|---|---|---|---|
| 6937. | —(NMeSO₂)-4-pyridyl | 7-[(4-methylpiperid-1-yl-CH₂CH₂—) | NH₂ |
| 6938. | —(NMeSO₂)-4-pyzidyl | 7-[(3-methylpiperid-1-yl-CH₂CH₂—)—] | NH₂ |
| 6939. | —(NMeSO₂)-4-pyridyl | 7-[(2-methylpiperid-1-yl-CH₂CH₃—)—] | NH₂ |
| 6940. | —(NMeSO₂)-4-pyridyl | 7-(1-piperidylcarbonyl) | NH₂ |
| 6941. | —(NMeSO₂)-4-pyridyl | 7-[(4-methylpiperazin-1-yl)carbonyl] | NH₂ |
| 6942. | —(NMeSO₂)-4-pyridyl | 7-(morpholin-4-ylcarbonyl) | NH₂ |
| 6943. | —(NMeSO₂)-4-pyridyl | 7-(diethylaminocarbonyl) | NH₂ |
| 6944. | —(NMeSO₂)-4-pyridyl | 7-(1-pyrrolidinylcarbonyl) | NH₂ |
| 6945. | —(NMeSO₂)-4-pyridyl | 7-(azaperhydroepinylcarbonyl) | NH₂ |
| 6946. | —(NMeSO₂)-4-pyridyl | 7-[(3,5-dimethylpiperid-1-yl)carbonyl) | NH₂ |
| 6947. | —(NMeSO₂)-4-pyridyl | 7-[(4-methylpiperid-1-ylcarbonyl) | NH₂ |
| 6948. | —(NMeSO₂)-4-pyridyl | 7-[(3-methylpiperid-1-ylcarbonyl) | NH₂ |
| 6949. | —(NMeSO₂)-4-pyridyl | 7-[(2-methylpiperid-1-ylcarbonyl) | NH₂ |
| 6950. | —(NMeSO₂)-4-pyridyl | 7-[2-(dimethylamino)ethoxy] | NH₂ |
| 6951. | —(NMeSO₂)-4-pyridyl | 7-[2-(methylamino)ethoxy] | NH₂ |
| 6952. | —(NMeSO₂)-4-pyridyl | 7-[((2R)pyrrolidin-2-yl)methoxy] | NH₂ |
| 6953. | —(NMeSO₂)-4-pyridyl | 7-[((2R)-1-methylpyrrolidin-2-yl)methoxy] | NH₂ |
| 6954. | —(NMeSO₂)-4-pyridyl | 7-[2-(piperid-1-yl)ethoxy) | NH₂ |
| 6955. | —(NMeSO₂)-4-pyridyl | 7-[2-(piperazin-1-yl)ethoxy] | NH₂ |
| 6956. | —(NMeSO₂)-4-pyridyl | 7-[2-(morpholin-4-yl)ethoxy] | NH₂ |
| 6957. | —(NMeSO₂)-4-pyridyl | 7-[2-(1-methyl(4-piperidyl))ethoxy] | NH₂ |
| 6958. | —(NMeSO₂)-4-pyridyl | 7-[2-(1-methyl(4-piperidyl))methoxy] | NH₂ |
| 6959. | —(NMeSO₂)-4-pyridyl | 7-(1-methyl(4-piperidyloxy)) | NH₂ |

TABLE 11

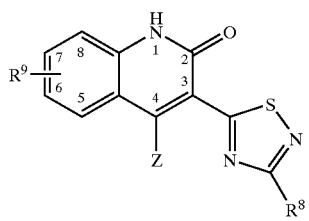

| # | R⁸ | R⁹ | Z |
|---|---|---|---|
| 6960. | 4-pyridyl | 7-(piperid-1-yl-CH₂—) | H |
| 6961. | 4-pyridyl | 7-(1-CH₃-piperazin-4-yl-CH₂—) | H |
| 6962. | 4-pyridyl | 7-(morpholin-4-yl-CH₂—) | H |
| 6963. | 4-pyridyl | 7-(diethylamino-CH₂—) | H |
| 6964. | 4-pyridyl | 7-(1-pyrrolidinyl-CH₂—) | H |
| 6965. | 4-pyridyl | 7-(azaperhydroepinyl-CH₂—) | H |
| 6966. | 4-pyridyl | 7-[(3,5-dimethylpiperid-1-yl)—CH₂—] | H |
| 6967. | 4-pyridyl | 7-[(4-methylpiperid-1-yl-CH₂—] | H |
| 6968. | 4-pyridyl | 7-[(3-methylpiperid-1-yl-CH₂—] | H |
| 6969. | 4-pyridyl | 7-[(2-methylpiperid-1-yl-CH₂—] | H |
| 6970. | 4-pyridyl | 7-(piperid-1-yl-CH₂CH₂—) | H |
| 6971. | 4-pyridyl | 7-(1-CH₃-piperazin-4-yl-CH₂CH₂—) | H |
| 6972. | 4-pyridyl | 7-(morpholin-4-yl-CH₂CH₂—) | H |
| 6973. | 4-pyridyl | 7-(diethylamino-CH₂CH₂—) | H |
| 6974. | 4-pyridyl | 7-(1-pyrrolidinyl-CH₂CH₂—) | H |
| 6975. | 4-pyridyl | 7-(azaperhydroepinyl-CH₂CH₂—) | H |
| 6976. | 4-pyridyl | 7-[(3,5-dimethylpiperid-1-yl)—CH₂CH₂—) | H |
| 6977. | 4-pyridyl | 7-[(4-methylpiperid-1-yl-CH₂CH₂—) | H |
| 6978. | 4-pyridyl | 7-[(3-methylpiperid-1-yl-CH₂CH₂—)—] | H |
| 6979. | 4-pyridyl | 7-[(2-methylpiperid-1-yl-CH₂CH₂—)—] | H |
| 6980. | 4-pyridyl | 7-(1-piperidylcarbonyl) | H |
| 6981. | 4-pyridyl | 7-[(4-methylpiperazin-1-yl)carbonyl] | H |
| 6982. | 4-pyridyl | 7-(morpholin-4-ylcarbonyl) | H |
| 6983. | 4-pyridyl | 7-(diethylaminocarbonyl) | H |

TABLE 11-continued

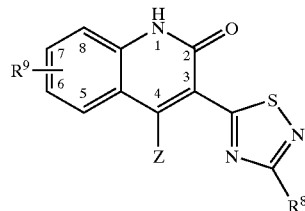

| # | R⁸ | R⁹ | Z |
|---|---|---|---|
| 6984. | 4-pyridyl | 7-(1-pyrrolidinylcarbonyl) | H |
| 6985. | 4-pyridyl | 7-(azaperhydroepinylcarbonyl) | H |
| 6986. | 4-pyridyl | 7-[(3,5-dimethylpiperid-1-yl)carbonyl] | H |
| 6987. | 4-pyridyl | 7-[(4-methylpiperid-1-ylcarbonyl] | H |
| 6988. | 4-pyridyl | 7-[(3-methylpiperid-1-ylcarbonyl] | H |
| 6989. | 4-pyridyl | 7-[(2-methylpiperid-1-ylcarbonyl] | H |
| 6990. | 4-pyridyl | 7-[2-(dimethylamino)ethoxy] | H |
| 6991. | 4-pyridyl | 7-[2-(methylamino)ethoxy] | H |
| 6992. | 4-pyridyl | 7-[((2R)pyrrolidin-2-yl)methoxy] | H |
| 6993. | 4-pyridyl | 7-[((2R)-1-methylpyrrolidin-2-yl)methoxy] | H |
| 6994. | 4-pyridyl | 7-[2-(piperid-1-yl)ethoxy] | H |
| 6995. | 4-pyridyl | 7-[2-(piperazin-1-yl)ethoxy] | H |
| 6996. | 4-pyridyl | 7-[2-(morpholin-4-yl)ethoxy] | H |
| 6997. | 4-pyridyl | 7-[2-(1-methyl(4-piperidyl))ethoxy] | H |
| 6998. | 4-pyridyl | 7-[2-(1-methyl(4-piperidyl))methoxy] | H |
| 6999. | 4-pyridyl | 7-(1-methyl(4-piperidyloxy)) | H |
| 7000. | 4-pyridyl | 7-(piperid-1-yl-CH₂—) | NH₂ |
| 7001. | 4-pyridyl | 7-(1-CH₃-piperazin-4-yl-CH₂—) | NH₂ |
| 7002. | 4-pyridyl | 7-(morpholin-4-yl-CH₂—) | NH₂ |
| 7003. | 4-pyridyl | 7-(diethylamino-CH₂—) | NH₂ |
| 7004. | 4-pyridyl | 7-(1-pyrrolidinyl-CH₂—) | NH₂ |
| 7005. | 4-pyridyl | 7-(azaperhydroepinyl-CH₂—) | NH₂ |
| 7006. | 4-pyridyl | 7-[(3,5-dimethylpiperid-1-yl)—CH₂—] | NH₂ |
| 7007. | 4-pyridyl | 7-[(4-methylpiperid-1-yl-CH₂—] | NH₂ |
| 7008. | 4-pyridyl | 7-[(3-methylpiperid-1-yl-CH₂—] | NH₂ |
| 7009. | 4-pyridyl | 7-[(2-methylpiperid-1-yl-CH₂—] | NH₂ |
| 7010. | 4-pyridyl | 7-(piperid-1-yl-CH₂CH₂—) | NH₂ |
| 7011. | 4-pyridyl | 7-(1-CH₃-piperazin-4-yl-CH₂CH₂—) | NH₂ |
| 7012. | 4-pyridyl | 7-(morpholin-4-yl-CH₂CH₂—) | NH₂ |
| 7013. | 4-pyridyl | 7-(diethylamino-CH₂CH₂—) | NH₂ |
| 7014. | 4-pyridyl | 7-(1-pyrrolidinyl-CH₂CH₂—) | NH₂ |
| 7015. | 4-pyridyl | 7-(azaperhydroepinyl-CH₂CH₂—) | NH₂ |
| 7016. | 4-pyridyl | 7-[(3,5-dimethylpiperid-1-yl)—CH₂CH₂—) | NH₂ |
| 7017. | 4-pyridyl | 7-[(4-methylpiperid-1-yl-CH₂CH₂—) | NH₂ |
| 7018. | 4-pyridyl | 7-[(3-methylpiperid-1-yl-CH₂CH₂—)—] | NH₂ |
| 7019. | 4-pyridyl | 7-[(2-methylpiperid-1-yl-CH₂CH₃—)—] | NH₂ |
| 7020. | 4-pyridyl | 7-(1-piperidylcarbonyl) | NH₂ |
| 7021. | 4-pyridyl | 7-[(4-methylpiperazin-1-yl)carbonyl] | NH₂ |
| 7022. | 4-pyridyl | 7-(morpholin-4-ylcarbonyl) | NH₂ |
| 7023. | 4-pyridyl | 7-(diethylaminocarbonyl) | NH₂ |
| 7024. | 4-pyridyl | 7-(1-pyrrolidinylcarbonyl) | NH₂ |
| 7025. | 4-pyridyl | 7-(azaperhydroepinylcarbonyl) | NH₂ |
| 7026. | 4-pyridyl | 7-[(3,5-dimethylpiperid-1-yl)carbonyl] | NH₂ |
| 7027. | 4-pyredyl | 7-[(4-methylpiperid-1-ylcarbonyl) | NH₂ |
| 7028. | 4-pyridyl | 7-[(3-methylpiperid-1-ylcarbonyl] | NH₂ |
| 7029. | 4-pyridyl | 7-[(2-methylpiperid-1-ylcarbonyl] | NH₂ |
| 7030. | 4-pyridyl | 7-[2-(dimethylamino)ethoxy] | NH₂ |
| 7031. | 4-pyridyl | 7-[2-(methylamino)ethoxy] | NH₂ |
| 7032. | 4-pyridyl | 7-[((2R)pyrrolidin-2-yl)methoxy] | NH₂ |
| 7033. | 4-pyridyl | 7-[((2R)-1-methylpyrrolidin-2-yl)methoxy] | NH₂ |
| 7034. | 4-pyridyl | 7-[2-(piperid-1-yl)ethoxy] | NH₂ |
| 7035. | 4-pyridyl | 7-[2-(piperazin-1-yl)ethoxy] | NH₂ |
| 7036. | 4-pyridyl | 7-[2-(morpholin-4-yl)ethoxy] | NH₂ |
| 7037. | 4-pyridyl | 7-[2-(1-methyl(4-piperidyl))ethoxy] | NH₂ |
| 7038. | 4-pyridyl | 7-[2-(1-methyl(4-piperidyl))methoxy] | NH₂ |
| 7039. | 4-pyridyl | 7-(1-methyl(4-piperidyloxy)) | NH₂ |
| 7040. | —(CH₂SO₂)-phenyl | 7-(piperid-1-yl-CH₂—) | H |
| 7041. | —(CH₂SO₂)-phenyl | 7-(1-CH₃-piperazin-4-yl-CH₂—) | H |
| 7042. | —(CH₂SO₂)-phenyl | 7-(morpholin-4-yl-CH₂—) | H |
| 7043. | —(CH₂SO₂)-phenyl | 7-(diethylamino-CH₂—) | H |
| 7044. | —(CH₂SO₂)-phenyl | 7-(1-pyrrolidinyl-CH₂—) | H |
| 7045. | —(CH₂SO₂)-phenyl | 7-(azaperhydroepinyl-CH₂—) | H |
| 7046. | —(CH₂SO₂)-phenyl | 7-[(3,5-dimethylpiperid-1-yl)—CH₂—] | H |
| 7047. | —(CH₂SO₂)-phenyl | 7-[(4-methylpiperid-1-yl-CH₂—] | H |
| 7048. | —(CH₂SO₂)-phenyl | 7-[(3-methylpiperid-1-yl-CH₂—] | H |

TABLE 11-continued

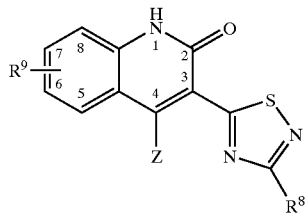

| # | R⁸ | R⁹ | Z |
|---|---|---|---|
| 7049. | —(CH₂SO₂)-phenyl | 7-[(2-methylpiperid-1-yl-CH₂—] | H |
| 7050. | —(CH₂SO₂)-phenyl | 7-(piperid-1-yl-CH₂CH₂—) | H |
| 7051. | —(CH₂SO₂)-phenyl | 7-(1-CH₃-piperazin-4-yl-CH₂CH₂—) | H |
| 7052. | —(CH₂SO₂)-phenyl | 7-(morpholin-4-yl-CH₂CH₂—) | H |
| 7053. | —(CH₂SO₂)-phenyl | 7-(diethylamino-CH₂CH₂—) | H |
| 7054. | —(CH₂SO₂)-phenyl | 7-(1-pyrrolidinyl-CH₂CH₂—) | H |
| 7055. | —(CH₂SO₂)-phenyl | 7-(azaperhydroepinyl-CH₂CH₂—) | H |
| 7056. | —(CH₂SO₂)-phenyl | 7-[(3,5-dimethylpiperid-1-yl)—CH₂CH₂—) | H |
| 7057. | —(CH₂SO₂)-phenyl | 7-[(4-methylpiperid-1-yl-CH₂CH₂—) | H |
| 7058. | —(CH₂SO₂)-phenyl | 7-[(3-methylpiperid-1-yl-CH₂CH₂—)—] | H |
| 7059. | —(CH₂SO₂)-phenyl | 7-[(2-methylpiperid-1-yl-CH₂CH₂—)—] | H |
| 7060. | —(CH₂SO₂)-phenyl | 7-(1-piperidylcarbonyl) | H |
| 7061. | —(CH₂SO₂)-phenyl | 7-[(4-methylpiperazin-1-yl)carbonyl] | H |
| 7062. | —(CH₂SO₂)-phenyl | 7-(morpholin-4-ylcarbonyl) | H |
| 7063. | —(CH₂SO₂)-phenyl | 7-(diethylaminocarbonyl) | H |
| 7064. | —(CH₂SO₂)-phenyl | 7-(1-pyrrolidinylcarbonyl) | H |
| 7065. | —(CH₂SO₂)-phenyl | 7-(azaperhydroepinylcarbonyl) | H |
| 7066. | —(CH₂SO₂)-phenyl | 7-[(3,5-dimethylpiperid-1-yl)carbonyl) | H |
| 7067. | —(CH₂SO₂)-phenyl | 7-[(4-methylpiperid-1-ylcarbonyl) | H |
| 7068. | —(CH₂SO₂)-phenyl | 7-[(3-methylpiperid-1-ylcarbonyl) | H |
| 7069. | —(CH₂SO₂)-phenyl | 7-[(2-methylpiperid-1-ylcarbonyl) | H |
| 7070. | —(CH₂SO₂)-phenyl | 7-[2-(dimethylanino)ethoxy] | H |
| 7071. | —(CH₂SO₂)-phenyl | 7-[2-(methylamino)ethoxy] | H |
| 7072. | —(CH₂SO₂)-phenyl | 7-[((2R)pyrrolidin-2-yl)methoxy] | H |
| 7073. | —(CH₂SO₂)-phenyl | 7-[((2R)-1-methylpyrrolidin-2-yl)methoxy] | H |
| 7074. | —(CH₂SO₂)-phenyl | 7-[2-(piperid-1-yl)ethoxy] | H |
| 7075. | —(CH₂SO₂)-phenyl | 7-(2-(piperazin-1-yl)ethoxy] | H |
| 7076. | —(CH₂SO₂)-phenyl | 7-(2-(morpholin-4-yl)ethoxy] | H |
| 7077. | —(CH₂SO₂)-phenyl | 7-[2-(1-methyl(4-piperidyl))ethoxy] | H |
| 7078. | —(CH₂SO₂)-phenyl | 7-[2-(1-methyl(4-piperidyl))methoxy] | H |
| 7079. | —(CH₂SO₂)-phenyl | 7-(1-methyl(4-piperidyloxy)) | H |
| 7080. | —(CH₂SO₂)-phenyl | 7-(piperid-1-yl-CH₂—) | NH₂ |
| 7081. | —(CH₂SO₂)-phenyl | 7-(1-CH₃-piperazin-4-yl-CH₂—) | NH₂ |
| 7082. | —(CH₂SO₂)-phenyl | 7-(morpholin-4-yl-CH₂—) | NH₂ |
| 7083. | —(CH₂SO₂)-phenyl | 7-(diethylamino-CH₂—) | NH₂ |
| 7084. | —(CH₂SO₂)-phenyl | 7-(1-pyrrolidinyl-CH₂—) | NH₂ |
| 7085. | —(CH₂SO₂)-phenyl | 7-(azaperhydroepinyl-CH₂—) | NH₂ |
| 7086. | —(CH₂SO₂)-phenyl | 7-[(3,5-dimethylpiperid-1-yl)—CH₂—] | NH₂ |
| 7087. | —(CH₂SO₂)-phenyl | 7-[(4-methylpiperid-1-yl-CH₂—] | NH₂ |
| 7088. | —(CH₂SO₂)-phenyl | 7-[(3-methylpiperid-1-yl-CH₂—] | NH₂ |
| 7089. | —(CH₂SO₂)-phenyl | 7-[(2-methylpiperid-1-yl-CH₂—] | NH₂ |
| 7090. | —(CH₂SO₂)-phenyl | 7-(piperid-1-yl-CH₂CH₂—) | NH₂ |
| 7091. | —(CH₂SO₂)-phenyl | 7-(1-CH₃-piperazin-4-yl-CH₂CH₂—) | NH₂ |
| 7092. | —(CH₂SO₂)-phenyl | 7-(morpholin-4-yl-CH₂CH₂—) | NH₂ |
| 7093. | —(CH₂SO₂)-phenyl | 7-(diethylamino-CH₂CH₂—) | NH₂ |
| 7094. | —(CH₂SO₂)-phenyl | 7-(1-pyrrolidinyl-CH₂CH₂—) | NH₂ |
| 7095. | —(CH₂SO₂)-phenyl | 7-(azaperhydroepinyl-CH₂CH₂—) | NH₂ |
| 7096. | —(CH₂SO₂)-phenyl | 7-[(3,5-dimethylpiperid-1-yl)—CH₂CH₂—) | NH₂ |
| 7097. | —(CH₂SO₂)-phenyl | 7-[(4-methylpiperid-1-yl-CH₂CH₂—) | NH₂ |
| 7098. | —(CH₂SO₂)-phenyl | 7-[(3-methylpiperid-1-yl-CH₂CH₂—)—] | NH₂ |
| 7099. | —(CH₂SO₂)-phenyl | 7-[(2-methylpiperid-1-yl-CH₂CH₂—)—] | NH₂ |
| 7100. | —(CH₂SO₂)-phenyl | 7-(1-piperidylcarbonyl) | NH₂ |
| 7101. | —(CH₂SO₂)-phenyl | 7-[(4-methylpiperazin-1-yl)carbonyl] | NH₂ |
| 7102. | —(CH₂SO₂)-phenyl | 7-(morpholin-4-ylcarbonyl) | NH₂ |
| 7103. | —(CH₂SO₂)-phenyl | 7-(diethylaminocarbonyl) | NH₂ |
| 7104. | —(CH₂SO₂)-phenyl | 7-(1-pyrrolidinylcarbonyl) | NH₂ |
| 7105. | —(CH₂SO₂)-phenyl | 7-(azaperhydroepinylcarbonyl) | NH₂ |
| 7106. | —(CH₂SO₂)-phenyl | 7-[(3,5-dimethylpiperid-1-yl)carbonyl) | NH₂ |
| 7107. | —(CH₂SO₂)-phenyl | 7-[(4-methylpiperid-1-ylcarbonyl) | NH₂ |
| 7108. | —(CH₂SO₂)-phenyl | 7-[(3-methylpiperid-1-ylcarbonyl) | NH₂ |
| 7109. | —(CH₂SO₂)-phenyl | 7-[(2-methylpiperid-1-ylcarbonyl) | NH₂ |
| 7110. | —(CH₂SO₂)-phenyl | 7-[2-(dimethylamino)ethoxy] | NH₂ |
| 7111. | —(CH₂SO₂)-phenyl | 7-[2-(methylamino)ethoxy] | NH₂ |
| 7112. | —(CH₂SO₂)-phenyl | 7-[((2R)pyrrolidin-2-yl)methoxy] | NH₂ |
| 7113. | —(CH₂SO₂)-phenyl | 7-[((2R)-1-methylpyrrolidin-2-yl)methoxy] | NH₂ |

TABLE 11-continued

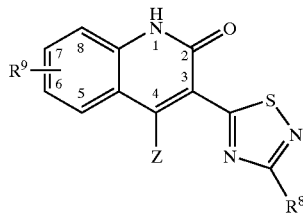

| # | R[8] | R[9] | Z |
|---|---|---|---|
| 7114. | —(CH$_2$SO$_2$)-phenyl | 7-[2-(piperid-1-yl)ethoxy] | NH$_2$ |
| 7115. | —(CH$_2$SO$_2$)-phenyl | 7-(2-(piperazin-1-yl)ethoxy] | NH$_2$ |
| 7116. | —(CH$_2$SO$_2$)-phenyl | 7-[2-(morpholin-4-yl)ethoxy] | NH$_2$ |
| 7117. | —(CH$_2$SO$_2$)-phenyl | 7-[2-(1-methyl(4-piperidyl))ethoxy] | NH$_2$ |
| 7118. | —(CH$_2$SO$_2$)-phenyl | 7-[2-(1-methyl(4-piperidyl))methoxy] | NH$_2$ |
| 7119. | —(CH$_2$SO$_2$)-phenyl | 7-(1-methyl(4-piperidyloxy)) | NH$_2$ |
| 7120. | —(CH$_2$SO$_2$)-2-thienyl | 7-(piperid-1-yl-CH$_2$—) | H |
| 7121. | —(CH$_2$SO$_2$)-2-thienyl | 7-(1-CH$_3$-piperazin-4-yl-CH$_2$—) | H |
| 7122. | —(CH$_2$SO$_2$)-2-thienyl | 7-(morpholin-4-yl-CH$_2$—) | H |
| 7123. | —(CH$_2$SO$_2$)-2-thienyl | 7-(diethylamino-CH$_2$—) | H |
| 7124. | —(CH$_2$SO$_2$)-2-thienyl | 7-(1-pyrrolidinyl-CH$_2$—) | H |
| 7125. | —(CH$_2$SO$_2$)-2-thienyl | 7-(azaperhydroepinyl-CH$_2$—) | H |
| 7126. | —(CH$_2$SO$_2$)-2-thienyl | 7-[(3,5-dimethylpiperid-1-yl)—CH$_2$—] | H |
| 7127. | —(CH$_2$SO$_2$)-2-thienyl | 7-[(4-methylpiperid-1-yl-CH$_2$—] | H |
| 7128. | —(CH$_2$SO$_2$)-2-thienyl | 7-[(3-methylpiperid-1-yl-CH$_2$—] | H |
| 7129. | —(CH$_2$SO$_2$)-2-thienyl | 7-[(2-methylpiperid-1-yl-CH$_2$—] | H |
| 7130. | —(CH$_2$SO$_2$)-2-thienyl | 7-(piperid-1-yl-CH$_2$CH$_2$—) | H |
| 7131. | —(CH$_2$SO$_2$)-2-thienyl | 7-(1-CH$_3$-piperazin-4-yl-CH$_2$CH$_2$—) | H |
| 7132. | —(CH$_2$SO$_2$)-2-thienyl | 7-(morpholin-4-yl-CH$_2$CH$_2$—) | H |
| 7133. | —(CH$_2$SO$_2$)-2-thienyl | 7-(diethylamino-CH$_2$CH$_2$—) | H |
| 7134. | —(CH$_2$SO$_2$)-2-thienyl | 7-(1-pyrrolidinyl-CH$_2$CH$_2$—) | H |
| 7135. | —(CH$_2$SO$_2$)-2-thienyl | 7-(azaperhydroepinyl-CH$_2$CH$_2$—) | H |
| 7136. | —(CH$_2$SO$_2$)-2-thienyl | 7-[(3,5-dimethylpiperid-1-yl)—CH$_2$CH$_2$—) | H |
| 7137. | —(CH$_2$SO$_2$)-2-thienyl | 7-[(4-methylpiperid-1-yl-CH$_2$CH$_2$—) | H |
| 7138. | —(CH$_2$SO$_2$)-2-thienyl | 7-[(3-methylpiperid-1-yl-CH$_2$CH$_2$—)—] | H |
| 7139. | —(CH$_2$SO$_2$)-2-thienyl | 7-[(2-methylpiperid-1-yl-CH$_2$CH$_2$—)—] | H |
| 7140. | —(CH$_2$SO$_2$)-2-thienyl | 7-(1-piperidylcarbonyl) | H |
| 7141. | —(CH$_2$SO$_2$)-2-thienyl | 7-[(4-methylpiperazin-1-yl)carbonyl] | H |
| 7142. | —(CH$_2$SO$_2$)-2-thienyl | 7-(morpholin-4-ylcarbonyl) | H |
| 7143. | —(CH$_2$SO$_2$)-2-thienyl | 7-(diethylaminocarbonyl) | H |
| 7144. | —(CH$_2$SO$_2$)-2-thienyl | 7-(1-pyrrolidinylcarbonyl) | H |
| 7145. | —(CH$_2$SO$_2$)-2-thienyl | 7-(azaperhydroepinylcarbonyl) | H |
| 7146. | —(CH$_2$SO$_2$)-2-thienyl | 7-[(3,5-dimethylpiperid-1-yl)carbonyl) | H |
| 7147. | —(CH$_2$SO$_2$)-2-thienyl | 7-[(4-methylpiperid-1-ylcarbonyl) | H |
| 7148. | —(CH$_2$SO$_2$)-2-thienyl | 7-[(3-methylpiperid-1-ylcarbonyl) | H |
| 7149. | —(CH$_2$SO$_2$)-2-thienyl | 7-[(2-methylpiperid-1-ylcarbonyl) | H |
| 7150. | —(CH$_2$SO$_2$)-2-thienyl | 7-[2-(dimethylamino)ethoxy] | H |
| 7151. | —(CH$_2$SO$_2$)-2-thienyl | 7-[2-(methylamino)ethoxy] | H |
| 7152. | —(CH$_2$SO$_2$)-2-thienyl | 7-[((2R)pyrrolidin-2-yl)methoxy] | H |
| 7153. | —(CH$_2$SO$_2$)-2-thienyl | 7-[((2R)-1-methylpyrrolidin-2-yl)methoxy] | H |
| 7154. | —(CH$_2$SO$_2$)-2-thienyl | 7-[2-(piperid-1-yl)ethoxy] | H |
| 7155. | —(CH$_2$SO$_2$)-2-thienyl | 7-[2-(piperazin-1-yl)ethoxy] | H |
| 7156. | —(CH$_2$SO$_2$)-2-thienyl | 7-[2-(morpholin-4-yl)ethoxy] | H |
| 7157. | —(CH$_2$SO$_2$)-2-thienyl | 7-[2-(1-methyl(4-piperidyl))ethoxy] | H |
| 7158. | —(CH$_2$SO$_2$)-2-thienyl | 7-[2-(1-methyl(4-piperidyl))methoxy] | H |
| 7159. | —(CH$_2$SO$_2$)-2-thienyl | 7-(1-methyl(4-piperidyloxy)) | H |
| 7160. | —(CH$_2$SO$_2$)-2-thienyl | 7-(piperid-1-yl-CH$_2$—) | NH$_2$ |
| 7161. | —(CH$_2$SO$_2$)-2-thienyl | 7-(1-CH$_3$-piperazin-4-yl-CH$_2$—) | NH$_2$ |
| 7162. | —(CH$_2$SO$_2$)-2-thienyl | 7-(morpholin-4-yl-CH$_2$—) | NH$_2$ |
| 7163. | —(CH$_2$SO$_2$)-2-thienyl | 7-(diethylamino-CH$_2$—) | NH$_2$ |
| 7164. | —(CH$_2$SO$_2$)-2-thienyl | 7-(1-pyrrolidinyl-CH$_2$—) | NH$_2$ |
| 7165. | —(CH$_2$SO$_2$)-2-thienyl | 7-(azaperhydroepinyl-CH$_2$—) | NH$_2$ |
| 7166. | —(CH$_2$SO$_2$)-2-thienyl | 7-[(3,5-dimethylpiperid-1-yl)—CH$_2$—) | NH$_2$ |
| 7167. | —(CH$_2$SO$_2$)-2-thienyl | 7-[(4-methylpiperid-1-yl-CH$_2$—] | NH$_2$ |
| 7168. | —(CH$_2$SO$_2$)-2-thienyl | 7-[(3-methylpiperid-1-yl-CH$_2$—] | NH$_2$ |
| 7169. | —(CH$_2$SO$_2$)-2-thienyl | 7-[(2-methylpiperid-1-yl-CH$_2$—] | NH$_2$ |
| 7170. | —(CH$_2$SO$_2$)-2-thienyl | 7-(piperid-1-yl-CH$_2$CH$_2$—) | NH$_2$ |
| 7171. | —(CH$_2$SO$_2$)-2-thienyl | 7-(1-CH$_3$-piperazin-4-yl-CH$_2$CH$_2$—) | NH$_2$ |
| 7172. | —(CH$_2$SO$_2$)-2-thienyl | 7-(morpholin-4-yl-CH$_2$CH$_2$—) | NH$_2$ |
| 7173. | —(CH$_2$SO$_2$)-2-thienyl | 7-(diethylamino-CH$_2$CH$_2$—) | NH$_2$ |
| 7174. | —(CH$_2$SO$_2$)-2-thienyl | 7-(1-pyrrolidinyl-CH$_2$CH$_2$—) | NH$_2$ |
| 7175. | —(CH$_2$SO$_2$)-2-thienyl | 7-(azaperhydroepinyl-CH$_2$CH$_2$—) | NH$_2$ |
| 7176. | —(CH$_2$SO$_2$)-2-thienyl | 7-[(3,5-dimethylpiperid-1-yl)—CH$_2$CH$_2$—) | NH$_2$ |
| 7177. | —(CH$_2$SO$_2$)-2-thienyl | 7-[(4-methylpiperid-1-yl-CH$_2$CH$_2$—) | NH$_2$ |
| 7178. | —(CH$_2$SO$_2$)-2-thienyl | 7-[(3-methylpiperid-1-yl-CH$_2$CH$_2$—)—] | NH$_2$ |

TABLE 11-continued

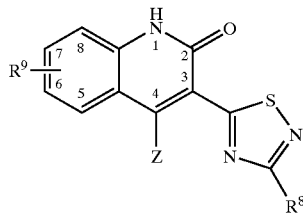

| # | R⁸ | R⁹ | Z |
|---|---|---|---|
| 7179. | —(CH₂SO₂)-2-thienyl | 7-[(2-methylpiperid-1-yl-CH₂CH₂—)—] | NH₂ |
| 7180. | —(CH₂SO₂)-2-thienyl | 7-(1-piperidylcarbonyl) | NH₂ |
| 7181. | —(CH₂SO₂)-2-thienyl | 7-[(4-methylpiperazin-1-yl)carbonyl] | NH₂ |
| 7182. | —(CH₂SO₂)-2-thienyl | 7-(morpholin-4-ylcarbonyl) | NH₂ |
| 7183. | —(CH₂SO₂)-2-thienyl | 7-(diethylaminocarbonyl) | NH₂ |
| 7184. | —(CH₂SO₂)-2-thienyl | 7-(1-pyrrolidinylcarbonyl) | NH₂ |
| 7185. | —(CH₂SO₂)-2-thienyl | 7-(azaperhydroepinylcarbonyl) | NH₂ |
| 7186. | —(CH₂SO₂)-2-thienyl | 7-[(3,5-dimethylpiperid-1-yl)carbonyl) | NH₂ |
| 7187. | —(CH₂SO₂)-2-thienyl | 7-[(4-methylpiperid-1-ylcarbonyl) | NH₂ |
| 7188. | —(CH₂SO₂)-2-thienyl | 7-[(3-methylpiperid-1-ylcarbonyl) | NH₂ |
| 7189. | —(CH₂SO₂)-2-thienyl | 7-[(2-methylpiperid-1-ylcarbonyl] | NH₂ |
| 7190. | —(CH₂SO₂)-2-thienyl | 7-[2-(dimethylamino)ethoxy] | NH₂ |
| 7191. | —(CH₂SO₂)-2-thienyl | 7-[2-(methylamino)ethoxy] | NH₂ |
| 7192. | —(CH₂SO₂)-2-thienyl | 7-[((2R)pyrrolidin-2-yl)methoxy] | NH₂ |
| 7193. | —(CH₂SO₂)-2-thienyl | 7-[((2R)-1-methylpyrrolidin-2-yl)methoxy] | NH₂ |
| 7194. | —(CH₂SO₂)-2-thienyl | 7-[2-(piperid-1-yl)ethoxy] | NH₂ |
| 7195. | —(CH₂SO₂)-2-thienyl | 7-[2-(piperazin-1-yl)ethoxy] | NH₂ |
| 7196. | —(CH₂SO₂)-2-thienyl | 7-[2-(morpholin-4-yl)ethoxy] | NH₂ |
| 7197. | —(CH₂SO₂)-2-thienyl | 7-[2-(1-methyl(4-piperidyl))ethoxy] | NH₂ |
| 7198. | —(CH₂SO₂)-2-thienyl | 7-[2-(1-methyl(4-piperidyl))methoxy] | NH₂ |
| 7199. | —(CH₂SO₂)-2-thienyl | 7-(1-methyl(4-piperidyloxy)) | NH₂ |
| 7200. | —(CH₂SO₂)-2-pyridyl | 7-(piperid-1-yl-CH₂—) | H |
| 7201. | —(CH₂SO₂)-2-pyridyl | 7-(1-CH₃-piperazin-4-yl-CH₂—) | H |
| 7202. | —(CH₂SO₂)-2-pyridyl | 7-(morpholin-4-yl-CH₂—) | H |
| 7203. | —(CH₂SO₂)-2-pyridyl | 7-(diethylamino-CH₂—) | H |
| 7204. | —(CH₂SO₂)-2-pyridyl | 7-(1-pyrrolidinyl-CH₂—) | H |
| 7205. | —(CH₂SO₂)-2-pyridyl | 7-(azaperhydroepinyl-CH₂—) | H |
| 7206. | —(CH₂SO₂)-2-pyridyl | 7-[(3,5-dimethylpiperid-1-yl)—CH₂—] | H |
| 7207. | —(CH₂SO₂)-2-pyridyl | 7-[(4-methylpiperid-1-yl-CH₂—] | H |
| 7208. | —(CH₂SO₂)-2-pyridyl | 7-[(3-methylpiperid-1-yl-CH₂—] | H |
| 7209. | —(CH₂SO₂)-2-pyridyl | 7-[(2-methylpiperid-1-yl-CH₂—] | H |
| 7210. | —(CH₂SO₂)-2-pyridyl | 7-(piperid-1-yl-CH₂CH₂—) | H |
| 7211. | —(CH₂SO₂)-2-pyridyl | 7-(1-CH₃-piperazin-4-yl-CH₂CH₂—) | H |
| 7212. | —(CH₂SO₂)-2-pyridyl | 7-(morpholin-4-yl-CH₂CH₂—) | H |
| 7213. | —(CH₂SO₂)-2-pyridyl | 7-(diethylamino-CH₂CH₂—) | H |
| 7214. | —(CH₂SO₂)-2-pyridyl | 7-(1-pyrrolidinyl-CH₂CH₂—) | H |
| 7215. | —(CH₂SO₂)-2-pyridyl | 7-(azaperhydroepinyl-CH₂CH₂—) | H |
| 7216. | —(CH₂SO₂)-2-pyridyl | 7-[(3,5-dimethylpiperid-1-yl)—CH₂CH₂—) | H |
| 7217. | —(CH₂SO₂)-2-pyridyl | 7-[(4-methylpiperid-1-yl-CH₂CH₂—) | H |
| 7218. | —(CH₂SO₂)-2-pyridyl | 7-[(3-methylpiperid-1-yl-CH₂CH₂—)—] | H |
| 7219. | —(CH₂SO₂)-2-pyridyl | 7-[(2-methylpiperid-1-yl-CH₂CH₂—)—] | H |
| 7220. | —(CH₂SO₂)-2-pyridyl | 7-(1-piperidylcarbonyl) | H |
| 7221. | —(CH₂SO₂)-2-pyridyl | 7-[(4-methylpiperazin-1-yl)carbonyl] | H |
| 7222. | —(CH₂SO₂)-2-pyridyl | 7-(morpholin-4-ylcarbonyl) | H |
| 7223. | —(CH₂SO₂)-2-pyridyl | 7-(diethylaminocarbonyl) | H |
| 7224. | —(CH₂SO₂)-2-pyridyl | 7-(1-pyrrolidinylcarbonyl) | H |
| 7225. | —(CH₂SO₂)-2-pyridyl | 7-(azaperhydroepinylcarbonyl) | H |
| 7226. | —(CH₂SO₂)-2-pyridyl | 7-[(3,5-dimethylpiperid-1-yl)carbonyl) | H |
| 7227. | —(CH₂SO₂)-2-pyridyl | 7-[(4-methylpiperid-1-ylcarbonyl) | H |
| 7228. | —(CH₂SO₂)-2-pyridyl | 7-[(3-methylpiperid-1-ylcarbonyl) | H |
| 7229. | —(CH₂SO₂)-2-pyridyl | 7-[(2-methylpiperid-1-ylcarbonyl) | H |
| 7230. | —(CH₂SO₂)-2-pyridyl | 7-[2-(dimethylamino)ethoxy] | H |
| 7231. | —(CH₂SO₂)-2-pyridyl | 7-[2-(methylamino)ethoxy] | H |
| 7232. | —(CH₂SO₂)-2-pyridyl | 7-[((2R)pyrrolidin-2-yl)methoxy] | H |
| 7233. | —(CH₂SO₂)-2-pyridyl | 7-[((2R)-1-methylpyrrolidin-2-yl)methoxy] | H |
| 7234. | —(CH₂SO₂)-2-pyridyl | 7-[2-(piperid-1-yl)ethoxy] | H |
| 7235. | —(CH₂SO₂)-2-pyridyl | 7-[2-(piperazin-1-yl)ethoxy] | H |
| 7236. | —(CH₂SO₂)-2-pyridyl | 7-[2-(morpholin-4-yl)ethoxy] | H |
| 7237. | —(CH₂SO₂)-2-pyridyl | 7-[2-(1-methyl(4-piperidyl))ethoxy] | H |
| 7238. | —(CH₂SO₂)-2-pyridyl | 7-[2-(1-methyl(4-piperidyl))methoxy] | H |
| 7239. | —(CH₂SO₂)-2-pyridyl | 7-(1-methyl(4-piperidyloxy)) | H |
| 7240. | —(CH₂SO₂)-2-pyridyl | 7-(piperid-1-yl-CH₂—) | NH₂ |
| 7241. | —(CH₂SO₂)-2-pyridyl | 7-(1-CH₃-piperazin-4-yl-CH₂—) | NH₂ |
| 7242. | —(CH₂SO₂)-2-pyridyl | 7-(morpholin-4-yl-CH₂—) | NH₂ |
| 7243. | —(CH₂SO₂)-2-pyridyl | 7-(diethylamino-CH₂—) | NH₂ |

TABLE 11-continued

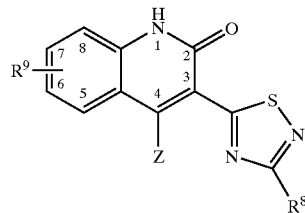

| # | R[8] | R[9] | Z |
|---|---|---|---|
| 7244. | —(CH$_2$SO$_2$)-2-pyridyl | 7-(1-pyrrolidinyl-CH$_2$—) | NH$_2$ |
| 7245. | —(CH$_2$SO$_2$)-2-pyridyl | 7-(azaperhydroepinyl-CH$_2$—) | NH$_2$ |
| 7246. | —(CH$_2$SO$_2$)-2-pyridyl | 7-[(3,5-dimethylpiperid-1-yl)—CH$_2$—] | NH$_2$ |
| 7247. | —(CH$_2$SO$_2$)-2-pyridyl | 7-[(4-methylpiperid-1-yl-CH$_2$—] | NH$_2$ |
| 7248. | —(CH$_2$SO$_2$)-2-pyridyl | 7-[(3-methylpiperid-1-yl-CH$_2$—] | NH$_2$ |
| 7249. | —(CH$_2$SO$_2$)-2-pyridyl | 7-[(2-methylpiperid-1-yl-CH$_2$—] | NH$_2$ |
| 7250. | —(CH$_2$SO$_2$)-2-pyridyl | 7-(piperid-1-yl-CH$_2$CH$_2$—) | NH$_2$ |
| 7251. | —(CH$_2$SO$_2$)-2-pyridyl | 7-(1-CH$_3$-piperazin-4-yl-CH$_2$CH$_2$—) | NH$_2$ |
| 7252. | —(CH$_2$SO$_2$)-2-pyridyl | 7-(morpholin-4-yl-CH$_2$CH$_2$—) | NH$_2$ |
| 7253. | —(CH$_2$SO$_2$)-2-pyridyl | 7-(diethylamino-CH$_2$CH$_2$—) | NH$_2$ |
| 7254. | —(CH$_2$SO$_2$)-2-pyridyl | 7-(1-pyrrolidinyl-CH$_2$CH$_2$—) | NH$_2$ |
| 7255. | —(CH$_2$SO$_2$)-2-pyridyl | 7-(azaperhydroepinyl-CH$_2$CH$_2$—) | NH$_2$ |
| 7256. | —(CH$_2$SO$_2$)-2-pyridyl | 7-[(3,5-dimethylpiperid-1-yl)—CH$_2$CH$_2$—) | NH$_2$ |
| 7257. | —(CH$_2$SO$_2$)-2-pyridyl | 7-[(4-methylpiperid-1-yl-CH$_2$CH$_2$—) | NH$_2$ |
| 7258. | —(CH$_2$SO$_2$)-2-pyridyl | 7-[(3-methylpiperid-1-yl-CH$_2$CH$_2$—)—] | NH$_2$ |
| 7259. | —(CH$_2$SO$_2$)-2-pyridyl | 7-[(2-methylpiperid-1-yl-CH$_2$CH$_2$—)—] | NH$_2$ |
| 7260. | —(CH$_2$SO$_2$)-2-pyridyl | 7-(1-piperidylcarbonyl) | NH$_2$ |
| 7261. | —(CH$_2$SO$_2$)-2-pyridyl | 7-[(4-methylpiperazin-1-yl)carbonyl] | NH$_2$ |
| 7262. | —(CH$_2$SO$_2$)-2-pyridyl | 7-(morpholin-4-ylcarbonyl) | NH$_2$ |
| 7263. | —(CH$_2$SO$_2$)-2-pyridyl | 7-(diethylaminocarbonyl) | NH$_2$ |
| 7264. | —(CH$_2$SO$_2$)-2-pyridyl | 7-(1-pyrrolidinylcarbonyl) | NH$_2$ |
| 7265. | —(CH$_2$SO$_2$)-2-pyridyl | 7-(azaperhydroepinylcarbonyl) | NH$_2$ |
| 7266. | —(CH$_2$SO$_2$)-2-pyridyl | 7-[(3,5-dimethylpiperid-1-yl)carbonyl] | NH$_2$ |
| 7267. | —(CH$_2$SO$_2$)-2-pyridyl | 7-[(4-methylpiperid-1-ylcarbonyl) | NH$_2$ |
| 7268. | —(CH$_2$SO$_2$)-2-pyridyl | 7-[(3-methylpiperid-1-ylcarbonyl) | NH$_2$ |
| 7269. | —(CH$_2$SO$_2$)-2-pyridyl | 7-[(2-methylpiperid-1-ylcarbonyl) | NH$_2$ |
| 7270. | —(CH$_2$SO$_2$)-2-pyridyl | 7-[2-(dimethylamino)ethoxy] | NH$_2$ |
| 7271. | —(CH$_2$SO$_2$)-2-pyridyl | 7-[2-(methylamino)ethoxy] | NH$_2$ |
| 7272. | —(CH$_2$SO$_2$)-2-pyridyl | 7-[((2R)pyrrolidin-2-yl)methoxy] | NH$_2$ |
| 7273. | —(CH$_2$SO$_2$)-2-pyridyl | 7-[((2R)-1-methylpyrrolidin-2-yl)methoxy] | NH$_2$ |
| 7274. | —(CH$_2$SO$_2$)-2-pyridyl | 7-[2-(piperid-1-yl)ethoxy] | NH$_2$ |
| 7275. | —(CH$_2$SO$_2$)-2-pyridyl | 7-[2-(piperazin-1-yl)ethoxy] | NH$_2$ |
| 7276. | —(CH$_2$SO$_2$)-2-pyridyl | 7-[2-(morpholin-4-yl)ethoxy] | NH$_2$ |
| 7277. | —(CH$_2$SO$_2$)-2-pyridyl | 7-[2-(1-methyl(4-piperidyl))ethoxy] | NH$_2$ |
| 7278. | —(CH$_2$SO$_2$)-2-pyridyl | 7-[2-(1-methyl(4-piperidyl))methoxy] | NH$_2$ |
| 7279. | —(CH$_2$SO$_2$)-2-pyridyl | 7-(1-methyl(4-piperidyloxy)) | NH$_2$ |
| 7280. | —(CH$_2$SO$_2$)-3-pyridyl | 7-(piperid-1-yl-CH$_2$—) | H |
| 7281. | —(CH$_2$SO$_2$)-3-pyridyl | 7-(1-CH$_3$-piperazin-4-yl-CH$_2$—) | H |
| 7282. | —(CH$_2$SO$_2$)-3-pyridyl | 7-(morpholin-4-yl-CH$_2$—) | H |
| 7283. | —(CH$_2$SO$_2$)-3-pyridyl | 7-(diethylamino-CH$_2$—) | H |
| 7284. | —(CH$_2$SO$_2$)-3-pyridyl | 7-(1-pyrrolidinyl-CH$_2$—) | H |
| 7285. | —(CH$_2$SO$_2$)-3-pyridyl | 7-(azaperhydroepinyl-CH$_2$—) | H |
| 7286. | —(CH$_2$SO$_2$)-3-pyridyl | 7-[(3,5-dimethylpiperid-1-yl)—CH$_2$—] | H |
| 7287. | —(CH$_2$SO$_2$)-3-pyridyl | 7-[(4-methylpiperid-1-yl-CH$_2$—] | H |
| 7288. | —(CH$_2$SO$_2$)-3-pyridyl | 7-[(3-methylpiperid-1-yl-CH$_2$—] | H |
| 7289. | —(CH$_2$SO$_2$)-3-pyridyl | 7-[(2-methylpiperid-1-yl-CH$_2$—] | H |
| 7290. | —(CH$_2$SO$_2$)-3-pyridyl | 7-(piperid-1-yl-CH$_2$CH$_2$—) | H |
| 7291. | —(CH$_2$SO$_2$)-3-pyridyl | 7-(1-CH$_3$-piperazin-4-yl-CH$_2$CH$_2$—) | H |
| 7292. | —(CH$_2$SO$_2$)-3-pyridyl | 7-(morpholin-4-yl-CH$_2$CH$_2$—) | H |
| 7293. | —(CH$_2$SO$_2$)-3-pyridyl | 7-(diethylamino-CH$_2$CH$_2$—) | H |
| 7294. | —(CH$_2$SO$_2$)-3-pyridyl | 7-(1-pyrrolidinyl-CH$_2$CH$_2$—) | H |
| 7295. | —(CH$_2$SO$_2$)-3-pyridyl | 7-(azaperhydroepinyl-CH$_2$CH$_2$—) | H |
| 7296. | —(CH$_2$SO$_2$)-3-pyridyl | 7-[(3,5-dimethylpiperid-1-yl)—CH$_2$CH$_2$—) | H |
| 7297. | —(CH$_2$SO$_2$)-3-pyridyl | 7-[(4-methylpiperid-1-yl-CH$_2$CH$_2$—) | H |
| 7298. | —(CH$_2$SO$_2$)-3-pyridyl | 7-[(3-methylpiperid-1-yl-CH$_2$CH$_2$—)—] | H |
| 7299. | —(CH$_2$SO$_2$)-3-pyridyl | 7-[(2-methylpiperid-1-yl-CH$_2$CH$_2$—)—] | H |
| 7300. | —(CH$_2$SO$_2$)-3-pyridyl | 7-(1-piperidylcarbonyl) | H |
| 7301. | —(CH$_2$SO$_2$)-3-pyridyl | 7-[(4-methylpiperazin-1-yl)carbonyl] | H |
| 7302. | —(CH$_2$SO$_2$)-3-pyridyl | 7-(morpholin-4-ylcarbonyl) | H |
| 7303. | —(CH$_2$SO$_2$)-3-pyridyl | 7-(diethylaminocarbonyl) | H |
| 7304. | —(CH$_2$SO$_2$)-3-pyridyl | 7-(1-pyrrolidinylcarbonyl) | H |
| 7305. | —(CH$_2$SO$_2$)-3-pyridyl | 7-(azaperhydroepinylcarbonyl) | H |
| 7306. | —(CH$_2$SO$_2$)-3-pyridyl | 7-[(3,5-dimethylpiperid-1-yl)carbonyl] | H |
| 7307. | —(CH$_2$SO$_2$)-3-pyridyl | 7-[(4-methylpiperid-1-ylcarbonyl) | H |
| 7308. | —(CH$_2$SO$_2$)-3-pyridyl | 7-[(3-methylpiperid-1-ylcarbonyl) | H |

TABLE 11-continued

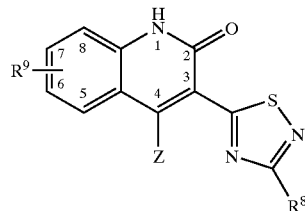

| # | R⁸ | R⁹ | Z |
|---|---|---|---|
| 7309. | —(CH₂SO₂)-3-pyridyl | 7-[(2-methylpiperid-1-ylcarbonyl) | H |
| 7310. | —(CH₂SO₂)-3-pyridyl | 7-[2-(dimethylamino)ethoxy] | H |
| 7311. | —(CH₂SO₂)-3-pyridyl | 7-[2-(methylamino)ethoxy] | H |
| 7312. | —(CH₂SO₂)-3-pyridyl | 7-[((2R)pyrrolidin-2-yl)methoxy] | H |
| 7313. | —(CH₂SO₂)-3-pyridyl | 7-[((2R)-1-methylpyrrolidin-2-yl)methoxy] | H |
| 7314. | —(CH₂SO₂)-3-pyridyl | 7-[2-(piperid-1-yl)ethoxy] | H |
| 7315. | —(CH₂SO₂)-3-pyridyl | 7-[2-(piperazin-1-yl)ethoxy] | H |
| 7316. | —(CH₂SO₂)-3-pyridyl | 7-[2-(morpholin-4-yl)ethoxy] | H |
| 7317. | —(CH₂SO₂)-3-pyridyl | 7-[2-(1-methyl(4-piperidyl))ethoxy] | H |
| 7318. | —(CH₂SO₂)-3-pyridyl | 7-[2-(1-methyl(4-piperidyl))methoxy] | H |
| 7319. | —(CH₂SO₂)-3-pyridyl | 7-(1-methyl(4-piperidyloxy)) | H |
| 7320. | —(CH₂SO₂)-3-pyridyl | 7-(piperid-1-yl-CH₂—) | NH₂ |
| 7321. | —(CH₂SO₂)-3-pyridyl | 7-(1-CH₃-piperazin-4-yl-CH₂—) | NH₂ |
| 7322. | —(CH₂SO₂)-3-pyridyl | 7-(morpholin-4-yl-CH₂—) | NH₂ |
| 7323. | —(CH₂SO₂)-3-pyridyl | 7-(diethylamino-CH₂—) | NH₂ |
| 7324. | —(CH₂SO₂)-3-pyridyl | 7-(1-pyrrolidinyl-CH₂—) | NH₂ |
| 7325. | —(CH₂SO₂)-3-pyridyl | 7-(azaperhydroepinyl-CH₂—) | NH₂ |
| 7326. | —(CH₂SO₂)-3-pyridyl | 7-[(3,5-dimethylpiperid-1-yl)—CH₂—] | NH₂ |
| 7327. | —(CH₂SO₂)-3-pyridyl | 7-[(4-methylpiperid-1-yl-CH₂—] | NH₂ |
| 7328. | —(CH₂SO₂)-3-pyridyl | 7-[(3-methylpiperid-1-yl-CH₂—] | NH₂ |
| 7329. | —(CH₂SO₂)-3-pyridyl | 7-[(2-methylpiperid-1-yl-CH₂—] | NH₂ |
| 7330. | —(CH₂SO₂)-3-pyridyl | 7-(piperid-1-yl-CH₂CH₂—) | NH₂ |
| 7331. | —(CH₂SO₂)-3-pyridyl | 7-(1-CH₃-piperazin-4-yl-CH₂CH₂—) | NH₂ |
| 7332. | —(CH₂SO₂)-3-pyridyl | 7-(morpholin-4-yl-CH₂CH₂—) | NH₂ |
| 7333. | —(CH₂SO₂)-3-pyridyl | 7-(diethylamino-CH₂CH₂—) | NH₂ |
| 7334. | —(CH₂SO₂)-3-pyridyl | 7-(1-pyrrolidinyl-CH₂CH₂—) | NH₂ |
| 7335. | —(CH₂SO₂)-3-pyridyl | 7-(azaperhydroepinyl-CH₂CH₂—) | NH₂ |
| 7336. | —(CH₂SO₂)-3-pyridyl | 7-[(3,5-dimethylpiperid-1-yl)—CH₂CH₂—) | NH₂ |
| 7337. | —(CH₂SO₂)-3-pyridyl | 7-[(4-methylpiperid-1-yl-CH₂CH₂—) | NH₂ |
| 7338. | —(CH₂SO₂)-3-pyridyl | 7-[(3-methylpiperid-1-yl-CH₂CH₂—)—] | NH₂ |
| 7339. | —(CH₂SO₂)-3-pyridyl | 7-[(2-methylpiperid-1-yl-CH₂CH₂—)—] | NH₂ |
| 7340. | —(CH₂SO₂)-3-pyridyl | 7-(1-piperidylcarbonyl) | NH₂ |
| 7341. | —(CH₂SO₂)-3-pyridyl | 7-[(4-methylpiperazin-1-yl)carbonyl] | NH₂ |
| 7342. | —(CH₂SO₂)-3-pyridyl | 7-(morpholin-4-ylcarbonyl) | NH₂ |
| 7343. | —(CH₂SO₂)-3-pyridyl | 7-(diethylaminocarbonyl) | NH₂ |
| 7344. | —(CH₂SO₂)-3-pyridyl | 7-(1-pyrrolidinylcarbonyl) | NH₂ |
| 7345. | —(CH₂SO₂)-3-pyridyl | 7-(azaperhydroepinylcarbonyl) | NH₂ |
| 7346. | —(CH₂SO₂)-3-pyridyl | 7-(3,5-dimethylpiperid-1-yl)carbonyl) | NH₂ |
| 7347. | —(CH₂SO₂)-3-pyridyl | 7-[(4-methylpiperid-1-ylcarbonyl) | NH₂ |
| 7348. | —(CH₂SO₂)-3-pyridyl | 7-[(3-methylpiperid-1-ylcarbonyl) | NH₂ |
| 7349. | —(CH₂SO₂)-3-pyridyl | 7-[(2-methylpiperid-1-ylcarbonyl) | NH₂ |
| 7350. | —(CH₂SO₂)-3-pyridyl | 7-[2-(dimethylamino)ethoxy] | NH₂ |
| 7351. | —(CH₂SO₂)-3-pyridyl | 7-[2-(methylamino)ethoxy] | NH₂ |
| 7352. | —(CH₂SO₂)-3-pyridyl | 7-[((2R)pyrrolidin-2-yl)methoxy] | NH₂ |
| 7353. | —(CH₂SO₂)-3-pyridyl | 7-[((2R)-1-methylpyrrolidin-2-yl)methoxy] | NH₂ |
| 7354. | —(CH₂SO₂)-3-pyridyl | 7-[2-(piperid-1-yl)ethoxy] | NH₂ |
| 7355. | —(CH₂SO₂)-3-pyridyl | 7-[2-(piperazin-1-yl)ethoxy] | NH₂ |
| 7356. | —(CH₂SO₂)-3-pyridyl | 7-[2-(morpholin-4-yl)ethoxy] | NH₂ |
| 7357. | —(CH₂SO₂)-3-pyridyl | 7-[2-(1-methyl(4-piperidyl))ethoxy] | NH₂ |
| 7358. | —(CH₂SO₂)-3-pyridyl | 7-[2-(1-methyl(4-piperidyl))methoxy] | NH₂ |
| 7359. | —(CH₂SO₂)-3-pyridyl | 7-(1-methyl(4-piperidyloxy)) | NH₂ |
| 7360. | —(CH₂SO₂)-4-pyridyl | 7-(piperid-1-yl-CH₂—) | H |
| 7361. | —(CH₂SO₂)-4-pyridyl | 7-(1-CH₃-piperazin-4-yl-CH₂—) | H |
| 7362. | —(CH₂SO₂)-4-pyridyl | 7-(morpholin-4-yl-CH₂—) | H |
| 7363. | —(CH₂SO₂)-4-pyridyl | 7-(diethylamino-CH₂—) | H |
| 7364. | —(CH₂SO₂)-4-pyridyl | 7-(1-pyrrolidinyl-CH₂—) | H |
| 7365. | —(CH₂SO₂)-4-pyridyl | 7-(azaperhydroepinyl-CH₂—) | H |
| 7366. | —(CH₂SO₂)-4-pyridyl | 7-[(3,5-dimethylpiperid-1-yl)—CH₂—] | H |
| 7367. | —(CH₂SO₂)-4-pyridyl | 7-[(4-methylpiperid-1-yl-CH₂—] | H |
| 7368. | —(CH₂SO₂)-4-pyridyl | 7-[(3-methylpiperid-1-yl-CH₂—] | H |
| 7369. | —(CH₂SO₂)-4-pyridyl | 7-[(2-methylpiperid-1-yl-CH₂—] | H |
| 7370. | —(CH₂SO₂)-4-pyridyl | 7-(piperid-1-yl-CH₂CH₂—) | H |
| 7371. | —(CH₂SO₂)-4-pyridyl | 7-(1-CH₃-piperazin-4-yl-CH₂CH₂—) | H |
| 7372. | —(CH₂SO₂)-4-pyridyl | 7-(morpholin-4-yl-CH₂CH₂—) | H |
| 7373. | —(CH₂SO₂)-4-pyridyl | 7-(diethylamino-CH₂CH₂—) | H |

TABLE 11-continued

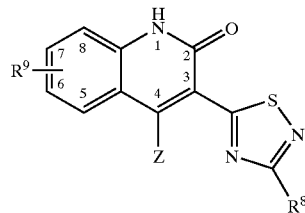

| # | R⁸ | R⁹ | Z |
|---|---|---|---|
| 7374. | —(CH₂SO₂)-4-pyridyl | 7-(1-pyrrolidinyl-CH₂CH₂—) | H |
| 7375. | —(CH₂SO₂)-4-pyridyl | 7-(azaperhydroepinyl-CH₂CH₂—) | H |
| 7376. | —(CH₂SO₂)-4-pyridyl | 7-[(3,5-dimethylpiperid-1-yl)—CH₂CH₂—] | H |
| 7377. | —(CH₂SO₂)-4-pyridyl | 7-[(4-methylpiperid-1-yl-CH₂CH₂—] | H |
| 7378. | —(CH₂SO₂)-4-pyridyl | 7-[(3-methylpiperid-1-yl-CH₂CH₂—)—] | H |
| 7379. | —(CH₂SO₂)-4-pyridyl | 7-[(2-methylpiperid-1-yl-CH₂CH₂—)—] | H |
| 7380. | —(CH₂SO₂)-4-pyridyl | 7-(1-piperidylcarbonyl) | H |
| 7381. | —(CH₂SO₂)-4-pyridyl | 7-[(4-methylpiperazin-1-yl)carbonyl] | H |
| 7382. | —(CH₂SO₂)-4-pyridyl | 7-(morpholin-4-ylcarbonyl) | H |
| 7383. | —(CH₂SO₂)-4-pyridyl | 7-(diethylaminocarbonyl) | H |
| 7384. | —(CH₂SO₂)-4-pyridyl | 7-(1-pyrrolidinylcarbonyl) | H |
| 7385. | —(CH₂SO₂)-4-pyridyl | 7-(azaperhydroepinylcarbonyl) | H |
| 7386. | —(CH₂SO₂)-4-pyridyl | 7-[(3,5-dimethylpiperid-1-yl)carbonyl] | H |
| 7387. | —(CH₂SO₂)-4-pyridyl | 7-(4-methylpiperid-1-ylcarbonyl) | H |
| 7388. | —(CH₂SO₂)-4-pyridyl | 7-[(3-methylpiperid-1-ylcarbonyl) | H |
| 7389. | —(CH₂SO₂)-4-pyridyl | 7-[(2-methylpiperid-1-ylcarbonyl) | H |
| 7390. | —(CH₂SO₂)-4-pyridyl | 7-[2-(dimethylamino)ethoxy] | H |
| 7391. | —(CH₂SO₂)-4-pyridyl | 7-[2-(methylamino)ethoxy] | H |
| 7392. | —(CH₂SO₂)-4-pyridyl | 7-[((2R)pyrrolidin-2-yl)methoxy] | H |
| 7393. | —(CH₂SO₂)-4-pyridyl | 7-[((2R)-1-methylpyrrolidin-2-yl)methoxy] | H |
| 7394. | —(CH₂SO₂)-4-pyridyl | 7-[2-(piperid-1-yl)ethoxy] | H |
| 7395. | —(CH₂SO₂)-4-pyridyl | 7-[2-(piperazin-1-yl)ethoxy] | H |
| 7396. | —(CH₂SO₂)-4-pyridyl | 7-[2-(morpholin-4-yl)ethoxy] | H |
| 7397. | —(CH₂SO₂)-4-pyridyl | 7-[2-(1-methyl(4-piperidyl))ethoxy] | H |
| 7398. | —(CH₂SO₂)-4-pyridyl | 7-[2-(1-methyl(4-piperidyl))methoxy] | H |
| 7399. | —(CH₂SO₂)-4-pyridyl | 7-(1-methyl(4-piperidyloxy)) | H |
| 7400. | —(CH₂SO₂)-4-pyridyl | 7-(piperid-1-yl-CH₂—) | NH₂ |
| 7401. | —(CH₂SO₂)-4-pyridyl | 7-(1-CH₃-piperazin-4-yl-CH₂—) | NH₂ |
| 7402. | —(CH₂SO₂)-4-pyridyl | 7-(morpholin-4-yl-CH₂—) | NH₂ |
| 7403. | —(CH₂SO₂)-4-pyridyl | 7-(diethylamino-CH₂—) | NH₂ |
| 7404. | —(CH₂SO₂)-4-pyridyl | 7-(1-pyrrolidinyl-CH₂—) | NH₂ |
| 7405. | —(CH₂SO₂)-4-pyridyl | 7-(azaperhydroepinyl-CH₂—) | NH₂ |
| 7406. | —(CH₂SO₂)-4-pyridyl | 7-[(3,5-dimethylpiperid-1-yl)—CH₂—] | NH₂ |
| 7407. | —(CH₂SO₂)-4-pyridyl | 7-[(4-methylpiperid-1-yl-CH₂—] | NH₂ |
| 7408. | —(CH₂SO₂)-4-pyridyl | 7-[(3-methylpiperid-1-yl-CH₂—] | NH₂ |
| 7409. | —(CH₂SO₂)-4-pyridyl | 7-[(2-methylpiperid-1-yl-CH₂—] | NH₂ |
| 7410. | —(CH₂SO₂)-4-pyridyl | 7-(piperid-1-yl-CH₂CH₂—) | NH₂ |
| 7411. | —(CH₂SO₂)-4-pyridyl | 7-(1-CH₃-piperazin-4-yl-CH₂CH₂—) | NH₂ |
| 7412. | —(CH₂SO₂)-4-pyridyl | 7-(morpholin-4-yl-CH₂CH₂—) | NH₂ |
| 7413. | —(CH₂SO₂)-4-pyridyl | 7-(diethylamino-CH₂CH₂—) | NH₂ |
| 7414. | —(CH₂SO₂)-4-pyridyl | 7-(1-pyrrolidinyl-CH₂CH₂—) | NH₂ |
| 7415. | —(CH₂SO₂)-4-pyridyl | 7-(azaperhydroepinyl-CH₂CH₂—) | NH₂ |
| 7416. | —(CH₂SO₂)-4-pyridyl | 7-[(3,5-dimethylpiperid-1-yl)—CH₂CH₂—) | NH₂ |
| 7417. | —(CH₂SO₂)-4-pyridyl | 7-[(4-methylpiperid-1-yl-CH₂CH₂—) | NH₂ |
| 7418. | —(CH₂SO₂)-4-pyridyl | 7-[(3-methylpiperid-1-yl-CH₂CH₂—)—] | NH₂ |
| 7419. | —(CH₂SO₂)-4-pyridyl | 7-[(2-methylpiperid-1-yl-CH₂CH₂—)—] | NH₂ |
| 7420. | —(CH₂SO₂)-4-pyridyl | 7-(1-piperidylcarbonyl) | NH₂ |
| 7421. | —(CH₂SO₂)-4-pyridyl | 7-[(4-methylpiperazin-1-yl)carbonyl] | NH₂ |
| 7422. | —(CH₂SO₂)-4-pyridyl | 7-(morpholin-4-ylcarbonyl) | NH₂ |
| 7423. | —(CH₂SO₂)-4-pyridyl | 7-(diethylaminocarbonyl) | NH₂ |
| 7424. | —(CH₂SO₂)-4-pyridyl | 7-(1-pyrrolidinylcarbonyl) | NH₂ |
| 7425. | —(CH₂SO₂)-4-pyridyl | 7-(azaperhydroepinylcarbonyl) | NH₂ |
| 7426. | —(CH₂SO₂)-4-pyridyl | 7-[(3,5-dimethylpiperid-1-yl)carbonyl] | NH₂ |
| 7427. | —(CH₂SO₂)-4-pyridyl | 7-[(4-methylpiperid-1-ylcarbonyl) | NH₂ |
| 7428. | —(CH₂SO₂)-4-pyridyl | 7-[(3-methylpiperid-1-ylcarbonyl) | NH₂ |
| 7429. | —(CH₂SO₂)-4-pyridyl | 7-[(2-methylpiperid-1-ylcarbonyl) | NH₂ |
| 7430. | —(CH₂SO₂)-4-pyridyl | 7-[2-(dimethylamino)ethoxy] | NH₂ |
| 7431. | —(CH₂SO₂)-4-pyridyl | 7-[2-(methylamino)ethoxy] | NH₂ |
| 7432. | —(CH₂SO₂)-4-pyridyl | 7-[((2R)pyrrolidin-2-yl)methoxy] | NH₂ |
| 7433. | —(CH₂SO₂)-4-pyridyl | 7-[((2R)-1-methylpyrrolidin-2-yl)methoxy] | NH₂ |
| 7434. | —(CH₂SO₂)-4-pyridyl | 7-[2-(piperid-1-yl)ethoxy] | NH₂ |
| 7435. | —(CH₂SO₂)-4-pyridyl | 7-[2-(piperazin-1-yl)ethoxy] | NH₂ |
| 7436. | —(CH₂SO₂)-4-pyridyl | 7-[2-(morpholin-4-yl)ethoxy] | NH₂ |
| 7437. | —(CH₂SO₂)-4-pyridyl | 7-[2-(1-methyl(4-piperidyl))ethoxy] | NH₂ |
| 7438. | —(CH₂SO₂)-4-pyridyl | 7-[2-(1-methyl(4-piperidyl))methoxy] | NH₂ |

TABLE 11-continued

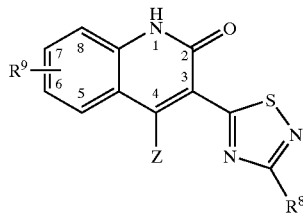

| # | R[8] | R[9] | Z |
|---|---|---|---|
| 7439. | —(CH$_2$SO$_2$)-4-pyridyl | 7-(1-methyl(4-piperidyloxy)) | NH$_2$ |
| 7440. | —(NMeSO$_2$)-phenyl | 7-(piperid-1-yl-CH$_2$—) | H |
| 7441. | —(NMeSO$_2$)-phenyl | 7-(1-CH$_3$-piperazin-4-yl-CH$_2$—) | H |
| 7442. | —(NMeSO$_2$)-phenyl | 7-(morpholin-4-yl-CH$_2$—) | H |
| 7443. | —(NMeSO$_2$)-phenyl | 7-(diethylamino-CH$_2$—) | H |
| 7444. | —(NMeSO$_2$)-phenyl | 7-(1-pyrrolidinyl-CH$_2$—) | H |
| 7445. | —(NMeSO$_2$)-phenyl | 7-(azaperhydroepinyl-CH$_2$—) | H |
| 7446. | —(NMeSO$_2$)-phenyl | 7-[(3,5-dimethylpiperid-1-yl)—CH$_2$—] | H |
| 7447. | —(NMeSO$_2$)-phenyl | 7-[(4-methylpiperid-1-yl-CH$_2$—] | H |
| 7448. | —(NMeSO$_2$)-phenyl | 7-[(3-methylpiperid-1-yl-CH$_2$—] | H |
| 7449. | —(NMeSO$_2$)-phenyl | 7-[(2-methylpiperid-1-yl-CH$_2$—] | H |
| 7450. | —(NMeSO$_2$)-phenyl | 7-(piperid-1-yl-CH$_2$—) | H |
| 7451. | —(NMeSO$_2$)-phenyl | 7-(1-CH$_3$-piperazin-4-yl-CH$_2$CH$_2$—) | H |
| 7452. | —(NMeSO$_2$)-phenyl | 7-(morpholin-4-yl-CH$_2$CH$_2$—) | H |
| 7453. | —(NMeSO$_2$)-phenyl | 7-(diethylamino-CH$_2$CH$_2$—) | H |
| 7454. | —(NMeSO$_2$)-phenyl | 7-(1-pyrrolidinyl-CH$_2$CH$_2$—) | H |
| 7455. | —(NMeSO$_2$)-phenyl | 7-(azaperhydroepinyl-CH$_2$CH$_2$—) | H |
| 7456. | —(NMeSO$_2$)-phenyl | 7-[(3,5-dimethylpiperid-1-yl)—CH$_2$CH$_2$—) | H |
| 7457. | —(NMeSO$_2$)-phenyl | 7-[(4-methylpiperid-1-yl-CH$_2$CH$_2$—) | H |
| 7458. | —(NMeSO$_2$)-phenyl | 7-[(3-methylpiperid-1-yl-CH$_2$CH$_2$—)—] | H |
| 7459. | —(NMeSO$_2$)-phenyl | 7-[(2-methylpiperid-1-yl-CH$_2$CH$_2$—)—] | H |
| 7460. | —(NMeSO$_2$)-phenyl | 7-(1-piperidylcarbonyl) | H |
| 7461. | —(NMeSO$_2$)-phenyl | 7-[(4-methylpiperazin-1-yl)carbonyl] | H |
| 7462. | —(NMeSO$_2$)-phenyl | 7-(morpholin-4-ylcarbonyl) | H |
| 7463. | —(NMeSO$_2$)-phenyl | 7-(diethylaminocarbonyl) | H |
| 7464. | —(NMeSO$_2$)-phenyl | 7-(1-pyrrolidinylcarbonyl) | H |
| 7465. | —(NMeSO$_2$)-phenyl | 7-(azaperhydroepinylcarbonyl) | H |
| 7466. | —(NMeSO$_2$)-phenyl | 7-[(3,5-dimethylpiperid-1-yl)carbonyl) | H |
| 7467. | —(NMeSO$_2$)-phenyl | 7-[(4-methylpiperid-1-ylcarbonyl) | H |
| 7468. | —(NMeSO$_2$)-phenyl | 7-[(3-methylpiperid-1-ylcarbonyl) | H |
| 7469. | —(NMeSO$_2$)-phenyl | 7-[(2-methylpiperid-1-ylcarbonyl) | H |
| 7470. | —(NMeSO$_2$)-phenyl | 7-[2-(dimethylamino)ethoxy] | H |
| 7471. | —(NMeSO$_2$)-phenyl | 7-[2-(methylamino)ethoxy] | H |
| 7472. | —(NMeSO$_2$)-phenyl | 7-[((2R)pyrrolidin-2-yl)methoxy] | H |
| 7473. | —(NMeSO$_2$)-phenyl | 7-[((2R)-1-methylpyrrolidin-2-yl)methoxy] | H |
| 7474. | —(NMeSO$_2$)-phenyl | 7-[2-(piperid-1-yl)ethoxy] | H |
| 7475. | —(NMeSO$_2$)-phenyl | 7-[2-(piperazin-1-yl)ethoxy] | H |
| 7476. | —(NMeSO$_2$)-phenyl | 7-[2-(morpholin-4-yl)ethoxy] | H |
| 7477. | —(NMeSO$_2$)-phenyl | 7-[2-(1-methyl(4-piperidyl))ethoxy] | H |
| 7478. | —(NMeSO$_2$)-phenyl | 7-[2-(1-methyl(4-piperidyl))methoxy] | H |
| 7479. | —(NMeSO$_2$)-phenyl | 7-(1-methyl(4-piperidyloxy)) | H |
| 7480. | —(NMeSO$_2$)-phenyl | 7-(piperid-1-yl-CH$_2$—) | NH$_2$ |
| 7481. | —(NMeSO$_2$)-phenyl | 7-(1-CH$_3$-piperazin-4-yl-CH$_2$—) | NH$_2$ |
| 7482. | —(NMeSO$_2$)-phenyl | 7-(morpholin-4-yl-CH$_2$—) | NH$_2$ |
| 7483. | —(NMeSO$_2$)-phenyl | 7-(diethylamino-CH$_2$—) | NH$_2$ |
| 7484. | —(NMeSO$_2$)-phenyl | 7-(1-pyrrolidinyl-CH$_2$—) | NH$_2$ |
| 7485. | —(NMeSO$_2$)-phenyl | 7-(azaperhydroepinyl-CH$_2$—) | NH$_2$ |
| 7486. | —(NMeSO$_2$)-phenyl | 7-[(3,5-dimethylpiperid-1-yl)—CH$_2$—] | NH$_2$ |
| 7487. | —(NMeSO$_2$)-phenyl | 7-[(4-methylpiperid-1-yl-CH$_2$—] | NH$_2$ |
| 7488. | —(NMeSO$_2$)-phenyl | 7-[(3-methylpiperid-1-yl-CH$_2$—] | NH$_2$ |
| 7489. | —(NMeSO$_2$)-phenyl | 7-[(2-methylpiperid-1-yl-CH$_2$—] | NH$_2$ |
| 7490. | —(NMeSO$_2$)-phenyl | 7-(piperid-1-yl-CH$_2$CH$_2$—) | NH$_2$ |
| 7491. | —(NMeSO$_2$)-phenyl | 7-(1-CH$_3$-piperazin-4-yl-CH$_2$CH$_2$—) | NH$_2$ |
| 7492. | —(NMeSO$_2$)-phenyl | 7-(morpholin-4-yl-CH$_2$CH$_2$—) | NH$_2$ |
| 7493. | —(NMeSO$_2$)-phenyl | 7-(diethylamino-CH$_2$CH$_2$—) | NH$_2$ |
| 7494. | —(NMeSO$_2$)-phenyl | 7-(1-pyrrolidinyl-CH$_2$CH$_2$—) | NH$_2$ |
| 7495. | —(NMeSO$_2$)-phenyl | 7-(azaperhydroepinyl-CH$_2$CH$_2$—) | NH$_2$ |
| 7496. | —(NMeSO$_2$)-phenyl | 7-[(3,5-dimethylpiperid-1-yl)—CH$_2$CH$_2$—) | NH$_2$ |
| 7497. | —(NMeSO$_2$)-phenyl | 7-[(4-methylpiperid-1-yl-CH$_2$CH$_2$—) | NH$_2$ |
| 7498. | —(NMeSO$_2$)-phenyl | 7-[(3-methylpiperid-1-yl-CH$_2$CH$_2$—)—] | NH$_2$ |
| 7499. | —(NMeSO$_2$)-phenyl | 7-[(2-methylpiperid-1-yl-CH$_2$CH$_2$—)—] | NH$_2$ |
| 7500. | —(NMeSO$_2$)-phenyl | 7-(1-piperidylcarbonyl) | NH$_2$ |
| 7501. | —(NMeSO$_2$)-phenyl | 7-[(4-methylpiperazin-1-yl)carbonyl] | NH$_2$ |
| 7502. | —(NMeSO$_2$)-phenyl | 7-(morpholin-4-ylcarbonyl) | NH$_2$ |
| 7503. | —(NMeSO$_2$)-phenyl | 7-(diethylaminocarbonyl) | NH$_2$ |

TABLE 11-continued

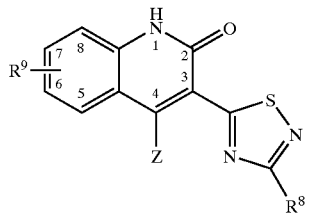

| # | R⁸ | R⁹ | Z |
|---|---|---|---|
| 7504. | —(NMeSO₂)-phenyl | 7-(1-pyrrolidinylcarbonyl) | NH₂ |
| 7505. | —(NMeSO₂)-phenyl | 7-(azaperhydroepinylcarbonyl) | NH₂ |
| 7506. | —(NMeSO₂)-phenyl | 7-[(3,5-dimethylpiperid-1-yl)carbonyl) | NH₂ |
| 7507. | —(NMeSO₂)-phenyl | 7-[(4-methylpiperid-1-ylcarbonyl) | NH₂ |
| 7508. | —(NMeSO₂)-phenyl | 7-[(3-methylpiperid-1-ylcarbonyl) | NH₂ |
| 7509. | —(NMeSO₂)-phenyl | 7-[(2-methylpiperid-1-ylcarbonyl) | NH₂ |
| 7510. | —(NMeSO₂)-phenyl | 7-[2-(dimethylamino)ethoxy] | NH₂ |
| 7511. | —(NMeSO₂)-phenyl | 7-[2-(methylamino)ethoxy] | NH₂ |
| 7512. | —(NMeSO₂)-phenyl | 7-[((2R)pyrrolidin-2-yl)methoxy] | NH₂ |
| 7513. | —(NMeSO₂)-phenyl | 7-[((2R)-1-methylpyrrolidin-2-yl)methoxy] | NH₂ |
| 7514. | —(NMeSO₂)-phenyl | 7-[2-(piperid-1-yl)ethoxy] | NH₂ |
| 7515. | —(NMeSO₂)-phenyl | 7-[2-(piperazin-1-yl)ethoxy] | NH₂ |
| 7516. | —(NMeSO₂)-phenyl | 7-[2-(morpholin-4-yl)ethoxy] | NH₂ |
| 7517. | —(NMeSO₂)-phenyl | 7-[2-(1-methyl(4-piperidyl))ethoxy] | NH₂ |
| 7518. | —(NMeSO₂)-phenyl | 7-[2-(1-methyl(4-piperidyl))methoxy] | NH₂ |
| 7519. | —(NMeSO₂)-phenyl | 7-(1-methyl(4-piperidyloxy)) | NH₂ |
| 7520. | —(NMeSO₂)-2-thienyl | 7-(piperid-1-yl-CH₂—) | H |
| 7521. | —(NMeSO₂)-2-thienyl | 7-(1-CH₃-piperazin-4-yl-CH₂—) | H |
| 7522. | —(NMeSO₂)-2-thienyl | 7-(morpholin-4-yl-CH₂—) | H |
| 7523. | —(NMeSO₂)-2-thienyl | 7-(diethylamino-CH₂—) | H |
| 7524. | —(NMeSO₂)-2-thienyl | 7-(1-pyrrolidinyl-CH₂—) | H |
| 7525. | —(NMeSO₂)-2-thienyl | 7-(azaperhydroepinyl-CH₂—) | H |
| 7526. | —(NMeSO₂)-2-thienyl | 7-[(3,5-dimethylpiperid-1-yl)—CH₂—] | H |
| 7527. | —(NMeSO₂)-2-thienyl | 7-[(4-methylpiperid-1-yl-CH₂—] | H |
| 7528. | —(NMeSO₂)-2-thienyl | 7-[(3-methylpiperid-1-yl-CH₂—] | H |
| 7529. | —(NMeSO₂)-2-thienyl | 7-[(2-methylpiperid-1-yl-CH₂—] | H |
| 7530. | —(NMeSO₂)-2-thienyl | 7-(piperid-1-yl-CH₂CH₂—) | H |
| 7531. | —(NMeSO₂)-2-thienyl | 7-(1-CH₃-piperazin-4-yl-CH₂CH₂—) | H |
| 7532. | —(NMeSO₂)-2-thienyl | 7-(morpholin-4-yl-CH₂CH₂—) | H |
| 7533. | —(NMeSO₂)-2-thienyl | 7-(diethylamino-CH₂CH₂—) | H |
| 7534. | —(NMeSO₂)-2-thienyl | 7-(1-pyrrolidinyl-CH₂CH₂—) | H |
| 7535. | —(NMeSO₂)-2-thienyl | 7-(azaperhydroepinyl-CH₂CH₂—) | H |
| 7536. | —(NMeSO₂)-2-thienyl | 7-[(3,5-dimethylpiperid-1-yl)—CH₂CH₂—) | H |
| 7537. | —(NMeSO₂)-2-thienyl | 7-[(4-methylpiperid-1-yl-CH₂CH₂—) | H |
| 7538. | —(NMeSO₂)-2-thienyl | 7-[(3-methylpiperid-1-yl-CH₂CH₂—)—] | H |
| 7539. | —(NMeSO₂)-2-thienyl | 7-[(2-methylpiperid-1-yl-CH₂CH₂—)—] | H |
| 7540. | —(NMeSO₂)-2-thienyl | 7-(1-piperidylcarbonyl) | H |
| 7541. | —(NMeSO₂)-2-thienyl | 7-[(4-methylpiperazin-1-yl)carbonyl] | H |
| 7542. | —(NMeSO₂)-2-thienyl | 7-(morpholin-4-ylcarbonyl) | H |
| 7543. | —(NMeSO₂)-2-thienyl | 7-(diethylaminocarbonyl) | H |
| 7544. | —(NMeSO₂)-2-thienyl | 7-(1-pyrrolidinylcarbonyl) | H |
| 7545. | —(NMeSO₂)-2-thienyl | 7-(azaperhydroepinylcarbonyl) | H |
| 7546. | —(NMeSO₂)-2-thienyl | 7-[(3,5-dimethylpiperid-1-yl)carbonyl) | H |
| 7547. | —(NMeSO₂)-2-thienyl | 7-[(4-methylpiperid-1-ylcarbonyl) | H |
| 7548. | —(NMeSO₂)-2-thienyl | 7-[(3-methylpiperid-1-ylcarbonyl) | H |
| 7549. | —(NMeSO₂)-2-thienyl | 7-[(2-methylpiperid-1-ylcarbonyl) | H |
| 7550. | —(NMeSO₂)-2-thienyl | 7-[2-(dimethylamino)ethoxy] | H |
| 7551. | —(NMeSO₂)-2-thienyl | 7-[2-(methylamino)ethoxy] | H |
| 7552. | —(NNeSO₂)-2-thienyl | 7-[((2-)pyrrolidin-2-yl)methoxy] | H |
| 7553. | —(NMeSO₂)-2-thienyl | 7-[((2R)-1-methylpyrrolidin-2-yl)methoxy] | H |
| 7554. | —(NMeSO₂)-2-thienyl | 7-[2-(piperid-1-yl)ethoxy] | H |
| 7555. | —(NMeSO₂)-2-thienyl | 7-[2-(piperazin-1-yl)ethoxy] | H |
| 7556. | —(NMeSO₂)-2-thienyl | 7-[2-(morpholin-4-yl)ethoxy] | H |
| 7557. | —(NMeSO₂)-2-thienyl | 7-[2-(1-methyl(4-piperidyl))ethoxy] | H |
| 7558. | —(NMeSO₂)-2-thienyl | 7-[2-(1-methyl(4-piperidyl))methoxy] | H |
| 7559. | —(NMeSO₂)-2-thienyl | 7-(1-methyl(4-piperidyloxy)) | H |
| 7560. | —(NMeSO₂)-2-thienyl | 7-(piperid-1-yl-CH₂—) | NH₂ |
| 7561. | —(NMeSO₂)-2-thienyl | 7-(1-CH₃-piperazin-4-yl-CH₂—) | NH₂ |
| 7562. | —(NMeSO₂)-2-thienyl | 7-(morpholin-4-yl-CH₂—) | NH₂ |
| 7563. | —(NMeSO₂)-2-thienyl | 7-(diethylamino-CH₂—) | NH₂ |
| 7564. | —(NMeSO₂)-2-thienyl | 7-(1-pyrrolidinyl-CH₂—) | NH₂ |
| 7565. | —(NMeSO₂)-2-thienyl | 7-(azaperhydroepinyl-CH₂—) | NH₂ |
| 7566. | —(NMeSO₂)-2-thienyl | 7-[(3,5-dimethylpiperid-1-yl)—CH₂—] | NH₂ |
| 7567. | —(NMeSO₂)-2-thienyl | 7-[(4-methylpiperid-1-yl-CH₂—] | NH₂ |
| 7568. | —(NMeSO₂)-2-thienyl | 7-[(3-methylpiperid-1-yl-CH₂—] | NH₂ |

TABLE 11-continued

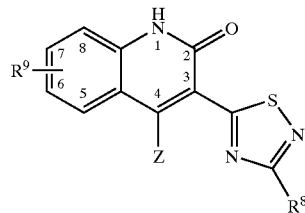

| # | R⁸ | R⁹ | Z |
|---|---|---|---|
| 7569. | —(NMeSO₂)-2-thienyl | 7-[(2-methylpiperid-1-yl-CH₂—] | NH₂ |
| 7570. | —(NMeSO₂)-2-thienyl | 7-(piperid-1-yl-CH₂CH₂—) | NH₂ |
| 7571. | —(NMeSO₂)-2-thienyl | 7-(1-CH₃-piperazin-4-yl-CH₂CH₂—) | NH₂ |
| 7572. | —(NMeSO₂)-2-thienyl | 7-(morpholin-4-yl-CH₂CH₂—) | NH₂ |
| 7573. | —(NMeSO₂)-2-thienyl | 7-(diethylamino-CH₂CH₂—) | NH₂ |
| 7574. | —(NMeSO₂)-2-thienyl | 7-(1-pyrrolidinyl-CH₂CH₂—) | NH₂ |
| 7575. | —(NMeSO₂)-2-thienyl | 7-(azaperhydroepinyl-CH₂CH₂—) | NH₂ |
| 7576. | —(NMeSO₂)-2-thienyl | 7-[(3,5-dimethylpiperid-1-yl)—CH₂CH₂—) | NH₂ |
| 7577. | —(NMeSO₂)-2-thienyl | 7-[(4-methylpiperid-1-yl-CH₂CH₂—) | NH₂ |
| 7578. | —(NMeSO₂)-2-thienyl | 7-[(3-methylpiperid-1-yl-CH₂CH₂—)—] | NH₂ |
| 7579. | —(NMeSO₂)-2-thienyl | 7-[(2-methylpiperid-1-yl-CH₂CH₂—)—] | NH₂ |
| 7580. | —(NMeSO₂)-2-thienyl | 7-(1-piperidylcarbonyl) | NH₂ |
| 7581. | —(NMeSO₂)-2-thienyl | 7-[(4-methylpiperazin-1-yl)carbonyl] | NH₂ |
| 7582. | —(NMeSO₂)-2-thienyl | 7-(morpholin-4-ylcarbonyl) | NH₂ |
| 7583. | —(NMeSO₂)-2-thienyl | 7-(diethylaminocarbonyl) | NH₂ |
| 7584. | —(NMeSO₂)-2-thienyl | 7-(1-pyrrolidinylcarbonyl) | NH₂ |
| 7585. | —(NMeSO₂)-2-thienyl | 7-(azaperhydroepinylcarbonyl) | NH₂ |
| 7586. | —(NMeSO₂)-2-thienyl | 7-(3,5-dimethylpiperid-1-yl)carbonyl) | NH₂ |
| 7587. | —(NMeSO₂)-2-thienyl | 7-[(4-methylpiperid-1-ylcarbonyl) | NH₂ |
| 7588. | —(NMeSO₂)-2-thienyl | 7-[(3-methylpiperid-1-ylcarbonyl) | NH₂ |
| 7589. | —(NMeSO₂)-2-thienyl | 7-[(2-methylpiperid-1-ylcarbonyl) | NH₂ |
| 7590. | —(NMeSO₂)-2-thienyl | 7-[2-(dimethylamino)ethoxy] | NH₂ |
| 7591. | —(NMeSO₂)-2-thienyl | 7-[2-(methylamino)ethoxy] | NH₂ |
| 7592. | —(NMeSO₂)-2-thienyl | 7-[((2R)pyrrolidin-2-yl)methoxy] | NH₂ |
| 7593. | —(NMeSO₂)-2-thienyl | 7-[((2R)-1-methylpyrrolidin-2-yl)methoxy] | NH₂ |
| 7594. | —(NMeSO₂)-2-thienyl | 7-[2-(piperid-1-yl)ethoxy] | NH₂ |
| 7595. | —(NMeSO₂)-2-thienyl | 7-[2-(piperazin-1-yl)ethoxy] | NH₂ |
| 7596. | —(NMeSO₂)-2-thienyl | 7-[2-(morpholin-4-yl)ethoxy] | NH₂ |
| 7597. | —(NMeSO₂)-2-thienyl | 7-[2-(1-methyl(4-piperidyl))ethoxy] | NH₂ |
| 7598. | —(NMeSO₂)-2-thienyl | 7-[2-(1-methyl(4-piperidyl))methoxy] | NH₂ |
| 7599. | —(NMeSO₂)-2-thienyl | 7-(1-methyl(4-piperidyloxy)) | NH₂ |
| 7600. | —(NMeSO₂)-2-pyridyl | 7-(piperid-1-yl-CH₂—) | H |
| 7601. | —(NMeSO₂)-2-pyridyl | 7-(1-CH₃-piperazin-4-yl-CH₂—) | H |
| 7602. | —(NMeSO₂)-2-pyridyl | 7-(morpholin-4-yl-CH₂—) | H |
| 7603. | —(NMeSO₂)-2-pyridyl | 7-(diethylamino-CH₂—) | H |
| 7604. | —(NMeSO₂)-2-pyridyl | 7-(1-pyrrolidinyl-CH₂—) | H |
| 7605. | —(NMeSO₂)-2-pyridyl | 7-(azaperhydroepinyl-CH₂—) | H |
| 7606. | —(NMeSO₂)-2-pyridyl | 7-[(3,5-dimethylpiperid-1-yl)—CH₂—] | H |
| 7607. | —(NMeSO₂)-2-pyridyl | 7-[(4-methylpiperid-1-yl-CH₂—] | H |
| 7608. | —(NMeSO₂)-2-pyridyl | 7-[(3-methylpiperid-1-yl-CH₂—] | H |
| 7609. | —(NMeSO₂)-2-pyridyl | 7-[(2-methylpiperid-1-yl-CH₂—] | H |
| 7610. | —(NMeSO₂)-2-pyridyl | 7-(piperid-1-yl-CH₂CH₂—) | H |
| 7611. | —(NMeSO₂)-2-pyridyl | 7-(1-CH₃-piperazin-4-yl-CH₂CH₂—) | H |
| 7612. | —(NMeSO₂)-2-pyridyl | 7-(morpholin-4-yl-CH₂CH₂—) | H |
| 7613. | —(NMeSO₂)-2-pyridyl | 7-(diethylamino-CH₂CH₂—) | H |
| 7614. | —(NMeSO₂)-2-pyridyl | 7-(1-pyrrolidinyl-CH₂CH₂—) | H |
| 7615. | —(NMeSO₂)-2-pyridyl | 7-(azaperhydroepinyl-CH₂CH₂—) | H |
| 7616. | —(NMeSO₂)-2-pyridyl | 7-[(3,5-dimethylpiperid-1-yl)—CH₂CH₂—) | H |
| 7617. | —(NMeSO₂)-2-pyridyl | 7-[(4-methylpiperid-1-yl-CH₂CH₂—) | H |
| 7618. | —(NMeSO₂)-2-pyridyl | 7-[(3-methylpiperid-1-yl-CH₂CH₂—)—] | H |
| 7619. | —(NMeSO₂)-2-pyridyl | 7-[(2-methylpiperid-1-yl-CH₂CH₂—)—] | H |
| 7620. | —(NMeSO₂)-2-pyridyl | 7-(1-piperidylcarbonyl) | H |
| 7621. | —(NMeSO₂)-2-pyridyl | 7-[(4-methylpiperazin-1-yl]carbonyl] | H |
| 7622. | —(NMeSO₂)-2-pyridyl | 7-(morpholin-4-ylcarbonyl) | H |
| 7623. | —(NMeSO₂)-2-pyridyl | 7-(diethylaminocarbonyl) | H |
| 7624. | —(NMeSO₂)-2-pyridyl | 7-(1-pyrrolidinylcarbonyl) | H |
| 7625. | —(NMeSO₂)-2-pyridyl | 7-(azaperhydroepinylcarbonyl] | H |
| 7626. | —(NMeSO₂)-2-pyridyl | 7-[(3,5-dimethylpiperid-1-yl)carbonyl) | H |
| 7627. | —(NMeSO₂)-2-pyridyl | 7-[(4-methylpiperid-1-ylcarbonyl) | H |
| 7628. | —(NMeSO₂)-2-pyridyl | 7-[(3-methylpiperid-1-ylcarbonyl) | H |
| 7629. | —(NMeSO₂)-2-pyridyl | 7-[(2-methylpiperid-1-ylcarbonyl) | H |
| 7630. | —(NMeSO₂)-2-pyridyl | 7-[2-(dimethylamino)ethoxy] | H |
| 7631. | —(NMeSO₂)-2-pyridyl | 7-[2-(methylamino)ethoxy] | H |
| 7632. | —(NMeSO₂)-2-pyridyl | 7-[((2R)pyrrolidin-2-yl)methoxy] | H |
| 7633. | —(NMeSO₂)-2-pyridyl | 7-[((2R)-1-methylpyrrolidin-2-yl)methoxy] | H |

TABLE 11-continued

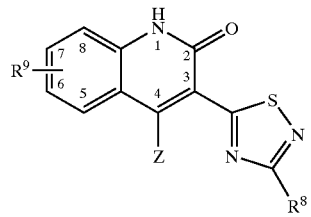

| # | R⁸ | R⁹ | Z |
|---|---|---|---|
| 7634. | —(NMeSO₂)-2-pyridyl | 7-[2-(piperid-1-yl)ethoxy] | H |
| 7635. | —(NMeSO₂)-2-pyridyl | 7-[2-(piperazin-1-yl)ethoxy] | H |
| 7636. | —(NMeSO₂)-2-pyridyl | 7-[2-(morpholin-4-yl)ethoxy] | H |
| 7637. | —(NMeSO₂)-2-pyridyl | 7-[2-(1-methyl(4-piperidyl))ethoxy] | H |
| 7638. | —(NMeSO₂)-2-pyridyl | 7-[2-(1-methyl(4-piperidyl))methoxy] | H |
| 7639. | —(NMeSO₂)-2-pyridyl | 7-(1-methyl(4-piperidyloxy)) | H |
| 7640. | —(NMeSO₂)-2-pyridyl | 7-(piperid-1-yl-CH₂—) | NH₂ |
| 7641. | —(NMeSO₂)-2-pyridyl | 7-(1-CH₃-piperazin-4-yl-CH₂—) | NH₂ |
| 7642. | —(NMeSO₂)-2-pyridyl | 7-(morpholin-4-yl-CH₂—) | NH₂ |
| 7643. | —(NMeSO₂)-2-pyridyl | 7-(diethylamino-CH₂—) | NH₂ |
| 7644. | —(NMeSO₂)-2-pyridyl | 7-(1-pyrrolidinyl-CH₂—) | NH₂ |
| 7645. | —(NMeSO₂)-2-pyridyl | 7-(azaperhydroepinyl-CH₂—) | NH₂ |
| 7646. | —(NMeSO₂)-2-pyridyl | 7-[(3,5-dimethylpiperid-1-yl)—CH₂—] | NH₂ |
| 7647. | —(NMeSO₂)-2-pyridyl | 7-[(4-methylpiperid-1-yl-CH₂—] | NH₂ |
| 7648. | —(NMeSO₂)-2-pyridyl | 7-[(3-methylpiperid-1-yl-CH₂—] | NH₂ |
| 7649. | —(NMeSO₂)-2-pyridyl | 7-[(2-methylpiperid-1-yl-CH₂—] | NH₂ |
| 7650. | —(NMeSO₂)-2-pyridyl | 7-(piperid-1-yl-CH₂CH₂—) | NH₂ |
| 7651. | —(NMeSO₂)-2-pyridyl | 7-(1-CH₃-piperazin-4-yl-CH₂CH₂—) | NH₂ |
| 7652. | —(NMeSO₂)-2-pyridyl | 7-(morpholin-4-yl-CH₂CH₂—) | NH₂ |
| 7653. | —(NMeSO₂)-2-pyridyl | 7-(diethylamino-CH₂CH₂—) | NH₂ |
| 7654. | —(NMeSO₂)-2-pyridyl | 7-(1-pyrrolidinyl-CH₂CH₂—) | NH₂ |
| 7655. | —(NMeSO₂)-2-pyridyl | 7-(azaperhydroepinyl-CH₂CH₂—) | NH₂ |
| 7656. | —(NMeSO₂)-2-pyridyl | 7-[(3,5-dimethylpiperid-1-yl)—CH₂CH₂—) | NH₂ |
| 7657. | —(NMeSO₂)-2-pyridyl | 7-[(4-methylpiperid-1-yl-CH₂CH₂—) | NH₂ |
| 7658. | —(NMeSO₂)-2-pyridyl | 7-[(3-methylpiperid-1-yl-CH₂CH₂—)—] | NH₂ |
| 7659. | —(NMeSO₂)-2-pyridyl | 7-[(2-methylpiperid-1-yl-CH₂CH₂—)—] | NH₂ |
| 7660. | —(NMeSO₂)-2-pyridyl | 7-(1-piperidylcarbonyl) | NH₂ |
| 7661. | —(NMeSO₂)-2-pyridyl | 7-[(4-methylpiperazin-1-yl)carbonyl) | NH₂ |
| 7662. | —(NMeSO₂)-2-pyridyl | 7-(morpholin-4-ylcarbonyl) | NH₂ |
| 7663. | —(NMeSO₂)-2-pyridyl | 7-(diethylaminocarbonyl) | NH₂ |
| 7664. | —(NMeSO₂)-2-pyridyl | 7-(1-pyrrolidinylcarbonyl) | NH₂ |
| 7665. | —(NMeSO₂)-2-pyridyl | 7-(azaperhydroepinylcarbonyl) | NH₂ |
| 7666. | —(NMeSO₂)-2-pyridyl | 7-[(3,5-dimethylpiperid-1-yl)carbonyl) | NH₂ |
| 7667. | —(NMeSO₂)-2-pyridyl | 7-(4-methylpiperid-1-ylcarbonyl) | NH₂ |
| 7668. | —(NMeSO₂)-2-pyridyl | 7-(3-methylpiperid-1-ylcarbonyl) | NH₂ |
| 7669. | —(NMeSO₂)-2-pyridyl | 7-(2-methylpiperid-1-ylcarbonyl) | NH₂ |
| 7670. | —(NMeSO₂)-2-pyridyl | 7-[2-(dimethylamino)ethoxy] | NH₂ |
| 7671. | —(NMeSO₂)-2-pyridyl | 7-[2-(methylamino)ethoxy] | NH₂ |
| 7672. | —(NMeSO₂)-2-pyridyl | 7-[((2R)pyrrolidin-2-yl)methoxy] | NH₂ |
| 7673. | —(NMeSO₂)-2-pyridyl | 7-[((2R)-1-methylpyrrolidin-2-yl)methoxy] | NH₂ |
| 7674. | —(NMeSO₂)-2-pyridyl | 7-[2-(piperid-1-yl)ethoxy] | NH₂ |
| 7675. | —(NMeSO₂)-2-pyridyl | 7-[2-(piperazin-1-yl)ethoxy] | NH₂ |
| 7676. | —(NMeSO₂)-2-pyridyl | 7-[2-(morpholin-4-yl)ethoxy] | NH₂ |
| 7677. | —(NMeSO₂)-2-pyridyl | 7-[2-(1-methyl(4-(piperidyl))ethoxy] | NH₂ |
| 7678. | —(NMeSO₂)-2-pyridyl | 7-[2-(1-methyl(4-piperidyl))methoxy] | NH₂ |
| 7679. | —(NMeSO₂)-2-pyridyl | 7-(1-methyl(4-piperidyloxy)) | NH₂ |
| 7680. | —(NMeSO₂)-3-pyridyl | 7-(piperid-1-yl-CH₂—) | H |
| 7681. | —(NMeSO₂)-3-pyridyl | 7-(1-CH₃-piperazin-4-yl-CH₂—) | H |
| 7682. | —(NMeSO₂)-3-pyridyl | 7-(morpholin-4-yl-CH₂—) | H |
| 7683. | —(NMeSO₂)-3-pyridyl | 7-(diethylamino-CH₂—) | H |
| 7684. | —(NMeSO₂)-3-pyridyl | 7-(1-pyrrolidinyl-CH₂—) | H |
| 7685. | —(NMeSO₂)-3-pyridyl | 7-(azaperhydroepinyl-CH₂—) | H |
| 7686. | —(NMeSO₂)-3-pyridyl | 7-[(3,5-dimethylpiperid-1-yl)—CH₂—] | H |
| 7687. | —(NMeSO₂)-3-pyridyl | 7-[(4-methylpiperid-1-yl-CH₂—] | H |
| 7688. | —(NMeSO₂)-3-pyridyl | 7-[(3-methylpiperid-1-yl-CH₂—] | H |
| 7689. | —(NMeSO₂)-3-pyridyl | 7-[(2-methylpiperid-1-yl-CH₂—] | H |
| 7690. | —(NMeSO₂)-3-pyridyl | 7-(piperid-1-yl-CH₂CH₂—) | H |
| 7691. | —(NMeSO₂)-3-pyridyl | 7-(1-CH₃-piperazin-4-yl-CH₂CH₂—) | H |
| 7692. | —(NMeSO₂)-3-pyridyl | 7-(morpholin-4-yl-CH₂CH₂—) | H |
| 7693. | —(NMeSO₂)-3-pyridyl | 7-(diethylamino-CH₂CH₂—) | H |
| 7694. | —(NMeSO₂)-3-pyridyl | 7-(1-pyrrolidinyl-CH₂CH₂—) | H |
| 7695. | —(NMeSO₂)-3-pyridyl | 7-(azaperhydroepinyl-CH₂CH₂—) | H |
| 7696. | —(NMeSO₂)-3-pyridyl | 7-[(3,5-dimethylpiperid-1-yl)—CH₂CH₂—) | H |
| 7697. | —(NMeSO₂)-3-pyridyl | 7-[(4-methylpiperid-1-yl-CH₂CH₂—) | H |
| 7698. | —(NMeSO₂)-3-pyridyl | 7-[(3-methylpiperid-1-yl-CH₂CH₂—)—] | H |

TABLE 11-continued

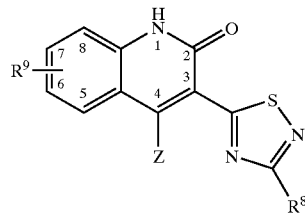

| # | R⁸ | R⁹ | Z |
|---|---|---|---|
| 7699. | —(NMeSO$_2$)-3-pyridyl | 7-[(2-methylpiperid-1-yl-CH$_2$CH$_2$—)—] | H |
| 7700. | —(NMeSO$_2$)-3-pyridyl | 7-(1-piperidylcarbonyl) | H |
| 7701. | —(NMeSO$_2$)-3-pyridyl | 7-[(4-methylpiperazin-1-yl)carbonyl] | H |
| 7702. | —(NMeSO$_2$)-3-pyridyl | 7-(morpholin-4-ylcarbonyl) | H |
| 7703. | —(NMeSO$_2$)-3-pyridyl | 7-(diethylaminocarbonyl) | H |
| 7704. | —(NMeSO$_2$)-3-pyridyl | 7-(1-pyrrolidinylcarbonyl) | H |
| 7705. | —(NMeSO$_2$)-3-pyridyl | 7-(azaperhydroepinylcarbonyl) | H |
| 7706. | —(NMeSO$_2$)-3-pyridyl | 7-[(3,5-dimethylpiperid-1-yl)carbonyl) | H |
| 7707. | —(NMeSO$_2$)-3-pyridyl | 7-[(4-methylpiperid-1-ylcarbonyl) | H |
| 7708. | —(NMeSO$_2$)-3-pyridyl | 7-[(3-methylpiperid-1-ylcarbonyl) | H |
| 7709. | —(NMeSO$_2$)-3-pyridyl | 7-[(2-methylpiperid-1-ylcarbonyl) | H |
| 7710. | —(NMeSO$_2$)-3-pyridyl | 7-[2-(dimethylamino)ethoxy] | H |
| 7711. | —(NMeSO$_2$)-3-pyridyl | 7-[2-(methylamino)ethoxy] | H |
| 7712. | —(NMeSO$_2$)-3-pyridyl | 7-[((2R)pyrrolidin-2-yl)methoxy] | H |
| 7713. | —(NMeSO$_2$)-3-pyridyl | 7-[((2R)-1-methylpyrrolidin-2-yl)methoxy] | H |
| 7714. | —(NMeSO$_2$)-3-pyridyl | 7-[2-(piperid-1-yl)ethoxy] | H |
| 7715. | —(NMeSO$_2$)-3-pyridyl | 7-[2-(piperazin-1-yl)ethoxy] | H |
| 7716. | —(NMeSO$_2$)-3-pyridyl | 7-[2-(morpholin-4-yl)ethoxy] | H |
| 7717. | —(NMeSO$_2$)-3-pyridyl | 7-[2-(1-methyl(4-piperidyl))ethoxy] | H |
| 7718. | —(NMeSO$_2$)-3-pyridyl | 7-[2-(1-methyl(4-piperidyl))methoxy] | H |
| 7719. | —(NMeSO$_2$)-3-pyridyl | 7-(1-methyl(4-piperidyloxy)) | H |
| 7720. | —(NMeSO$_2$)-3-pyridyl | 7-(piperid-1-yl-CH$_2$—) | NH$_2$ |
| 7721. | —(NMeSO$_2$)-3-pyridyl | 7-(1-CH$_3$-piperazin-4-yl-CH$_2$—) | NH$_2$ |
| 7722. | —(NMeSO$_2$)-3-pyridyl | 7-(morpholin-4-yl-CH$_2$—) | NH$_2$ |
| 7723. | —(NMeSO$_2$)-3-pyridyl | 7-(diethylamino-CH$_2$—) | NH$_2$ |
| 7724. | —(NMeSO$_2$)-3-pyridyl | 7-(1-pyrrolidinyl-CH$_2$—) | NH$_2$ |
| 7725. | —(NMeSO$_2$)-3-pyridyl | 7-(azaperhydroepinyl-CH$_2$—) | NH$_2$ |
| 7726. | —(NMeSO$_2$)-3-pyridyl | 7-[(3,5-dimethylpiperid-1-yl)—CH$_2$—] | NH$_2$ |
| 7727. | —(NMeSO$_2$)-3-pyridyl | 7-[(4-methylpiperid-1-yl-CH$_2$—] | NH$_2$ |
| 7728. | —(NMeSO$_2$)-3-pyridyl | 7-[(3-methylpiperid-1-yl-CH$_2$—] | NH$_2$ |
| 7729. | —(NMeSO$_2$)-3-pyridyl | 7-[(2-methylpiperid-1-yl-CH$_2$—] | NH$_2$ |
| 7730. | —(NMeSO$_2$)-3-pyridyl | 7-(piperid-1-yl-CH$_2$CH$_2$—) | NH$_2$ |
| 7731. | —(NMeSO$_2$)-3-pyridyl | 7-(1-CH$_3$-piperazin-4-yl-CH$_2$CH$_2$—) | NH$_2$ |
| 7732. | —(NMeSO$_2$)-3-pyridyl | 7-(morpholin-4-yl-CH$_2$CH$_2$—) | NH$_2$ |
| 7733. | —(NMeSO$_2$)-3-pyridyl | 7-(diethylamino-CH$_2$CH$_2$—) | NH$_2$ |
| 7734. | —(NMeSO$_2$)-3-pyridyl | 7-(1-pyrrolidinyl-CH$_2$CH$_2$—) | Nh$_2$ |
| 7735. | —(NMeSO$_2$)-3-pyridyl | 7-(azaperhydroepinyl-CH$_2$CH$_2$—) | NH$_2$ |
| 7736. | —(NMeSO$_2$)-3-pyridyl | 7-[(3,5-dimethylpiperid-1-yl)—CH$_2$CH$_2$—) | NH$_2$ |
| 7737. | —(NMeSO$_2$)-3-pyridyl | 7-[(4-methylpiperid-1-yl-CH$_2$CH$_2$—) | NH$_2$ |
| 7738. | —(NMeSO$_2$)-3-pyridyl | 7-[(3-methylpiperid-1-yl-CH$_2$CH$_2$—)—] | NH$_2$ |
| 7739. | —(NMeSO$_2$)-3-pyridyl | 7-[(2-methylpiperid-1-yl-CH$_2$CH$_2$—)—] | NH$_2$ |
| 7740. | —(NMeSO$_2$)-3-pyridyl | 7-(1-piperidylcarbonyl) | NH$_2$ |
| 7741. | —(NMeSO$_2$)-3-pyridyl | 7-[(4-methylpiperazin-1-yl)carbonyl] | NH$_2$ |
| 7742. | —(NMeSO$_2$)-3-pyridyl | 7-(morpholin-4-ylcarbonyl) | NH$_2$ |
| 7743. | —(NMeSO$_2$)-3-pyridyl | 7-(diethylaminocarbonyl) | NH$_2$ |
| 7744. | —(NMeSO$_2$)-3-pyridyl | 7-(1-pyrrolidinylcarbonyl) | NH$_2$ |
| 7745. | —(NMeSO$_2$)-3-pyridyl | 7-(azaperhydroepinylcarbonyl) | NH$_2$ |
| 7746. | —(NMeSO$_2$)-3-pyridyl | 7-[(3,5-dimethylpiperid-1-yl)carbonyl) | NH$_2$ |
| 7747. | —(NMeSO$_2$)-3-pyridyl | 7-[(4-methylpiperid-1-ylcarbonyl) | NH$_2$ |
| 7748. | —(NMeSO$_2$)-3-pyridyl | 7-[(3-methylpiperid-1-ylcarbonyl) | NH$_2$ |
| 7749. | —(NMeSO$_2$)-3-pyridyl | 7-[(2-methylpiperid-1-ylcarbonyl) | NH$_2$ |
| 7750. | —(NMeSO$_2$)-3-pyridyl | 7-[2-(dimethylamino)ethoxy] | NH$_2$ |
| 7751. | —(NMeSO$_2$)-3-pyridyl | 7-[2-(methylamino)ethoxy] | NH$_2$ |
| 7752. | —(NMeSO$_2$)-3-pyridyl | 7-[((2R)pyrrolidin-2-yl)methoxy] | NH$_2$ |
| 7753. | —(NMeSO$_2$)-3-pyridyl | 7-[((2R)-1-methylpyrrolidin-2-yl)methoxy] | NH$_2$ |
| 7754. | —(NMeSO$_2$)-3-pyridyl | 7-[2-(piperid-1-yl)ethoxy] | NH$_2$ |
| 7755. | —(NMeSO$_2$)-3-pyridyl | 7-[2-(piperazin-1-yl)ethoxy] | NH$_2$ |
| 7756. | —(NMeSO$_2$)-3-pyridyl | 7-[2-(morpholin-4-yl)ethoxy] | NH$_2$ |
| 7757. | —(NMeSO$_2$)-3-pyridyl | 7-[2-(1-methyl(4-piperidyl))ethoxy] | NH$_2$ |
| 7758. | —(NMeSO$_2$)-3-pyridyl | 7-[2-(1-methyl(4-piperidyl))methoxy] | NH$_2$ |
| 7759. | —(NMeSO$_2$)-3-pyridyl | 7-(1-methyl(4-piperidyloxy)) | NH$_2$ |
| 7760. | —(NMeSO$_2$)-4-pyridyl | 7-(piperid-1-yl-CH$_2$—) | H |
| 7761. | —(NMeSO$_2$)-4-pyridyl | 7-(1-CH$_3$-piperazin-4-yl-CH$_2$—) | H |
| 7762. | —(NMeSO$_2$)-4-pyridyl | 7-(morpholin-4-yl-CH$_2$—) | H |
| 7763. | —(NMeSO$_2$)-4-pyridyl | 7-(diethylamino-CH$_2$—) | H |

TABLE 11-continued

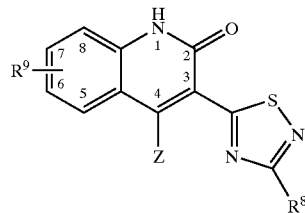

| # | R8 | R9 | Z |
|---|---|---|---|
| 7764. | —(NMeSO$_2$)-4-pyridyl | 7-(1-pyrrolidinyl-CH$_2$—) | H |
| 7765. | —(NMeSO$_2$)-4-pyridyl | 7-(azaperhydroepinyl-CH$_2$—) | H |
| 7766. | —(NMeSO$_2$)-4-pyridyl | 7-[(3,5-dimethylpiperid-1-yl)—CH$_2$—] | H |
| 7767. | —(NMeSO$_2$)-4-pyridyl | 7-[(4-methylpiperid-1-yl-CH$_2$—] | H |
| 7768. | —(NMeSO$_2$)-4-pyridyl | 7-[(3-methylpiperid-1-yl-CH$_2$—] | H |
| 7769. | —(NMeSO$_2$)-4-pyridyl | 7-[(2-methylpiperid-1-yl-CH$_2$—] | H |
| 7770. | —(NMeSO$_2$)-4-pyridyl | 7-(piperid-1-yl-CH$_2$CH$_2$—) | H |
| 7771. | —(NMeSO$_2$)-4-pyridyl | 7-(1-CH$_3$-piperazin-4-yl-CH$_2$CH$_2$—) | H |
| 7772. | —(NMeSO$_2$)-4-pyridyl | 7-(morpholin-4-yl-CH$_2$CH$_2$—) | H |
| 7773. | —(NMeSO$_2$)-4-pyridyl | 7-(diethylamino-CH$_2$CH$_2$—) | H |
| 7774. | —(NMeSO$_2$)-4-pyridyl | 7-(1-pyrrolidinyl-CH$_2$CH$_2$—) | H |
| 7775. | —(NMeSO$_2$)-4-pyridyl | 7-(azaperhydroepinyl-CH$_2$CH$_2$—) | H |
| 7776. | —(NMeSO$_2$)-4-pyridyl | 7-[(3,5-dimethylpiperid-1-yl)—CH$_2$CH$_2$—) | H |
| 7777. | —(NMeSO$_2$)-4-pyridyl | 7-[(4-methylpiperid-1-yl-CH$_2$CH$_2$—) | H |
| 7778. | —(NMeSO$_2$)-4-pyridyl | 7-[(3-methylpiperid-1-yl-CH$_2$CH$_2$—)—] | H |
| 7779. | —(NMeSO$_2$)-4-pyridyl | 7-[(2-methylpiperid-1-yl-CH$_2$CH$_2$—)—] | H |
| 7780. | —(NMeSO$_2$)-4-pyridyl | 7-(1-piperidylcarbonyl) | H |
| 7781. | —(NMeSO$_2$)-4-pyridyl | 7-[(4-methylpiperazin-1-yl)carbonyl] | H |
| 7782. | —(NMeSO$_2$)-4-pyridyl | 7-(morpholin-4-ylcarbonyl) | H |
| 7783. | —(NMeSO$_2$)-4-pyridyl | 7-(diethylaminocarbonyl) | H |
| 7784. | —(NMeSO$_2$)-4-pyridyl | 7-(1-pyrrolidinylcarbonyl) | H |
| 7785. | —(NMeSO$_2$)-4-pyridyl | 7-(azaperhydroepinylcarbonyl) | H |
| 7786. | —(NMeSO$_2$)-4-pyridyl | 7-[(3,5-dimethylpiperid-1-yl)carbonyl) | H |
| 7787. | —(NMeSO$_2$)-4-pyridyl | 7-[(4-methylpiperid-1-ylcarbonyl) | H |
| 7788. | —(NMeSO$_2$)-4-pyridyl | 7-[(3-methylpiperid-1-ylcarbonyl) | H |
| 7789. | —(NMeSO$_2$)-4-pyridyl | 7-[(2-methylpiperid-1-ylcarbonyl) | H |
| 7790. | —(NMeSO$_2$)-4-pyridyl | 7-[2-(dimethylamino)ethoxy] | H |
| 7791. | —(NMeSO$_2$)-4-pyridyl | 7-[2-(methylamino)ethoxy] | H |
| 7792. | —(NMeSO$_2$)-4-pyridyl | 7-[((2R)pyrrolidin-2-yl)methoxy] | H |
| 7793. | —(NMeSO$_2$)-4-pyridyl | 7-[((2R)-1-methylpyrrolidin-2-yl)methoxy] | H |
| 7794. | —(NMeSO$_2$)-4-pyridyl | 7-[2-(piperid-1-yl)ethoxy] | H |
| 7795. | —(NMeSO$_2$)-4-pyridyl | 7-[2-(piperazin-1-yl)ethoxy] | H |
| 7796. | —(NMeSO$_2$)-4-pyridyl | 7-[2-(morpholin-4-yl)ethoxy] | H |
| 7797. | —(NMeSO$_2$)-4-pyridyl | 7-[2-(1-methyl(4-piperidyl))ethoxy] | H |
| 7798. | —(NMeSO$_2$)-4-pyridyl | 7-[2-(1-methyl(4-piperidyl))methoxy] | H |
| 7799. | —(NMeSO$_2$)-4-pyridyl | 7-(1-methyl(4-piperidyloxy)) | H |
| 7800. | —(NMeSO$_2$)-4-pyridyl | 7-(piperid-1-yl-CH$_2$—) | NH$_2$ |
| 7801. | —(NMeSO$_2$)-4-pyridyl | 7-(1-CH$_3$-piperazin-4-yl-CH$_2$—) | NH$_2$ |
| 7802. | —(NMeSO$_2$)-4-pyridyl | 7-(morpholin-4-yl-CH$_2$—) | NH$_2$ |
| 7803. | —(NMeSO$_2$)-4-pyridyl | 7-(diethylamino-CH$_2$—) | NH$_2$ |
| 7804. | —(NMeSO$_2$)-4-pyridyl | 7-(1-pyrrolidinyl-CH$_2$—) | NH$_2$ |
| 7805. | —(NMeSO$_2$)-4-pyridyl | 7-(azaperhydroepinyl-CH$_2$—) | NH$_2$ |
| 7806. | —(NMeSO$_2$)-4-pyridyl | 7-[(3,5-dimethylpiperid-1-yl)—CH$_2$—] | NH$_2$ |
| 7807. | —(NMeSO$_2$)-4-pyridyl | 7-[(4-methylpiperid-1-yl-CH$_2$—] | NH$_2$ |
| 7808. | —(NMeSO$_2$)-4-pyridyl | 7-[(3-methylpiperid-1-yl-CH$_2$—] | NH$_2$ |
| 7809. | —(NMeSO$_2$)-4-pyridyl | 7-[(2-methylpiperid-1-yl-CH$_2$—] | NH$_2$ |
| 7810. | —(NMeSO$_2$)-4-pyridyl | 7-(piperid-1-yl-CH$_2$CH$_2$—) | NH$_2$ |
| 7811. | —(NMeSO$_2$)-4-pyridyl | 7-(1-CH$_3$-piperazin-4-yl-CH$_2$CH$_2$—) | NH$_2$ |
| 7812. | —(NMeSO$_2$)-4-pyridyl | 7-(morpholin-4-yl-CH$_2$CH$_2$—) | NH$_2$ |
| 7813. | —(NMeSO$_2$)-4-pyridyl | 7-(diethylamino-CH$_2$CH$_2$—) | NH$_2$ |
| 7814. | —(NMeSO$_2$)-4-pyridyl | 7-(1-pyrrolidinyl-CH$_2$CH$_2$—) | NH$_2$ |
| 7815. | —(NMeSO$_2$)-4-pyridyl | 7-(azaperhydroepinyl-CH$_2$CH$_2$—) | NH$_2$ |
| 7816. | —(NMeSO$_2$)-4-pyridyl | 7-[(3,5-dimethylpiperid-1-yl)—CH$_2$CH$_2$—) | NH$_2$ |
| 7817. | —(NMeSO$_2$)-4-pyridyl | 7-[(4-methylpiperid-1-yl-CH$_2$CH$_2$—) | NH$_2$ |
| 7818. | —(NMeSO$_2$)-4-pyridyl | 7-[(3-methylpiperid-1-yl-CH$_2$CH$_2$—)—] | NH$_2$ |
| 7819. | —(NMeSO$_2$)-4-pyridyl | 7-[(2-methylpiperid-1-yl-CH$_2$CH$_2$—)—] | NH$_2$ |
| 7820. | —(NMeSO$_2$)-4-pyridyl | 7-(1-piperidylcarbonyl) | NH$_2$ |
| 7821. | —(NMeSO$_2$)-4-pyridyl | 7-[(4-methylpiperazin-1-yl)carbonyl] | NH$_2$ |
| 7822. | —(NMeSO$_2$)-4-pyridyl | 7-(morpholin-4-ylcarbonyl) | NH$_2$ |
| 7823. | —(NMeSO$_2$)-4-pyridyl | 7-(diethylaminocarbonyl) | NH$_2$ |
| 7824. | —(NMeSO$_2$)-4-pyridyl | 7-(1-pyrrolidinylcarbonyl) | NH$_2$ |
| 7825. | —(NMeSO$_2$)-4-pyridyl | 7-(azaperhydroepinylcarbonyl) | NH$_2$ |
| 7826. | —(NMeSO$_2$)-4-pyridyl | 7-[(3,5-dimethylpiperid-1-yl)carbonyl) | NH$_2$ |
| 7827. | —(NMeSO$_2$)-4-pyridyl | 7-[(4-methylpiperid-1-ylcarbonyl) | NH$_2$ |
| 7828. | —(NMeSO$_2$)-4-pyridyl | 7-[(3-methylpiperid-1-ylcarbonyl) | NH$_2$ |

TABLE 11-continued

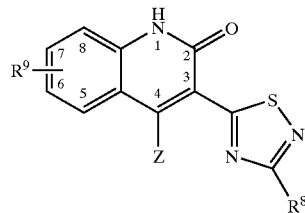

| # | R⁸ | R⁹ | Z |
|---|---|---|---|
| 7829. | —(NMeSO₂)-4-pyridyl | 7-[(2-methylpiperid-1-ylcarbonyl) | NH₂ |
| 7830. | —(NMeSO₂)-4-pyridyl | 7-[2-(dimethylamino)ethoxy] | NH₂ |
| 7831. | —(NMeSO₂)-4-pyridyl | 7-[2-(methylamino)ethoxy] | NH₂ |
| 7832. | —(NMeSO₂)-4-pyridyl | 7-[((2R)pyrrolidin-2-yl)methoxy] | NH₂ |
| 7833. | —(NMeSO₂)-4-pyridyl | 7-[((2R)-1-methylpyrrolidin-2-yl)methoxy] | NH₂ |
| 7834. | —(NMeSO₂)-4-pyridyl | 7-[2-(piperid-1-yl)ethoxy] | NH₂ |
| 7835. | —(NMeSO₂)-4-pyridyl | 7-[2-(piperazin-1-yl)ethoxy] | NH₂ |
| 7836. | —(NMeSO₂)-4-pyridyl | 7-[2-(morpholin-4-yl)ethoxy] | NH₂ |
| 7837. | —(NMeSO₂)-4-pyridyl | 7-[2-(1-methyl(4-piperidyl))ethoxy] | NH₂ |
| 7838. | —(NMeSO₂)-4-pyridyl | 7-[2-(1-methyl(4-piperidyl))methoxy] | NH₂ |
| 7839. | —(NMeSO₂)-4-pyridyl | 7-(1-methyl(4-piperidyloxy)) | NH₂ |

TABLE 12

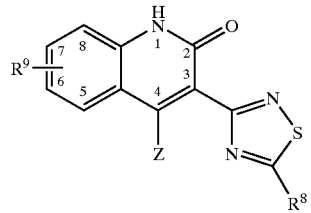

| # | R⁸ | R⁹ | Z |
|---|---|---|---|
| 7840. | 4-pyridyl | 7-(piperid-1-yl-CH₂—) | H |
| 7841. | 4-pyridyl | 7-(1-CH₃-piperazin-4-yl-CH₂—) | H |
| 7842. | 4-pyridyl | 7-(morpholin-4-yl-CH₂—) | H |
| 7843. | 4-pyridyl | 7-(diethylamino-CH₂—) | H |
| 7844. | 4-pyridyl | 7-(1-pyrrolidinyl-CH₂—) | H |
| 7845. | 4-pyridyl | 7-(azaperhydroepinyl-CH₂—) | H |
| 7846. | 4-pyridyl | 7-[(3,5-dimethylpiperid-1-yl)—CH₂—] | H |
| 7847. | 4-pyridyl | 7-[(4-methylpiperid-1-yl-CH₂—] | H |
| 7848. | 4-pyridyl | 7-[(3-methylpiperid-1-yl-CH₂—] | H |
| 7849. | 4-pyridyl | 7-[(2-methylpiperid-1-yl-CH₂—] | H |
| 7850. | 4-pyridyl | 7-(piperid-1-yl-CH₂CH₂—) | H |
| 7851. | 4-pyridyl | 7-(1-CH₃-piperazin-4-yl-CH₂CH₂—) | H |
| 7852. | 4-pyridyl | 7-(morpholin-4-yl-CH₂CH₂—) | H |
| 7853. | 4-pyridyl | 7-(diethylamino-CH₂CH₂—) | H |
| 7854. | 4-pyridyl | 7-(1-pyrrolidinyl-CH₂CH₂—) | H |
| 7855. | 4-pyridyl | 7-(azaperhydroepinyl-CH₂CH₂—) | H |
| 7856. | 4-pyridyl | 7-[(3,5-dimethylpiperid-1-yl)—CH₂CH₂—] | H |
| 7857. | 4-pyridyl | 7-[(4-methylpiperid-1-yl-CH₂CH₂—) | H |
| 7858. | 4-pyridyl | 7-[(3-methylpiperid-1-yl-CH₂CH₂—)—] | H |
| 7859. | 4-pyridyl | 7-[(2-methylpiperid-1-yl-CH₂CH₂—)—] | H |
| 7860. | 4-pyridyl | 7-(1-piperidylcarbonyl) | H |
| 7861. | 4-pyridyl | 7-[(4-methylpiperazin-1-yl)carbonyl] | H |
| 7862. | 4-pyridyl | 7-(morpholin-4-ylcarbonyl) | H |
| 7863. | 4-pyridyl | 7-(diethylaminocarbonyl) | H |
| 7864. | 4-pyridyl | 7-(1-pyrrolidinylcarbonyl) | H |
| 7865. | 4-pyridyl | 7-(azaperhydroepinylcarbonyl) | H |
| 7866. | 4-pyridyl | 7-[(3,5-dimethylpiperid-1-yl)carbonyl) | H |
| 7867. | 4-pyridyl | 7-[(4-methylpiperid-1-ylcarbonyl) | H |
| 7868. | 4-pyridyl | 7-[(3-methylpiperid-1-ylcarbonyl) | H |
| 7869. | 4-pyridyl | 7-[(2-methylpiperid-1-ylcarbonyl) | H |
| 7870. | 4-pyridyl | 7-[2-(dimethylamino)ethoxy] | H |
| 7871. | 4-pyridyl | 7-[2-(methylamino)ethoxy] | H |
| 7872. | 4-pyridyl | 7-[((2R)pyrrolidin-2-yl)methoxy] | H |
| 7873. | 4-pyridyl | 7-[((2R)-1-methylpyrrolidin-2-yl)methoxy] | H |
| 7874. | 4-pyridyl | 7-[2-(piperid-1-yl)ethoxy] | H |
| 7875. | 4-pyridyl | 7-[2-(piperazin-1-yl)ethoxy] | H |

TABLE 12-continued

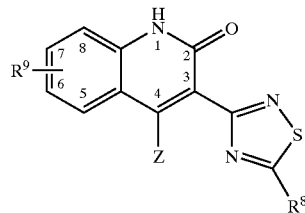

| # | R[8] | R[9] | Z |
|---|------|------|---|
| 7876. | 4-pyridyl | 7-[2-(morpholin-4-yl)ethoxy] | H |
| 7877. | 4-pyridyl | 7-[2-(1-methyl(4-piperidyl))ethoxy] | H |
| 7878. | 4-pyridyl | 7-[2-(1-methyl(4-piperidyl))methoxy] | H |
| 7879. | 4-pyridyl | 7-(1-methyl(4-piperidyloxy)) | H |
| 7880. | 4-pyridyl | 7-(piperid-1-yl-CH$_2$—) | NH$_2$ |
| 7881. | 4-pyridyl | 7-(1-CH$_3$-piperazin-4-yl-CH$_2$—) | NH$_2$ |
| 7882. | 4-pyridyl | 7-(morpholin-4-yl-CH$_2$—) | NH$_2$ |
| 7883. | 4-pyridyl | 7-(diethylamino-CH$_2$—) | NH$_2$ |
| 7884. | 4-pyridyl | 7-(1-pyrrolidinyl-CH$_2$—) | NH$_2$ |
| 7885. | 4-pyridyl | 7-(azaperhydroepinyl-CH$_2$—) | NH$_2$ |
| 7886. | 4-pyridyl | 7-[(3,5-dimethylpiperid-1-yl)—CH$_2$—] | NH$_2$ |
| 7887. | 4-pyridyl | 7-[(4-methylpiperid-1-yl-CH$_2$—] | NH$_2$ |
| 7888. | 4-pyridyl | 7-[(3-methylpiperid-1-yl-CH$_2$—] | NH$_2$ |
| 7889. | 4-pyridyl | 7-[(2-methylpiperid-1-yl-CH$_2$—] | NH$_2$ |
| 7890. | 4-pyridyl | 7-(piperid-1-yl-CH$_2$CH$_2$—) | NH$_2$ |
| 7891. | 4-pyridyl | 7-(1-CH$_3$-piperazin-4-yl-CH$_2$CH$_2$—) | NH$_2$ |
| 7892. | 4-pyridyl | 7-(morpholin-4-yl-CH$_2$CH$_2$—) | NH$_2$ |
| 7893. | 4-pyridyl | 7-(diethylamino-CH$_2$CH$_2$—) | NH$_2$ |
| 7894. | 4-pyridyl | 7-(1-pyrrolidinyl-CH$_2$CH$_2$—) | NH$_2$ |
| 7895. | 4-pyridyl | 7-(azaperhydroepinyl-CH$_2$CH$_2$—) | NH$_2$ |
| 7896. | 4-pyridyl | 7-[(3,5-dimethylpiperid-1-yl)—CH$_2$CH$_2$—) | NH$_2$ |
| 7897. | 4-pyridyl | 7-[(4-methylpiperid-1-yl-CH$_2$CH$_2$—) | NH$_2$ |
| 7898. | 4-pyridyl | 7-[(3-methylpiperid-1-yl-CH$_2$CH$_2$—)—] | NH$_2$ |
| 7899. | 4-pyridyl | 7-[(2-methylpiperid-1-yl-CH$_2$CH$_3$—)—] | NH$_2$ |
| 7900. | 4-pyridyl | 7-(1-piperidylcarbonyl) | NH$_2$ |
| 7901. | 4-pyridyl | 7-[(4-methylpiperazin-1-yl)carbonyl] | NH$_2$ |
| 7902. | 4-pyridyl | 7-(morpholin-4-ylcarbonyl) | NH$_2$ |
| 7903. | 4-pyridyl | 7-(diethylaminocarbonyl) | NH$_2$ |
| 7904. | 4-pyridyl | 7-(1-pyrrolidinylcarbonyl) | NH$_2$ |
| 7905. | 4-pyridyl | 7-(azaperhydroepinylcarbonyl) | NH$_2$ |
| 7906. | 4-pyridyl | 7-[(3,5-dimethylpiperid-1-yl)carbonyl) | NH$_2$ |
| 7907. | 4-pyredyl | 7-[(4-methylpiperid-1-ylcarbonyl) | NH$_2$ |
| 7908. | 4-pyridyl | 7-[(3-methylpiperid-1-ylcarbonyl) | NH$_2$ |
| 7909. | 4-pyridyl | 7-[(2-methylpiperid-1-ylcarbonyl) | NH$_2$ |
| 7910. | 4-pyridyl | 7-[2-(dimethylamino)ethoxy] | NH$_2$ |
| 7911. | 4-pyridyl | 7-[2-(methylamino)ethoxy] | NH$_2$ |
| 7912. | 4-pyridyl | 7-[((2R)pyrrolidin-2-yl)methoxy] | NH$_2$ |
| 7913. | 4-pyridyl | 7-[((2R)-1-methylpyrrolidin-2-yl)methoxy] | NH$_2$ |
| 7914. | 4-pyridyl | 7-[2-(piperid-1-yl)ethoxy] | NH$_2$ |
| 7915. | 4-pyridyl | 7-[2-(piperazin-1-yl)ethoxy] | NH$_2$ |
| 7916. | 4-pyridyl | 7-[2-(morpholin-4-yl)ethoxy] | NH$_2$ |
| 7917. | 4-pyridyl | 7-[2-(1-methyl(4-piperidyl))ethoxy] | NH$_2$ |
| 7918. | 4-pyridyl | 7-[2-(1-methyl(4-piperidyl))methoxy] | NH$_2$ |
| 7919. | 4-pyridyl | 7-(1-methyl(4-piperidyloxy)) | NH$_2$ |
| 7920. | —(CH$_2$SO$_2$)-phenyl | 7-(piperid-1-yl-CH$_2$—) | H |
| 7921. | —(CH$_2$SO$_2$)-phenyl | 7-(1-CH$_3$-piperazin-4-yl-CH$_2$—) | H |
| 7922. | —(CH$_2$SO$_2$)-phenyl | 7-(morpholin-4-yl-CH$_2$—) | H |
| 7923. | —(CH$_2$SO$_2$)-phenyl | 7-(diethylamino-CH$_2$—) | H |
| 7924. | —(CH$_2$SO$_2$)-phenyl | 7-(1-pyrrolidinyl-CH$_2$—) | H |
| 7925. | —(CH$_2$SO$_2$)-phenyl | 7-(azaperhydroepinyl-CH$_2$—) | H |
| 7926. | —(CH$_2$SO$_2$)-phenyl | 7-[(3,5-dimethylpiperid-1-yl)—CH$_2$—] | H |
| 7927. | —(CH$_2$SO$_2$)-phenyl | 7-[(4-methylpiperid-1-yl-CH$_2$—] | H |
| 7928. | —(CH$_2$SO$_2$)-phenyl | 7-[(3-methylpiperid-1-yl-CH$_2$—] | H |
| 7929. | —(CH$_2$SO$_2$)-phenyl | 7-[(2-methylpiperid-1-yl-CH$_2$—] | H |
| 7930. | —(CH$_2$SO$_2$)-phenyl | 7-(piperid-1-yl-CH$_2$CH$_2$—) | H |
| 7931. | —(CH$_2$SO$_2$)-phenyl | 7-(1-CH$_3$-piperazin-4-yl-CH$_2$CH$_2$—) | H |
| 7932. | —(CH$_2$SO$_2$)-phenyl | 7-(morpholin-4-yl-CH$_2$CH$_2$—) | H |
| 7933. | —(CH$_2$SO$_2$)-phenyl | 7-(diethylamino-CH$_2$CH$_2$—) | H |
| 7934. | —(CH$_2$SO$_2$)-phenyl | 7-(1-pyrrolidinyl-CH$_2$CH$_2$—) | H |
| 7935. | —(CH$_2$SO$_2$)-phenyl | 7-(azaperhydroepinyl-CH$_2$CH$_2$—) | H |
| 7936. | —(CH$_2$SO$_2$)-phenyl | 7-[(3,5-dimethylpiperid-1-yl)—CH$_2$CH$_2$—) | H |
| 7937. | —(CH$_2$SO$_2$)-phenyl | 7-[(4-methylpiperid-1-yl-CH$_2$CH$_2$—) | H |
| 7938. | —(CH$_2$SO$_2$)-phenyl | 7-[(3-methylpiperid-1-yl-CH$_2$CH$_2$—)—] | H |
| 7939. | —(CH$_2$SO$_2$)-phenyl | 7-[(2-methylpiperid-1-yl-CH$_2$CH$_2$—)—] | H |
| 7940. | —(CH$_2$SO$_2$)-phenyl | 7-(1-piperidylcarbonyl) | H |

TABLE 12-continued

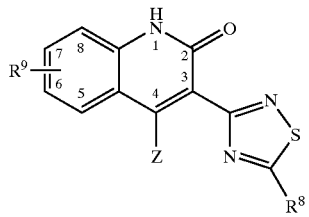

| # | R⁸ | R⁹ | Z |
|---|---|---|---|
| 7941. | —(CH₂SO₂)-phenyl | 7-[(4-methylpiperazin-1-yl)carbonyl] | H |
| 7942. | —(CH₂SO₂)-phenyl | 7-(morpholin-4-ylcarbonyl) | H |
| 7943. | —(CH₂SO₂)-phenyl | 7-(diethylaminocarbonyl) | H |
| 7944. | —(CH₂SO₂)-phenyl | 7-(1-pyrrolidinylcarbonyl) | H |
| 7945. | —(CH₂SO₂)-phenyl | 7-(azaperhydroepinylcarbonyl) | H |
| 7946. | —(CH₂SO₂)-phenyl | 7-[(3,5-dimethylpiperid-1-yl)carbonyl] | H |
| 7947. | —(CH₂SO₂)-phenyl | 7-[(4-methylpiperid-1-yl)carbonyl] | H |
| 7948. | —(CH₂SO₂)-phenyl | 7-[(3-methylpiperid-1-yl)carbonyl] | H |
| 7949. | —(CH₂SO₂)-phenyl | 7-[(2-methylpiperid-1-yl)carbonyl] | H |
| 7950. | —(CH₂SO₂)-phenyl | 7-[2-(dimethylamino)ethoxy] | H |
| 7951. | —(CH₂SO₂)-phenyl | 7-[2-(methylamino)ethoxy] | H |
| 7952. | —(CH₂SO₂)-phenyl | 7-[((2R)pyrrolidin-2-yl)methoxy] | H |
| 7953. | —(CH₂SO₂)-phenyl | 7-[((2R)-1-methylpyrrolidin-2-yl)methoxy] | H |
| 7954. | —(CH₂SO₂)-phenyl | 7-[2-(piperid-1-yl)ethoxy] | H |
| 7955. | —(CH₂SO₂)-phenyl | 7-(2-(piperazin-1-yl)ethoxy] | H |
| 7956. | —(CH₂SO₂)-phenyl | 7-[2-(morpholin-4-yl)ethoxy] | H |
| 7957. | —(CH₂SO₂)-phenyl | 7-[2-(1-methyl(4-piperidyl))ethoxy] | H |
| 7958. | —(CH₂SO₂)-phenyl | 7-[2-(1-methyl(4-piperidyl))methoxy] | H |
| 7959. | —(CH₂SO₂)-phenyl | 7-(1-methyl(4-piperidyloxy)) | H |
| 7960. | —(CH₂SO₂)-phenyl | 7-(piperid-1-yl-CH₂—) | NH₂ |
| 7961. | —(CH₂SO₂)-phenyl | 7-(1-CH₃-piperazin-4-yl-CH₂—) | NH₂ |
| 7962. | —(CH₂SO₂)-phenyl | 7-(morpholin-4-yl-CH₂—) | NH₂ |
| 7963. | —(CH₂SO₂)-phenyl | 7-(diethylamino-CH₂—) | NH₂ |
| 7964. | —(CH₂SO₂)-phenyl | 7-(1-pyrrolidinyl-CH₂—) | NH₂ |
| 7965. | —(CH₂SO₂)-phenyl | 7-(azaperhydroepinyl-CH₂—) | NH₂ |
| 7966. | —(CH₂SO₂)-phenyl | 7-[(3,5-dimethylpiperid-1-yl)—CH₂—] | NH₂ |
| 7967. | —(CH₂SO₂)-phenyl | 7-[(4-methylpiperid-1-yl-CH₂—] | NH₂ |
| 7968. | —(CH₂SO₂)-phenyl | 7-[(3-methylpiperid-1-yl-CH₂—] | NH₂ |
| 7969. | —(CH₂SO₂)-phenyl | 7-[(2-methylpiperid-1-yl-CH₂—] | NH₂ |
| 7970. | —(CH₂SO₂)-phenyl | 7-(piperid-1-yl-CH₂CH₂—) | NH₂ |
| 7971. | —(CH₂SO₂)-phenyl | 7-(1-CH₃-piperazin-4-yl-CH₂CH₂—) | NH₂ |
| 7972. | —(CH₂SO₂)-phenyl | 7-(morpholin-4-yl-CH₂CH₂—) | NH₂ |
| 7973. | —(CH₂SO₂)-phenyl | 7-(diethylamino-CH₂CH₂—) | NH₂ |
| 7974. | —(CH₂SO₂)-phenyl | 7-(1-pyrrolidinyl-CH₂CH₂—) | NH₂ |
| 7975. | —(CH₂SO₂)-phenyl | 7-(azaperhydroepinyl-CH₂CH₂—) | NH₂ |
| 7976. | —(CH₂SO₂)-phenyl | 7-[(3,5-dimethylpiperid-1-yl)—CH₂CH₂—) | NH₂ |
| 7977. | —(CH₂SO₂)-phenyl | 7-[(4-methylpiperid-1-yl-CH₂CH₂—) | NH₂ |
| 7978. | —(CH₂SO₂)-phenyl | 7-[(3-methylpiperid-1-yl-CH₂CH₂—)—] | NH₂ |
| 7979. | —(CH₂SO₂)-phenyl | 7-[(2-methylpiperid-1-yl-CH₂CH₂—)—] | NH₂ |
| 7980. | —(CH₂SO₂)-phenyl | 7-(1-piperidylcarbonyl) | NH₂ |
| 7981. | —(CH₂SO₂)-phenyl | 7-[(4-methylpiperazin-1-yl)carbonyl] | NH₂ |
| 7982. | —(CH₂SO₂)-phenyl | 7-(morpholin-4-ylcarbonyl) | NH₂ |
| 7983. | —(CH₂SO₂)-phenyl | 7-(diethylaminocarbonyl) | NH₂ |
| 7984. | —(CH₂SO₂)-phenyl | 7-(1-pyrrolidinylcarbonyl) | NH₂ |
| 7985. | —(CH₂SO₂)-phenyl | 7-(azaperhydroepinylcarbonyl) | NH₂ |
| 7986. | —(CH₂SO₂)-phenyl | 7-[(3,5-dimethylpiperid-1-yl)carbonyl) | NH₂ |
| 7987. | —(CH₂SO₂)-phenyl | 7-[(4-methylpiperid-1-ylcarbonyl) | NH₂ |
| 7988. | —(CH₂SO₂)-phenyl | 7-[(3-methylpiperid-1-ylcarbonyl) | NH₂ |
| 7989. | —(CH₂SO₂)-phenyl | 7-[(2-methylpiperid-1-ylcarbonyl) | NH₂ |
| 7990. | —(CH₂SO₂)-phenyl | 7-[2-(dimethylamino)ethoxy] | NH₂ |
| 7991. | —(CH₂SO₂)-phenyl | 7-[2-(methylamino)ethoxy] | NH₂ |
| 7992. | —(CH₂SO₂)-phenyl | 7-[((2R)pyrrolidin-2-yl)methoxy] | NH₂ |
| 7993. | —(CH₂SO₂)-phenyl | 7-[((2R)-1-methylpyrrolidin-2-yl)methoxy] | NH₂ |
| 7994. | —(CH₂SO₂)-phenyl | 7-[2-(piperid-1-yl)ethoxy] | NH₂ |
| 7995. | —(CH₂SO₂)-phenyl | 7-(2-(piperazin-1-yl)ethoxy] | NH₂ |
| 7996. | —(CH₂SO₂)-phenyl | 7-[2-(morpholin-4-yl)ethoxy] | NH₂ |
| 7997. | —(CH₂SO₂)-phenyl | 7-[2-(1-methyl(4-piperidyl))ethoxy] | NH₂ |
| 7998. | —(CH₂SO₂)-phenyl | 7-[2-(1-methyl(4-piperidyl))methoxy] | NH₂ |
| 7999. | —(CH₂SO₂)-phenyl | 7-(1-methyl(4-piperidyloxy)) | NH₂ |
| 8000. | —(CH₂SO₂)-2-thienyl | 7-(piperid-1-yl-CH₂—) | H |
| 8001. | —(CH₂SO₂)-2-thienyl | 7-(1-CH₃-piperazin-4-yl-CH₂—) | H |
| 8002. | —(CH₂SO₂)-2-thienyl | 7-(morpholin-4-yl-CH₂—) | H |
| 8003. | —(CH₂SO₂)-2-thienyl | 7-(diethylamino-CH₂—) | H |
| 8004. | —(CH₂SO₂)-2-thienyl | 7-(1-pyrrolidinyl-CH₂—) | H |
| 8005. | —(CH₂SO₂)-2-thienyl | 7-(azaperhydroepinyl-CH₂—) | H |

TABLE 12-continued

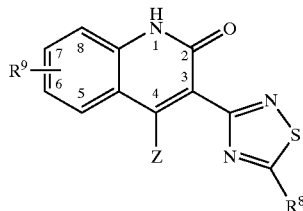

| # | R⁸ | R⁹ | Z |
|---|---|---|---|
| 8006. | —(CH₂SO₂)-2-thienyl | 7-[(3,5-dimethylpiperid-1-yl)—CH₂—] | H |
| 8007. | —(CH₂SO₂)-2-thienyl | 7-[(4-methylpiperid-1-yl-CH₂—] | H |
| 8008. | —(CH₂SO₂)-2-thienyl | 7-[(3-methylpiperid-1-yl-CH₂—] | H |
| 8009. | —(CH₂SO₂)-2-thienyl | 7-[(2-methylpiperid-1-yl-CH₂—] | H |
| 8010. | —(CH₂SO₂)-2-thienyl | 7-(piperid-1-yl-CH₂CH₂—) | H |
| 8011. | —(CH₂SO₂)-2-thienyl | 7-(1-CH₃-piperazin-4-yl-CH₂CH₂—) | H |
| 8012. | —(CH₂SO₂)-2-thienyl | 7-(morpholin-4-yl-CH₂—) | H |
| 8013. | —(CH₂SO₂)-2-thienyl | 7-(diethylamino-CH₂CH₂—) | H |
| 8014. | —(CH₂SO₂)-2-thienyl | 7-(1-pyrrolidinyl-CH₂CH₂—) | H |
| 8015. | —(CH₂SO₂)-2-thienyl | 7-(azaperhydroepinyl-CH₂CH₂—) | H |
| 8016. | —(CH₂SO₂)-2-thienyl | 7-[(3,5-dimethylpiperid-1-yl)—CH₂CH₂—) | H |
| 8017. | —(CH₂SO₂)-2-thienyl | 7-[(4-methylpiperid-1-yl-CH₂CH₂—) | H |
| 8018. | —(CH₂SO₂)-2-thienyl | 7-[(3-methylpiperid-1-yl-CH₂CH₂—)—] | H |
| 8019. | —(CH₂SO₂)-2-thienyl | 7-[(2-methylpiperid-1-yl-CH₂CH₂—)—] | H |
| 8020. | —(CH₂SO₂)-2-thienyl | 7-(1-piperidylcarbonyl) | H |
| 8021. | —(CH₂SO₂)-2-thienyl | 7-[(4-methylpiperazin-1-yl)carbonyl] | H |
| 8022. | —(CH₂SO₂)-2-thienyl | 7-(morpholin-4-ylcarbonyl) | H |
| 8023. | —(CH₂SO₂)-2-thienyl | 7-(diethylaminocarbonyl) | H |
| 8024. | —(CH₂SO₂)-2-thienyl | 7-(1-pyrrolidinylcarbonyl) | H |
| 8025. | —(CH₂SO₂)-2-thienyl | 7-(azaperhydroepinylcarbonyl) | H |
| 8026. | —(CH₂SO₂)-2-thienyl | 7-[(3,5-dimethylpiperid-1-yl)carbonyl) | H |
| 8027. | —(CH₂SO₂)-2-thienyl | 7-[(4-methylpiperid-1-ylcarbonyl) | H |
| 8028. | —(CH₂SO₂)-2-thienyl | 7-[(3-methylpiperid-1-ylcarbonyl) | H |
| 8029. | —(CH₂SO₂)-2-thienyl | 7-[(2-methylpiperid-1-ylcarbonyl) | H |
| 8030. | —(CH₂SO₂)-2-thienyl | 7-[2-(dimethylamino)ethoxy] | H |
| 8031. | —(CH₂SO₂)-2-thienyl | 7-[2-(methylamino)ethoxy] | H |
| 8032. | —(CH₂SO₂)-2-thienyl | 7-[((2R)pyrrolidin-2-yl)methoxy] | H |
| 8033. | —(CH₂SO₂)-2-thienyl | 7-[((2R)-1-methylpyrrolidin-2-yl)methoxy] | H |
| 8034. | —(CH₂SO₂)-2-thienyl | 7-[2-(piperid-1-yl)ethoxy] | H |
| 8035. | —(CH₂SO₂)-2-thienyl | 7-[2-(piperazin-1-yl)ethoxy] | H |
| 8036. | —(CH₂SO₂)-2-thienyl | 7-[2-(morpholin-4-yl)ethoxy] | H |
| 8037. | —(CH₂SO₂)-2-thienyl | 7-[2-(1-methyl(4-piperidyl))ethoxy] | H |
| 8038. | —(CH₂SO₂)-2-thienyl | 7-[2-(1-methyl(4-piperidyl))methoxy] | H |
| 8039. | —(CH₂SO₂)-2-thienyl | 7-(1-methyl(4-piperidyloxy)) | H |
| 8040. | —(CH₂SO₂)-2-thienyl | 7-(piperid-1-yl-CH₂—) | NH₂ |
| 8041. | —(CH₂SO₂)-2-thienyl | 7-(1-CH₃-piperazin-4-yl-CH₂—) | NH₂ |
| 8042. | —(CH₂SO₂)-2-thienyl | 7-(morpholin-4-yl-CH₂—) | NH₂ |
| 8043. | —(CH₂SO₂)-2-thienyl | 7-(diethylamino-CH₂—) | NH₂ |
| 8044. | —(CH₂SO₂)-2-thienyl | 7-(1-pyrrolidinyl-CH₂—) | NH₂ |
| 8045. | —(CH₂SO₂)-2-thienyl | 7-(azaperhydroepinyl-CH₂—) | NH₂ |
| 8046. | —(CH₂SO₂)-2-thienyl | 7-[(3,5-dimethylpiperid-1-yl)—CH₂—] | NH₂ |
| 8047. | —(CH₂SO₂)-2-thienyl | 7-[(4-methylpiperid-1-yl-CH₂—] | NH₂ |
| 8048. | —(CH₂SO₂)-2-thienyl | 7-[(3-methylpiperid-1-yl-CH₂—] | NH₂ |
| 8049. | —(CH₂SO₂)-2-thienyl | 7-[(2-methylpiperid-1-yl-CH₂—] | NH₂ |
| 8050. | —(CH₂SO₂)-2-thienyl | 7-(piperid-1-yl-CH₂CH₂—) | NH₂ |
| 8051. | —(CH₂SO₂)-2-thienyl | 7-(1-CH₃-piperazin-4-yl-CH₂CH₂—) | NH₂ |
| 8052. | —(CH₂SO₂)-2-thienyl | 7-(morpholin-4-yl-CH₂CH₂—) | NH₂ |
| 8053. | —(CH₂SO₂)-2-thienyl | 7-(diethylamino-CH₂CH₂—) | NH₂ |
| 8054. | —(CH₂SO₂)-2-thienyl | 7-(1-pyrrolidinyl-CH₂CH₂—) | NH₂ |
| 8055. | —(CH₂SO₂)-2-thienyl | 7-(azaperhydroepinyl-CH₂CH₂—) | NH₂ |
| 8056. | —(CH₂SO₂)-2-thienyl | 7-[(3,5-dimethylpiperid-1-yl)—CH₂CH₂—) | NH₂ |
| 8057. | —(CH₂SO₂)-2-thienyl | 7-[(4-methylpiperid-1-yl-CH₂CH₂—) | NH₂ |
| 8058. | —(CH₂SO₂)-2-thienyl | 7-[(3-methylpiperid-1-yl-CH₂CH₂—)—] | NH₂ |
| 8059. | —(CH₂SO₂)-2-thienyl | 7-[(2-methylpiperid-1-yl-CH₂CH₂—)—] | NH₂ |
| 8060. | —(CH₂SO₂)-2-thienyl | 7-(1-piperidylcarbonyl) | NH₂ |
| 8061. | —(CH₂SO₂)-2-thienyl | 7-[(4-methylpiperazin-1-yl)carbonyl] | NH₂ |
| 8062. | —(CH₂SO₂)-2-thienyl | 7-(morpholin-4-ylcarbonyl) | NH₂ |
| 8063. | —(CH₂SO₂)-2-thienyl | 7-(diethylaminocarbonyl) | NH₂ |
| 8064. | —(CH₂SO₂)-2-thienyl | 7-(1-pyrrolidinylcarbonyl) | NH₂ |
| 8065. | —(CH₂SO₂)-2-thienyl | 7-(azaperhydroepinylcarbonyl) | NH₂ |
| 8066. | —(CH₂SO₂)-2-thienyl | 7-[(3,5-dimethylpiperid-1-yl)carbonyl) | NH₂ |
| 8067. | —(CH₂SO₂)-2-thienyl | 7-[(4-methylpiperid-1-ylcarbonyl) | NH₂ |
| 8068. | —(CH₂SO₂)-2-thienyl | 7-[(3-methylpiperid-1-ylcarbonyl) | NH₂ |
| 8069. | —(CH₂SO₂)-2-thienyl | 7-[(2-methylpiperid-1-ylcarbonyl) | NH₂ |
| 8070. | —(CH₂SO₂)-2-thienyl | 7-[2-(dimethylamino)ethoxy] | NH₂ |

TABLE 12-continued

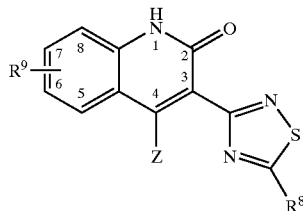

| # | R⁸ | R⁹ | Z |
|---|---|---|---|
| 8071. | —(CH₂SO₂)-2-thienyl | 7-[2-(methylamino)ethoxy] | NH₂ |
| 8072. | —(CH₂SO₂)-2-thienyl | 7-[((2R)pyrrolidin-2-yl)methoxy] | NH₂ |
| 8073. | —(CH₂SO₂)-2-thienyl | 7-[((2R)-1-methylpyrrolidin-2-yl)methoxy] | NH₂ |
| 8074. | —(CH₂SO₂)-2-thienyl | 7-[2-(piperid-1-yl)ethoxy] | NH₂ |
| 8075. | —(CH₂SO₂)-2-thienyl | 7-[2-(piperazin-1-yl)ethoxy] | NH₂ |
| 8076. | —(CH₂SO₂)-2-thienyl | 7-[2-(morpholin-4-yl)ethoxy] | NH₂ |
| 8077. | —(CH₂SO₂)-2-thienyl | 7-[2-(1-methyl(4-piperidyl))ethoxy] | NH₂ |
| 8078. | —(CH₂SO₂)-2-thienyl | 7-[2-(1-methyl(4-piperidyl))methoxy] | NH₂ |
| 8079. | —(CH₂SO₂)-2-thienyl | 7-(1-methyl(4-piperidyloxy)) | NH₂ |
| 8080. | —(CH₂SO₂)-2-pyridyl | 7-(piperid-1-yl-CH₂—) | H |
| 8081. | —(CH₂SO₂)-2-pyridyl | 7-(1-CH₃-piperazin-4-yl-CH₂—) | H |
| 8082. | —(CH₂SO₂)-2-pyridyl | 7-(morpholin-4-yl-CH₂—) | H |
| 8083. | —(CH₂SO₂)-2-pyridyl | 7-(diethylamino-CH₂—) | H |
| 8084. | —(CH₂SO₂)-2-pyridyl | 7-(1-pyrrolidinyl-CH₂—) | H |
| 8085. | —(CH₂SO₂)-2-pyridyl | 7-(azaperhydroepinyl-CH₂—) | H |
| 8086. | —(CH₂SO₂)-2-pyridyl | 7-[(3,5-dimethylpiperid-1-yl)—CH₂—] | H |
| 8087. | —(CH₂SO₂)-2-pyridyl | 7-[(4-methylpiperid-1-yl-CH₂—] | H |
| 8088. | —(CH₂SO₂)-2-pyridyl | 7-[(3-methylpiperid-1-yl-CH₂—] | H |
| 8089. | —(CH₂SO₂)-2-pyridyl | 7-[(2-methylpiperid-1-yl-CH₂—] | H |
| 8090. | —(CH₂SO₂)-2-pyridyl | 7-(piperid-1-yl-CH₂CH₂—) | H |
| 8091. | —(CH₂SO₂)-2-pyridyl | 7-(1-CH₃-piperazin-4-yl-CH₂CH₂—) | H |
| 8092. | —(CH₂SO₂)-2-pyridyl | 7-(morpholin-4-yl-CH₂CH₂—) | H |
| 8093. | —(CH₂SO₂)-2-pyridyl | 7-(diethylamino-CH₂CH₂—) | H |
| 8094. | —(CH₂SO₂)-2-pyridyl | 7-(1-pyrrolidinyl-CH₂CH₂—) | H |
| 8095. | —(CH₂SO₂)-2-pyridyl | 7-(azaperhydroepinyl-CH₂CH₂—) | H |
| 8096. | —(CH₂SO₂)-2-pyridyl | 7-[(3,5-dimethylpiperid-1-yl)—CH₂CH₂—) | H |
| 8097. | —(CH₂SO₂)-2-pyridyl | 7-[(4-methylpiperid-1-yl-CH₂CH₂—) | H |
| 8098. | —(CH₂SO₂)-2-pyridyl | 7-[(3-methylpiperid-1-yl-CH₂CH₂—)—] | H |
| 8099. | —(CH₂SO₂)-2-pyridyl | 7-[(2-methylpiperid-1-yl-CH₂CH₂—)—] | H |
| 8100. | —(CH₂SO₂)-2-pyridyl | 7-(1-piperidylcarbonyl) | H |
| 8101. | —(CH₂SO₂)-2-pyridyl | 7-[(4-methylpiperazin-1-yl)carbonyl] | H |
| 8102. | —(CH₂SO₂)-2-pyridyl | 7-(morpholin-4-ylcarbonyl) | H |
| 8103. | —(CH₂SO₂)-2-pyridyl | 7-(diethylaminocarbonyl) | H |
| 8104. | —(CH₂SO₂)-2-pyridyl | 7-(1-pyrrolidinylcarbonyl) | H |
| 8105. | —(CH₂SO₂)-2-pyridyl | 7-(azaperhydroepinylcarbonyl) | H |
| 8106. | —(CH₂SO₂)-2-pyridyl | 7-[(3,5-dimethylpiperid-1-yl)carbonyl] | H |
| 8107. | —(CH₂SO₂)-2-pyridyl | 7-[(4-methylpiperid-1-ylcarbonyl) | H |
| 8108. | —(CH₂SO₂)-2-pyridyl | 7-(3-methylpiperid-1-ylcarbonyl) | H |
| 8109. | —(CH₂SO₂)-2-pyridyl | 7-(2-methylpiperid-1-ylcarbonyl) | H |
| 8110. | —(CH₂SO₂)-2-pyridyl | 7-[2-(dimethylamino)ethoxy] | H |
| 8111. | —(CH₂SO₂)-2-pyridyl | 7-[2-(methylamino)ethoxy] | H |
| 8112. | —(CH₂SO₂)-2-pyridyl | 7-[((2R)pyrrolidin-2-yl)methoxy] | H |
| 8113. | —(CH₂SO₂)-2-pyridyl | 7-[((2R)-1-methylpyrrolidin-2-yl)methoxy] | H |
| 8114. | —(CH₂SO₂)-2-pyridyl | 7-[2-(piperid-1-yl)ethoxy] | H |
| 8115. | —(CH₂SO₂)-2-pyridyl | 7-[2-(piperazin-1-yl)ethoxy] | H |
| 8116. | —(CH₂SO₂)-2-pyridyl | 7-[2-(morpholin-4-yl)ethoxy] | H |
| 8117. | —(CH₂SO₂)-2-pyridyl | 7-[2-(1-methyl(4-piperidyl))ethoxy] | H |
| 8118. | —(CH₂SO₂)-2-pyridyl | 7-[2-(1-methyl(4-piperidyl))methoxy] | H |
| 8119. | —(CH₂SO₂)-2-pyridyl | 7-(1-methyl(4-piperidyloxy)) | H |
| 8120. | —(CH₂SO₂)-2-pyridyl | 7-(piperid-1-yl-CH₂—) | NH₂ |
| 8121. | —(CH₂SO₂)-2-pyridyl | 7-(1-CH₃-piperazin-4-yl-CH₂—) | NH₂ |
| 8122. | —(CH₂SO₂)-2-pyridyl | 7-(morpholin-4-yl-CH₂—) | NH₂ |
| 8123. | —(CH₂SO₂)-2-pyridyl | 7-(diethylamino-CH₂—) | NH₂ |
| 8124. | —(CH₂SO₂)-2-pyridyl | 7-(1-pyrrolidinyl-CH₂—) | NH₂ |
| 8125. | —(CH₂SO₂)-2-pyridyl | 7-(azaperhydroepinyl-CH₂—) | NH₂ |
| 8126. | —(CH₂SO₂)-2-pyridyl | 7-[(3,5-dimethylpiperid-1-yl)—CH₂—] | NH₂ |
| 8127. | —(CH₂SO₂)-2-pyridyl | 7-[(4-methylpiperid-1-yl-CH₂—] | NH₂ |
| 8128. | —(CH₂SO₂)-2-pyridyl | 7-[(3-methylpiperid-1-yl-CH₂—] | NH₂ |
| 8129. | —(CH₂SO₂)-2-pyridyl | 7-[(2-methylpiperid-1-yl-CH₂—] | NH₂ |
| 8130. | —(CH₂SO₂)-2-pyridyl | 7-(piperid-1-yl-CH₂CH₂—) | NH₂ |
| 8131. | —(CH₂SO₂)-2-pyridyl | 7-(1-CH₃-piperazin-4-yl-CH₂CH₂—) | NH₂ |
| 8132. | —(CH₂SO₂)-2-pyridyl | 7-(morpholin-4-yl-CH₂CH₂—) | NH₂ |
| 8133. | —(CH₂SO₂)-2-pyridyl | 7-(diethylamino-CH₂CH₂—) | NH₂ |
| 8134. | —(CH₂SO₂)-2-pyridyl | 7-(1-pyrrolidinyl-CH₂CH₂—) | NH₂ |
| 8135. | —(CH₂SO₂)-2-pyridyl | 7-(azaperhydroepinyl-CH₂CH₂—) | NH₂ |

TABLE 12-continued

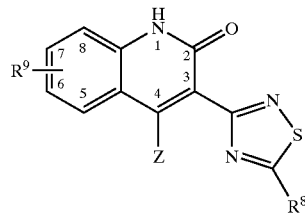

| # | R8 | R9 | Z |
|---|---|---|---|
| 8136. | —(CH2SO2)-2-pyridyl | 7-[(3,5-dimethylpiperid-1-yl)—CH2CH2—) | NH2 |
| 8137. | —(CH2SO2)-2-pyridyl | 7-[(4-methylpiperid-1-yl-CH2CH2—) | NH2 |
| 8138. | —(CH2SO2)-2-pyridyl | 7-[(3-methylpiperid-1-yl-CH2CH2—)—] | NH2 |
| 8139. | —(CH2SO2)-2-pyridyl | 7-[(2-methylpiperid-1-yl-CH2CH2—)—] | NH2 |
| 8140. | —(CH2SO2)-2-pyridyl | 7-(1-piperidylcarbonyl) | NH2 |
| 8141. | —(CH2SO2)-2-pyridyl | 7-[(4-methylpiperazin-1-yl)carbonyl] | NH2 |
| 8142. | —(CH2SO2)-2-pyridyl | 7-(morpholin-4-ylcarbonyl) | NH2 |
| 8143. | —(CH2SO2)-2-pyridyl | 7-(diethylaminocarbonyl) | NH2 |
| 8144. | —(CH2SO2)-2-pyridyl | 7-(1-pyrrolidinylcarbonyl) | NH2 |
| 8145. | —(CH2SO2)-2-pyridyl | 7-(azaperhydroepinylcarbonyl) | NH2 |
| 8146. | —(CH2SO2)-2-pyridyl | 7-[(3,5-dimethylpiperid-1-yl)carbonyl] | NH2 |
| 8147. | —(CH2SO2)-2-pyridyl | 7-[(4-methylpiperid-1-ylcarbonyl) | NH2 |
| 8148. | —(CH2SO2)-2-pyridyl | 7-(3-methylpiperid-1-ylcarbonyl) | NH2 |
| 8149. | —(CH2SO2)-2-pyridyl | 7-(2-methylpiperid-1-ylcarbonyl) | NH2 |
| 8150. | —(CH2SO2)-2-pyridyl | 7-[2-(dimethylamino)ethoxy] | NH2 |
| 8151. | —(CH2SO2)-2-pyridyl | 7-[2-(methylamino)ethoxy] | NH2 |
| 8152. | —(CH2SO2)-2-pyridyl | 7-[((2R)pyrrolidin-2-yl)methoxy] | NH2 |
| 8153. | —(CH2SO2)-2-pyridyl | 7-[((2R)-1-methylpyrrolidin-2-yl)methoxy] | NH2 |
| 8154. | —(CH2SO2)-2-pyridyl | 7-[2-(piperid-1-yl)ethoxy] | NH2 |
| 8155. | —(CH2SO2)-2-pyridyl | 7-[2-(piperazin-1-yl)ethoxy] | NH2 |
| 8156. | —(CH2SO2)-2-pyridyl | 7-[2-(morpholin-4-yl)ethoxy] | NH2 |
| 8157. | —(CH2SO2)-2-pyridyl | 7-[2-(1-methyl(4-piperidyl))ethoxy] | NH2 |
| 8158. | —(CH2SO2)-2-pyridyl | 7-[2-(1-methyl(4-piperidyl))methoxy] | NH2 |
| 8159. | —(CH2SO2)-2-pyridyl | 7-(1-methyl(4-piperidyloxy)) | NH2 |
| 8160. | —(CH2SO2)-3-pyridyl | 7-(piperid-1-yl-CH2—) | H |
| 8161. | —(CH2SO2)-3-pyridyl | 7-(1-CH3-piperazin-4-yl-CH2—) | H |
| 8162. | —(CH2SO2)-3-pyridyl | 7-(morpholin-4-yl-CH2—) | H |
| 8163. | —(CH2SO2)-3-pyridyl | 7-(diethylamino-CH2—) | H |
| 8164. | —(CH2SO2)-3-pyridyl | 7-(1-pyrrolidinyl-CH2—) | H |
| 8165. | —(CH2SO2)-3-pyridyl | 7-(azaperhydroepinyl-CH2—) | H |
| 8166. | —(CH2SO2)-3-pyridyl | 7-[(3,5-dimethylpiperid-1-yl)—CH2—] | H |
| 8167. | —(CH2SO2)-3-pyridyl | 7-[(4-methylpiperid-1-yl-CH2—] | H |
| 8168. | —(CH2SO2)-3-pyridyl | 7-[(3-methylpiperid-1-yl-CH2—] | H |
| 8169. | —(CH2SO2)-3-pyridyl | 7-[(2-methylpiperid-1-yl-CH2—] | H |
| 8170. | —(CH2SO2)-3-pyridyl | 7-(piperid-1-yl-CH2CH2—) | H |
| 8171. | —(CH2SO2)-3-pyridyl | 7-(1-CH3-piperazin-4-yl-CH2CH2—) | H |
| 8172. | —(CH2SO2)-3-pyridyl | 7-(morpholin-4-yl-CH2CH2—) | H |
| 8173. | —(CH2SO2)-3-pyridyl | 7-(diethylamino-CH2CH2—) | H |
| 8174. | —(CH2SO2)-3-pyridyl | 7-(1-pyrrolidinyl-CH2CH2—) | H |
| 8175. | —(CH2SO2)-3-pyridyl | 7-(azaperhydroepinyl-CH2CH2—) | H |
| 8176. | —(CH2SO2)-3-pyridyl | 7-[(3,5-dimethylpiperid-1-yl)—CH2CH2—) | H |
| 8177. | —(CH2SO2)-3-pyridyl | 7-[(4-methylpiperid-1-yl-CH2CH2—) | H |
| 8178. | —(CH2SO2)-3-pyridyl | 7-[(3-methylpiperid-1-yl-CH2CH2—)—] | H |
| 8179. | —(CH2SO2)-3-pyridyl | 7-[(2-methylpiperid-1-yl-CH2CH2—)—] | H |
| 8180. | —(CH2SO2)-3-pyridyl | 7-(1-piperidylcarbonyl) | H |
| 8181. | —(CH2SO2)-3-pyridyl | 7-[(4-methylpiperazin-1-yl)carbonyl] | H |
| 8182. | —(CH2SO2)-3-pyridyl | 7-(morpholin-4-ylcarbonyl) | H |
| 8183. | —(CH2SO2)-3-pyridyl | 7-(diethylaminocarbonyl) | H |
| 8184. | —(CH2SO2)-3-pyridyl | 7-(1-pyrrolidinylcarbonyl) | H |
| 8185. | —(CH2SO2)-3-pyridyl | 7-(azaperhydroepinylcarbonyl) | H |
| 8186. | —(CH2SO2)-3-pyridyl | 7-[(3,5-dimethylpiperid-1-yl)carbonyl] | H |
| 8187. | —(CH2SO2)-3-pyridyl | 7-(4-methylpiperid-1-ylcarbonyl) | H |
| 8188. | —(CH2SO2)-3-pyridyl | 7-(3-methylpiperid-1-ylcarbonyl) | H |
| 8189. | —(CH2SO2)-3-pyridyl | 7-(2-methylpiperid-1-ylcarbonyl) | H |
| 8190. | —(CH2SO2)-3-pyridyl | 7-[2-(dimethylamino)ethoxy] | H |
| 8191. | —(CH2SO2)-3-pyridyl | 7-[2-(methylamino)ethoxy] | H |
| 8192. | —(CH2SO2)-3-pyridyl | 7-[((2R)pyrrolidin-2-yl)methoxy] | H |
| 8193. | —(CH2SO2)-3-pyridyl | 7-[((2R)-1-methylpyrrolidin-2-yl)methoxy] | H |
| 8194. | —(CH2SO2)-3-pyridyl | 7-[2-(piperid-1-yl)ethoxy] | H |
| 8195. | —(CH2SO2)-3-pyridyl | 7-[2-(piperazin-1-yl)ethoxy] | H |
| 8196. | —(CH2SO2)-3-pyridyl | 7-[2-(morpholin-4-yl)ethoxy] | H |
| 8197. | —(CH2SO2)-3-pyridyl | 7-[2-(1-methyl(4-piperidyl))ethoxy] | H |
| 8198. | —(CH2SO2)-3-pyridyl | 7-[2-(1-methyl(4-piperidyl))methoxy] | H |
| 8199. | —(CH2SO2)-3-pyridyl | 7-(1-methyl(4-piperidyloxy)) | H |
| 8200. | —(CH2SO2)-3-pyridyl | 7-(piperid-1-yl-CH2—) | NH2 |

TABLE 12-continued

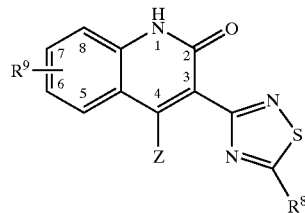

| # | R⁸ | R⁹ | Z |
|---|---|---|---|
| 8201. | —(CH₂SO₂)-3-pyridyl | 7-(1-CH₂-piperazin-4-yl-CH₂—) | NH₂ |
| 8202. | —(CH₂SO₂)-3-pyridyl | 7-(morpholin-4-yl-CH₂—) | NH₂ |
| 8203. | —(CH₂SO₂)-3-pyridyl | 7-(diethylamino-CH₂—) | NH₂ |
| 8204. | —(CH₂SO₂)-3-pyridyl | 7-(1-pyrrolidinyl-CH₂—) | NH₂ |
| 8205. | —(CH₂SO₂)-3-pyridyl | 7-(azaperhydroepinyl-CH₂—) | NH₂ |
| 8206. | —(CH₂SO₂)-3-pyridyl | 7-[(3,5-dimethylpiperid-1-yl)—CH₂—] | NH₂ |
| 8207. | —(CH₂SO₂)-3-pyridyl | 7-[(4-methylpiperid-1-yl-CH₂—] | NH₂ |
| 8208. | —(CH₂SO₂)-3-pyridyl | 7-[(3-methylpiperid-1-yl-CH₂—] | NH₂ |
| 8209. | —(CH₂SO₂)-3-pyridyl | 7-[(2-methylpiperid-1-yl-CH₂—] | NH₂ |
| 8210. | —(CH₂SO₂)-3-pyridyl | 7-(piperid-1-yl-CH₂CH₂—) | NH₂ |
| 8211. | —(CH₂SO₂)-3-pyridyl | 7-(1-CH₃-piperazin-4-yl-CH₂CH₂—) | NH₂ |
| 8212. | —(CH₂SO₂)-3-pyridyl | 7-(morpholin-4-yl-CH₂CH₂—) | NH₂ |
| 8213. | —(CH₂SO₂)-3-pyridyl | 7-(diethylamino-CH₂CH₂—) | NH₂ |
| 8214. | —(CH₂SO₂)-3-pyridyl | 7-(1-pyrrolidinyl-CH₂CH₂—) | NH₂ |
| 8215. | —(CH₂SO₂)-3-pyridyl | 7-(azaperhydroepinyl-CH₂CH₂—) | NH₂ |
| 8216. | —(CH₂SO₂)-3-pyridyl | 7-[(3,5-dimethylpiperid-1-yl)—CH₂CH₂—) | NH₂ |
| 8217. | —(CH₂SO₂)-3-pyridyl | 7-[(4-methylpiperid-1-yl-CH₂CH₂—) | NH₂ |
| 8218. | —(CH₂SO₂)-3-pyridyl | 7-[(3-methylpiperid-1-yl-CH₂CH₂—)—] | NH₂ |
| 8219. | —(CH₂SO₂)-3-pyridyl | 7-[(2-methylpiperid-1-yl-CH₂CH₂—)—] | NH₂ |
| 8220. | —(CH₂SO₂)-3-pyridyl | 7-(1-piperidylcarbonyl) | NH₂ |
| 8221. | —(CH₂SO₂)-3-pyridyl | 7-[(4-methylpiperazin-1-yl)carbonyl] | NH₂ |
| 8222. | —(CH₂SO₂)-3-pyridyl | 7-(morpholin-4-ylcarbonyl) | NH₂ |
| 8223. | —(CH₂SO₂)-3-pyridyl | 7-(diethylaminocarbonyl) | NH₂ |
| 8224. | —(CH₂SO₂)-3-pyridyl | 7-(1-pyrrolidinylcarbonyl) | NH₂ |
| 8225. | —(CH₂SO₂)-3-pyridyl | 7-(azaperhydroepinylcarbonyl) | NH₂ |
| 8226. | —(CH₂SO₂)-3-pyridyl | 7-[(3,5-dimethylpiperid-1-yl)carbonyl) | NH₂ |
| 8227. | —(CH₂SO₂)-3-pyridyl | 7-[(4-methylpiperid-1-ylcarbonyl) | NH₂ |
| 8228. | —(CH₂SO₂)-3-pyridyl | 7-[(3-methylpiperid-1-ylcarbonyl) | NH₂ |
| 8229. | —(CH₂SO₂)-3-pyridyl | 7-[(2-methylpiperid-1-ylcarbonyl) | NH₂ |
| 8230. | —(CH₂SO₂)-3-pyridyl | 7-[2-(dimethylamino)ethoxy] | NH₂ |
| 8231. | —(CH₂SO₂)-3-pyridyl | 7-[2-(methylamino)ethoxy] | NH₂ |
| 8232. | —(CH₂SO₂)-3-pyridyl | 7-[((2R)pyrrolidin-2-yl)methoxy] | NH₂ |
| 8233. | —(CH₂SO₂)-3-pyridyl | 7-[((2R)-1-methylpyrrolidin-2-yl)methoxy] | NH₂ |
| 8234. | —(CH₂SO₂)-3-pyridyl | 7-[2-(piperid-1-yl)ethoxy] | NH₂ |
| 8235. | —(CH₂SO₂)-3-pyridyl | 7-[2-(piperazin-1-yl)ethoxy] | NH₂ |
| 8236. | —(CH₂SO₂)-3-pyridyl | 7-[2-(morpholin-4-yl)ethoxy] | NH₂ |
| 8237. | —(CH₂SO₂)-3-pyridyl | 7-[2-(1-methyl(4-piperidyl))ethoxy] | NH₂ |
| 8238. | —(CH₂SO₂)-3-pyridyl | 7-(2-(1-methyl(4-piperidyl))methoxy] | NH₂ |
| 8239. | —(CH₂SO₂)-3-pyridyl | 7-(1-methyl(4-piperidyloxy)) | NH₂ |
| 8240. | —(CH₂SO₂)-4-pyridyl | 7-(piperid-1-yl-CH₂—) | H |
| 8241. | —(CH₂SO₂)-4-pyridyl | 7-(1-CH₃-piperazin-4-yl-CH₂—) | H |
| 8242. | —(CH₂SO₂)-4-pyridyl | 7-(morpholin-4-yl-CH₂—) | H |
| 8243. | —(CH₂SO₂)-4-pyridyl | 7-(diethylamino-CH₂—) | H |
| 8244. | —(CH₂SO₂)-4-pyridyl | 7-(1-pyrrolidinyl-CH₂—) | H |
| 8245. | —(CH₂SO₂)-4-pyridyl | 7-(azaperhydroepinyl-CH₂—) | H |
| 8246. | —(CH₂SO₂)-4-pyridyl | 7-[(3,5-dimethylpiperid-1-yl)—CH₂—] | H |
| 8247. | —(CH₂SO₂)-4-pyridyl | 7-[(4-methylpiperid-1-yl-CH₂—] | H |
| 8248. | —(CH₂SO₂)-4-pyridyl | 7-[(3-methylpiperid-1-yl-CH₂—] | H |
| 8249. | —(CH₂SO₂)-4-pyridyl | 7-[(2-methylpiperid-1-yl-CH₂—] | H |
| 8250. | —(CH₂SO₂)-4-pyridyl | 7-(piperid-1-yl-CH₂CH₂—) | H |
| 8251. | —(CH₂SO₂)-4-pyridyl | 7-(1-CH₃-piperazin-4-yl-CH₂CH₂—) | H |
| 8252. | —(CH₂SO₂)-4-pyridyl | 7-(morpholin-4-yl-CH₂CH₂—) | H |
| 8253. | —(CH₂SO₂)-4-pyridyl | 7-(diethylamino-CH₂CH₂—) | H |
| 8254. | —(CH₂SO₂)-4-pyridyl | 7-(1-pyrrolidinyl-CH₂CH₂—) | H |
| 8255. | —(CH₂SO₂)-4-pyridyl | 7-(azaperhydroepinyl-CH₂CH₂—) | H |
| 8256. | —(CH₂SO₂)-4-pyridyl | 7-[(3,5-dimethylpiperid-1-yl)—CH₂CH₂—) | H |
| 8257. | —(CH₂SO₂)-4-pyridyl | 7-[(4-methylpiperid-1-yl-CH₂CH₂—) | H |
| 8258. | —(CH₂SO₂)-4-pyridyl | 7-[(3-methylpiperid-1-yl-CH₂CH₂—)—] | H |
| 8259. | —(CH₂SO₂)-4-pyridyl | 7-[(2-methylpiperid-1-yl-CH₂CH₂—)—] | H |
| 8260. | —(CH₂SO₂)-4-pyridyl | 7-(1-piperidylcarbonyl) | H |
| 8261. | —(CH₂SO₂)-4-pyridyl | 7-[(4-methylpiperazin-1-yl)carbonyl] | H |
| 8262. | —(CH₂SO₂)-4-pyridyl | 7-(morpholin-4-ylcarbonyl) | H |
| 8263. | —(CH₂SO₂)-4-pyridyl | 7-(diethylaminocarbonyl) | H |
| 8264. | —(CH₂SO₂)-4-pyridyl | 7-(1-pyrrolidinylcarbonyl) | H |
| 8265. | —(CH₂SO₂)-4-pyridyl | 7-(azaperhydroepinylcarbonyl) | H |

TABLE 12-continued

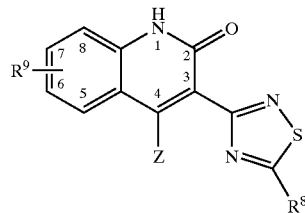

| # | R⁸ | R⁹ | Z |
|---|---|---|---|
| 8266. | —(CH₂SO₂)-4-pyridyl | 7-[(3,5-dimethylpiperid-1-yl)carbonyl) | H |
| 8267. | —(CH₂SO₂)-4-pyridyl | 7-[(4-methylpiperid-1-ylcarbonyl) | H |
| 8268. | —(CH₂SO₂)-4-pyridyl | 7-[(3-methylpiperid-1-ylcarbonyl) | H |
| 8269. | —(CH₂SO₂)-4-pyridyl | 7-[(2-methylpiperid-1-ylcarbonyl) | H |
| 8270. | —(CH₂SO₂)-4-pyridyl | 7-[2-(dimethylamino)ethoxy] | H |
| 8271. | —(CH₂SO₂)-4-pyridyl | 7-[2-(methylamino)ethoxy] | H |
| 8272. | —(CH₂SO₂)-4-pyridyl | 7-[((2R)pyrrolidin-2-yl)methoxy] | H |
| 8273. | —(CH₂SO₂)-4-pyridyl | 7-[((2R)-1-methylpyrrolidin-2-yl)methoxy] | H |
| 8274. | —(CH₂SO₂)-4-pyridyl | 7-[2-(piperid-1-yl)ethoxy] | H |
| 8275. | —(CH₂SO₂)-4-pyridyl | 7-[2-(piperazin-1-yl)ethoxy] | H |
| 8276. | —(CH₂SO₂)-4-pyridyl | 7-[2-(morpholin-4-yl)ethoxy] | H |
| 8277. | —(CH₂SO₂)-4-pyridyl | 7-[2-(1-methyl(4-piperidyl))ethoxy] | H |
| 8278. | —(CH₂SO₂)-4-pyridyl | 7-[2-(1-methyl(4-piperidyl))methoxy] | H |
| 8279. | —(CH₂SO₂)-4-pyridyl | 7-(1-methyl(4-piperidyloxy)) | H |
| 8280. | —(CH₂SO₂)-4-pyridyl | 7-(piperid-1-yl-CH₂—) | NH₂ |
| 8281. | —(CH₂SO₂)-4-pyridyl | 7-(1-CH₃-piperazin-4-yl-CH₂—) | NH₂ |
| 8282. | —(CH₂SO₂)-4-pyridyl | 7-(morpholin-4-yl-CH₂—) | NH₂ |
| 8283. | —(CH₂SO₂)-4-pyridyl | 7-(diethylamino-CH₂—) | NH₂ |
| 8284. | —(CH₂SO₂)-4-pyridyl | 7-(1-pyrrolidinyl-CH₂—) | NH₂ |
| 8285. | —(CH₂SO₂)-4-pyridyl | 7-(azaperhydroepinyl-CH₂—) | NH₂ |
| 8286. | —(CH₂SO₂)-4-pyridyl | 7-[(3,5-dimethylpiperid-1-yl)—CH₂—] | NH₂ |
| 8287. | —(CH₂SO₂)-4-pyridyl | 7-[(4-methylpiperid-1-yl-CH₂—] | NH₂ |
| 8288. | —(CH₂SO₂)-4-pyridyl | 7-[(3-methylpiperid-1-yl-CH₂—] | NH₂ |
| 8289. | —(CH₂SO₂)-4-pyridyl | 7-[(2-methylpiperid-1-yl-CH₂—] | NH₂ |
| 8290. | —(CH₂SO₂)-4-pyridyl | 7-(piperid-1-yl-CH₂CH₂—) | NH₂ |
| 8291. | —(CH₂SO₂)-4-pyridyl | 7-(1-CH₃-piperazin-4-yl-CH₂CH₂—) | NH₂ |
| 8292. | —(CH₂SO₂)-4-pyridyl | 7-(morpholin-4-yl-CH₂CH₂—) | NH₂ |
| 8293. | —(CH₂SO₂)-4-pyridyl | 7-(diethylamino-CH₂CH₂—) | NH₂ |
| 8294. | —(CH₂SO₂)-4-pyridyl | 7-(1-pyrrolidinyl-CH₂CH₂—) | NH₂ |
| 8295. | —(CH₂SO₂)-4-pyridyl | 7-(azaperhydroepinyl-CH₂CH₂—) | NH₂ |
| 8296. | —(CH₂SO₂)-4-pyridyl | 7-[(3,5-dimethylpiperid-1-yl)—CH₂CH₂—) | NH₂ |
| 8297. | —(CH₂SO₂)-4-pyridyl | 7-[(4-methylpiperid-1-yl-CH₂CH₂—) | NH₂ |
| 8298. | —(CH₂SO₂)-4-pyridyl | 7-[(3-methylpiperid-1-yl-CH₂CH₂—)—] | NH₂ |
| 8299. | —(CH₂SO₂)-4-pyridyl | 7-[(2-methylpiperid-1-yl-CH₂CH₂—)—] | NH₂ |
| 8300. | —(CH₂SO₂)-4-pyridyl | 7-(1-piperidylcarbonyl) | NH₂ |
| 8301. | —(CH₂SO₂)-4-pyridyl | 7-[(4-methylpiperazin-1-yl)carbonyl] | NH₂ |
| 8302. | —(CH₂SO₂)-4-pyridyl | 7-(morpholin-4-ylcarbonyl) | NH₂ |
| 8303. | —(CH₂SO₂)-4-pyridyl | 7-(diethylaminocarbonyl) | NH₂ |
| 8304. | —(CH₂SO₂)-4-pyridyl | 7-(1-pyrrolidinylcarbonyl) | NH₂ |
| 8305. | —(CH₂SO₂)-4-pyridyl | 7-(azaperhydroepinylcarbonyl) | NH₂ |
| 8306. | —(CH₂SO₂)-4-pyridyl | 7-[(3,5-dimethylpiperid-1-yl)carbonyl) | NH₂ |
| 8307. | —(CH₂SO₂)-4-pyridyl | 7-[(4-methylpiperid-1-ylcarbonyl) | NH₂ |
| 8308. | —(CH₂SO₂)-4-pyridyl | 7-[(3-methylpiperid-1-ylcarbonyl) | NH₂ |
| 8309. | —(CH₂SO₂)-4-pyridyl | 7-[(2-methylpiperid-1-ylcarbonyl) | NH₂ |
| 8310. | —(CH₂SO₂)-4-pyridyl | 7-[2-(dimethylamino)ethoxy] | NH₂ |
| 8311. | —(CH₂SO₂)-4-pyridyl | 7-[2-(methylamino)ethoxy] | NH₂ |
| 8312. | —(CH₂SO₂)-4-pyridyl | 7-[((2R)pyrrolidin-2-yl)methoxy] | NH₂ |
| 8313. | —(CH₂SO₂)-4-pyridyl | 7-[((2R)-1-methylpyrrolidin-2-yl)methoxy] | NH₂ |
| 8314. | —(CH₂SO₂)-4-pyridyl | 7-[2-(piperid-1-yl)ethoxy] | NH₂ |
| 8315. | —(CH₂SO₂)-4-pyridyl | 7-[2-(piperazin-1-yl)ethoxy] | NH₂ |
| 8316. | —(CH₂SO₂)-4-pyridyl | 7-[2-(morpholin-4-yl)ethoxy] | NH₂ |
| 8317. | —(CH₂SO₂)-4-pyridyl | 7-[2-(1-methyl(4-piperidyl))ethoxy] | NH₂ |
| 8318. | —(CH₂SO₂)-4-pyridyl | 7-[2-(1-methyl(4-piperidyl))methoxy] | NH₂ |
| 8319. | —(CH₂SO₂)-4-pyridyl | 7-(1-methyl(4-piperidyloxy)) | NH₂ |
| 8320. | —(NMeSO₂)-phenyl | 7-(piperid-1-yl-CH₂—) | H |
| 8321. | —(NMeSO₂)-phenyl | 7-(1-CH₃-piperazin-4-yl-CH₂—) | H |
| 8322. | —(NMeSO₂)-phenyl | 7-(morpholin-4-yl-CH₂—) | H |
| 8323. | —(NMeSO₂)-phenyl | 7-(diethylamino-CH₂—) | H |
| 8324. | —(NMeSO₂)-phenyl | 7-(1-pyrrolidinyl-CH₂—) | H |
| 8325. | —(NMeSO₂)-phenyl | 7-(azaperhydroepinyl-CH₂—) | H |
| 8326. | —(NMeSO₂)-phenyl | 7-[(3,5-dimethylpiperid-1-yl)—CH₂—] | H |
| 8327. | —(NMeSO₂)-phenyl | 7-[(4-methylpiperid-1-yl-CH₂—] | H |
| 8328. | —(NMeSO₂)-phenyl | 7-[(3-methylpiperid-1-yl-CH₂—] | H |
| 8329. | —(NMeSO₂)-phenyl | 7-[(2-methylpiperid-1-yl-CH₂—] | H |
| 8330. | —(NMeSO₂)-phenyl | 7-(piperid-1-yl-CH₂CH₂—) | H |

TABLE 12-continued

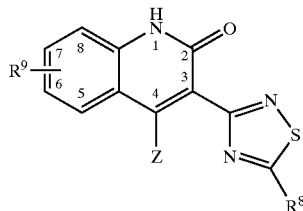

| # | R⁸ | R⁹ | Z |
|---|---|---|---|
| 8331. | —(NMeSO₂)-phenyl | 7-(1-CH₃-piperazin-4-yl-CH₂CH₂—) | H |
| 8332. | —(NMeSO₂)-phenyl | 7-(morpholin-4-yl-CH₂CH₂—) | H |
| 8333. | —(NMeSO₂)-phenyl | 7-(diethylamino-CH₂CH₂—) | H |
| 8334. | —(NMeSO₂)-phenyl | 7-(1-pyrrolidinyl-CH₂CH₂—) | H |
| 8335. | —(NMeSO₂)-phenyl | 7-(azaperhydroepinyl-CH₂CH₂—) | H |
| 8336. | —(NMeSO₂)-phenyl | 7-[(3,5-dimethylpiperid-1-yl)—CH₂CH₂—) | H |
| 8337. | —(NMeSO₂)-phenyl | 7-[(4-methylpiperid-1-yl-CH₂CH₂—) | H |
| 8338. | —(NMeSO₂)-phenyl | 7-[(3-methylpiperid-1-yl-CH₂CH₂—)—] | H |
| 8339. | —(NMeSO₂)-phenyl | 7-[(2-methylpiperid-1-yl-CH₂CH₂—)—] | H |
| 8340. | —(NMeSO₂)-phenyl | 7-(1-piperidylcarbonyl) | H |
| 8341. | —(NMeSO₂)-phenyl | 7-[(4-methylpiperazin-1-yl)carbonyl] | H |
| 8342. | —(NMeSO₂)-phenyl | 7-(morpholin-4-ylcarbonyl) | H |
| 8343. | —(NMeSO₂)-phenyl | 7-(diethylaminocarbonyl) | H |
| 8344. | —(NMeSO₂)-phenyl | 7-(1-pyrrolidinylcarbonyl) | H |
| 8345. | —(NMeSO₂)-phenyl | 7-(azaperhydroepinylcarbonyl) | H |
| 8346. | —(NMeSO₂)-phenyl | 7-[(3,5-dimethylpiperid-1-yl)carbonyl] | H |
| 8347. | —(NMeSO₂)-phenyl | 7-[(4-methylpiperid-1-ylcarbonyl) | H |
| 8348. | —(NMeSO₂)-phenyl | 7-[(3-methylpiperid-1-ylcarbonyl) | H |
| 8349. | —(NMeSO₂)-phenyl | 7-[(2-methylpiperid-1-ylcarbonyl) | H |
| 8350. | —(NMeSO₂)-phenyl | 7-[2-(dimethylamino)ethoxy] | H |
| 8351. | —(NMeSO₂)-phenyl | 7-[2-(methylamino)ethoxy] | H |
| 8352. | —(NMeSO₂)-phenyl | 7-[((2R)pyrrolidin-2-yl)methoxy] | H |
| 8353. | —(NMeSO₂)-phenyl | 7-[((2R)-1-methylpyrrolidin-2-yl)methoxy] | H |
| 8354. | —(NMeSO₂)-phenyl | 7-[2-(piperid-1-yl)ethoxy] | H |
| 8355. | —(NMeSO₂)-phenyl | 7-[2-(piperazin-1-yl)ethoxy] | H |
| 8356. | —(NMeSO₂)-phenyl | 7-[2-(morpholin-4-yl)ethoxy] | H |
| 8357. | —(NMeSO₂)-phenyl | 7-[2-(1-methyl(4-piperidyl))ethoxy] | H |
| 8358. | —(NMeSO₂)-phenyl | 7-[2-(1-methyl(4-piperidyl))methoxy] | H |
| 8359. | —(NMeSO₂)-phenyl | 7-(1-methyl(4-piperidyloxy)) | H |
| 8360. | —(NMeSO₂)-phenyl | 7-(piperid-1-yl-CH₂—) | NH₂ |
| 8361. | —(NMeSO₂)-phenyl | 7-(1-CH₃-piperazin-4-yl-CH₂—) | NH₂ |
| 8362. | —(NMeSO₂)-phenyl | 7-(morpholin-4-yl-CH₂—) | NH₂ |
| 8363. | —(NMeSO₂)-phenyl | 7-(diethylamino-CH₂—) | NH₂ |
| 8364. | —(NMeSO₂)-phenyl | 7-(1-pyrrolidinyl-CH₂—) | NH₂ |
| 8365. | —(NMeSO₂)-phenyl | 7-(azaperhydroepinyl-CH₂—) | NH₂ |
| 8366. | —(NMeSO₂)-phenyl | 7-[(3,5-dimethylpiperid-1-yl)—CH₂—] | NH₂ |
| 8367. | —(NMeSO₂)-phenyl | 7-[(4-methylpiperid-1-yl-CH₂—] | NH₂ |
| 8368. | —(NMeSO₂)-phenyl | 7-[(3-methylpiperid-1-yl-CH₂—] | NH₂ |
| 8369. | —(NMeSO₂)-phenyl | 7-[(2-methylpiperid-1-yl-CH₂—] | NH₂ |
| 8370. | —(NMeSO₂)-phenyl | 7-(piperid-1-yl-CH₂CH₂—) | NH₂ |
| 8371. | —(NMeSO₂)-phenyl | 7-(1-CH₃-piperazin-4-yl-CH₂CH₂—) | NH₂ |
| 8372. | —(NMeSO₂)-phenyl | 7-(morpholin-4-yl-CH₂CH₂—) | NH₂ |
| 8373. | —(NMeSO₂)-phenyl | 7-(diethylamino-CH₂CH₂—) | NH₂ |
| 8374. | —(NMeSO₂)-phenyl | 7-(1-pyrrolidinyl-CH₂CH₂—) | NH₂ |
| 8375. | —(NMeSO₂)-phenyl | 7-(azaperhydroepinyl-CH₂CH₂—) | NH₂ |
| 8376. | —(NMeSO₂)-phenyl | 7-[(3,5-dimethylpiperid-1-yl)—CH₂CH₂—) | NH₂ |
| 8377. | —(NMeSO₂)-phenyl | 7-[(4-methylpiperid-1-yl-CH₂CH₂—) | NH₂ |
| 8378. | —(NMeSO₂)-phenyl | 7-[(3-methylpiperid-1-yl-CH₂CH₂—)—] | NH₂ |
| 8379. | —(NMeSO₂)-phenyl | 7-[(2-methylpiperid-1-yl-CH₂CH₂—)—] | NH₂ |
| 8380. | —(NMeSO₂)-phenyl | 7-(1-piperidylcarbonyl) | NH₂ |
| 8381. | —(NMeSO₂)-phenyl | 7-[(4-methylpiperazin-1-yl)carbonyl] | NH₂ |
| 8382. | —(NMeSO₂)-phenyl | 7-(morpholin-4-ylcarbonyl) | NH₂ |
| 8383. | —(NMeSO₂)-phenyl | 7-(diethylaminocarbonyl) | NH₂ |
| 8384. | —(NMeSO₂)-phenyl | 7-(1-pyrrolidinylcarbonyl) | NH₂ |
| 8385. | —(NMeSO₂)-phenyl | 7-(azaperhydroepinylcarbonyl) | NH₂ |
| 8386. | —(NMeSO₂)-phenyl | 7-[(3,5-dimethylpiperid-1-yl)carbonyl] | NH₂ |
| 8387. | —(NMeSO₂)-phenyl | 7-[(4-methylpiperid-1-ylcarbonyl) | NH₂ |
| 8388. | —(NMeSO₂)-phenyl | 7-[(3-methylpiperid-1-ylcarbonyl) | NH₂ |
| 8389. | —(NMeSO₂)-phenyl | 7-[(2-methylpiperid-1-ylcarbonyl) | NH₂ |
| 8390. | —(NMeSO₂)-phenyl | 7-[2-(dimethylamino)ethoxy] | NH₂ |
| 8391. | —(NMeSO₂)-phenyl | 7-[2-(methylamino)ethoxy] | NH₂ |
| 8392. | —(NMeSO₂)-phenyl | 7-[((2R)pyrrolidin-2-yl)methoxy] | NH₂ |
| 8393. | —(NMeSO₂)-phenyl | 7-[((2R)-1-methylpyrrolidin-2-yl)methoxy] | NH₂ |
| 8394. | —(NMeSO₂)-phenyl | 7-[2-(piperid-1-yl)ethoxy] | NH₂ |
| 8395. | —(NMeSO₂)-phenyl | 7-[2-(piperazin-1-yl)ethoxy] | NH₂ |

TABLE 12-continued

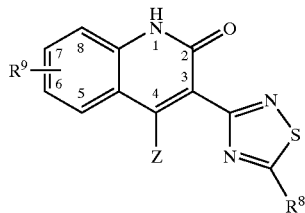

| # | R⁸ | R⁹ | Z |
|---|---|---|---|
| 8396. | —(NMeSO₂)-phenyl | 7-[2-(morpholin-4-yl)ethoxy] | NH₂ |
| 8397. | —(NMeSO₂)-phenyl | 7-[2-(1-methyl(4-piperidyl))ethoxy] | NH₂ |
| 8398. | —(NMeSO₂)-phenyl | 7-[2-(1-methyl(4-piperidyl))methoxy] | NH₂ |
| 8399. | —(NMeSO₂)-phenyl | 7-(1-methyl(4-piperidyloxy)) | NH₂ |
| 8400. | —(NMeSO₂)-2-thienyl | 7-(piperid-1-yl-CH₂—) | H |
| 8401. | —(NMeSO₂)-2-thienyl | 7-(1-CH₃-piperazin-4-yl-CH₂—) | H |
| 8402. | —(NMeSO₂)-2-thienyl | 7-(morpholin-4-yl-CH₂—) | H |
| 8403. | —(NMeSO₂)-2-thienyl | 7-(diethylamino-CH₂—) | H |
| 8404. | —(NMeSO₂)-2-thienyl | 7-(1-pyrrolidinyl-CH₂—) | H |
| 8405. | —(NMeSO₂)-2-thienyl | 7-(azaperhydroepinyl-CH₂—) | H |
| 8406. | —(NMeSO₂)-2-thienyl | 7-[(3,5-dimethylpiperid-1-yl)—CH₂—] | H |
| 8407. | —(NMeSO₂)-2-thienyl | 7-[(4-methylpiperid-1-yl-CH₂—] | H |
| 8408. | —(NMeSO₂)-2-thienyl | 7-[(3-methylpiperid-1-yl-CH₂—] | H |
| 8409. | —(NMeSO₂)-2-thienyl | 7-[(2-methylpiperid-1-yl-CH₂—] | H |
| 8410. | —(NMeSO₂)-2-thienyl | 7-(piperid-1-yl-CH₂CH₂—) | H |
| 8411. | —(NMeSO₂)-2-thienyl | 7-(1-CH₃-piperazin-4-yl-CH₂CH₂—) | H |
| 8412. | —(NMeSO₂)-2-thienyl | 7-(morpholin-4-yl-CH₂CH₂—) | H |
| 8413. | —(NMeSO₂)-2-thienyl | 7-(diethylamino-CH₂CH₂—) | H |
| 8414. | —(NMeSO₂)-2-thienyl | 7-(1-pyrrolidinyl-CH₂CH₂—) | H |
| 8415. | —(NMeSO₂)-2-thienyl | 7-(azaperhydroepinyl-CH₂CH₂—) | H |
| 8416. | —(NMeSO₂)-2-thienyl | 7-[(3,5-dimethylpiperid-1-yl)—CH₂CH₂—) | H |
| 8417. | —(NMeSO₂)-2-thienyl | 7-[(4-methylpiperid-1-yl-CH₂CH₂—) | H |
| 8418. | —(NMeSO₂)-2-thienyl | 7-[(3-methylpiperid-1-yl-CH₂CH₂—)—] | H |
| 8419. | —(NMeSO₂)-2-thienyl | 7-[(2-methylpiperid-1-yl-CH₂CH₂—)—] | H |
| 8420. | —(NMeSO₂)-2-thienyl | 7-(1-piperidylcarbonyl) | H |
| 8421. | —(NMeSO₂)-2-thienyl | 7-[(4-methylpiperazin-1-yl)carbonyl] | H |
| 8422. | —(NMeSO₂)-2-thienyl | 7-(morpholin-4-ylcarbonyl) | H |
| 8423. | —(NMeSO₂)-2-thienyl | 7-(diethylaminocarbonyl) | H |
| 8424. | —(NMeSO₂)-2-thienyl | 7-(1-pyrrolidinylcarbonyl) | H |
| 8425. | —(NMeSO₂)-2-thienyl | 7-(azaperhydroepinylcarbonyl) | H |
| 8426. | —(NMeSO₂)-2-thienyl | 7-[(3,5-dimethylpiperid-1-yl)carbonyl) | H |
| 8427. | —(NMeSO₂)-2-thienyl | 7-[(4-methylpiperid-1-ylcarbonyl) | H |
| 8428. | —(NMeSO₂)-2-thienyl | 7-[(3-methylpiperid-1-ylcarbonyl) | H |
| 8429. | —(NMeSO₂)-2-thienyl | 7-[(2-methylpiperid-1-ylcarbonyl) | H |
| 8430. | —(NMeSO₂)-2-thienyl | 7-[2-(dimethylamino)ethoxy] | H |
| 8431. | —(NMeSO₂)-2-thienyl | 7-[2-(methylamino)ethoxy] | H |
| 8432. | —(NNeSO₂)-2-thienyl | 7-[((2R)pyrrolidin-2-yl)methoxy] | H |
| 8433. | —(NMeSO₂)-2-thienyl | 7-[((2R)-1-methylpyrrolidin-2-yl)methoxy] | H |
| 8434. | —(NMeSO₂)-2-thienyl | 7-[2-(piperid-1-yl)ethoxy] | H |
| 8435. | —(NMeSO₂)-2-thienyl | 7-[2-(piperazin-1-yl)ethoxy] | H |
| 8436. | —(NMeSO₂)-2-thienyl | 7-[2-(morpholin-4-yl)ethoxy] | H |
| 8437. | —(NMeSO₂)-2-thienyl | 7-[2-(1-methyl(4-piperidyl))ethoxy] | H |
| 8438. | —(NMeSO₂)-2-thienyl | 7-[2-(1-methyl(4-piperidyl))methoxy] | H |
| 8439. | —(NMeSO₂)-2-thienyl | 7-(1-methyl(4-piperidyloxy)) | H |
| 8440. | —(NMeSO₂)-2-thienyl | 7-(piperid-1-yl-CH₂—) | NH₂ |
| 8441. | —(NMeSO₂)-2-thienyl | 7-(1-CH₃-piperazin-4-yl-CH₂—) | NH₂ |
| 8442. | —(NMeSO₂)-2-thienyl | 7-(morpholin-4-yl-CH₂—) | NH₂ |
| 8443. | —(NMeSO₂)-2-thienyl | 7-(diethylamino-CH₂—) | NH₂ |
| 8444. | —(NMeSO₂)-2-thienyl | 7-(1-pyrrolidinyl-CH₂—) | NH₂ |
| 8445. | —(NMeSO₂)-2-thienyl | 7-(azaperhydroepinyl-CH₂—) | NH₂ |
| 8446. | —(NMeSO₂)-2-thienyl | 7-[(3,5-dimethylpiperid-1-yl)—CH₂—] | NH₂ |
| 8447. | —(NMeSO₂)-2-thienyl | 7-[(4-methylpiperid-1-yl-CH₂—] | NH₂ |
| 8448. | —(NMeSO₂)-2-thienyl | 7-[(3-methylpiperid-1-yl-CH₂—] | NH₂ |
| 8449. | —(NMeSO₂)-2-thienyl | 7-[(2-methylpiperid-1-yl-CH₂—] | NH₂ |
| 8450. | —(NMeSO₂)-2-thienyl | 7-(piperid-1-yl-CH₂CH₂—) | NH₂ |
| 8451. | —(NMeSO₂)-2-thienyl | 7-(1-CH₃-piperazin-4-yl-CH₂CH₂—) | NH₂ |
| 8452. | —(NMeSO₂)-2-thienyl | 7-(morpholin-4-yl-CH₂CH₂—) | NH₂ |
| 8453. | —(NMeSO₂)-2-thienyl | 7-(diethylamino-CH₂CH₂—) | NH₂ |
| 8454. | —(NMeSO₂)-2-thienyl | 7-(1-pyrrolidinyl-CH₂CH₂—) | NH₂ |
| 8455. | —(NMeSO₂)-2-thienyl | 7-(azaperhydroepinyl-CH₂CH₂—) | NH₂ |
| 8456. | —(NMeSO₂)-2-thienyl | 7-[(3,5-dimethylpiperid-1-yl)—CH₂CH₂—) | NH₂ |
| 8457. | —(NMeSO₂)-2-thienyl | 7-[(4-methylpiperid-1-yl-CH₂CH₂—) | NH₂ |
| 8458. | —(NMeSO₂)-2-thienyl | 7-[(3-methylpiperid-1-yl-CH₂CH₂—)—] | NH₂ |
| 8459. | —(NMeSO₂)-2-thienyl | 7-[(2-methylpiperid-1-yl-CH₂CH₂—)—] | NH₂ |
| 8460. | —(NMeSO₂)-2-thienyl | 7-(1-piperidylcarbonyl) | NH₂ |

TABLE 12-continued

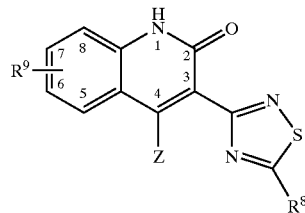

| # | R⁸ | R⁹ | Z |
|---|---|---|---|
| 8461. | —(NMeSO₂)-2-thienyl | 7-[(4-methylpiperazin-1-yl)carbonyl] | NH₂ |
| 8462. | —(NMeSO₂)-2-thienyl | 7-(morpholin-4-ylcarbonyl) | NH₂ |
| 8463. | —(NMeSO₂)-2-thienyl | 7-(diethylaminocarbonyl) | NH₂ |
| 8464. | —(NMeSO₂)-2-thienyl | 7-(1-pyrrolidinylcarbonyl) | NH₂ |
| 8465. | —(NMeSO₂)-2-thienyl | 7-(azaperhydroepinylcarbonyl) | NH₂ |
| 8466. | —(NMeSO₂)-2-thienyl | 7-[(3,5-dimethylpiperid-1-yl)carbonyl] | NH₂ |
| 8467. | —(NMeSO₂)-2-thienyl | 7-[(4-methylpiperid-1-yl)carbonyl] | NH₂ |
| 8468. | —(NMeSO₂)-2-thienyl | 7-[(3-methylpiperid-1-yl)carbonyl] | NH₂ |
| 8469. | —(NMeSO₂)-2-thienyl | 7-[(2-methylpiperid-1-yl)carbonyl] | NH₂ |
| 8470. | —(NMeSO₂)-2-thienyl | 7-[2-(dimethylamino)ethoxy] | NH₂ |
| 8471. | —(NMeSO₂)-2-thienyl | 7-[2-(methylamino)ethoxy] | NH₂ |
| 8472. | —(NMeSO₂)-2-thienyl | 7-[((2R)pyrrolidin-2-yl)methoxy] | NH₂ |
| 8473. | —(NMeSO₂)-2-thienyl | 7-[((2R)-1-methylpyrrolidin-2-yl)methoxy] | NH₂ |
| 8474. | —(NMeSO₂)-2-thienyl | 7-[2-(piperid-1-yl)ethoxy] | NH₂ |
| 8475. | —(NMeSO₂)-2-thienyl | 7-[2-(piperazin-1-yl)ethoxy] | NH₂ |
| 8476. | —(NMeSO₂)-2-thienyl | 7-[2-(morpholin-4-yl)ethoxy] | NH₂ |
| 8477. | —(NMeSO₂)-2-thienyl | 7-[2-(1-methyl(4-piperidyl))ethoxy] | NH₂ |
| 8478. | —(NMeSO₂)-2-thienyl | 7-[2-(1-methyl(4-piperidyl))methoxy] | NH₂ |
| 8479. | —(NMeSO₂)-2-thienyl | 7-(1-methyl(4-piperidyloxy)) | NH₂ |
| 8480. | —(NMeSO₂)-2-pyridyl | 7-(piperid-1-yl-CH₂—) | H |
| 8481. | —(NMeSO₂)-2-pyridyl | 7-(1-CH₃-piperazin-4-yl-CH₂—) | H |
| 8482. | —(NMeSO₂)-2-pyridyl | 7-(morpholin-4-yl-CH₂—) | H |
| 8483. | —(NMeSO₂)-2-pyridyl | 7-(diethylamino-CH₂—) | H |
| 8484. | —(NMeSO₂)-2-pyridyl | 7-(1-pyrrolidinyl-CH₂—) | H |
| 8485. | —(NMeSO₂)-2-pyridyl | 7-(azaperhydroepinyl-CH₂—) | H |
| 8486. | —(NMeSO₂)-2-pyridyl | 7-[(3,5-dimethylpiperid-1-yl)—CH₂—] | H |
| 8487. | —(NMeSO₂)-2-pyridyl | 7-[(4-methylpiperid-1-yl-CH₂—] | H |
| 8488. | —(NMeSO₂)-2-pyridyl | 7-[(3-methylpiperid-1-yl-CH₂—] | H |
| 8489. | —(NMeSO₂)-2-pyridyl | 7-[(2-methylpiperid-1-yl-CH₂—] | H |
| 8490. | —(NMeSO₂)-2-pyridyl | 7-(piperid-1-yl-CH₂CH₂—) | H |
| 8491. | —(NMeSO₂)-2-pyridyl | 7-(1-CH₃-piperazin-4-yl-CH₂CH₂—) | H |
| 8492. | —(NMeSO₂)-2-pyridyl | 7-(morpholin-4-yl-CH₂CH₂—) | H |
| 8493. | —(NMeSO₂)-2-pyridyl | 7-(diethylamino-CH₂CH₂—) | H |
| 8494. | —(NMeSO₂)-2-pyridyl | 7-(1-pyrrolidinyl-CH₂CH₂—) | H |
| 8495. | —(NMeSO₂)-2-pyridyl | 7-(azaperhydroepinyl-CH₂CH₂—) | H |
| 8496. | —(NMeSO₂)-2-pyridyl | 7-[(3,5-dimethylpiperid-1-yl)—CH₂CH₂—) | H |
| 8497. | —(NMeSO₂)-2-pyridyl | 7-[(4-methylpiperid-1-yl-CH₂CH₂—) | H |
| 8498. | —(NMeSO₂)-2-pyridyl | 7-[(3-methylpiperid-1-yl-CH₂CH₂—)—] | H |
| 8499. | —(NMeSO₂)-2-pyridyl | 7-[(2-methylpiperid-1-yl-CH₂CH₂—)—] | H |
| 8500. | —(NMeSO₂)-2-pyridyl | 7-(1-piperidylcarbonyl) | H |
| 8501. | —(NMeSO₂)-2-pyridyl | 7-[(4-methylpiperazin-1-yl]carbonyl] | H |
| 8502. | —(NMeSO₂)-2-pyridyl | 7-(morpholin-4-ylcarbonyl) | H |
| 8503. | —(NMeSO₂)-2-pyridyl | 7-(diethylaminocarbonyl) | H |
| 8504. | —(NMeSO₂)-2-pyridyl | 7-(1-pyrrolidinylcarbonyl) | H |
| 8505. | —(NMeSO₂)-2-pyridyl | 7-(azaperhydroepinylcarbonyl) | H |
| 8506. | —(NMeSO₂)-2-pyridyl | 7-[(3,5-dimethylpiperid-1-yl)carbonyl] | H |
| 8507. | —(NMeSO₂)-2-pyridyl | 7-[(4-methylpiperid-1-yl)carbonyl] | H |
| 8508. | —(NMeSO₂)-2-pyridyl | 7-[(3-methylpiperid-1-yl)carbonyl] | H |
| 8509. | —(NMeSO₂)-2-pyridyl | 7-[(2-methylpiperid-1-yl)carbonyl] | H |
| 8510. | —(NMeSO₂)-2-pyridyl | 7-[2-(dimethylamino)ethoxy] | H |
| 8511. | —(NMeSO₂)-2-pyridyl | 7-[2-(methylamino)ethoxy] | H |
| 8512. | —(NMeSO₂)-2-pyridyl | 7-[((2R)pyrrolidin-2-yl)methoxy] | H |
| 8513. | —(NMeSO₂)-2-pyridyl | 7-[((2R)-1-methylpyrrolidin-2-yl)methoxy] | H |
| 8514. | —(NMeSO₂)-2-pyridyl | 7-[2-(piperid-1-yl)ethoxy] | H |
| 8515. | —(NMeSO₂)-2-pyridyl | 7-[2-(piperazin-1-yl)ethoxy] | H |
| 8516. | —(NMeSO₂)-2-pyridyl | 7-[2-(morpholin-4-yl)ethoxy] | H |
| 8517. | —(NMeSO₂)-2-pyridyl | 7-[2-(1-methyl(4-piperidyl))ethoxy] | H |
| 8518. | —(NMeSO₂)-2-pyridyl | 7-[2-(1-methyl(4-piperidyl))methoxy] | H |
| 8519. | —(NMeSO₂)-2-pyridyl | 7-(1-methyl(4-piperidyloxy)) | H |
| 8520. | —(NMeSO₂)-2-pyridyl | 7-(piperid-1-yl-CH₂—) | NH₂ |
| 8521. | —(NMeSO₂)-2-pyridyl | 7-(1-CH₃-piperazin-4-yl-CH₂—) | NH₂ |
| 8522. | —(NMeSO₂)-2-pyridyl | 7-(morpholin-4-yl-CH₂—) | NH₂ |
| 8523. | —(NMeSO₂)-2-pyridyl | 7-(diethylamino-CH₂—) | NH₂ |
| 8524. | —(NMeSO₂)-2-pyridyl | 7-(1-pyrrolidinyl-CH₂—) | NH₂ |
| 8525. | —(NMeSO₂)-2-pyridyl | 7-(azaperhydroepinyl-CH₂—) | NH₂ |

TABLE 12-continued

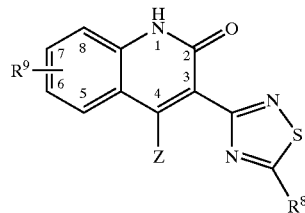

| # | R⁸ | R⁹ | Z |
|---|---|---|---|
| 8526. | —(NMeSO₂)-2-pyridyl | 7-[(3,5-dimethylpiperid-1-yl)—CH₂—] | NH₂ |
| 8527. | —(NMeSO₂)-2-pyridyl | 7-[(4-methylpiperid-1-yl-CH₂—] | NH₂ |
| 8528. | —(NMeSO₂)-2-pyridyl | 7-[(3-methylpiperid-1-yl-CH₂—] | NH₂ |
| 8529. | —(NMeSO₂)-2-pyridyl | 7-[(2-methylpiperid-1-yl-CH₂—] | NH₂ |
| 8530. | —(NMeSO₂)-2-pyridyl | 7-(piperid-1-yl-CH₂CH₂—) | NH₂ |
| 8531. | —(NMeSO₂)-2-pyridyl | 7-(1-CH₃-piperazin-4-yl-CH₂CH₂—) | NH₂ |
| 8532. | —(NMeSO₂)-2-pyridyl | 7-(morpholin-4-yl-CH₂CH₂—) | NH₂ |
| 8533. | —(NMeSO₂)-2-pyridyl | 7-(diethylamino-CH₂CH₂—) | NH₂ |
| 8534. | —(NMeSO₂)-2-pyridyl | 7-(1-pyrrolidinyl-CH₂CH₂—) | NH₂ |
| 8535. | —(NMeSO₂)-2-pyridyl | 7-(azaperhydroepinyl-CH₂CH₂—) | NH₂ |
| 8536. | —(NMeSO₂)-2-pyridyl | 7-[(3,5-dimethylpiperid-1-yl)—CH₂CH₂—) | NH₂ |
| 8537. | —(NMeSO₂)-2-pyridyl | 7-[(4-methylpiperid-1-yl-CH₂CH₂—) | NH₂ |
| 8538. | —(NMeSO₂)-2-pyridyl | 7-[(3-methylpiperid-1-yl-CH₂CH₂—)—] | NH₂ |
| 8539. | —(NMeSO₂)-2-pyridyl | 7-[(2-methylpiperid-1-yl-CH₂CH₂—)—] | NH₂ |
| 8540. | —(NMeSO₂)-2-pyridyl | 7-(1-piperidylcarbonyl) | NH₂ |
| 8541. | —(NMeSO₂)-2-pyridyl | 7-[(4-methylpiperazin-1-yl)carbonyl] | NH₂ |
| 8542. | —(NMeSO₂)-2-pyridyl | 7-(morpholin-4-ylcarbonyl) | NH₂ |
| 8543. | —(NMeSO₂)-2-pyridyl | 7-(diethylaminocarbonyl) | NH₂ |
| 8544. | —(NMeSO₂)-2-pyridyl | 7-(1-pyrrolidinylcarbonyl) | NH₂ |
| 8545. | —(NMeSO₂)-2-pyridyl | 7-(azaperhydroepinylcarbonyl) | NH₂ |
| 8546. | —(NMeSO₂)-2-pyridyl | 7-(3,5-dimethylpiperid-1-yl)carbonyl) | NH₂ |
| 8547. | —(NMeSO₂)-2-pyridyl | 7-[(4-methylpiperid-1-ylcarbonyl) | NH₂ |
| 8548. | —(NMeSO₂)-2-pyridyl | 7-[(3-methylpiperid-1-ylcarbonyl) | NH₂ |
| 8549. | —(NMeSO₂)-2-pyridyl | 7-[(2-methylpiperid-1-ylcarbonyl) | NH₂ |
| 8550. | —(NMeSO₂)-2-pyridyl | 7-[2-(dimethylamino)ethoxy] | NH₂ |
| 8551. | —(NMeSO₂)-2-pyridyl | 7-[2-(methylamino)ethoxy] | NH₂ |
| 8552. | —(NMeSO₂)-2-pyridyl | 7-[((2R)pyrrolidin-2-yl)methoxy] | NH₂ |
| 8553. | —(NMeSO₂)-2-pyridyl | 7-[((2R)-1-methylpyrrolidin-2-yl)methoxy] | NH₂ |
| 8554. | —(NMeSO₂)-2-pyridyl | 7-[2-(piperid-1-yl)ethoxy] | NH₂ |
| 8555. | —(NMeSO₂)-2-pyridyl | 7-[2-(piperazin-1-yl)ethoxy] | NH₂ |
| 8556. | —(NMeSO₂)-2-pyridyl | 7-[2-(morpholin-4-yl)ethoxy] | NH₂ |
| 8557. | —(NMeSO₂)-2-pyridyl | 7-[2-(1-methyl(4-(piperidyl))ethoxy] | NH₂ |
| 8558. | —(NMeSO₂)-2-pyridyl | 7-[2-(1-methyl(4-piperidyl))methoxy] | NH₂ |
| 8559. | —(NMeSO₂)-2-pyridyl | 7-(1-methyl(4-piperidyloxy)) | NH₂ |
| 8560. | —(NMeSO₂)-3-pyridyl | 7-(piperid-1-yl-CH₂—) | H |
| 8561. | —(NMeSO₂)-3-pyridyl | 7-(1-CH₃-piperazin-4-yl-CH₂—) | H |
| 8562. | —(NMeSO₂)-3-pyridyl | 7-(morpholin-4-yl-CH₂—) | H |
| 8563. | —(NMeSO₂)-3-pyridyl | 7-(diethylamino-CH₂—) | H |
| 8564. | —(NMeSO₂)-3-pyridyl | 7-(1-pyrrolidinyl-CH₂—) | H |
| 8565. | —(NMeSO₂)-3-pyridyl | 7-(azaperhydroepinyl-CH₂—) | H |
| 8566. | —(NMeSO₂)-3-pyridyl | 7-[(3,5-dimethylpiperid-1-yl)—CH₂—] | H |
| 8567. | —(NMeSO₂)-3-pyridyl | 7-[(4-methylpiperid-1-yl-CH₂—] | H |
| 8568. | —(NMeSO₂)-3-pyridyl | 7-[(3-methylpiperid-1-yl-CH₂—] | H |
| 8569. | —(NMeSO₂)-3-pyridyl | 7-[(2-methylpiperid-1-yl-CH₂—] | H |
| 8570. | —(NMeSO₂)-3-pyridyl | 7-(piperid-1-yl-CH₂—) | H |
| 8571. | —(NMeSO₂)-3-pyridyl | 7-(1-CH₃-piperazin-4-yl-CH₂CH₂—) | H |
| 8572. | —(NMeSO₂)-3-pyridyl | 7-(morpholin-4-yl-CH₂CH₂—) | H |
| 8573. | —(NMeSO₂)-3-pyridyl | 7-(diethylamino-CH₂CH₂—) | H |
| 8574. | —(NMeSO₂)-3-pyridyl | 7-(1-pyrrolidinyl-CH₂CH₂—) | H |
| 8575. | —(NMeSO₂)-3-pyridyl | 7-(azaperhydroepinyl-CH₂CH₂—) | H |
| 8576. | —(NMeSO₂)-3-pyridyl | 7-[(3,5-dimethylpiperid-1-yl)—CH₂CH₂—) | H |
| 8577. | —(NMeSO₂)-3-pyridyl | 7-[(4-methylpiperid-1-yl-CH₂CH₂—) | H |
| 8578. | —(NMeSO₂)-3-pyridyl | 7-[(3-methylpiperid-1-yl-CH₂CH₂—)—] | H |
| 8579. | —(NMeSO₂)-3-pyridyl | 7-[(2-methylpiperid-1-yl-CH₂CH₂—)—] | H |
| 8580. | —(NMeSO₂)-3-pyridyl | 7-(1-piperidylcarbonyl) | H |
| 8581. | —(NMeSO₂)-3-pyridyl | 7-[(4-methylpiperazin-1-yl)carbonyl] | H |
| 8582. | —(NMeSO₂)-3-pyridyl | 7-(morpholin-4-ylcarbonyl) | H |
| 8583. | —(NMeSO₂)-3-pyridyl | 7-(diethylaminocarbonyl) | H |
| 8584. | —(NMeSO₂)-3-pyridyl | 7-(1-pyrrolidinylcarbonyl) | H |
| 8585. | —(NMeSO₂)-3-pyridyl | 7-(azaperhydroepinylcarbonyl) | H |
| 8586. | —(NMeSO₂)-3-pyridyl | 7-(3,5-dimethylpiperid-1-yl)carbonyl) | H |
| 8587. | —(NMeSO₂)-3-pyridyl | 7-[(4-methylpiperid-1-ylcarbonyl) | H |
| 8588. | —(NMeSO₂)-3-pyridyl | 7-[(3-methylpiperid-1-ylcarbonyl) | H |
| 8589. | —(NMeSO₂)-3-pyridyl | 7-[(2-methylpiperid-1-ylcarbonyl) | H |
| 8590. | —(NMeSO₂)-3-pyridyl | 7-[2-(dimethylamino)ethoxy] | H |

TABLE 12-continued

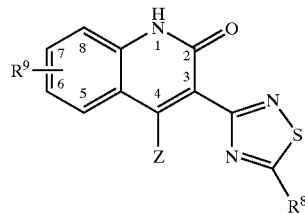

| # | R⁸ | R⁹ | Z |
|---|---|---|---|
| 8591. | —(NMeSO₂)-3-pyridyl | 7-[2-(methylamino)ethoxy] | H |
| 8592. | —(NMeSO₂)-3-pyridyl | 7-[((2R)pyrrolidin-2-yl)methoxy] | H |
| 8593. | —(NMeSO₂)-3-pyridyl | 7-[((2R)-1-methylpyrrolidin-2-yl)methoxy] | H |
| 8594. | —(NMeSO₂)-3-pyridyl | 7-[2-(piperid-1-yl)ethoxy] | H |
| 8595. | —(NMeSO₂)-3-pyridyl | 7-[2-(piperazin-1-yl)ethoxy] | H |
| 8596. | —(NMeSO₂)-3-pyridyl | 7-[2-(morpholin-4-yl)ethoxy] | H |
| 8597. | —(NMeSO₂)-3-pyridyl | 7-[2-(1-methyl(4-piperidyl))ethoxy] | H |
| 8598. | —(NMeSO₂)-3-pyridyl | 7-[2-(1-methyl(4-piperidyl))methoxy] | H |
| 8599. | —(NMeSO₂)-3-pyridyl | 7-(1-methyl(4-piperidyloxy)) | H |
| 8600. | —(NMeSO₂)-3-pyridyl | 7-(piperid-1-yl-CH₂—) | NH₂ |
| 8601. | —(NMeSO₂)-3-pyridyl | 7-(1-CH₃-piperazin-4-yl-CH₂—) | NH₂ |
| 8602. | —(NMeSO₂)-3-pyridyl | 7-(morpholin-4-yl-CH₂—) | NH₂ |
| 8603. | —(NMeSO₂)-3-pyridyl | 7-(diethylamino-CH₂—) | NH₂ |
| 8604. | —(NMeSO₂)-3-pyridyl | 7-(1-pyrrolidinyl-CH₂—) | NH₂ |
| 8605. | —(NMeSO₂)-3-pyridyl | 7-(azaperhydroepinyl-CH₂—) | NH₂ |
| 8606. | —(NMeSO₂)-3-pyridyl | 7-[(3,5-dimethylpiperid-1-yl)—CH₂—] | NH₂ |
| 8607. | —(NMeSO₂)-3-pyridyl | 7-[(4-methylpiperid-1-yl-CH₂—] | NH₂ |
| 8608. | —(NMeSO₂)-3-pyridyl | 7-[(3-methylpiperid-1-yl-CH₂—] | NH₂ |
| 8609. | —(NMeSO₂)-3-pyridyl | 7-[(2-methylpiperid-1-yl-CH₂—] | NH₂ |
| 8610. | —(NMeSO₂)-3-pyridyl | 7-(piperid-1-yl-CH₂CH₂—) | NH₂ |
| 8611. | —(NMeSO₂)-3-pyridyl | 7-(1-CH₃-piperazin-4-yl-CH₂CH₂—) | NH₂ |
| 8612. | —(NMeSO₂)-3-pyridyl | 7-(morpholin-4-yl-CH₂CH₂—) | NH₂ |
| 8613. | —(NMeSO₂)-3-pyridyl | 7-(diethylamino-CH₂CH₂—) | NH₂ |
| 8614. | —(NMeSO₂)-3-pyridyl | 7-(1-pyrrolidinyl-CH₂CH₂—) | Nh₂ |
| 8615. | —(NMeSO₂)-3-pyridyl | 7-(azaperhydroepinyl-CH₂CH₂—) | NH₂ |
| 8616. | —(NMeSO₂)-3-pyridyl | 7-[(3,5-dimethylpiperid-1-yl)—CH₂CH₂—) | NH₂ |
| 8617. | —(NMeSO₂)-3-pyridyl | 7-[(4-methylpiperid-1-yl-CH₂CH₂—) | NH₂ |
| 8618. | —(NMeSO₂)-3-pyridyl | 7-[(3-methylpiperid-1-yl-CH₂CH₂—)—] | NH₂ |
| 8619. | —(NMeSO₂)-3-pyridyl | 7-[(2-methylpiperid-1-yl-CH₂CH₂—)—] | NH₂ |
| 8620. | —(NMeSO₂)-3-pyridyl | 7-(1-piperidylcarbonyl) | NH₂ |
| 8621. | —(NMeSO₂)-3-pyridyl | 7-[(4-methylpiperazin-1-yl)carbonyl] | NH₂ |
| 8622. | —(NMeSO₂)-3-pyridyl | 7-(morpholin-4-ylcarbonyl) | NH₂ |
| 8623. | —(NMeSO₂)-3-pyridyl | 7-(diethylaminocarbonyl) | NH₂ |
| 8624. | —(NMeSO₂)-3-pyridyl | 7-(1-pyrrolidinylcarbonyl) | NH₂ |
| 8625. | —(NMeSO₂)-3-pyridyl | 7-(azaperhydroepinylcarbonyl) | NH₂ |
| 8626. | —(NMeSO₂)-3-pyridyl | 7-[(3,5-dimethylpiperid-1-yl)carbonyl] | NH₂ |
| 8627. | —(NMeSO₂)-3-pyridyl | 7-[(4-methylpiperid-1-ylcarbonyl) | NH₂ |
| 8628. | —(NMeSO₂)-3-pyridyl | 7-(3-methylpiperid-1-ylcarbonyl) | NH₂ |
| 8629. | —(NMeSO₂)-3-pyridyl | 7-(2-methylpiperid-1-ylcarbonyl) | NH₂ |
| 8630. | —(NMeSO₂)-3-pyridyl | 7-[2-(dimethylamino)ethoxy] | NH₂ |
| 8631. | —(NMeSO₂)-3-pyridyl | 7-[2-(methylamino)ethoxy] | NH₂ |
| 8632. | —(NMeSO₂)-3-pyridyl | 7-[((2R)pyrrolidin-2-yl)methoxy] | NH₂ |
| 8633. | —(NMeSO₂)-3-pyridyl | 7-[((2R)-1-methylpyrrolidin-2-yl)methoxy] | NH₂ |
| 8634. | —(NMeSO₂)-3-pyridyl | 7-[2-(piperid-1-yl)ethoxy] | NH₂ |
| 8635. | —(NMeSO₂)-3-pyridyl | 7-[2-(piperazin-1-yl)ethoxy] | NH₂ |
| 8636. | —(NMeSO₂)-3-pyridyl | 7-[2-(morpholin-4-yl)ethoxy] | NH₂ |
| 8637. | —(NMeSO₂)-3-pyridyl | 7-[2-(1-methyl(4-piperidyl))ethoxy] | NH₂ |
| 8638. | —(NMeSO₂)-3-pyridyl | 7-[2-(1-methyl(4-piperidyl))methoxy] | NH₂ |
| 8639. | —(NMeSO₂)-3-pyridyl | 7-(1-methyl(4-piperidyloxy)) | NH₂ |
| 8640. | —(NMeSO₂)-4-pyridyl | 7-(piperid-1-yl-CH₂—) | H |
| 8641. | —(NMeSO₂)-4-pyridyl | 7-(1-CH₃-piperazin-4-yl-CH₂—) | H |
| 8642. | —(NMeSO₂)-4-pyridyl | 7-(morpholin-4-yl-CH₂—) | H |
| 8643. | —(NMeSO₂)-4-pyridyl | 7-(diethylamino-CH₂—) | H |
| 8644. | —(NMeSO₂)-4-pyridyl | 7-(1-pyrrolidinyl-CH₂—) | H |
| 8645. | —(NMeSO₂)-4-pyridyl | 7-(azaperhydroepinyl-CH₂—) | H |
| 8646. | —(NMeSO₂)-4-pyridyl | 7-[(3,5-dimethylpiperid-1-yl)—CH₂—] | H |
| 8647. | —(NMeSO₂)-4-pyridyl | 7-[(4-methylpiperid-1-yl-CH₂—] | H |
| 8648. | —(NMeSO₂)-4-pyridyl | 7-[(3-methylpiperid-1-yl-CH₂—] | H |
| 8649. | —(NMeSO₂)-4-pyridyl | 7-[(2-methylpiperid-1-yl-CH₂—] | H |
| 8650. | —(NMeSO₂)-4-pyridyl | 7-(piperid-1-yl-CH₂CH₂—) | H |
| 8651. | —(NMeSO₂)-4-pyridyl | 7-(1-CH₃-piperazin-4-yl-CH₂CH₂—) | H |
| 8652. | —(NMeSO₂)-4-pyridyl | 7-(morpholin-4-yl-CH₂CH₂—) | H |
| 8653. | —(NMeSO₂)-4-pyridyl | 7-(diethylamino-CH₂CH₂—) | H |
| 8654. | —(NMeSO₂)-4-pyridyl | 7-(1-pyrrolidinyl-CH₂CH₂—) | H |
| 8655. | —(NMeSO₂)-4-pyridyl | 7-(azaperhydroepinyl-CH₂CH₂—) | H |

TABLE 12-continued

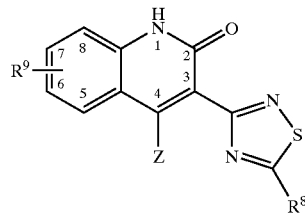

| # | R⁸ | R⁹ | Z |
|---|---|---|---|
| 8656. | —(NMeSO₂)-4-pyridyl | 7-[(3,5-dimethylpiperid-1-yl)—CH₂CH₂—) | H |
| 8657. | —(NMeSO₂)-4-pyridyl | 7-[(4-methylpiperid-1-yl-CH₂CH₂—) | H |
| 8658. | —(NMeSO₂)-4-pyridyl | 7-[(3-methylpiperid-1-yl-CH₂CH₂—)—] | H |
| 8659. | —(NMeSO₂)-4-pyridyl | 7-[(2-methylpiperid-1-yl-CH₂CH₂—)—] | H |
| 8660. | —(NMeSO₂)-4-pyridyl | 7-(1-piperidylcarbonyl) | H |
| 8661. | —(NMeSO₂)-4-pyridyl | 7-[(4-methylpiperazin-1-yl)carbonyl] | H |
| 8662. | —(NMeSO₂)-4-pyridyl | 7-(morpholin-4-ylcarbonyl) | H |
| 8663. | —(NMeSO₂)-4-pyridyl | 7-(diethylaminocarbonyl) | H |
| 8664. | —(NMeSO₂)-4-pyridyl | 7-(1-pyrrolidinylcarbonyl) | H |
| 8665. | —(NMeSO₂)-4-pyridyl | 7-(azaperhydroepinylcarbonyl) | H |
| 8666. | —(NMeSO₂)-4-pyridyl | 7-[(3,5-dimethylpiperid-1-yl)carbonyl) | H |
| 8667. | —(NMeSO₂)-4-pyridyl | 7-[(4-methylpiperid-1-ylcarbonyl) | H |
| 8668. | —(NMeSO₂)-4-pyridyl | 7-[(3-methylpiperid-1-ylcarbonyl) | H |
| 8669. | —(NMeSO₂)-4-pyridyl | 7-[(2-methylpiperid-1-ylcarbonyl) | H |
| 8670. | —(NMeSO₂)-4-pyridyl | 7-[(2-(dimethylamino)ethoxy] | H |
| 8671. | —(NMeSO₂)-4-pyridyl | 7-[2-(methylamino)ethoxy] | H |
| 8672. | —(NMeSO₂)-4-pyridyl | 7-[((2R)pyrrolidin-2-yl)methoxy] | H |
| 8673. | —(NMeSO₂)-4-pyridyl | 7-[((2R)-1-methylpyrrolidin-2-yl)methoxy] | H |
| 8674. | —(NMeSO₂)-4-pyridyl | 7-[2-(piperid-1-yl)ethoxy] | H |
| 8675. | —(NMeSO₂)-4-pyridyl | 7-[2-(piperazin-1-yl)ethoxy] | H |
| 8676. | —(NMeSO₂)-4-pyridyl | 7-[2-(morpholin-4-yl)ethoxy] | H |
| 8677. | —(NMeSO₂)-4-pyridyl | 7-[2-(1-methyl(4-piperidyl))ethoxy] | H |
| 8678. | —(NMeSO₂)-4-pyridyl | 7-[2-(1-methyl(4-piperidyl))methoxy] | H |
| 8679. | —(NMeSO₂)-4-pyridyl | 7-(1-methyl(4-piperidyloxy)) | H |
| 8680. | —(NMeSO₂)-4-pyridyl | 7-(piperid-1-yl-CH₂—) | NH₂ |
| 8681. | —(NMeSO₂)-4-pyridyl | 7-(1-CH₃-piperazin-4-yl-CH₂—) | NH₂ |
| 8682. | —(NMeSO₂)-4-pyridyl | 7-(morpholin-4-yl-CH₂—) | NH₂ |
| 8683. | —(NMeSO₂)-4-pyridyl | 7-(diethylamino-CH₂—) | NH₂ |
| 8684. | —(NMeSO₂)-4-pyridyl | 7-(1-pyrrolidinyl-CH₂—) | NH₂ |
| 8685. | —(NMeSO₂)-4-pyridyl | 7-(azaperhydroepinyl-CH₂—) | NH₂ |
| 8686. | —(NMeSO₂)-4-pyridyl | 7-[(3,5-dimethylpiperid-1-yl)—CH₂—] | NH₂ |
| 8687. | —(NMeSO₂)-4-pyridyl | 7-[(4-methylpiperid-1-yl-CH₂—] | NH₂ |
| 8688. | —(NMeSO₂)-4-pyridyl | 7-[(3-methylpiperid-1-yl-CH₂—] | NH₂ |
| 8689. | —(NMeSO₂)-4-pyridyl | 7-[(2-methylpiperid-1-yl-CH₂—] | NH₂ |
| 8690. | —(NMeSO₂)-4-pyridyl | 7-piperid-1-yl-CH₂CH₂—) | NH₂ |
| 8691. | —(NMeSO₂)-4-pyridyl | 7-(1-CH₃-piperazin-4-yl-CH₂CH₂—) | NH₂ |
| 8692. | —(NMeSO₂)-4-pyridyl | 7-(morpholin-4-yl-CH₂CH₂—) | NH₂ |
| 8693. | —(NMeSO₂)-4-pyridyl | 7-(diethylamino-CH₂CH₂—) | NH₂ |
| 8694. | —(NMeSO₂)-4-pyridyl | 7-(1-pyrrolidinyl-CH₂CH₂—) | NH₂ |
| 8695. | —(NMeSO₂)-4-pyridyl | 7-(azaperhydroepinyl-CH₂CH₂—) | NH₂ |
| 8696. | —(NMeSO₂)-4-pyridyl | 7-[(3,5-dimethylpiperid-1-yl)—CH₂CH₂—) | NH₂ |
| 8697. | —(NMeSO₂)-4-pyridyl | 7-[(4-methylpiperid-1-yl-CH₂CH₂—) | NH₂ |
| 8698. | —(NMeSO₂)-4-pyridyl | 7-[(3-methylpiperid-1-yl-CH₂CH₂—)—] | NH₂ |
| 8699. | —(NMeSO₂)-4-pyridyl | 7-[(2-methylpiperid-1-yl-CH₂CH₂—)—] | NH₂ |
| 8700. | —(NMeSO₂)-4-pyridyl | 7-(1-piperidylcarbonyl) | NH₂ |
| 8701. | —(NMeSO₂)-4-pyridyl | 7-[(4-methylpiperazin-1-yl)carbonyl] | NH₂ |
| 8702. | —(NMeSO₂)-4-pyridyl | 7-(morpholin-4-ylcarbonyl) | NH₂ |
| 8703. | —(NMeSO₂)-4-pyridyl | 7-(diethylaminocarbonyl) | NH₂ |
| 8704. | —(NMeSO₂)-4-pyridyl | 7-(1-pyrrolidinylcarbonyl) | NH₂ |
| 8705. | —(NMeSO₂)-4-pyridyl | 7-(azaperhydroepinylcarbonyl) | NH₂ |
| 8706. | —(NMeSO₂)-4-pyridyl | 7-[(3,5-dimethylpiperid-1-yl)carbonyl) | NH₂ |
| 8707. | —(NMeSO₂)-4-pyridyl | 7-[(4-methylpiperid-1-ylcarbonyl) | NH₂ |
| 8708. | —(NMeSO₂)-4-pyridyl | 7-[(3-methylpiperid-1-ylcarbonyl) | NH₂ |
| 8709. | —(NMeSO₂)-4-pyridyl | 7-[(2-methylpiperid-1-ylcarbonyl) | NH₂ |
| 8710. | —(NMeSO₂)-4-pyridyl | 7-[2-(dimethylamino)ethoxy] | NH₂ |
| 8711. | —(NMeSO₂)-4-pyridyl | 7-[2-(methylamino)ethoxy] | NH₂ |
| 8712. | —(NMeSO₂)-4-pyridyl | 7-[((2R)pyrrolidin-2-yl)methoxy] | NH₂ |
| 8713. | —(NMeSO₂)-4-pyridyl | 7-[((2R)-1-methylpyrrolidin-2-yl)methoxy] | NH₂ |
| 8714. | —(NMeSO₂)-4-pyridyl | 7-[2-(piperid-1-yl)ethoxy] | NH₂ |
| 8715. | —(NMeSO₂)-4-pyridyl | 7-[2-(piperazin-1-yl)ethoxy] | NH₂ |
| 8716. | —(NMeSO₂)-4-pyridyl | 7-[2-(morpholin-4-yl)ethoxy] | NH₂ |
| 8717. | —(NMeSO₂)-4-pyridyl | 7-[2-(1-methyl(4-piperidyl))ethoxy] | NH₂ |
| 8718. | —(NMeSO₂)-4-pyridyl | 7-[2-(1-methyl(4-piperidyl))methoxy] | NH₂ |
| 8719. | —(NMeSO₂)-4-pyridyl | 7-(1-methyl(4-piperidyloxy)) | NH₂ |

EXAMPLE 8721

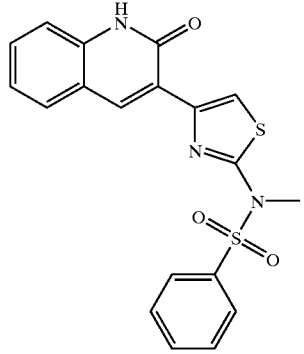

N-Methyl-N-(4-(2-oxo-1,2-dihydro-3-quinolinyl)-1,3-thiazol-2-yl)benzenesulfonamide To a solution of 3-[2-(methylamino)-1,3-thiazol-4-yl] hydroquinolin-2-one (180 mg, 0.7 mmol) in 5 mL pyridine was added benzenesulfonyl chloride (0.28 mL, 2.2 mmol) and a few crystals of DMAP. After 6 h, an amount of benzenesulfonyl chloride (0.10 mL, 0.8 mmol) was added. After 16 h, the reaction was quenched with water and the solvent was concentrated in vacuo. The crude material was purified by reverse phase HPLC to give a white solid. Mp: 242–244° C. MS m/z: 439(M+1).

EXAMPLE 8722

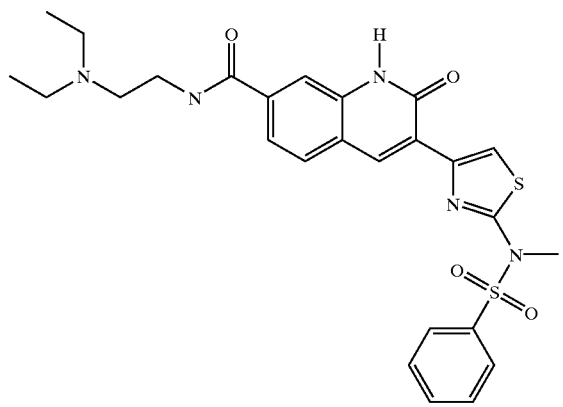

3-[2-(Benzenesulfonyl-methyl-amino)-thiazol-4-yl]-2-oxo-1,2-dihydro-quinoline-7-carboxylic acid (2-diethylamino-ethyl)-amide This compound was prepared analogous to Example 8734 using N,N-diethylethylendiamine. MS m/z: 540(M+1).

EXAMPLE 8723

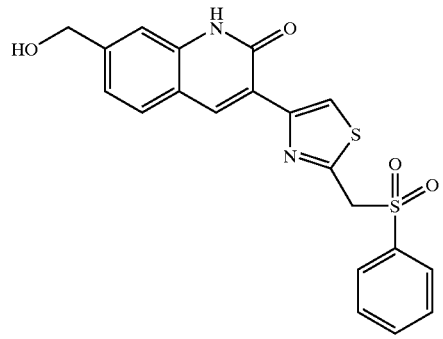

7-(Hydroxymethyl)-3-(2-((phenylsulfonyl)methyl)-1,3-thiazol-4-yl)-2(1H)-quinolinone The compound was prepared according to the procedure described for Examples 110(d) by employing 4-tert-butyldimethylsiloxymethyl-3-(2-bromoacetyl)-1H-quinolin-2-one (Example 110(c), 5.0 mmol) and 2-phenylsulfonylethanethiocarboxamide (Maybridge, 1.1 g, 5.0 mmol). Precipitates were collected by filtration to provide 0.95 g of solid. A 200 mg fraction was recrystalized from MeOH and $CH_2Cl_2$ to yield the title compound as a light yellow solid. MS m/z: 413.3 (M+1).

EXAMPLE 8724

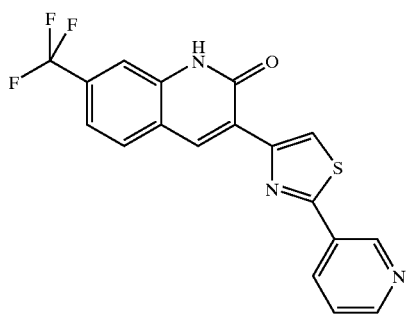

3-(2-(3-Pyridinyl)-1,3-thiazol-4-yl)-7-(trifluoromethyl)-2(1H)-quinolinone

This compound was prepared according to the method described in Example 104 by employing 7-(α, α, α-trifluoromethyl-3-(2-bromoacetyl)-1H-quinolin-2-one and thionicotinamide. MS m/z: 374.0 (M+1).

EXAMPLE 8725

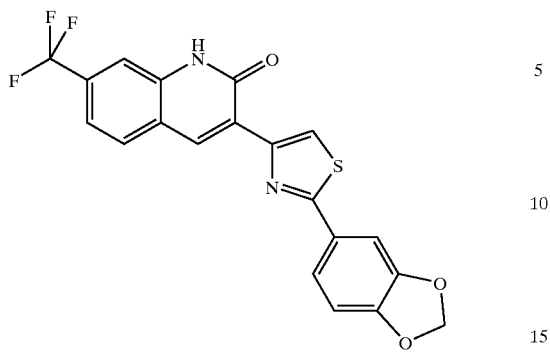

3-(2-(1,3-Benzodioxol-5-yl)-1,3-thiazol-4-yl)-7-(trifluoromethyl)-2(1H)-quinolinone This compound was prepared according to the method described in Example 104 by employing 7-(α,α,α-trifluoromethyl-3-(2-bromoacetyl)-1H-quinolin-2-one and benzo[1,3]dioxole-5-carbothioic acid amide. MS m/z: 417.1 (M+1).

EXAMPLE 8726

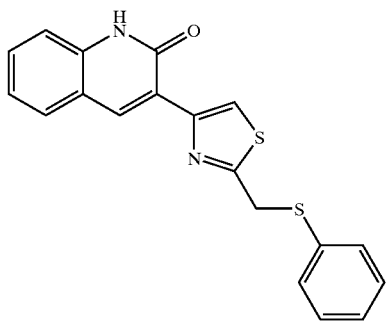

3-(2-Phenylthiomethyl-thiazol-4-yl)-1H-quinolin-2-one

EXAMPLE 8727

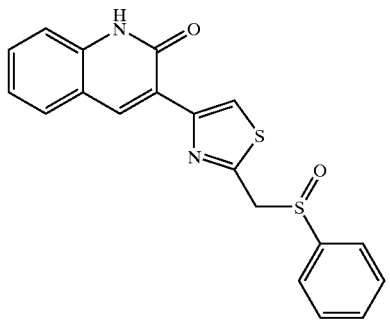

3-(2-Benzenesulfinylmethyl-thiazol-4-yl)-1H-quinolin-2-one

EXAMPLE 8728

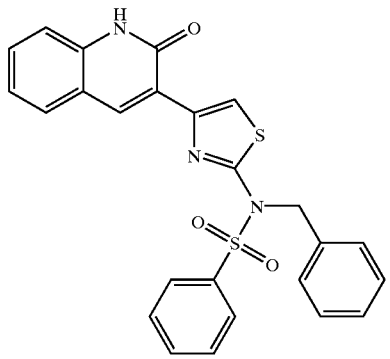

N-Benzyl-N-[4-(2-oxo-1,2-dihydro-quinolin-3-yl)-thiazol-2-yl]-benzenesulfonamide To a slurry of 3-(2-[(phenylsulfonyl)amino]-1,3-thiazol-4-yl)hydroquinolin-2-one in 5 ml DMF was added 60% NAH (29 mg, 0.7 mmol) resulting in gas evolution. After 15 min, benzyl bromide (0.08 ml, 0.67 mmol) was added. After 5 h the reaction solvent was removed to provide a yellow solid. The solid was washed with hot DMF, filtered, and washed consecutively with DMF, water, MeOH, and CH$_2$Cl$_2$. Drying in vacuo gave a pale yellow amorphous solid. Mp: 228–232° C. Ms m/z: 474 (m+1); 472 (m−1).

EXAMPLE 8729

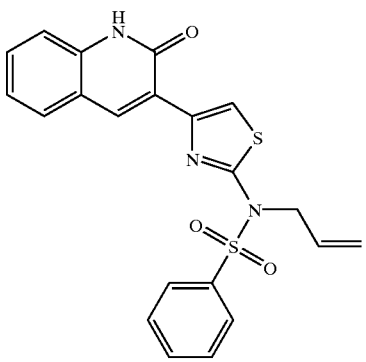

N-Allyl-N-[4-(2-oxo-1,2-dihydro-quinolin-3-yl)-thiazol-2-yl]-benzenesulfonamide

This compound was prepared analogous to Example 8728 using allyl bromide. Mp: 214–216° C. MS m/z: 424 (M+1); 422 (M−1).

EXAMPLE 8730

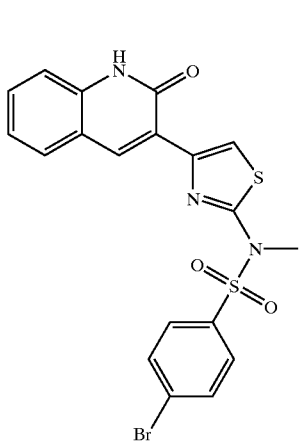

4-Bromo-N-methyl-N-[4-(2-oxo-1,2-dihydro-quinolin-3-yl)-thiazol-2-yl]-benzenesulfonamide This compound was prepared analogous to Example 8721 using 4-bromobenzenesulfonyl chloride. Mp: 280–282° C. MS m/z: 478(M+1).

EXAMPLE 8731

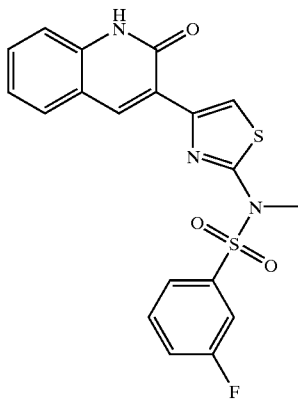

3-Fluoro-N-methyl-N-[4-(2-oxo-1,2-dihydro-quinolin-3-yl)-thiazol-2-yl]-benzenesulfonamide This compound was prepared analogous to Example 8721 using 3-fluorobenzenesulfonyl chloride. Mp: 247–249° C. MS m/z: 416 (M+1), 414 (M−1).

EXAMPLE 8732

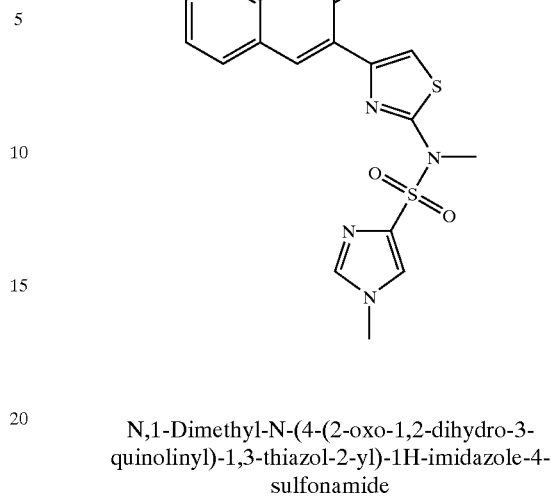

N,1-Dimethyl-N-(4-(2-oxo-1,2-dihydro-3-quinolinyl)-1,3-thiazol-2-yl)-1H-imidazole-4-sulfonamide This compound was prepared analogous to Example 8721 using 1-methyl-1H-imidazole-4-sulfonyl chloride (Maybridge). Mp:>300° C. MS m/z: 402 (M+1), 400 (M−1).

EXAMPLE 8733

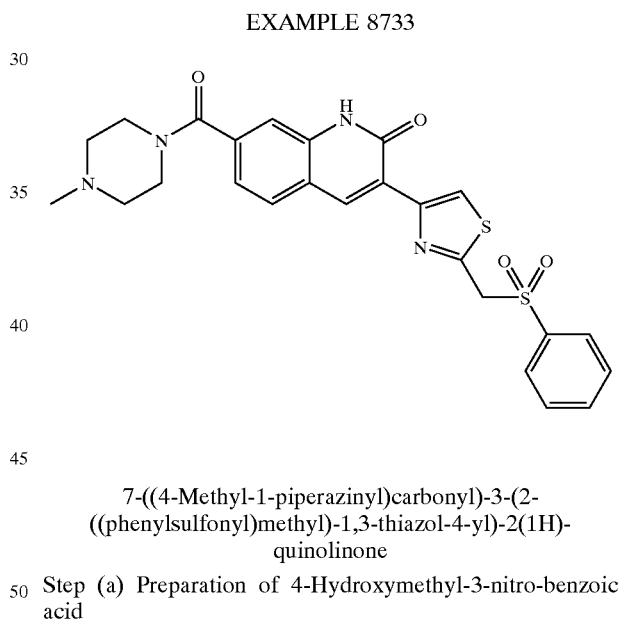

7-((4-Methyl-1-piperazinyl)carbonyl)-3-(2-((phenylsulfonyl)methyl)-1,3-thiazol-4-yl)-2(1H)-quinolinone Step (a) Preparation of 4-Hydroxymethyl-3-nitro-benzoic acid To a suspension of 1-methyl-2-nitroterephthalate (10.2 g, 45.1 mmol) and 150 mL of anhydrous ether was added 5.2 mL of anhydrous MeOH at which point most of the solid went into solution. The solution was cooled to 0° C. and LiBH$_4$ (in THF, 57.0 mL, 114.0 mmol, Aldrich) was added slowly over 50 min. Bubbles were generated. The resulting mixture was stirred at RT for 5 h, then heated to 35° C. TLC showed ~20% conversion. 100 mL of anhydrous THF was added and the reaction was heated to 55° C. After 3 days, TLC showed reactions to be complete. The reaction was carefully quenched with the addition of H$_2$O, and neutralized with 1N HCl. The organic layer was separated and the aqueous layer was extracted with ether (3×). The combined organic layers were washed with brine, dried over MgSO$_4$, and concentrated in vacuo to give a light yellow solid. MS m/z: 196.1 (M−1).

Step (b) Preparation of 4-Hydroxymethyl-3-nitro-benzoic acid methyl ester

4-Hydroxymethyl-3-nitro-benzoic acid (step (a), 2.0 g, 10.2 mmol) was dissolved in 100 mL of MeOH, treated with 10 drops of concentrated $H_2SO_4$ and stirred at 70° C. After 36 h, the solution was concentrated in vacuo and redissolved in EtOAc. The EtOAc solution was washed with 1N NaOH and brine, dried over $MgSO_4$, and concentrated to afford the title compound as a light-yellow solid upon drying under vacuum. MS m/z: 210.1 (M−1).

Step (c) Preparation of 3-Amino-4-hydroxymethyl-benzoic acid methyl ester

To a solution of 4-hydroxymethyl-3-nitro-benzoic acid methyl ester (step (b), 5.6 g, 26.5 mmol) in 60 mL EtOH/30 mL $H_2O$ was added Fe powder (7.5 g, 134.3 mmol) and $NH_4Cl$ (0.75 g, 14.0 mmol). The reaction mixture was stirred at 75° C. for 3 h, then filtered while hot through Celite. The Celite was washed with EtOAc and MeOH. The filtrate was concentrated in vacuo and partitioned between EtOAc/$H_2O$. The EtOAc layers was dried over $MgSO_4$ and concentrated in vacuo to give a yellow solid. MS m/z: 179.9 (M−1).

Step (d) Preparation of 3-Amino-4-formyl-benzoic acid methyl ester

Dissolve 3-amino-4-hydroxymethyl-benzoic acid methyl ester (step (c), 4.2 g, 23.3 mmol) in 125 mL of anhydrous $CH_2Cl_2$ and add $MnO_2$ (20.2 g, 232.8 mmol) and stirred at RT. After 5 h, the solution was filtered through Celite and concentrated to afford the title compound as a yellow solid upon drying under vacuum. MS m/z: 180.1 (M+1).

Step (e) Preparation of 3-Acetyl-2-oxo-1,2-dihydro-quinolinone-7-carboxylic acid methyl ester To a solution of 3-amino-4-formyl-benzoic acid methyl ester (step (d), 4.0 g, 22.1 mmol), DMAP (0.3 g, 2.4 mmol) and 100 mL of anhydrous dichloroethane was added diketene (1.9 mL, 24.7 mmol) dropwise over 2 min. The solution was stirred at 50° C. After 30 min, the reaction had thickened and a yellow ppt came out of solution. The ppt was filtered and washed with $CH_2Cl_2$ and dried on vacuum to give a fluffy yellow solid. MS m/z: 246.3 (M+1).

Step (f) Preparation of 3-(2-bromoacetyl)-2-oxo-1,2-dihydro-quinolinone-7-carboxylic acid methyl ester A solution of 3-acetyl-2-oxo-1,2-dihydro-quinolinone-7-carboxylic acid methyl ester (step (e), 2.8 g, 11.3 mmol), 5,5-dibromobarbaturic acid (1.9 g, 6.8 mmol), and THF (125 mL) was stirred at reflux. After 2 h, 5,5-dibromobarbaturic acid (100 mg) was added. After an additional 3 h, the ppt was filtered and rinsed with THF to give a yellow solid. MS m/z: 325.7 (M+1).

Step (g) Preparation of 3-(2-benzenesulfonylmethyl-thiazol-4-yl)-1H-quinolin-2-one-7-carboxylic acid methyl ester A solution of 3-(2-bromoacetyl)-2-oxo-1,2-dihydro-quinolinone-7-carboxylic acid methyl ester (step (f), 2.8 g, 8.6 mmol), 2-benzenesulfonylthioacetamide (2.5 g, 11.4 mmol), and MeOH (150 mL) were stirred at reflux for 4 days. LC-MS shows a mixture of title compound and starting materials. The reaction was cooled and filtered. The solid was repeatedly filtered from boiling THF to give the title compound. Starting material and crude product were also recovered. MS m/z: 440.9 (M+1).

Step (h) Preparation of 3-(2-benzenesulfonylmethyl-thiazol-4-yl)-1H-quinolin-2-one-7-carboxylic acid To a solution of 3-(2-benzenesulfonylmethyl-thiazol-4-yl)-1H-quinolin-2-one-7-carboxylic acid methyl ester (step (g), 0.9 g, 2.1 mmol) and THF (200 mL) was added 1N NaOH (4 mL). The solution was stirred at RT. After 2 h, an additional 4 mL of 1N NaOH was added. After an additional 3 h, 4 mL of 1N NaOH was added. After 24 h, TLC shows complete conversion. The solution was concentrated in vacuo and diluted with 100 mL of $H_2O$. The aqueous solution was acidified with 2N HCl (aq) and a precipitate formed. The precipitate was filtered and dried in vacuo at 60° C. to give an off-white solid. MS m/z: 427.0 (M+1).

Step (i) Preparation of 3-(2-benzenesulfonylmethyl-thiazol-4-yl)-7-(4-methyl-piperazine-1-carbonyl)-1H-quinolin-2-one A solution of 3-(2-benzenesulfonylmethyl-thiazol-4-yl)-1H-quinolin-2-one-7-carboxylic acid (step (h), 0.1 g, 0.2 mmol), EDC (0.08 g, 0.4 mmol), HOBt (0.08 g, 0.6 mmol), DMAP (4 mg), and 4 mL of DMF were stirred for 15 min, and then 1-methyl piperazine (0.13 mL, 1.2 mmol) was added. The reaction was stirred at RT for 24 h. The reaction was diluted with 50 mL of $H_2O$ and extracted with EtOAc (4×). The combined EtOAc layers were washed with 0.5N HCl, saturated $NaHCO_3$, and brine. The acidic aqueous layer was neutralized with 1N NaOH and extracted with EtOAc (3×). The combined organic layers were dried over $MgSO_4$ and concentrated in vacuo. The resulting solid was suspended in a minimum of EtOAc and filtered to give a solid. MS m/z: 509.4 (M+1). Anal. Calc'd for $C_{25}H_{24}N_4O_4S_2$: C, 59.04; H, 4.76; N, 11.02. Found: C, 58.75; H, 4.87; N, 10.90.

EXAMPLE 8734

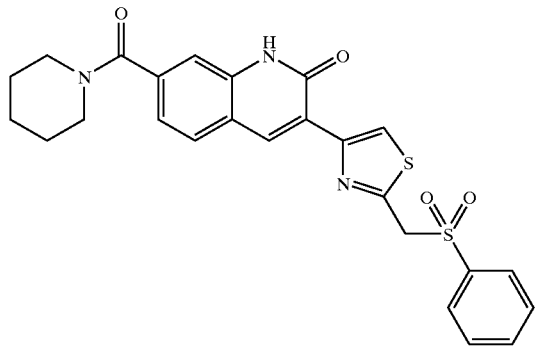

3-(2-((Phenylsulfonyl)methyl)-1,3-thiazol-4-yl)-7-(1-piperidinylcarbonyl)-2(1H)-quinolinone To a suspension of 3-(2-benzenesulfonylmethyl-thiazol-4-yl)-1H-quinolin-2-one-7-carboxylic acid (Example 8733 step (h), 0.1 g, 0.2 mmol) and 5 mL of anhydrous $CH_2Cl_2$ was added TEA (0.2 mL, 1.4 mmol) and pivaloyl chloride (0.1 mL, 0.8 mmol). The solution was stirred overnight at RT. The reaction was now homogenous and piperidine (0.5 mL, 5.1 mmol) was added. After 6 h, the reaction was diluted with $H_2O$. The aqueous solution was extracted with EtOAc (6×). The combined EtOAc layers were washed with brine, dried over $MgSO_4$, and concentrated in vacuo. The solid was suspended in a minimum of EtOAc and filtered to give a solid. MS m/z: 494.1 (M+1). Anal. Calc'd for $C_{25}H_{23}N_3O_4S_2 \cdot 0.5H_2O$: C, 59.74; H, 4.81; N, 8.36. Found: C, 59.64; H, 4.82; N, 8.30.

EXAMPLE 8735

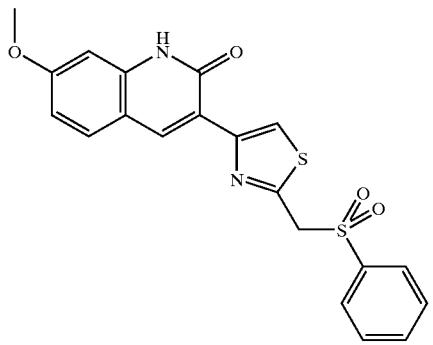

7-(Methoxy)-3-(2-((phenylsulfonyl)methyl)-1,3-thiazol-4-yl)-2(1H)-quinolinone

A mixture of 3-(2-bromo-acetyl)-7-methoxy-1H-quinolin-2-one (0.25 g, 0.84 mmole) and 2-benzenethioacetamide (0.24 g, 1.1 mmole) in EtOH (5 mL) was heated by Microwave Synthesizer in 7 min. at 150° C. The mixture was cooled. The precipitated solid was filtered and triturated with EtOH to give a tan solid. MS (m/z): 413.0 (m+1).

EXAMPLE 8736

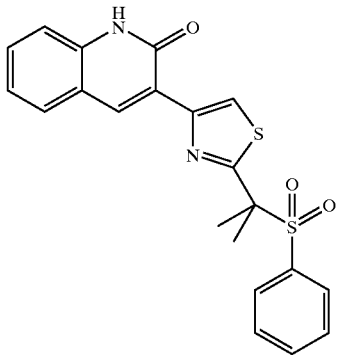

3-(2-(1-Methyl-1-(phenylsulfonyl)ethyl)-1,3-thiazol-4-yl)-2(1H)-quinolinone

Step (a) Preparation of 2-benzenesulfonyl-2-methyl-propionitrile

To a solution of 2-(phenylsulfonyl)acetonitrile (Aldrich, 2.70 g, 15.0 mmol) in 20 mL of $CH_2Cl_2$ were added 10 mL of 5 N NaOH, tetra-n-butylammonium iodide (0.75 g, 2.1 mmol), and 5.0 mL of MeI. The resulting mixture was stirred vigorously at RT for 1 h. Diluted with 40 mL of $CH_2Cl_2$ and the layers were carefully separated to avoid emulsion. The organic layer was washed with 50 mL of $H_2O$ (2×), dried ($Na_2SO_4$), and concentrated to provide the title compound as a white solid. MS m/z: 231.9 (M+23).

Step (b) Preparation of 2-amino-1,1-dimethyl-1-(phenylsulfonyl)ethane-2-thione

A solution of 2-methyl-2-(phenylsulfonyl)propanenitrile (Step a, 3.0 g, 14.4 mmol) in 20 mL of pyridine and 4 mL of TEA was purged with $H_2S$ gas for 3 h. The resulting mixture was stirred at RT overnight. Solvents were removed under vacuum and the oily residue was azeotroped with 3×50 mL of toluene. A stock solution in 25 mL of anhydrous MeOH was then prepared and used in next step. MS m/z: 242.2 (M−1).

Step (c) Preparation of 3-(2-(1-methyl-1-(phenylsulfonyl)ethyl)-1,3-thiazol-4-yl)-2(1h)-quinolinone A mixture of 3-(2-bromoacetyl)-1h-quinolin-2-one (Example 27(b), 270 mg, 1.0 mmol) and 2-amino-1,1-dimethyl-1-(phenylsulfonyl)ethane-2-thione (step b, 1.7 ml, 1.0 mmol) in 3.5 ml of anhydrous MeOH was heated at 120° C. for 5 min by microwave synthesizer. The reaction mixture was cooled to RT. The precipitates were collected by filtration and washed with MeOH and $CH_2Cl_2$ to provide the title compound as a light yellow solid. Ms m/z: 411.3 (m+1).

EXAMPLE 8737

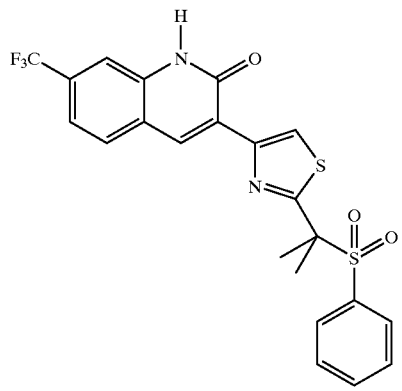

3-(2-(1-Methyl-1-(phenylsulfonyl)ethyl)-1,3-thiazol-4-yl)-7-(trifluoromethyl)-2(1H)-quinolinone This compound was prepared according to the method described in Example 8734 by employing morpholine (Aldrich). MS m/z: 496.1 (M+1). Anal. Calc'd for $C_{24}H_{23}N_3O_5S_2$: C, 58.17; H, 4.27; N, 8.48. Found: C, 58.07; H, 4.54; N, 8.25.

EXAMPLE 8738

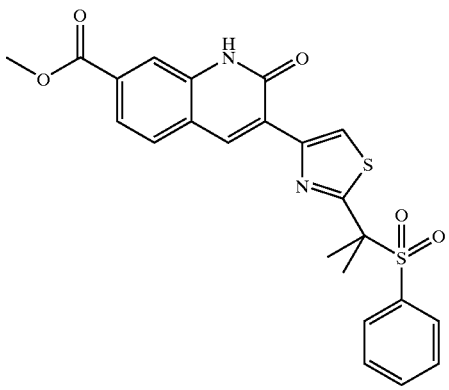

Methyl 3-(2-(1-methyl-1-(phenylsulfonyl)ethyl)-1,3-thiaxol-4-yl)-2-oxo-1,2-dihydro-7-quinolinecarboxylate The compound was prepared according to the procedure described for Example 8836(c) by employing 3-(2-bromoacetyl)-2-oxo-1,2-dihydro-quinolinone-7-carboxylic acid methyl ester (Example 8733(f), 300 mg, 0.92 mmol) and 2-amino-1,1-dimethyl-1-(phenylsulfonyl)ethane-2-thione (Step b, 1.7 mL, 1.0 mmol) in 3.5 mL of anhydrous MeOH was heated at 120° C. for 5 min by microwave synthesizer. The reaction mixture was cooled to RT. The precipitates were collected by filtration and washed with MeOH and CH₂Cl₂ to provide the title compound as a light yellow solid. MS m/z: 469.2 (M+1).

EXAMPLE 8739

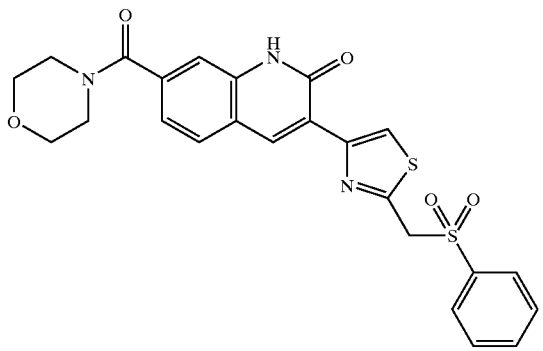

7-(4-Morpholinylcarbonyl)-3-(2-((phenylsulfonyl)methyl)-1,3-thiazol-4-yl)-2(1H)-quinolinone

EXAMPLE 8740

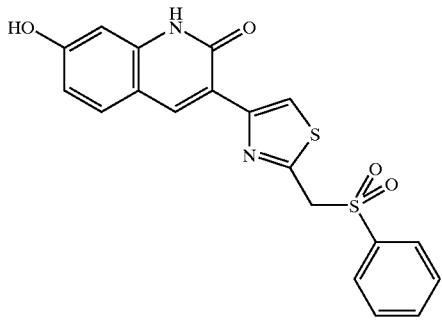

7-hydroxy-3-(2-((phenylsulfonyl)methyl)-1,3-thiazol-4-yl)-2(1H)-quinolinone

To a stirred suspension of 7-(methoxy)-3-(2-((phenylsulfonyl)methyl)-1,3-thiazol-4-yl)-2(1h)-quinolinone (Example 8735) (0.1 g, 0.24 mmole) in EtSH (1 mL) was added AlBr3. Stirring was continued in 14 h. The mixture was poured onto ice water and the solid was filtered. The solid was purified by RP-HPLC to give a tan solid. MS (m/z): 399.50 (m+1).

EXAMPLE 8741

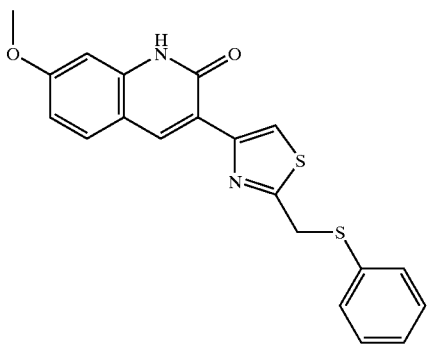

7-(Methoxy)-3-(2-((phenylthio)methyl)-1,3-thiazol-4-yl)-2(1H)-quinolinone

Following the Example 8735 to give the title compound as a tan solid. MS (m/z): 381.5 (m+1).

EXAMPLE 8742

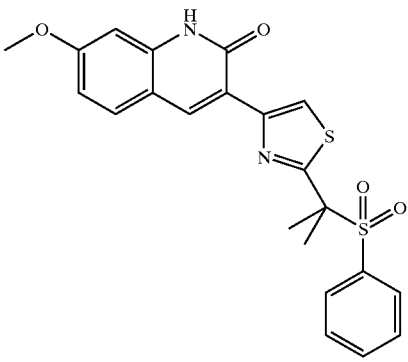

7-(Methoxy)-3-(2-(1-methyl-1-(phenylsulfonyl)ethyl)-1,3-thiazol-4-yl)-2(1H)-quinolinone This compound was prepared according to the procedure described for Example 8836(c) by employing 3-(2-bromoacetyl)-7-methoxy-1H-quinolin-2-one (Example 8741, 250 mg, 0.84 mmol) and 2-amino-1,1-dimethyl-1-(phenylsulfonyl)ethane-2-thione (Step b, 1.7 mL, 1.0 mmol) in 3.5 mL of anhydrous MeOH was heated at 120° C. for 3×5 min by microwave synthesizer. The reaction mixture was cooled to RT. The precipitates were collected by filtration and washed with MeOH and CH₂Cl₂ to provide the title compound as a white solid. MS m/z: 441 (M+1).

EXAMPLE 8743

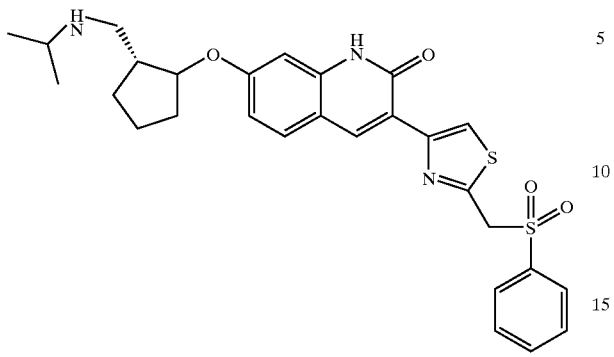

7-(((2R)-2-(((1-Methylethyl)amino)methyl)-1-pyrrolidinyl)methyl)-3-(2-((phenylsulfonyl)methyl)-1,3-thiazol-4-yl)-2(1H)-quinolinone Step (a) 3-(2-Benzenesulfonylmethyl-thiazol-4-yl)-2-oxo-1,2-dihydro-quinoline-7-carbaldehyde.

To a solution of 7-(hydroxymethyl)-3-(2-((phenylsulfonyl)methyl)-1,3-thiazol-4-yl)-2(1H)-quinolinone (Example 8723, 1.7 g, 4.12 mmol) in 150 mL of DMF was added 25 g of MnO$_2$. The mixture was stirred at RT for 24 h. The solids were filtered off through Celite®. 20 mL of DMF was used to rinse the solid. The combined filtrate containing the intermediate aldehyde was stored in refrigerator until being used for the next step without further purification. MS m/z: 411.0 (M+1).

Step (b) 7-(((2r)-2-(((1-Methylethyl)amino)methyl)-1-pyrrolidinyl)methyl)-3-(2-((phenylsulfonyl)methyl)-1,3-thiazol-4-yl)-2(1h)-quinolinone.

A solution of 3-(2-benzenesulfonylmethyl-thiazol-4-yl)-2-oxo-1,2-dihydro-quinoline-7-carbaldehyde in DMF (Example 8743(a)), 0.1 mL of the corresponding secondary alkyamine, 0.5 mL of HOAc, 1.0 mL of CH$_2$Cl$_2$, 0.1 mL of trimethyl orthoformate was stirred at RT for 2 h. 0.9 g of polymer bounded MP-NEt$_3$:BH$_3$(CN) (Argonaut, 1 mmol/g) was added and the resulting mixture was stirred at RT for 24 h. The polymer beads were filtered off and the filtrate was concentrated. Residues were dissolved in minimal amount of DMSO. Final compounds were purified using a mass-triggered preparative HPLC system and dried via lyophilization. Treatment of the residues with ammonium hydroxide provided the title compounds as a light yellow solid after lyophilization. MS m/z: 537 (M+1).

Examples 8744–8756 were prepared by the procedure described in Example 8743.

EXAMPLE 8744

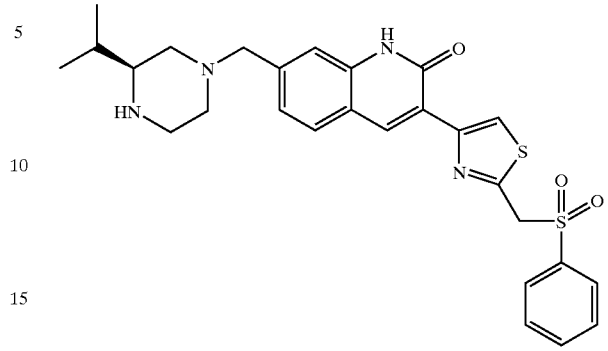

7-(((3S)-3-(1-Methylethyl)-1-piperazinyl)methyl)-3-(2-((phenylsulfonyl)methyl)-1,3-thiazol-4-yl)-2(1H)-quinolinone Tan solid. MS m/z: 523.4 (M+1).

EXAMPLE 8745

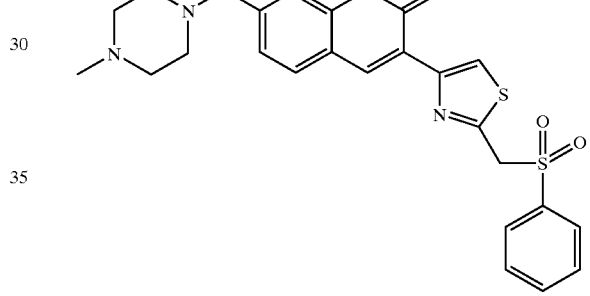

7-((4-Methyl-1-piperazinyl)methyl)-3-(2-((phenylsulfonyl)methyl)-1,3-thiazol-4-yl)-2(1H)-quinolinone Light yellow solid. MS m/z: 495.4 (M+1).

EXAMPLE 8746

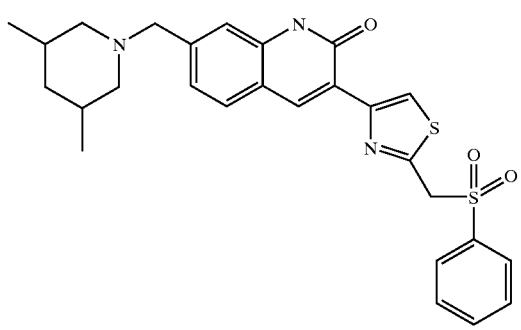

7-((3,5-Dimethyl-1-piperidinyl)methyl)-3-(2-((phenylsulfonyl)methyl)-1,3-thiazol-4-yl)-2(1H)-quinolinone Light yellow solid. MS m/z: 508.6 (M+1).

EXAMPLE 8747

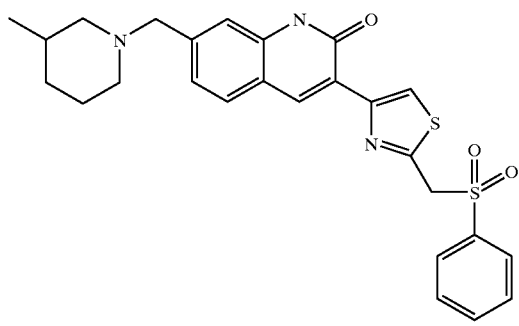

7-((3-Methyl-1-piperidinyl)methyl)-3-(2-((phenylsulfonyl)methyl)-1,3-thiazol-4-yl)-2(1H)-quinolinone Off-white solid. MS m/z: 494.4 (M+1).

EXAMPLE 8748

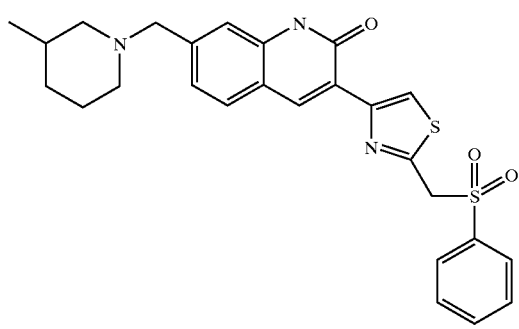

7-((3-methyl-1-piperazinyl)methyl)-3-(2-((phenylsulfonyl)methyl)-1,3-thiazol-4-yl)-2(1H)-quinolinone Off-white solid. MS m/z: 495.3 (M+1).

EXAMPLE 8749

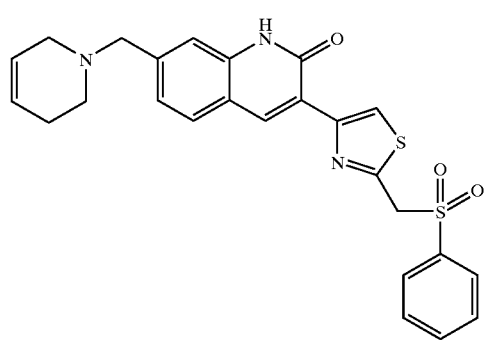

7-(3,6-Dihydro-1(2H)-pyridinylmethyl)-3-(2-((phenylsulfonyl)methyl)-1,3-thiazol-4-yl)-2(1H)-quinolinone Off-white solid. MS m/z: 478.2 (M+1).

EXAMPLE 8750

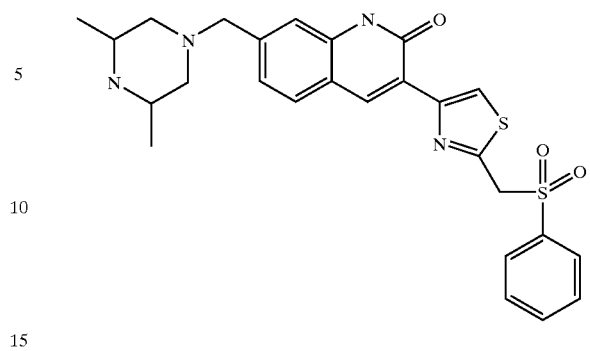

7-((cis-3,5-Dimethyl-1-piperazinyl-methyl)-3-(2-((phenylsulfonyl)methyl)-1,3-thiazol-4-yl)-2(1H)-quinolinone Off-white solid. MS m/z: 509.3 (M+1).

EXAMPLE 8751

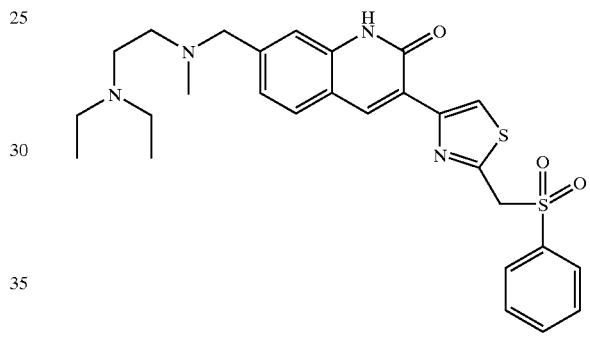

7-(((2-(Diethylamino)ethyl)(methyl)amino)methyl)-3-(2-((phenylsulfonyl)methyl)-1,3-thiazol-4-yl)-2(1H)-quinolinone Yellow solid. MS m/z: 525.3 (M+1).

EXAMPLE 8752

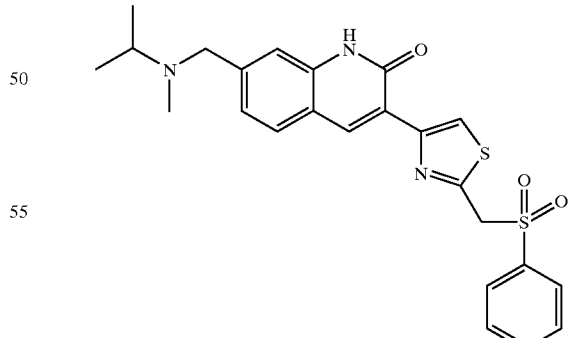

7-((Methyl(1-methylethyl)amino)methyl)-3-(2-((phenylsulfonyl)methyl)-1,3-thiazol-4-yl)-2(1H)-quinolinone White solid. MS m/z: 468 (M+1).

EXAMPLE 8753

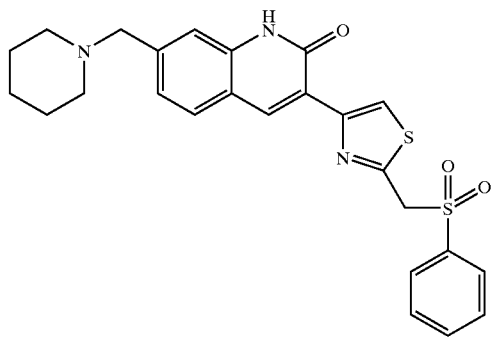

3-(2-((Phenylsulfonyl)methyl)-1,3-thiazol-4-yl)-7-(1-piperidinylmethyl)-2(1H)-quinolinone Light yellow solid. MS m/z: 480.3 (M+1).

EXAMPLE 8754

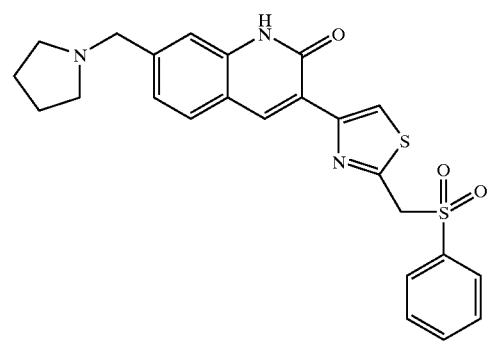

3-(2-((Phenylsulfonyl)methyl)-1,3-thiazol-4-yl)-7-(1-pyrrolidinylmethyl)-2(1H)-quinolinone Off-white solid. MS m/z: 466 (M+1).

EXAMPLE 8755

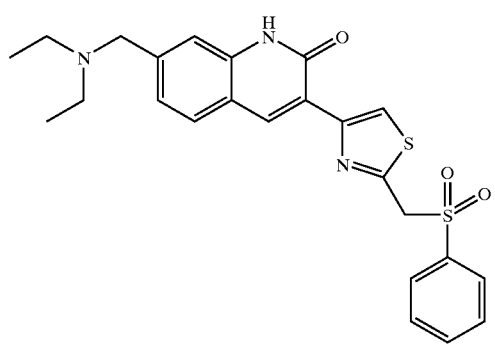

7-((Diethylamino)methyl)-3-(2-((phenylsulfonyl)methyl)-1,3-thiazol-4-yl)-2(1H)-quinolinone Light yellow solid. MS m/z: 4680.3 (M+1).

EXAMPLE 8756

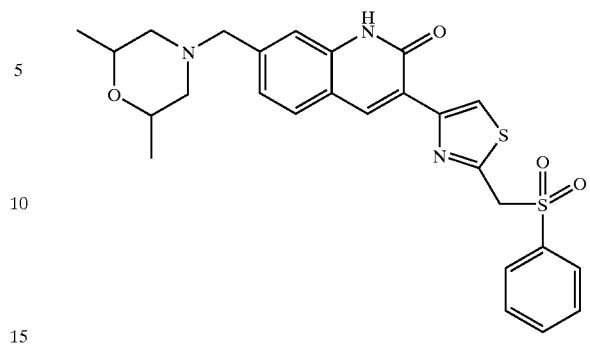

7-((2,6-Dimethyl-4-morpholinyl)methyl)-3-(2-((phenylsulfonyl)methyl)-1,3-thiazol-4-yl)-2(1H)-quinolinone Light yellow solid. MS m/z: 510.3 (M+1).

EXAMPLE 8757

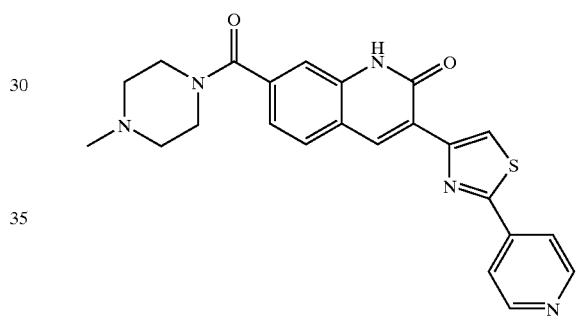

7-((4-Methyl-1-piperazinyl)carbonyl)-3-(2-(4-pyridinyl)-1,3-thiazol-4-yl)-2(1H)-quinolinone Step (a) Preparation of 3-(2-pyridin-4-yl-thiazol-4-yl)-1H-quinolin-2-one-7-carboxylic acid methyl ester A solution of 3-(2-bromoacetyl)-2-oxo-1,2-dihydro-quinolinone-7-carboxylic acid methyl ester (Example 8733 (f), 1.1 g, 3.3 mmol), isothionicotinamide (0.5 g, 3.3 mmol), and MeOH (65 mL) were stirred at 65° C. overnight. A catalytic amount of p-toluenesulfonic acid was added. After an additional 24 h, the reaction was cooled and filtered to give crude compound. MS m/z: 364.2 (M+1).

Step (b) Preparation of 3-(2-pyridin-4-yl-thiazol-4-yl)-1H-quinolin-2-one-7-carboxylic acid This compound was prepared according to the method described in Example 8733 step (h). MS m/z: 350.0 (M+1).

Step (c) Preparation of 7-(4-methyl-piperazine-1-carbonyl)-3-(2-pyridin-4-yl-thiazol-4-yl)-1H-quinolin-2-one This compound was prepared according to the method described in Example 8734 employing 1-methyl piperazine. MS m/z: 432.2 (M+1). Anal. Calc'd for $C_{23}H_{21}N_5O_2S \cdot 0.7H_2O$: C, 62.20; H, 5.08; N, 15.77. Found: C, 62.28; H, 4.84; N, 15.80.

EXAMPLE 8758

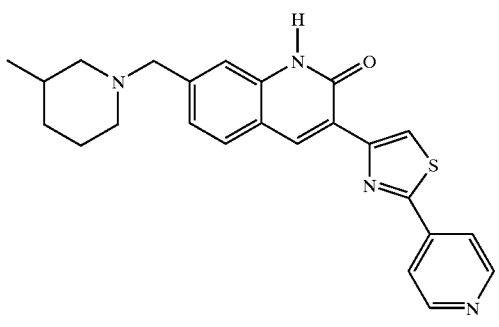

7-(3-Methyl-piperidin-1-ylmethyl)-3-(2-pyridin-4-yl-thiazol-4-yl)-1H-quinolin-2-one Step (a) Preparation of 3-(2-pyridin-4-yl-thiazol-4-yl)-1H-quinolin-2-one-7-carbaldehyde To a solution of 7-hydroxymethyl-3-(2-pyridin-4-yl-thiazol-4-yl)-1H-quinolin-2-one (Example 103(d), 1.78 g, 5.3 mmol) was added 100 mL of anhydrous DMF and Dess-Martin periodinane (2.69 g, 6.3 mmol, Omega). The reaction was stirred at RT for 5 h. The precipitate was filtered and washed with $CH_2Cl_2$ (2×) to give a quantitative amount of tan solid. MS m/z: 334.3 (M+1).

Step (b) General procedure for reductive amination with 3-(2-pyridin-4-yl-thiazol-4-yl)-1H-quinolin-2-one-7-carbaldehyde A solution of 3-(2-pyridin-4-yl-thiazol-4-yl)-1H-quinolin-2-one-7-carbaldehyde (step (a), 60 mg, 0.18 mmol), 1 mL of $CH_2Cl_2$, 0.5 mL of trimethyl orthoformate, 3-methylpiperidine (0.2 mL), and 10 mL of 5% HOAc in DMF was allowed to stir for 2 h. At this time, 0.9 g of polymer bounded MP-$NEt_3$:$BH_3$(CN) (Argonaut, 1 mmol/g) was added and the mixture was stirred at RT overnight. The resins were carefully removed by filtration and the filtrate was concentrated. The resulting residue was dissolved in DMSO and purified by preparative HPLC. The solid obtained after lyophilization was neutralized with aqueous ammonium hydroxide and subsequently lyophilized. Treatment with excess 1 N HCl solution afforded the title compound as a yellow solid after lyophilization (HCl salt). MS m/z: 417.0 (M+1).

EXAMPLE 8759

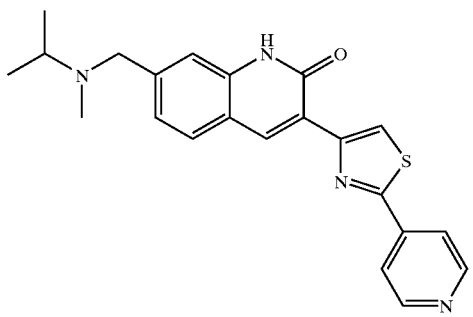

7-[(Isopropyl-methyl-amino)-methyl]-3-(2-pyridin-4-yl-thiazol-4-yl)-1H-quinolin-2-one This compound was prepared according to the method described in example 8758 step (b) employing 3-(2-pyridin-4-yl-thiazol-4-yl)-1H-quinolin-2-one-7-carbaldehyde and N-isopropyl-N-methylamine to provide the desired compound as a yellow solid. MS m/z; 391.0 (M+1).

EXAMPLE 8760

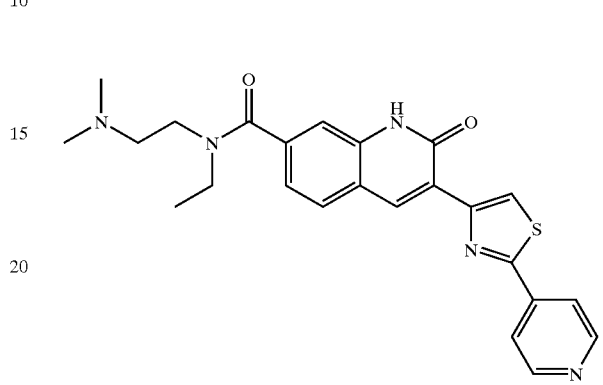

2-Oxo-3-(2-pyridin-4-yl-thiazol-4-yl)-1,2-dihydro-quinoline-7-carboxylic acid (2-dimethylamino-ethyl)-ethyl-amide This compound was prepared according to the method described in Example 8734 employing N'-ethyl-N,N-dimethylethane-1,2-diamine (Aldrich) and 3-(2-pyridin-4-yl-thiazol-4-yl)-1H-quinolin-2-one-7-carboxylic acid. MS m/z: 448.2 (M+1). Anal. Calc'd for $C_{24}H_{25}N_5O_2S \cdot 1.7H_2O$: C, 60.28; H, 5.99; N, 14.65. Found: C, 60.03; H, 5.61; N, 14.39.

EXAMPLE 8761

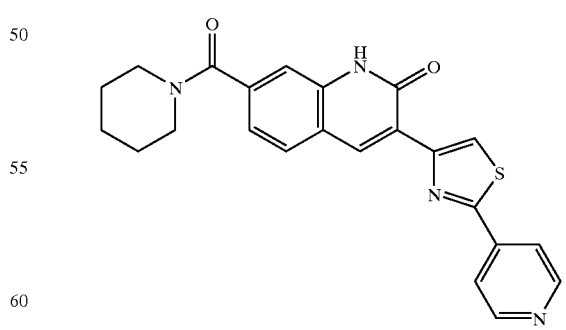

7-(Piperidine-1-carbonyl)-3-(2-pyridin-4-yl-thiazol-4-yl)-1H-quinolin-2-one

This compound was prepared according to the method described in Example 8734 employing N'-ethyl-N,N-dimethylethane-1,2-diamine (Aldrich) and 3-(2-pyridin-4-yl-thiazol-4-yl)-1H-quinolin-2-one-7-carboxylic acid. MS m/z: 417.2 (M+1). Anal. Calc'd for $C_{23}H_{20}N_4O_2S \cdot 0.1H_2O$: C, 66.04; H, 4.87; N, 13.39. Found: C, 65.74; H, 4.71; N, 13.21.

EXAMPLE 8762

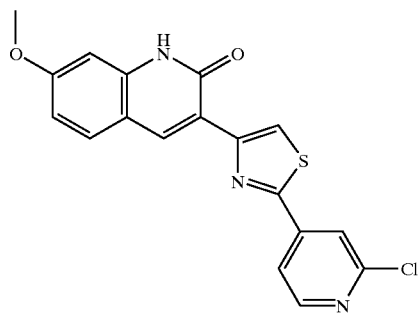

3-(2-(2-Chloro-4-pyridinyl)-1,3-thiazol-4-yl)-7-(methoxy)-2(1H)-quinolinone

Following the Example 8735 to give the title compound as a tan solid. MS (m/z): 370.5 (m+1).

EXAMPLE 8763

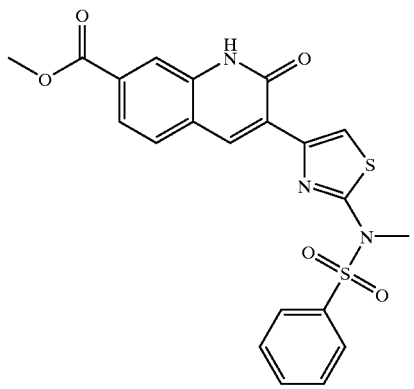

Methyl 3-(2-methyl(phenylsulfonyl)amino)-1,3-thiazol-4-yl)-2-oxo-1,2-dihydro-7-quinolinecarboxylate Step (A) Preparation of 3-(2-methylamino-thiazol-4-yl)-2-oxo-1,2-dihydro-quinoline-7-carboxylic acid methyl ester This compound was made analogous to Example 8733, step G. 3-(2-Bromo-acetyl)-2-oxo-1,2-dihydro-quinoline-7-carboxylic acid methyl ester (497 mg, 1.5 mmol) and 1-methyl-2-thiourea (130 mg, 1.4 mmol) in MeOH were heated to 150° C. for 400 seconds in the microwave. MS m/z: 316 (M+1), 314 (M−1).

Step (B) Preparation of methyl 3-(2-(methyl (phenylsulfonyl)amino)-1,3-thiazol-4-yl)-2-oxo-1,2-dihydro-7-quinolinecarboxylate This compound was prepared in a similar fashion to Example 8721. Mp. >300° C. MS m/z: 456(M+1), 454 (M−1).

EXAMPLE 8764

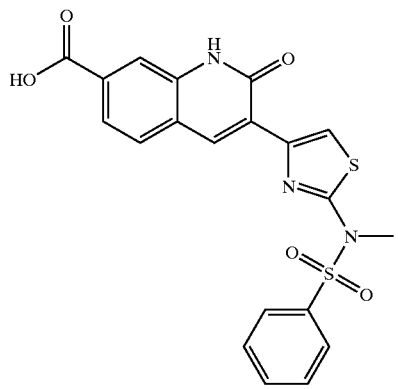

3-(2-(Methyl(phenylsulfonyl)amino)-1,3-thiazol-4-yl)-2-oxo-1,2-dihydro-7-quinolinecarboxylic Acid This compound was prepared analogous to Example 8733,step H. MS m/z: 442(M+1), 440 (M−1).

EXAMPLE 8765

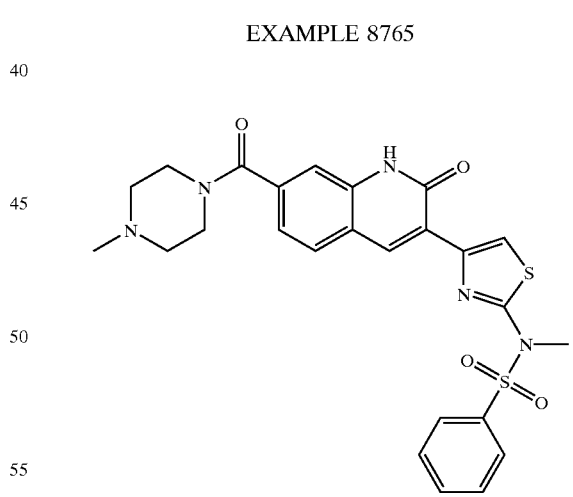

N-Methyl-N-{4-[7-(4-methyl-piperazine-1-carbonyl)-2-oxo-1,2-dihydro-quinolin-3-yl]-thiazol-2-yl}-benzenesulfonamide This compound was prepared analogous to Example 8734 using N-methyl-piperazine. Mp. 242–247° C. MS m/z: 524(M+1), 522 (M−1).

EXAMPLE 8766

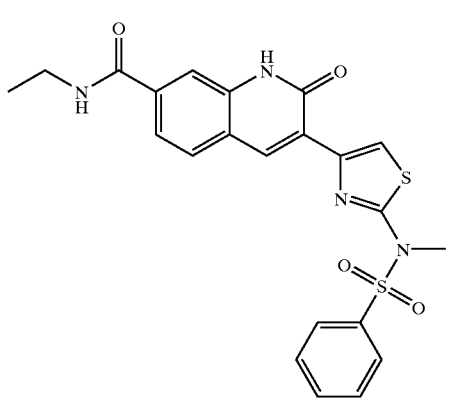

3-[2-(Benzenesulfonyl-methyl-amino)-thiazol-4-yl]-2-oxo-1,2-dihydro-quinoline-7-carboxylic acid ethylamide This compound was prepared analogous to Example 8734 using ethyl amine. Mp. >300° C. MS m/z: 469(M+1), 467(M−1).

EXAMPLE 8767

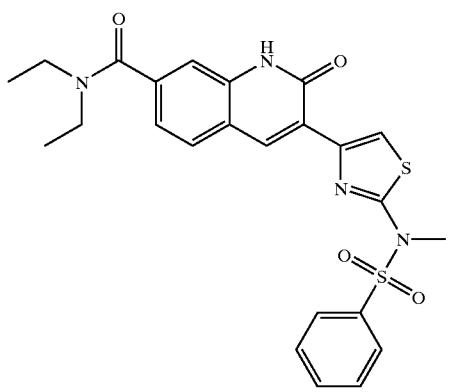

N,N-Diethyl-3-(2-(methyl(phenylsulfonyl)amino)-1,3-thiazol-4-yl)-2-oxo-1,2-dihydro-7-quinolinecarboxamide This compound was prepared analogous to Example 8734 using diethyl amine. Mp. 200–202° C. MS m/z: 497(M+1), 495(M−1).

EXAMPLE 8768

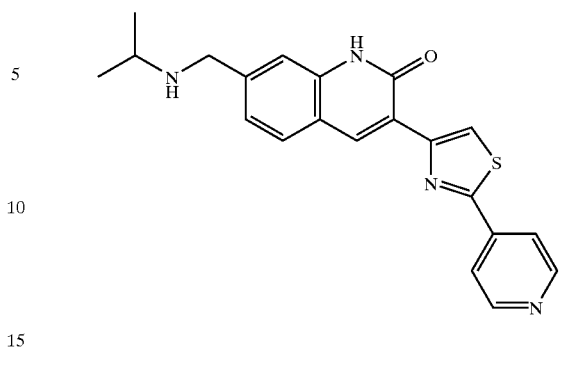

7-(Isopropylamino-methyl)-3-(2-pyridin-4-yl-thiazol-4-yl)-1H-quinolin-2-one

A solution of 3-(2-pyridin-4-yl-thiazol-4-yl)-1H-quinolin-2-one-7-carbaldehyde (step (a), 100 mg, 0.3 mmol), 1.5 mL AcOH, 1.5 mL of triethyl orthoformate, isopropylamine (0.5 mL), and 30 mL of DMF was stirred for 3 h. Gentle heating was be used to bring about a homogenous solution. After 3 h, NaBH(OAc)$_3$ (0.5 g, Aldrich) was added and the reaction was stirred for 3 days at RT. The solution was concentrated in genevac overnight to remove DMF. The resulting solid was dissolved in a minimal amount of DMSO and purified by mass triggered HPLC to give a yellow solid after drying in genevac (TFA salt). MS m/z: 377.3 (M+1).

EXAMPLE 8769

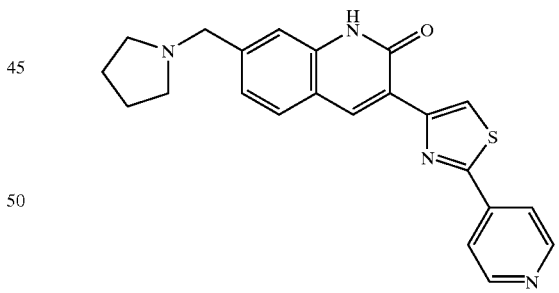

3-(2-Pyridin-4-yl-thiazol-4-yl)-7-pyrrolidin-1-ylmethyl-1H-quinolin-2-one

This compound was prepared according to the method described in example 8768 employing 3-(2-pyridin-4-yl-thiazol-4-yl)-1H-quinolin-2-one-7-carbaldehyde and pyrrolidine to give a yellow solid. MS m/z: 389.2 (M+1).

EXAMPLE 8770

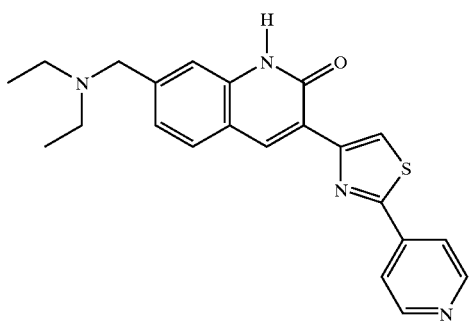

7-Diethylaminomethyl-3-(2-pyridin-4-yl-thiazol-4-yl)-1H-quinolin-2-one

This compound was prepared according to the method described in example 8768 employing 3-(2-pyridin-4-yl-thiazol-4-yl)-1H-quinolin-2-one-7-carbaldehyde and N,N-diethylamine to give a yellow solid. MS m/z: 391.3 (M+1).

EXAMPLE 8771

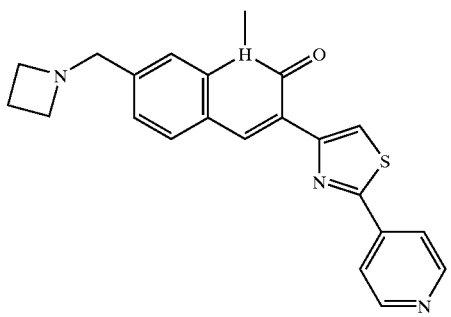

7-Azetidin-1-ylmethyl-3-(2-pyridin-4-yl-thiazol-4-yl)-1H-quinolin-2-one

This compound was prepared according to the method described in example 8768 employing 3-(2-pyridin-4-yl-thiazol-4-yl)-1H-quinolin-2-one-7-carbaldehyde and azetidine to give a yellow solid. MS m/z: 375.1 (M+1).

EXAMPLE 8772

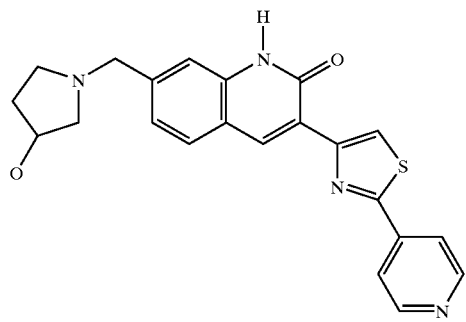

7-(3-Hydroxy-pyrrolidin-1-ylmethyl)-3-(2-pyridin-4-yl-thiazol-4-yl)-1H-quinolin-2-one This compound was prepared according to the method described in example 8768 employing 3-(2-pyridin-4-yl-thiazol-4-yl)-1H-quinolin-2-one-7-carbaldehyde and 3-hydroxypyrrolidine to give a yellow solid. MS m/z: 405.4 (M+1).

EXAMPLE 8773

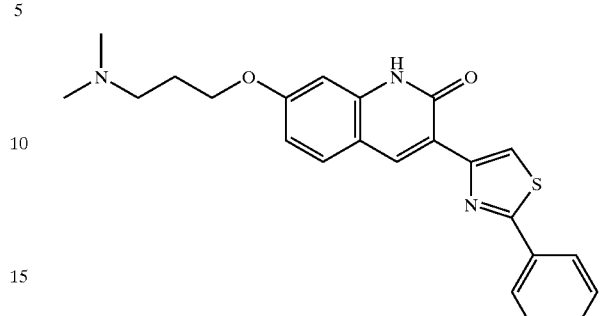

7-((3-(Dimethylamino)propyl)oxy)-3-(2-(4-pyridinyl)-1,3-thiazol-4-yl)-2(1H)-quinolinone A mixture of 7-hydroxy-3(2-(4-pyridinyl)-1,3-thiazol-4-yl)-2 (1H)-quinolinone (0.1 g, 0.37 mmole), potassium carbonate (0.15 g, 1.14 mmole), and N,N,-dimethylpropyl chloride hydrochloride (0.06 g, 0.45 mmole) in DMF (3 mL) was heated at 80° C. in 24 h. The mixture was cooled, concentrated, taken up in $H_2O$, and filtered to isolate a solid which was purified by flash column chromatography (15% MeOH/$CH_2Cl_2$) to give a tan solid. MS (m/z): 407.5 (m+1).

EXAMPLE 8774

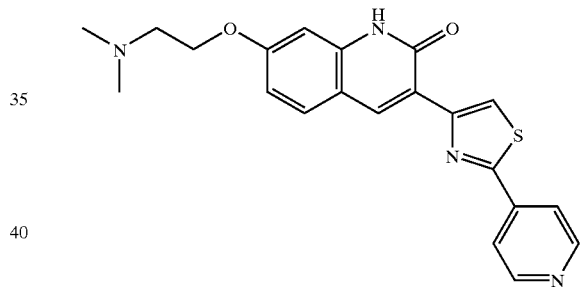

7-((2-(Dimethylamino)ethyl)oxy)-3-(2-(4-pyridinyl)-1,3-thiazol-4-yl)-2(1H)-quinolinone Following the Example 8773 to give a tan solid. MS (m/z): 393.5 (m+1).

EXAMPLE 8775

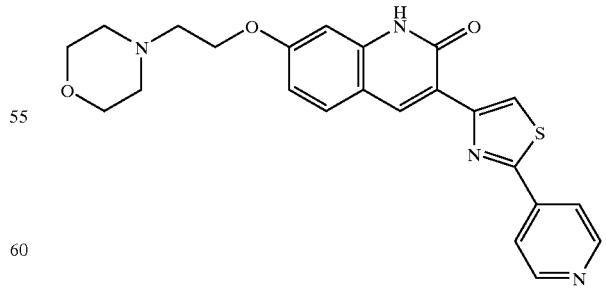

7-((2-(4-Morpholinyl)ethyl)oxy)-3-(2-(4-pyridinyl)-1,3-thiazol-4-yl)-2(1H)-quinolinone Following the Example 8773 to give a tan solid. MS (m/z): 435.5 (m+1).

EXAMPLE 8776

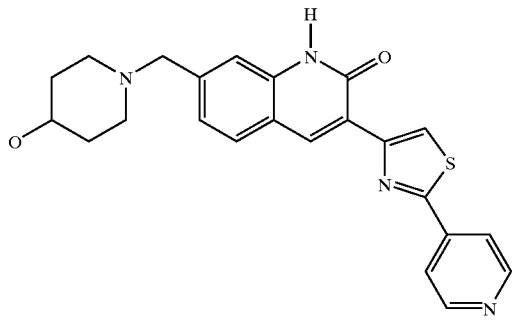

7-(4-Hydroxy-piperidin-1-ylmethyl)-3-(2-pyridin-4-yl-thiazol-4-yl)-1H-quinolin-2-one

This compound was prepared according to the method described in example 8768 employing 3-(2-pyridin-4-yl-thiazol-4-yl)-1H-quinolin-2-one-7-carbaldehyde and 4-hydroxypiperidine. To give a yellow solid. MS m/z: 419.0 (M+1).

EXAMPLE 8777

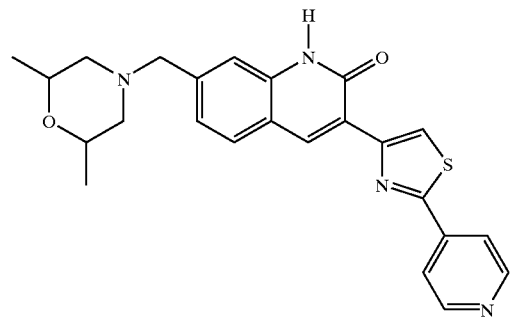

7-(2,6-Dimethyl-morpholin-4-ylmethyl)-3-(2-pyridin-4-yl-thiazol-4-yl)-1H-quinolin-2-one

This compound was prepared according to the method described in example 8768 employing 3-(2-pyridin-4-yl-thiazol-4-yl)-1H-quinolin-2-one-7-carbaldehyde and 2,6-dimethylmorpholine to give a yellow solid. MS m/z: 433.1 (M+1).

EXAMPLE 8778

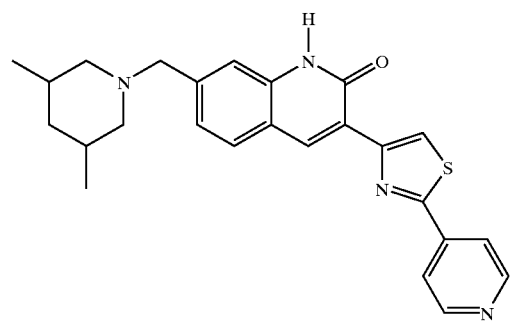

7-(3,5-Dimethyl-piperidin-1-ylmethyl)-3-(2-pyridin-4-yl-thiazol-4-yl)-1H-quinolin-2-one

This compound was prepared according to the method described in example 8768 employing 3-(2-pyridin-4-yl-thiazol-4-yl)-1H-quinolin-2-one-7-carbaldehyde and 3,5-dimethylpiperidine to give a yellow solid. MS m/z: 431.1 (M+1).

EXAMPLE 8779

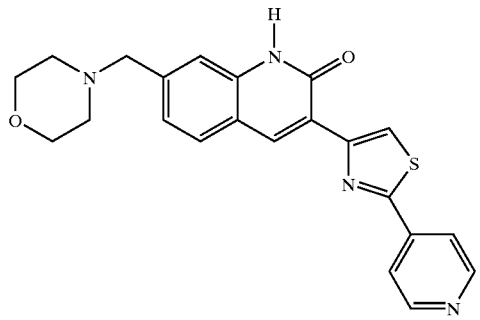

7-Morpholin-4-ylmethyl-3-(2-pyridin-4-yl-thiazol-4-yl)-1H-quinolin-2-one

This compound was prepared according to the method described in example 8768 employing 3-(2-pyridin-4-yl-thiazol-4-yl)-1H-quinolin-2-one-7-carbaldehyde and morpholine to give a yellow solid. MS m/z: 405.0 (M+1).

EXAMPLE 8780

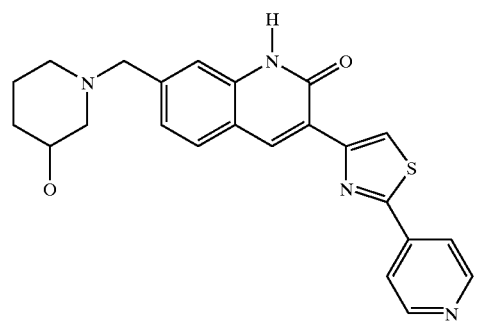

7-(3-Hydroxy-piperidin-1-ylmethyl)-3-(2-pyridin-4-yl-thiazol-4-yl)-1H-quinolin-2-one

This compound was prepared according to the method described in example 8768 employing 3-(2-pyridin-4-yl-thiazol-4-yl)-1H-quinolin-2-one-7-carbaldehyde and 3-hydroxypiperidine to give a yellow solid. MS m/z: 419.2 (M+1).

EXAMPLE 8781

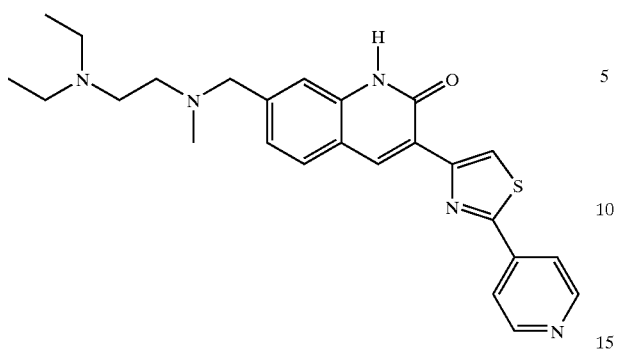

7-{([(2-Diethylamino-ethyl)-methyl-amino]-methyl}-3-(2-pyridin-4-yl-thiazol-4-yl)-1H-quinolin-2-one This compound was prepared according to the method described in example 8768 employing 3-(2-pyridin-4-yl-thiazol-4-yl)-1H-quinolin-2-one-7-carbaldehyde and N,N-diethyl-N'-methyl-ethane-1,2-diamine to give a yellow solid. MS m/z: 448.2 (M+1).

EXAMPLE 8782

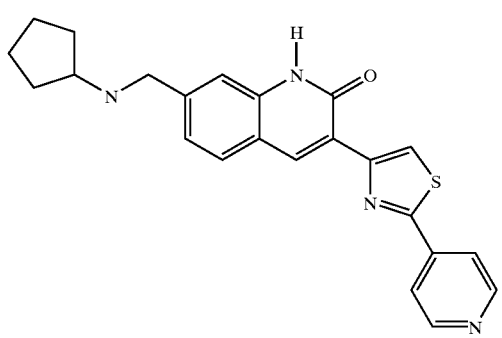

7-Cyclopentylaminomethyl-3-(2-pyridin-4-yl-thiazol-4-yl)-1H-quinolin-2-one

This compound was prepared according to the method described in example 8768 employing 3-(2-pyridin-4-yl-thiazol-4-yl)-1H-quinolin-2-one-7-carbaldehyde and cyclopentylamine to give a yellow solid. MS m/z: 403.2 (M+1).

EXAMPLE 8783

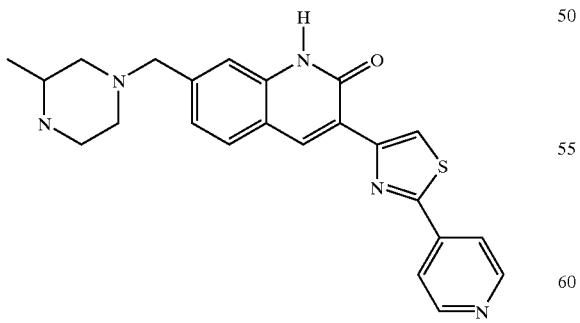

7-(3-Methyl-piperazin-1-ylmethyl)-3-(2-pyridin-4-yl-thiazol-4-yl)-1H-quinolin-2-one This compound was prepared according to the method described in example 8768 employing 3-(2-pyridin-4-yl-thiazol-4-yl)-1H-quinolin-2-one-7-carbaldehyde and 3-methylpiperazine to give a yellow solid. MS m/z: 418.3 (M+1).

EXAMPLE 8784

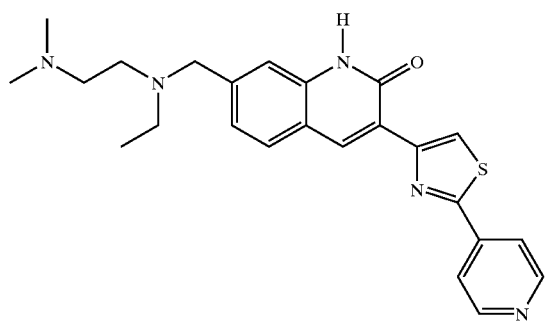

7-{[(2-Dimethylamino-ethyl)-ethyl-amino]-methyl}-3-(2-pyridin-4-yl-thiazol-4-yl)-1H-quinolin-2-one This compound was prepared according to the method described in example 8768 employing 3-(2-pyridin-4-yl-thiazol-4-yl)-1H-quinolin-2-one-7-carbaldehyde and N'-ethyl-N,N-dimethyl-ethane-1,2-diamine to give a yellow solid. MS m/z: 434.2 (M+1).

EXAMPLE 8785

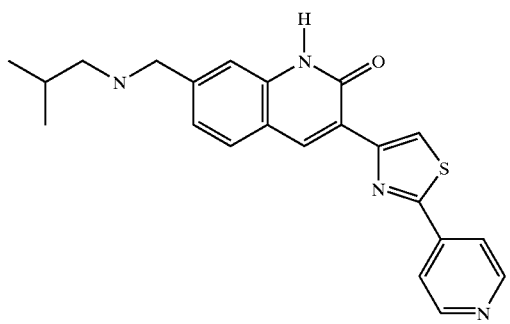

7-(Isobutylamino-methyl)-3-(2-pyridin-4-yl-thiazol-4-yl)-1H-quinolin-2-one

This compound was prepared according to the method described in example 8768 employing 3-(2-pyridin-4-yl-thiazol-4-yl)-1H-quinolin-2-one-7-carbaldehyde and isobutylamine to give a yellow solid. MS m/z: 391.3 (M+1).

EXAMPLE 8786

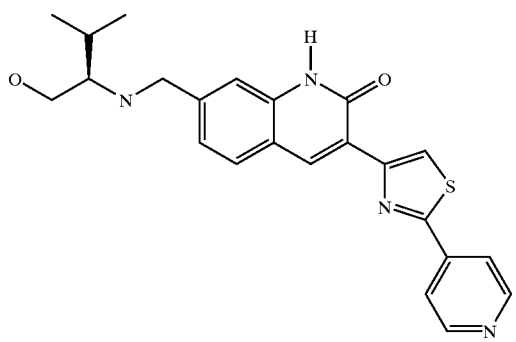

7-[(1-Hydroxymethyl-2-methyl-propylamino)-methyl]-3-(2-pyridin-4-yl-thiazol-4-yl)-1H-quinolin-2-one This compound was prepared according to the method described in example 8768 employing 3-(2-pyridin-4-yl-thiazol-4-yl)-1H-quinolin-2-one-7-carbaldehyde and 2-amino-3-methyl-butan-1-ol to give a yellow solid. MS m/z: 421.3 (M+1).

EXAMPLE 8787

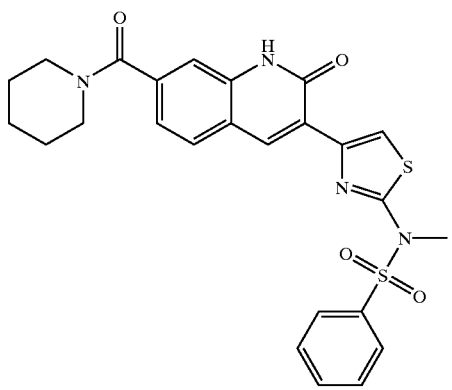

N-Methyl-N-(4-(2-oxo-7-(1-piperidinylcarbonyl)-1,2-dihydro-3-quinolinyl)-1,3-thiazol-2-yl)benzenesulfonamide This compound was prepared analogous to Example 8734 using piperidine. MS m/z: 509(M+1).

EXAMPLE 8788

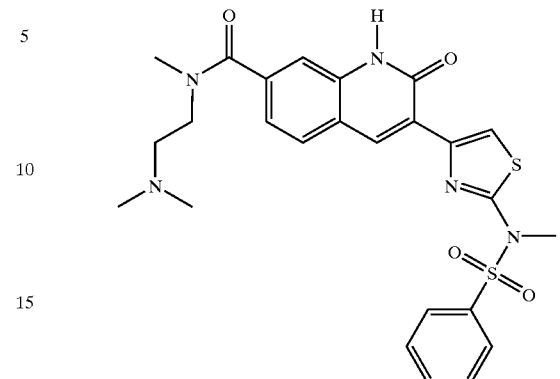

3-[2-(Benzenesulfonyl-methyl-amino)-thiazol-4-yl]-2-oxo-1,2-dihydro-quinoline-7-carboxylic acid (2-dimethylamino-ethyl)-methyl-amide This compound was prepared analogous to Example 8734 using N,N,N'-trimethylethylenediamine. Mp. 144–148° C. MS m/z: 526(M+1).

EXAMPLE 8789

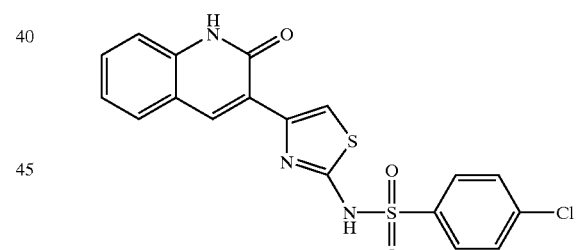

4-Chloro-N-(4-(2-oxo-1,2-dihydro-3-quinolinyl)-1,3-thiazol-2-yl)benzenesulfonamide To a suspension of 3-(2-amino-1,3-thiazol-4-yl) hydroquinolin-2-one hydrobromide (45 mg, 0.14 mmol) in 1 mL pyridine was added 4-chloro-benzenesulfonyl chloride (Aldrich) (78 mg, 0.37 mmol) followed by a few crystals of DMAP (Aldrich). The reaction was heated to 63° C. for 7 h then cooled to RT. To the mixture was added MeOH. The solids were filtered, washed with MeOH and dried in vacuo to give an off-white amorphous solid. Mp: >300° C. MS m/z: 418 (M+1); 416 (M−1).

EXAMPLE 8790

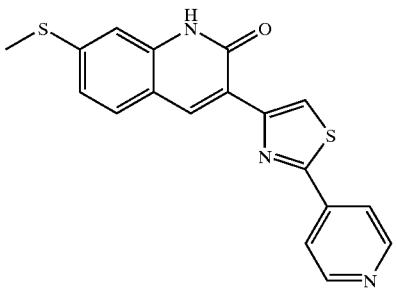

2-Methylthio-6-(2-pyridin-4-yl-thiazol-4-yl)-8H-pyrido[2,3-d]pyrimidin-7-one

Step a—4-Amino-2-methylthio-pyrimidine-5-carboxylic acid ethyl ester

A mixture of 4-chloro-2-methylthio-pyrimidine-5-carboxylic acid ethyl ester (10.0 g, 43.10 mmole) and NH$_4$OH (40%, 100 mL) in THF (100 mL) was stirred at RT in a sealed bottle. The mixture was concentrated, taken up in water, and the white solid was filtered and dried by air).

Step b—(4-Amino-2-methylthio-pyrimidin-5-yl)-methanol

To a stirred, cooled mixture of 4-amino-2-methylthio-pyrimidine-5-carboxylic acid ethyl ester (7.68 g, 36.02 mmole) was added 1.0M LAH (54 mL) in THF. The reaction was stirred at RT in 1 h, cooled and quenched slowly with H$_2$O and 1N NaOH. The solid was filtered off. The filtrate was concentrated, extracted with CH$_2$Cl$_2$ (3×), dried over MgSO$_4$, and concentrated to give a yellow foam.

Step c—4-Amino-2-methylthio-pyrimidine-5-carbaldehyde

To a stirred solution of (4-amino-2-methylthio-pyrimidin-5-yl)-methanol (3.68 g, 21.51 mmole) in CHCl$_3$ (100 mL) was added MnO2 (13.1 g, 150.6 mmole). Stirring was continued in 14 h. The solid was filtered and the filtrate was concentrated to give a yellow solid.

Step d—6-Acetyl-2-methylsulfanyl-8H-pyrido[2,3-d]pyrimidin-7-one

A mixture of 4-amino-2-methylthio-pyrimidine-5-carbaldehyde (1.5 g, 8.87 mmole) and diketene (1.12 g, 13.31 mmole) in p-dioxane (30 mL) was heated at reflux for 24 h. The mixture was cooled and the yellow solid was filtered, and washed with EtOAc.

Step e—6-Bromoacetyl-2-methylthio-8H-pyrido[2,3-d]pyrimidin-7-one

A mixture of 6-acetyl-2-methylsulfanyl-8H-pyrido[2,3-d]pyrimidin-7-one (1.55 g, 6.59 mmole) and 5,5-dibromobarbituric acid (1.32 g, 4.61 mmole) in anhydrous p-dioxane (40 mL) was heated at reflux for 24 h. The mixture was cooled, concentrated, taken up in H$_2$O, stirred and filtered to give a brown solid.

Step f—2-Methylthio-6-(2-pyridin-4-yl-thiazol-4-yl)-8H-pyrido[2,3-d]pyrimidin-7-one A mixture of 6-bromoacetyl)-2-methylsulfanyl-8H-pyrido[2,3-d]pyrimidin-7-one (1.0 g, 3.18 mmole), and isothionicotinamide (0.45 g, 4.14 mmole) in p-dioxane (40 mL) was heated at reflux for 24 h. The mixture was cooled and the solid was filtered, triturated with EtOAc to give a yellow solid. MS (m/z): 354.3 (M+1).

EXAMPLE 8791

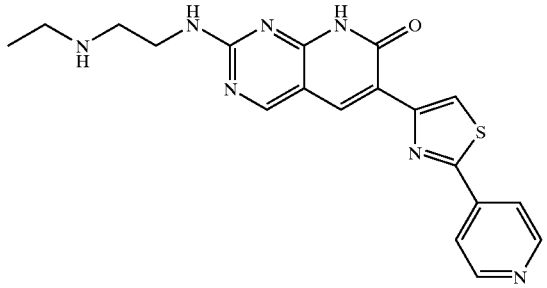

2-(2-Ethylamino-ethylamino)-6-(2-pyridyl-4-yl-thiazol-4-yl)-8H-pyrido[2,3-d]pyrimidin-7-one A mixture of 2-methylsulfanyl-6-(2-pyridin-4-yl-thiazol-4-yl)-8H-pyrido[2,3-d]pyrimidin-7-one (0.15 g, 0.425 mmole) and N-ethylaminoethylamine (0.075 g, 0.85 mmole) in DMSO (1 mL) was heated by microwave Synthesizer in 10 min at 180° C. The mixture was cooled and quenched with H$_2$O. The brown solid was filtered and purified by ISO (20% MeOH/CH$_2$Cl$_2$) to give a yellow solid. MS (m/z): 394.4 (m+1).

Additional compounds made include those in Table 13, prepared similar to the methods disclosed above.

TABLE 13

| # | Ar | Q | Z | M+H |
|---|----|----|----|-----|
| 8792. | 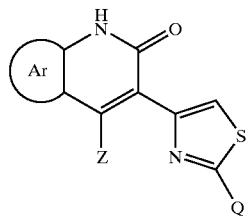 | | 4-pyridyl | H |

TABLE 13-continued

| # | Ar | Q | Z | M+H |
|---|----|---|---|-----|
| 8793. | thienyl | 4-pyridyl | amino | |
| 8794. | thienyl | 4-pyridyl | H | |
| 8795. | 2-(morpholinoethylamino)thiazolyl | 4-pyridyl | H | |
| 8796. | 2-(morpholinopropylamino)thiazolyl | 4-pyridyl | H | |
| 8797. | 2-(piperidinoethylamino)thiazolyl | 4-pyridyl | H | |
| 8798. | 2-(dimethylaminopropylamino)thiazolyl | 4-pyridyl | H | |

TABLE 13-continued
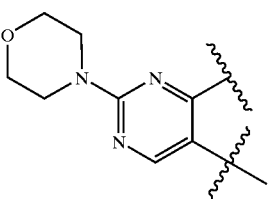
| # | Ar | Q | Z | M+H |
|---|----|---|---|-----|
| 8799. | 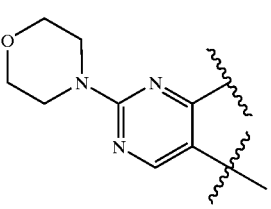 | 2-dimethylamino-4-pyridyl | H | MS (m/z): 436.5 (m + 1) |
| 8800. | 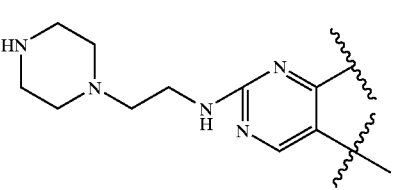 | pyridyl | H | MS (m/z): 393.4 (m + 1) |
| 8801. | 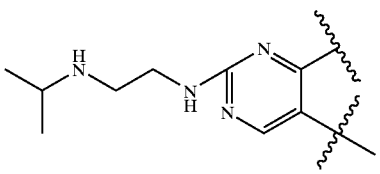 | 2-dimethylamino-4-pyridyl | H | MS (m/z): 478.5 (m + 1) |
| 8802. | 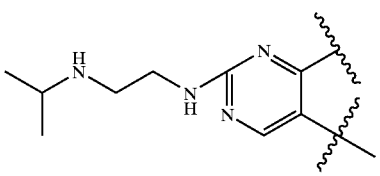 | 2-dimethylamino-4-pyridyl | H | MS (m/z): 451.5 (m + 1) |
| 8803. | 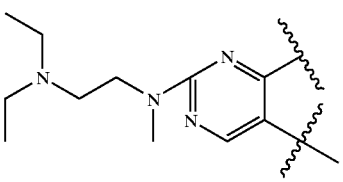 | 4-pyridyl | H | MS (m/z): 408.5 (m + 1) |
| 8804. |  | 4-pyridyl | H | MS (m/z): 436.5 (m + 1) |

TABLE 13-continued

| # | Ar | Q | Z | M+H |
|---|----|---|---|-----|
| 8805. | (ethylaminoethyl-aminopyrimidinyl group) | 2-dimethylamino-4-pyridyl | H | |

The pharmacological properties of the compounds of this invention may be confirmed by a number of pharmacological assays. The exemplified pharmacological assays which follow have been carried out with the compounds according to the invention and their salts. The compounds of invention exhibited more than 10% cdk5/p25 or cdk2/cyclin inhibition at 10 μM.

Biological Evaluation
Protocols for Cyclin E2/CDK2
Cloning of Cdk2 and cyclin 2/Generation of Cdk2 and cyclin 2 Recombinant Baculovirus The following oligonucleotide primers flanking the coding sequence of the human Cdk2 cDNA clone were used to amplify the gene and place EcoRI and HindIII restriction sites at the 5' and 3' ends of the gene respectively. [5' oligo-5'-AAGCGCGCGGAATTCATAAATATGGAGAA-CTTCCAAAAGGTGGAA-3'; 3' oligo-5'-CTCGACAAGCTTATTAGAGTCGAAGATGGGGTAC-3']

The following oligonucleotide primers flanking the coding sequence of the human CycE2 cDNA clone were used to amplify the gene and place XhoI and SphI restriction sites at the 5' and 3' ends of the gene respectively. A His tag was also placed at the N-terminus of the CycE2 protein. [5' oligo-5'-CCCGGGATCTCGAGATAAATATGCATCATCATCA-TCATTCAAGACGAAGTAGCCGTTTACAA-3'; 3' oligo-5'-CCCGGTACCGCATGCTTAGTGTTTTCCTGGTGG-TTTTTC-3']

CycE-2 and Cdk2 PCR fragments were subcloned into the vector pFastBacDual (Gibco/LifeTechnologies) using the restriction sites indicated above. Recombinant virus was made following protocols supplied by the manufacturer.
Expression of Cyclin 2/CDK2 in Insect Cells Hi5 cells were grown to a cell density of 1×10⁶ cells per ml in 800 ml of Excell 405 media (JRH). Cells were infected with virus at a multiplicity of 1. Infected cultures were incubated with shaking at 28° C. Cells were harvested by centrifugation.
Cloning of Cdk5 and p25/Generation of CDK5 and p25 Recombinant Baculovirus Based on the reported sequences of human CDK5 and p35, GenBank accession numbers X66364 and X80343 respectively, oligonucleotide primers flanking the coding sequence of each gene were used to amplify CDK5 (5'-GCGATGCAGAAATACGAGAAACT-3'; 5'-CCCCACTGTCTCACCCTCTCAA-3') and p35 (5'-CGGTGAGCGGTTTTATCCC-TCC-3'; 5'-GCATTGAATCCTTGAGCCATGACG-3') from a human fetal brain cDNA library (Clontech). p25, a C-terminal proteolytic fragment corresponding to amino acids 99–307 of full-length p35 (Lew, et. al), was PCR subcloned from the p35 sequence using oligonucleotide primers (5'-CGGGATCCATGGCCCAGCCCCCACCGGCCCA-3'; 5'-CCAAGCTTTCACCGATCCAGGCCTAG-3'). The p25 PCR product (629 bp) was cloned into the pFastBacHTb baculovirus expression vector (Gibco BRL) using BamHI and HindIII. CDK5 was PCR subcloned using oligonucleotide primers (5'-CGGGATCCGCCACCATGCAGAAATACGAGAAACTGG-3'; 5'-GGACTAGTCTAGGGCGGACAGAAGTCG-3'). The CDK5 PCR product (879 bp) was cloned into the pFastBacl baculovirus expression vector (Gibco BRL) using BamHI and SpeI. Recombinant baculovirus expressing human Cdk5 and N-terminally six histidine tagged p25 were generated using the Bac-to-Bac system (Gibco BRL).
Expression of P25/CDK5 in Insect Cells Co-infections of Hi5 cells by recombinant baculovirus containing the P25 gene and another containing the CDK5 gene were done at a multiplicity of infection of 5 (each virus). The Hi5 cultures were set to a cell concentration of 1×10⁶ cells per ml in 800 ml of Excell media by JRH. The cultures were grown in 2.6L fernbach flasks with shaking (110 rpm) at 27° C. for 60 h. The cells were harvested by centrifugation.
Purification of Complexes All steps were performed at 4° C. Insect cells expressing either cyclin E2/CDK2 or p25/CDK5 were lysed using a micro-fluidizer (Microfluidics Corporation.) The lysis buffer contained 10 mM Hepes, 150 mM NaCl, 20 mM MgCl₂, 20 mm imidazole, 0.5 mM EDTA, 10% glycerol, 25 μg/ml Aprotinin, 25 μg/ml Leupeptin, 1 mM Pefabloc, pH 7.5). Total protein was determined on the resulting lysate using the Bradford method with a BSA standard curve. Protamine sulfate was added to the lysate to give a final 30:1 protein-:protamine sulfate, incubated for 15–20 min and centrifuged at 14000×g for 30 min to remove insoluble material. Ni-NTA superflow resin (Qiagen Inc) was equilibrated in lysis buffer and incubated with the centrifugation supernatant for 1 h while rotating. The slurry was packed in a glass column and washed until a stable UV baseline was reached. Proteins were eluted with a linear gradient of 20–300 mM imidazole over 15 column volumes. Fractions were analyzed by SDS-PAGE and Western blot. Appropriate fractions were pooled, total protein determined, and submitted for kinase assay.

CDK2 Kinase Assay

CDK2 kinase assays were carried out with inhibitor (dissolved in DMSO) in a total volume of 50 μl with 1 nM enzyme (His-tagged cyclin 2/CDK2), 1 μM Histone-H1 (Gibco), 25 μM ATP, 20 μCi/ml $^{33}$P-ATP (Amersham; 2500 Ci/mmole) in kinase buffer (50 mM Tris-HCl, pH 7.5, 5 mM $MgCl_2$, 1 mM EGTA, 5 mM DTT, 200 μg/ml BSA and 20 mM β-glycerophosphate for 60 min at 25° C. Reactions were stopped by the addition of an equal volume of 30% trichloroacetic acid (Sigma). Precipitates were formed by incubation at 4° C. for 60 min then collected by filtration on Millipore® filter plates (MAFC NOB10). MicroScint-20 (40 μL, Packard) was added, and counted on a Packard Top-Count®. Raw cpms were analyzed with a four-parameter logistic fit using the Levenburg Marquardt algorithm (Xlfit software IDBS LTD). Kinetic parameters were calculated by non-linear regression analysis using Grafit (Erithacus Software LTD). Riscovitine (BIOMOL Research Labs Inc., Plymouth Meeting, Pa.) and staurosporin (Sigma, St. Louis Mo.) were used as standards.

CDK5 Kinase Assay

CDK5 kinase assays were carried out with inhibitor (dissolved in DMSO) in a total volume of 50 μl with 1 nM enzyme (His-tagged p25/CDK5), 1 μM Histone-H1 (Gibco), 25 μM ATP, 20 μCi/ml $^{33}$P-ATP (Amersham; 2500 Ci/mmole) in kinase buffer (50 mM Tris-HCl, pH 7.5, 5 mM MgCl2, 1 mM EGTA, 5 mM DTT, 200 μg/ml BSA and 20 mM β-glycerophosphate) for 60 min at 25° C. Reactions were stopped by the addition of an equal volume of 30% trichloroacetic acid (Sigma). Precipitates were formed by incubation at 4° C. for 60 min then collected by filtration on Millipore® filter plates (MAFC NOB10). MicroScint-20 (40 μL, Packard) was added, and counted on a Packard Top-Count®. Raw cpms were analyzed with a four-parameter logistic fit using the Levenburg Marquardt algorithm (Xlfit software IDBS LTD). Kinetic parameters were calculated by non-linear regression analysis using Grafit (Erithacus Software LTD). Riscovitine (BIOMOL Research Labs Inc., Plymouth Meeting, Pa.) and staurosporin (Sigma) were used as standards.

Examples 1–2, 5–8, 11–12, 14–16, 18–19, 21–22, 25–26, 29, 42, 46, 54, 62, 64, 81, 91, 96, 98, 100–102, 105, 107–109, 111, 114, 116, 8721, 8723, 8725, 8727, 8729–8731, 8733–8736, 8739–8740, 8742–8750, 8752–8753, 8755–8765, 8767–8772, 8774–8786, 8790–8792 and 8804 exhibited cdk2/cyclin kinase activity with $IC_{50}$ values less than 1 μM. The compounds of examples 1–2, 4–9, 11–12, 15, 17–22, 24–26, 35, 39–40, 43, 46–48, 50–51, 53–55, 64, 67–682, 81, 85, 87–91, 95–96, 103, 111, 116, 8721, 8723–8724, 8726–8727, 8731–8735, 8737, 8739–8740, 8742–8743, 8745–8762, 8764–8786, and 8790–8799 exhibited cdk5/p25 kinase activity with $IC_{50}$ values less than 1 μM.

Cell Proliferation Assay

Cell Proliferation was measured using a colorimetric immunoassay (B/M Roche #164 7229), based on the measurement of pyrimidine analog BrdU incorporation during DNA synthesis in proliferating cells. Cells, e.g., human PC-3 prostate carcinoma cells, huFSF normal human foreskin fibroblast cells, HCT 116 human colon carcinoma cells or HT 29 human colon carcinoma cells, were cultured in a 96-well plate for 24 h, until a cell count of $3 \times 10^3$ to $6 \times 10^3$ cells per well in duplicate wells were achieved, in a well volume of 200 μl. The media was changed and 1 μl of 200× control inhibitors or compounds were added to each well. Cells are incubated for 48 h at 37° C. The cells were labeled with BrdU for 4 h at 37° C. The labeling medium was removed and in one step, the cells were fixed and the DNA was denatured (30 min at RT). Anti-BrdU-POD antibody was added to bind to the BrdU incorporated in newly synthesized cellular DNA (60–90 min at RT). The cells were washed 3× with washing buffer, substrate (100 μl) was added and the cells were incubated for 10 min at RT. The substrate reaction was stopped by adding 25 μl of 1M $H_2SO_4$. The amount of BrdU incorporated was quantified by measuring the absorbance at 450 nm using ELISA reader. $IC_{50}$'s were calculated using GraFit (Sigma).

Ischemic Stoke Model: Middle Cerebral Artery Occlusion (MCAO) in vivo

The compounds' effect on treating stroke was measured in a MCAO rat model. (L. Belayev et al., Stroke, 27, 1616–23 (1996). Male Sprague-Dawley rats (300–330 g body weight) were anesthetized with halothane and MCAO was induced by inserting a poly-L-lysine coated monofilament suture to the beginning of the middle cerebral artery (MCA),. After various time points (60, 90 or 120 min), the intraluminal suture was carefully removed to start reperfusion. Physiological conditions (blood $O_2$, $CO_2$, pH, glucose, blood pressure) were monitored and kept stable during the surgery. The compound was dissolved in 20% Captisol in phosphate buffered saline and administered (orally, IV or IP) 90 min after ischemia onset, at the beginning of reperfusion. Further dosing occurred at 4–8 h and twice a day thereafter.

The use of behavioral tests was directly analogous to the clinical neurological examination for assessing ischemic deficits and rates of behavioral recovery. The battery consisted of four tests: (1) postural reflex test, (2) forelimb placing test (JB Bederson et al., Stroke, 17:472–76 (1986) (L. Belayev et al., Stroke, 26:2313–20 (1995), (3) contralateral foot fault index (A. Tamura et al., J. Cereb Blood Flow Metab., 1:53–60 (1981) (DM Freeney, Science, 217:855–57 (1982), and (4) cylinder asymmetry (T A Jones and T. Schallert, J. Neurosci., 14:2140–52 (1994). Tests were performed once a day for three days and then once a week for a period of 30 days. These tests are useful in assessing neurological deficits for short-term studies; the cylinder asymmetry test appeared to be the most useful for long term experiments.

At the end of the experiment, the infarct volume was measured (J B Bederson et al., Stroke, 17:1304–8 (1986) (K A Osborne et al, J. Neurol Neurosurg. Psychiatry, 50:402 (1987) (R A Swanson et al., J. Cereb. Blood Flow Metab., 10:290–3 (1990). The brains were removed and sliced coronally at 1 mm thickness. The brain slices were stained with 2% (w/vol) 2,3,5-triphenyltetrazolium chloride (TTC) which stains the infarcted areas of the brain in white and allows for the measurement of infarct volume by an image-analysis system. Edema volume that contributes to infarct volume was subtracted by comparison with the total volume of the contralateral hemisphere.

Formulations

Also embraced within this invention is a class of pharmaceutical compositions comprising the active compounds of Formula I-V in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.5 and about 50 mg/kg body weight and most preferably between about 0.1 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono-or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e.Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:
1. A compound of Formula I

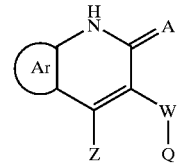

wherein

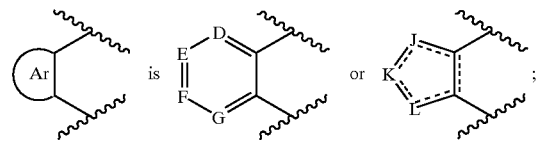

wherein A is O, S or NH;
wherein D is $CR^1$ or N;
wherein E is $CR^2$ or N;
wherein F is $CR^3$ or N;
wherein G is $CR^4$ or N;
wherein J is selected from $NR^6$, S, O, and $CR^1$;
wherein K is selected from $NR^6$, S, O, and $CR^2$;
wherein L is selected from $NR^6$, S, O, and $CR^3$;
wherein Q is selected from hydroxy, $-N(R^5)_2$, $-NR^5C(O)R^5$, $-(C_1-C_8)$alkyl-$OR^5$, $-(C_1-C_8)$alkyl-$S(O)_nR^5$, $-N(C_1-C_8\text{-alkyl})$-$S(O)_nR^5$, $-NHS(O)_nR^5$, aryl, a monocyclic or bicyclic, non-aromatic carbocyclic ring, heteroaryl and a monocyclic or bicyclic, non-aromatic heterocyclic ring; wherein the ring is unsubstituted or substituted with one or more groups selected from H, halo, aryl, alkynyl, alkenyl, $-OR^5$, $-N(R^5)_2$, $-(C_1-C_8)$alkyl-$N(R^5)_2$, lower alkoxyalkyl, $-O-C_1-C_2$-alkyl-$O-$, $-S(O)_nR^5$, cyano, $(C_1-C_8)$ alkyl, lower cyanoalkyl, lower alkylaminoalkoxy, lower aminoalkoxyalkyl $(C_3-C_{10})$cycloalkyl, nitro, optionally substituted 4–7 membered heterocyclyl, optionally substituted phenoxyalkyl, optionally substituted heterocyclyloxyalkyl, $-SO_2NR^5R^5$, $-NR^5SO_2R^5$, $-C(O)N(R^5)_2$, $-CO_2R^5$, $-CO_2NR^5R^5$, $-SO_2NHC(O)R^5$, optionally substituted phenylalkyl, optionally substituted heterocyclylalkyl, $-NR^5C(O)N(R^5)_2$, $-NR^5C(O)R^5$, $-NR^5CO_2R^5$ and $-C(O)R^5$;
wherein W is thiazolyl that is unsubstituted or substituted with one or more groups selected from halo, aryl, cycloalkyl, $-OR^5$, $(C_2-C_8)$alkenyl, $(C_2-C_8)$alkynyl, $-N(R^5)_2$, $-(C_1-C_8)$alkyl-$N(R^5)_2$, $-SO_2NR^5R^5$, $-(C_1-C_8)$alkyl$SO_2R^5$, $-(C_1-C_8)$alkyl$SO_2-(C_1-C_8)$ alkyl-$R^5$, $(C_1-C_8)$alkyl, $(C_3-C_{10})$cycloalkyl, nitro, cyano, optionally substituted 5-6 membered heterocyclyl, formyl, alkylcarbonyl, cycloalkylcarbonyl, heterocyclylcarbonyl, arylcarbonyl, $-NR^5SO_2R^5$, $-C(O)N(R5)_2$, $-C(O)NR^5R^{5a}$, $-CO_2R^5$, optionally substituted phenylalkyl, optionally substituted heterocyclylalkyl, $-NR^5C(O)N(R^5)_2$, $-NR^5C(O)R^5$ and $-NR^5CO_2R^5$;
wherein Z is selected from H, $-N(R^5)_2$, $-SR^5$, $-OR^5$, $-C(R^5)_3$ and aryl;
wherein n is 0, 1 or 2;
wherein m is 0 or 1;

wherein $R^1$, $R^2$, $R^3$, and $R^4$ are independently selected from H, —$OR^5$, —$OR^{5a}$, halo, aryl, alkenyl, alkynyl, —$NR^5_2$, —$(C_1-C_8)$alkyl-$N(R^5)_2$, —$S(O)_n$—$NR^5R^5$, —$S(O)_nR^5$, $(C_1-C_8)$alkyl, $(C_3-C_{10})$cycloalkyl, nitro, cyano, optionally substituted 4–10 membered heterocyclyl, —$C(O)R^5$, —$NR^5SO_2R^5$, —$C(O)N(R^5)_2$, —$CO_2R^5$, optionally substituted arylalkyl, optionally substituted 4–10 membered heterocyclylalkyl, —$NR^5C(O)N(R^5)_2$, —$NR^5C(O)R^5$ and —$NR^5CO_2R^5$; wherein $R^1$ and $R^2$ may be joined to form a 5–10 membered saturated or unsaturated carbocyclic or heterocyclic ring; wherein $R^2$ and $R^3$ may be joined to form a 5–10 membered saturated or unsaturated carbocyclic or heterocyclic ring; or wherein $R^3$ and $R^4$ may be joined to form a 5–10 membered saturated or unsaturated carbocyclic or heterocyclic ring;

wherein $R^5$ is independently selected from H, lower alkyl, optionally substituted aryl, optionally substituted aralkyl, optionally substituted heterocyclyl, optionally substituted heterocyclylalkyl, optionally substituted cycloalkyl, optionally substituted cycloalkyl-alkyl, and lower haloalkyl;

wherein $R^{5a}$ is alkylaminoalkyl;

wherein $R^6$ is selected from H, $(C_1-C_2)$alkyl, and a lone pair of electrons;

wherein a solid line with a dashed line (- - -) represents either a single or a double bond;

wherein each alkyl, aryl, heteroaryl, heterocyclyl, cycloalkyl, alkynyl, alkynyl, and alkoxy moiety of any $R^1$, $R^2$, $R^3$, $R^4$, or $R^5$ can optionally join with another $R^1$, $R^2$, $R^3$, $R^4$, or $R^5$ to form a 3–7 membered ring; and wherein each alkyl, aryl, heteroaryl, cycloalkyl, alkynyl, alkynyl, heterocyclyl, and alkoxy moiety of any $R^1$, $R^2$, $R^3$, $R^4$, $R^5$, Q and W is optionally substituted with one or more groups selected from halo, —$NH_2$, —OH, —$CO_2H$, $(C_1-C_6)$alkylamino, $(C_1-C_6)$alkyl, $C_1-C_6$ alkoxy, $C_1-C_6$haloalkyl, di$(C_1-C_6)$alkylamino, $(C_1-C_6)$alkylamino-$(C_1-C_6)$alkyl, $(C_1-C_6)$hydroxyalkylamino, $(C_1-C_6)$alkylamino-$(C_1-C_6)$alkylamino, phenyl, and heterocyclyl;

provided Z is not OH when Ar is aryl; further provided Q is not unsubstituted phenyl when W is thiazol-4-yl, when Z is H and when F is C—$OCH_3$; further provided Q is not 3,4-dimethoxyphenyl when W is thiazol-4-yl, when Z is H and when $R^1$, $R^2$, $R^3$ and $R^4$ are H; and further provided Q is not 3,4-dihydroxyphenyl when W is thiazol-2-yl, when Z is H and when $R^1$, $R^2$, $R^3$ and $R^4$ are H;

and pharmaceutically acceptable derivatives thereof.

2. Compound of claim 1 wherein Q is selected from hydroxy, —$N(R^5)_2$, —$NR^5C(O)R^5$, —$(C_1-C_8)$alkyl-$OR^5$, —$(C_1-C_8)$alkyl-$S(O)_nR^5$, —$N(C_1-C_8$-alkyl)-$S(O)_nR^5$, —$NHS(O)_nR^5$, aryl, a monocyclic or bicyclic, non-aromatic carbocyclic ring, heteroaryl and a monocyclic or bicyclic, non-aromatic heterocyclic ring, wherein the ring is unsubstituted or substituted with one or more groups selected from H, halo, aryl, alkynyl, alkenyl, —$OR^5$, —$N(R^5)_2$, —$(C_1-C_8)$alkyl-$N(R^5)_2$, lower alkoxyalkyl, —$S(O)_nR^5$, cyano, $(C_1-C_8)$alkyl, lower cyanoalkyl, lower alkylaminoalkoxy, lower aminoalkoxyalkyl $(C_3-C_{10})$cycloalkyl, nitro, optionally substituted 4–7 membered heterocyclyl, optionally substituted phenoxyalkyl, optionally substituted heterocyclyloxyalkyl, —$SO_2NR^5R^5$, —$NR^5SO_2R^5$, —$C(O)N(R^5)_2$, —$CO_2R^5$, —$CO_2NR^5R^5$, —$SO_2NHC(O)R^5$, optionally substituted phenylalkyl, optionally substituted heterocyclylalkyl, —$NR^5C(O)N(R^5)_2$, —$NR^5C(O)R^5$, —$NR^5CO_2R^5$ and —$C(O)R^5$;

wherein W is a thiazol-4-yl or thiazol-2-yl ring that is unsubstituted or substituted with one or more groups selected from halo, aryl, cycloalkyl, —$OR^5$, $(C_2-C_8)$alkenyl, $(C_2-C_8)$alkynyl, —$N(R^5)_2$, —$(C_1-C_8)$alkyl-$N(R^5)_2$, —$SO_2NR^5R^5$, —$(C_1-C_8)$alkyl$SO_2R^5$, —$(C_1-C_8)$alkyl$SO_2$—$(C_1-C_8)$alkyl-$R^5$, $(C_1-C_8)$alkyl, $(C_3-C_{10})$cycloalkyl, nitro, cyano, optionally substituted 5–6 membered heterocyclyl, formyl, alkylcarbonyl, cycloalkylcarbonyl, heterocyclylcarbonyl, arylcarbonyl, —$NR^5SO_2R^5$, —$C(O)N(R^5)_2$, —$CO_2R^5$, optionally substituted phenylalkyl, optionally substituted heterocyclylalkyl, —$NR^5C(O)N(R^5)_2$, —$NR^5C(O)R^5$ and —$NR^5CO_2R^5$;

wherein Z is selected from H, —$N(R^5)_2$, —$SR^5$, —$OR^5$, —$C(R^5)_3$ and aryl;

wherein n is 0, 1 or 2;

wherein m is 0 or 1;

wherein $R^1$, $R^2$, $R^3$, and $R^4$ are independently selected from H, —$OR^5$, halo, aryl, alkenyl, alkynyl, —$NR^5_2$, —$(C_1-C_8)$alkyl-$N(R^5)_2$, —$S(O)_n$—$NR^5R^5$, —$S(O)_nR^5$, $(C_1-C_8)$alkyl, $(C_3-C_{10})$cycloalkyl, nitro, cyano, optionally substituted 4–10 membered heterocyclyl, –$C(O)R^5$, —$SO_2R^5$, —$NR^5SO_2R^5$, —$C(O)N(R^5)_2$, —$CO_2R^5$, optionally substituted arylalkyl, optionally substituted 4–10 membered heterocyclylalkyl, —$NR^5C(O)N(R^5)_2$, —$NR^5C(O)R^5$ and —$NR^5CO_2R^5$; wherein $R^1$ and $R^2$ may be joined to form a 5–10 membered saturated or unsaturated carbocyclic or heterocyclic ring; wherein $R^2$ and $R^3$ may be joined to form a 5–10 membered saturated or unsaturated carbocyclic or heterocyclic ring; or wherein $R^3$ and $R^4$ may be joined to form a 5–10 membered saturated or unsaturated carbocyclic or heterocyclic ring;

wherein $R^5$ is independently selected from H, lower alkyl, optionally substituted aryl, optionally substituted aralkyl, optionally substituted heterocyclyl, optionally substituted heterocyclylalkyl, optionally substituted $C_3-C_6$ cycloalkyl, optionally substituted $C_3-C_6$ cycloalkyl-alkyl, and lower haloalkyl;

wherein $R^6$ is selected from H, $(C_1-C_2)$alkyl, and a lone pair of electrons;

wherein each alkyl, aryl, heteroaryl, heterocyclyl, cycloalkyl, alkynyl, alkynyl, and alkoxy moiety of any $R^1$, $R^2$, $R^3$, $R^4$, or $R^5$ can optionally join with another $R^1$, $R^2$, $R^3$, $R^4$, or $R^5$ to form a 3–7 membered ring; and wherein each alkyl, aryl, heteroaryl, cycloalkyl, alkynyl, alkynyl, heterocyclyl, and alkoxy moiety of any $R^1$, $R^2$, $R^3$, $R^4$, $R^5$, Q and W is optionally substituted with one or more groups selected from halo, —$NH_2$, —OH, —$CO_2H$, $(C_1-C_6)$alkylamino, $(C_1-C_6)$alkyl, di$(C_1-C_6)$alkylamino, phenyl, and heterocyclyl;

and pharmaceutically acceptable derivatives thereof.

3. Compound of claim 1 wherein Q is selected from hydroxy, —N $(R^5)_2$, $R^5SO_2$—$(C_1-C_6)$alkyl, —$N(C_1-C_6$-alkyl)-$S(O)_nR^5$, substituted or unsubstituted phenyl, substituted or unsubstituted 5–6 member e d heteroaryl, substituted or unsubstituted $C_3-C_6$ cycloalkyl, and substituted or unsubstituted non-aromatic heterocyclyl.

4. Compound of claim 3 wherein A is O; wherein Q is selected from —$N(R^5)_2$, $R^5S(O)_n$—$(C_1-C_3)$alkyl, —$N(C_1-C_3$-alkyl)-$S(O)_nR^5$, optionally substituted phenyl, benzodioxolyl, and substituted or unsubstituted 6-membered heteroaryl.

5. Compound of claim 4, and pharmaceutically acceptable derivatives thereof, wherein Ar is selected from phenyl, thienyl, pyrimidinyl, pyridyl and thiazolyl, wherein Ar is optionally substituted with one or more radicals selected from —OR$^5$, chloro, fluoro, phenyl, $C_2$–$C_6$ alkenyl, $C_2$–$C_6$ alkynyl, —N(R$^5$)$_2$, —($C_1$–$C_6$)alkyl-N(R$^5$)$_2$, —S(O)$_n$—NR$^5$R$^5$, —S(O)$_n$R$^5$, ($C_1$–$C_6$)alkyl, ($C_3$–$C_6$)cycloalkyl, nitro, cyano, optionally substituted 4–6 membered heterocyclyl, —C(O)R$^5$, —NR$^5$SO$_2$R$^5$, —C(O)N(R$^5$)$_2$, —CO$_2$R$^5$, optionally substituted phenyl-$C_1$–$C_6$-alkyl, optionally substituted 4–6 membered heterocyclyl-$C_1$–$C_6$-alkyl, —NR$^5$C(O)N(R$^5$)$_2$, —NR$^5$C(O)R$^5$ and —NR$^5$CO$_2$R$^5$;

wherein Q is selected from —N(R$^5$)$_2$, R$^5$-carbonyl-HN—, R$^5$-carbonyl-N(CH$_3$)—, phenyl-O—($C_1$–$C_2$)alkyl, R$^5$SO$_2$—($C_1$–$C_2$)alkyl, —N($C_1$–$C_2$-alkyl)-S(O)$_n$R$^5$, substituted or unsubstituted phenyl and substituted or unsubstituted 5–6 membered heteroaryl;

wherein Z is selected from H, —N(R$^5$)$_2$, —OR$^5$, ($C_1$–$C_3$) alkyl and phenyl;

wherein R$^5$ is independently selected from H, ($C_1$–$C_6$) alkyl, optionally substituted phenyl, optionally substituted phenyl-($C_1$–$C_4$)alkyl, optionally substituted 4–10 membered heterocyclyl, optionally substituted 4–10 membered heterocyclyl-($C_1$–$C_4$)alkyl, optionally substituted $C_3$–$C_6$ cycloalkyl, optionally substituted $C_3$–$C_6$ cycloalkyl-($C_1$–$C_4$)alkyl, and ($C_1$–$C_4$)haloalkyl; and wherein each alkyl, aryl, heteroaryl, cycloalkyl, alkynyl, alkynyl, and alkoxy moiety is optionally substituted with one or more groups selected from halo, —NH$_2$, —OH, —CO$_2$H, ($C_1$–$C_4$)alkylamino, ($C_1$–$C_4$)alkyl, di($C_1$–$C_4$)alkylamino, pyrrolidinyl, piperazinyl, piperidinyl, morpholinyl, and azetidinyl.

6. Compound of claim 5, and pharmaceutically acceptable derivatives thereof, wherein Ar is phenyl optionally substituted with one or more radicals selected from —OR$^5$, chloro, fluoro, phenyl, —N(R$^5$)$_2$, —($C_1$–$C_2$)alkyl-N(R$^5$)$_2$, —S(O)$_n$—NR$^5$R$^5$, —S(O)$_n$R$^5$, ($C_1$–$C_4$)alkyl, ($C_1$–$C_2$) haloalkyl, hydroxy-($C_1$–$C_2$)alkyl, hydroxy-($C_1$–$C_4$)-alkylamino, ($C_1$–$C_2$)-alkylamino-($C_1$–$C_2$)-alkylamino, ($C_1$–$C_2$)-alkylamino-($C_1$–$C_2$)-alkoxy, ($C_3$–$C_6$)cycloalkyl, optionally substituted heterocyclyl selected from pyrrolidinyl, piperazinyl, piperidinyl, and morpholinyl, —C(O)R$^5$, —NR$^5$SO$_2$R$^5$, —C(O)N(R$^5$)$_2$, —CO$_2$R$^5$, optionally substituted benzyl, optionally substituted 4–6 membered heterocyclyl-$C_1$–$C_2$-alkyl, —NR$^5$C(O)R$^5$ and —NR$^5$CO$_2$R$^5$;

wherein Q is selected from —N(R$^5$)$_2$, R$^5$-carbonyl-HN—, R$^5$-carbonyl—N(CH$_3$)—, phenyl-O-methyl, R$^5$S(O)$_n$—($C_1$–$C_3$)alkyl, —N($C_1$–$C_2$-alkyl)-S(O)$_n$R$^5$, optionally substituted phenyl, optionally substituted pyridyl, optionally substituted pyrazinyl, optionally substituted pyrimidinyl and optionally substituted pyridazinyl; wherein n is 0, 1 or 2;

wherein Z is selected from H, —N(R$^5$)$_2$, —OR$^5$, and phenyl;

wherein R$^5$ is independently selected from H, ($C_1$–$C_6$) alkyl, optionally substituted $C_3$–$C_6$ cycloalkyl, $C_3$–$C_6$ cycloalkyl-($C_1$–$C_4$)alkyl, optionally substituted phenyl, optionally substituted phenyl-($C_1$–$C_3$)alkyl, optionally substituted 4–6 membered heterocyclyl-($C_1$–$C_4$)alkyl, ($C_1$–$C_2$)haloalkyl, and optionally substituted 4–6 membered heterocyclyl; and wherein each alkyl, aryl, heteroaryl, cycloalkyl, alkynyl, alkynyl, and alkoxy moiety is optionally substituted with one or more groups selected from chloro, fluoro, —NH$_2$, —OH, —CO$_2$H, ($C_1$–$C_2$)alkylamino, ($C_1$–$C_2$) alkyl, di($C_1$–$C_2$)alkylamino, pyrrolidinyl, piperazinyl, piperidinyl, morpholinyl and azetidinyl.

7. Compound of claim 6, and pharmaceutically acceptable derivatives thereof, wherein Ar is phenyl optionally substituted with one or more radicals selected from H, cyclopropylmethylamino, 3-hydroxypropylamino, 2-(piperidin-1-yl)ethylamino, (1-piperidylmethyl)amino, 2-(pyrrolidin-1-yl)ethylamino, 2-(morpholin-4-yl) ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino)ethylamino, aminomethyl, dimethylaminoethyl, isopropylaminomethyl, diethylaminomethyl, N-methyl-N-(isopropyl)aminomethyl, N-methyl-N-(diethylaminoethyl)aminomethyl, N-ethyl-N-(dimethylaminoethyl)aminomethyl, (1-hydroxymethyl-2-methylpropyl)amino, cyclopentylaminomethyl, 2-(dimethylamino)ethoxy, 3-(dimethylamino)propoxy, 2-(methylamino)ethoxy, ((2R)pyrrolidin-2-yl)methoxy, ((2R)-1-methylpyrrolidin-2-yl)methoxy, 2-(piperid-1-yl) ethoxy, 2-(piperazin-1-yl)ethoxy, 2-(morpholin-4-yl)ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4-ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 3-aminopyrrolidin-1-yl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl; wherein Q is selected from amino, 2-pyridylamino, 3-pyridylamino, 4-pyridylamino, phenylsulfonylamino, N-methyl-N-(3-fluorobenzylsulfonyl)amino, N-methyl-N-(2-pyridylsulfonyl)amino, N-methyl-N-(3-pyridylsulfonyl) amino, N-methyl-N-(4-pyridylsulfonyl)amino, N-methyl-N-(2-thienylsulfonyl)amino, N-methyl-N-(phenylsulfonyl) amino, N-methyl-N-(1-methylimidazol-4-ylsulfonyl)amino, 2-pyridylsulfonylmethyl, 3-pyridylsulfonylmethyl, 4-pyridylsulfonylmethyl, 2-thienylsulfonylmethyl, phenylsulfonylmethyl, 1-phenylsulfonyl-1-methylethyl, 2-furylmethylsulfonylmethyl, 3-trifluoromethylphenylmethylsulfonylmethyl, methylsulfonylmethyl, tert-butylsulfonylmethyl, 4-fluorophenyl-methylsulfonylmethyl, 4-chlorophenyl-methylsulfonylmethyl, phenyl substituted with one or more substituents selected from H, hydroxyl, chloro, fluoro, methoxy, amino, aminomethyl, methylsulfonyl, methyl, cyano, trifluoromethyl, and pyrrolyl, unsubstituted pyridyl, and pyridyl substituted with one or more substituents selected from chloro, fluoro, —NH$_2$, —OH, —CO$_2$H, methylamino, methyl, ethyl, diethyl-amino, pyrrolidinyl, piperazinyl, piperidinyl, morpholinyl and azetidinyl; substituted or unsubstituted pyridyl; and wherein Z is selected from H, amino and phenyl.

8. Compound of claim 1 wherein W is thiazol-4-yl.
9. Compound of claim 1 wherein W is thiazol-2-yl.
10. Compound of claim 1 wherein Q is phenylsulfonylmethyl.
11. Compound of claim 1 wherein Q is N-methyl-N-(phenylsulfonyl)amino.
12. Compound of claim 1 wherein Q is 4-pyridyl.
13. A compound of claim 1 having Formula II

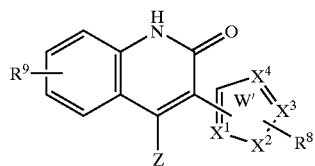

II wherein ring W' is 4-thiazolyl or 2-thiazolyl;

wherein Z is selected from H, —N($R^{11}$)$_2$, —O$R^{11}$, ($C_1$–$C_4$)alkyl and phenyl;

wherein $R^8$ is selected from —N($R^{11}$)$_2$, $R^{11}$S(O)$_n$— ($C_1$–$C_8$)alkyl, N—($C_1$–$C_8$-alkyl)-N—[$R^{11}$S(O)$_n$] amino, optionally substituted phenyl, benzodioxolyl, optionally substituted pyridyl, optionally substituted pyrazinyl, optionally substituted pyrimidinyl and optionally substituted pyridazinyl;

wherein $R^9$ is one or more substituents selected from H, —O$R^{11}$, chloro, fluoro, phenyl, —N($R^{11}$)$_2$, —($C_1$–$C_2$) alkyl-N($R^{11}$)$_2$, —S(O)$_n$—N($R^{11}$)$_2$, —S(O)$_n$$R^{11}$, ($C_1$–$C_4$)alkyl, ($C_3$–$C_6$)cycloalkyl, hydroxy-($C_1$–$C_4$)-alkylamino, ($C_1$–$C_2$)-alkylamino-($C_1$–$C_2$)-alkylamino, ($C_1$–$C_2$)-alkylamino-($C_1$–$C_2$)-alkoxy, optionally substituted heterocyclyl selected from pyrrolidinyl, piperazinyl, piperidinyl, and morpholinyl, —C(O)$R^{11}$, —N$R^{11}$SO$_2$$R^{11}$, —C(O)N($R^{11}$)$_2$, —CO$_2$$R^{11}$, optionally substituted benzyl, optionally substituted 4–6 membered heterocyclyl-$C_1$–$C_2$-alkyl, —N$R^{11}$C(O)$R^{11}$ and —N$R^{11}$CO$_2$$R^{11}$;

wherein n is 0, 1 or 2;

wherein $R^{10}$ is selected from H, halo, aryl, cycloalkyl, —O$R^{11}$, ($C_2$–$C_8$)alkenyl, ($C_2$–$C_8$)alkynyl, —N($R^{11}$)$_2$, —($C_1$–$C_8$)alkyl-N($R^{11}$)$_2$, —SO$_2$N$R^{11}$$R^{11}$, ($C_1$–$C_8$) alkyl, cycloalkylalkyl, nitro, cyano, heteroaryl, optionally substituted 5–6 membered heterocyclyl, formyl, alkylcarbonyl, cycloalkylcarbonyl, arylcarbonyl, heterocyclylcarbonyl, —N$R^{11}$SO$_2$$R^{11}$, —C(O)N ($R^{11}$)$_2$, —CO$_2$$R^{11}$, optionally substituted phenylalkyl, optionally substituted heteroarylalkyl, —N$R^{11}$C(O)N ($R^{11}$)$_2$, —N$R^{11}$C(O)$R^{11}$ and —N$R^{11}$CO$_2$$R^{11}$; and wherein $R^{11}$ is selected from H, ($C_1$–$C_6$)alkyl, optionally substituted phenyl, optionally substituted phenyl-($C_1$–$C_4$)alkyl, optionally substituted 4–6 membered heterocyclyl, optionally substituted 4–6 membered heterocyclyl-($C_1$–$C_4$)alkyl, $C_3$–$C_6$ cycloalkyl, $C_3$–$C_6$ cycloalkyl-($C_1$–$C_4$)alkyl and ($C_1$–$C_2$)haloalkyl;

wherein each alkyl, phenyl, cycloalkyl, and heterocyclyl moiety is optionally substituted with one or more groups selected from halo, —NH$_2$, —OH, —CO$_2$H, ($C_1$–$C_4$)alkylamino, ($C_1$–$C_4$)alkyl, di($C_1$–$C_4$) alkylamino, ($C_1$–$C_4$)haloalkyl, pyrrolidinyl, piperazinyl, piperidinyl, morpholinyl, and azetidinyl;

provided Z is not OH; further provided $R^8$ is not unsubstituted 2-phenyl when Z is H, when ring W' is thiazol-4-yl and when $R^9$ is 6-methoxy; further provided $R^8$ is not 2-phenyl or 2-[3,4-dimethoxyphenyl] when Z is H, ring W' is thiazol-4-yl and when $R^9$ is H; and further provided $R^8$ is not 4-[3,4-dihydroxyphenyl] when Z is H, ring W' is thiazol-2-yl and when $R^9$ is H;

and pharmaceutically acceptable derivatives thereof.

14. Compound of claim 13 wherein Z is selected from H, amino and phenyl; wherein $R^8$ is selected from amino, 2-pyridylamino, 3-pyridylamino, 4-pyridylamino, phenylsulfonylamino, N-methyl-N-(3-fluorobenzylsulfonyl)amino, N-methyl-N-(2-pyridylsulfonyl)amino, N-methyl-N-(3-pyridylsulfonyl) amino, N-methyl-N-(4-pyridylsulfonyl)amino, N-methyl-N-(2-thienylsulfonyl)amino, N-methyl-N-(phenylsulfonyl) amino, N-methyl-N-(1-methylimidazol-4-ylsulfonyl)amino, 2-pyridylsulfonylmethyl, 3-pyridylsulfonylmethyl, 4-pyridylsulfonylmethyl, 2-thienylsulfonylmethyl, phenylsulfonylmethyl, 1-phenylsulfonyl-1-methylethyl, 2-furylmethylsulfonylmethyl, 3-trifluoromethylphenylmethylsulfonylmethyl, methylsulfonylmethyl, tert-butylsulfonylmethyl, 4-fluorophenyl-methylsulfonylmethyl, 4-chlorophenyl-methylsulfonylmethyl, phenyl substituted with one or more substituents selected from H, hydroxyl, chloro, fluoro, methoxy, amino, aminomethyl, methylsulfonyl, methyl, cyano, trifluoromethyl, and pyrrolyl, unsubstituted pyridyl, and pyridyl substituted with one or more substituents selected from chloro, fluoro, —NH$_2$, —OH, —CO$_2$H, methylamino, methyl, ethyl, diethyl-amino, pyrrolidinyl, piperazinyl, piperidinyl, morpholinyl and azetidinyl;

wherein $R^9$ is one or more radicals selected from H, cyclopropylmethylamino, 3-hydroxypropylamino, 2-(piperidin-1-yl)ethylamino, 2-(pyrrolidin-1-yl) ethylamino, 2-(morpholin-4-yl)ethylamino, 3-(piperidin-1-yl)propylamino, 3-(pyrrolidin-1-yl) propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino) ethylamino, aminomethyl, dimethylaminoethyl, isopropylaminomethyl, diethylaminomethyl, N-methyl-N-(isopropyl)aminomethyl, N-methyl-N-(diethylaminoethyl)aminomethyl, N-ethyl-N-(dimethylaminoethyl)aminomethyl, (1-hydroxymethyl-2-methylpropyl)amino, cyclopentylaminomethyl, 2-(dimethylamino)ethoxy, 3-(dimethylamino)propoxy, 2-(methylamino)ethoxy, ((2R)pyrrolidin-2-yl)methoxy, ((2R)-1-methylpyrrolidin-2-yl)methoxy, 2-(piperid-1-yl) ethoxy, 2-(piperazin-1-yl)ethoxy, 2-(morpholin-4-yl) ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4- ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl; and wherein $R^{10}$ is H; and pharmaceutically acceptable derivatives thereof.

15. Compound of claim 1 and pharmaceutically acceptable derivatives thereof selected from:

3-[2-(6-methoxy-3-pyridyl)-1,3-thiazol-4-yl]hydroquinolin-2-one;
6-chloro-3-[2-(2-ethyl(4-pyridyl))(1,3-thiazol-4-yl)]hydroquinolin-2-one;
3-[2-(4-(1,2,3-thiadiazol-4-yl)phenyl)-1,3-thiazol-4-yl]hydroquinolin-2-one;
3-[2-(2,3-dichlorophenyl)-1,3-thiazol-4-yl]hydroquinolin-2-one;
3-(2-benzenesulfonylmethyl-thiazol-4-yl)-7-trifluoromethyl-1H-quinolin-2-one;
3-[2-(4-chloro-benzenesulfonylmethyl)-thiazol-4-yl]-7-trifluoromethyl-1H-quinolin-2-one;
3-[2-(thienyl-2-sulfonylmethyl)-thiazol-4-yl]-7-trifluoromethyl-1H-quinolin-2-one;
7-piperidin-1-ylmethyl-3-(2-pyridin-4-yl-thiazol-4-yl)-1H-quinolin-2-one;
7-{4-methyl-piperazin-1-ylmethyl)-3-2-pyridin-4-yl-thiazol-4-yl)-1H-quinolin-2-one;
3-[2-(3,4,5,6-tetrahydro-2H-[1,2']bipyridinyl-40-yl)-thiazol-4-yl]-1H-quinolin-2-one;
3-{2-[2-(3-hydroxy-propylamino)-pyridin-4-yl]-thiazol-4-yl}-1H-quinolin-2-one;
7-hydroxymethyl-3-(2-pyridin-4-yl-thiazol-4-yl)-1H-quinolin-2-one;
3-[2-(4-amino-phenyl)-thiazol-4-yl]-1H-quinolin-2-one;
3-{2-[2-(2-piperidin-1-yl-ethoxy)-pyridin-4-yl]-thiazol-4-yl}-1H-quinolin-2-one;
3-{2-[2-(2-morpholin-4-yl-ethoxy)-pyridin-4-yl]-thiazol-4-yl}-1H-quinolin-2-one;
3-(2-[2-(2-diethylamino-ethoxy)-pyridin-4-yl]-thiazol-4-yl}-1H-quinolin-2-one;
3-{2-[2-(1-ethyl-pyrrolidin-3-yloxy)-pyridin-4-yl]-thiazol-4-yl}-1H-quinolin-2-one;
2-methylene-3-{2-[2-(5-methyl-tetrahydro-furan-2-ylmethoxy)-pyridin-4-yl]-thiazol-4-yl}-1,2-dihydro-quinoline;
3-{2-[2-(tetrahydro-furan-2-ylmethoxy)-pyridin-4-yl]-thiazol-4-yl}-1H-quinolin-2-one;
3-(2-{2-[2-(2-ethoxy-ethoxy)-ethoxy]-pyridin-4-yl}-thiazol-4-yl)-1H-quinolin-2-one;
3-[2-(2-chloro-pyridin-4-yl)-thiazol-4-yl]-1H-quinolin-2-one;
3-[2-(4-hydroxy-phenyl)-thiazol-4-yl]-1H-quinolin-2-one;
5-(piperidine-1-carbonyl)-3-(2-pyridin-4-yl-thiazol-4-yl)-1H-quinolin-2-one;
3-(4-pyridin-4-yl-thiazol-2-yl)-1H-quinolin-2-one;
3-[4-(3-nitro-phenyl)-thiazol-2-yl]-1H-quinolin-2-one;
3-[2-(4-pyridyl)]-4-thiazolyl]-2(1H)-quinolinone;
3-[2-(3-pyridyl)-4-thiazolyl]-2(1H)-quinolinone;
3-[2-(4-pyridyl)-4-thiazolyl]-4-phenyl-2(1H)-quinolinone;
4-hydroxy-3-(2-pyridin-4-yl-thiazol-4-yl)-1H-quinolin-2-one;
3-[2-(4-pyridyl)-4-thiazolyl]-4-amino-2(1H)-quinolinone;
3-[2-(4-pyridyl)-4-thiazolyl]-4-amino-6-(1-piperidinyl)-2(1H)-quinolinone;
1,2-dihydro-2-oxo-3-[2-(4-pyridyl)-4-thiazolyl]-5-quinolinecarboxylic acid methyl ester;
3-[2-(3-pyridyl)-4-thiazolyl]-6,7-(methylenedioxyl)-2(1H)-quinolinone;
N,N-diethyl-1,2-dihydro-2-oxo-3-[2-(4-pyridyl)-4-thiazolyl]-5-quinolinecarboxamide;.
3-[2-(2-ethyl-4-pyridyl)-1,3-thiazol-4-yl]hydroquinolin-2-one;
3-[2-(6-oxo-3-hydropyridyl)-1,3-thiazol-4-yl]hydroquinolin-2-one;
6-chloro-3-(2-(4-pyridyl)(1,3-thiazol-4-yl))hydroquinolin-2-one;
3-[2-(4-pyridyl)-4-thiazolyl]-6,7-(methylenedioxyl)-2(1H)-quinolinone;
3-[2-(4-pyridyl)-4-thiazolyl]-4-amino-6,7-dimethoxy-2(1H)-quinolinone;
3-[2-(3-oyridyl)-4-thiazolyl]-4-amino-6,7-dimethoxy-2(1H)-quinolinone;
3-[2-(4-pyridyl)-4-thiazolyl]-4-amino-6-chloro-2(1H)-quinolinone;
3-[2-(4-pyridyl)-4-thiazolyl]-4-amino-6-(4-methyl-1-piperazinyl)-2(1H)-quinolinone;
3-[2-(2-ethyl(4-pyridyl))(1,3-thiazol-4-yl)]-6-fluorohydroquinolin-2-one;
6-fluoro-3-(2-(4-pyridyl)(1,3-thiazol-4-yl))hydroquinolin-2-one;
3-(2-(4-pyridyl)(1,3-thiazol-4-yl))-7-(trifluoromethyl)hydroquinolin-2-one;
3-[2-(2,6-dichlorophenyl)-1,3-thiazol-4-yl]hydroquinolin-2-one;
3-(2-(2,3-dihydrobenzo[b]furan-5-yl)-1,3-thiazol-4-yl)hydroquinolin-2-one;
3-(2-(3-thienyl)-1,3-thiazol-4-yl)hydroquinolin-2-one;
3-[2-(3,5-dichloro-4-pyridyl)-1,3-thiazol-4-yl]hydroquinolin-2-one;
3-{2-[(2-pyridylsulfonyl)methyl]-1,3-thiazol-4-yl}hydroquinolin-2-one;
3-{2-([(2-furylmethyl)sulfonyl]methyl}-1,3-thiazol-4-yl)hydroquinolin-2-one;
3-{2-[({[3-(trifluoromethyl)phenyl]methyl}sulfonyl)-methyl]-1,3-thiazol-4-yl}hydroquinolin-2-one;
3-[2-({[(4-fluorophenyl)methyl]sulfonyl}methyl)-1,3-thiazol-4-yl]hydroquinolin-2-one;
3-(2-(2-thienyl)-1,3-thiazol-4-yl)hydroquinolin-2-one;
3-(2-{[(4-chlorophenyl)sulfonyl]methyl}-1,3-thiazol-4-yl)hydroquinolin-2-one;
3-{2-[(2-thienylsulfonyl)methyl]-1,3-thiazol-4-yl}hydroquinolin-2-one;
3-{2-[(methylsulfonyl)methyl]-1,3-thiazol-4-yl}hydroquinolin-2-one;
3-{2-[(phenylsulfonyl)methyl]-1,3-thiazol-4-yl}hydroquinolin-2-one;
3-[2-(2-pyridylamino)-1,3-thiazol-4-yl]hydroquinolin-2-one hydrobromide;
3-[2-(3-pyridylamino)-1,3-thiazol-4-yl]hydroquinolin-2-one hydrobromide;
N-methyl-N-(4-(2-oxo-1,2-dihydro-3-quinolinyl)-1,3-thiazol-2-yl)benzenesulfonamide;
7-(Hydroxymethyl)-3-(2-((phenylsulfonyl)methyl)-1,3-thiazol-4-yl)-2(1H)-quinolinone;
3-(2-(3-Pyridinyl)-1,3-thiazol-4-yl)-7-(trifluoromethyl)-2(1H)-quinolinone;

3-(2-(1,3-Benzodioxol-5-yl)-1,3-thiazol-4-yl)-7-(trifluoromethyl)-2(1H)-quinolinone;
3-(2-Phenylthiomethyl-thiazol-4-yl)-1H-quinolin-2-one;
3-(2-Benzenesulfinylmethyl-thiazol-4-yl)-1H-quinolin-2-one;
N-Allyl-N-[4-(2-oxo-1,2-dihydro-quinolin-3-yl)-thiazol-2-yl]-benzenesulfonamide;
4-Bromo-N-methyl-N-[4-(2-oxo-1,2-dihydro-quinolin-3-yl)-thiazol-2-yl]-benzenesulfonamide;
3-Fluoro-N-methyl-N-[4-(2-oxo-1,2-dihydro-quinolin-3-yl)-thiazol-2-yl]-benzenesulfonamide;
N,1-Dimethyl-N-(4-(2-oxo-1,2-dihydro-3-quinolinyl)-1,3-thiazol-2-yl)-1H-imidazole-4-sulfonamide;
7-((4-Methyl-1-piperazinyl)carbonyl)-3-(2-((phenylsulfonyl)methyl)-1,3-thiazol-4-yl)-2(1H)-quinolinone;
3-(2-((Phenylsulfonyl)methyl)-1,3-thiazol-4-yl)-7-(1-piperidinylcarbonyl)-2(1H)-quinolinone
7-(Methoxy)-3-(2-((phenylsulfonyl)methyl)-1,3-thiazol-4-yl)-2(1H)-quinolinone;
3-(2-(1-Methyl-1-(phenylsulfonyl)ethyl)-1,3-thiazol-4-yl)-2(1H)-quinolinone;
3-(2-(1-Methyl-1-(phenylsulfonyl)ethyl)-1,3-thiazol-4-yl)-7-(trifluoromethyl)-2(1H)-quinolinone;
7-(4-Morpholinylcarbonyl)-3-(2-((phenylsulfonyl)methyl)-1,3-thiazol-4-yl)-2(1H)-quinolinone;
7-hydroxy-3-(2-((phenylsulfonyl)methyl)-1,3-thiazol-4-yl)-2(1H)-quinolinone;
7-(Methoxy)-3-(2-(1-methyl-1-(phenylsulfonyl)ethyl)-1,3-thiazol-4-yl)-2(1H)-quinolinone;
7-(((2R)-2-(((1-Methylethyl)amino)methyl)-1-pyrrolidinyl)methyl)-3-(2-((phenylsulfonyl)methyl)-1,3-thiazol-4-yl)-2(1H)-quinolinone;
7-(((3S)-3-(1-Methylethyl)-1-piperazinyl)methyl)-3-(2-((phenylsulfonyl)methyl)-1,3-thiazol-4-yl)-2(1H)-quinolinone;
7-((4-Methyl-1-piperazinyl)methyl)-3-(2-((phenylsulfonyl)methyl)-1,3-thiazol-4-yl)-2(1H)-quinolinone;
7-((3,5-Dimethyl-1-piperidinyl)methyl)-3-(2-((phenylsulfonyl)methyl)-1,3-thiazol-4-yl)-2(1H)-quinolinone;
7-((3-Methyl-1-piperidinyl)methyl)-3-(2-((phenylsulfonyl)methyl)-1,3-thiazol-4-yl)-2(1H)-quinolinone;
7-((3-methyl-1-piperazinyl)methyl)-3-(2-((phenylsulfonyl)methyl)-1,3-thiazol-4-yl)-2(1H)-quinolinone;
7-(3,6-Dihydro-1(2H)-pyridinylmethyl)-3-(2-((phenylsulfonyl)methyl)-1,3-thiazol-4-yl)-2(1H)-quinolinone;
7-((3,5-Dimethyl-1-piperazinyl)methyl)-3-(2-((phenylsulfonyl)methyl)-1,3-thiazol-4-yl)-2(1H)-quinolinone;
7-(((2-(Diethylamino)ethyl)(methyl)amino)methyl)-3-(2-((phenylsulfonyl)methyl)-1,3-thiazol-4-yl)-2(1H)-quinolinone;
7-((Methyl(1-methylethyl)amino)methyl)-3-(2-((phenylsulfonyl)methyl)-1,3-thiazol-4-yl)-2(1H)-quinolinone;
3-(2-((Phenylsulfonyl)methyl)-1,3-thiazol-4-yl)-7-(1-piperidinylmethyl)-2(1H)-quinolinone;
3-(2-((Phenylsulfonyl)methyl)-1,3-thiazol-4-yl)-7-(1-pyrrolidinylmethyl)-2(1H)-quinolinone;
7-((Diethylamino)methyl)-3-(2-((phenylsulfonyl)methyl)-1,3-thiazol-4-yl)-2(1H)-quinolinone;
7-((2,6-Dimethyl-4-morpholinyl)methyl)-3-(2-((phenylsulfonyl)methyl)-1,3-thiazol-4-yl)-2(1H)-quinolinone;
7-((4-Methyl-1-piperazinyl)carbonyl)-3-(2-(4-pyridinyl)-1,3-thiazol-4-yl)-2(1H)-quinolinone;
7-(3-Methyl-piperidin-1-ylmethyl)-3-(2-pyridin-4-yl-thiazol-4-yl)-1H-quinolin-2-one;
7-[(Isopropyl-methyl-amino)-methyl]-3-(2-pyridin-4-yl-thiazol-4-yl)-1H-quinolin-2-one;
2-Oxo-3-2-pyridin-4-yl-thiazol-4-yl)-1,2-dihydro-quinoline-7-carboxylic acid (2-dimethylamino-ethyl)-ethyl-amide;
7-(Piperidine-1-carbonyl)-3-(2-pyridin-4-yl-thiazol-4-yl)-1H-quinolin-2-one;
3-(2-(2-Chloro-4-pyridinyl)-1,3-thiazol-4-yl)-7-(methoxy)-2(1H)-quinolinone;
Methyl 3-(2-(methyl(phenylsulfonyl)amino)-1,3-thiazol-4-yl)-2-oxo-1,2-dihydro-7-quinolinecarboxylate;
3-(2-(Methyl(phenylsulfonyl)amino)-1,3-thiazol-4-yl)-2-oxo-1,2-dihydro-7-quinolinecarboxylic acid;
N-Methyl-N-{4-[7-(4-methyl-piperazine-1-carbonyl)-2-oxo-1,2-dihydro-quinolin-3-yl]-thiazol-2-yl}-benzenesulfonamide;
3-[2-(Benzenesulfonyl-methyl-amino)-thiazol-4-yl]-2-oxo-1,2-dihydro-quinoline-7-carboxylic acid ethylamide;
N,N-Diethyl-3-(2-(methyl(phenylsulfonyl)amino)-1,3-thiazol-4-yl)-2-oxo-1,2-dihydro-7-quinolinecarboxamide;
7-(Isopropylamino-methyl)-3-(2-pyridin-4-yl-thiazol-4-yl)-1H-quinolin-2-one;
3-(2-Pyridin-4-yl-thiazol-4-yl)-7-pyrrolidin-1-ylmethyl-1H-quinolin-2-one;
7-Diethylaminomethyl-3-(2-pyridin-4-yl-thiazol-4-yl)-1H-quinolin-2-one;
7-Azetidin-1-ylmethyl-3-(2-pyridin-4-yl-thiazol-4-yl)-1H-quinolin-2-one;
7-(3-Hydroxy-pyrrolidin-1-ylmethyl)-3-(2-pyridin-4-yl-thiazol-4-yl)-1H-quinolin-2-one;
7-((3-(Dimethylamino)propyl)oxy)-3-(2-(4-pyridinyl)-1,3-thiazol-4-yl)-2(1H)-quinolinone;
7-((2-(Dimethylamino)ethyl)oxy)-3-(2-(4-pyridinyl)-1,3-thiazol-4-yl)-2(1H)-quinolinone;
7-((2-(4-morpholinyl)ethyl)oxy)-3-(2-(4-pyridinyl)-1,3-thiazol-4-yl)-2(1H)-quinolinone;
7-(4-Hydroxy-piperidin-1-ylmethyl)-3-(2-pyridin-4-yl-thiazol-4-yl)-1H-quinolin-2-one;
7-(2,6-Dimethyl-morpholin-4-ylmethyl)-3-(2-pyridin-4-yl-thiazol-4-yl)-1H-quinolin-2-one;
7-(3,5-Dimethyl-piperidin-1-ylmethyl)-3-(2-pyridin-4-yl-thiazol-4-yl)-1H-quinolin-2-one;
7-Morpholin-4-ylmethyl-3-(2-pyridin-4-yl-thiazol-4-yl)-1H-quinolin-2-one;
7-(3-Hydroxy-piperidin-1-ylmethyl)-3-(2-pyridin-4-yl-thiazol-4-yl)-1H-quinolin-2-one;
7-{[(2-Diethylamino-ethyl)-methyl-amino]-methyl}-3-(2-pyridin-4-yl-thiazol-4-yl)-1H-quinolin-2-one;
7-Cyclopentylaminomethyl-3-(2-pyridin-4-yl-thiazol-4-yl)-1H-quinolin-2-one;
7-(3-Methyl-piperazin-1-ylmethyl)-3-(2-pyridin-4-yl-thiazol-4-yl)-1H-quinolin-2-one;
7-{[(2-Dimethylamino-ethyl)-ethyl-amino]-methyl}-3-(2-pyridin-4-yl-thiazol-4-yl)-1H-quinolin-2-one;
7-(Isobutylamino-methyl)-3-(2-pyridin-4-yl-thiazol-4-yl)-1H-quinolin-2-one; and
7-[(1-Hydroxymethyl-2-methyl-propylamino)-methyl]-3-(2-pyridin-4-yl-thiazol-4-yl)-1H-quinolin-2-one.

16. A compound of claim 1 having Formula III

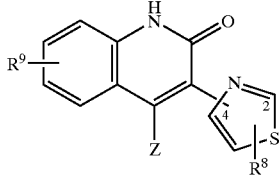

III wherein Z is selected from H, amino, hydroxy and phenyl;
wherein $R^8$ is selected from pyridyl, pyrazinyl, pyrimidinyl and pyridazinyl; wherein $R^8$ is unsubstituted or substituted with one or more substituents selected from chloro, fluoro, —$NH_2$, —OH, —$CO_2H$, ($C_1$–$C_2$) alkylamino, ($C_1$–$C_2$)alkyl, di($C_1$–$C_2$)alkylamino, ($C_1$–$C_2$)alkylamino($C_1$–$C_2$)alkyl, hydroxy-($C_1$–$C_2$) alkylamino, 5–6-membered heterocyclyloxy, 5–6-membered heterocyclyl-($C_1$–$C_2$)alkoxy, [($C_1$–$C_2$) alkoxy]$_{1-3}$, phenyl, pyrrolidinyl, piperazinyl, piperidinyl, morpholinyl and azetidinyl;
wherein $R^9$ is one or more substituents selected from H, —$OR^{11}$, chloro, fluoro, phenyl, —$N(R^{11})_2$, —($C_1$–$C_2$) alkyl-$N(R^{11})_2$, —$S(O)_n$—$N(R^{11})_2$, —$S(O)_nR^{11}$, ($C_1$–$C_4$)alkyl, ($C_3$–$C_6$)cycloalkyl, hydroxy-($C_1$–$C_4$)-alkylamino, ($C_1$–$C_2$)-alkylamino-($C_1$–$C_2$)-alkylamino, ($C_1$–$C_2$)-alkylamino-($C_1$–$C_2$)-alkoxy, optionally substituted heterocyclyl selected from pyrrolidinyl, piperazinyl, piperidinyl, and morpholinyl, —$C(O)R^{11}$, —$NR^{11}SO_2R^{11}$, —$C(O)N(R^{11})_2$, —$CO_2R^{11}$, optionally substituted benzyl, optionally substituted 4–6 membered heterocyclyl-$C_1$–$C_2$-alkyl, —$NR^{11}C(O)R^{11}$ and —$NR^{11}CO_2R^{11}$;
wherein $R^{11}$ is selected from H, ($C_1$–$C_6$)alkyl, optionally substituted phenyl, optionally substituted phenyl-($C_1$–$C_4$)alkyl, optionally substituted 4–6 membered heterocyclyl, optionally substituted 4–6 membered heterocyclyl-($C_1$–$C_4$)alkyl, $C_3$–$C_6$ cycloalkyl, $C_3$–$C_6$ cycloalkyl-($C_1$–$C_4$)alkyl and ($C_1$–$C_2$)haloalkyl;
wherein n is 0, 1 or 2; and
wherein each alkyl, phenyl, cycloalkyl, and heterocyclyl moiety is optionally substituted with one or more groups selected from halo, —$NH_2$, —OH, —$CO_2H$, ($C_1$–$C_4$)alkylamino, ($C_1C_4$)alkyl, di($C_1$–$C_4$) alkylamino, ($C_1$–$C_4$)haloalkyl, pyrrolidinyl, piperazinyl, piperidinyl, morpholinyl, and azetidinyl;
and pharmaceutically acceptable derivatives thereof
provided $R^8$ is attached at thiazole ring position 2 or 4, and the quinolinone ring is attached at the other of thiazole ring positions 2 or 4.

17. Compound of claim 16 wherein Z is selected from H, amino and phenyl; wherein $R^8$ is unsubstituted pyridyl or pyridyl substituted with one or more substituents selected from chloro, fluoro, —$NH_2$, —OH, —$CO_2H$, methylamino, methyl, ethyl, diethyl-amino, pyrrolidinyl, piperazinyl, piperidinyl, morpholinyl and azetidinyl; and wherein $R^9$ is one or more radicals selected from H, cyclopropylmethylamino, 3-hydroxypropylamino, 2-(piperidin-1-yl)ethylamino, 2-(pyrrolidin-1-yl) ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino) ethylamino, aminomethyl, dimethylaminoethyl, isopropylaminomethyl, diethylaminomethyl, N-methyl-N-(isopropyl)aminomethyl, N-methyl-N-(diethylaminoethyl) aminomethyl, N-ethyl-N-(dimethylaminoethyl) aminomethyl, (1-hydroxymethyl-2-methylpropyl)amino, cyclopentylaminomethyl, 2-(dimethylamino)ethoxy, 3-(dimethylamino)propoxy, 2-(methylamino)ethoxy, ((2R) pyrrolidin-2-yl)methoxy, ((2R)-1-methylpyrrolidin-2-yl) methoxy, 2-(piperid-1-yl)ethoxy, 2-(piperazin-1-yl)ethoxy, 2-(morpholin-4-yl)ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4-ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl; and pharmaceutically acceptable derivatives thereof.

18. Compound of claim 16 wherein $R^8$ is 4-pyridyl or 3-pyridyl; wherein $R^8$ is unsubstituted or substituted.

19. Compound of claim 16 wherein Z is H.

20. Compound of claim 16 wherein $R^8$ is 4-pyridyl.

21. Compound of claim 16 wherein the $R^8$ substituent is attached at thiazole ring position 2 and the quinolinone ring is attached at thiazole ring position 4.

22. Compound of claim 16 wherein the $R^8$ substituent is attached at thiazole ring position 4 and the quinolinone ring is attached at thiazole ring position 2.

23. Compound of claim 16 wherein $R^9$ is attached at quinolinone ring position 7.

24. A compound of claim 1 having Formula IV

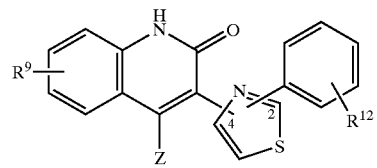

IV wherein Z is selected from H, amino and phenyl;
wherein $R^9$ is one or more substituents selected from H, —$OR^{11}$, chloro, fluoro, phenyl, —$N(R^{11})_2$, —($C_1$–$C_2$) alkyl-$N(R^{11})_2$, —$S(O)_n$—$N(R^{11})_2$, —$S(O)_nR^{11}$, ($C_1$–$C_4$)alkyl, ($C_3$–$C_6$)cycloalkyl, hydroxy-($C_1$–$C_4$)-alkylamino, ($C_1$–$C_2$)-alkylamino-($C_1$–$C_2$)-alkylamino, ($C_1$–$C_2$)-alkylamino-($C_1$–$C_2$)-alkoxy, optionally substituted heterocyclyl selected from pyrrolidinyl, piperazinyl, piperidinyl, and morpholinyl, —$C(O)R^{11}$, —$NR^{11}SO_2R^{11}$, —$C(O)N(R^{11})_2$, —$CO_2R^{11}$, optionally substituted benzyl, optionally substituted 4–6 membered heterocyclyl-$C_1$–$C_2$-alkyl, —$NR^{11}C(O)R^{11}$ and —$NR^{11}CO_2R^{11}$;

wherein R¹¹ is selected from H, (C₁–C₆)alkyl, optionally substituted phenyl, optionally substituted phenyl-(C₁–C₄)alkyl, optionally substituted 4–6 membered heterocyclyl, optionally substituted 4–6 membered heterocyclyl-(C₁–C₄)alkyl, C₃–C₆ cycloalkyl, C₃–C₆ cycloalkyl-(C₁–C₄)alkyl and (C₁–C₂)haloalkyl;

wherein R¹² is one or more substituents selected from H, hydroxyl, halo, aryl, (C₂–C₄)alkynyl, (C₂–C₄)alkenyl, —OR¹¹, —O—C₁₋₂-alkyl-O—, —N(R¹¹)₂, —(C₁–C₄)alkyl-N(R¹¹)₂, lower alkoxyalkyl, R¹¹—SO₂—, (C₁–C₄)alkyl, cyano, nitro, lower cyanoalkyl, lower haloalkyl, lower hydroxyalkyl, lower aminoalkyl, lower alkylaminoalkyl, lower alkylaminoalkoxy, lower aminoalkoxyalkyl (C₃–C₆)cycloalkyl, optionally substituted 4–6 membered heterocyclyl, optionally substituted phenoxyalkyl, optionally substituted heterocyclyloxyalkyl, —SO₂NR¹¹R¹¹, —NR¹¹SO₂R¹¹, —C(O)N(R¹¹)₂, —CO₂R¹¹, —CO₂NR¹¹R¹¹, —SO₂NHC(O)R¹¹, optionally substituted phenyl-(C₁–C₄)alkyl, optionally substituted heterocyclyl-(C₁–C₄)alkyl, —NR¹¹C(O)N(R¹¹)₂, —NR¹¹C(O)R¹¹, —NR¹¹CO₂R¹¹ and —C(O)R¹¹;

wherein n is 0, 1 or 2; and wherein each alkyl, phenyl, cycloalkyl, and heterocyclyl moiety is optionally substituted with one or more groups selected from halo, —NH₂, —OH, —CO₂H, (C₁–C₄)alkylamino, (C₁–C₄)alkyl, di(C₁–C₄)alkylamino, (C₁–C₄)haloalkyl, pyrrolidinyl, piperazinyl, piperidinyl, morpholinyl, and azetidinyl;

provided the compound of Formula IV is not 6-methoxy-3-(2-phenyl-thiazol-4-yl)-1H-quinolin-2-one, 3-(2-phenyl-thiazol-4-yl)-1H-quinolin-2-one, 3-(4-(3,4-dihydroxyphenyl)thiazol-2-yl)-1H-quinolin-2-one or 3-(2-(3,4-dimethoxyphenyl)thiazol-4-yl)-1H-quinolin-2-one;

and pharmaceutically acceptable derivatives thereof.

25. Compound of claim 24 wherein Z is H or amino;

wherein R⁹ is one or more radicals selected from H, cyclopropylmethylamino, 3-hydroxypropylamino, 2-(piperidin-1-yl)ethylamino, 2-(pyrrolidin-1-yl)ethylamino, 2-(morpholin-4-yl)ethylamino, 3-(piperidin-1-yl)propylamino, 3-(pyrrolidin-1-yl)propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino)ethylamino, aminomethyl, dimethylaminoethyl, isopropylaminomethyl, diethylaminomethyl, N-methyl-N-(isopropyl)aminomethyl, N-methyl-N-(diethylaminoethyl)aminomethyl, N-ethyl-N-(dimethylaminoethyl)aminomethyl, (1-hydroxymethyl-2-methylpropyl)amino, cyclopentylaminomethyl, 2-(dimethylamino)ethoxy, 3-(dimethylamino)propoxy, 2-(dimethylamino)ethoxy, ((2R)pyrrolidin-2-yl)methoxy, ((2R)-1-methylpyrrolidin-2-yl)methoxy, 2-(piperid-1-yl)ethoxy, 2-(piperazin-1-yl)ethoxy, 2-(morpholin-4-yl)ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4-ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl; and wherein R¹² is one or more radicals selected from H, hydroxyl, chloro, fluoro, methoxy, —OCH₂O—, amino, aminomethyl, methylsulfonyl, methyl, cyano, trifluoromethyl and pyrrolyl; and pharmaceutically acceptable derivatives thereof.

26. Compound of claim 24 wherein Z is H.

27. Compound of claim 24 wherein the phenyl substituent is attached at thiazole ring position 2 and the quinolinone ring is attached at thiazole ring position 4.

28. Compound of claim 24 wherein the phenyl substituent is attached at thiazole ring position 4 and the quinolinone ring is attached at thiazole ring position 2.

29. Compound of claim 24 wherein R⁹ is attached at quinolinone ring position 7.

30. A compound of claim 1 having Formula V

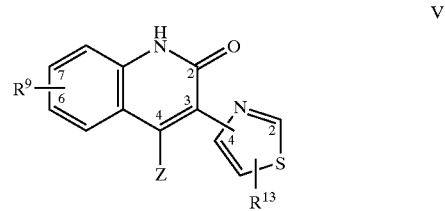

wherein Z is selected from H, amino, hydroxyl and phenyl;

wherein R⁹ is one or more substituents selected from H, —OR¹¹, chloro, fluoro, phenyl, —N(R¹¹)₂, —(C₁–C₂)alkyl-N(R¹¹)₂, —S(O)ₙ—N(R¹¹)₂, —S(O)ₙR¹¹, (C₁–C₄)alkyl, (C₃–C₆)cycloalkyl, hydroxy-(C₁–C₄)-alkylamino, (C₁–C₂)-alkylamino-(C₁–C₂)-alkylamino, (C₁–C₂)-alkylamino-(C₁–C₂)-alkoxy, optionally substituted heterocyclyl selected from pyrrolidinyl, piperazinyl, piperidinyl, and morpholinyl, —C(O)R¹¹, —NR¹¹SO₂R¹¹, —C(O)N(R¹¹)₂, —CO₂R¹¹, optionally substituted benzyl, optionally substituted 4–6 membered heterocyclyl-C₁–C₂-alkyl, —NR¹¹C(O)R¹¹ and —NR¹¹CO₂R¹¹;

wherein R¹¹ is selected from H, (C₁–C₆)alkyl, optionally substituted phenyl, optionally substituted phenyl-(C₁–C₄)alkyl, optionally substituted 4–6 membered heterocyclyl, optionally substituted 4–6 membered heterocyclyl-(C₁–C₄)alkyl, C₃–C₆ cycloalkyl, C₃–C₆ cycloalkyl-(C₁–C₄)alkyl and (C₁–C₂)haloalkyl;

wherein R¹³ is selected from amino, 5–6-membered heteroarylamino, R¹¹sulfonyl-C₁₋₃-alkyl and N—(R¹¹sulfonyl)-N—(R¹⁴) amino;

wherein R¹⁴ is C₁₋₂ alkyl;

wherein n is 0, 1 or 2; and wherein each alkyl, phenyl, cycloalkyl, and heterocyclyl moiety is optionally substituted with one or more groups selected from halo, —NH₂, —OH, —CO₂H, (C₁–C₄)alkylamino, (C₁–C₄)alkyl, di(C₁–C₄)alkylamino, (C₁–C₄)haloalkyl, pyrrolidinyl, piperazinyl, piperidinyl, morpholinyl, and azetidinyl;

and pharmaceutically acceptable derivatives thereof.

31. Compound of claim 30 wherein Z is H or amino; wherein $R^9$ is one or more radicals selected from H, cyclopropylmethylamino, 3-hydroxypropylamino, 2-(piperidin-1-yl)ethylamino, 2-(pyrrolidin-1-yl) ethylamino, 2-(morpholin-4-yl)ethylamino, 3-(piperidin-1-yl)propylamino, 3-(pyrrolidin-1-yl) propylamino, 3-(morpholin-4-yl)propylamino, N-methyl-N-(2-piperid-1-ylethyl)amino, N-methyl-N-(2-pyrrolidin-1-ylethyl)amino, N-methyl-N-(2-morpholin-4-ylethyl)amino, ((2S)-2-amino-3-phenylpropyl)amino, 4-methylpiperazin-1-ylamino, N-methyl-N-((tetrahydrofur-2-yl)methyl)amino, (4-piperidylmethyl)amino, amino, methylamino, (2-methylbutyl)amino, diethylamino, (diethylamino) ethylamino, aminomethyl, dimethylaminoethyl, isopropylaminomethyl, diethylaminomethyl, N-methyl-N-(isopropyl)aminomethyl, N-methyl-N-(diethylaminoethyl)aminomethyl, N-ethyl-N-(dimethylaminoethyl)aminomethyl, (1-hydroxymethyl-2-methylpropyl)amino, cyclopentylaminomethyl, 2-(dimethylamino)ethoxy, 3-(dimethylamino)propoxy, 2-(methylamino)ethoxy, ((2R)pyrrolidin-2-yl)methoxy, ((2R)-1-methylpyrrolidin-2-yl)methoxy, 2-(piperid-1-yl) ethoxy, 2-(piperazin-1-yl)ethoxy, 2-(morpholin-4-yl) ethoxy, hydroxy, benzyloxy, methoxy, chloro, fluoro, phenyl, aminosulfonyl, piperazinylsulfonyl, methylthio, methylsulfonyl, methyl, cyclopropyl, pyrrolidinyl, piperazinyl, piperidin-1-yl, morpholinyl, 4-methylpiperazin-1-yl, 3-aminopyrrolidin-1-yl, 3,5-dimethylpiperazin-1-yl, methylcarbonyl, phenylcarbonyl, piperidin-1-ylcarbonyl, 4-methylpiperazin-1-ylcarbonyl, morpholin-4-ylcarbonyl, trifluoromethyl, hydroxymethyl, hydroxyethyl, diethylaminocarbonyl, ethylaminocarbonyl, methoxycarbonyl, carboxy, optionally substituted benzyl, piperazinylmethyl, azetidin-1-ylmethyl, pyrrolidin-1-ylmethyl, 3-hydroxypyrrolidin-1-ylmethyl, 4-methylpiperazin-1-ylmethyl, 3-methylpiperazin-1-ylmethyl, 3,5-dimethylpiperazin-1-ylmethyl, 3-isopropylpiperazin-1-ylmethyl, 3,6-dihydropyridin-1-ylmethyl, 3-methylpiperidin-1-ylmethyl, 3,5-dimethylpiperidin-1-ylmethyl, 3-hydroxypiperidin-1-ylmethyl, 4-hydroxypiperidin-1-ylmethyl, piperidin-1-ylmethyl, 2,6-dimethylmorpholin-4-ylmethyl and morpholin-4-ylmethyl; and wherein $R^{13}$ is selected from amino, 2-pyridylamino, 3-pyridylamino, 4-pyridylamino, phenylsulfonylamino, N-methyl-N-(3-fluorobenzylsulfonyl amino, N-methyl-N-(2-pyridylsulfonyl)amino, N-methyl-N-(3-pyridylsulfonyl)amino, N-methyl-N-(4-pyridylsulfonyl)amino, N-methyl-N-(2-thienylsulfonyl)amino, N-methyl-N-(phenylsulfonyl) amino, N-methyl-N-(1-methylimidazol-4-ylsulfonyl) amino, 2-pyridylsulfonylmethyl, 3-pyridylsulfonylmethyl, 4-pyridylsulfonylmethyl, 2-thienylsulfonylmethyl, phenylsulfonylmethyl, 1-phenylsulfonyl-1-methylethyl, 2-furylmethylsulfonylmethyl, 3-trifluoromethylphenylmethyl-sulfonylmethyl, methylsulfonylmethyl, tert-butylsulfonylmethyl, 4-fluorophenyl-methylsulfonylmethyl and 4-chlorophenyl-methylsulfonylmethyl; and pharmaceutically acceptable derivatives thereof.

32. Compound of claim 30 wherein Z is H.

33. Compound of claim 30 wherein the $R^{13}$ substituent is attached at thiazole ring position 2 and the quinolinone ring is attached at thiazole ring position 4.

34. Compound of claim 30 wherein the $R^{13}$ substituent is attached at thiazole ring position 4 and the quinolinone ring is attached at thiazole ring position 2.

35. Compound of claim 30 wherein $R^{13}$ is phenylsulfonylmethyl.

36. Compound of claim 30 wherein $R^{13}$ is N-methyl-N-(phenylsulfonyl)amino.

37. Compound of claim 30 wherein $R^9$ is attached at quinolinone ring position 7.

38. A pharmaceutically acceptable salt of a compound of claim 1.

39. A pharmaceutical composition comprising a pharmaceutically acceptable carrier and a compound of claim 1.

40. Compound of claim 5, wherein Ar is selected from

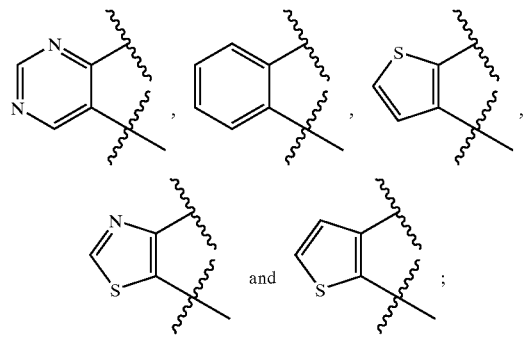

and and pharmaceutically acceptable derivatives thereof.

41. Compound of claim 5 wherein Ar is

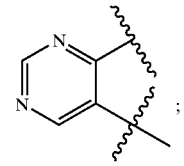

and pharmaceutically acceptable derivatives thereof.

42. Compound of claim 5 wherein Ar is phenyl; and pharmaceutically acceptable derivatives thereof.

43. Compound of claim 5 wherein Ar is selected from,

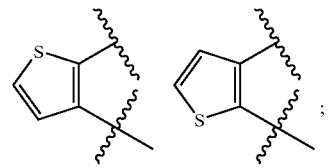

and pharmaceutically acceptable derivatives thereof.

44. Compound of claim 5 wherein Ar is

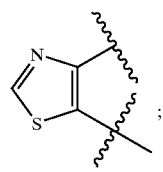

and pharmaceutically acceptable derivatives thereof.

* * * * *